US012465603B2

(12) United States Patent
Ahmad et al.

(10) Patent No.: US 12,465,603 B2
(45) Date of Patent: Nov. 11, 2025

(54) PHTHALAZINONE BASED MODULATORS FOR THE TREATMENT OF DISEASE

(71) Applicant: Soley Therapeutics, Inc., South San Francisco, CA (US)

(72) Inventors: Nadia Mamoona Ahmad, Essex (GB); Christopher Charles Rennie, Essex (GB); William Rameshchandra Krishna Esmieu, Saffron Walden (GB); Mark Chambers, Saffron Walden (GB); Toby Jonathan Blench, Essex (GB); Susan Mary Cramp, Essex (GB); Toby Matthew Grover Mullins, Essex (GB); Terry Aaron Panchal, Essex (GB); Joseph Leo Mckenna, Essex (GB)

(73) Assignee: SOLEY THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 18/770,015

(22) Filed: Jul. 11, 2024

(65) Prior Publication Data

US 2024/0374589 A1 Nov. 14, 2024

Related U.S. Application Data

(63) Continuation of application No. PCT/US2023/080304, filed on Nov. 17, 2023.

(60) Provisional application No. 63/426,670, filed on Nov. 18, 2022.

(51) Int. Cl.

| | |
|---|---|
| ***C07D 237/32*** | (2006.01) |
| ***A61K 31/502*** | (2006.01) |
| ***A61K 31/5025*** | (2006.01) |
| ***A61K 31/506*** | (2006.01) |
| ***C07D 401/06*** | (2006.01) |
| ***C07D 401/12*** | (2006.01) |
| ***C07D 403/12*** | (2006.01) |
| ***C07D 405/04*** | (2006.01) |
| ***C07D 413/12*** | (2006.01) |
| ***C07D 471/04*** | (2006.01) |

(52) U.S. Cl.

CPC ........ *A61K 31/5025* (2013.01); *A61K 31/502* (2013.01); *A61K 31/506* (2013.01); *C07D 237/32* (2013.01); *C07D 401/06* (2013.01); *C07D 401/12* (2013.01); *C07D 403/12* (2013.01); *C07D 405/04* (2013.01); *C07D 413/12* (2013.01); *C07D 471/04* (2013.01)

(58) Field of Classification Search

CPC ... C07D 237/32; C07D 401/12; C07D 413/12

See application file for complete search history.

(56) References Cited

FOREIGN PATENT DOCUMENTS

| | | | |
|---|---|---|---|
| EP | 1664023 | B1 | 8/2008 |
| WO | WO-2022051569 | A1 | 3/2022 |
| WO | WO-2024108131 | A1 | 5/2024 |

OTHER PUBLICATIONS

RN 1054065-32-5, Registry of STNext, 2008.*
RN 1054063-96-5, Registry of STNext, 2008.*
RN 1054026-39-9, Registry of STNext, 2008.*
1054025-99-8, Registry of STNext, 2008.*
RN 1952684-17-1 in Registry of STNext. Registry of STNext, 2016.*
Ballell et al., Fueling Open-Source Drug Discovery: 177 Small-Molecule Leads against Tuberculosis. ChemMedChem 8:313-321 (2013).
Deodhar K. D. et al., A convenient synthesis of some phthalazine derivatives from azocoupled homophthalic anhydride. Synthesis 421-422 (1983).
Giannini, Giuseppe, et al. Novel PARP-1 inhibitors based on a 2-propanoyl-3H-quinazolin-4-one scaffold. Bioorganic & Medicinal Chemistry Letters, vol. 24, No. 2, 462-466 (2013).
PCT/US2023/080304 International Search Report and Written Opinion dated Mar. 25, 2024.

* cited by examiner

*Primary Examiner* — Brian E Mcdowell
(74) *Attorney, Agent, or Firm* — WILSON SONSINI GOODRICH & ROSATI

(57) ABSTRACT

The disclosure herein provides compounds and pharmaceutical compositions of Formula (II)

(II)

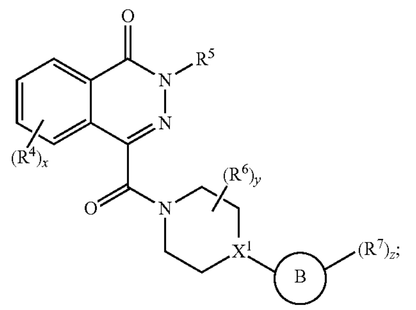

for killing a cancer cell or inhibiting cancer cell proliferation. Further, the compounds and pharmaceutical compositions of Formula (II) are useful in methods for the inhibition of cancer cell proliferation.

10 Claims, No Drawings

PHTHALAZINONE BASED MODULATORS FOR THE TREATMENT OF DISEASE

CROSS-REFERENCE

This application is a continuation of International Application No. PCT/US2023/080304, filed on Nov. 17, 2023, which claims the benefit of U.S. Provisional Application No. 63/426,670 filed on Nov. 18, 2022, each of which is hereby incorporated by reference in its entirety.

BACKGROUND OF THE INVENTION

In 2020, there were an estimated 19.3 million new cancer cases around the world. This number is expected to increase to 30.2 million by 2040. In 2022, there will be an estimated 1.9 million new cancer cases diagnosed and 609,360 cancer deaths in the United States. Although medical advances have improved cancer survival rates, certain patient populations and particular cancers still require further research. Thus, there exists an unmet need for new and more effective treatments for cancer patients.

SUMMARY OF THE INVENTION

In some aspects, the present disclosure provides a compound represented by the structure of Formula (I):

(I)

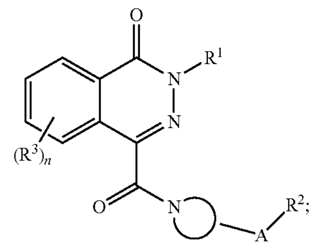

or a pharmaceutically acceptable salt thereof wherein:

$R^1$ is selected from (i) and (ii):

(i) $C_{1-6}$ alkyl optionally substituted with one or more substituents independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN; and (ii) optionally substituted $C_{3-10}$ saturated carbocycle and optionally substituted 3- to 10-membered heterocycle, wherein the optional substituents are independently selected from:

halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN; and $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN;

$R^2$ is selected from hydrogen, optionally substituted $C_{3-10}$ saturated carbocycle, and optionally substituted 3- to 10-membered heterocycle, wherein the optional substituents are independently selected from:

halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN; and $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, $OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN;

wherein at least one of $R^1$ and $R^2$ is selected from optionally substituted $C_{3-10}$ carbocycle and optionally substituted 3- to 10-membered heterocycle;

$R^3$ is independently selected at each occurrence from:

halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, and —CN; and $C_{1-6}$ alkyl optionally substituted with one or more substituents independently selected from halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, =S, =O, and —CN;

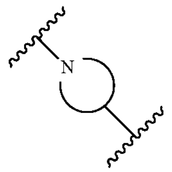

is 3- to 10-membered heterocyclene optionally substituted with one or more substituents independently selected from:

halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$ —$S(O)R^{13}$, —$S(O)_2R^{13}$, —$S(O)_2N(R^{13})_2$, —$NO_2$, and —CN; and $C_{1-6}$ alkyl optionally substituted with one or more substituents independently selected from halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, =S, =O, and —CN;

A is selected from optionally substituted $C_{3-10}$ carbocyclene and optionally substituted 3- to 10-membered heterocyclene, wherein the optional substituents are independently selected from:

halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^4$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, ═S, ═O, and —CN;

wherein when A is a 5-membered heteroaryl, the 5-membered heteroaryl includes one or more heteroatoms selected from O, S, and N, and no more than two N atoms in the ring;

$R^{10}$, $R^{11}$, $R^{12}$, $R^{13}$, and $R^{14}$ are each independently selected at each occurrence from (iii), (iv) and (v):

(iii) hydrogen;

(iv) $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN; and (v) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, ═O, and —CN; and n is selected from 0, 1, 2, 3, and 4.

In another aspect, the present disclosure provides a compound represented by the structure of Formula (II):

(II)

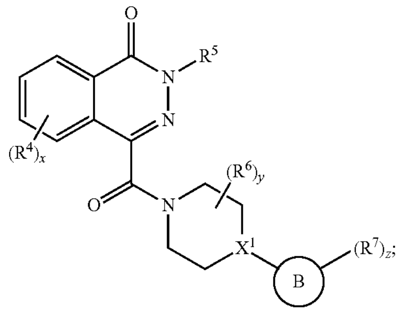

or a pharmaceutically acceptable salt thereof wherein:

$X^1$ is selected from N and $C(R^8)$;

$R^4$ is independently selected at each occurrence from (a), (b) and (c):

(a) halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, and —CN;

(b) $C_{1-6}$ alkyl optionally substituted with one or more substituents independently selected from halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, ═S, ═O, and —CN; and (c) $C_{3-10}$ carbocycle and 3- to 10-membered heterocycle, any of which is optionally substituted with one or more substituents independently selected from halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, ═S, ═O, and —CN;

$R^5$ is $C_{1-6}$ alkyl optionally substituted with one or more substituents independently selected from: halogen, —$OR^{21}$, —$SR^{21}$, —$N(R^{21})_2$, —$C(O)R^{21}$, —$C(O)OR^{21}$, —$OC(O)R^{21}$, —$OC(O)N(R^{21})_2$, —$C(O)N(R^{21})_2$, —$N(R^{21})C(O)R^{21}$, —$N(R^{21})C(O)OR^{21}$, —$N(R^{21})C(O)N(R^{21})_2$, —$N(R^{21})S(O)_2(R^{21})$, —$S(O)R^{21}$, —$S(O)_2R^{21}$, —$S(O)_2N(R^{21})_2$, —$NO_2$, ═S, ═O, and —CN;

$R^6$ is independently selected at each occurrence from:

halogen, —$OR^{22}$, —$SR^{22}$, —$N(R^{22})_2$, —$C(O)R^{22}$, —$C(O)OR^{22}$, —$OC(O)R^{22}$, —$OC(O)N(R^{22})_2$, —$C(O)N(R^{22})_2$, —$N(R^{22})C(O)R^{22}$, —$N(R^{22})C(O)OR^{22}$, —$N(R^{22})C(O)N(R^{22})_2$, —$N(R^{22})S(O)_2(R^{22})$, —$S(O)R^{22}$, —$S(O)_2R^{22}$, —$S(O)_2N(R^{21})_2$, —$NO_2$, ═S, ═O, and —CN; and $C_{1-6}$ alkyl optionally substituted with one or more substituents independently selected from halogen-$OR^{22}$, —$SR^{22}$, —$N(R^{22})_2$, —$C(O)R^{22}$, —$C(O)OR^{22}$, —$OC(O)R^{22}$, —$OC(O)N(R^{22})_2$, —$C(O)N(R^{22})_2$, —$N(R^{22})C(O)R^{22}$, —$N(R^{22})C(O)OR^{22}$, —$N(R^{22})C(O)N(R^{22})_2$, —$N(R^{22})S(O)_2(R^{22})$, —$S(O)R^{22}$, —$S(O)_2R^{22}$, —$S(O)_2N(R^{21})_2$, —$NO_2$, ═S, ═O, and —CN;

Ring B is selected from $C_{3-10}$ carbocyclene and 3- to 10-membered heterocyclene;

$R^7$ is independently selected at each occurrence from:

hydrogen, halogen, —$OR^{23}$, —$SR^{23}$, —$N(R^{23})_2$, —$C(O)R^{23}$, —$OC(O)R^{23}$, —$OC(O)N(R^{23})_2$, —$C(O)N(R^{23})_2$, —$N(R^{23})C(O)R^{23}$, —$N(R^{23})C(O)OR^{23}$, —$N(R^{23})C(O)N(R^{23})_2$, —$N(R^{12})S(O)_2(R^{23})$, —$S(O)R^{23}$, —$S(O)_2R^{23}$, —$S(O)_2N(R^{23})_2$, —$NO_2$, and —CN; and $C_{1-6}$ alkyl optionally substituted with one or more substituents independently selected from halogen, —$OR^{23}$, —$SR^{23}$, $N(R^{23})_2$, —$C(O)R^{23}$, —$C(O)OR^{23}$, —$OC(O)R^{23}$, —$OC(O)N(R^{23})_2$, —$C(O)N(R^{23})_2$, —$N(R^{23})C(O)R^{23}$, —$N(R^{23})C(O)OR^{23}$, —$N(R^{23})C(O)N(R^{23})_2$, —$N(R^{23})S(O)_2(R^{23})$, —$S(O)R^{23}$, —$S(O)_2R^{23}$, —$S(O)_2N(R^{23})_2$, —$NO_2$, ═S, ═O, and —CN;

$R^8$, $R^{20}$, $R^{21}$, $R^{22}$, and $R^{23}$, are each independently selected at each occurrence from (d), (e), and (f):

(d) hydrogen;

(e) $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and (f) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN;

x is selected from 0, 1, 2, 3, and 4;

y is selected from 0, 1, 2, 3, and 4;

z is selected from 0, 1, 2, 3, 4 and 5; and at least one of x or y is selected from 1, 2, 3, and 4.

In another aspect, the present disclosure provides a compound represented by the structure of Formula (III):

(III)

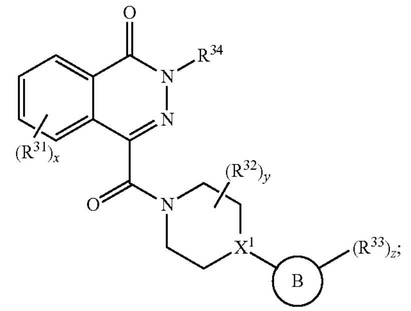

or a pharmaceutically acceptable salt thereof wherein:

$X^1$ is selected from N and C($R^{35}$);

$R^{31}$ is independently selected at each occurrence from (I), (II) and (III):

(I) halogen, —$OR^{40}$, —$SR^{40}$, —$N(R^{40})_2$, —$C(O)R^{40}$, —$C(O)OR^{40}$, —$OC(O)R^{40}$, —$OC(O)N(R^{40})_2$, —$C(O)N(R^{40})_2$, —$N(R^{40})C(O)R^{40}$, —$N(R^{40})C(O)OR^{40}$, —$N(R^{40})C(O)N(R^{40})_2$, —$N(R^{40})S(O)_2(R^{40})$, —$S(O)R^{40}$, —$S(O)_2R^{40}$, —$S(O)_2N(R^{40})_2$, —$NO_2$, and —CN;

(II) $C_{1-6}$ alkyl optionally substituted with one or more substituents independently selected from halogen, —$OR^{40}$, —$SR^{40}$, —$N(R^{40})_2$, —$C(O)R^{40}$, —$C(O)OR^{40}$, —$OC(O)R^{40}$, —$OC(O)N(R^{40})_2$, —$C(O)N(R^{40})_2$, —$N(R^{40})C(O)R^{40}$, —$N(R^{40})C(O)OR^{40}$, —$N(R^{40})C(O)N(R^{40})_2$, —$N(R^{40})S(O)_2(R^{40})$, —$S(O)R^{40}$, —$S(O)_2R^{40}$, —$S(O)_2N(R^{40})_2$, —$NO_2$, =S, =O, and —CN; and (III) $C_{3-10}$ carbocycle and 3- to 10-membered heterocycle, any of which is optionally substituted with one or more substituents independently selected from halogen, —$OR^{40}$, —$SR^{40}$, —$N(R^{40})_2$, —$C(O)R^{40}$, —$C(O)OR^{40}$, —$OC(O)R^{40}$, —$OC(O)N(R^{40})_2$, —$C(O)N(R^{40})_2$, —$N(R^{40})C(O)R^{40}$, —$N(R^{40})C(O)OR^{40}$, —$N(R^{40})C(O)N(R^{40})_2$, —$N(R^{40})S(O)_2(R^{40})$, —$S(O)R^{40}$, —$S(O)_2R^{40}$, —$S(O)_2N(R^{40})_2$, —$NO_2$, =S, =O, and —CN;

$R^{32}$ is independently selected at each occurrence from: halogen, —$OR^{41}$, —$SR^{41}$, —$N(R^{41})_2$, —$C(O)R^{41}$, —$C(O)OR^{41}$, —$OC(O)R^{41}$, —$OC(O)N(R^{41})_2$, —$C(O)N(R^{41})_2$, —$N(R^{41})C(O)R^{41}$, —$N(R^{41})C(O)OR^{41}$, —$N(R^{41})C(O)N(R^{41})_2$, —$N(R^{41})S(O)_2(R^{41})$, —$S(O)R^{41}$, —$S(O)_2R^{41}$, —$S(O)_2N(R^{41})_2$, —$NO_2$, =S, =O, and —CN; and $C_{1-6}$ alkyl optionally substituted with one or more substituents independently selected from halogen, —$OR^{41}$, —$SR^{41}$, —$N(R^{41})_2$, —$C(O)R^{41}$, —$C(O)OR^{41}$, —$OC(O)R^{41}$, —$OC(O)N(R^{41})_2$, —$C(O)N(R^{41})_2$, —$N(R^{41})C(O)R^{41}$, —$N(R^{41})C(O)OR^{41}$, —$N(R^{41})C(O)N(R^{41})_2$, —$N(R^{41})S(O)_2(R^{41})$, —$S(O)R^{41}$, —$S(O)_2R^{41}$, —$S(O)_2N(R^{41})_2$, —$NO_2$, =S, =O, and —CN; and $R^{33}$ is independently selected at each occurrence from: halogen, —$OR^{42}$, —$SR^{42}$, —$N(R^{42})_2$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, and —$S(O)_2N(R^{42})_2$; and $C_{1-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, and —CN;

wherein when one $R^{33}$ is methyl, each additional $R^{33}$ is independently selected from (IV), (V), and (VI);

(IV) halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, and —CN;

(V) $C_1$ alkyl substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, =O, and —CN; and (VI) $C_{2-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, =O, and —CN; or two $R^{33}$ on adjacent atoms may come together to form a $C_{3-8}$ carbocycle or 3- to 8-membered heterocycle, each of which is optionally substituted with one or more substituents independently selected from:

halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =O, and —CN; and $C_{1-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, =O, and —CN;

$R^{34}$ is selected from $C_{1-6}$ alkyl and $C_{2-6}$ alkenyl, each of which is optionally substituted with one or more substituents independently selected from halogen, —$OR^{43}$, —$SR^{43}$, —$N(R^{43})_2$, —$C(O)R^{43}$, —$C(O)OR^{43}$, —$OC(O)R^{43}$, —$OC(O)N(R^{43})_2$, —$C(O)N(R^{43})_2$, —$N(R^{43})C(O)R^{43}$, —$N(R^{43})C(O)OR^{43}$, $—N(R^{43})C(O)N(R^{43})_2$, $—N(R^{43})S(O)_2(R^{43})$, $—S(O)R^{43}$, $—S(O)_2R^{43}$, $—S(O)_2N(R^{43})_2$, $—NO_2$, =S, =O, and —CN;

Ring B is selected from $C_{3-6}$ carbocyclene and 4- to 6-membered heterocyclene;

$R^{35}$, $R^{40}$, $R^{41}$, $R^{42}$, and $R^{43}$ are each independently selected at each occurrence from (VII), (VIII), and (IX):

(VII) hydrogen;

(VII) $C_{1-6}$ alkyl optionally substituted with one more substituents independently selected from halogen, —O—$C_{1-6}$ alkyl, —O—$C_{1-6}$ haloalkyl, $—NH_2$, $—NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, $—NH_2$, $—NO_2$, =O, and —CN; and (IX) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, $—NH_2$, $—NO_2$, =O, and —CN;

x is selected from 0, 1, 2, 3, and 4;

y is selected from 0, 1, 2, 3, and 4; and z is selected from 2, 3, 4 and 5.

In another aspect, the present disclosure provides a compound represented by the structure of Formula (IV):

(IV)

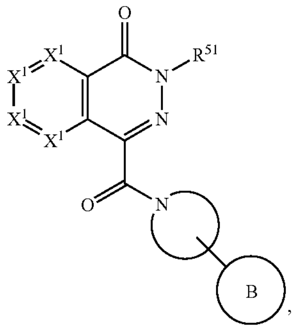

or a pharmaceutically acceptable salt wherein:

each $X^1$ is selected from $C(R^{50})$ and N, and at least one $X^1$ is N;

$R^{50}$ is independently selected at each occurrence from: hydrogen, halogen, $—OR^{60}$, $—SR^{60}$, $—N(R^{60})_2$, $—C(O)R^{60}$, $—C(O)OR^{60}$, $—OC(O)R^{60}$, $—OC(O)N(R^{60})_2$, $—C(O)N(R^{60})_2$, $—N(R^{60})C(O)R^{60}$, $—N(R^{60})C(O)OR^{60}$, $—N(R^{60})C(O)N(R^{60})_2$, $—N(R^{60})S(O)_2(R^{60})$, $—S(O)R^{60}$, $—S(O)_2R^{60}$, $—S(O)_2N(R^{60})_2$, $—NO_2$, and —CN; and $C_{1-6}$ alkyl optionally substituted with one or more substituents independently selected from halogen, $—OR^{60}$, $—SR^{60}$, $—N(R^{60})_2$, $—C(O)R^{60}$, $—C(O)OR^{60}$, $—OC(O)R^{60}$, $—OC(O)N(R^{60})_2$, $—C(O)N(R^{60})_2$, $—N(R^{60})C(O)R^{60}$, $—N(R^{60})C(O)OR^{60}$, $—N(R^{60})C(O)N(R^{60})_2$, $—N(R^{60})S(O)_2(R^{60})$, $—S(O)R^{60}$, $—S(O)_2R^{60}$, $—S(O)_2N(R^{60})_2$, $—NO_2$, =S, =O, and —CN;

$R^{51}$ is independently selected from:

$C_{1-6}$ alkyl optionally substituted with one or more substituents independently selected from halogen, $—OR^{61}$, $—SR^{61}$, $—N(R^{61})_2$, $—C(O)R^{61}$, $—C(O)OR^{61}$, $—OC(O)R^{61}$, $—OC(O)N(R^{61})_2$, $—C(O)N(R^{61})_2$, $—N(R^{61})C(O)R^{61}$, $—N(R^{61})C(O)OR^{61}$, $—N(R^{61})C(O)N(R^{61})_2$, $—N(R^{61})S(O)_2(R^{61})$, $—S(O)R^{61}$, $—S(O)_2R^{61}$, $—S(O)_2N(R^{61})_2$, $—NO_2$, =S, =O, and —CN; and $C_{3-10}$ carbocycle and 3- to 10-membered heterocycle, any of which is optionally substituted with one or more substituents independently selected from halogen, $—OR^{61}$, $—SR^{61}$, $—N(R^{61})_2$, $—C(O)R^{61}$, $—C(O)OR^{61}$, $—OC(O)R^{61}$, $—OC(O)N(R^{61})_2$, $—C(O)N(R^{61})_2$, $—N(R^{61})C(O)R^{61}$, $—N(R^{61})C(O)OR^{61}$, $—N(R^{61})C(O)N(R^{61})_2$, $—N(R^{61})S(O)_2(R^{61})$, $—S(O)R^{61}$, $—S(O)_2R^{61}$, $—S(O)_2N(R^{61})_2$, $—NO_2$, =S, =O, and —CN;

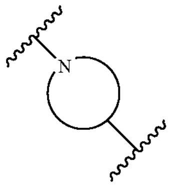

is 3- to 12-membered heterocyclene optionally substituted with one or more substituents independently selected from:

halogen, $—OR^{62}$, $—SR^{62}$, $—N(R^{62})_2$, $—C(O)R^{62}$, $—C(O)OR^{62}$, $—OC(O)R^{62}$, $—OC(O)N(R^{62})_2$, $—C(O)N(R^{62})_2$, $—N(R^{62})C(O)R^{62}$, $—N(R^{62})C(O)OR^{62}$, $—N(R^{62})C(O)N(R^{62})_2$, $—N(R^{62})S(O)_2(R^{62})$, $—S(O)R^{62}$, $—S(O)_2R^{62}$, $—S(O)_2N(R^{62})_2$, $—NO_2$, and —CN;

$C_{1-6}$ alkyl optionally substituted with one or more substituents independently selected from halogen, $—OR^{62}$, $—SR^{62}$, $—N(R^{62})_2$, $—C(O)R^{62}$, $—C(O)OR^{62}$, $—OC(O)R^{62}$, $—OC(O)N(R^{62})_2$, $—C(O)N(R^{62})_2$, $—N(R^{62})C(O)R^{62}$, $—N(R^{62})C(O)OR^{62}$, $—N(R^{62})C(O)N(R^{62})_2$, $—N(R^{62})S(O)_2(R^{62})$, $—S(O)R^{62}$, $—S(O)_2R^{62}$, $—S(O)_2N(R^{62})_2$, $—NO_2$, =S, =O, and —CN; and Ring B is selected from $C_{3-10}$ carbocycle and 3- to 10-membered heterocycle, any of which is optionally substituted with one or more substituents independently selected from:

halogen, $—OR^{63}$, $—SR^{63}$, $—N(R^{63})_2$, $—C(O)R^{63}$, $—C(O)OR^{63}$, $—OC(O)R^{63}$, $—OC(O)N(R^{63})_2$, $—C(O)N(R^{63})_2$, $—N(R^{63})C(O)R^{63}$, $—N(R^{63})C(O)OR^{63}$, $—N(R^{63})C(O)N(R^{63})_2$, $—N(R^{63})S(O)_2(R^{63})$, $—S(O)R^{63}$, $—S(O)_2R^{63}$, $—S(O)_2N(R^{63})_2$, $—NO_2$, and —CN; and $C_{1-6}$ alkyl optionally substituted with one or more substituents independently selected from halogen, $—OR^{63}$, $—SR^{63}$, $—N(R^{63})_2$, $—C(O)R^{63}$, $—C(O)OR^{63}$, $—OC(O)R^{63}$, $—OC(O)N(R^{63})_2$, $—C(O)N(R^{63})_2$, $—N(R^{63})C(O)R^{63}$, $—N(R^{63})C(O)OR^{63}$, $—N(R^{63})C(O)N(R^{63})_2$, $—N(R^{63})S(O)_2(R^{63})$, $—S(O)R^{63}$, $—S(O)_2R^{63}$, $—S(O)_2N(R^{63})_2$, $—NO_2$, =S, =O, and —CN;

$R^{60}$, $R^{61}$, $R^{62}$, and $R^{63}$ are independently selected at each occurrence from: hydrogen;

$C_{1-6}$ alkyl optionally substituted with one more substituents independently selected from halogen, —O—$C_{1-6}$ alkyl, —O—$C_{1-6}$ haloalkyl, $—NH_2$, $—NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some aspects, the present disclosure provides a method for killing a cancer cell or inhibiting cancer cell proliferation comprising contacting a cell with a compound represented by the structure of Formula (V):

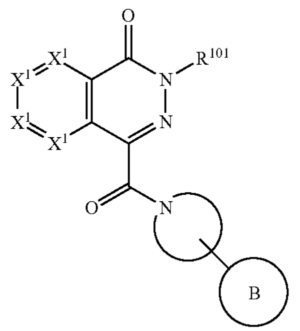

or a pharmaceutically acceptable salt wherein:

each $X^1$ is selected from $C(R^{100})$ and N;

$R^{100}$ is independently selected at each occurrence from:

hydrogen, halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, and —CN;

$C_{1-6}$ alkyl optionally substituted with one or more substituents independently selected from halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, =S, =O, and —CN; and $C_{3-10}$ carbocycle and 3- to 10-membered heterocycle, any of which is optionally substituted with one or more substituents independently selected from halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, =S, =O, and —CN;

$R^{101}$ is independently selected from:

$C_{1-6}$ alkyl and $C_{2-6}$ alkenyl, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $C_{3-10}$ carbocycle and 3- to 10-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN;

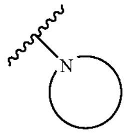 [SMILES: *N]

is 3- to 12-membered heterocyclene optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN;

Ring B is selected from $C_{3-12}$ carbocycle and 3- to 12-membered heterocycle, any of which is optionally substituted with one or more substituents independently selected from:

halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, and —CN;

$C_{1-6}$ alkyl optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, =S, =O, and —CN; and $C_{3-10}$ carbocycle and 3- to 10-membered heterocycle, any of which is optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —C(O)N($R^{105}$)$_2$, —N($R^{105}$)C(O)$R^{105}$, —N($R^{105}$)C(O)O$R^{105}$, —N($R^{105}$)C(O)N($R^{105}$)$_2$, —N($R^{105}$)S(O)$_2$($R^{105}$), —S(O)$R^{105}$, —S(O)$_2R^{105}$, —S(O)$_2$N($R^{105}$)$_2$, —$NO_2$, =S, =O, and —CN;

$R^{102}$, $R^{103}$, $R^{104}$, and $R^{105}$ are independently selected at each occurrence from:

hydrogen;

$C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

"Alkyl" refers to a straight or branched hydrocarbon chain monovalent radical consisting solely of carbon and hydrogen atoms, containing no unsaturation, and preferably having from one to twelve carbon atoms (i.e., $C_1$-$C_{12}$ alkyl). The alkyl is attached to the remainder of the molecule through a single bond. In certain embodiments, an alkyl comprises one to twelve carbon atoms (i.e., $C_1$-$C_{12}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). For example, the alkyl group may be attached to the rest of the molecule by a single bind, such as, methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl), and the like.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like.

"Alkylene" refers to a straight divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. Alkylene chain may be optionally substituted by one or more substituents such as those substituents described herein. In certain embodiments, an alkylene comprises one to ten carbon atoms (i.e., $C_1$-$C_{10}$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene).

"Alkenylene" refers to a straight divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. Alkenylene chain may be optionally substituted by one or more substituents such as those substituents described herein. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene).

"Alkynylene" refers to a straight divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. Alkynylene chain may be optionally substituted by one or more substituents such as those substituents described herein. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene).

The term "$C_{x-y}$" when used in conjunction with a chemical moiety, such as alkyl, alkenyl, or alkynyl is meant to include groups that contain from x to y carbons in the chain. For example, the term "$C_{1-6}$ alkyl" refers to substituted or unsubstituted saturated hydrocarbon groups, including straight-chain alkyl and branched-chain alkyl groups that contain from 1 to 6 carbons. The term —$C_{x-y}$ alkylene- refers to a substituted or unsubstituted alkylene chain with from x to y carbons in the alkylene chain. For example, —$C_{1-6}$ alkylene- may be selected from methylene, ethylene, propylene, butylene, pentylene, and hexylene, any one of which is optionally substituted.

The terms "$C_{x-y}$ alkenyl" and "$C_{x-y}$ alkynyl" refer to unsaturated aliphatic groups analogous in length and possible substitution to the alkyls described above, but that contain at least one double or triple bond, respectively. The term —$C_{x-y}$ alkenylene- refers to a substituted or unsubstituted alkenylene chain with from x to y carbons in the alkenylene chain. For example, —$C_{2-6}$ alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$ alkynylene-refers to a substituted or unsubstituted alkynylene chain with from x to y carbons in the alkynylene chain. For example, —$C_{2-6}$ alkynylene- may be selected from ethynylene, propynylene, butynylene, pentynylene, and hexynylene, any one of which is optionally substituted. An alkynylene chain may have one triple bond or more than one triple bond in the alkynylene chain.

The term "carbocycle" as used herein refers to a saturated, unsaturated or aromatic ring in which each atom of the ring is carbon. Carbocycle include 3- to 10-membered monocyclic rings and 6- to 12-membered bicyclic rings. Each ring of a bicyclic carbocycle may be selected from saturated, unsaturated, and aromatic rings. Bicyclic carbocycles may be fused, bridged or spiro-ring systems. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Carbocycle may be optionally substituted by one or more substituents such as those substituents described herein.

"Cycloalkyl" refers to a stable fully saturated monocyclic or polycyclic hydrocarbon radical consisting solely of carbon and hydrogen atoms, which includes fused or bridged ring systems, and preferably having from three to twelve carbon atoms (i.e., $C_{3-12}$ cycloalkyl). In certain embodiments, a cycloalkyl comprises three to ten carbon atoms (i.e., $C_{3-10}$ cycloalkyl). In other embodiments, a cycloalkyl comprises five to seven carbon atoms (i.e., $C_{5-7}$ cycloalkyl). The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Cycloalkyl may be optionally substituted by one or more substituents such as those substituents described herein.

"Cycloalkenyl" refers to a stable unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond (i.e., $C_{3-12}$ cycloalkenyl). In certain embodiments, a cycloalkenyl comprises three to ten carbon atoms (i.e., $C_{3-10}$ cycloalkenyl). In other embodiments, a cycloalkenyl comprises five to seven carbon atoms (i.e., $C_{5-7}$ cycloalkenyl).

The cycloalkenyl may be attached to the rest of the molecule by a single bond. Examples of monocyclic cycloalkenyls include, e.g., cyclopentenyl, cyclohexenyl, cycloheptenyl, and cyclooctenyl. Cycloalkenyl may be optionally substituted by one or more substituents such as those substituents described herein.

The term "carbocyclene" refers to a divalent ring, linking the rest of the molecule to a radical group, consisting solely of carbon and hydrogen atoms. The carbocyclene is attached to the rest of the molecule through a single bond and to the radical group through a single bond. The points of attachment of the carbocyclene are to the rest of the molecule and to the radical group are through any two carbons respectively. Carbocyclene includes arylene and cycloalkylene. The term therefore distinguishes carbocyclene from heterocyclene in which the divalent ring comprises at least one atom that is different from a carbon atom. The heterocyclene is attached to the rest of the molecule through a single bond and to the radical group through a single bond. The points of attachment of the heterocyclene are to the rest of the molecule and to the radical group through any two atoms respectively, valency permitting. Heterocyclene includes heteroarylene and heterocycloalkylene. Carbocyclene and heterocyclene may each be optionally substituted by one or more substituents such as those substituents described herein.

"Aryl" refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Aryl may be optionally substituted by one or more substituents such as those substituents described herein.

A "$C_{x-y}$ carbocycle" is meant to include groups that contain from x to y carbons in a ring. For example, the term "$C_{3-6}$ carbocycle" can be a saturated, unsaturated or aromatic ring system that contains from 3 to 6 carbon atoms-any of which is optionally substituted as provided herein.

The term "heterocycle" as used herein refers to a saturated, unsaturated, non-aromatic or aromatic ring comprising one or more heteroatoms. Exemplary heteroatoms include N, O, Si, P, B, and S atoms. Heterocycles include 3- to 10-membered monocyclic rings and 6- to 12-membered bicyclic rings. Each ring of a bicyclic heterocycle may be selected from saturated, unsaturated, and aromatic rings. In some embodiments, the heterocycle comprises at least one heteroatom selected from oxygen, nitrogen, sulfur, or any combination thereof. In some embodiments, the heterocycle comprises at least one heteroatom selected from oxygen, nitrogen, or any combination thereof. In some embodiments, the heterocycle comprises at least one heteroatom selected from oxygen, sulfur, or any combination thereof. In some embodiments, the heterocycle comprises at least one heteroatom selected from nitrogen, sulfur, or any combination thereof. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Heterocycle may be optionally substituted by one or more substituents such as those substituents described herein. Bicyclic heterocycles may be fused, bridged or spiro-ring systems. In an exemplary embodiment, a heterocycle, e.g., pyridyl, may be fused to a saturated or unsaturated ring, e.g., cyclohexane, cyclopentane, or cyclohexene. Heterocycle may be optionally substituted by one or more substituents such as those substituents described herein.

"Heterocycloalkyl" refers to a stable 3- to 12-membered non-aromatic ring radical that comprises two to twelve carbon atoms and at least one heteroatom wherein each heteroatom may be selected from N, O, Si, P, B, and S atoms. In some embodiments, the heterocycloalkyl comprises at least one heteroatom selected from oxygen, nitrogen, sulfur, or any combination thereof. In some embodiments, the heterocycloalkyl comprises at least one heteroatom selected from oxygen, nitrogen, or any combination thereof. In some embodiments, the heterocycloalkyl comprises at least one heteroatom selected from oxygen, sulfur, or any combination thereof. In some embodiments, the heterocycloalkyl comprises at least one heteroatom selected from nitrogen, sulfur, or any combination thereof. The heterocycloalkyl may be selected from monocyclic or bicyclic, and fused or bridged ring systems. The heteroatoms in the heterocycloalkyl radical are optionally oxidized. One or more nitrogen atoms, if present, are optionally quaternized. The heterocycloalkyl radical is partially or fully saturated. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Heterocycloalkyl may be optionally substituted by one or more substituents such as those substituents described herein.

The term "heteroaryl" refers to a radical derived from a 5- to 12-membered aromatic ring radical whose ring structure comprise at least one heteroatom, preferably between one to four heteroatoms. In some embodiments, the heteroaryl comprises at least one heteroatom selected from oxygen, nitrogen, sulfur, or any combination thereof. In some embodiments, the heteroaryl comprises at least one heteroatom selected from oxygen, nitrogen, or any combination thereof. In some embodiments, the heteroaryl comprises at least one heteroatom selected from oxygen, sulfur, or any combination thereof. In some embodiments, the heteroaryl comprises at least one heteroatom selected from nitrogen, sulfur, or any combination thereof. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl.

As used herein, the heteroaryl ring may be selected from monocyclic or polycyclic (bicyclic and fused or bridged) systems rings wherein at least one of the rings in the ring system is aromatic, i.e., it contains a cyclic, delocalized (4n+2) π-electron system in accordance with the Hückel theory. Heteroaryl includes aromatic single ring structures, preferably 5- to 6-membered rings, whose ring structures include at least one heteroatom, preferably one to four heteroatoms, more preferably one or two heteroatoms. Heteroaryl groups include, for example, pyrrole, furan, thiophene, imidazole, oxazole, thiazole, pyrazole, pyridine, pyrazine, pyridazine, and pyrimidine, and the like. Heteroaryl may be optionally substituted by one or more substituents such as those substituents described herein. Heteroaryl also includes polycyclic ring systems having two or more rings in which two or more atoms are common to two adjoining rings wherein at least one of the rings is heteroaromatic, e.g., the other rings can be aromatic or non-aromatic carbocyclic, or heterocyclic.

An "X-membered heterocycle" refers to the number of endocylic atoms, i.e., X, in the ring. For example, a 5-membered heteroaryl ring or 5-membered aromatic heterocycle has 5 endocyclic atoms, e.g., triazole, oxazole, thiophene, etc.

"Alkoxy" refers to a radical bonded through an oxygen atom of the formula —O-alkyl, where alkyl is an alkyl chain as defined above.

"Halo" or "halogen" refers to halogen substituents such as bromo, chloro, fluoro and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, and I). When an alkyl group is substituted with more than one halogen radicals, each halogen may be independently selected for example, 1-chloro,2-fluoroethane.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—OW, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^a$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)O$R^a$ (where t is 1 or 2), and —$R^b$—S(O)$_t$N($R^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo(=N—OH), hydrazine(=N—$NH_2$), —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine(=N—$NH_2$), —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$_t$O$R^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain. It will be understood by those skilled in the art that substituents can themselves be substituted, if appropriate.

The term "salt" or "pharmaceutically acceptable salt" refers to salts derived from a variety of organic and inorganic counter ions well known in the art. Pharmaceutically acceptable acid addition salts can be formed with inorganic acids and organic acids. Pharmaceutically acceptable base addition salts can be formed with inorganic and organic bases.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

The terms "administer", "administered", "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The terms "administer", "administered", "administers" and "administering" a compound should be understood to mean providing a compound of the invention or a prodrug of a compound of the invention to the individual in need.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition, and can contemplate a range of results directed to that end, including but not restricted to prevention of the condition entirely.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

Compounds

Compounds of Formula (I).

In some aspects, the present disclosure provides a compound represented by the structure of Formula (I):

(I)

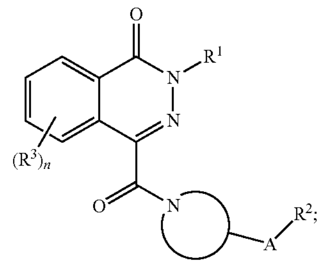

or a pharmaceutically acceptable salt thereof wherein:

$R^1$ is selected from (i) and (ii):

(i) $C_{1-6}$ alkyl optionally substituted with one or more substituents independently selected from: halogen, $—OR^{10}$, $—SR^{10}$, $—N(R^{10})_2$, $—C(O)R^{10}$, $—C(O)OR^{10}$, $—OC(O)R^{10}$, $—OC(O)N(R^{10})_2$, $—C(O)N(R^{10})_2$, $—N(R^{10})C(O)R^{10}$, $—N(R^{10})C(O)OR^{10}$, $—N(R^{10})C(O)N(R^{10})_2$, $—N(R^{10})S(O)_2(R^{10})$, $—S(O)R^{10}$, $—S(O)_2R^{10}$, $—S(O)_2N(R^{10})_2$, $—NO_2$, $=S$, $=O$, and —CN; and (ii) optionally substituted $C_{3-10}$ saturated carbocycle and optionally substituted 3- to 10-membered heterocycle, wherein the optional substituents are independently selected from:

halogen, $—OR^{10}$, $—SR^{10}$, $—N(R^{10})_2$, $—C(O)R^{10}$, $—C(O)OR^{10}$, $—OC(O)R^{10}$, $—OC(O)N(R^{10})_2$, $—C(O)N(R^{10})_2$, $—N(R^{10})C(O)R^{10}$, $—N(R^{10})C(O)OR^{10}$, $—N(R^{10})C(O)N(R^{10})_2$, $—N(R^{10})S(O)_2(R^{10})$, $—S(O)R^{10}$, $—S(O)_2R^{10}$, $—S(O)_2N(R^{10})_2$, $—NO_2$, $=S$, $=O$, and —CN; and $C_{1-6}$ alkyl optionally substituted with one or more substituents independently selected from halogen, $—OR^{10}$, $—SR^{10}$, $—N(R^{10})_2$, $—C(O)R^{10}$, $—C(O)OR^{10}$, $—OC(O)R^{10}$, $—OC(O)N(R^{10})_2$, $—C(O)N(R^{10})_2$, $—N(R^{10})C(O)R^{10}$, $—N(R^{10})C(O)OR^{10}$, $—N(R^{10})C(O)N(R^{10})_2$, $—N(R^{10})S(O)_2(R^{10})$, $—S(O)R^{10}$, $—S(O)_2R^{10}$, $—S(O)_2N(R^{10})_2$, $—NO_2$, $=S$, $=O$, and —CN;

$R^2$ is selected from hydrogen, optionally substituted $C_{3-10}$ saturated carbocycle, and optionally substituted 3- to 10-membered heterocycle, wherein the optional substituents are independently selected from:

halogen, $—OR^{11}$, $—SR^{11}$, $—N(R^{11})_2$, $—C(O)R^{11}$, $—C(O)OR^{11}$, $—OC(O)R^{11}$, $—OC(O)N(R^{11})_2$, $—C(O)N(R^{11})_2$, $—N(R^{11})C(O)R^{11}$, $—N(R^{11})C(O)OR^{11}$, $—N(R^{11})C(O)N(R^{11})_2$, $—N(R^{11})S(O)_2(R^{11})$, $—S(O)R^{11}$, $—S(O)_2R^{11}$, $—S(O)_2N(R^{11})_2$, $—NO_2$, $=S$, $=O$, and —CN; and $C_{1-6}$ alkyl optionally substituted with one or more substituents independently selected from halogen, $—OR^{11}$, $—SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN;

wherein at least one of $R^1$ and $R^2$ is selected from optionally substituted $C_{3-10}$ carbocycle and optionally substituted 3- to 10-membered heterocycle;

$R^3$ is independently selected at each occurrence from: halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, and —CN; and $C_{1-6}$ alkyl optionally substituted with one or more substituents independently selected from halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, =S, =O, and —CN;

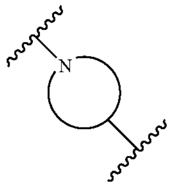

is 3- to 10-membered heterocyclene optionally substituted with one or more substituents independently selected from:

halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, and —CN; and $C_{1-6}$ alkyl optionally substituted with one or more substituents independently selected from halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, =S, =O, and —CN;

A is selected from optionally substituted $C_{3-10}$ carbocyclene and optionally substituted 3- to 10-membered heterocyclene, wherein the optional substituents are independently selected from:

halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN;

wherein when A is a 5-membered heteroaryl, the 5-membered heteroaryl includes one or more heteroatoms selected from O, S, and N, and no more than two N atoms in the ring;

$R^{10}$, $R^{11}$, $R^{12}$, $R^{13}$, and $R^{14}$ are each independently selected at each occurrence from (iii), (iv) and (v):

(iii) hydrogen;

(iv) $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and (v) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and n is selected from 0, 1, 2, 3, and 4.

In some embodiments, for the compound or salt of Formula (I), n is selected from 0, 1, 2, and 3. In some embodiments, n is selected from 0, 1, and 2. In some aspects, n is selected from 1, 2, 3, and 4. In some embodiments, n is selected from 1, 2, and 3. In some embodiments, n is selected from 2, 3, and 4. In some embodiments, n is selected from 1 and 2. In some embodiments, n is selected from 0 and 1. In some embodiments, n is 4. In some embodiments, n is 3. In some embodiments, n is 2. In some embodiments, n is 1. In some embodiments, n is 0.

In some embodiments, for the compound or salt of Formula (I), n is selected from 1, and the compound of Formula (I) is selected from Formula (I-a), (I-b), (I-c), and (I-d):

(I-a)

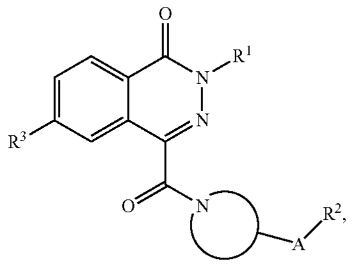

(I-b)

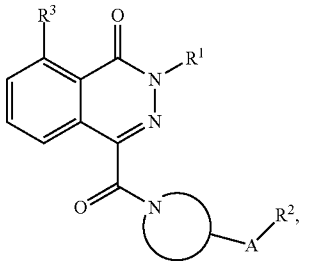

-continued (I-c)

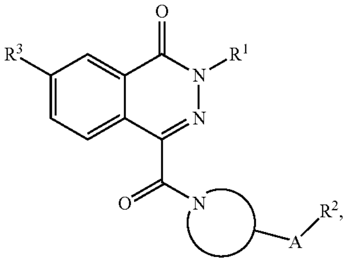

and (I-d)

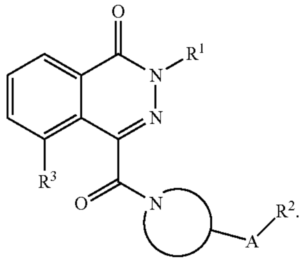

In some embodiments, for the compound or salt of Formula (I), the compound of Formula (I) is selected from Formula (I-a):

(I-a)

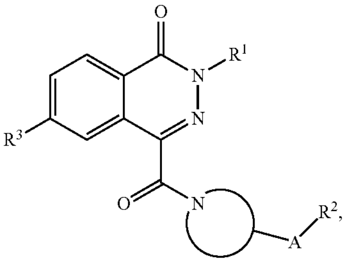

(I-b)

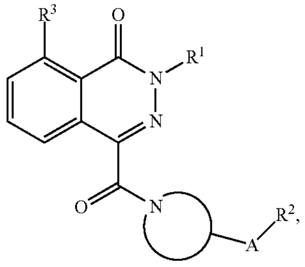

(I-c)

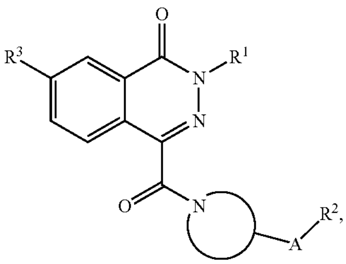

and

-continued (I-d)

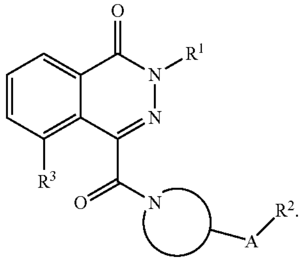

In some embodiments, a compound or salt of the disclosure is represented by Formula (I-a):

(I-a)

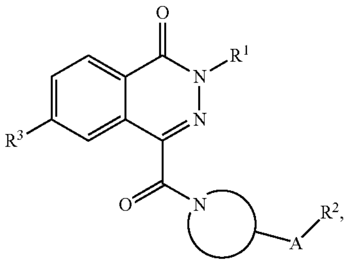

or a pharmaceutically acceptable salt thereof, wherein $R^1$, $R^2$, $R^3$, A, and

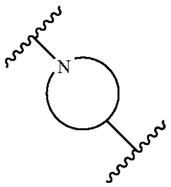

are as defined in Formula (I).

In some embodiments, a compound or salt of the disclosure is represented by Formula (I-b):

(I-b)

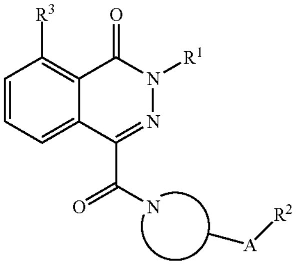

or a pharmaceutically acceptable salt thereof, wherein $R^1$, $R^2$, $R^3$, A, and

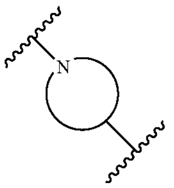

are as defined in Formula (I).

In some embodiments, a compound or salt of the disclosure is represented by Formula (I-c):

(I-c)

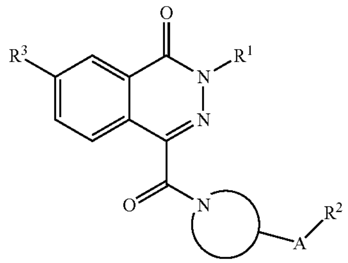

or a pharmaceutically acceptable salt thereof, wherein $R^1$, $R^2$, $R^3$, A, and

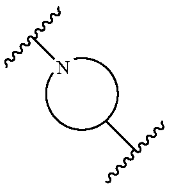

are as defined in Formula (I).

In some embodiments, a compound or salt of the disclosure is represented by Formula (I-d):

(I-d)

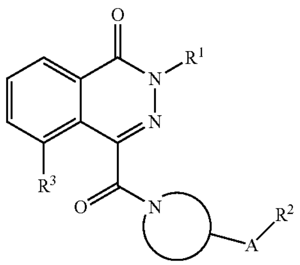

or a pharmaceutically acceptable salt thereof, wherein $R^1$, $R^2$, $R^3$, A, and

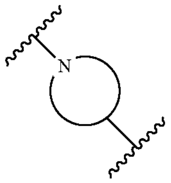

are as defined in Formula (I).

In some embodiments, for the compound or salt of Formula (I), (I-a), (I-b), (I-c), or (I-d), $R^1$ is selected from $C_{1-6}$ alkyl optionally substituted with one or more substituents independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from $C_{1-6}$ alkyl optionally substituted with one or more substituents independently selected from: halogen, —$OR^{10}$, —$N(R^{10})_2$, —$C(O)R^{10}$, —$NO_2$, =S, =O, and —CN.

In some embodiments, for the compound or salt of Formula (I), (I-a), (I-b), (I-c), or (I-d), $R^1$ is selected from $C_{1-3}$ alkyl optionally substituted with one or more substituents independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from $C_{1-3}$ alkyl optionally substituted with one or more substituents independently selected from: halogen, —$OR^{10}$, —$N(R^{10})_2$, —$C(O)R^{10}$, —$NO_2$, =S, =O, and —CN.

In some embodiments, for the compound or salt of Formula (I), (I-a), (I-b), (I-c), or (I-d), $R^1$ is selected from methyl, ethyl, propyl, and isopropyl, each of which is optionally substituted with one or more substituents independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from methyl, ethyl, propyl, and isopropyl, each of which is optionally substituted with one or more substituents independently selected from: halogen, —$OR^{10}$, —$N(R^{10})_2$, —$C(O)R^{10}$, —$NO_2$, =S, =O, and —CN. In some embodiments, $R^1$ is selected from optionally substituted methyl and optionally substituted ethyl.

In some embodiments, for the compound or salt of Formula (I), (I-a), (I-b), (I-c), or (I-d), $R^1$ is selected from optionally substituted $C_{3-10}$ saturated carbocycle and optionally substituted 3- to 10-membered heterocycle. In some embodiments, $R^1$ is selected from optionally substituted $C_{3-10}$ saturated carbocycle and optionally substituted 3- to 10-membered heterocycle, wherein the optional substituents are independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN; and $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-10}$ saturated carbocycle and optionally substituted 3- to 10-membered heterocycle, wherein the optional substituents are independently selected from: halogen, —$OR^{10}$, —$N(R^{10})_2$, —$C(O)R^{10}$, —$C(O)OR^{10}$, —$NO_2$, =S, =O, and —CN; and $C_{1-6}$ alkyl optionally substituted with one or more substituents independently selected from halogen, —$OR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-10}$ saturated carbocycle and optionally substituted 3- to 10-membered heterocycle, wherein the optional substituents are independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-10}$ saturated carbocycle and optionally substituted 3- to 10-membered heterocycle, wherein the optional substituents are independently selected from: halogen, —$OR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-10}$ saturated carbocycle and optionally substituted 3- to 10-membered heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-10}$ saturated carbocycle and optionally substituted 3- to 10-membered heterocycle, wherein the optional substituents are independently selected from $C_{1-6}$ alkyl optionally substituted with one or more substituents independently selected from halogen, —$OR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-6}$ saturated carbocycle and optionally substituted 3- to 6-membered heterocycle. In some embodiments, $R^1$ is selected from optionally substituted $C_{3-6}$ saturated carbocycle and optionally substituted 3- to 6-membered heterocycle, wherein the optional substituents are independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN; and $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-6}$ saturated carbocycle and optionally substituted 3- to 6-membered heterocycle, wherein the optional substituents are independently selected from: halogen, —$OR^{10}$, —$N(R^{10})_2$, —$C(O)R^{10}$, —$C(O)OR^{10}$, —$NO_2$, =S, =O, and —CN; and $C_{1-6}$ alkyl optionally substituted with one or more substituents independently selected from halogen, —$OR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-6}$ saturated carbocycle and optionally substituted 3- to 6-membered heterocycle, wherein the optional substituents are independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-6}$ saturated carbocycle and optionally substituted 3- to 6-membered heterocycle, wherein the optional substituents are independently selected from: halogen, —$OR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-6}$ saturated carbocycle and optionally substituted 3- to 6-membered heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-6}$ saturated carbocycle and optionally substituted 3- to 6-membered heterocycle, wherein the optional substituents are independently selected from $C_{1-6}$ alkyl optionally substituted with one or more substituents independently selected from halogen, —$OR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-10}$ saturated carbocycle. In some embodiments, the optionally substituted $C_{3-10}$ saturated carbocycle of $R^1$ is selected from: optionally substituted $C_3$ saturated carbocycle, optionally substituted $C_4$ saturated carbocycle, optionally substituted $C_5$ saturated carbocycle, optionally substituted $C_6$ saturated carbocycle, optionally substituted $C_7$ saturated carbocycle, optionally substituted $C_8$ saturated carbocycle, optionally substituted $C_9$ saturated carbocycle, and optionally substituted $C_{10}$ saturated carbocycle. In some embodiments, the optionally substituted $C_{3-10}$ saturated carbocycle of $R^1$ is selected from: optionally substituted $C_{3-4}$ saturated carbocycle, optionally substituted $C_{3-5}$ saturated carbocycle, optionally substituted $C_{3-6}$ saturated carbocycle, optionally substituted $C_{3-7}$ saturated carbocycle, optionally substituted $C_{3-8}$ saturated carbocycle, and optionally substituted $C_{3-9}$ saturated carbocycle.

In some embodiments, for the compound or salt of Formula (I), (I-a), (I-b), (I-c), or (I-d), $R^1$ is selected from optionally substituted $C_{3-10}$ saturated carbocycle, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-10}$ saturated carbocycle, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-10}$ saturated carbocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-10}$ saturated carbocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-6}$ saturated carbocycle, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-6}$ saturated carbocycle, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted $C_{3-6}$ saturated carbocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-6}$ saturated carbocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted cyclopropyl, optionally substituted cyclobutyl, optionally substituted cyclopentyl, and optionally substituted cyclohexyl, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted $C_{3-6}$ saturated carbocycle, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted cyclopropyl, optionally substituted cyclobutyl, optionally substituted cyclopentyl, and optionally substituted cyclohexyl, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted cyclopropyl, optionally substituted cyclobutyl, optionally substituted cyclopentyl, and optionally substituted cyclohexyl, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is cyclopropyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ cyclopropyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN. In some embodiments, $R^1$ is cyclopropyl.

In some embodiments, for the compound or salt of Formula (I), (I-a), (I-b), (I-c), or (I-d), $R^1$ is cyclopropyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is cyclopropyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN. In some embodiments, $R^1$ is cyclopropyl.

In some embodiments, for the compound or salt of Formula (I), (I-a), (I-b), (I-c), or (I-d), $R^1$ is selected from optionally substituted 3- to 10-membered heterocycle. In some embodiments, the optionally substituted 3- to 10-membered heterocycle of $R^1$ is selected from: optionally substituted 3-membered heterocycle, optionally substituted 4-membered heterocycle, optionally substituted 5-membered heterocycle, optionally substituted 6-membered heterocycle, optionally substituted 7-membered heterocycle, optionally substituted 8-membered heterocycle, optionally substituted 9-membered heterocycle, and optionally substituted 10-membered heterocycle. In some embodiments, the optionally substituted 3- to 10-membered heterocycle of $R^1$ is selected from: optionally substituted 3- to 4-membered heterocycle, optionally substituted 3- to 5-membered heterocycle, optionally substituted 3- to 6-membered heterocycle, optionally substituted 3- to 7-membered heterocycle, optionally substituted 3- to 8-membered heterocycle, and optionally substituted 3- to 9-membered heterocycle.

In some embodiments, for the compound or salt of Formula (I), (I-a), (I-b), (I-c), or (I-d), $R^1$ is selected from optionally substituted 3- to 10-membered heterocycle, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted 3- to 10-membered heterocycle, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted 3- to 10-membered heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted 3- to 10-membered heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted 3- to 6-membered heterocycle, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted 3- to 6-membered heterocycle, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted 3- to 6-membered heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted 3- to 6-membered heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted 4- to 6-membered saturated heterocycle, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted 4- to 6-membered saturated heterocycle, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted 4- to 6-membered saturated heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted 4- to 6-membered saturated heterocycle, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted azirdidinyl, optionally substituted oxiranyl, optionally substituted azetidinyl, optionally substituted diazaetidinyl, and optionally substituted oxetanyl, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted azirdidinyl, optionally substituted oxiranyl, optionally substituted azetidinyl, optionally substituted diazaetidinyl, and optionally substituted oxetanyl, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is selected from optionally substituted optionally substituted azirdidinyl, optionally substituted oxiranyl, optionally substituted azetidinyl, optionally substituted diazaetidinyl, and optionally substituted oxetanyl, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is selected from optionally substituted azirdidinyl, optionally substituted oxiranyl, optionally substituted azetidinyl, optionally substituted diazaetidinyl, and optionally substituted oxetanyl, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is optionally substituted oxetanyl, wherein the optional substituents are independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is optionally substituted oxetanyl, wherein the optional substituents are independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^1$ is optionally substituted oxetanyl, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN. In some embodiments, $R^1$ is optionally substituted oxetanyl, wherein the optional substituents are independently selected from $C_{1-6}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =S, =O, and —CN.

In some embodiments, for the compound or salt of Formula (I), (I-a), (I-b), (I-c), or (I-d), $R^2$ is hydrogen.

In some embodiments, for the compound or salt of Formula (I), (I-a), (I-b), (I-c), or (I-d), $R^2$ is optionally substituted $C_{3-10}$ saturated carbocycle, and optionally substituted 3- to 10-membered heterocycle, wherein the optional substituents are independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-10}$ saturated carbocycle, and optionally substituted 3- to 10-membered heterocycle, wherein the optional substituents are independently selected from: halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted $C_{3-10}$ saturated carbocycle, and optionally substituted 3- to 10-membered heterocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-10}$ saturated carbocycle, and optionally substituted 3- to 10-membered heterocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted $C_{3-6}$ saturated carbocycle, and optionally substituted 3- to 6-membered heterocycle, wherein the optional substituents are independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-6}$ saturated carbocycle, and optionally substituted 3- to 6-membered heterocycle, wherein the optional substituents are independently selected from: halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted $C_{3-6}$ saturated carbocycle, and optionally substituted 3- to 10-membered heterocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-6}$ saturated carbocycle, and optionally substituted 3- to 6-membered heterocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is selected from optionally substituted $C_{3-10}$ saturated carbocycle. In some embodiments, the optionally substituted $C_{3-10}$ saturated carbocycle of $R^2$ is selected from: optionally substituted $C_3$ saturated carbocycle, optionally substituted $C_4$ saturated carbocycle, optionally substituted $C_5$ saturated carbocycle, optionally substituted $C_6$ saturated carbocycle, optionally substituted $C_7$ saturated carbocycle, optionally substituted $C_8$ saturated carbocycle, optionally substituted $C_9$ saturated carbocycle, and optionally substituted $C_{10}$ saturated carbocycle. In some embodiments, the optionally substituted $C_{3-10}$ saturated carbocycle of $R^2$ is selected from: optionally substituted $C_{3-4}$ saturated carbocycle, optionally substituted $C_{3-5}$ saturated carbocycle, optionally substituted $C_{3-6}$ saturated carbocycle, optionally substituted $C_{3-7}$ saturated carbocycle, optionally substituted $C_{3-8}$ saturated carbocycle, and optionally substituted $C_{3-9}$ saturated carbocycle.

In some embodiments, for the compound or salt of Formula (I), (I-a), (I-b), (I-c), or (I-d), $R^2$ is optionally substituted $C_{3-10}$ saturated carbocycle wherein the optional substituents are independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-10}$ saturated carbocycle, wherein the optional substituents are independently selected from: halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted $C_{3-10}$ saturated carbocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-10}$ saturated carbocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted $C_{3-6}$ saturated carbocycle, wherein the optional substituents are independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-6}$ saturated carbocycle, wherein the optional substituents are independently selected from: halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted $C_{3-6}$ saturated carbocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted $C_{3-6}$ saturated carbocycle, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted cyclopropyl, optionally substituted cyclobutyl, optionally substituted cyclopentyl, and optionally substituted cyclohexyl, wherein the optional substituents are independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted cyclopropyl, optionally substituted cyclobutyl, optionally substituted cyclopentyl, and optionally substituted cyclohexyl, wherein the optional substituents are independently selected from: halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is optionally substituted cyclopropyl, optionally substituted cyclobutyl, optionally substituted cyclopentyl, and optionally substituted cyclohexyl, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is optionally substituted cyclopropyl, optionally substituted cyclobutyl, optionally substituted cyclopentyl, and optionally substituted cyclohexyl, wherein the optional substituents are independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$—$NO_2$, =S, =O, and —CN.

In some embodiments, for the compound or salt of Formula (I), (I-a), (I-b), (I-c), or (I-d), $R^2$ is cyclopropyl optionally substituted with one or more substituents independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is cyclopropyl optionally substituted with one or more substituents independently selected from: halogen, —$OR^{11}$, —$SR^{11}$, —$N(R^{11})_2$, —$C(O)R^{11}$, —$C(O)OR^{11}$—$NO_2$, =S, =O, and —CN. In some embodiments, $R^2$ is cyclopropyl.

In some embodiments, for the compound or salt of Formula (I), (I-a), (I-b), (I-c), or (I-d), $R^2$ is cyclopropyl optionally substituted with one or more substituents independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})C(O)R^{11}$, —$N(R^{11})C(O)OR^{11}$, —$N(R^{11})C(O)N(R^{11})_2$, —$N(R^{11})S(O)_2(R^{11})$, —$S(O)R^{11}$, —$S(O)_2R^{11}$, —$S(O)_2N(R^{11})_2$, —$NO_2$, =S, =O, and —CN. In some embodiments, $R^2$ is cyclopropyl optionally substituted with one or more substituents independently selected from $C_{1-6}$ alkyl optionally substituted with one or more substituents independently selected from halogen, —$OR^{11}$, —$SR^{11}$, —$N(R^{11})_2$, —$C(O)R^{11}$, —$C(O)OR^{11}$—$NO_2$, =S, =O, and —CN. In some embodiments, $R^2$ is cyclopropyl.

In some embodiments, for the compound or salt of Formula (I), (I-a), (I-b), (I-c), or (I-d), $R^2$ is selected from optionally substituted 3- to 10-membered heterocycle. In some embodiments, the optionally substituted 3- to 10-membered heterocycle of $R^2$ is selected from: optionally substituted 3-membered heterocycle, optionally substituted 4-membered heterocycle, optionally substituted 5-membered heterocycle, optionally substituted 6-membered heterocycle, optionally substituted 7-membered heterocycle, optionally substituted 8-membered heterocycle, optionally substituted 9-membered heterocycle, and optionally substituted 10-membered heterocycle. In some embodiments, the optionally substituted 3- to 10-membered heterocycle of $R^2$ is selected from: optionally substituted 3- to 4-membered heterocycle, optionally substituted 3- to 5-membered heterocycle, optionally substituted 3- to 6-membered heterocycle, optionally substituted 3- to 7-membered heterocycle, optionally substituted 3- to 8-membered heterocycle, and optionally substituted 3- to 9-membered heterocycle.

In some embodiments, for the compound or salt of Formula (I), (I-a), (I-b), (I-c), or (I-d), $R^2$ is optionally substituted 3- to 10-membered heterocycle, wherein the optional substituents are independently selected from: halogen, —$OR^{11}$, —$SR^{11}$, —$N(R^{11})_2$, —$C(O)R^{11}$, —$C(O)OR^{11}$, —$OC(O)R^{11}$, —$OC(O)N(R^{11})_2$, —$C(O)N(R^{11})_2$, —$N(R^{11})$ $C(O)R^{11}$, $—N(R^{11})C(O)OR^{11}$, $—N(R^{11})C(O)N(R^{11})_2$, $—N(R^{11})S(O)_2(R^{11})$, $—S(O)R^{11}$, $—S(O)_2R^{11}$, $—S(O)_2N(R^{11})_2$, $—NO_2$, $═S$, $═O$, and —CN. In some embodiments, $R^2$ is optionally substituted 3- to 10-membered heterocycle, wherein the optional substituents are independently selected from: halogen, $—OR^{11}$, $—SR^{11}$, $—N(R^{11})_2$, $—C(O)R^{11}$, $—C(O)OR^{11}—NO_2$, $═S$, $═O$, and —CN.

In some embodiments, for the compound or salt of Formula (I), (I-a), (I-b), (I-c), or (I-d), $R^2$ is optionally substituted 3- to 10-membered heterocycle, wherein the optional substituents are independently selected from $C_{1-6}$ alkyl optionally substituted with one or more substituents independently selected from halogen, $—OR^{11}$, $—SR^{11}$, $—N(R^{11})_2$, $—C(O)R^{11}$, $—C(O)OR^{11}$, $—OC(O)R^{11}$, $—OC(O)N(R^{11})_2$, $—C(O)N(R^{11})_2$, $—N(R^{11})C(O)R^{11}$, $—N(R^{11})C(O)OR^{11}$, $—N(R^{11})C(O)N(R^{11})_2$, $—N(R^{11})S(O)_2(R^{11})$, $—S(O)R^{11}$, $—S(O)_2R^{11}$, $—S(O)_2N(R^{11})_2$, $—NO_2$, $═S$, $═O$, and —CN. In some embodiments, $R^2$ is optionally substituted 3- to 10-membered heterocycle, wherein the optional substituents are independently selected from $C_{1-6}$ alkyl optionally substituted with one or more substituents independently selected from halogen, $—OR^{11}$, $—SR^{11}$, $—N(R^{11})_2$, $—C(O)R^{11}$, $—C(O)OR^{11}—NO_2$, $═S$, $═O$, and —CN.

In some embodiments, for the compound or salt of Formula (I), (I-a), (I-b), (I-c), or (I-d), $R^2$ is optionally substituted 3- to 6-membered heterocycle, wherein the optional substituents are independently selected from: halogen, $—OR^{11}$, $—SR^{11}$, $—N(R^{11})_2$, $—C(O)R^{11}$, $—C(O)OR^{11}$, $—OC(O)R^{11}$, $—OC(O)N(R^{11})_2$, $—C(O)N(R^{11})_2$, $—N(R^{11})C(O)R^{11}$, $—N(R^{11})C(O)OR^{11}$, $—N(R^{11})C(O)N(R^{11})_2$, $—N(R^{11})S(O)_2(R^{11})$, $—S(O)R^{11}$, $—S(O)_2R^{11}$, $—S(O)_2N(R^{11})_2$, $—NO_2$, $═S$, $═O$, and —CN. In some embodiments, $R^2$ is 3- to 6-membered heterocycle, wherein the optional substituents are independently selected from: halogen, $—OR^{11}$, $—SR^{11}$, $—N(R^{11})_2$, $—C(O)R^{11}$, $—C(O)OR^{11}—NO_2$, $═S$, $═O$, and —CN.

In some embodiments, for the compound or salt of Formula (I), (I-a), (I-b), (I-c), or (I-d), $R^2$ is optionally substituted 3- to 6-membered heterocycle, wherein the optional substituents are independently selected from $C_{1-6}$ alkyl optionally substituted with one or more substituents independently selected from halogen, $—OR^{11}$, $—SR^{11}$, $—N(R^{11})_2$, $—C(O)R^{11}$, $—C(O)OR^{11}$, $—OC(O)R^{11}$, $—OC(O)N(R^{11})_2$, $—C(O)N(R^{11})_2$, $—N(R^{11})C(O)R^{11}$, $—N(R^{11})C(O)OR^{11}$, $—N(R^{11})C(O)N(R^{11})_2$, $—N(R^{11})S(O)_2(R^{11})$, $—S(O)R^{11}$, $—S(O)_2R^{11}$, $—S(O)_2N(R^{11})_2$, $—NO_2$, $═S$, $═O$, and —CN. In some embodiments, $R^2$ is optionally substituted 3- to 6-membered heterocycle, wherein the optional substituents are independently selected from $C_{1-6}$ alkyl optionally substituted with one or more substituents independently selected from halogen, $—OR^{11}$, $—SR^{11}$, $—N(R^{11})_2$, $—C(O)R^{11}$, $—C(O)OR^{11}—NO_2$, $═S$, $═O$, and —CN.

In some embodiments, for the compound or salt of Formula (I), (I-a), (I-b), (I-c), or (I-d), $R^1$ is selected from $C_{1-3}$ alkyl, $C_{1-3}$ haloalkyl, optionally substituted saturated $C_{3-6}$ carbocycle, and optionally substituted 3- to 6-membered heterocycle; and $R^2$ is selected from hydrogen, optionally substituted $C_{3-6}$ saturated carbocycle, and optionally substituted 3- to 6-membered heterocycle; wherein at least one of $R^1$ and $R^2$ is selected from optionally substituted $C_{3-6}$ saturated carbocycle, and optionally substituted 3- to 6-membered heterocycle. In some embodiments, $R^1$ is $C_{1-3}$ alkyl and $R^2$ is selected from optionally substituted $C_{3-6}$ saturated carbocycle, and optionally substituted 3- to 6-membered heterocycle. In some embodiments, $R^1$ is $C_{1-3}$ haloalkyl and $R^2$ is selected from optionally substituted $C_{3-6}$ saturated carbocycle, and optionally substituted 3- to 6-membered heterocycle. In some embodiments, $R^1$ is optionally substituted saturated $C_{3-6}$ carbocycle and $R^2$ is selected from hydrogen, optionally substituted $C_{3-6}$ saturated carbocycle, and optionally substituted 3- to 6-membered heterocycle. In some embodiments, $R^1$ is optionally substituted 3- to 6-membered heterocycle and $R^2$ is selected from hydrogen, optionally substituted $C_{3-6}$ saturated carbocycle, and optionally substituted 3- to 6-membered heterocycle.

In some embodiments, for the compound or salt of Formula (I), (I-a), (I-b), (I-c), or (I-d), $R^1$ is selected from $C_{1-3}$ alkyl, $C_{1-3}$ haloalkyl, optionally substituted saturated $C_{3-6}$ carbocycle, and optionally substituted 3- to 6-membered heterocycle; and $R^2$ is selected from hydrogen, optionally substituted $C_{3-6}$ saturated carbocycle, and optionally substituted 3- to 6-membered heterocycle; wherein at least one of $R^1$ and $R^2$ is selected from optionally substituted $C_{3-6}$ saturated carbocycle, and optionally substituted 3- to 6-membered heterocycle. In some embodiments, $R^1$ is selected from optionally substituted saturated $C_{3-6}$ carbocycle, and optionally substituted 3- to 6-membered heterocycle; and $R^2$ is hydrogen. In some embodiments, $R^1$ is selected from $C_{1-3}$ alkyl, $C_{1-3}$ haloalkyl, optionally substituted saturated $C_{3-6}$ carbocycle, and optionally substituted 3- to 6-membered heterocycle; and $R^2$ is optionally substituted $C_{3-6}$ saturated carbocycle. In some embodiments, $R^1$ is selected from $C_{1-3}$ alkyl, $C_{1-3}$ haloalkyl, optionally substituted saturated $C_{3-6}$ carbocycle, and optionally substituted 3- to 6-membered heterocycle; and $R^2$ is optionally substituted 3- to 6-membered heterocycle.

In some embodiments, for the compound or salt of Formula (I), (I-a), (I-b), (I-c), or (I-d), $R^1$ is optionally substituted saturated $C_{3-6}$ carbocycle or optionally substituted saturated 3- to 6-membered heterocycle; and $R^2$ is selected from hydrogen, optionally substituted $C_{3-6}$ saturated carbocycle, and optionally substituted saturated 3- to 6-membered heterocycle. In some embodiments, $R^1$ is optionally substituted saturated $C_{3-4}$ carbocycle or optionally substituted saturated 3- to 4-membered heterocycle; and $R^2$ is selected from hydrogen, optionally substituted saturated $C_{3-6}$ carbocycle, and optionally substituted saturated 3- to 6-membered heterocycle. In some embodiments, $R^1$ is optionally substituted $C_{3-4}$ cycloalkyl or optionally substituted 3- to 4-membered heterocycloalkyl; and $R^2$ is hydrogen.

In some embodiments, for the compound or salt of Formula (I), (I-a), (I-b), (I-c), or (I-d), $R^2$ is optionally substituted $C_{3-6}$ saturated carbocycle, and optionally substituted 3- to 6-membered heterocycle; and $R^1$ is selected from $C_{1-3}$ alkyl, $C_{1-3}$ haloalkyl, optionally substituted saturated $C_{3-6}$ carbocycle, and optionally substituted 3- to 6-membered heterocycle. In some embodiments, $R^2$ is optionally substituted saturated $C_{3-4}$ carbocycle or optionally substituted saturated 3- to 4-membered heterocycle; and $R^1$ is selected from $C_{1-3}$ alkyl, $C_{1-3}$ haloalkyl, optionally substituted saturated $C_{3-6}$ carbocycle, and optionally substituted 3- to 6-membered heterocycle.

In some embodiments, for the compound or salt of Formula (I), (I-a), (I-b), (I-c), or (I-d), $R^1$ is selected from methyl, ethyl,

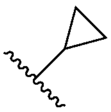 and 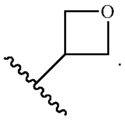 [SMILES: *C1COC1]

In some embodiments, $R^1$ is selected from

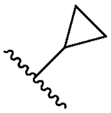 and 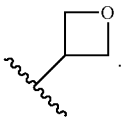

In some embodiments, $R^1$ is selected from methyl and ethyl.

In some embodiments, for the compound or salt of Formula (I), (I-a), (I-b), (I-c), or (I-d), $R^2$ is hydrogen or

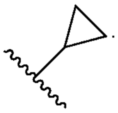

In some embodiments, $R^2$ is hydrogen. In some embodiments, $R^2$ is

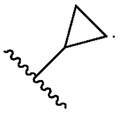

In some embodiments, for the compound or salt of Formula (I), (I-a), (I-b), (I-c), or (I-d), at least one of $R^1$ and $R^2$ is selected from

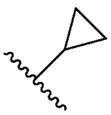 and 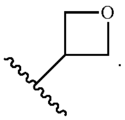

In some embodiments, at least one of $R^1$ and $R^2$ is selected from

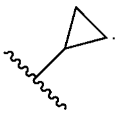

In some embodiments, at least one of $R^1$ and $R^2$ is selected from

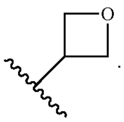

In some embodiments, for the compound or salt of Formula (I), (I-a), (I-b), (I-c), or (I-d), A is selected from optionally substituted $C_{3-10}$ saturated carbocyclene. In some embodiments, the optionally substituted $C_{3-10}$ saturated carbocyclene of A is selected from: optionally substituted $C_3$ saturated carbocyclene, optionally substituted $C_4$ saturated carbocyclene, optionally substituted $C_5$ saturated carbocyclene, optionally substituted $C_6$ saturated carbocyclene, optionally substituted $C_7$ saturated carbocyclene, optionally substituted $C_8$ saturated carbocyclene, optionally substituted $C_9$ saturated carbocyclene, and optionally substituted $C_{10}$ saturated carbocyclene. In some embodiments, the optionally substituted $C_{3-10}$ saturated carbocyclene of A is selected from: optionally substituted $C_{3-4}$ saturated carbocyclene, optionally substituted $C_{3-5}$ saturated carbocyclene, optionally substituted $C_{3-6}$ saturated carbocyclene, optionally substituted $C_{3-7}$ saturated carbocyclene, optionally substituted $C_{3-8}$ saturated carbocyclene, and optionally substituted $C_{3-9}$ saturated carbocyclene.

In some embodiments, for the compound or salt of Formula (I), (I-a), (I-b), (I-c), or (I-d), A is optionally substituted $C_{3-10}$ carbocyclene, wherein the optional substituents are independently selected from: halogen, $—OR^4$, $—SR^{14}$, $—N(R^{14})_2$, $—C(O)R^{14}$, $—C(O)OR^{14}$, $—OC(O)R^{14}$, $—OC(O)N(R^{14})_2$, $—C(O)N(R^{14})_2$, $—N(R^{14})C(O)R^{14}$, $—N(R^{14})C(O)OR^{14}$, $—N(R^{14})C(O)N(R^{14})_2$, $—N(R^{14})S(O)_2(R^{14})$, $—S(O)R^{14}$, $—S(O)_2R^{14}$, $—S(O)_2N(R^{14})_2$, $—NO_2$, and —CN; and $C_{1-6}$ alkyl optionally substituted with one or more substituents independently selected from halogen, $—OR^{14}$, $—SR^{14}$, $—N(R^{14})_2$, $—C(O)R^{14}$, $—C(O)OR^{14}$, $—OC(O)R^{14}$, $—OC(O)N(R^{14})_2$, $—C(O)N(R^{14})_2$, $—N(R^{14})C(O)R^{14}$, $—N(R^{14})C(O)OR^{14}$, $—N(R^{14})C(O)N(R^{14})_2$, $—N(R^{14})S(O)_2(R^{14})$, $—S(O)R^{14}$, $—S(O)_2R^{14}$, $—S(O)_2N(R^{14})_2$, $—NO_2$, =S, =O, and —CN. In some embodiments, A is optionally substituted $C_{3-10}$ carbocyclene, wherein the optional substituents are independently selected from: halogen, $—OR^{14}$, $—N(R^{14})_2$, $—C(O)R^{14}$, $—C(O)OR^{14}$, $—NO_2$, and —CN; and $C_{1-6}$ alkyl optionally substituted with one or more substituents independently selected from halogen, $—OR^{14}$, $—N(R^{14})_2$, $—C(O)R^{14}$, $—C(O)OR^{14}$, $—NO_2$, and —CN.

In some embodiments, for the compound or salt of Formula (I), (I-a), (I-b), (I-c), or (I-d), A is optionally substituted $C_{3-6}$ carbocyclene, wherein the optional substituents are independently selected from: halogen, $—OR^{14}$, $—SR^{14}$, $—N(R^{14})_2$, $—C(O)R^{14}$, $—C(O)OR^{14}$, $—OC(O)R^{14}$, $—OC(O)N(R^{14})_2$, $—C(O)N(R^{14})_2$, $—N(R^{14})C(O)R^{14}$, $—N(R^{14})C(O)OR^{14}$, $—N(R^{14})C(O)N(R^{14})_2$, $—N(R^{14})S(O)_2(R^{14})$, $—S(O)R^{14}$, $—S(O)_2R^{14}$, $—S(O)_2N(R^{14})_2$, $—NO_2$, and —CN; and $C_{1-6}$ alkyl optionally substituted with one or more substituents independently selected from halogen, $—OR^{14}$, $—SR^{14}$, $—N(R^{14})_2$, $—C(O)R^{14}$, $—C(O)OR^{14}$, $—OC(O)R^{14}$, $—OC(O)N(R^{14})_2$, $—C(O)N(R^{14})_2$, $—N(R^{14})C(O)R^{14}$, $—N(R^{14})C(O)OR^{14}$, $—N(R^{14})C(O)N(R^{14})_2$, $—N(R^{14})S(O)_2(R^{14})$, $—S(O)R^{14}$, $—S(O)_2R^{14}$, $—S(O)_2N(R^{14})_2$, $—NO_2$, =S, =O, and —CN. In some embodiments, A is optionally substituted $C_{3-6}$ carbocyclene, wherein the optional substituents are independently selected from: halogen, $—OR^{14}$, $—N(R^{14})_2$, $—C(O)R^{14}$, $—C(O)OR^{14}$, $—NO_2$, and —CN; and $C_{1-6}$ alkyl optionally substituted with one or more substituents independently selected from halogen, $—OR^{14}$, $—N(R^{14})_2$, $—C(O)R^{14}$, $—C(O)OR^{14}$, $—NO_2$, and —CN.

In some embodiments, for the compound or salt of Formula (I), (I-a), (I-b), (I-c), or (I-d), A is optionally substituted phenylene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted phenylene, wherein the optional substituents are independently selected from: halogen, —$OR^{14}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN.

In some embodiments, for the compound or salt of Formula (I), (I-a), (I-b), (I-c), or (I-d), A is optionally substituted phenylene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN. In some embodiments, A is optionally substituted phenylene, wherein the optional substituents are independently selected from: halogen, —$OR^{14}$, —$N(R^{14})_2$, —$C(O)R^{14}$, —$C(O)OR^{14}$, —$NO_2$, and —CN.

In some embodiments, for the compound or salt of Formula (I), (I-a), (I-b), (I-c), or (I-d), A is optionally substituted phenylene, wherein the optional substituents are independently selected from: $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted phenylene, wherein the optional substituents are independently selected from: $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN.

In some embodiments, for the compound or salt of Formula (I), (I-a), (I-b), (I-c), or (I-d),

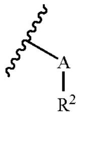

is selected from:

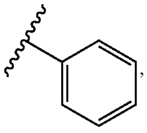, 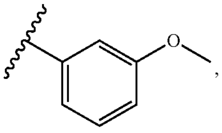, 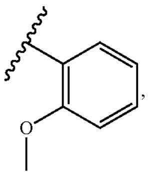,

-continued

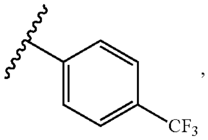, 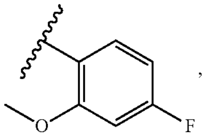,

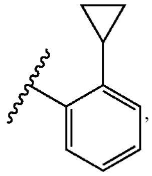, 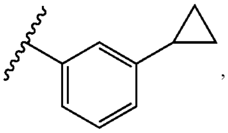,

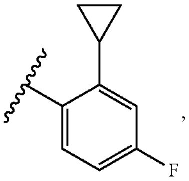, and

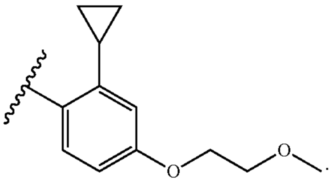.

In some embodiments, for the compound or salt of Formula (I), (I-a), (I-b), (I-c), or (I-d), $R^1$ is selected from optionally substituted $C_{3-10}$ carbocycle and optionally substituted 3- to 10-membered heterocycle; $R^2$ is selected hydrogen; and A is selected from

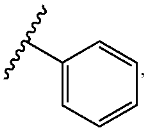, 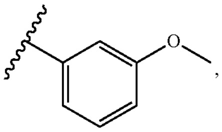, 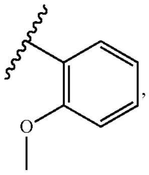,

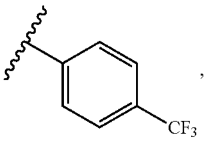, and 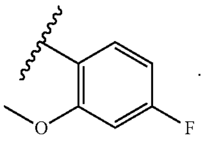.

In some embodiments, for the compound or salt of Formula (I), (I-a), (I-b), (I-c), or (I-d),

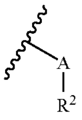

is selected from:

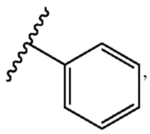, 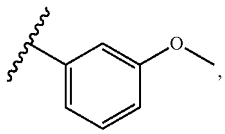, 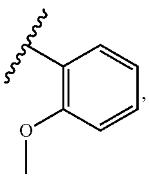, 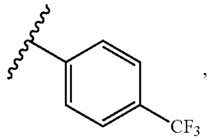, 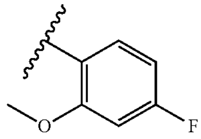, 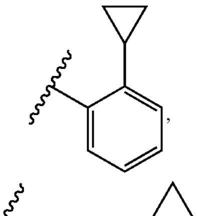, 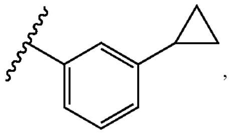, 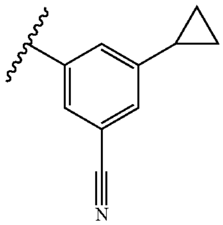, 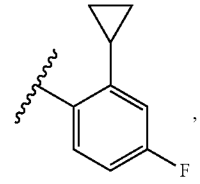, and 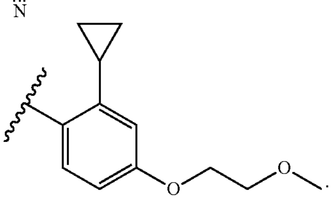.

In some embodiments, for the compound or salt of Formula (I), (I-a), (I-b), (I-c), or (I-d), A is selected from optionally substituted 3- to 10-membered heterocyclene, wherein when A is a 5-membered heteroaryl, the 5-membered heteroaryl includes one or more heteroatoms selected from O, S, and N, and no more than two N atoms in the ring. In some embodiments, the optionally substituted 3- to 10-membered heterocyclene of A is selected from: optionally substituted 3-membered heterocyclene, optionally substituted 4-membered heterocyclene, optionally substituted 5-membered heterocyclene, optionally substituted 6-membered heterocyclene, optionally substituted 7-membered heterocyclene, optionally substituted 8-membered heterocyclene, optionally substituted 9-membered heterocyclene, and optionally substituted 10-membered heterocyclene. In some embodiments, the optionally substituted 3- to 10-membered heterocyclene of A is selected from: optionally substituted 3- to 4-membered heterocyclene, optionally substituted 3- to 5-membered heterocyclene, optionally substituted 3- to 6-membered heterocyclene, optionally substituted 3- to 7-membered heterocyclene, optionally substituted 3- to 8-membered heterocyclene, and optionally substituted 3- to 9-membered heterocyclene.

In some embodiments, for the compound or salt of Formula (I), (I-a), (I-b), (I-c), or (I-d), A is optionally substituted 3- to 10-membered heterocyclene, wherein the optional substituents are independently selected from: halogen, —$OR^{11}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted 3- to 10-membered heterocyclene, wherein the optional substituents are independently selected from: halogen, —$OR^{11}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN.

In some embodiments, for the compound or salt of Formula (I), (I-a), (I-b), (I-c), or (I-d), A is optionally substituted 3- to 6-membered heterocyclene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted 3- to 6-membered heterocyclene, wherein the optional substituents are independently selected from: halogen, —$OR^{14}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN.

In some embodiments, for the compound or salt of Formula (I), (I-a), (I-b), (I-c), or (I-d), A is optionally substituted 3- to 6-membered heterocyclene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted 3- to 6-membered heterocyclene, wherein the optional substituents are independently selected from: halogen, —$OR^{14}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN; wherein when A is a 5-membered heteroaryl, the 5-membered heteroaryl includes one or more heteroatoms selected from O, S, and N, and no more than two N atoms in the ring.

In some embodiments, for the compound or salt of Formula (I), (I-a), (I-b), (I-c), or (I-d), A is optionally substituted 6-membered heteroarylene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted 6-membered heteroarylene, wherein the optional substituents are independently selected from: halogen, —$OR^{14}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN; wherein when A is a 5-membered heteroaryl, the 5-membered heteroaryl includes one or more heteroatoms selected from O, S, and N, and no more than two N atoms in the ring.

In some embodiments, for the compound or salt of Formula (I), (I-a), (I-b), (I-c), or (I-d), A is optionally substituted pyridinylene, optionally substituted pyrimidinylene, and optionally substituted pyrazinylene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, =S, =O, and —CN. In some embodiments, A is optionally substituted pyridinylene, optionally substituted pyrimidinylene, and optionally substituted pyrazinylene, wherein the optional substituents are independently selected from: halogen, —$OR^{14}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{14}$, —$N(R^{14})_2$, —$C(O)R^{14}$, —$C(O)OR^{14}$, —$NO_2$, and —CN; wherein when A is a 5-membered heteroaryl, the 5-membered heteroaryl includes one or more heteroatoms selected from O, S, and N, and no more than two N atoms in the ring. In some embodiments,

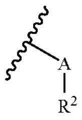

is selected from

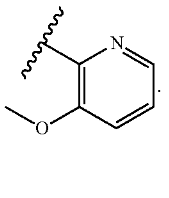 [SMILES: *c1ncccc1OC]

In some embodiments, for the compound or salt of Formula (I), (I-a), (I-b), (I-c), or (I-d), $R^1$ is selected from $C_{1-6}$ alkyl optionally substituted with one or more substituents independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2(R^{10})$, —$S(O)R^{10}$, —$S(O)_2R^{10}$, —$S(O)_2N(R^{10})_2$, —$NO_2$, =S, =O, and —CN; and

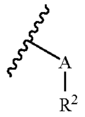

is selected from

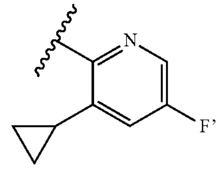
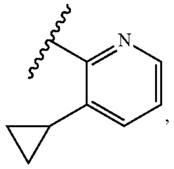
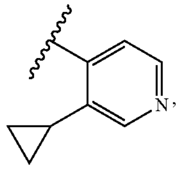
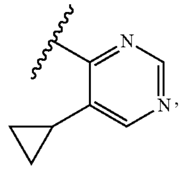
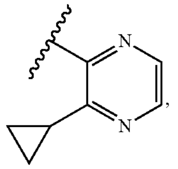
and
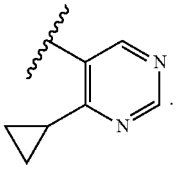

In some embodiments, for the compound or salt of Formula (I), (I-a), (I-b), (I-c), or (I-d),

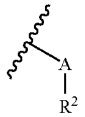

is selected from

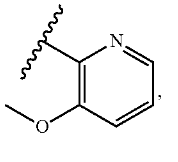
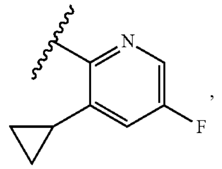
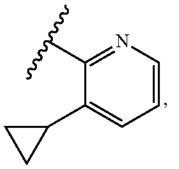
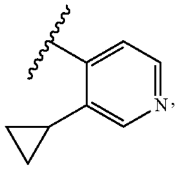
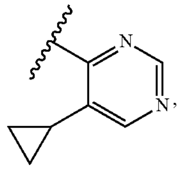

-continued

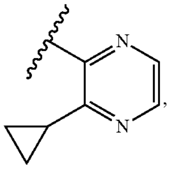, and 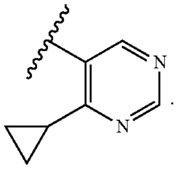.

In some embodiments, for the compound or salt of Formula (I), (I-a), (I-b), (I-c), or (I-d), $R^1$ is selected from $C_{1-6}$ alkyl optionally substituted with one or more substituents independently selected from: halogen, —$OR^{10}$, —$SR^{10}$, —$N(R^{10})_2$, —$C(O)R^{10}$, —$C(O)OR^{10}$, —$OC(O)R^{10}$, —$OC(O)N(R^{10})_2$, —$C(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)_2R^{10}$), —$S(O)R^{10}$, —$S(O)_2R^{10}$, —$S(O)_2N(R^{10})_2$, —$NO_2$, ═S, ═O, and —CN; and

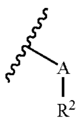

is selected from

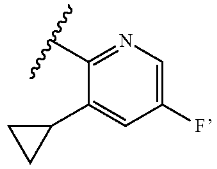 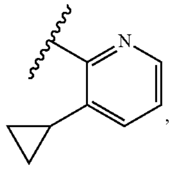,

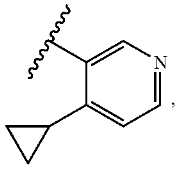, 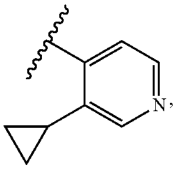, 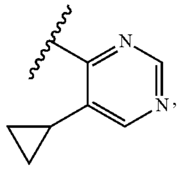,

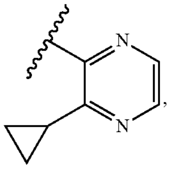, and 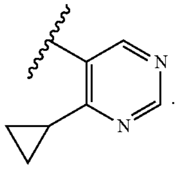.

In some embodiments, for the compound or salt of Formula (I), (I-a), (I-b), (I-c), or (I-d),

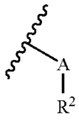

is selected from

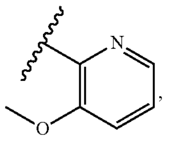, 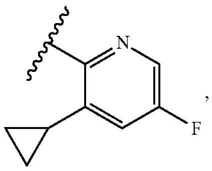,

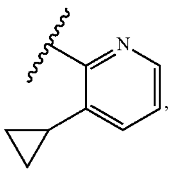, 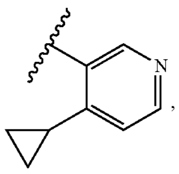, 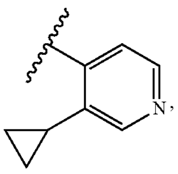,

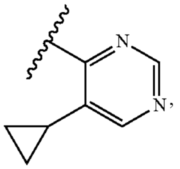, 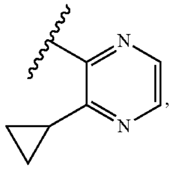, and

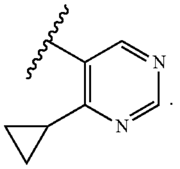.

In some embodiments, for the compound or salt of Formula (I), (I-a), (I-b), (I-c), or (I-d), A is selected from optionally substituted phenylene and optionally substituted 6-membered heteroarylene, wherein the optional substituents are independently selected from: halogen, —$OR^{14}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, and —CN; and $C_{1-6}$ alkyl optionally substituted with one or more substituents independently selected from halogen, —$OR^{11}$, —$SR^{14}$, —$N(R^{14})_2$, —$C(O)R^{14}$, —$C(O)OR^{14}$, —$OC(O)R^{14}$, —$OC(O)N(R^{14})_2$, —$C(O)N(R^{14})_2$, —$N(R^{14})C(O)R^{14}$, —$N(R^{14})C(O)OR^{14}$, —$N(R^{14})C(O)N(R^{14})_2$, —$N(R^{14})S(O)_2(R^{14})$, —$S(O)R^{14}$, —$S(O)_2R^{14}$, —$S(O)_2N(R^{14})_2$, —$NO_2$, ═S, ═O, and —CN. In some embodiments, A is selected from optionally substituted phenylene and optionally substituted 6-membered heteroarylene, wherein the optional substituents are independently selected from: halogen, —$OR^{11}$, —$N(R^{14})_2$, —$C(O)R^{14}$, —$C(O)OR^{14}$, —$NO_2$, and —CN; and $C_{1-6}$ alkyl optionally substituted with one or more substituents independently selected from halogen, —$OR^{11}$, —$N(R^{14})_2$, —$C(O)R^{14}$, —$C(O)OR^{14}$, —$NO_2$, and —CN.

In some embodiments, for the compound or salt of Formula (I), (I-a), (I-b), (I-c), or (I-d),

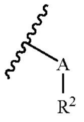

is selected from:
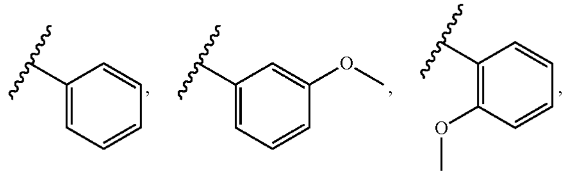
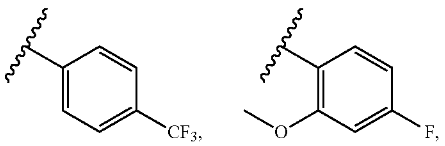
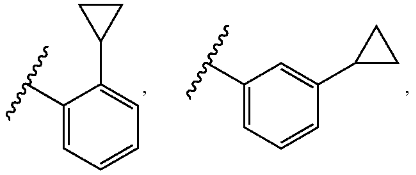
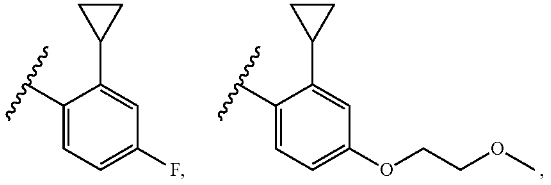
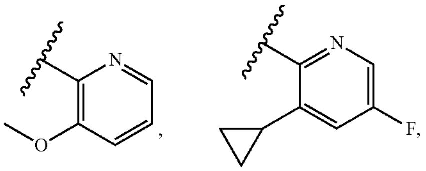
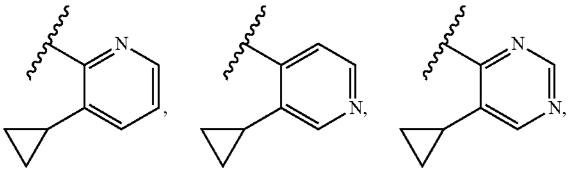
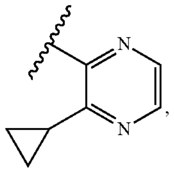
and
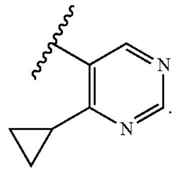
In some embodiments, for the compound or salt of Formula (I), (I-a), (I-b), (I-c), or (I-d),
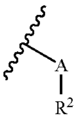
is selected from:
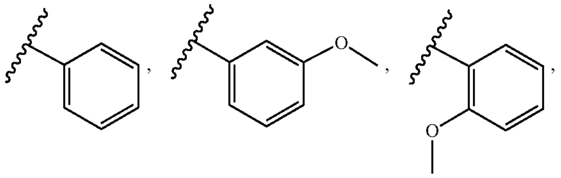
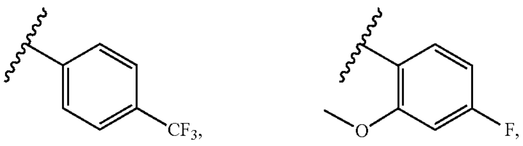
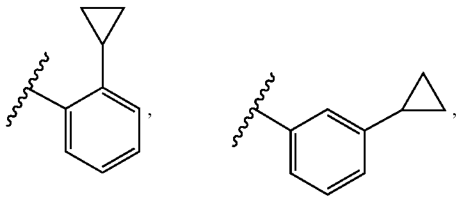
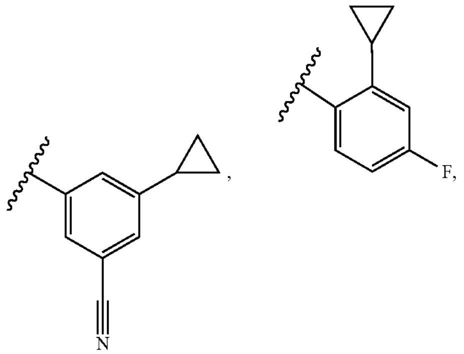
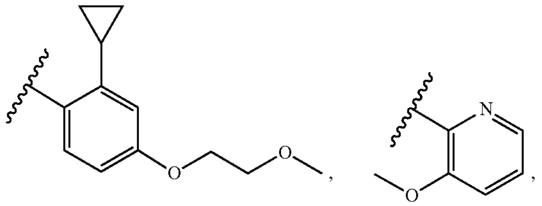
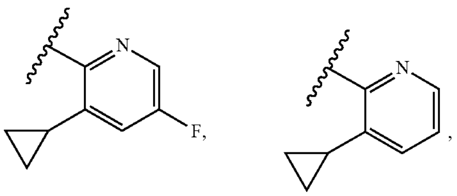
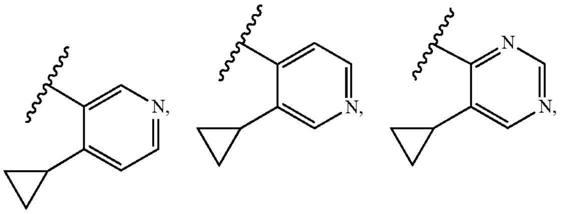

-continued

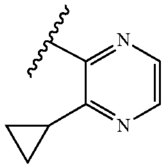

,

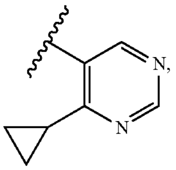

In some embodiments, for the compound or salt of Formula (I), (I-a), (I-b), (I-c), or (I-d), the optionally substituted 3- to 10-membered heterocyclene of

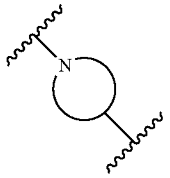

is selected from: optionally substituted 3-membered heterocyclene, optionally substituted 4-membered heterocyclene, optionally substituted 5-membered heterocyclene, optionally substituted 6-membered heterocyclene, optionally substituted 7-membered heterocyclene, optionally substituted 8-membered heterocyclene, optionally substituted 9-membered heterocyclene, and optionally substituted 10-membered heterocyclene. In some embodiments,

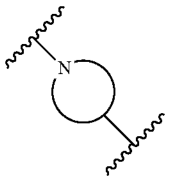

is selected from: optionally substituted 3- to 4-membered heterocyclene, optionally substituted 3- to 5-membered heterocyclene, optionally substituted 3- to 6-membered heterocyclene, optionally substituted 3- to 7-membered heterocyclene, optionally substituted 3- to 8-membered heterocyclene, and optionally substituted 3- to 9-membered heterocyclene. In some embodiments,

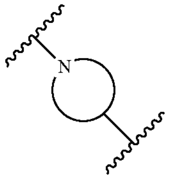

is optionally substituted 3- to 7-membered heterocyclene. In some embodiments,

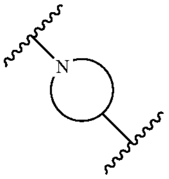

is optionally substituted 4- to 7-membered heterocyclene. In some embodiments,

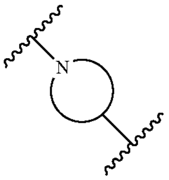

is optionally substituted 5- to 7-membered heterocyclene.

In some embodiments, for the compound or salt of Formula (I), (I-a), (I-b), (I-c), or (I-d),

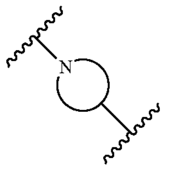

is selected from 4- to 7-membered heterocyclene optionally substituted with one or more substituents independently selected from: halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, and —CN; and $C_{1-6}$ alkyl optionally substituted with one or more substituents independently selected from halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, ═S, ═O, and —CN; and $R^{13}$ is selected from hydrogen, $C_{1-3}$ alkyl, and $C_{1-3}$ haloalkyl. In some embodiments,

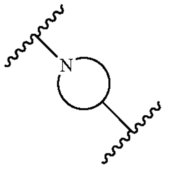

is selected from 4- to 7-membered heterocyclene optionally substituted with one or more substituents independently selected from: halogen, —$OR^{13}$, —$N(R^{13})_2$, —$C(O)R^{13}$, —$C(O)OR^{13}$, —$NO_2$, and —CN; and $C_{1-6}$ alkyl optionally substituted with one or more substituents independently selected from: halogen, —$OR^{13}$, —$N(R^{13})_2$, —$C(O)R^{13}$, —$C(O)OR^{13}$, —$NO_2$, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

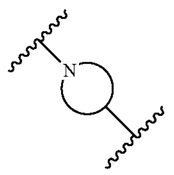

is selected from 4- to 7-membered heterocyclene, each of which is optionally substituted with one or more substituents independently selected from halogen, —$OR^{13}$, —$N(R^{13})_2$, —$C(O)R^{13}$, —$C(O)OR^{13}$, —$C(O)N(R^{13})_2$, —$NO_2$, —CN; and $C_{1-6}$ alkyl optionally substituted with one or more substituents independently selected from halogen, —$OR^{13}$, —$N(R^{13})_2$, —$C(O)R^{13}$, —$C(O)OR^{13}$, —$C(O)N(R^{13})_2$, —$NO_2$, =S, =O, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

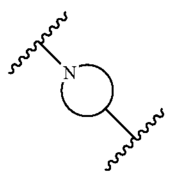

is selected from 5- to 6-membered saturated heterocyclene optionally substituted with one or more substituents independently selected from: halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, and —CN; and $C_{1-6}$ alkyl optionally substituted with one or more substituents independently selected from halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, =S, =O, and —CN; and $R^{13}$ is selected from hydrogen, $C_{1-3}$ alkyl, and $C_{1-3}$ haloalkyl. In some embodiments,

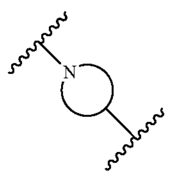

is selected from 5- to 6-membered saturated heterocyclene optionally substituted with one or more substituents independently selected from: halogen, —$OR^{13}$, —$N(R^{13})_2$, —$C(O)R^{13}$, —$C(O)OR^{13}$, —$NO_2$, and —CN; and $C_{1-6}$ alkyl optionally substituted with one or more substituents independently selected from: halogen, —$OR^{13}$, —$N(R^{13})_2$, —$C(O)R^{13}$, —$C(O)OR^{13}$, —$NO_2$, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

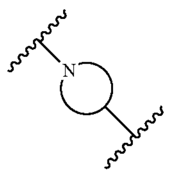

is selected from 5- to 6-membered saturated heterocyclene, optionally substituted with one or more substituents independently selected from halogen, —$OR^{13}$, —$N(R^{13})_2$, —$C(O)R^{13}$, —$C(O)OR^{13}$, —$C(O)N(R^{13})_2$, —$NO_2$, —CN; and $C_{1-6}$ alkyl optionally substituted with one or more substituents independently selected from halogen, —$OR^{13}$, —$N(R^{13})_2$, —$C(O)R^{13}$, —$C(O)OR^{13}$, —$C(O)N(R^{13})_2$, —$NO_2$, =S, =O, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

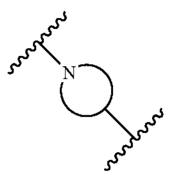

is selected from pyrrolidinylene, piperidinylene and piperazinylene, each of which is optionally substituted with one or more substituents independently selected from: halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, and —CN; and $C_{1-6}$ alkyl optionally substituted with one or more substituents independently selected from halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, =S, =O, and —CN; and $R^{13}$ is selected from hydrogen, $C_{1-3}$ alkyl, and $C_{1-3}$ haloalkyl. In some embodiments,

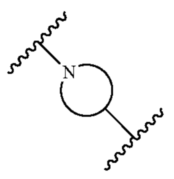

is selected from piperidinylene and piperazinylene, each of which is optionally substituted with one or more substituents independently selected from: halogen, —$OR^{13}$, —$N(R^{13})_2$, —$C(O)R^{13}$, —$C(O)OR^{13}$, —$NO_2$, and —CN; and $C_{1-6}$ alkyl optionally substituted with one or more substituents independently selected from: halogen, —$OR^{13}$, —$N(R^{13})_2$, —$C(O)R^{13}$, —$C(O)OR^{13}$, —$NO_2$, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

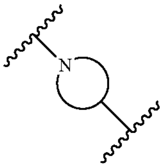

is selected from piperidinylene and piperazinylene, each of which is optionally substituted with one or more substituents independently selected from: halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, and —CN; and $C_{1-6}$ alkyl optionally substituted with one or more substituents independently selected from halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, =S, =O, and —CN; and $R^{13}$ is selected from hydrogen, $C_{1-3}$ alkyl, and $C_{1-3}$ haloalkyl. In some embodiments,

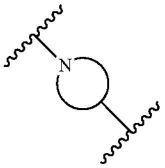

is selected from piperidinylene and piperazinylene, each of which is optionally substituted with one or more substituents independently selected from: halogen, —$OR^{13}$, —$N(R^{13})_2$, —$C(O)R^{13}$, —$C(O)OR^{13}$, —$NO_2$, and —CN; and $C_{1-6}$ alkyl optionally substituted with one or more substituents independently selected from: halogen, —$OR^{13}$, —$N(R^{13})_2$, —$C(O)R^{13}$, —$C(O)OR^{13}$, —$NO_2$, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

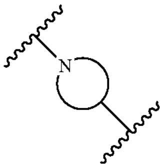

is selected from piperidinylene and piperazinylene, each of which is optionally substituted with one or more substituents independently selected from: halogen, —$OR^{13}$, —$SR^{13}$, —$N(R^{13})_2$, —$C(O)R^{13}$, —$C(O)OR^{13}$, —$OC(O)R^{13}$, —$OC(O)N(R^{13})_2$, —$C(O)N(R^{13})_2$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$S(O)R^{13}$, —$S(O)_2R^{13}$, —$S(O)_2N(R^{13})_2$, —$NO_2$, and —CN; and $R^{13}$ is selected from hydrogen, $C_{1-3}$ alkyl, and $C_{1-3}$ haloalkyl. In some embodiments,

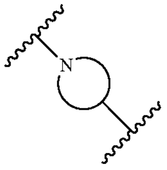

is selected from piperidinylene and piperazinylene, each of which is optionally substituted with one or more substituents independently selected from: halogen, —$OR^{13}$, —$N(R^{13})_2$, —$C(O)R^{13}$, —$C(O)OR^{13}$, —$NO_2$, and —CN; and $R^{13}$ is selected from hydrogen, $C_{1-3}$ alkyl, and $C_{1-3}$ haloalkyl.

In some embodiments, for the compound or salt of Formula (I), (I-a), (I-b), (I-c), or (I-d),

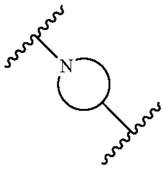

is unsubstituted. In some embodiments,

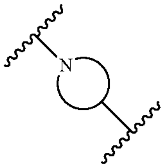

is

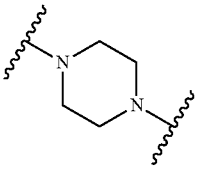

.

In some embodiments,

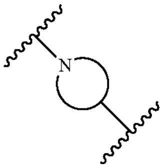

is

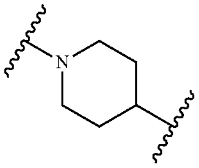

.

In some embodiments, for the compound or salt of Formula (I), (I-a), (I-b), (I-c), or (I-d), $R^3$ is selected from halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, and —CN; and $C_{1-3}$ alkyl optionally substituted with one or more substituents independently selected from halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, =S, =O, and —CN. In some embodiments, $R^3$ is selected from halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, and —CN. In some embodiments, $R^3$ is selected from halogen, —$OR^{12}$, —$N(R^{12})_2$, —$C(O)R^{12}$, —$C(O)OR^{12}$, —$NO_2$, and —CN. In some embodiments, $R^3$ is selected from $C_{1-3}$ alkyl optionally substituted with one or more substituents independently selected from halogen, —$OR^{12}$, —$SR^{12}$, —$N(R^{12})_2$, —$C(O)R^{12}$, —$C(O)OR^{12}$, —$OC(O)R^{12}$, —$OC(O)N(R^{12})_2$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})S(O)_2(R^{12})$, —$S(O)R^{12}$, —$S(O)_2R^{12}$, —$S(O)_2N(R^{12})_2$, —$NO_2$, =S, =O, and —CN. In some embodiments, $R^3$ is selected from $C_{1-3}$ alkyl optionally substituted with one or more substituents independently selected from halogen, —$OR^{12}$, —$N(R^{12})_2$, —$C(O)R^{12}$, —$C(O)OR^{12}$, —$NO_2$, and —CN. In some embodiments, $R^3$ is selected from halogen, —$OR^{12}$, —$N(R^{12})_2$, —$C(O)R^{12}$, —$C(O)OR^{12}$, —$NO_2$, —CN, $C_{1-3}$ alkyl, and $C_{1-3}$ haloalkyl; and $R^{12}$ is selected from hydrogen, $C_{1-3}$ alkyl, and $C_{1-3}$ haloalkyl.

In some embodiments, for the compound or salt of Formula (I), (I-a), (I-b), (I-c), or (I-d), $R^{10}$ is hydrogen. In some embodiments, $R^{10}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{10}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{10}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (I), (I-a), (I-b), (I-c), or (I-d), $R^{11}$ is hydrogen. In some embodiments, $R^{11}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{11}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{11}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (I), (I-a), (I-b), (I-c), or (I-d), $R^{12}$ is hydrogen. In some embodiments, $R^{12}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{12}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{12}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (I), (I-a), (I-b), (I-c), or (I-d), $R^{13}$ is hydrogen. In some embodiments, $R^{13}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{13}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{13}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (I), (I-a), (I-b), (I-c), or (I-d), $R^{14}$ is hydrogen. In some embodiments, $R^{14}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{14}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{14}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, the compound of Formula (I) is:
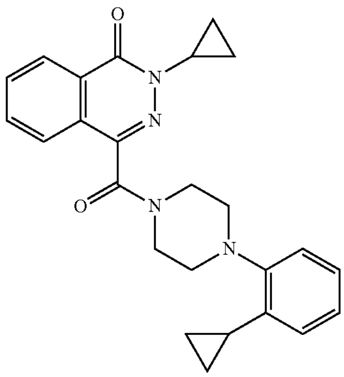
,
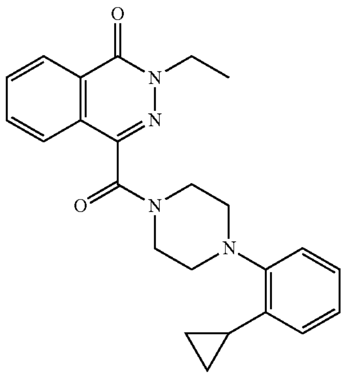
,
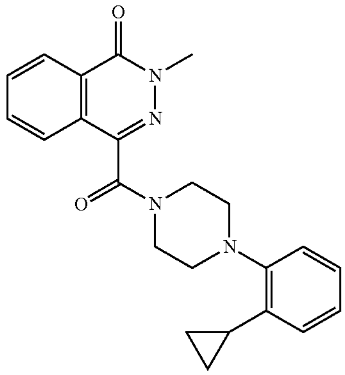
,
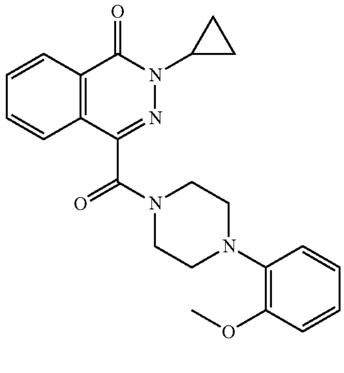
,
-continued
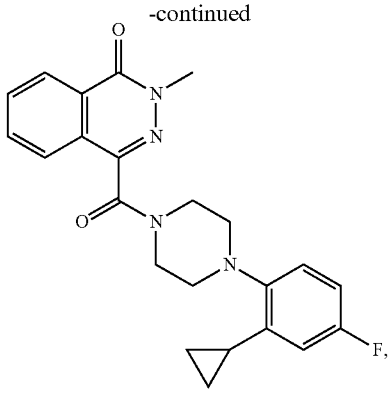
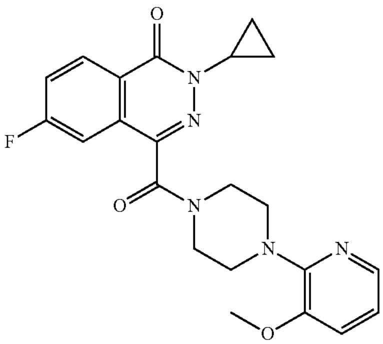
,
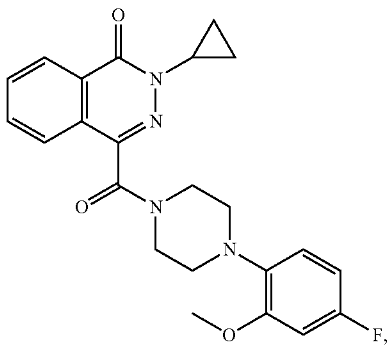
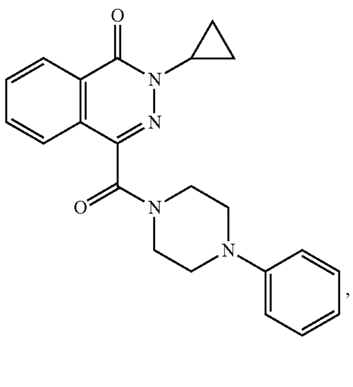
, -continued
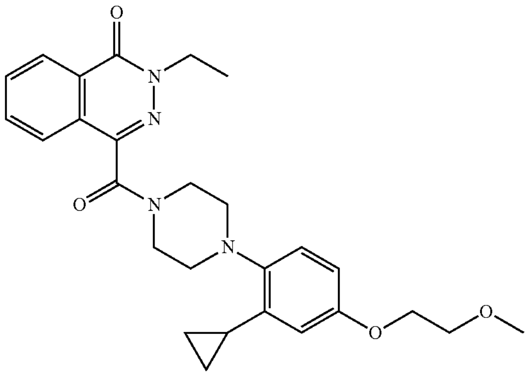
,
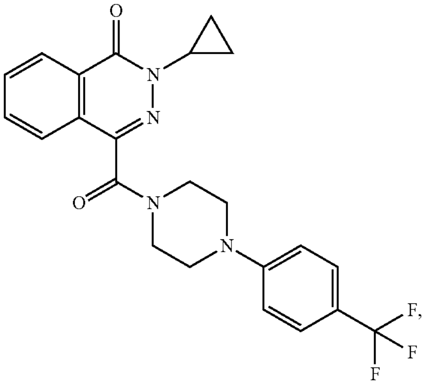
,
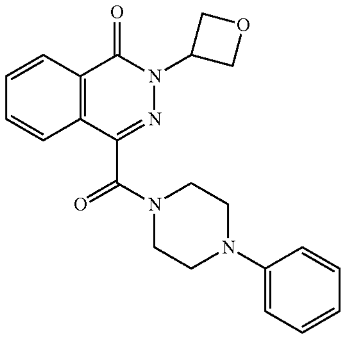
,
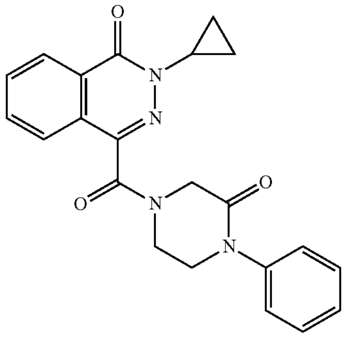
,
-continued
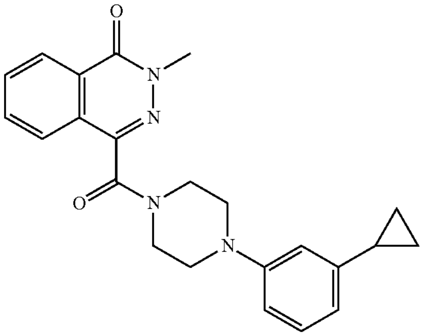
,
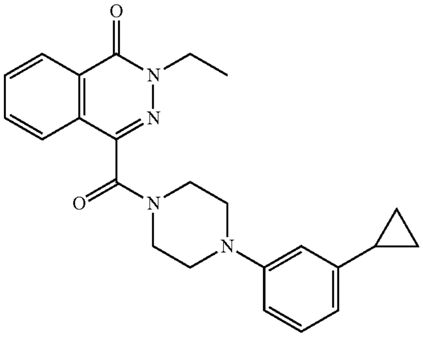
,
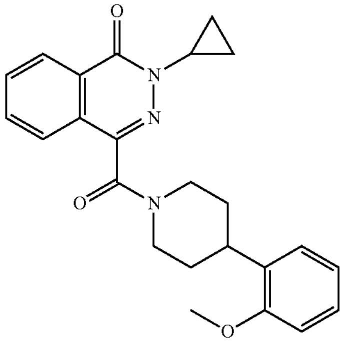
,
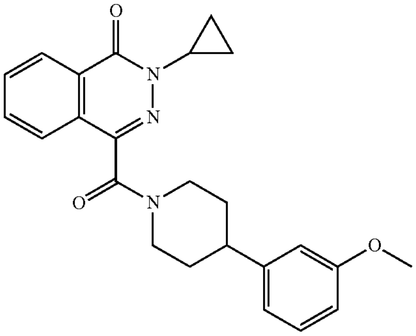
,
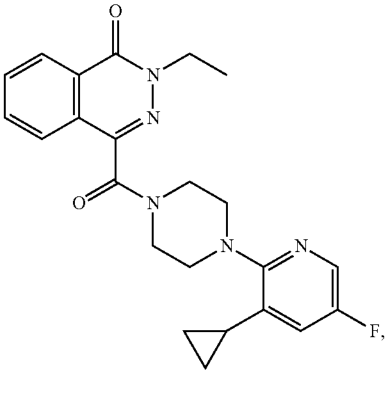
, -continued
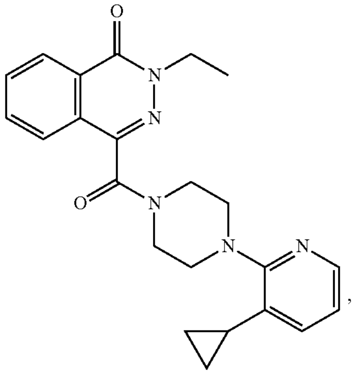
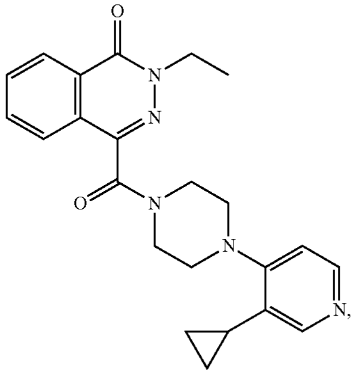
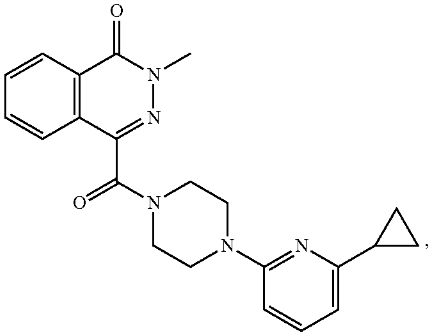
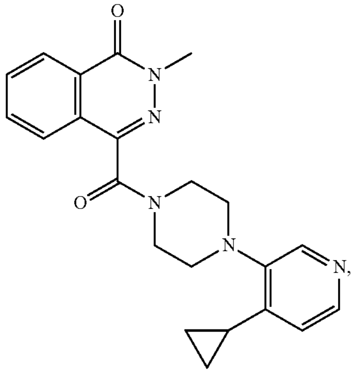
-continued
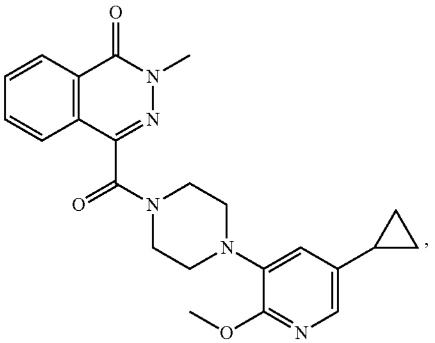
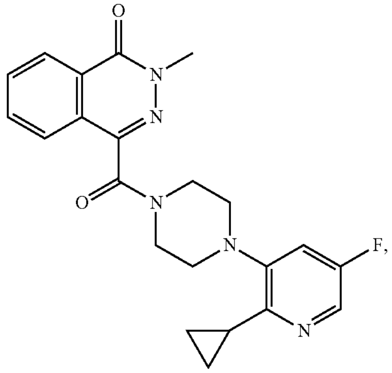
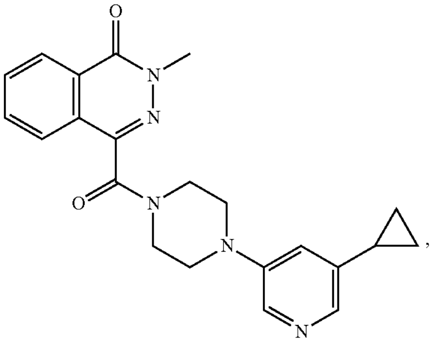
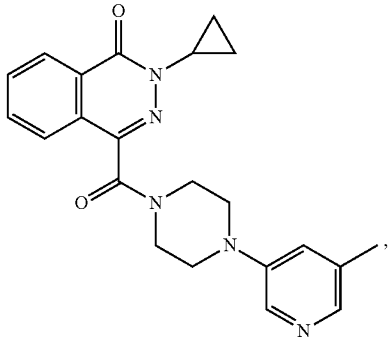

-continued
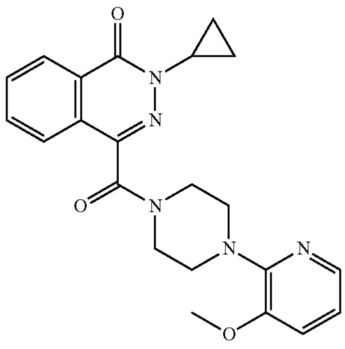
,
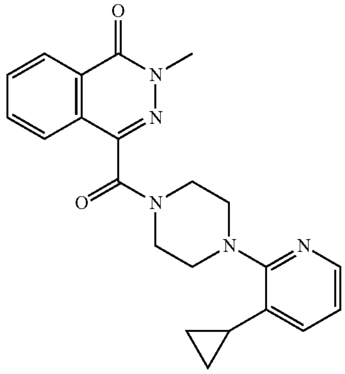
,
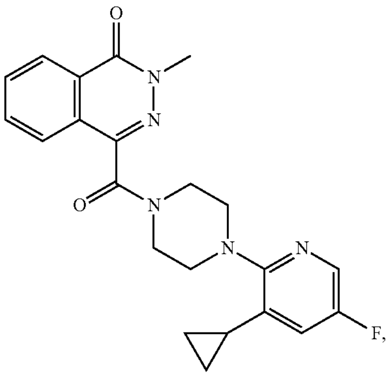
,
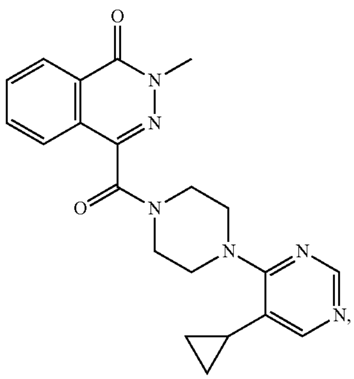
,
-continued
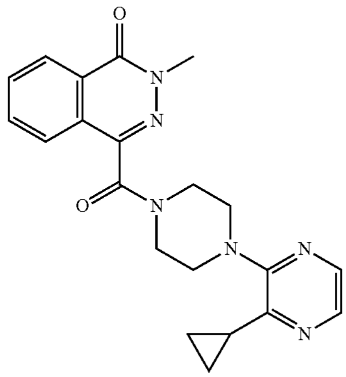
,
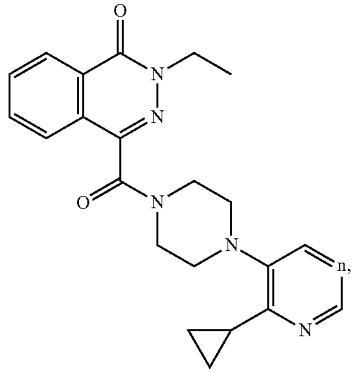
,
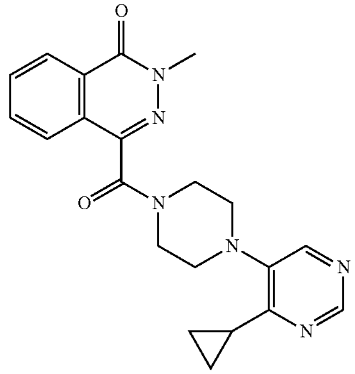
or a salt of any one thereof.
In some embodiments, the compound of Formula (I) is:
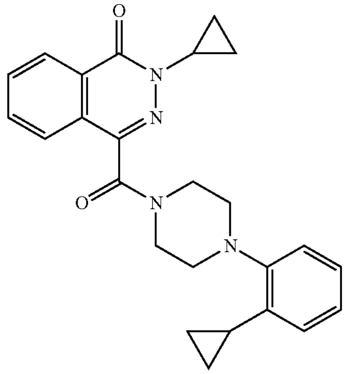
, -continued
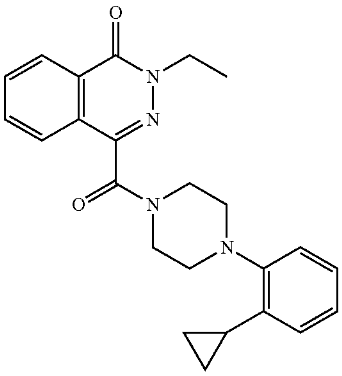
,
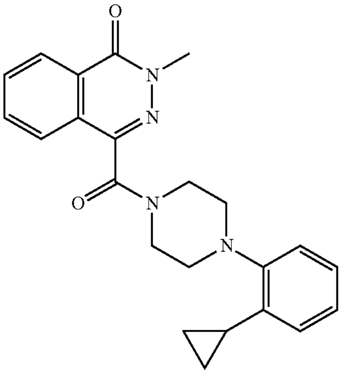
,
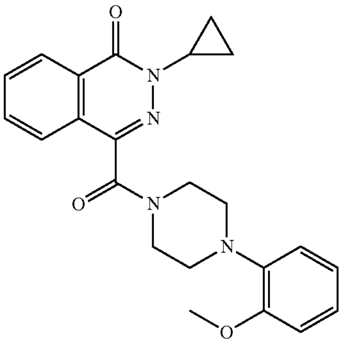
,
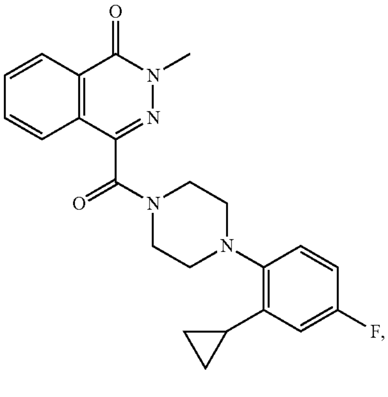
,
-continued
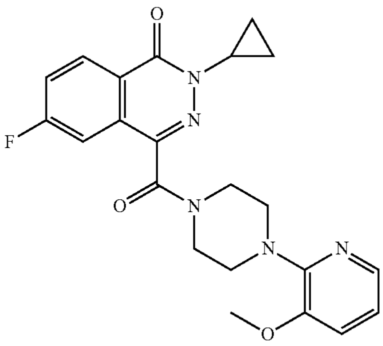
,
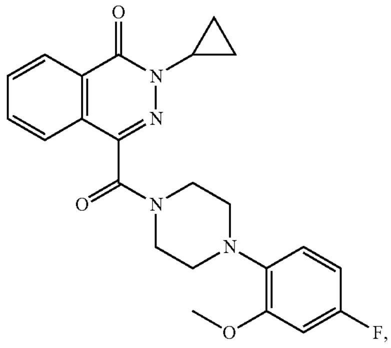
,
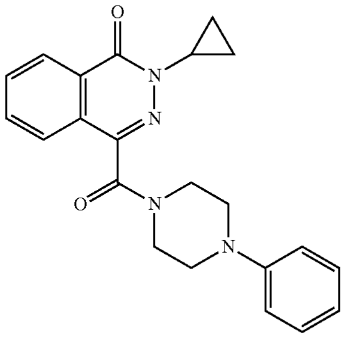
,
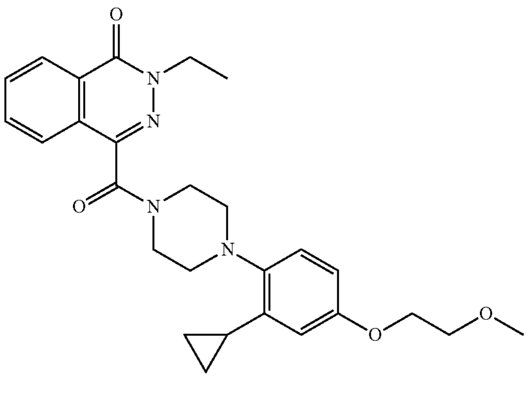
, -continued
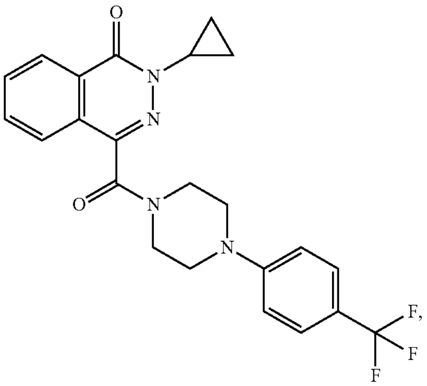
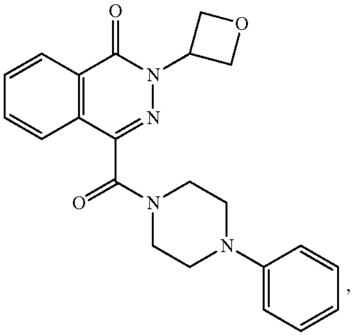
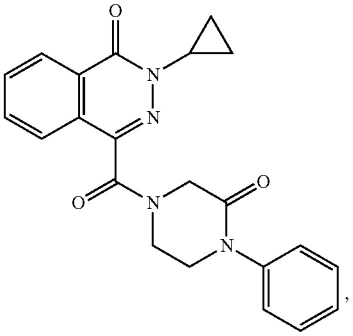
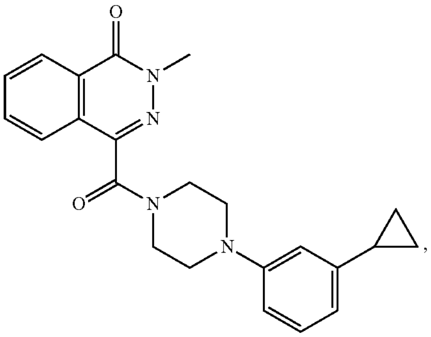
-continued
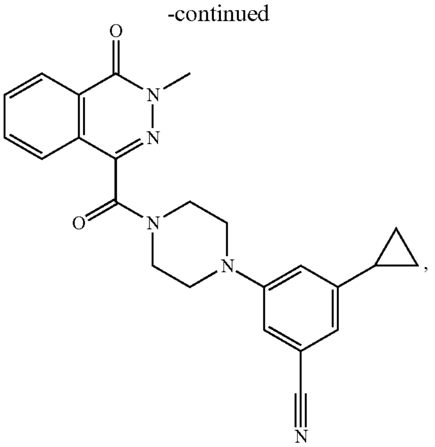
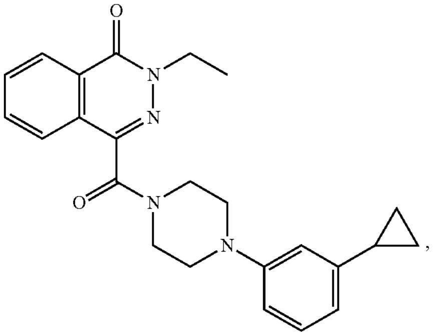
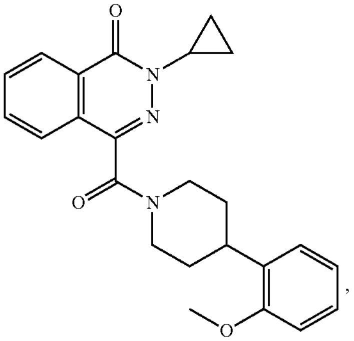
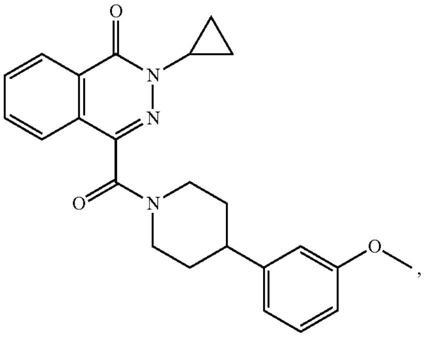

-continued
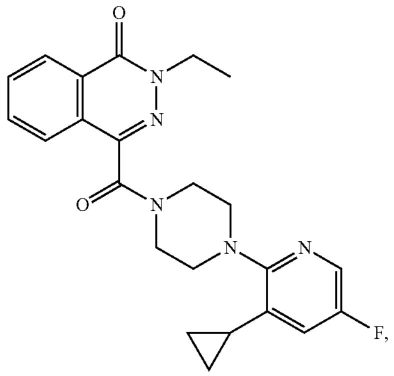
,
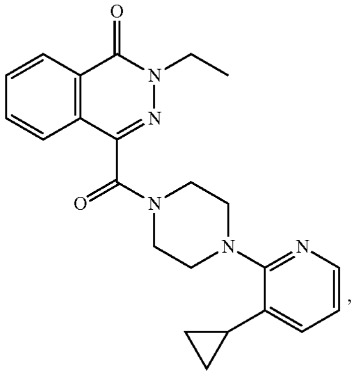
,
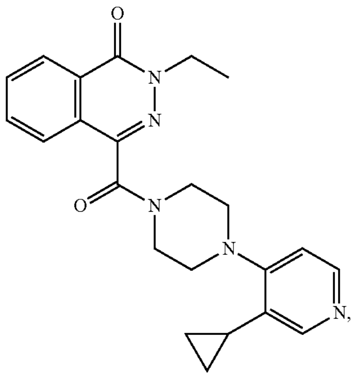
,
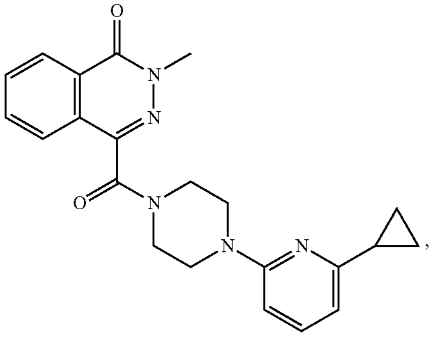
,
-continued
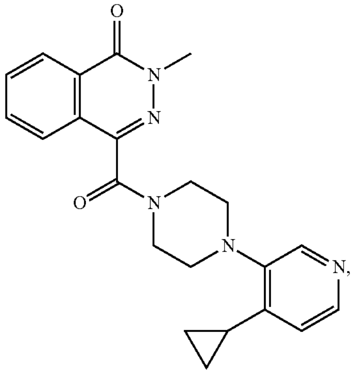
,
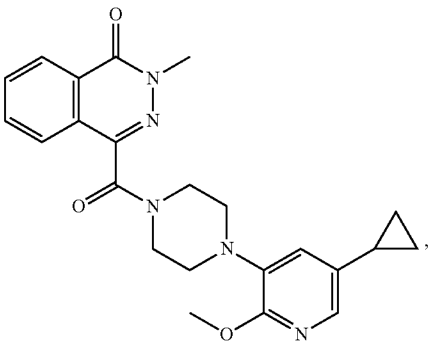
,
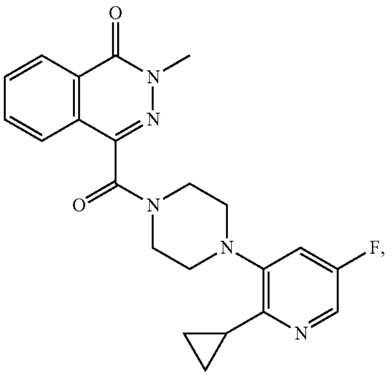
,
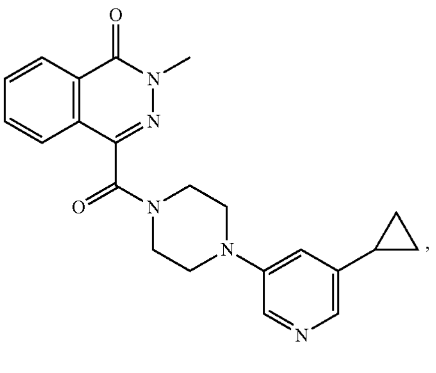
,

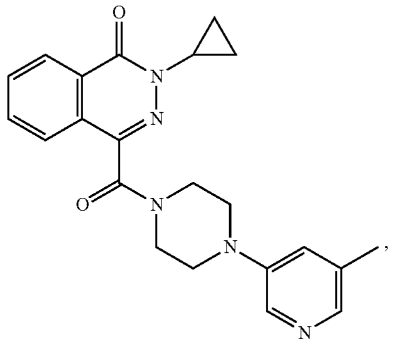
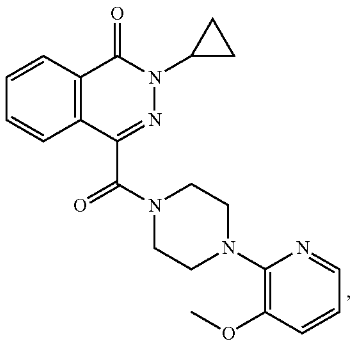
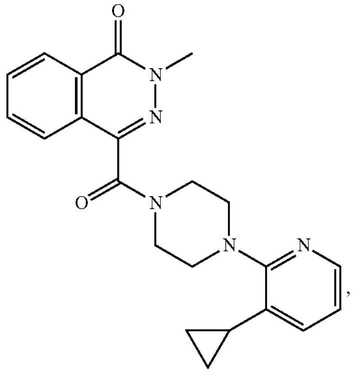
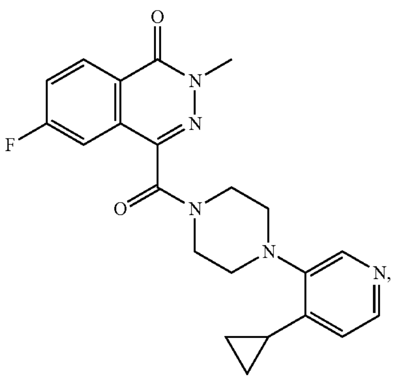
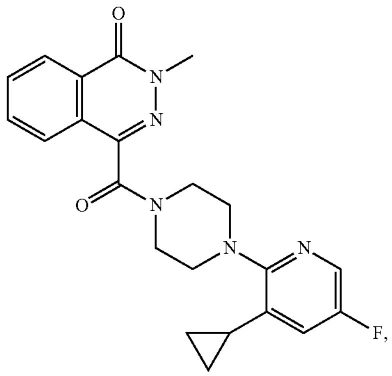
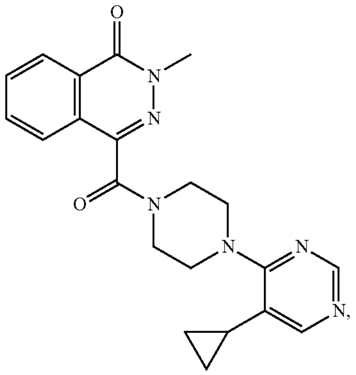
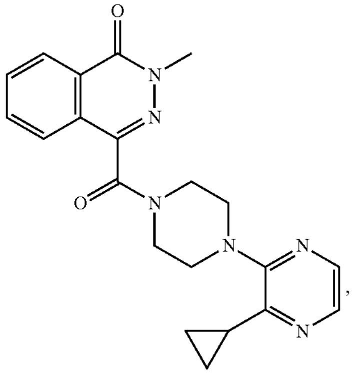
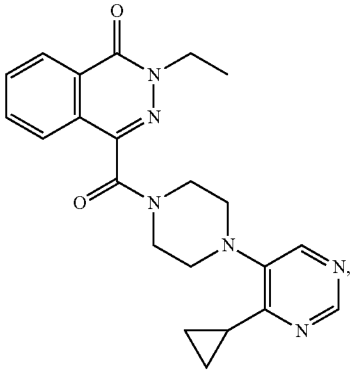

-continued

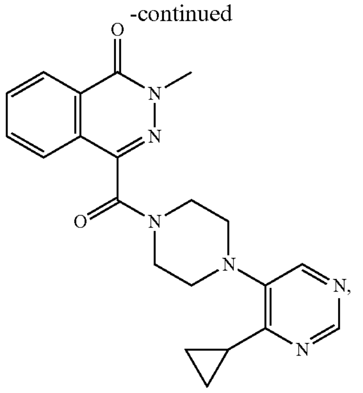

or a salt of any one thereof.

Compounds of Formula (II).

In some aspects, the present disclosure provides a compound represented by the structure of Formula (II):

(II)

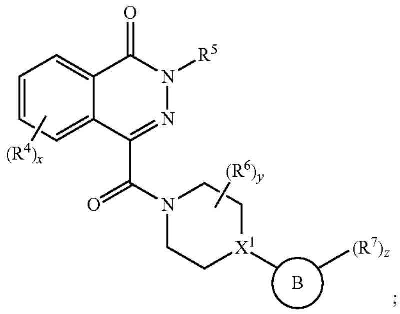

;

or a pharmaceutically acceptable salt thereof wherein:

$X^1$ is selected from N and $C(R^8)$;

$R^4$ is independently selected at each occurrence from (a), (b) and (c):

(a) halogen, $—OR^{20}$, $—SR^{20}$, $—N(R^{20})_2$, $—C(O)R^{20}$, $—C(O)OR^{20}$, $—OC(O)R^{20}$, $—OC(O)N(R^{20})_2$, $—C(O)N(R^{20})_2$, $—N(R^{20})C(O)R^{20}$, $—N(R^{20})C(O)OR^{20}$, $—N(R^{20})C(O)N(R^{20})_2$, $—N(R^{20})S(O)_2(R^{20})$, $—S(O)R^{20}$, $—S(O)_2R^{20}$, $—S(O)_2N(R^{20})_2$, $—NO_2$, and —CN;

(b) $C_{1-6}$ alkyl optionally substituted with one or more substituents independently selected from halogen, $—OR^{20}$, $—SR^{20}$, $—N(R^{20})_2$, $—C(O)R^{20}$, $—C(O)OR^{20}$, $—OC(O)R^{20}$, $—OC(O)N(R^{20})_2$, $—C(O)N(R^{20})_2$, $—N(R^{20})C(O)R^{20}$, $—N(R^{20})C(O)OR^{20}$, $—N(R^{20})C(O)N(R^{20})_2$, $—N(R^{20})S(O)_2(R^{20})$, $—S(O)R^{20}$, $—S(O)_2R^{20}$, $—S(O)_2N(R^{20})_2$, $—NO_2$, =S, =O, and —CN; and (c) $C_{3-10}$ carbocycle and 3- to 10-membered heterocycle, any of which is optionally substituted with one or more substituents independently selected from halogen, $—OR^{20}$, $—SR^{20}$, $—N(R^{20})_2$, $—C(O)R^{20}$, $—C(O)OR^{20}$, $—OC(O)R^{20}$, $—OC(O)N(R^{20})_2$, $—C(O)N(R^{20})_2$, $—N(R^{20})C(O)R^{20}$, $—N(R^{20})C(O)OR^{20}$, $—N(R^{20})C(O)N(R^{20})_2$, $—N(R^{20})S(O)_2(R^{20})$, $—S(O)R^{20}$, $—S(O)_2R^{20}$, $—S(O)_2N(R^{20})_2$, $—NO_2$, =S, =O, and —CN;

$R^5$ is $C_{1-6}$ alkyl optionally substituted with one or more substituents independently selected from: halogen, $—OR^{21}$, $—SR^{21}$, $—N(R^{21})_2$, $—C(O)R^{21}$, $—C(O)OR^{21}$, $—OC(O)R^{21}$, $—OC(O)N(R^{21})_2$, $—C(O)N(R^{21})_2$, $—N(R^{21})C(O)R^{21}$, $—N(R^{21})C(O)OR^{21}$, $—N(R^{21})C(O)N(R^{21})_2$, $—N(R^{21})S(O)_2(R^{21})$, $—S(O)R^{21}$, $—S(O)_2R^{21}$, $—S(O)_2N(R^{21})_2$, $—NO_2$, =S, =O, and —CN;

$R^6$ is independently selected at each occurrence from: halogen, $—OR^{22}$, $—SR^{22}$, $—N(R^{22})_2$, $—C(O)R^{22}$, $—C(O)OR^{22}$, $—OC(O)R^{22}$, $—OC(O)N(R^{22})_2$, $—C(O)N(R^{22})_2$, $—N(R^{22})C(O)R^{22}$, $—N(R^{22})C(O)OR^{22}$, $—N(R^{22})C(O)N(R^{22})_2$, $—N(R^{22})S(O)_2(R^{22})$, $—S(O)R^{22}$, $—S(O)_2R^{22}$, $—S(O)_2N(R^{21})_2$, $—NO_2$, =S, =O, and —CN; and $C_{1-6}$ alkyl optionally substituted with one or more substituents independently selected from halogen-$OR^{22}$, $—SR^{22}$, $—N(R^{22})_2$, $—C(O)R^{22}$, $—C(O)OR^{22}$, $—OC(O)R^{22}$, $—OC(O)N(R^{22})_2$, $—C(O)N(R^{22})_2$, $—N(R^{22})C(O)R^{22}$, $—N(R^{22})C(O)OR^{22}$, $—N(R^{22})C(O)N(R^{22})_2$, $—N(R^{22})S(O)_2(R^{22})$, $—S(O)R^{22}$, $—S(O)_2R^{22}$, $—S(O)_2N(R^{21})_2$, $—NO_2$, =S, =O, and —CN;

Ring B is selected from $C_{3-10}$ carbocyclene and 3- to 10-membered heterocyclene;

$R^7$ is independently selected at each occurrence from: hydrogen, halogen, $—OR^{23}$, $—SR^{23}$, $—N(R^{23})_2$, $—C(O)R^{23}$, $—OC(O)R^{23}$, $—OC(O)N(R^{23})_2$, $—C(O)N(R^{23})_2$, $—N(R^{23})C(O)R^{23}$, $—N(R^{23})C(O)OR^{23}$, $—N(R^{23})C(O)N(R^{23})_2$, $—N(R^{12})S(O)_2(R^{23})$, $—S(O)R^{23}$, $—S(O)_2R^{23}$, $—S(O)_2N(R^{23})_2$, $—NO_2$, and —CN; and $C_{1-6}$ alkyl optionally substituted with one or more substituents independently selected from halogen, $—OR^{23}$, $—SR^{23}$, $N(R^{23})_2$, $—C(O)R^{23}$, $—C(O)OR^{23}$, $—OC(O)R^{23}$, $—OC(O)N(R^{23})_2$, $—C(O)N(R^{23})_2$, $—N(R^{23})C(O)R^{23}$, $—N(R^{23})C(O)OR^{23}$, $—N(R^{23})C(O)N(R^{23})_2$, $—N(R^{23})S(O)_2(R^{23})$, $—S(O)R^{23}$, $—S(O)_2R^{23}$, $—S(O)_2N(R^{23})_2$, $—NO_2$, =S, =O, and —CN;

$R^8$, $R^{20}$, $R^{21}$, $R^{22}$, and $R^{23}$, are each independently selected at each occurrence from (d), (e), and (f:

(d) hydrogen;

(e) $C_{1-6}$ alkyl optionally substituted with one more substituents independently selected from halogen, $—O—C_{1-6}$ alkyl, $—O—C_{1-6}$ haloalkyl, $—NH_2$, $—NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, $—O—C_{1-6}$ alkyl, $—O—C_{1-6}$ haloalkyl, $—NH_2$, $—NO_2$, =O, and —CN; and (f) $C_{3-10}$ carbocycle and 3- to 10-membered heterocycle optionally substituted with one or more substituents independently selected from: halogen, —OH, $—O—C_{1-6}$ alkyl, $—O—C_{1-6}$ haloalkyl, $—NH_2$, $—NO_2$, =O, and —CN;

x is selected from 0, 1, 2, 3, and 4;

y is selected from 0, 1, 2, 3, and 4;

z is selected from 0, 1, 2, 3, 4 and 5; and at least one of x or y is selected from 1, 2, 3, and 4.

In some embodiments, for the compound or salt of Formula (II), x is selected from 0, 1, 2, and 3. In some embodiments, x is selected from 0, 1, and 2. In some embodiments, x is selected from 1 and 2. In some embodiments, x is selected from 0 and 1. In some embodiments, x is 4. In some embodiments, x is 3. In some embodiments, x is 2. In some embodiments, x is 1. In some embodiments, x is 0.

In some embodiments, Formula (I) is represented by a structure selected from Formula (II-a), (II-b), (II-c), (II-d) and (II-e):

(II-a)

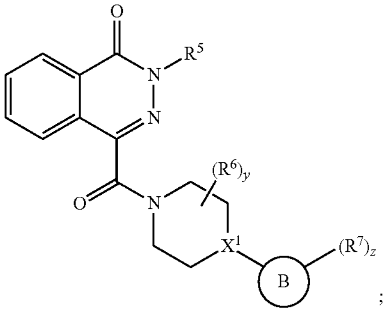

;

(II-b)

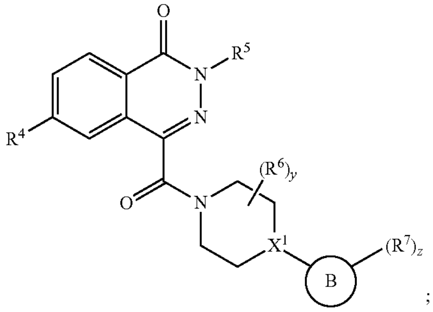

;

(II-c)

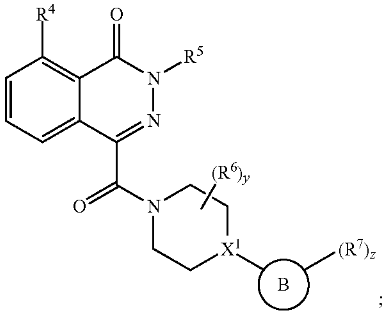

;

(II-d)

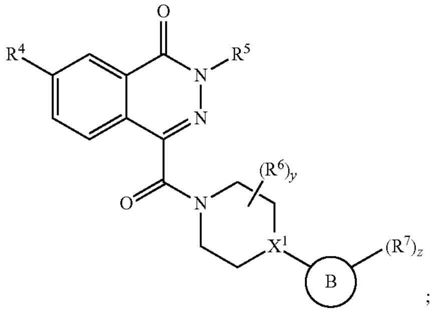

;

-continued (II-e)

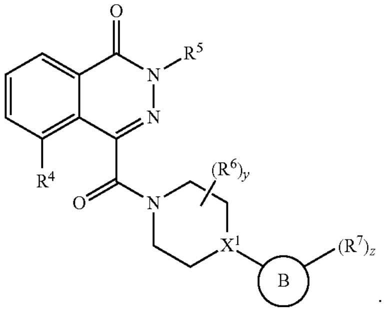

.

In some embodiments, a compound or salt of the disclosure is represented by Formula (II-a):

(II-a)

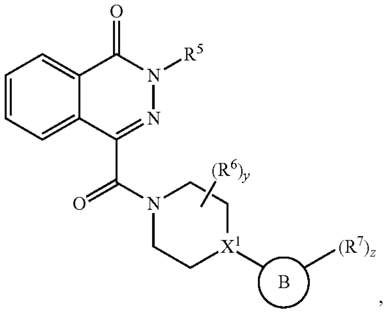

, or a pharmaceutically acceptable salt thereof, wherein $R^5$, $R^6$, $R^7$, $X^1$, Ring B, y, and z are as defined in Formula (II).

In some embodiments, a compound or salt of the disclosure is represented by Formula (II-b):

(II-b)

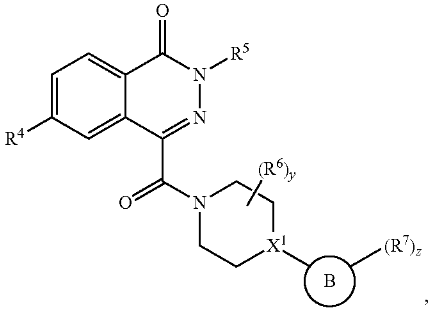

, or a pharmaceutically acceptable salt thereof, wherein $R^4$, $R^5$, $R^6$, $R^7$, $X^1$, Ring B, y, and z are as defined in Formula (II).

In some embodiments, a compound or salt of the disclosure is represented by Formula (II-c):

(II-c)

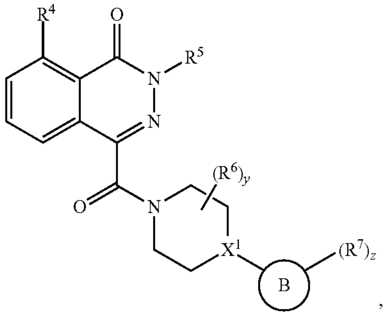

, or a pharmaceutically acceptable salt thereof, wherein $R^4$, $R^5$, $R^6$, $R^7$, $X^1$, Ring B, y, and z are as defined in Formula (II).

In some embodiments, a compound or salt of the disclosure is represented by Formula (II-d):

(II-d)

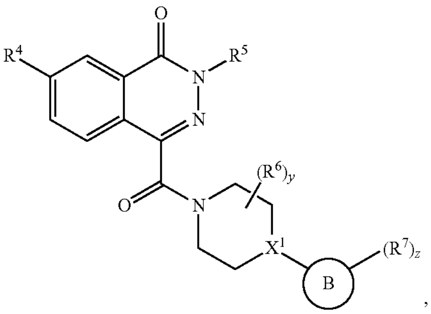

, or a pharmaceutically acceptable salt thereof, wherein $R^4$, $R^5$, $R^6$, $R^7$, $X^1$, Ring B, y, and z are as defined in Formula (II).

In some embodiments, a compound or salt of the disclosure is represented by Formula (II-e):

(II-e)

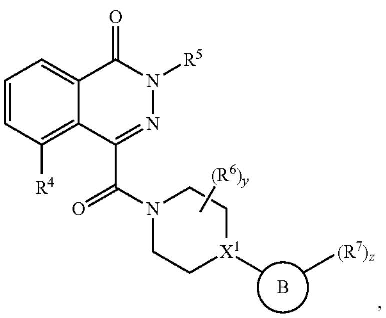

, or a pharmaceutically acceptable salt thereof, wherein $R^4$, $R^5$, $R^6$, $R^7$, $X^1$, Ring B, y, and z are as defined in Formula (II).

In some embodiments, the structure of Formula (II) is represented by the structure of Formula (II-a) or (II-b):

(II-a)

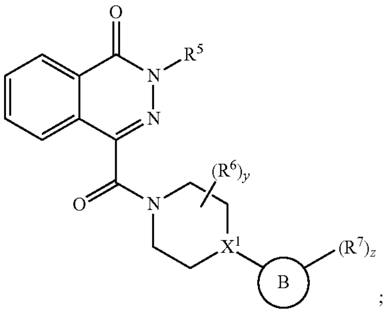

;

(II-b)

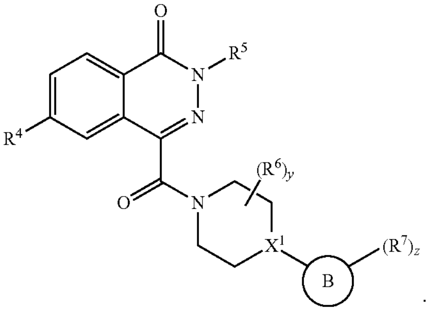

.

In some embodiments, for the compound or salt of Formula (II), (II-b), (II-c), (II-d), or (II-e), $R^4$ is selected from halogen, $—OR^{20}$, $—SR^{20}$, $—N(R^{20})_2$, $—C(O)R^{20}$, $—C(O)OR^{20}$, $—OC(O)R^{20}$, $—OC(O)N(R^{20})_2$, $—C(O)N(R^{20})_2$, $—N(R^{20})C(O)R^{20}$, $—N(R^{20})C(O)OR^{20}$, $—N(R^{20})C(O)N(R^{20})_2$, $—N(R^{20})S(O)_2(R^{20})$, $—S(O)R^{20}$, $—S(O)_2R^{20}$, $—S(O)_2N(R^{20})_2$, $—NO_2$, and —CN. In some embodiments, $R^4$ is selected from halogen, $—OR^{20}$, $—N(R^{20})_2$, $—C(O)R^{20}$, $—C(O)OR^{20}$, $—NO_2$, and —CN.

In some embodiments, for the compound or salt of Formula (II), (II-b), (II-c), (II-d), or (II-e), $R^4$ is $C_{1-6}$ alkyl optionally substituted with one or more substituents independently selected from halogen, $—OR^{20}$, $—SR^{20}$, $—N(R^{20})_2$, $—C(O)R^{20}$, $—C(O)OR^{20}$, $—OC(O)R^{20}$, $—OC(O)N(R^{20})_2$, $—C(O)N(R^{20})_2$, $—N(R^{20})C(O)R^{20}$, $—N(R^{20})C(O)OR^{20}$, $—N(R^{20})C(O)N(R^{20})_2$, $—N(R^{20})S(O)_2(R^{20})$, $—S(O)R^{20}$, $—S(O)_2R^{20}$, $—S(O)_2N(R^{20})_2$, $—NO_2$, =S, =O, and —CN. In some embodiments, $R^4$ is $C_{1-6}$ alkyl optionally substituted with one or more substituents independently selected from halogen, $—OR^{20}$, $—N(R^{20})_2$, $—C(O)R^{20}$, $—C(O)OR^{20}$, $—NO_2$, and —CN.

In some embodiments, for the compound or salt of Formula (II), (II-b), (II-c), (II-d), or (II-e), $R^4$ is selected from $C_{3-10}$ carbocycle and 3- to 10-membered heterocycle, any of which is optionally substituted with one or more substituents independently selected from halogen, $—OR^{20}$, $—SR^{20}$, $—N(R^{20})_2$, $—C(O)R^{20}$, $—C(O)OR^{20}$, $—OC(O)R^{20}$, $—OC(O)N(R^{20})_2$, $—C(O)N(R^{20})_2$, $—N(R^{20})C(O)R^{20}$, $—N(R^{20})C(O)OR^{20}$, $—N(R^{20})C(O)N(R^{20})_2$, $—N(R^{20})S(O)_2(R^{20})$, $—S(O)R^{20}$, $—S(O)_2R^{20}$, $—S(O)_2N(R^{20})_2$, $—NO_2$, =S, =O, and —CN. In some embodiments, $R^4$ is selected from $C_{3-10}$ carbocycle and 3- to 10-membered heterocycle, any of which is optionally substituted with one or more substituents independently selected from halogen, $—OR^{20}$, $—N(R^{20})_2$, $—C(O)R^{20}$, $—C(O)OR^{20}$, $—NO_2$, and —CN.

In some embodiments, for the compound or salt of Formula (II), (II-b), (II-c), (II-d), or (II-e), $R^4$ is selected from: halogen, $—OR^{20}$, $—N(R^{20})_2$, $—C(O)R^{20}$, $—NO_2$, and —CN; $C_{1-3}$ alkyl, $C_{3-6}$ carbocycle, and 3- to 6-membered heterocycle, any of which is optionally substituted with one or more substituents independently selected from: halogen, —$OR^{20}$, —$N(R^{20})_2$, —$C(O)R^{20}$, —$NO_2$, and —CN; and each $R^{20}$ is independently selected from hydrogen, $C_{1-4}$ alkyl, and $C_{1-4}$ haloalkyl. In some embodiments, $R^4$ is selected from: halogen, —$OR^{20}$, —$N(R^{20})_2$, and —CN; $C_{3-6}$ carbocycle, and 3- to 6-membered heterocycle, any of which is optionally substituted with one or more substituents independently selected from: halogen, —$OR^{20}$, and —$N(R^{20})_2$; and each $R^{20}$ is independently selected hydrogen, $C_{1-4}$ alkyl, and $C_{1-4}$ haloalkyl.

In some embodiments, for the compound or salt of Formula (II), (II-b), (II-c), (II-d), or (II-e), $R^4$ is selected from: halogen, —$OR^{20}$, —$N(R^{20})_2$, —$C(O)R^{20}$, —$NO_2$, and —CN; $C_{1-3}$ alkyl, $C_{3-6}$ saturated carbocycle, and 3- to 6-membered saturated heterocycle, any of which is optionally substituted with one or more substituents independently selected from: halogen, —$OR^{20}$, —$N(R^{20})_2$, —$C(O)R^{20}$, —$NO_2$, and —CN; and each $R^{20}$ is independently selected from hydrogen, $C_{1-4}$ alkyl, and $C_{1-4}$ haloalkyl. In some embodiments, $R^4$ is selected from: halogen, —$OR^{20}$, —$N(R^{20})_2$, and —CN; $C_{3-6}$ saturated carbocycle, and 3- to 6-membered saturated heterocycle, any of which is optionally substituted with one or more substituents independently selected from: halogen, —$OR^{20}$, and —$N(R^{20})_2$; and each $R^{20}$ is independently selected hydrogen, $C_{1-4}$ alkyl, and $C_{1-4}$ haloalkyl.

In some embodiments, for the compound or salt of Formula (II), (II-b), (II-c), (II-d), or (II-e), $R^4$ is selected from: halogen, —$OR^{20}$, —$N(R^{20})_2$, and —CN; $C_{3-4}$ carbocycle, and 4- to 5-membered heterocycle; and each $R^{20}$ is independently selected from hydrogen and $C_{1-4}$ alkyl. In some embodiments, $R^4$ is selected from: fluoro, bromo, —O—$C_{1-6}$ alkyl, —$N(CH_3)_2$, —CN,

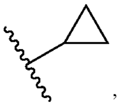 , and 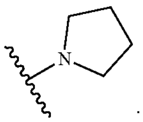 .

In some embodiments, for the compound or salt of Formula (II), (II-b), (II-c), (II-d), or (II-e), $R^4$ is selected from: halogen, —$OR^{20}$, —$N(R^{20})_2$, and —CN; $C_{3-4}$ saturated carbocycle, and 4- to 5-membered saturated heterocycle; and each $R^{20}$ is independently selected from hydrogen and $C_{1-4}$ alkyl. In some embodiments, $R^4$ is selected from: fluoro, chloro, bromo, —O—$C_{1-6}$ alkyl, —$N(CH_3)_2$, —CN,

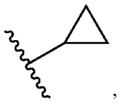 , and 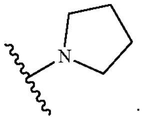 .

In some embodiments, $R^4$ is selected from: fluoro, bromo, —O—$C_{1-6}$ alkyl, —$N(CH_3)_2$, —CN

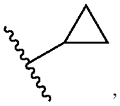 , and 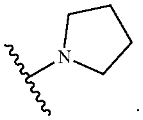 .

In some embodiments, $R^4$ is selected from: fluoro and bromo. In some embodiments, $R^4$ is selected from: O—$C_{1-6}$ alkyl, —$N(CH_3)_2$, and —CN. In some embodiments, $R^4$ is selected from:

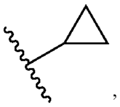 , and 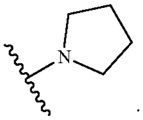 .

In some embodiments, for the compound or salt of Formula (II), (II-a), (II-b), (II-c), (II-d), or (II-e), y is selected from 0, 1, 2, and 3. In some embodiments, x is selected from 0, 1, and 2. In some embodiments, y is selected from 1 and 2. In some embodiments, y is selected from 0 and 1. In some embodiments, y is 4. In some embodiments, y is 3. In some embodiments, y is 2. In some embodiments, y is 1. In some embodiments, y is 0.

In some embodiments, for the compound or salt of Formula (II), (II-a), (II-b), (II-c), (II-d), or (II-e), x is selected from 1, 2, 3 and 4; and y is selected from 0, 1, 2, 3, and 4. In some embodiments, x is selected from 2, 3 and 4; and y is selected from 0, 1, 2, 3, and 4. In some embodiments, x is selected from 3 and 4; and y is selected from 0, 1, 2, 3, and 4. In some embodiments, x is selected from 4; and y is selected from 0, 1, 2, 3, and 4. In some embodiments, x is selected from 3; and y is selected from 0, 1, 2, 3, and 4. In some embodiments, x is selected from 2; and y is selected from 0, 1, 2, 3, and 4. In some embodiments, x is selected from 1; and y is selected from 0, 1, 2, 3, and 4.

In some embodiments, for the compound or salt of Formula (II), (II-a), (II-b), (II-c), (II-d), or (II-e), y is selected from 1, 2, 3, and 4; and x is selected from 0, 1, 2, 3, and 4. In some embodiments, y is selected from 2, 3, and 4; and x is selected from 0, 1, 2, 3, and 4. In some embodiments, y is selected from 3, and 4; and x is selected from 0, 1, 2, 3, and 4. In some embodiments, y is selected from 4; and x is selected from 0, 1, 2, 3, and 4. In some embodiments, y is selected from 3; and x is selected from 0, 1, 2, 3, and 4. In some embodiments, y is selected from 2; and x is selected from 0, 1, 2, 3, and 4. In some embodiments, y is selected from 1; and x is selected from 0, 1, 2, 3, and 4.

In some embodiments, for the compound or salt of Formula (II), (II-a), (II-b), (II-c), (III-d), or (II-e), $R^6$ is selected at each occurrence from: halogen, —$OR^{22}$, —$SR^{22}$, —$N(R^{22})_2$, —$C(O)R^{22}$, —$C(O)OR^{22}$, —$OC(O)R^{22}$, —$OC(O)N(R^{22})_2$, —$C(O)N(R^{22})_2$, —$N(R^{22})C(O)R^{22}$, —$N(R^{22})C(O)OR^{22}$, —$N(R^{22})C(O)N(R^{22})_2$, —$N(R^{22})S(O)_2(R^{22})$, —$S(O)R^{22}$, —$S(O)_2R^{22}$, —$S(O)_2N(R^{21})_2$, —$NO_2$, ═S, ═O, and —CN. In some embodiments, $R^6$ is selected at each occurrence from: halogen, —$OR^{22}$, —$N(R^{22})_2$, —$C(O)R^{22}$, —$C(O)OR^{22}$, —$NO_2$, ═S, ═O, and —CN. In some embodiments, $R^6$ is selected at each occurrence from $C_{1-6}$ alkyl optionally substituted with one or more substituents independently selected from halogen, —$OR^{22}$, —$SR^{22}$, —$N(R^{22})_2$, —$C(O)R^{22}$, —$C(O)OR^{22}$, —$OC(O)R^{22}$, —$OC(O)N(R^{22})_2$, —$C(O)N(R^{22})_2$, —$N(R^{22})C(O)R^{22}$, —$N(R^{22})C(O)OR^{22}$, —$N(R^{22})C(O)N(R^{22})_2$, —$N(R^{22})S(O)_2(R^{22})$, —$S(O)R^{22}$, —$S(O)_2R^{22}$, —$S(O)_2N(R^{21})_2$, —$NO_2$, ═S, ═O, and —CN. In some embodiments, $R^6$ is selected at each occurrence from $C_{1-6}$ alkyl optionally substituted with one or more substituents independently selected from: halogen, —$OR^{22}$, —$N(R^{22})_2$, —$C(O)R^{22}$, —$C(O)OR^{22}$, —$NO_2$, ═S, ═O, and —CN.

In some embodiments, for the compound or salt of Formula (II), (II-a), (II-b), (II-c), (II-d), or (II-e), $R^6$ is $C_{1-3}$ alkyl optionally substituted with one or more substituents independently selected from halogen, —$OR^{22}$, —$N(R^{22})_2$, —$C(O)R^{22}$, —$NO_2$, and —CN; and $R^{22}$ is selected from hydrogen and $C_{1-3}$ alkyl. In some embodiments, $R^6$ is unsubstituted $C_{1-3}$ alkyl. In some embodiments, $R^6$ is selected from methyl, ethyl, propyl, and isopropyl. In some embodiments, $R^6$ is selected from methyl and ethyl.

In some embodiments, for the compound or salt of Formula (II), (II-a), (II-b), (II-c), (II-d), or (II-e), $X^1$ is nitrogen.

In some embodiments, for the compound or salt of Formula (II), (II-a), (II-b), (II-c), (II-d), or (II-e), $X^1$ is $C(R^8)$; and $R^8$ is selected from: hydrogen, $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN. In some embodiments, $X^1$ is $C(R^8)$; and $R^8$ is selected from: hydrogen, $C_{1-6}$ alkyl optionally substituted with one more substituents independently selected from halogen, —O—$C_{1-6}$ alkyl, —O—$C_{1-6}$ haloalkyl, —$NH_2$, —$NO_2$, and —CN.

In some embodiments, for the compound or salt of Formula (II), (II-a), (II-b), (II-c), (II-d), or (II-e), Ring B is selected from $C_{3-6}$ carbocyclene 3- to 9-membered heterocyclene. In some embodiments, Ring B is selected from $C_{3-6}$ carbocyclene and 5- to 9-membered heterocyclene. In some embodiments, Ring B is selected from phenylene and 3- to 9-membered heterocyclene. In some embodiments, Ring B is selected from phenylene and 6-membered heteroarylene. In some embodiments, Ring B is selected from phenylene, pyridinylene, and benzoxazolylene. In some embodiments, Ring B is phenylene. In some embodiments, Ring B is selected from pyridinylene, and benzoxazolylene.

In some embodiments, for the compound or salt of Formula (II), (II-a), (II-b), (II-c), (II-d), or (II-e), Ring B is selected from $C_{3-10}$ carbocyclene. In some embodiments, the $C_{3-10}$ carbocyclene of Ring B is selected from: $C_3$ carbocyclene, $C_4$ carbocyclene, $C_5$ carbocyclene, $C_6$ carbocyclene, $C_7$ carbocyclene, $C_8$ carbocyclene, $C_9$ carbocyclene, and $C_{10}$ carbocyclene. In some embodiments, the $C_{3-10}$ carbocyclene of Ring B is selected from: $C_{3-4}$ carbocyclene, $C_{3-5}$ carbocyclene, $C_{3-6}$ carbocyclene, $C_{3-7}$ carbocyclene, $C_{3-8}$ carbocyclene, and $C_{3-9}$ carbocyclene.

In some embodiments, for the compound or salt of Formula (II), (II-a), (II-b), (II-c), (II-d), or (II-e), Ring B is selected from 3- to 10-membered heterocyclene. In some embodiments, the 3- to 10-membered heterocyclene of Ring B is selected from: 3-membered heterocyclene, 4-membered heterocyclene, 5-membered heterocyclene, 6-membered heterocyclene, 7-membered heterocyclene, 8-membered heterocyclene, 9-membered heterocyclene, and 10-membered heterocyclene. In some embodiments, the 3- to 10-membered heterocyclene of Ring B is selected from: 3- to 4-membered heterocyclene, 3- to 5-membered heterocyclene, 3- to 6-membered heterocyclene, 3- to 7-membered heterocyclene, 3- to 8-membered heterocyclene, and 3- to 9-membered heterocyclene. In some embodiments, the 3- to 10-membered heterocyclene of Ring B is 7- to 10-membered bicyclic heterocyclene. In some embodiments, Ring B is phenyl or pyridyl. In some embodiments, Ring B is phenyl. In some embodiments, Ring B is pyridyl.

In some embodiments, for the compound or salt of Formula (II), (II-a), (II-b), (II-c), (II-d), or (II-e), Ring B is selected from:

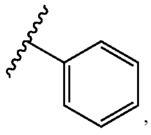,
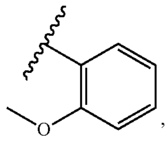,
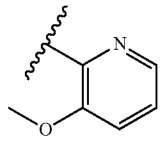, and
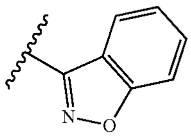.

In some embodiments, Ring B is

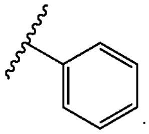 [SMILES: *c1ccccc1].

In some embodiments, Ring B is

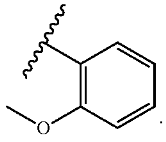 [SMILES: *c1ccccc1OC].

In some embodiments, Ring B is

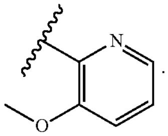 [SMILES: *c1ncccc1OC].

In some embodiments, Ring B is

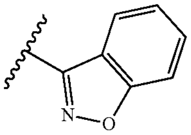.

In some embodiments, for the compound or salt of Formula (II), (II-a), (II-b), (II-c), (II-d) or (II-e), Ring B is selected from:

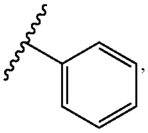, 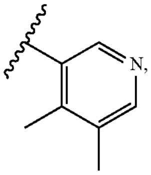, 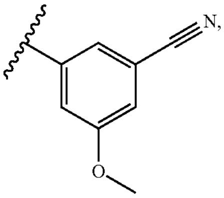,
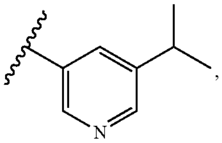, 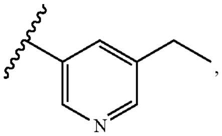,
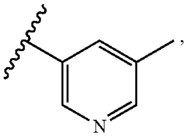, 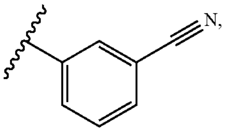,
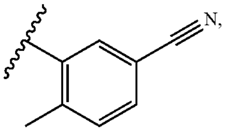, 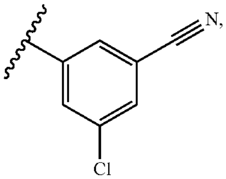,
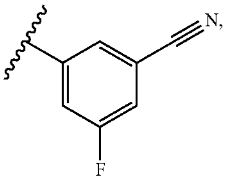, 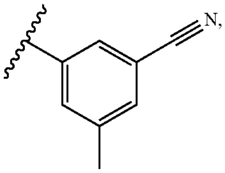,
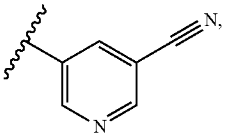, 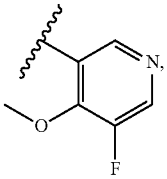,
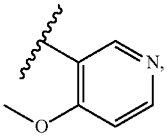, 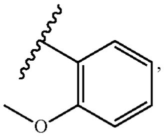, 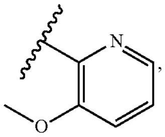, and
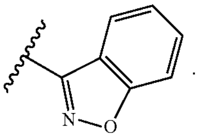.
In some embodiments, Ring B is
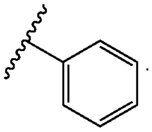 [SMILES: *c1ccccc1].
In some embodiments, Ring B is
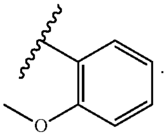 [SMILES: *c1ccccc1OC].
In some embodiments, Ring B is
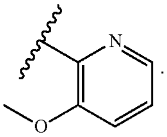 [SMILES: *c1ncccc1OC].
In some embodiments, Ring B is
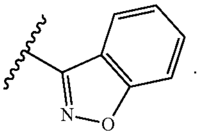 [SMILES: *c1noc2ccccc12].
In some embodiments, Ring B is
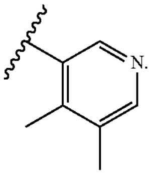 [SMILES: *c1cncc(C)c1C].
In some embodiments, Ring B is
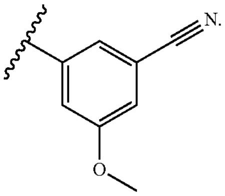 [SMILES: *c1cc(C#N)cc(OC)c1].
In some embodiments, Ring B is
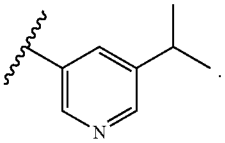 [SMILES: *c1cncc(C(C)C)c1].

In some embodiments, Ring B is

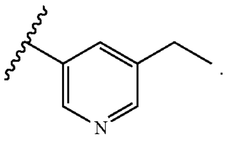 [SMILES: *c1cncc(CC)c1]

In some embodiments, Ring B is

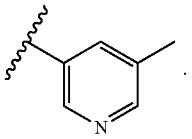 [SMILES: *c1cncc(C)c1]

In some embodiments, Ring B is

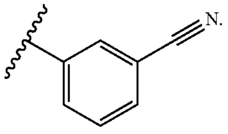 [SMILES: *c1cccc(C#N)c1]

In some embodiments, Ring B is

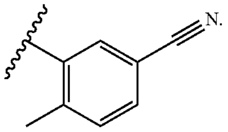 [SMILES: *c1cc(C#N)ccc1C]

In some embodiments, Ring B is

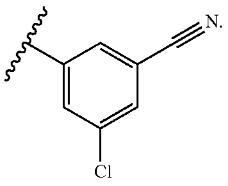 [SMILES: *c1cc(Cl)cc(C#N)c1]

In some embodiments, Ring B is

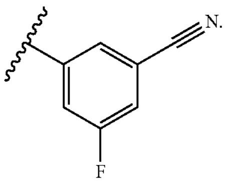 [SMILES: *c1cc(F)cc(C#N)c1]

In some embodiments, Ring B is

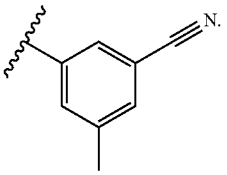 [SMILES: *c1cc(C)cc(C#N)c1]

In some embodiments, Ring B is

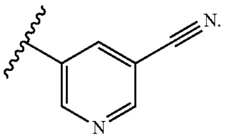 [SMILES: *c1cncc(C#N)c1]

In some embodiments, Ring B is

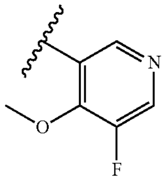 [SMILES: *c1cncc(F)c1OC]

In some embodiments, Ring B is

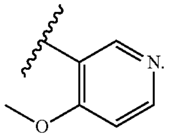 [SMILES: *c1cnccc1OC]

In some embodiments, for the compound or salt of Formula (II), (II-a), (II-b), (II-c), (II-d), or (II-e), z is selected from 0, 1, 2, and 3. In some embodiments, z is selected from 0, 1, and 2. In some embodiments, z is selected from 0 and 1. In some embodiments, z is selected from 1, 2, 3, and 4. In some embodiments, z is selected from 2, 3, and 4. In some embodiments, z is selected from 3 and 4. In some embodiments, z is selected from 1 and 2. In some embodiments, z is 1 or 2. In some embodiments, z is 0. In some embodiments, z is 1. In some embodiments, z is 2. In some embodiments, z is 3. In some embodiments, z is 4.

In some embodiments, for the compound or salt of Formula (II), (II-a), (II-b), (II-c), (II-d), or (II-e), $R^7$ is selected from: hydrogen, halogen, $—OR^{23}$, $—SR^{23}$, $—N(R^{23})_2$, $—C(O)R^{23}$, $—OC(O)R^{23}$, $—OC(O)N(R^{23})_2$, $—C(O)N(R^{23})_2$, $—N(R^{23})C(O)R^{23}$, $—N(R^{23})C(O)OR^{23}$, $—N(R^{23})C(O)N(R^{23})_2$, $—N(R^{12})S(O)_2(R^{23})$, $—S(O)R^{23}$, $—S(O)_2R^{23}$, $—S(O)_2N(R^{23})_2$, $—NO_2$, and —CN. In some embodiments, $R^7$ is selected from: hydrogen, halogen, $—OR^{23}$, $—N(R^{23})_2$, $—C(O)R^{23}$, $—NO_2$, and —CN. In some embodiments, $R^7$ is selected from $C_{1-6}$ alkyl optionally substituted with one or more substituents independently selected from halogen, $—OR^{23}$, $—SR^{23}$, $—N(R^{23})_2$, $—C(O)R^{23}$, $—C(O)OR^{23}$, $—OC(O)R^{23}$, $—OC(O)N(R^{23})_2$, $—C(O)N(R^{23})_2$, $—N(R^{23})C(O)R^{23}$, $—N(R^{23})C(O)OR^{23}$, $—N(R^{23})$ $C(O)N(R^{23})_2$, —$N(R^{23})S(O)_2(R^{23})$, —$S(O)R^{23}$, —$S(O)_2R^{23}$, —$S(O)_2N(R^{23})_2$, —$NO_2$, =S, =O, and —CN. In some embodiments, $R^7$ is selected from $C_{1-6}$ alkyl optionally substituted with one or more substituents independently selected from halogen, —$OR^{23}$, —$N(R^{23})_2$, —$C(O)R^{23}$, —$C(O)OR^{23}$, —$NO_2$, =S, =O, and —CN.

In some embodiments, for the compound or salt of Formula (II), (II-a), (II-b), (II-c), (II-d), or (II-e), $R^7$ is selected from: hydrogen, halogen, —$OR^{23}$, —$N(R^{23})_2$, —$C(O)R^{23}$, —$NO_2$, —CN; and from $C_{1-6}$ alkyl optionally substituted with one or more substituents independently selected from halogen, —$OR^{23}$, —$N(R^{23})_2$, —$C(O)R^{23}$, —$C(O)OR^{23}$, —$NO_2$, =S, =O, and —CN. In some embodiments, $R^7$ is selected from halogen, —$OR^{23}$, —$N(R^{23})_2$, —$C(O)R^{23}$, —$NO_2$, —CN; and $C_{1-6}$ alkyl optionally substituted with one or more substituents independently selected from halogen, —$OR^{23}$, —$N(R^{23})_2$, —$C(O)R^{23}$, —$NO_2$, and —CN; and $R^{23}$ is selected from hydrogen and $C_{1-3}$ alkyl. In some embodiments, $R^7$ is selected from —$OR^{23}$ and $C_{1-3}$ haloalkyl.

In some embodiments, for the compound or salt of Formula (II), (II-a), (II-b), (II-c), (II-d), or (II-e), $R^{20}$ is hydrogen. In some embodiments, $R^{20}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{20}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{20}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (II), (II-a), (II-b), (II-c), (II-d), or (II-e), $R^{21}$ is hydrogen. In some embodiments, $R^{21}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{21}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{21}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (II), (II-a), (II-b), (II-c), (II-d), or (II-e), $R^{22}$ is hydrogen. In some embodiments, $R^{22}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{22}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{22}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (II), (II-a), (II-b), (II-c), (II-d), or (II-e), $R^{23}$ is hydrogen. In some embodiments, $R^{23}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{23}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{23}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In another aspect, the disclosure provides a compound or salt represented by the structure of Formula (II) wherein:

$X^1$ is selected from N;

$R^4$ is independently selected at each occurrence from (a) and (b):

(a) halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, and —CN; and (b) $C_{1-6}$ alkyl optionally substituted with one or more substituents independently selected from halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, =S, =O, and —CN; for example, $R^4$ is halogen;

$R^5$ is $C_{1-6}$ alkyl or $C_{1-6}$ haloalkyl; for example, $R^5$ is methyl;

Ring B is 3- to 10-membered heterocyclene; for example Ring B is 6-membered heterocyclene;

$R^7$ is independently selected at each occurrence from: hydrogen, halogen, —$OR^{23}$, —$SR^{23}$, —$N(R^{23})_2$, —$C(O)R^{23}$, —$OC(O)R^{23}$, —$OC(O)N(R^{23})_2$, —$C(O)N$ $(R^{23})_2$, —$N(R^{23})C(O)R^{23}$, —$N(R^{23})C(O)OR^{23}$, —$N(R^{23})C(O)N(R^{23})_2$, —$N(R^{12})S(O)_2(R^{23})$, —$S(O)R^{23}$, —$S(O)_2R^{23}$, —$S(O)_2N(R^{23})_2$, —$NO_2$, and —CN; and $C_{1-6}$ alkyl optionally substituted with one or more substituents independently selected from halogen, —$OR^{23}$, —$SR^{23}$, $N(R^{23})_2$, —$C(O)R^{23}$, —$C(O)OR^{23}$, —$OC(O)R^{23}$, —$OC(O)N(R^{23})_2$, —$C(O)N(R^{23})_2$, —$N(R^{23})C(O)R^{23}$, —$N(R^{23})C(O)OR^{23}$, —$N(R^{23})C(O)N(R^{23})_2$, —$N(R^{23})S(O)_2(R^{23})$, —$S(O)R^{23}$, —$S(O)_2R^{23}$, —$S(O)_2N(R^{23})_2$, —$NO_2$, =S, =O, and —CN; for example $R^7$ is —$OR^{23}$;

$R^{20}$ and $R^{23}$ are each independently selected at each occurrence from (d), (e), and (f):

(d) hydrogen;

(e) $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and (f) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN;

x is selected from 1 or 2;

y is 0; and z is selected from 0, 1, and 2.

In some embodiments, the compound of Formula (II) is:

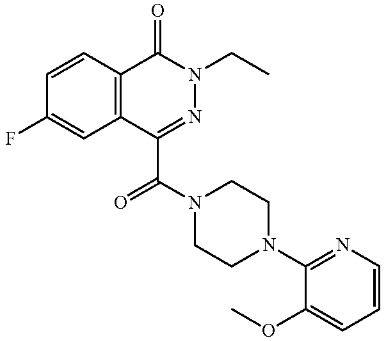

,

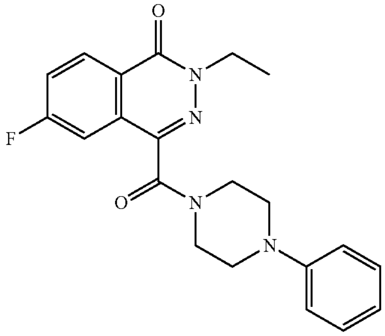

,

-continued

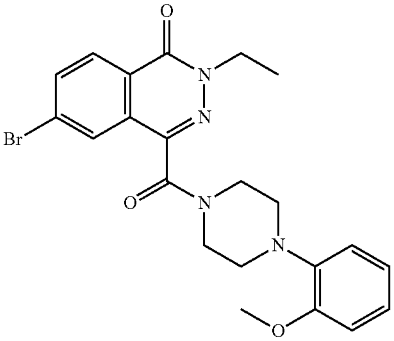

,

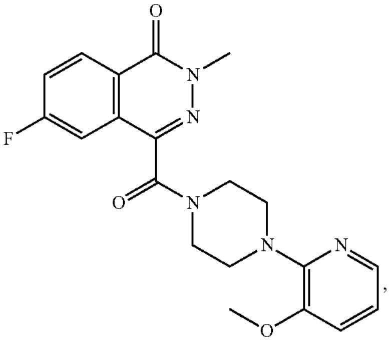

,

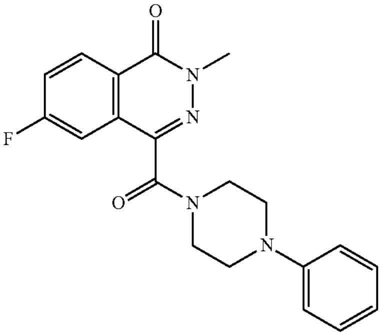

,

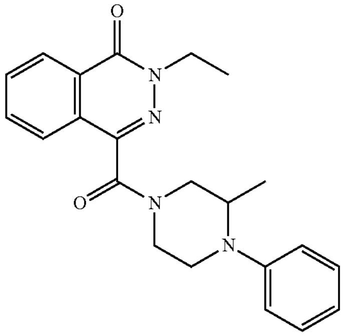

,

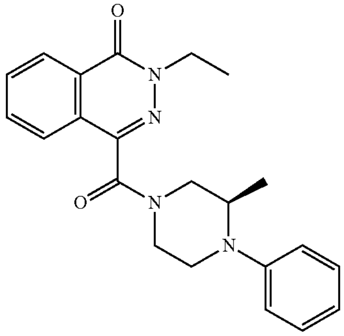

,

-continued
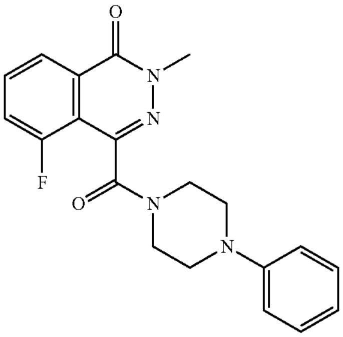
,
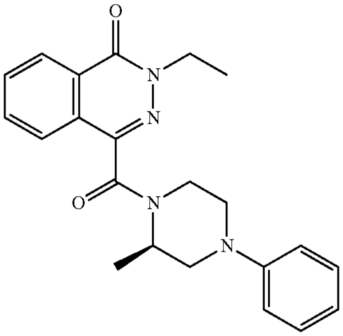
,
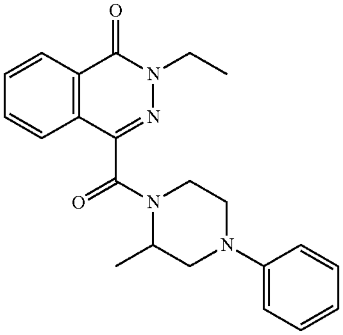
,
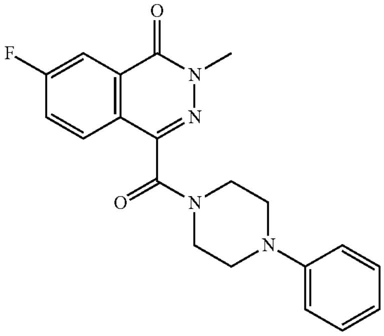
,
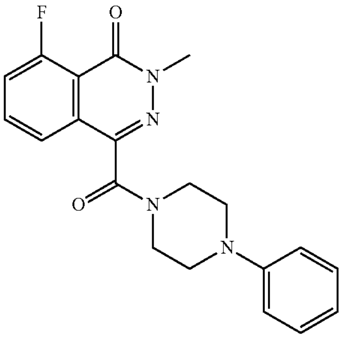
,
-continued
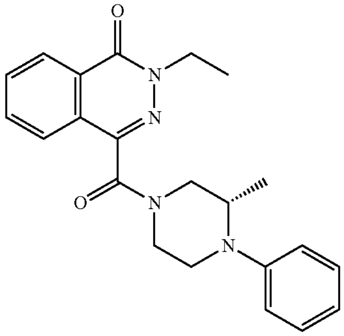
,
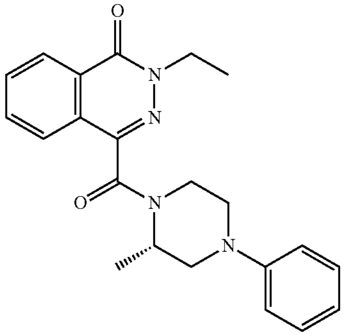
,
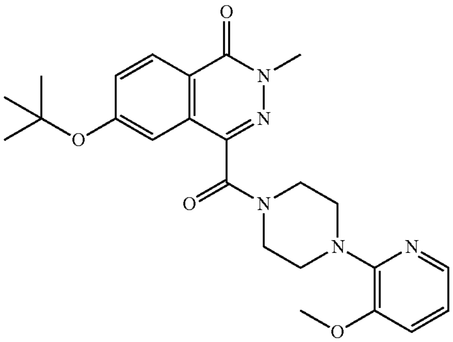
,
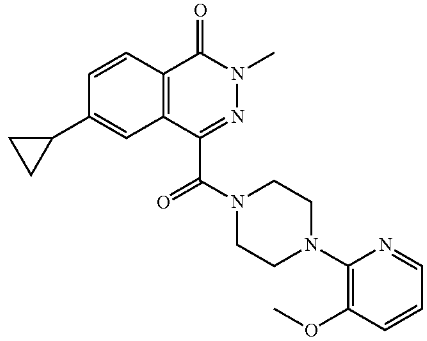
,
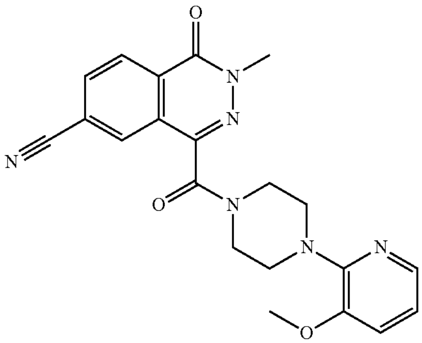
, -continued
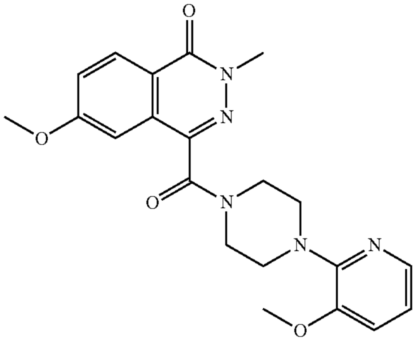
,
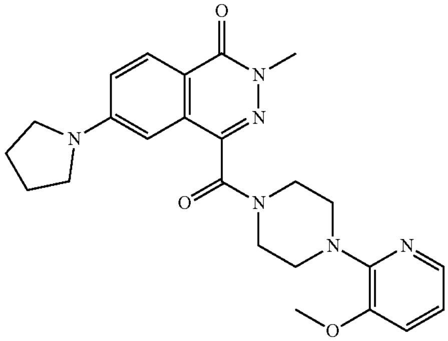
,
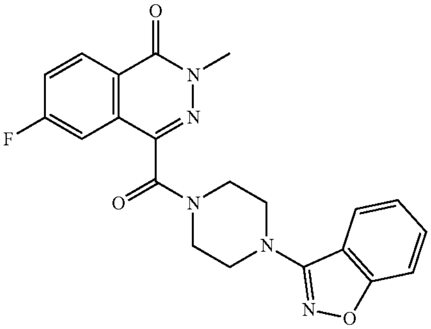
,
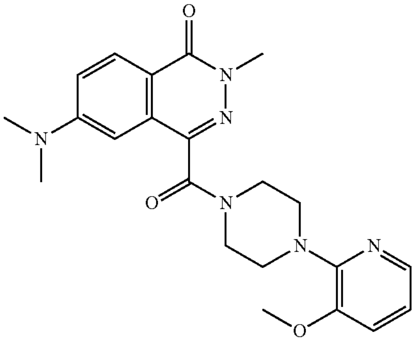
,
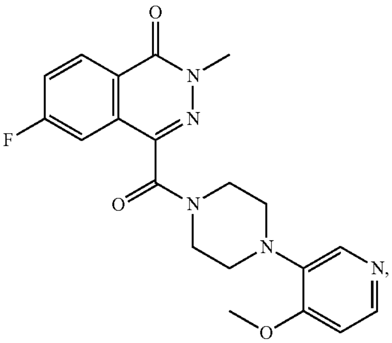
,
-continued
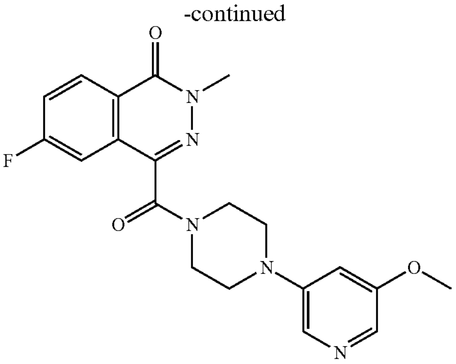
,
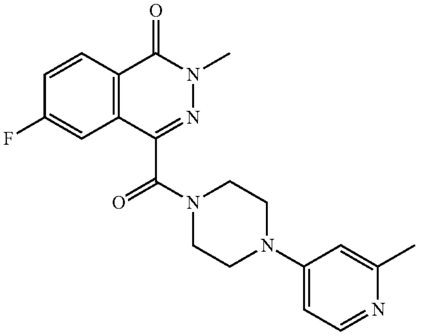
,
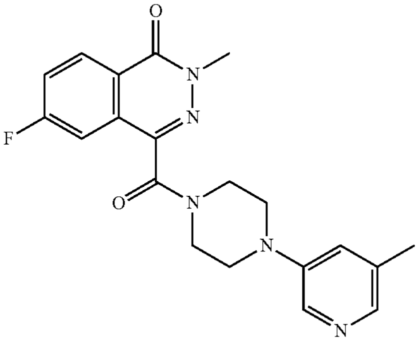
,
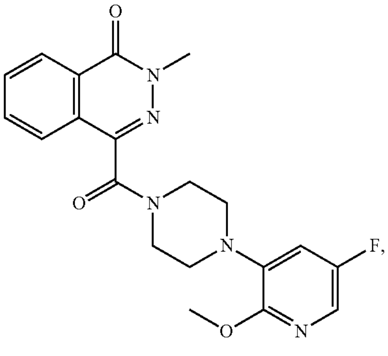
, -continued
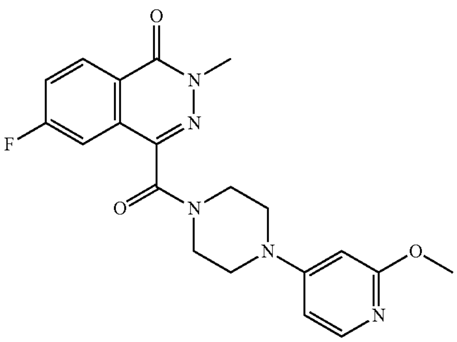,
or a salt of any one thereof.
In some embodiments, the compound of Formula (II) is:
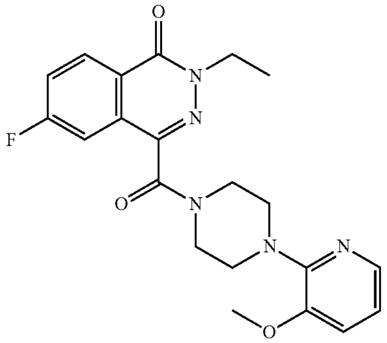,
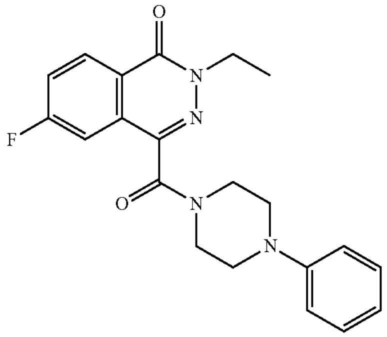,
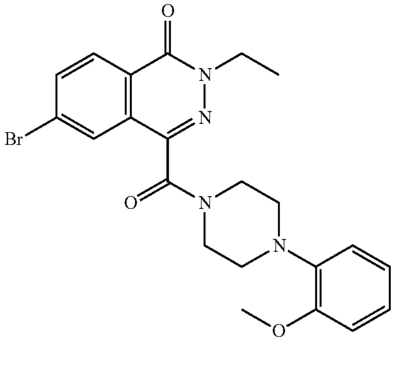,
-continued
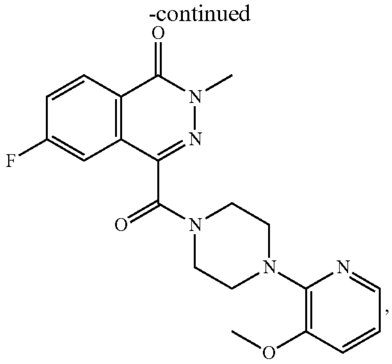,
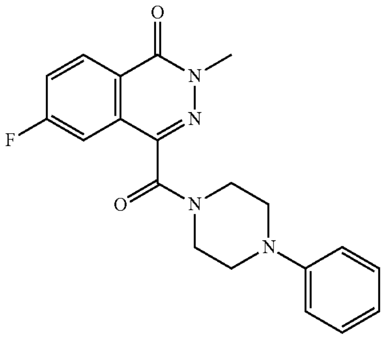,
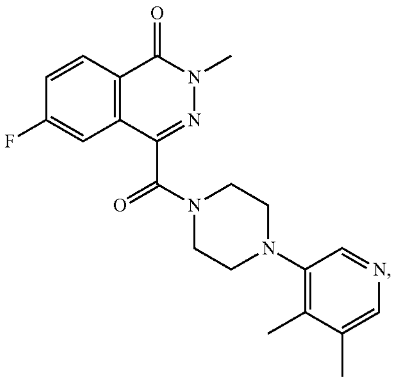,
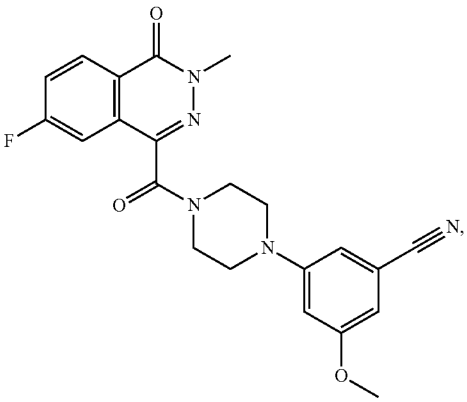, -continued
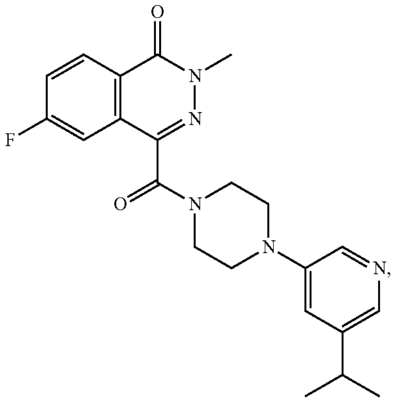
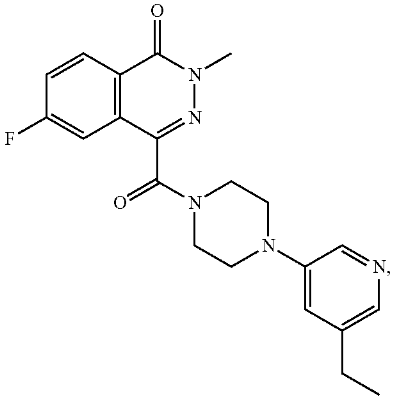
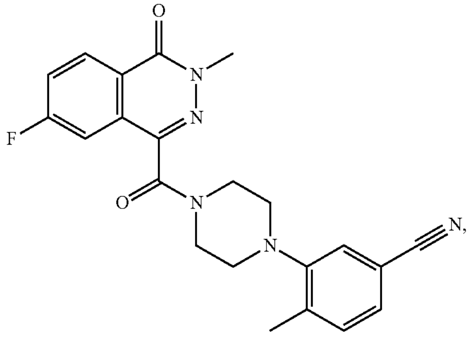
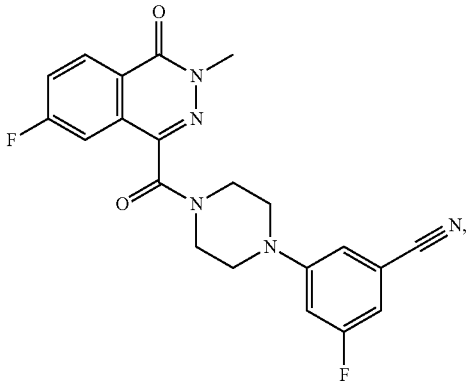
-continued
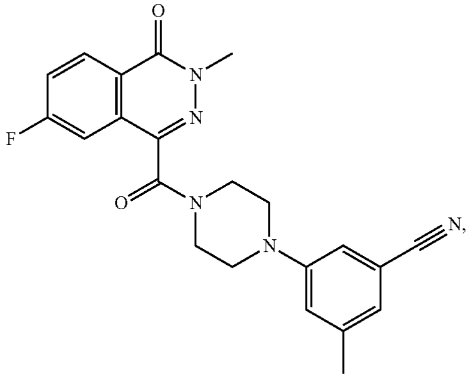
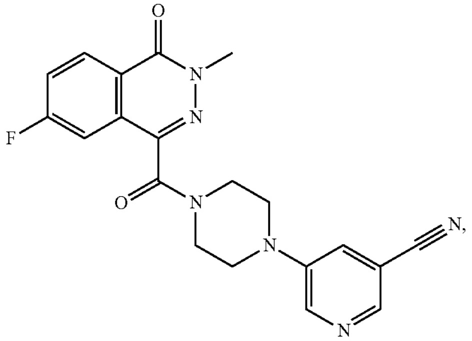
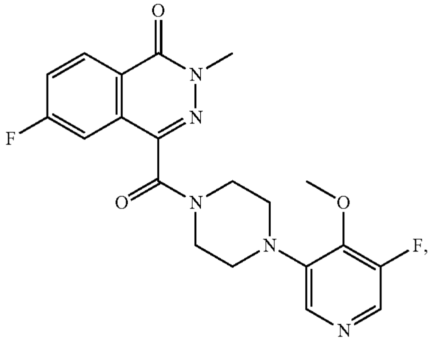
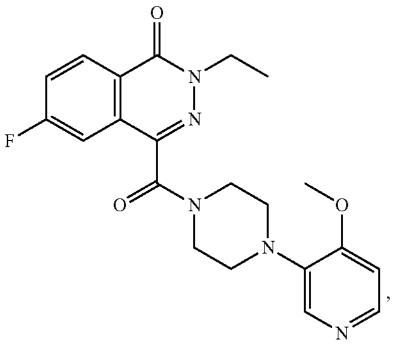

-continued
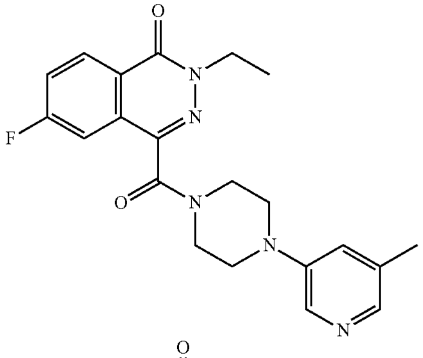
,
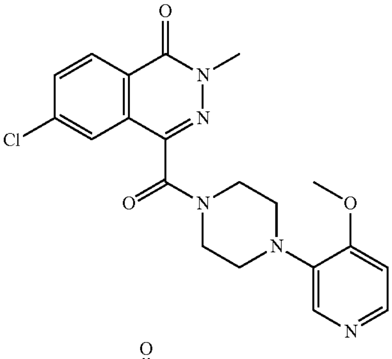
,
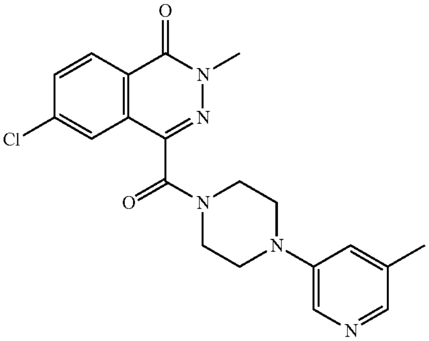
,
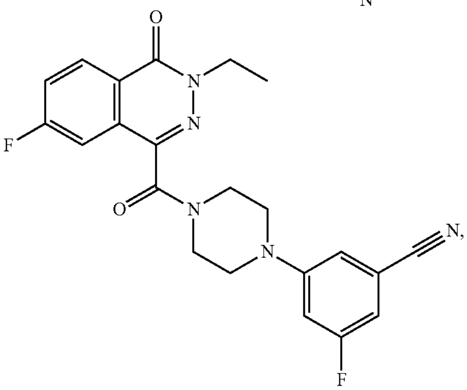
,
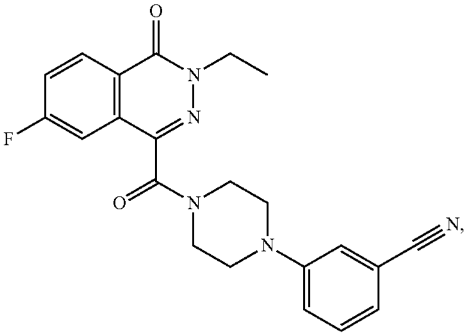
,
-continued
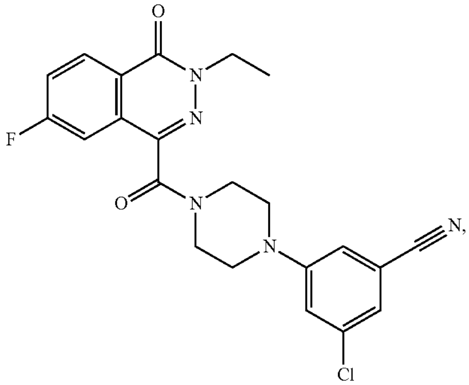 [SMILES: CCn1nc(C(=O)N2CCN(c3cc(Cl)cc(C#N)c3)CC2)c2cc(F)ccc2c1=O]
,
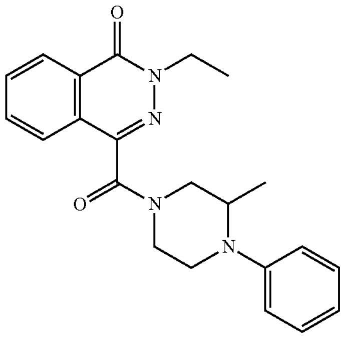
,
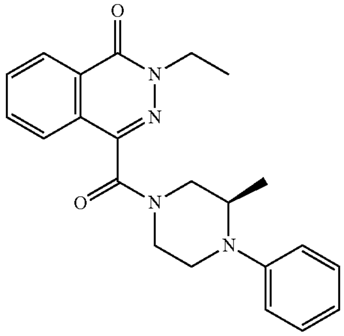
,
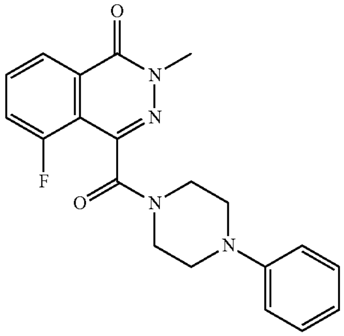
,
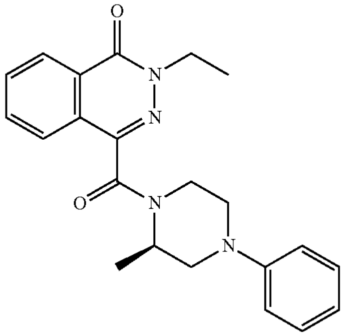
, -continued
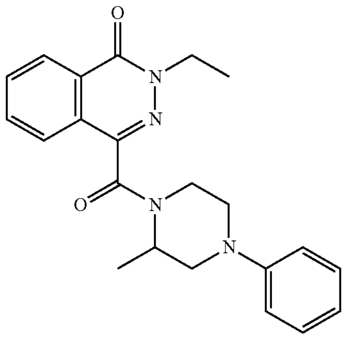
,
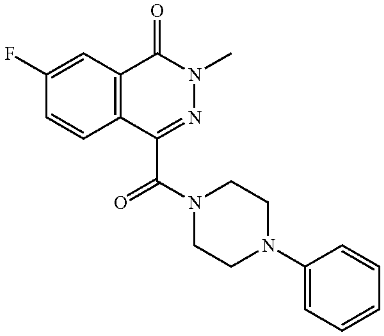
,
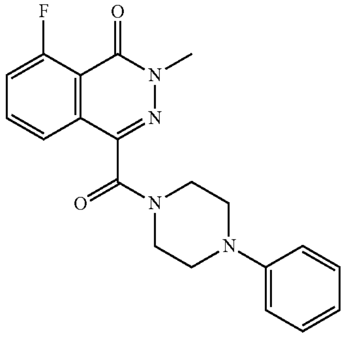
,
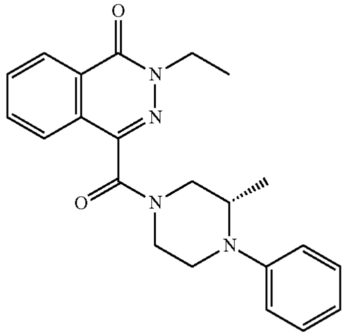
,
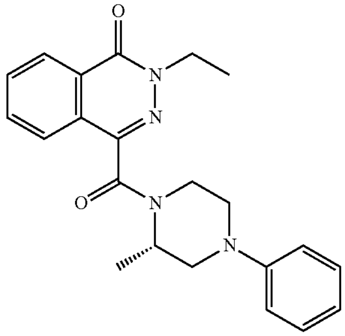
,
-continued
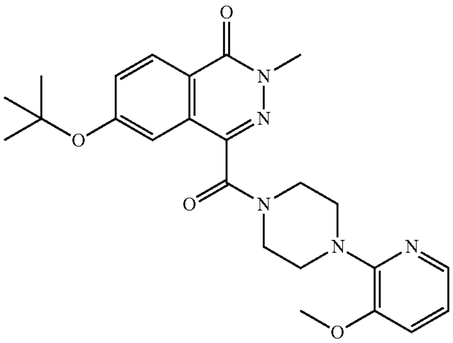
,
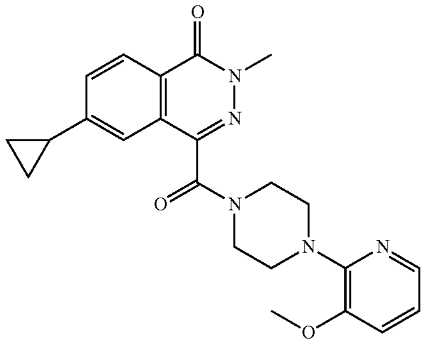
,
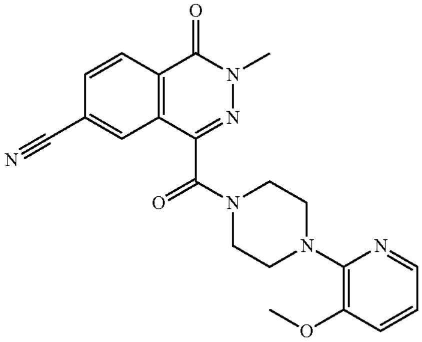
,
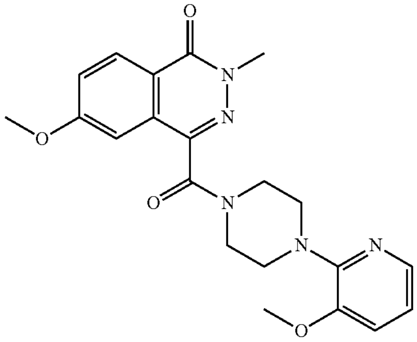
,
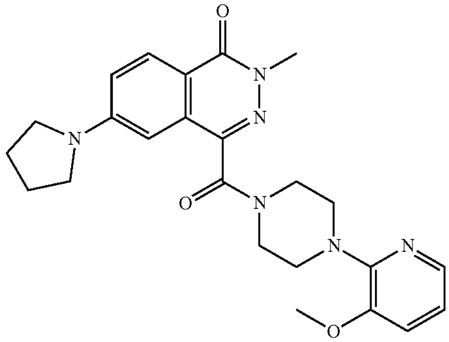
, -continued

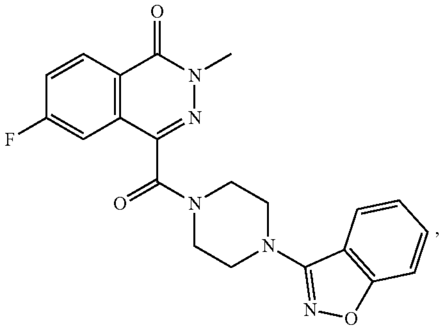

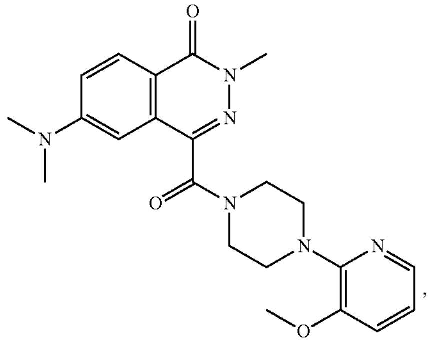

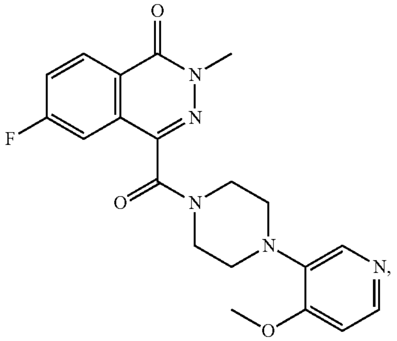

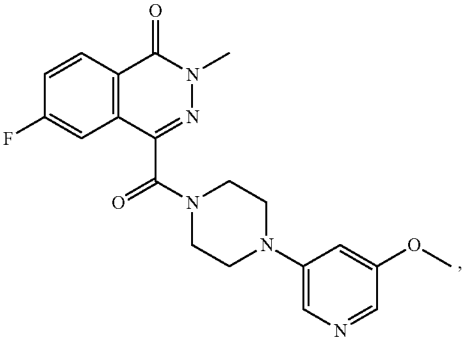

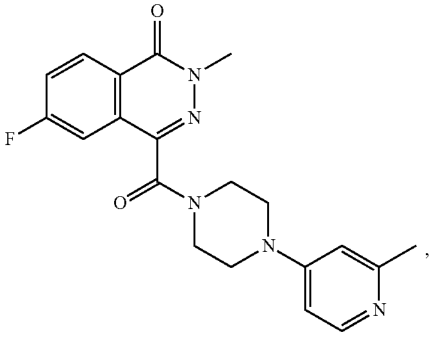

-continued

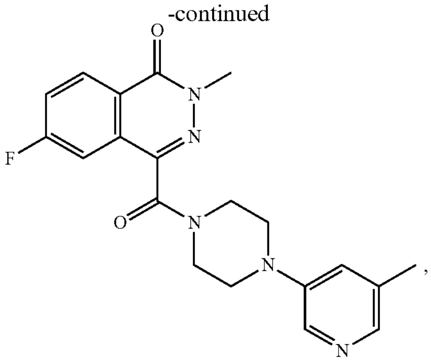

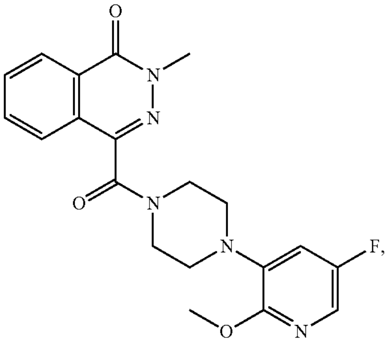

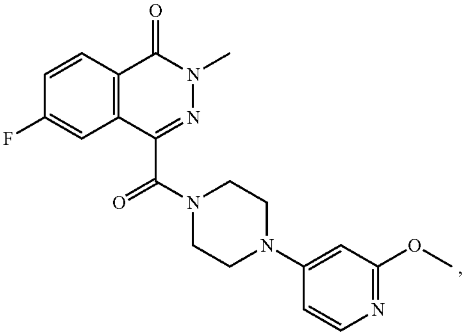

or a salt of any one thereof.

Compounds of Formula (III).

In some aspects, the present disclosure provides a compound represented by the structure of Formula (III):

(III)

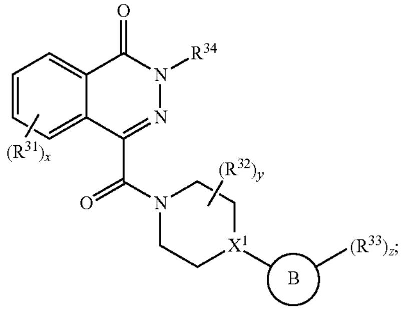

or a pharmaceutically acceptable salt thereof wherein:

$X^1$ is selected from N and $C(R^{35})$;

$R^{31}$ is independently selected at each occurrence from (I), (II) and (III):

(I) halogen, $—OR^{40}$, $—SR^{40}$, $—N(R^{40})_2$, $—C(O)R^{40}$, $—C(O)OR^{40}$, $—OC(O)R^{40}$, $—OC(O)N(R^{40})_2$, —C(O)N($R^{40}$)$_2$, —N($R^{40}$)C(O)$R^{40}$, —N($R^{40}$)C(O)O$R^{40}$, —N($R^{40}$)C(O)N($R^{40}$)$_2$, —N($R^{40}$)S(O)$_2$($R^{40}$), —S(O)$R^{40}$, —S(O)$_2R^{40}$, —S(O)$_2$N($R^{40}$)$_2$, —$NO_2$, and —CN;

(II) $C_{1-6}$ alkyl optionally substituted with one or more substituents independently selected from halogen, —O$R^{40}$, —S$R^{40}$, —N($R^{40}$)$_2$, —C(O)$R^{40}$, —C(O)O$R^{40}$, —OC(O)$R^{40}$, —OC(O)N($R^{40}$)$_2$, —C(O)N($R^{40}$)$_2$, —N($R^{40}$)C(O)$R^{40}$, —N($R^{40}$)C(O)O$R^{40}$, —N($R^{40}$)C(O)N($R^{40}$)$_2$, —N($R^{40}$)S(O)$_2$($R^{40}$), —S(O)$R^{40}$, —S(O)$_2R^{40}$, —S(O)$_2$N($R^{40}$)$_2$, —$NO_2$, ═S, ═O, and —CN; and (III) $C_{3-10}$ carbocycle and 3- to 10-membered heterocycle, any of which is optionally substituted with one or more substituents independently selected from halogen, —O$R^{40}$, —S$R^{40}$, —N($R^{40}$)$_2$, —C(O)$R^{40}$, —C(O)O$R^{40}$, —OC(O)$R^{40}$, —OC(O)N($R^{40}$)$_2$, —C(O)N($R^{40}$)$_2$, —N($R^{40}$)C(O)$R^{40}$, —N($R^{40}$)C(O)O$R^{40}$, —N($R^{40}$)C(O)N($R^{40}$)$_2$, —N($R^{40}$)S(O)$_2$($R^{40}$), —S(O)$R^{40}$, —S(O)$_2R^{40}$, —S(O)$_2$N($R^{40}$)$_2$, —$NO_2$, ═S, ═O, and —CN;

$R^{32}$ is independently selected at each occurrence from: halogen, —O$R^{41}$, —S$R^{41}$, —N($R^{41}$)$_2$, —C(O)$R^{41}$, —C(O)O$R^{41}$, —OC(O)$R^{41}$, —OC(O)N($R^{41}$)$_2$, —C(O)N($R^{41}$)$_2$, —N($R^{41}$)C(O)$R^{41}$, —N($R^{41}$)C(O)O$R^{41}$, —N($R^{41}$)C(O)N($R^{41}$)$_2$, —N($R^{41}$)S(O)$_2$($R^{41}$), —S(O)$R^{41}$, —S(O)$_2R^{41}$, —S(O)$_2$N($R^{41}$)$_2$, —$NO_2$, ═S, ═O, and —CN; and $C_{1-6}$ alkyl optionally substituted with one or more substituents independently selected from halogen, —O$R^{41}$, —S$R^{41}$, —N($R^{41}$)$_2$, —C(O)$R^{41}$, —C(O)O$R^{41}$, —OC(O)$R^{41}$, —OC(O)N($R^{41}$)$_2$, —C(O)N($R^{41}$)$_2$, —N($R^{41}$)C(O)$R^{41}$, —N($R^{41}$)C(O)O$R^{41}$, —N($R^{41}$)C(O)N($R^{41}$)$_2$, —N($R^{41}$)S(O)$_2$($R^{41}$), —S(O)$R^{41}$, —S(O)$_2R^{41}$, —S(O)$_2$N($R^{41}$)$_2$, —$NO_2$, ═S, ═O, and —CN; and $R^{33}$ is independently selected at each occurrence from: halogen, —O$R^{42}$, —S$R^{42}$, —N($R^{42}$)$_2$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, and —S(O)$_2$N($R^{42}$)$_2$; and $C_{1-6}$ alkyl optionally substituted with one or more substituents independently selected from halogen, —O$R^{42}$, —S$R^{42}$, —N($R^{42}$)$_2$, —C(O)$R^{42}$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, —S(O)$_2$N($R^{42}$)$_2$, —$NO_2$, ═S, and —CN;

wherein when one $R^{33}$ is methyl, each additional $R^{33}$ is independently selected from (IV), (V), and (VI):

(IV) halogen, —O$R^{42}$, —S$R^{42}$, —N($R^{42}$)$_2$, —C(O)$R^{42}$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, —S(O)$_2$N($R^{42}$)$_2$, —$NO_2$, and —CN;

(V) $C_1$ alkyl substituted with one or more substituents independently selected from halogen, —O$R^{42}$, —S$R^{42}$, —N($R^{42}$)$_2$, —C(O)$R^{42}$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, —S(O)$_2$N($R^{42}$)$_2$, —$NO_2$, ═S, ═O, and —CN; and (VI) $C_{2-6}$ alkyl optionally substituted with one or more substituents independently selected from halogen, —O$R^{42}$, —S$R^{42}$, —N($R^{42}$)$_2$, —C(O)$R^{42}$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, —S(O)$_2$N($R^{42}$)$_2$, —$NO_2$, ═S, ═O, and —CN; or two $R^{33}$ on adjacent atoms may come together to form a $C_{3-8}$ carbocycle or 3- to 8-membered heterocycle, each of which is optionally substituted with one or more substituents independently selected from:

halogen, —O$R^{42}$, —S$R^{42}$, —N($R^{42}$)$_2$, —C(O)$R^{42}$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, —S(O)$_2$N($R^{42}$)$_2$, —$NO_2$, ═O, and —CN; and $C_{1-6}$ alkyl optionally substituted with one or more substituents independently selected from halogen, —O$R^{42}$, —S$R^{42}$, —N($R^{42}$)$_2$, —C(O)$R^{42}$, —C(O)O$R^{42}$, —OC(O)$R^{42}$, —OC(O)N($R^{42}$)$_2$, —C(O)N($R^{42}$)$_2$, —N($R^{42}$)C(O)$R^{42}$, —N($R^{42}$)C(O)O$R^{42}$, —N($R^{42}$)C(O)N($R^{42}$)$_2$, —N($R^{42}$)S(O)$_2$($R^{42}$), —S(O)$R^{42}$, —S(O)$_2R^{42}$, —S(O)$_2$N($R^{42}$)$_2$, —$NO_2$, ═S, ═O, and —CN;

$R^{34}$ is selected from $C_{1-6}$ alkyl and $C_{2-6}$ alkenyl, each of which is optionally substituted with one or more substituents independently selected from halogen, —O$R^{43}$, —S$R^{43}$, —N($R^{43}$)$_2$, —C(O)$R^{43}$, —C(O)O$R^{43}$, —OC(O)$R^{43}$, —OC(O)N($R^{43}$)$_2$, —C(O)N($R^{43}$)$_2$, —N($R^{43}$)C(O)$R^{43}$, —N($R^{43}$)C(O)O$R^{43}$, —N($R^{43}$)C(O)N($R^{43}$)$_2$, —N($R^{43}$)S(O)$_2$($R^{43}$), —S(O)$R^{43}$, —S(O)$_2R^{43}$, —S(O)$_2$N($R^{43}$)$_2$, —$NO_2$, ═S, ═O, and —CN;

Ring B is selected from $C_{3-6}$ carbocyclene and 4- to 6-membered heterocyclene;

$R^{35}$, $R^{40}$, $R^{41}$, $R^{42}$, and $R^{43}$ are each independently selected at each occurrence from (VII), (VIII), and (IX):

(VII) hydrogen;

(VII) $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN; and (IX) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, ═O, and —CN;

x is selected from 0, 1, 2, 3, and 4;

y is selected from 0, 1, 2, 3, and 4; and z is selected from 2, 3, 4 and 5.

In some embodiments, for the compound or salt of Formula (III), $X^1$ is C($R^{35}$). In some embodiments, $R^{35}$ of C($R^{35}$) is selected from hydrogen; and $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{35}$ of C($R^{35}$) is $C_{1-6}$ alkyl optionally substituted with one more substituents independently selected from halogen, —O—$C_{1-6}$ alkyl, —O—$C_{1-6}$ haloalkyl, —$NH_2$, —$NO_2$, and —CN. In some embodiments, $R^{35}$ of C($R^{35}$) is selected from hydrogen, methyl, ethyl, propyl, and isopropyl. In some embodiments, $R^{35}$ of C($R^{35}$) is selected from methyl, ethyl, propyl, and isopropyl. In some embodiments, $R^{35}$ of C($R^{35}$) is hydrogen.

In some embodiments, for the compound or salt of Formula (III), $R^{35}$ is hydrogen. In some embodiments, $R^{35}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{35}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{35}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (III), $X^1$ is N.

In some embodiments, for the compound or salt of Formula (III), y is selected from 0, 1, 2, and 3. In some embodiments, y is selected from 0, 1, and 2. In some embodiments, y is selected from 0 and 1. In some embodiments, y is selected from 1, 2, 3, and 4. In some embodiments, y is selected from 2, 3, and 4. In some embodiments, y is selected from 3 and 4. In some embodiments, y is selected from 1 and 2. In some embodiments, y is 1 or 2. In some embodiments, y is 0. In some embodiments, y is 1. In some embodiments, y is 2. In some embodiments, y is 3. In some embodiments, y is 4.

In some embodiments, for the compound or salt of Formula (III), each $R^{32}$ is selected from halogen, —$OR^{41}$, —$SR^{41}$, —$N(R^{41})_2$, —$C(O)R^{41}$, —$C(O)OR^{41}$, —$OC(O)R^{41}$, —$OC(O)N(R^{41})_2$, —$C(O)N(R^{41})_2$, —$N(R^{41})C(O)R^{41}$, —$N(R^{41})C(O)OR^{41}$, —$N(R^{41})C(O)N(R^{41})_2$, —$N(R^{41})S(O)_2(R^{41})$, —$S(O)R^{41}$, —$S(O)_2R^{41}$, —$S(O)_2N(R^{41})_2$, —$NO_2$, =S, =O, and —CN. In some embodiments, each $R^{32}$ is selected from halogen, —$OR^{41}$, —$N(R^{41})_2$, —$C(O)R^{41}$, —$C(O)OR^{41}$, —$NO_2$, =S, =O, and —CN.

In some embodiments, for the compound or salt of Formula (III), each $R^{32}$ is selected from $C_{1-6}$ alkyl optionally substituted with one or more substituents independently selected from halogen, —$OR^{41}$, —$SR^{41}$, —$N(R^{41})_2$, —$C(O)R^{41}$, —$C(O)OR^{41}$, —$OC(O)R^{41}$, —$OC(O)N(R^{41})_2$, —$C(O)N(R^{41})_2$, —$N(R^{41})C(O)R^{41}$, —$N(R^{41})C(O)OR^{41}$, —$N(R^{41})C(O)N(R^{41})_2$, —$N(R^{41})S(O)_2(R^{41})$, —$S(O)R^{41}$, —$S(O)_2R^{41}$, —$S(O)_2N(R^{41})_2$, —$NO_2$, =S, =O, and —CN. In some embodiments, each $R^{32}$ is selected from $C_{1-6}$ alkyl optionally substituted with one or more substituents independently selected from halogen, —$OR^{41}$, —$N(R^{41})_2$, —$C(O)R^{41}$, —$C(O)OR^{41}$, —$NO_2$, =S, =O, and —CN. In some embodiments, each $R^{32}$ is selected from $C_{1-3}$ alkyl optionally substituted with one or more substituents independently selected from halogen, —$OR^{41}$, —$N(R^{41})_2$, —$C(O)R^{41}$, —$C(O)OR^{41}$, —$NO_2$, =S, =O, and —CN.

In some embodiments, for the compound or salt of Formula (III), x is selected from 0, 1, 2, and 3. In some embodiments, x is selected from 0, 1, and 2. In some embodiments, x is selected from 0 and 1. In some embodiments, x is selected from 1, 2, 3, and 4. In some embodiments, x is selected from 2, 3, and 4. In some embodiments, x is selected from 3 and 4. In some embodiments, x is selected from 1 and 2. In some embodiments, x is 1 or 2. In some embodiments, x is 0. In some embodiments, x is 1. In some embodiments, x is 2. In some embodiments, x is 3. In some embodiments, x is 4.

In some embodiments, for the compound or salt of Formula (III), for the compound or salt of formula (III), each $R^{31}$ is selected from halogen, —$OR^{40}$, —$SR^{40}$, —$N(R^{40})_2$, —$C(O)R^{40}$, —$C(O)OR^{40}$, —$OC(O)R^{40}$, —$OC(O)N(R^{40})_2$, —$C(O)N(R^{40})_2$, —$N(R^{40})C(O)R^{40}$, —$N(R^{40})C(O)OR^{40}$, —$N(R^{40})C(O)N(R^{40})_2$, —$N(R^{40})S(O)_2(R^{40})$, —$S(O)R^{40}$, —$S(O)_2R^{40}$, —$S(O)_2N(R^{40})_2$, —$NO_2$, and —CN. In some embodiments, each $R^{31}$ is selected from halogen, —$OR^{40}$, —$N(R^{40})_2$, —$C(O)R^{40}$, —$C(O)OR^{40}$, —$NO_2$, and —CN.

In some embodiments, for the compound or salt of Formula (III), each $R^{31}$ is selected from $C_{1-6}$ alkyl optionally substituted with one or more substituents independently selected from halogen, —$OR^{40}$, —$SR^{40}$, —$N(R^{40})_2$, —$C(O)R^{40}$, —$C(O)OR^{40}$, —$OC(O)R^{40}$, —$OC(O)N(R^{40})_2$, —$C(O)N(R^{40})_2$, —$N(R^{40})C(O)R^{40}$, —$N(R^{40})C(O)OR^{40}$, —$N(R^{40})C(O)N(R^{40})_2$, —$N(R^{40})S(O)_2(R^{40})$, —$S(O)R^{40}$, —$S(O)_2R^{40}$, —$S(O)_2N(R^{40})_2$, —$NO_2$, =S, =O, and —CN. In some embodiments, each $R^{31}$ is selected from $C_{1-6}$ alkyl optionally substituted with one or more substituents independently selected from halogen, —$OR^{40}$, —$N(R^{40})_2$, —$C(O)R^{40}$, —$C(O)OR^{40}$, —$NO_2$, =S, =O, and —CN. In some embodiments, each $R^{31}$ is selected from $C_{1-3}$ alkyl optionally substituted with one or more substituents independently selected from halogen, —$OR^{40}$, —$N(R^{40})_2$, —$C(O)R^{40}$, —$C(O)OR^{40}$, —$NO_2$, =S, =O, and —CN.

In some embodiments, for the compound or salt of Formula (III), each $R^{31}$ is selected from $C_{3-10}$ carbocycle and 3- to 10-membered heterocycle, any of which is optionally substituted with one or more substituents independently selected from halogen, —$OR^{40}$, —$SR^{40}$, —$N(R^{40})_2$, —$C(O)R^{40}$, —$C(O)OR^{40}$, —$OC(O)R^{40}$, —$OC(O)N(R^{40})_2$, —$C(O)N(R^{40})_2$, —$N(R^{40})C(O)R^{40}$, —$N(R^{40})C(O)OR^{40}$, —$N(R^{40})C(O)N(R^{40})_2$, —$N(R^{40})S(O)_2(R^{40})$, —$S(O)R^{40}$, —$S(O)_2R^{40}$, —$S(O)_2N(R^{40})_2$, —$NO_2$, =S, =O, and —CN. In some embodiments, each $R^{31}$ is selected from $C_{3-10}$ carbocycle and 3- to 10-membered heterocycle, any of which is optionally substituted with one or more substituents independently selected from halogen, —$OR^{40}$, —$N(R^{40})_2$, —$C(O)R^{40}$, —$C(O)OR^{40}$, —$NO_2$, =S, =O, and —CN. In some embodiments, each $R^{31}$ is selected from $C_{3-6}$ carbocycle and 3- to 6-membered heterocycle, any of which is optionally substituted with one or more substituents independently selected from halogen, —$OR^{40}$, —$N(R^{40})_2$, —$C(O)R^{40}$, —$C(O)OR^{40}$, —$NO_2$, =S, =O, and —CN.

In some embodiments, for the compound or salt of Formula (III), each $R^{31}$ is independently selected from halogen, —$OR^{40}$, —$N(R^{40})_2$, —$C(O)R^{40}$, —$C(O)OR^{40}$, —$NO_2$, —CN; and $C_{1-6}$ alkyl, $C_{3-10}$ carbocycle and 3- to 10-membered heterocycle, each of which is optionally substituted with one or more substituents independently selected from halogen, —$OR^{40}$, —$N(R^{40})_2$, —$C(O)R^{40}$, —$C(O)OR^{40}$, —$NO_2$, =S, =O, and —CN; and each $R^{40}$ is independently selected from hydrogen and $C_{1-3}$ alkyl optionally substituted with one or more substituents independently selected from halogen and —O—$C_{1-3}$ alkyl.

In some embodiments, for the compound or salt of Formula (III), $R^{34}$ is selected from $C_{1-6}$ alkyl optionally substituted with one or more substituents independently selected from halogen, —$OR^{43}$, —$SR^{43}$, —$N(R^{43})_2$, —$C(O)R^{43}$, —$C(O)OR^{43}$, —$OC(O)R^{43}$, —$OC(O)N(R^{43})_2$, —$C(O)N(R^{43})_2$, —$N(R^{43})C(O)R^{43}$, —$N(R^{43})C(O)OR^{43}$, —$N(R^{43})C(O)N(R^{43})_2$, —$N(R^{43})S(O)_2(R^{43})$, —$S(O)R^{43}$, —$S(O)_2R^{43}$, —$S(O)_2N(R^{43})_2$, —$NO_2$, =S, =O, and —CN. In some embodiments, $R^{34}$ is selected from $C_{1-6}$ alkyl optionally substituted with one or more substituents independently selected from halogen, —$OR^{43}$, —$N(R^{43})_2$, —$C(O)R^{43}$, —$C(O)OR^{43}$, —$NO_2$, =S, =O, and —CN. In some embodiments, $R^{34}$ is selected from $C_{1-3}$alkyl optionally substituted with one or more substituents independently selected from halogen, —$OR^{43}$, —$N(R^{43})_2$, —$C(O)R^{43}$, —$C(O)OR^{43}$, —$NO_2$, =S, =O, and —CN.

In some embodiments, for the compound or salt of Formula (III), $R^{34}$ is selected from $C_{2-6}$ alkenyl optionally substituted with one or more substituents independently selected from halogen, —$OR^{43}$, —$SR^{43}$, —$N(R^{43})_2$, —$C(O)R^{43}$, —$C(O)OR^{43}$, —$OC(O)R^{43}$, —$OC(O)N(R^{43})_2$, —$C(O)N(R^{43})_2$, —$N(R^{43})C(O)R^{43}$, —$N(R^{43})C(O)OR^{43}$, —$N(R^{43})C(O)N(R^{43})_2$, —$N(R^{43})S(O)_2(R^{43})$, —$S(O)R^{43}$, —$S(O)_2R^{43}$, —$S(O)_2N(R^{43})_2$, —$NO_2$, =S, =O, and —CN. In some embodiments, $R^{34}$ is selected from $C_{2-6}$ alkenyl optionally substituted with one or more substituents independently selected from halogen, —$OR^{43}$, —$N(R^{43})_2$, —$C(O)R^{43}$, —$C(O)OR^{43}$, —$NO_2$, =S, =O, and —CN. In some embodiments, $R^{34}$ is selected from $C_{24}$ alkenyl optionally substituted with one or more substituents independently selected from halogen, —$OR^{43}$, —$N(R^{43})_2$, —$C(O)R^{43}$, —$C(O)OR^{43}$, —$NO_2$, =S, =O, and —CN.

In some embodiments, for the compound or salt of Formula (III), $R^{34}$ is selected from $C_{1-4}$ alkyl and $C_{24}$ alkenyl, each of which is optionally substituted with one or more substituents independently selected from halogen, —$OR^{43}$, —$N(R^{43})_2$, —$C(O)R^{43}$, and —CN, and each $R^{43}$ is independently selected from hydrogen, $C_{1-3}$ alkyl, and $C_{1-3}$ haloalkyl. In some embodiments, $R^{34}$ is selected from methyl, ethyl, propyl, isopropyl, and propenyl.

In some embodiments, for the compound or salt of Formula (III), z is selected from 2, 3, and 4. In some embodiments, z is selected from 3 and 4. In some embodiments, z is selected from 2 and 3. In some embodiments, z is selected from 3, 4, and 5. In some embodiments, z is selected from 4 and 5. In some embodiments, z selected from 3 and 4. In some embodiments, z is 5. In some embodiments, z is 4. In some embodiments, z is 3. In some embodiments, z is 2.

In some embodiments, Formula (III) is represented by a structure selected from Formula (III-a), (III-b), (III-c), (III-d), and (III-e).

(III-a)

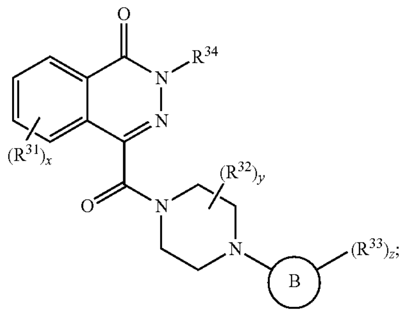

(III-b)

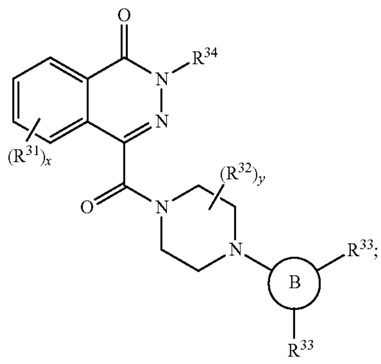

(III-c)

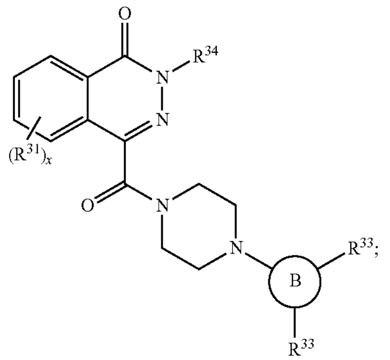

(III-d)

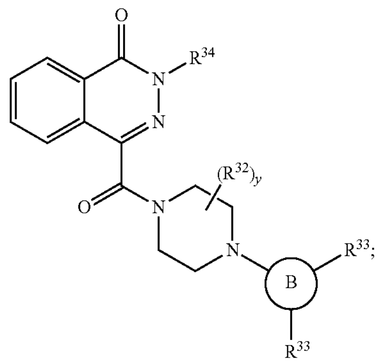

-continued (III-e)

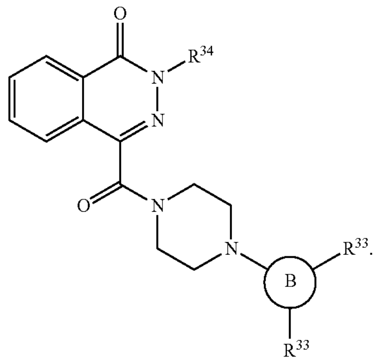

In some embodiments, a compound or salt of the disclosure is represented by Formula (III-a):

(III-a)

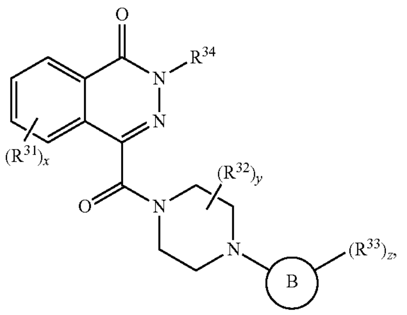

or a pharmaceutically acceptable salt thereof, wherein $R^{31}$, $R^{32}$, $R^{33}$, $R^{34}$, Ring B, x, y, and z are as defined in Formula (III).

In some embodiments, a compound or salt of the disclosure is represented by Formula (III-b):

(III-b)

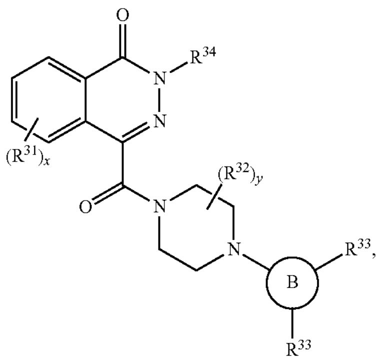

or a pharmaceutically acceptable salt thereof, wherein $R^{31}$, $R^{32}$, $R^{33}$, $R^{34}$, Ring B, x, and y, are as defined in Formula (III).

In some embodiments, a compound or salt of the disclosure is represented by Formula (III-c):

(III-c)

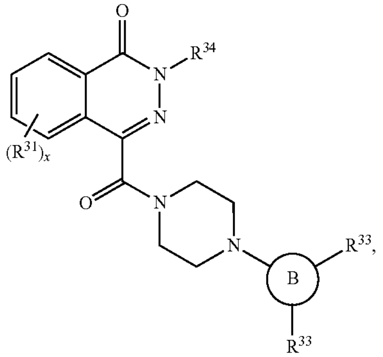

or a pharmaceutically acceptable salt thereof, wherein $R^{31}$, $R^{33}$, $R^{34}$, Ring B, and x are as defined in Formula (III).

In some embodiments, a compound or salt of the disclosure is represented by Formula (III-d):

(III-d)

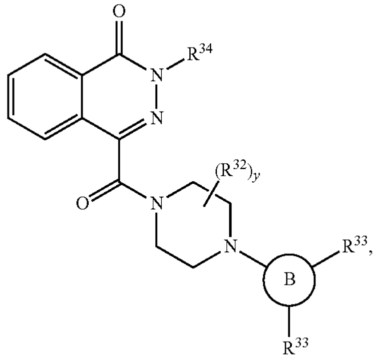

or a pharmaceutically acceptable salt thereof, wherein $R^{32}$, $R^{33}$, $R^{34}$, Ring B, and y, are as defined in Formula (III).

In some embodiments, a compound or salt of the disclosure is represented by Formula (III-e):

(III-e)

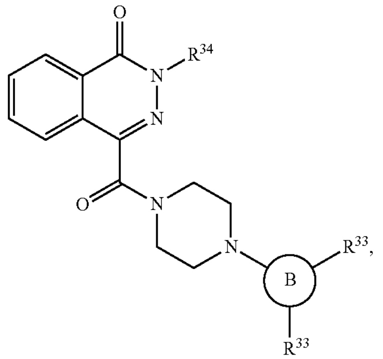

or a pharmaceutically acceptable salt thereof, wherein $R^{33}$, $R^{34}$, and Ring B, are as defined in Formula (III).

In some embodiments, for the compound or salt of Formula (III), (III-a), (III-b), (III-c), (III-d), or (III-e), Ring B is selected from $C_{3-10}$ carbocyclene. In some embodiments, the $C_{3-10}$ carbocyclene of Ring B is selected from: $C_3$ carbocyclene, $C_4$ carbocyclene, $C_5$ carbocyclene, $C_6$ carbocyclene, $C_7$ carbocyclene, $C_8$ carbocyclene, $C_9$ carbocyclene, and $C_{10}$ carbocyclene. In some embodiments, Ring B is selected from: $C_{3-4}$ carbocyclene, $C_{3-5}$ carbocyclene, $C_{3-6}$ carbocyclene, $C_{3-7}$ carbocyclene, $C_{3-8}$ carbocyclene, and $C_{3-9}$ carbocyclene.

In some embodiments, for the compound or salt of Formula (III), (III-a), (III-b), (III-c), (III-d), or (III-e), Ring B is selected from 3- to 10-membered heterocyclene. In some embodiments, the 3- to 10-membered heterocyclene of Ring B is selected from 3-membered heterocyclene, 4-membered heterocyclene, 5-membered heterocyclene, 6-membered heterocyclene, 7-membered heterocyclene, 8-membered heterocyclene, 9-membered heterocyclene, and 10-membered heterocyclene. In some embodiments, Ring B is selected from: 3- to 4-membered heterocyclene, 3- to 5-membered heterocyclene, 3- to 6-membered heterocyclene, 3- to 7-membered heterocyclene, 3- to 8-membered heterocyclene, and 3- to 9-membered heterocyclene.

In some embodiments, for the compound or salt of Formula (III), (III-a), (III-b), (III-c), (III-d), or (III-e), Ring B is selected from $C_{3-6}$ carbocyclene and 5- to 6-membered heterocyclene. In some embodiments, Ring B is selected from phenylene and 6-membered heteroarylene. In some embodiments, Ring B is selected from phenylene and pyridinylene.

In some embodiments, for the compound or salt of Formula (III), (III-a), (III-b), (III-c), (III-d), or (III-e), Ring B is selected from $C_{3-6}$ carbocyclene and 5- to 6-membered heterocyclene and z is 2. In some embodiments, Ring B is selected from phenylene and pyridinylene and z is 2

In some embodiments, for the compound or salt of Formula (III) or (III-a), Ring B is selected from $C_{3-6}$ carbocyclene and 5- to 6-membered heterocyclene and z is 3. In some embodiments, Ring B is selected from phenylene and pyridinylene and z is 3

In some embodiments, for the compound or salt of Formula (III) or (III-a), Ring B is selected from $C_{3-6}$ carbocyclene and 5- to 6-membered heterocyclene and z is 4. In some embodiments, Ring B is selected from phenylene and pyridinylene and z is 4.

In some embodiments, for the compound or salt of Formula (III), (III-a), (III-b), (III-c), (III-d), or (III-e), each $R^{33}$ is selected from halogen, —$OR^{42}$, —$SR^{42}$, —$N(R^{42})_2$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, and —$S(O)_2N(R^{42})_2$. In some embodiments, each $R^{33}$ is selected from halogen, —$OR^{42}$, —$SR^{42}$, —$N(R^{42})_2$, —$C(O)OR^{42}$, —$C(O)N(R^{42})_2$, —$N(R^{42})C(O)R^{42}$, —$N(R^{42})S(O)_2(R^{42})$, and —$S(O)_2N(R^{42})_2$. In some embodiments, each $R^{33}$ is selected from halogen $OR^{42}$, —$N(R^{42})_2$, and —$C(O)OR^{42}$.

In some embodiments, for the compound or salt of Formula (III), (III-a), (III-b), (III-c), (III-d), or (III-e), each $R^{33}$ is selected from $C_{1-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, and —CN. In some embodiments, each $R^{33}$ is selected from $C_{1-6}$ alkyl optionally substituted with one or more substituents independently selected from halogen, —$OR^{42}$, —$SR^{42}$, —$N(R^{42})_2$, —$C(O)OR^{42}$, $C(O)N(R^{42})_2$, —$N(R^{42})C(O)R^{42}$, —$N(R^{42})S(O)_2(R^{42})$, —$S(O)_2N(R^{42})_2$, —$NO_2$, =S, and —CN. In some embodiments, each $R^{33}$ is selected from $C_{1-3}$ alkyl optionally substituted with one or more substituents independently selected from halogen, —$OR^{42}$, —$N(R^{42})_2$, —$C(O)OR^{42}$, —$NO_2$, =S, and —CN.

In some embodiments, for the compound or salt of Formula (III), (III-a), (III-b), (III-c), (III-d), or (III-e), each $R^{33}$ is selected from halogen, —$OR^{42}$, —$SR^{42}$, —$N(R^{42})_2$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, and —$S(O)_2N(R^{42})_2$; and each $R^{42}$ is independently selected from hydrogen and $C_{1-3}$ alkyl optionally substituted with one or more substituents independently selected from halogen and —O—$C_{1-3}$ alkyl. In some embodiments, each $R^{33}$ is selected from halogen, —$OR^{42}$, —$SR^{42}$, —$N(R^{42})_2$, —$C(O)OR^{42}$, —$C(O)N(R^{42})_2$, —$N(R^{42})C(O)R^{42}$, —$N(R^{42})S(O)_2(R^{42})$, and —$S(O)_2N(R^{42})_2$; and each $R^{42}$ is independently selected from hydrogen and $C_{1-3}$ alkyl optionally substituted with one or more substituents independently selected from halogen and —O—$C_{1-3}$ alkyl. In some embodiments, each $R^{33}$ is selected from halogen $OR^{42}$, —$N(R^{42})_2$, and —$C(O)OR^{42}$; and each $R^{42}$ is independently selected from hydrogen and $C_{1-3}$ alkyl optionally substituted with one or more substituents independently selected from halogen and —O—$C_{1-3}$ alkyl.

In some embodiments, for the compound or salt of Formula (III), (III-a), (III-b), (III-c), (III-d), or (III-e), each $R^{33}$ is selected from $C_{1-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, and —CN; and each $R^{42}$ is independently selected from hydrogen and $C_{1-3}$ alkyl optionally substituted with one or more substituents independently selected from halogen and —O—$C_{1-3}$ alkyl. In some embodiments, each $R^{33}$ is selected from $C_{1-6}$ alkyl optionally substituted with one or more substituents independently selected from halogen, —$OR^{42}$, —$SR^{42}$, —$N(R^{42})_2$, —$C(O)OR^{42}$, —$C(O)N(R^{42})_2$, —$N(R^{42})C(O)R^{42}$, —$N(R^{42})S(O)_2(R^{42})$, —$S(O)_2N(R^{42})_2$, —$NO_2$, =S, and —CN; and each $R^{42}$ is independently selected from hydrogen and $C_{1-3}$ alkyl optionally substituted with one or more substituents independently selected from halogen and —O—$C_{1-3}$ alkyl. In some embodiments, each $R^{33}$ is selected from $C_{1-3}$ alkyl optionally substituted with one or more substituents independently selected from halogen, —$OR^{42}$, —$N(R^{42})_2$, —$C(O)OR^{42}$, —$NO_2$, =S, and —CN; and each $R^{42}$ is independently selected from hydrogen and $C_{1-3}$ alkyl optionally substituted with one or more substituents independently selected from halogen and —O—$C_{1-3}$ alkyl.

In some embodiments, for the compound or salt of Formula (III), (III-a), (III-b), (III-c), (III-d), or (III-e), each $R^{33}$ is independently selected from halogen, —$OR^{42}$, —$SR^{42}$, —$N(R^{42})_2$, —$C(O)OR^{42}$, —$C(O)N(R^{42})_2$, —$N(R^{42})C(O)R^{42}$, —$N(R^{42})S(O)_2(R^{42})$, —$S(O)_2N(R^{42})_2$; and $C_{1-6}$ alkyl optionally substituted with one or more substituents independently selected from halogen, —$OR^{42}$, —$SR^{42}$, —$N(R^{42})_2$, —$C(O)OR^{42}$, —$C(O)N(R^{42})_2$, —$N(R^{42})C(O)R^{42}$, —$N(R^{42})S(O)_2(R^{42})$, —$S(O)_2N(R^{42})_2$, —$NO_2$, =S, and —CN; and each $R^{42}$ is independently selected from hydrogen and $C_{1-3}$ alkyl optionally substituted with one or more substituents independently selected from halogen and —O—$C_{1-3}$ alkyl.

In some embodiments, for the compound or salt of Formula (III), (III-a), (III-b), (III-c), (III-d), or (III-e), each $R^{33}$ is independently selected from: halogen, —$OR^{42}$, —$N(R^{42})_2$; and $C_{1-6}$ alkyl optionally substituted with one or more substituents independently selected from halogen, —$OR^{42}$, —$N(R^{42})_2$, —$NO_2$, and —CN; and each $R^{42}$ is independently selected from hydrogen and $C_{1-3}$ alkyl optionally substituted with one or more substituents independently selected from halogen and —O—$C_{1-3}$ alkyl. In some embodiments, each $R^{33}$ is independently selected from: halogen, —$OR^{42}$, and $C_{1-6}$ alkyl optionally substituted with one or more substituents independently selected from halogen and —$OR^{42}$; and each $R^{42}$ is independently selected from hydrogen and $C_{1-3}$ alkyl optionally substituted with one or more substituents independently selected from halogen and —O—$C_{1-3}$ alkyl. In some embodiments, each $R^{33}$ is independently selected from chloro, fluoro, bromo, methyl, —$CF_3$,

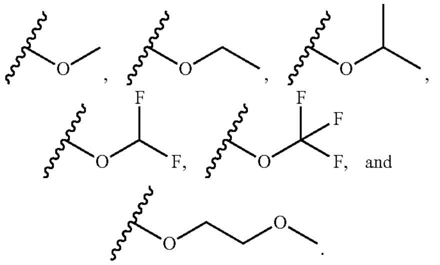

In some embodiments, each $R^{33}$ is independently selected from chloro, fluoro, and bromo. In some embodiments, each $R^{33}$ is independently selected from methyl and —$CF_3$. In some embodiments, each $R^{33}$ is independently selected from

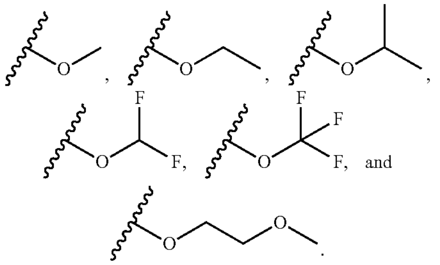

In some embodiments, each $R^{33}$ is independently selected from chloro, fluoro, bromo

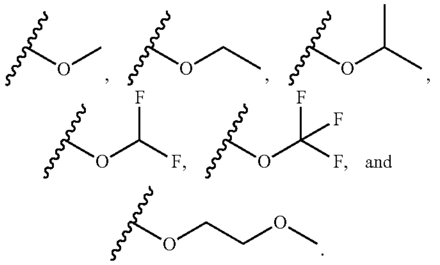

In some embodiments, each $R^{33}$ is independently selected from methyl, —$CF_3$,

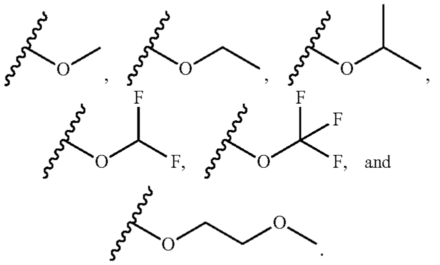

In some embodiments, each $R^{33}$ is independently selected from methyl, —$CF_3$, chloro, fluoro, and bromo.

In some embodiments, for the compound or salt of Formula (III), (III-a), (III-b), (III-c), (III-d), or (III-e), one $R^{33}$ is methyl and each additional $R^{33}$ is selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, and —CN. In some embodiments, one $R^{33}$ is methyl and each additional $R^{33}$ is selected from halogen, —$OR^{42}$, —$N(R^{42})_2$, —$C(O)R^{42}$, —$C(O)OR^{42}$, —$NO_2$, and —CN.

In some embodiments, for the compound or salt of Formula (III), (III-a), (III-b), (III-c), (III-d), or (III-e), one $R^{33}$ is methyl and each additional $R^{33}$ is selected from $C_1$ alkyl substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, =O, and —CN. In some embodiments, one $R^{33}$ is methyl and each additional $R^{33}$ is selected from $C_1$ alkyl substituted with one or more substituents independently selected from halogen, —$OR^{42}$, —$N(R^{42})_2$, —$C(O)R^{42}$, —$C(O)OR^{42}$, —$NO_2$, =S, =O, and —CN.

In some embodiments, for the compound or salt of Formula (III), (III-a), (III-b), (III-c), (III-d), or (III-e), one $R^{33}$ is methyl and each additional $R^{33}$ is selected from $C_{2-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, =O, and —CN. In some embodiments, one $R^{33}$ is methyl and each additional $R^{33}$ is selected from $C_{2-6}$ alkyl optionally substituted with one or more substituents independently selected from halogen, —$OR^{42}$, —$N(R^{42})_2$, —$C(O)R^{42}$, —$C(O)OR^{42}$, —$NO_2$, =S, =O, and —CN.

In some embodiments, for the compound or salt of Formula (III), (III-a), (III-b), (III-c), (III-d), or (III-e), one $R^{33}$ is methyl and each additional $R^{33}$ is selected from halogen, —$OR^{42}$, —$N(R^{42})_2$, —$C(O)R^{42}$, —$C(O)OR^{42}$, —$NO_2$, —CN; $C_1$ alkyl substituted with one or more substituents independently selected from halogen, —$OR^{42}$, —$N(R^{42})_2$, —$C(O)R^{42}$, —$C(O)OR^{42}$, —$NO_2$, =S, =O, and —CN; and $C_{2-6}$ alkyl optionally substituted with one or more substituents independently selected from halogen, —$OR^{42}$, —$N(R^{42})_2$, —$C(O)R^{42}$, —$C(O)OR^{42}$, —$NO_2$, =S, =O, and —CN. In some embodiments, one $R^{33}$ is methyl and each additional $R^{33}$ is selected from halogen, —$OR^{42}$, —$N(R^{42})_2$, —$C(O)R^{42}$, —$C(O)OR^{42}$, —$NO_2$, —CN; and $C_1$ alkyl substituted with one or more substituents independently selected from halogen, —$OR^{42}$, —$N(R^{42})_2$, —C(O)$R^{42}$, —$C(O)OR^{42}$, —$NO_2$, =S, =O, and —CN. In some embodiments, one $R^{33}$ is methyl and each additional $R^{33}$ is selected from halogen, —$OR^{42}$, —$N(R^{42})_2$, —$C(O)R^{42}$, —$C(O)OR^{42}$, —$NO_2$, —CN; and $C_{2-6}$ alkyl substituted with one or more substituents independently selected from halogen, —$OR^{42}$, —$N(R^{42})_2$, —$C(O)R^{42}$, —$C(O)OR^{42}$, —$NO_2$, =S, =O, and —CN.

In some embodiments, for the compound or salt of Formula (III), (III-a), (III-b), (III-c), (III-d), or (III-e),

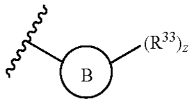

is selected from:

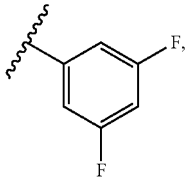 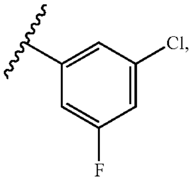

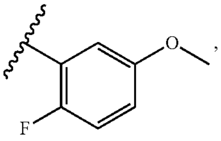 , 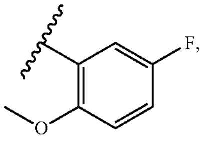

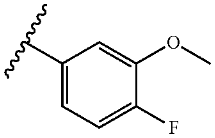 , 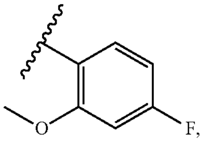

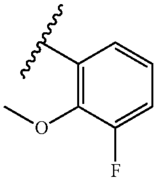 , 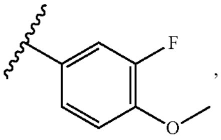 ,

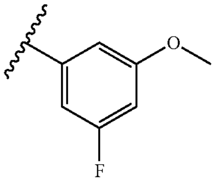 , 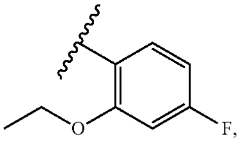

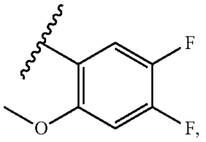 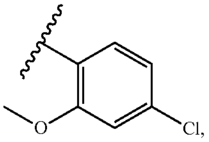

-continued

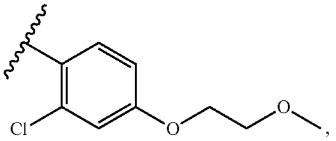 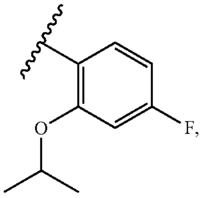

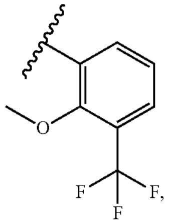 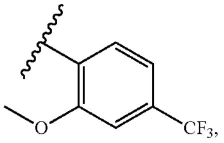

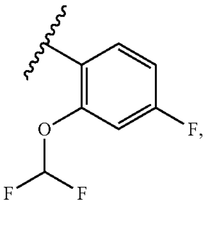 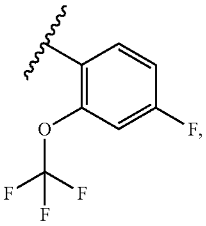

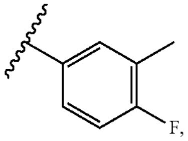 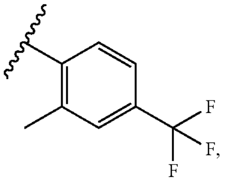

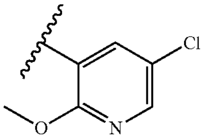 , 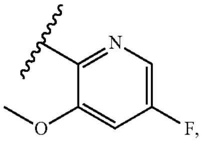

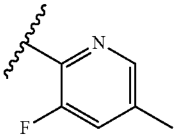 , 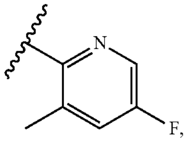

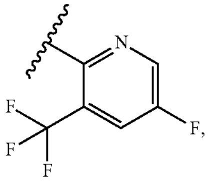 and 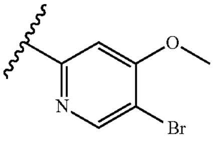 .

In some embodiments, for the compound or salt of Formula (III), (III-a), (III-b), (III-c), (III-d), or (III-e),

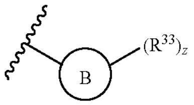

is selected from:
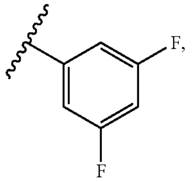 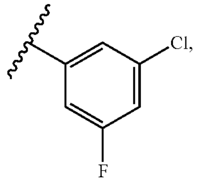
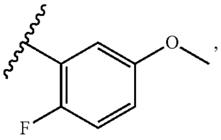 , 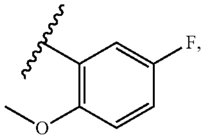
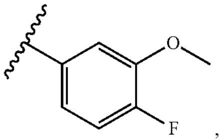 , 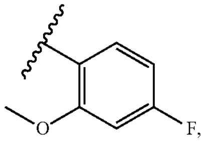
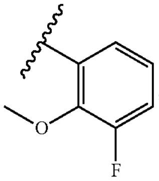 , 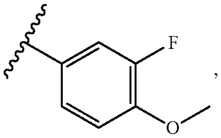 ,
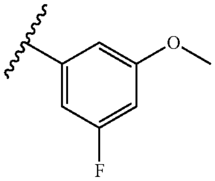 , 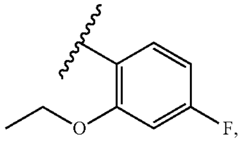
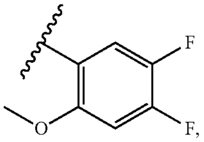 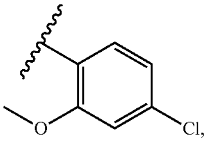
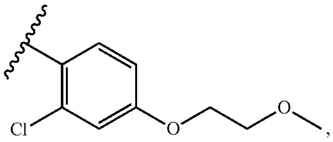 , 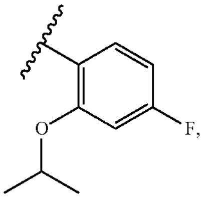
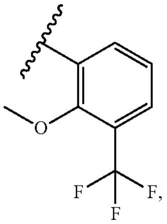 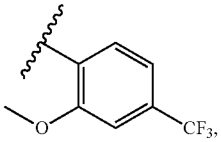
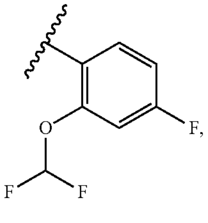 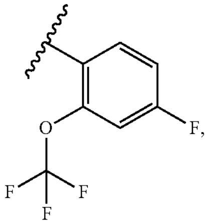
-continued
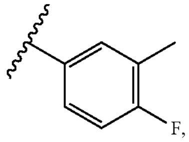 and 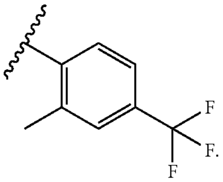
In some embodiments, for the compound or salt of Formula (III), (III-a), (III-b), (III-c), (III-d), or (III-e),
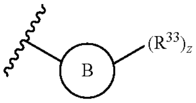
is selected from:
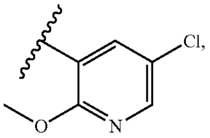 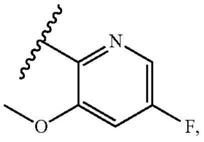
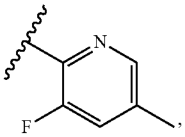 , 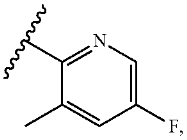
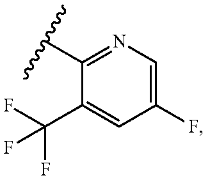 and 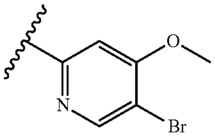
In some embodiments, for the compound or salt of Formula (III), (III-a), (III-b), (III-c), (III-d), or (III-e),
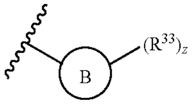
is selected from:
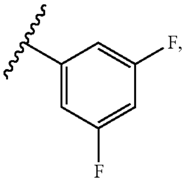 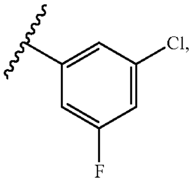

-continued
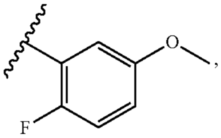
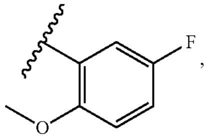
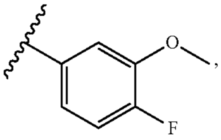
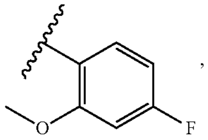
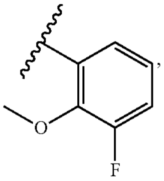
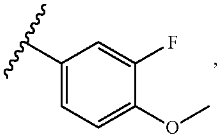
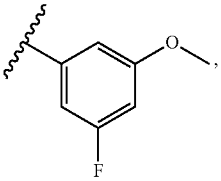
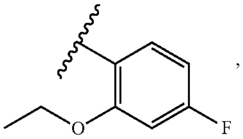
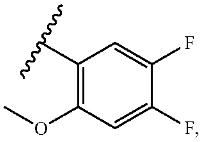
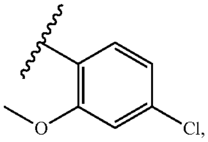
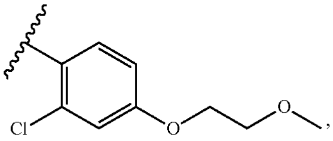
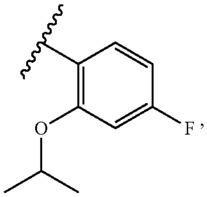
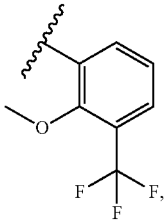
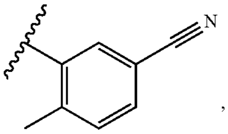
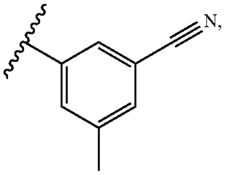
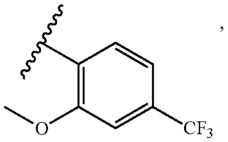
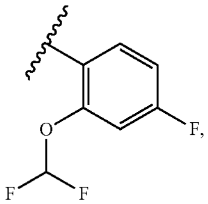
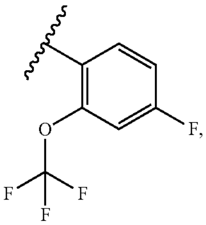
-continued
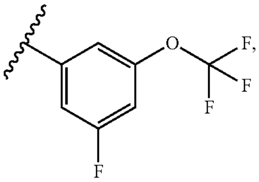
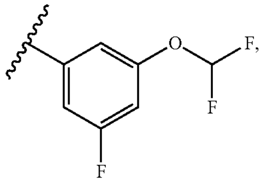
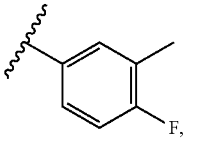
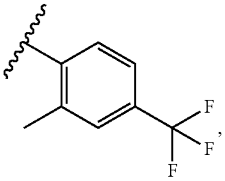
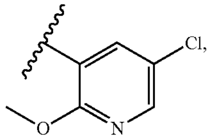
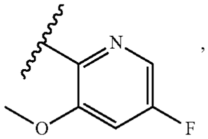
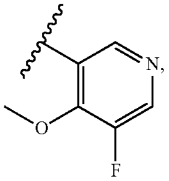
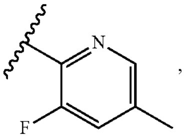
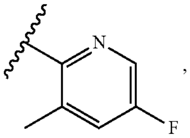
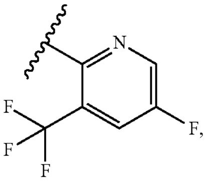
and
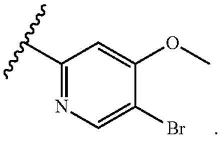
.
In some embodiments, for the compound or salt of Formula (III), (III-a), (III-b), (III-c), (III-d), or (III-e),
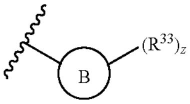
is selected from:
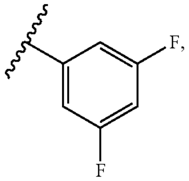
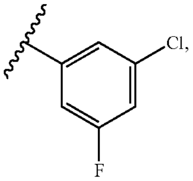
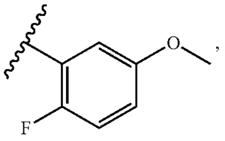
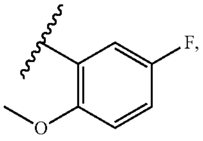
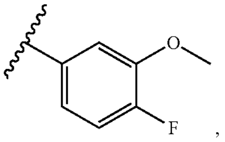
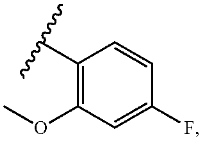

-continued

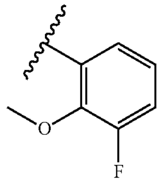,
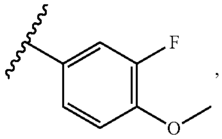,
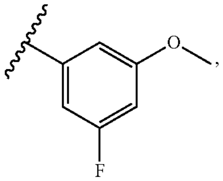
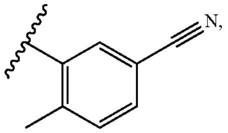
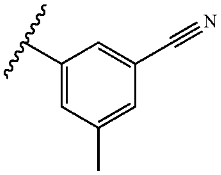,
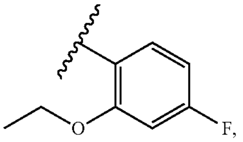
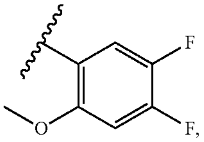
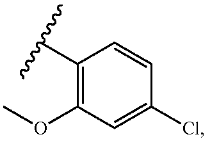
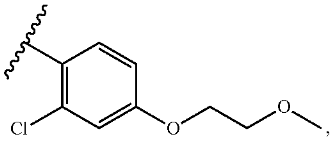
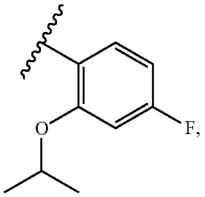
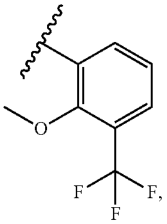
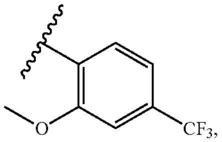
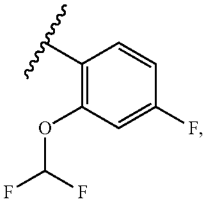
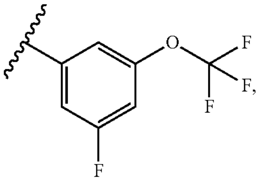
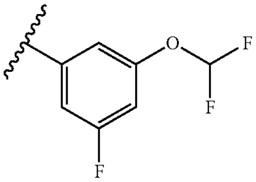,
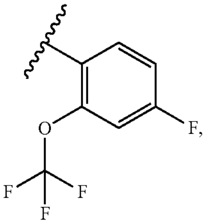

-continued

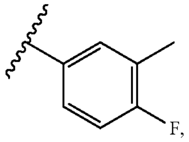
and
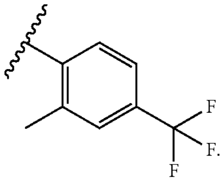

In some embodiments, for the compound or salt of Formula (III), (III-a), (III-b), (III-c), (III-d), or (III-e),

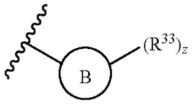

is selected from:

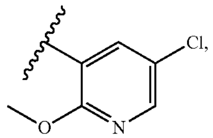
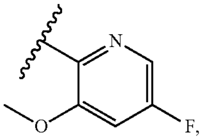
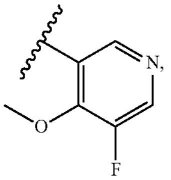
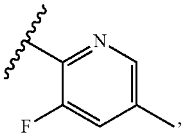
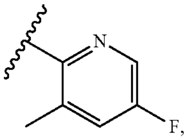
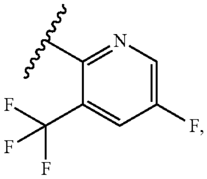
and
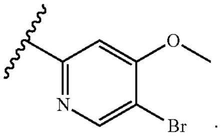

In some embodiments, for the compound or salt of Formula (III), (III-a), (III-b), (III-c), (III-d), or (III-e), two $R^{33}$ on adjacent atoms may come together to form a $C_{3-8}$ carbocycle optionally substituted with one or more substituents independently selected from: halogen, $—OR^{42}$, $—SR^{42}$, $—N(R^{42})_2$, $—C(O)R^{42}$, $—C(O)OR^{42}$, $—OC(O)R^{42}$, $—OC(O)N(R^{42})_2$, $—C(O)N(R^{42})_2$, $—N(R^{42})C(O)R^{42}$, $—N(R^{42})C(O)OR^{42}$, $—N(R^{42})C(O)N(R^{42})_2$, $—N(R^{42})S(O)_2(R^{42})$, $—S(O)R^{42}$, $—S(O)_2R^{42}$, $—S(O)_2N(R^{42})_2$, $—NO_2$, =O, and —CN; and $C_{1-6}$ alkyl optionally substituted with one or more substituents independently selected from halogen, $—OR^{42}$, $—SR^{42}$, $—N(R^{42})_2$, $—C(O)R^{42}$, $—C(O)OR^{42}$, $—OC(O)R^{42}$, $—OC(O)N(R^{42})_2$, $—C(O)N(R^{42})_2$, $—N(R^{42})C(O)R^{42}$, $—N(R^{42})C(O)OR^{42}$, $—N(R^{42})C(O)N(R^{42})_2$, $—N(R^{42})S(O)_2(R^{42})$, $—S(O)R^{42}$, $—S(O)_2R^{42}$, $—S(O)_2N(R^{42})_2$, $—NO_2$, =S, =O, and —CN. In some embodiments, two $R^{33}$ on adjacent atoms may come together to form a $C_{3-8}$ carbocycle optionally substituted with one or more substituents independently selected from: halogen, $—OR^{42}$, $—SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =O, and —CN. In some embodiments, two $R^{33}$ on adjacent atoms may come together to form a $C_{3-8}$ carbocycle optionally substituted with one or more $C_{1-6}$ alkyl optionally substituted with one or more substituents independently selected from halogen, —$OR^{42}$, —$SR^{42}$, —$N(R^{42})_2$, —$C(O)R^{42}$, —$C(O)OR^{42}$, —$OC(O)R^{42}$, —$OC(O)N(R^{42})_2$, —$C(O)N(R^{42})_2$, —$N(R^{42})C(O)R^{42}$, —$N(R^{42})C(O)OR^{42}$, —$N(R^{42})C(O)N(R^{42})_2$, —$N(R^{42})S(O)_2(R^{42})$, —$S(O)R^{42}$, —$S(O)_2R^{42}$, —$S(O)_2N(R^{42})_2$, —$NO_2$, =S, =O, and —CN.

In some embodiments, for the compound or salt of Formula (III), (III-a), (III-b), (III-c), (III-d), or (III-e), two $R^{33}$ on adjacent atoms may come together to form a $C_{3-8}$ carbocycle optionally substituted with one or more substituents independently selected from halogen, —$OR^{42}$, —$N(R^{42})_2$, —$C(O)R^{42}$, —$C(O)OR^{42}$, —$NO_2$, =O, and —CN; and $C_{1-6}$ alkyl optionally substituted with one or more substituents independently selected from halogen, —$OR^{42}$, —$N(R^{42})_2$, —$C(O)R^{42}$, —$C(O)OR^{42}$, —$NO_2$, =O, and —CN. In some embodiments, two $R^{33}$ on adjacent atoms may come together to form a $C_{3-8}$ carbocycle optionally substituted with one or more substituents independently selected from halogen, —$OR^{42}$, —$N(R^{42})_2$, —$C(O)R^{42}$, —$C(O)OR^{42}$, —$NO_2$, =O, and —CN. In some embodiments, two $R^{33}$ on adjacent atoms may come together to form a $C_{3-8}$ carbocycle optionally substituted with one or more $C_{1-6}$ alkyl optionally substituted with one or more substituents independently selected from halogen, —$OR^{42}$, —$N(R^{42})_2$, —$C(O)R^{42}$, —$C(O)OR^{42}$, —$NO_2$, =O, and —CN.

In some embodiments, for the compound or salt of Formula (III), (III-a), (III-b), (III-c), (III-d), or (III-e), two $R^{33}$ on adjacent atoms may come together to form a 4- to 6-membered heterocycle, each of which is optionally substituted with one or more substituents independently selected from halogen, —$OR^{42}$, —$N(R^{42})_2$, —$C(O)R^{42}$, —$NO_2$, —CN; and $C_{1-3}$ alkyl optionally substituted with one or more substituents independently selected from halogen, —$OR^{42}$, —$N(R^{42})_2$, —$C(O)R^{42}$, —$NO_2$, and —CN; and each $R^{42}$ is independently selected from hydrogen, $C_{1-3}$ alkyl, and $C_{1-3}$ haloalkyl.

In some embodiments, for the compound or salt of Formula (III), (III-a), (III-b), (III-c), (III-d), or (III-e), two $R^{33}$ on adjacent atoms may come together to form a $C_{3-8}$ carbocycle, each of which is optionally substituted with one or more substituents independently selected from halogen, —$OR^{42}$, —$N(R^{42})_2$, —$C(O)R^{42}$, —$NO_2$, —CN; and $C_{1-3}$ alkyl optionally substituted with one or more substituents independently selected from halogen, —$OR^{42}$, —$N(R^{42})_2$, —$C(O)R^{42}$, —$NO_2$, and —CN; and each $R^{42}$ is independently selected from hydrogen, $C_{1-3}$ alkyl, and $C_{1-3}$ haloalkyl.

In some embodiments, for the compound or salt of Formula (III), (III-a), (III-b), (III-c), (III-d), or (III-e), two $R^{33}$ on adjacent atoms may come together to form a 3- to 8-membered heterocycle, each of which is optionally substituted with one or more substituents independently selected from halogen, —$OR^{42}$, —$N(R^{42})_2$, —$C(O)R^{42}$, —$NO_2$, —CN; and $C_{1-3}$ alkyl optionally substituted with one or more substituents independently selected from halogen, —$OR^{42}$, —$N(R^{42})_2$, —$C(O)R^{42}$, —$NO_2$, and —CN; and each $R^{42}$ is independently selected from hydrogen, $C_{1-3}$ alkyl, and $C_{1-3}$ haloalkyl.

In some embodiments, for the compound or salt of Formula (III), (III-a), (III-b), (III-c), (III-d), or (III-e),

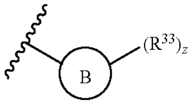

is selected from dihydrobenzofuranylene, benzofuranylene, and benzdioxazolylene, each of which is optionally substituted with one or more substituents independently selected from halogen, —$OR^{42}$, —$N(R^{42})_2$, —$C(O)R^{42}$, —$NO_2$, —CN; and $C_{1-3}$ alkyl optionally substituted with one or more substituents independently selected from halogen, —$OR^{42}$, —$N(R^{42})_2$, —$C(O)R^{42}$, —$NO_2$, and —CN; and each $R^{42}$ is independently selected from hydrogen, $C_{1-3}$ alkyl, and $C_{1-3}$ haloalkyl. In some embodiments,

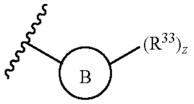

is selected from dihydrobenzofuranylene, benzofuranylene, and benzodioxolylene, each of which is optionally substituted with one or more substituents independently selected from halogen and unsubstituted $C_{1-3}$ alkyl. In some embodiments,

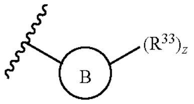

is selected from dihydrobenzofuranylene, benzofuranylene, and benzodioxolylene, each of which is optionally substituted with one or more substituents independently selected from fluoro and methyl.

In some embodiments, for the compound or salt of Formula (III), (III-a), (III-b), (III-c), (III-d), or (III-e),

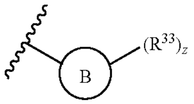

is selected from

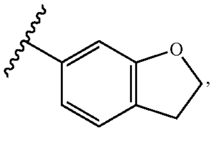,
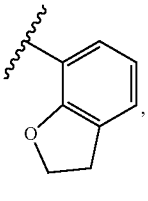,
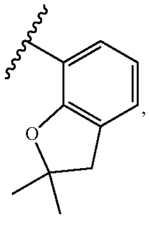,

-continued

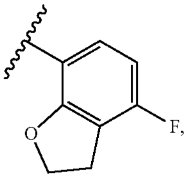,

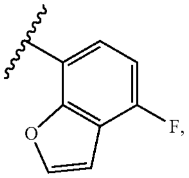, and

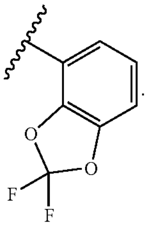

In some embodiments,

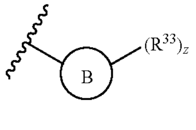

is selected from

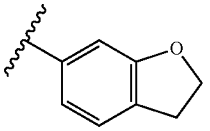

and

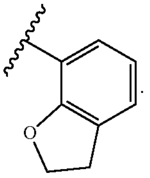

In some embodiments,

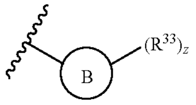

is selected from

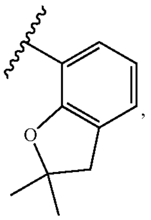

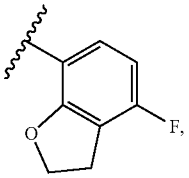

-continued

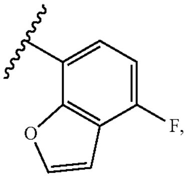

and

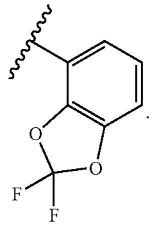

In some embodiments, for the compound or salt of Formula (III), (III-a), (III-b), (III-c), (III-d), or (III-e),

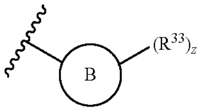

is selected from furopyridinyl, thienopyridinyl, indazolyl, pyrazolo[4,3-b]pyridinyl, imidazo[1,2-a]pyridinyl, imidazo[1,2-a]pyrazinyl, and pyrazolo[1,5-a]pyridinyl, each of which is optionally substituted with one or more substituents independently selected from halogen, —$OR^{42}$, —$N(R^{42})_2$, —$C(O)R^{42}$, —$NO_2$, —CN; and $C_{1-3}$ alkyl optionally substituted with one or more substituents independently selected from halogen, —$OR^{42}$, —$N(R^{42})_2$, —$C(O)R^{42}$, —$NO_2$, and —CN; and each $R^{42}$ is independently selected from hydrogen, $C_{1-3}$ alkyl, and $C_{1-3}$ haloalkyl. In some embodiments,

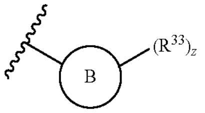

is selected from furopyridinyl, thienopyridinyl, indazolyl, pyrazolo[4,3-b]pyridinyl, imidazo[1,2-a]pyridinyl, imidazo[1,2-a]pyrazinyl, and pyrazolo[1,5-a]pyridinyl, each of which is optionally substituted with one or more substituents independently selected from halogen and unsubstituted $C_{1-3}$ alkyl. In some embodiments,

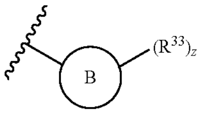

is selected from furopyridinyl, thienopyridinyl, indazolyl, pyrazolo[4,3-b]pyridinyl, imidazo[1,2-a]pyridinyl, imidazo[1,2-a]pyrazinyl, and pyrazolo[1,5-a]pyridinyl, each of which is optionally substituted with one or more substituents independently selected from fluoro and methyl. In some embodiments,

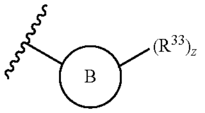

is selected from furopyridinyl, thienopyridinyl, indazolyl, pyrazolo[4,3-b]pyridinyl, imidazo[1,2-a]pyridinyl, imidazo[1,2-a]pyrazinyl, and pyrazolo[1,5-a]pyridinyl, each of which is optionally substituted with one substituent selected from methyl.

In some embodiments, for the compound or salt of Formula (III), (III-a), (III-b), (III-c), (III-d), or (III-e),

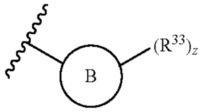

is selected from

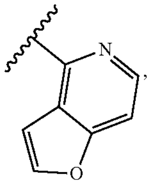,
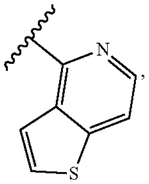,
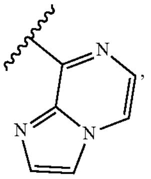,
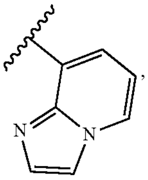,
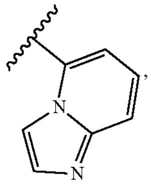,
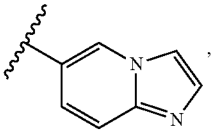,
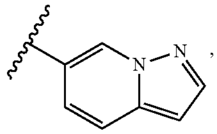,
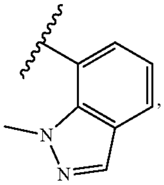, and
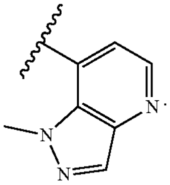.

In some embodiments, for the compound or salt of Formula (III), (III-a), (III-b), (III-c), (III-d), or (III-e), $R^{40}$ is hydrogen. In some embodiments, $R^{40}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{40}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{40}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (III), (III-a), (III-b), (III-c), (III-d), or (III-e), $R^{41}$ is hydrogen. In some embodiments, $R^{41}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{41}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{41}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (III), (III-a), (III-b), (III-c), (III-d), or (III-e), $R^{42}$ is hydrogen. In some embodiments, $R^{42}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{42}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{42}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (III), (III-a), (III-b), (III-c), (III-d), or (III-e), $R^{43}$ is hydrogen. In some embodiments, $R^{43}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{43}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{43}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.
In some embodiments, the compound of Formula (III) is
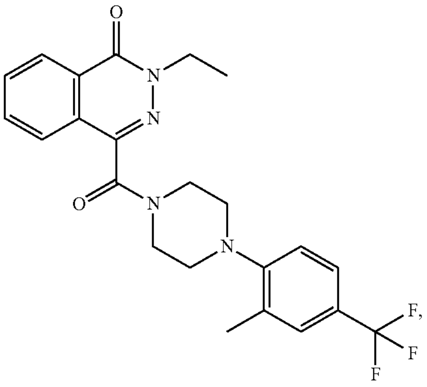
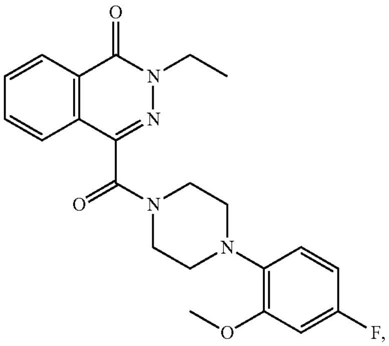
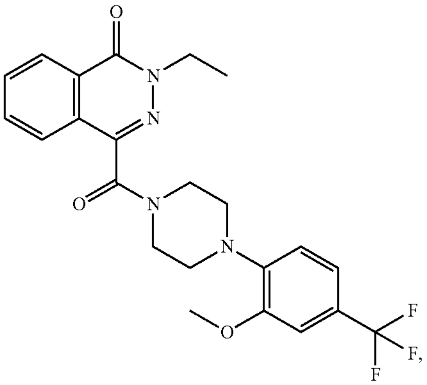
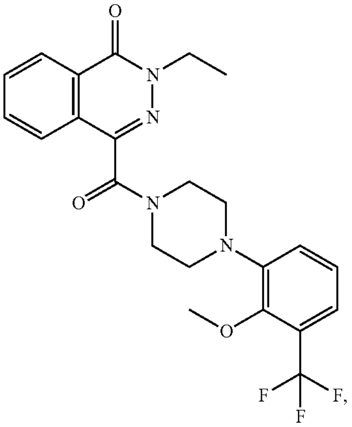
-continued
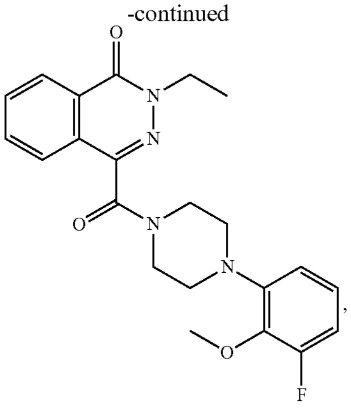
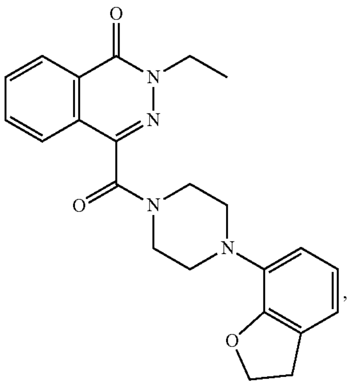
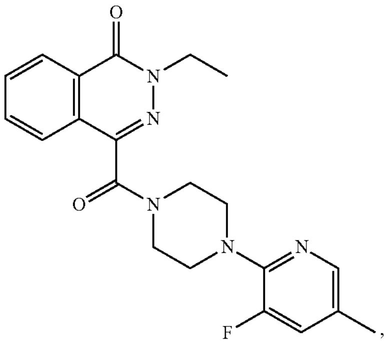
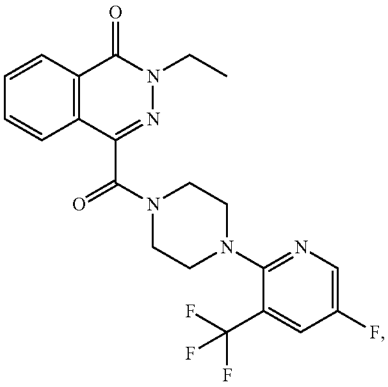

-continued
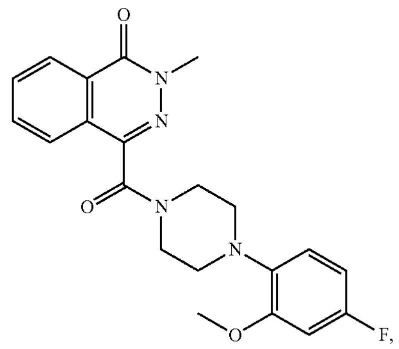
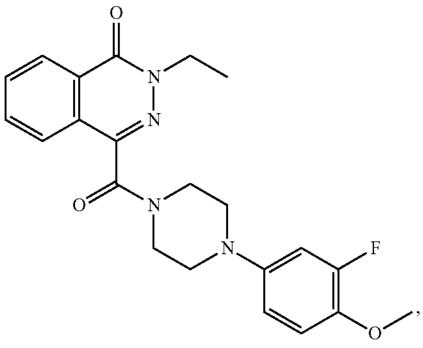
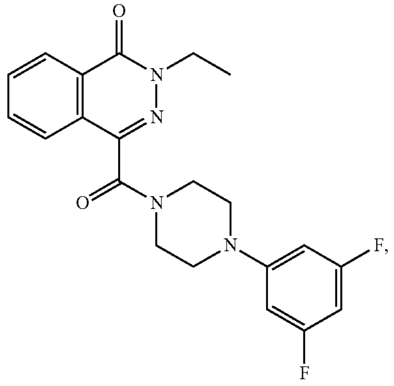
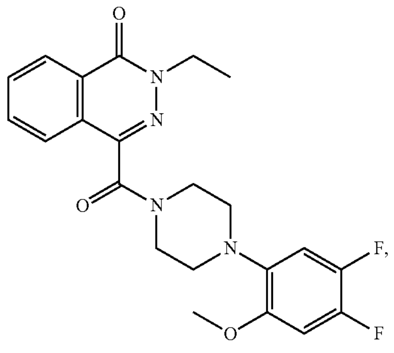
-continued
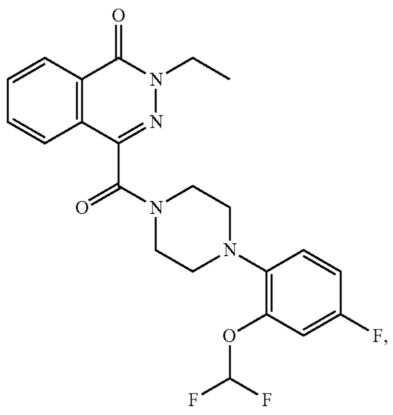
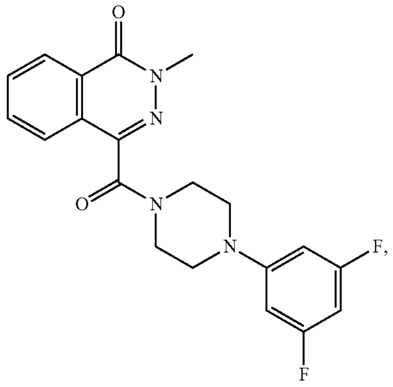
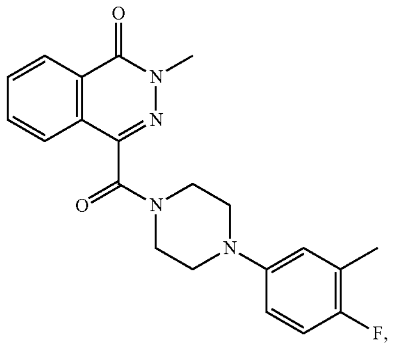
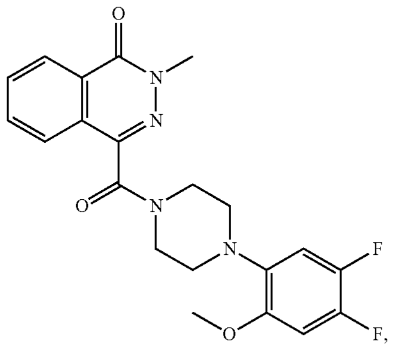

-continued
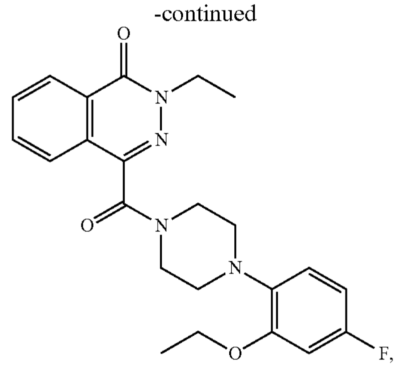
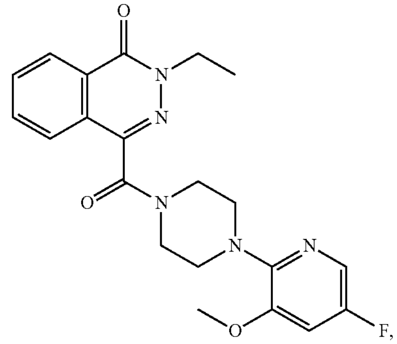
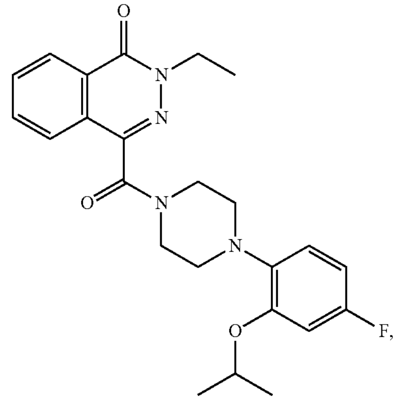
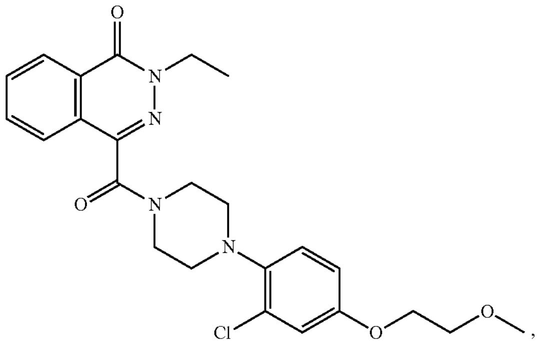
-continued
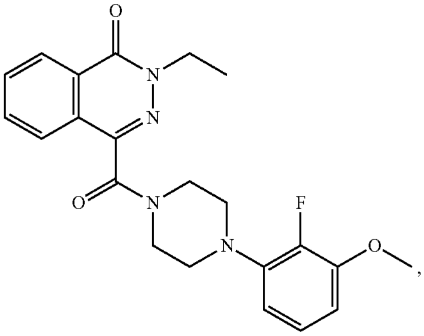
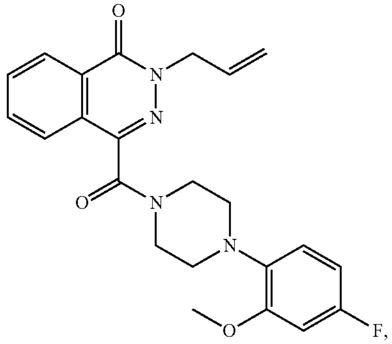
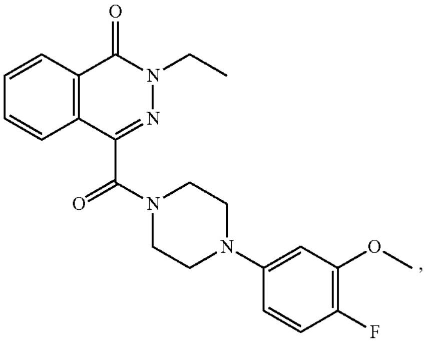
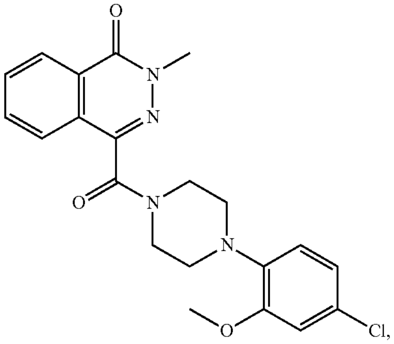
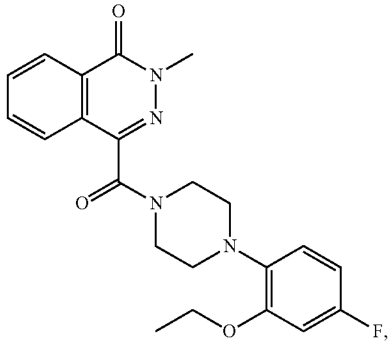

-continued
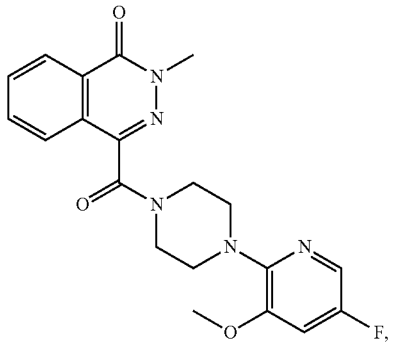
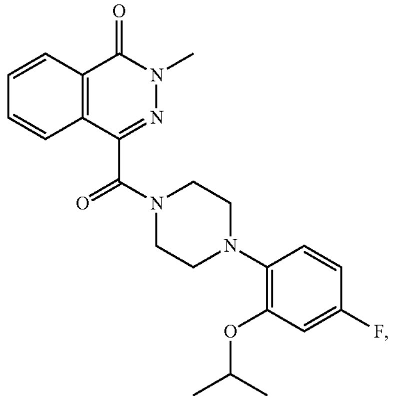
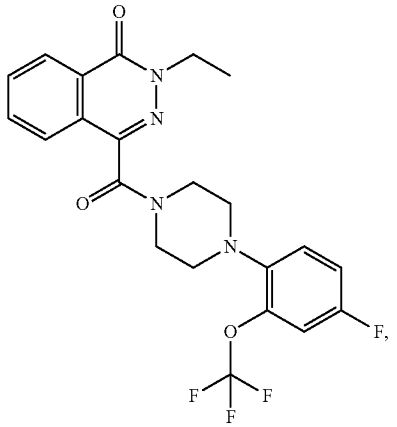
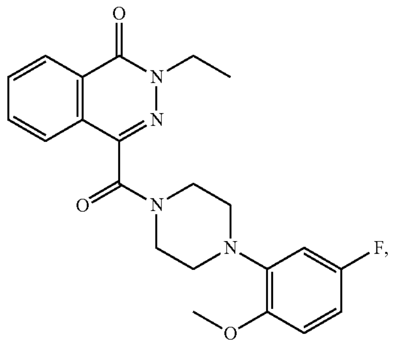
-continued
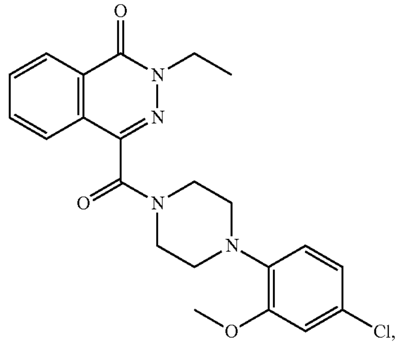
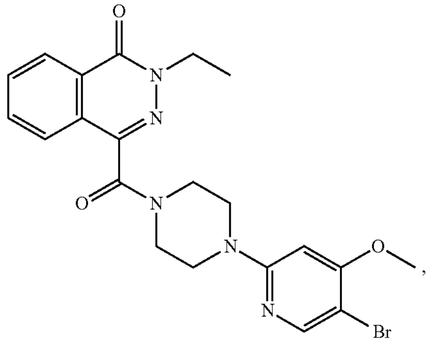
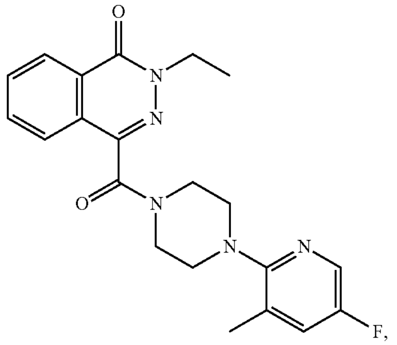
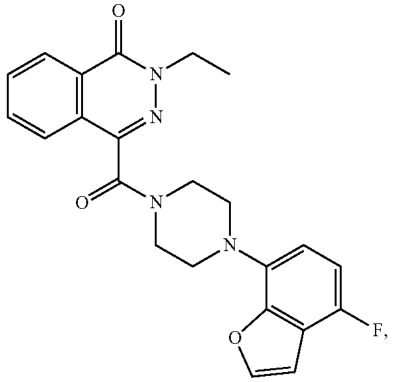

-continued
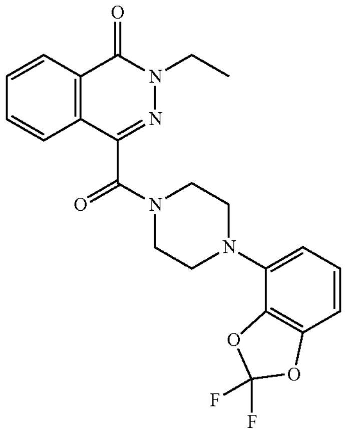
,
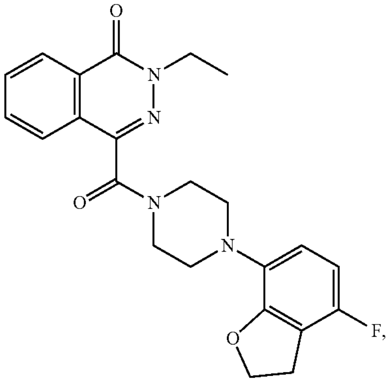
F,
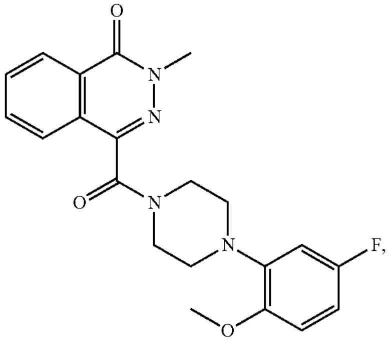
F,
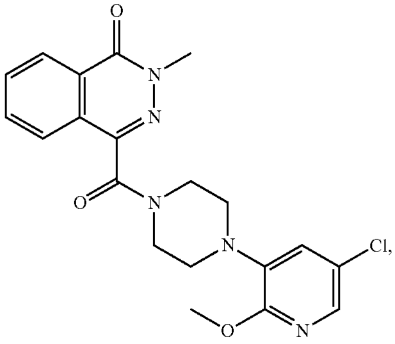
Cl,
-continued
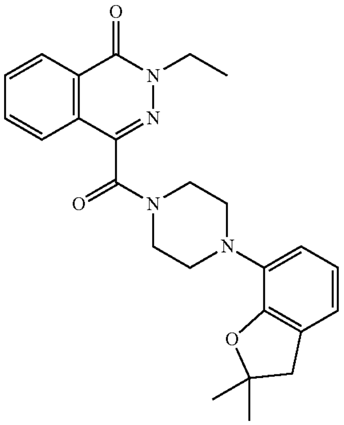
,
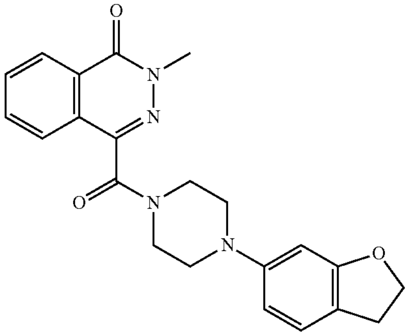
,
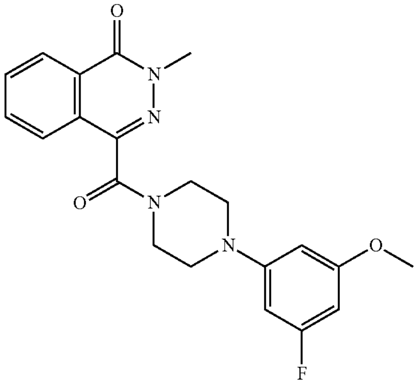
,
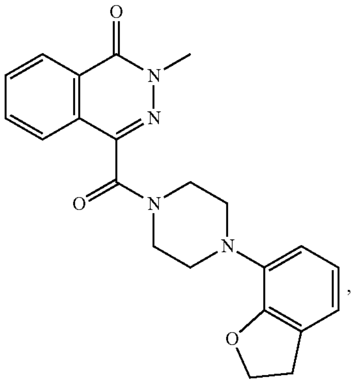
, -continued
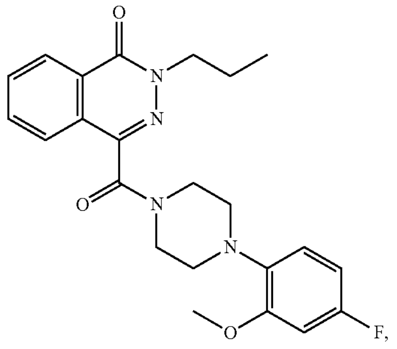
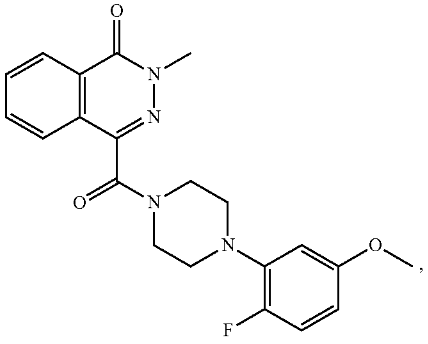
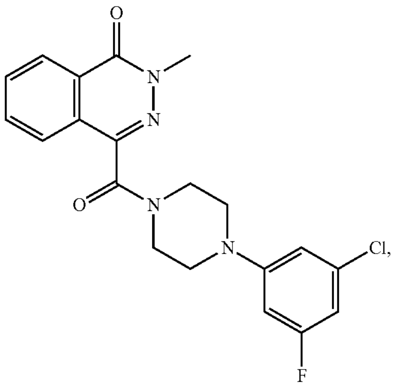
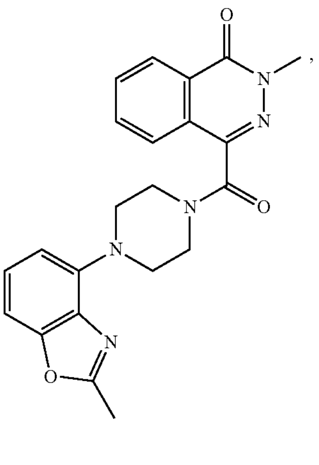
-continued
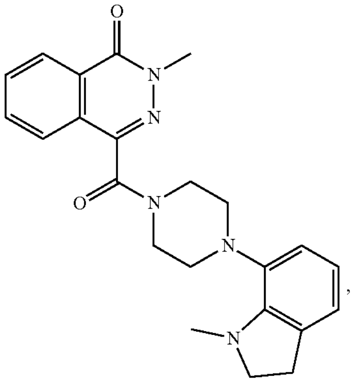
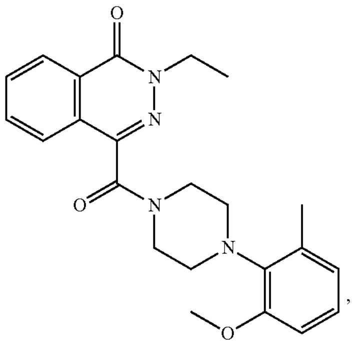
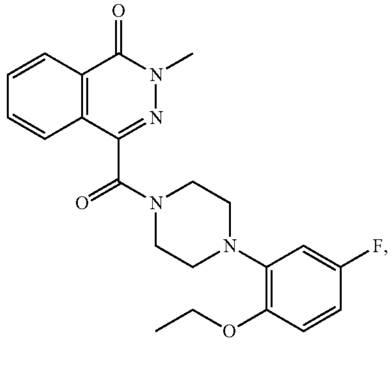
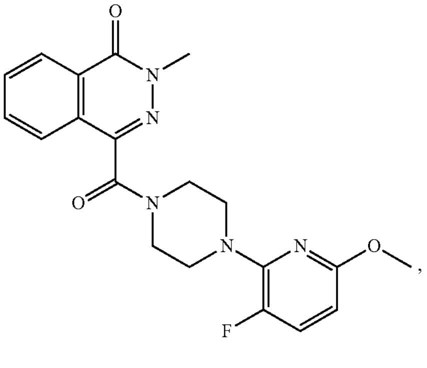

-continued
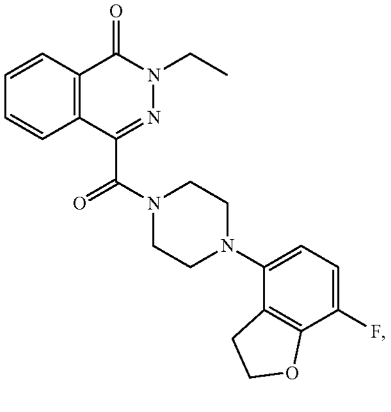
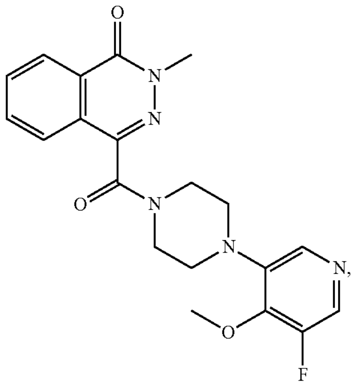
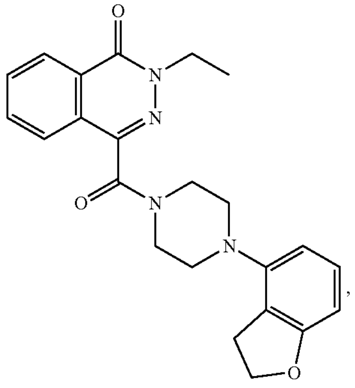
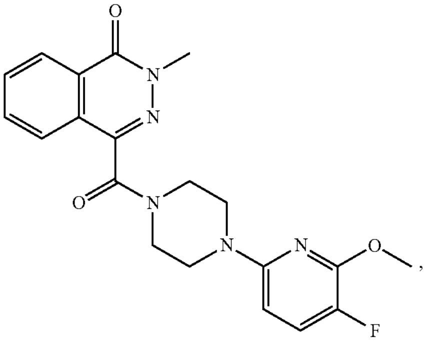
-continued
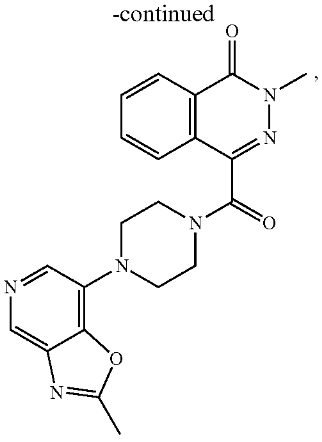
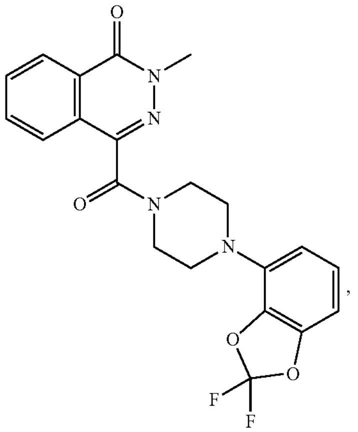
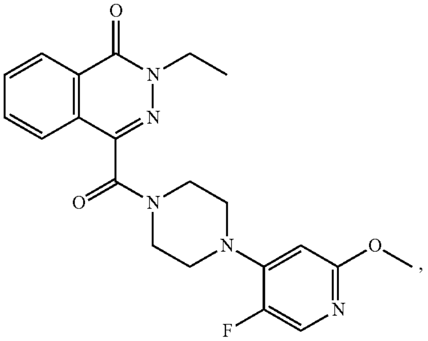
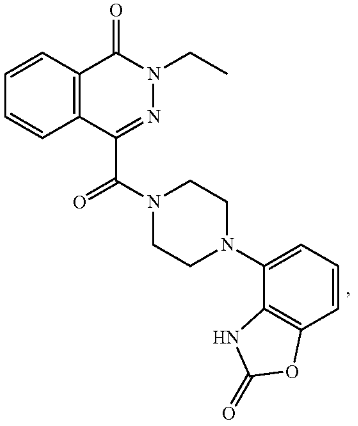

-continued
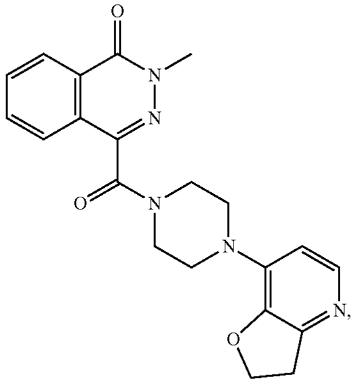
,
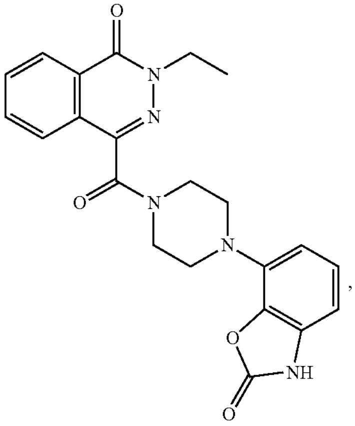
,
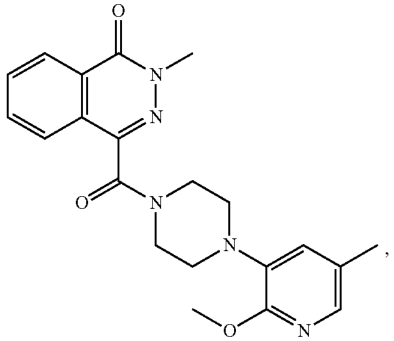
,
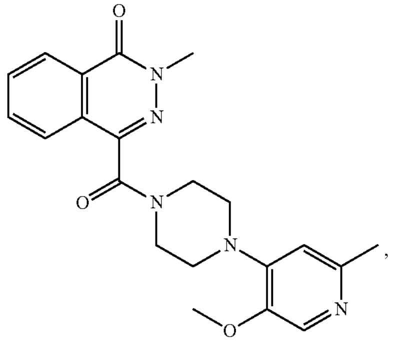
,
-continued
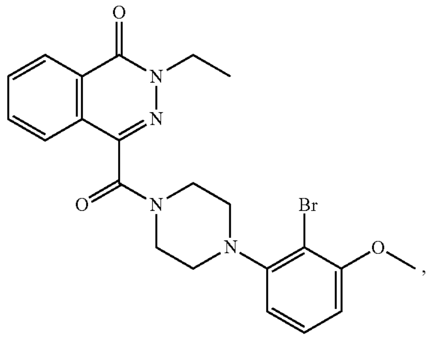
,
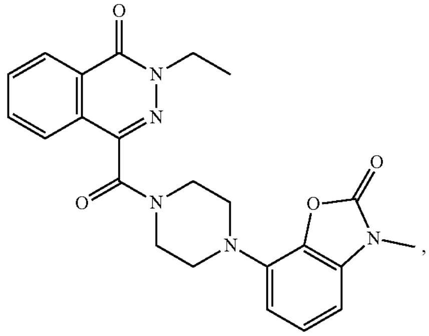
,
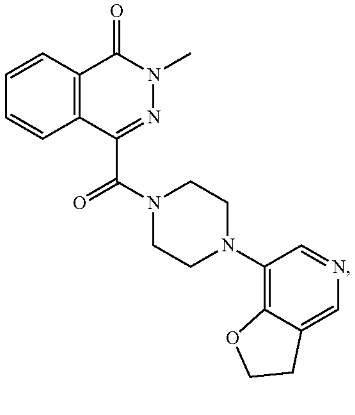
,
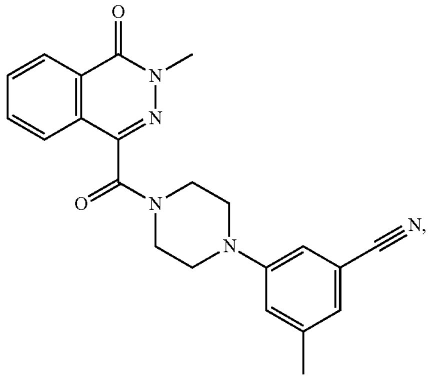
, -continued
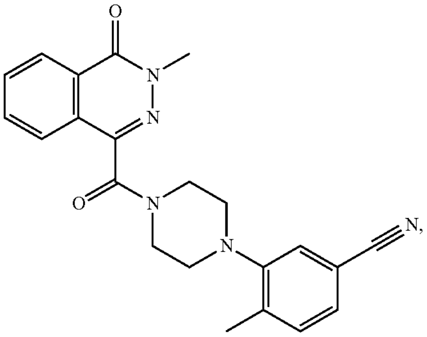
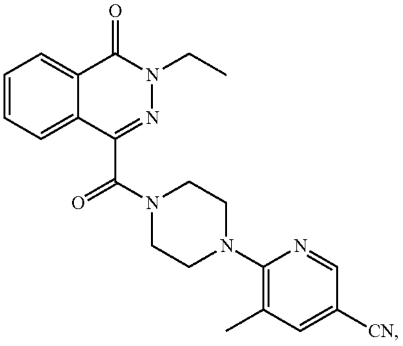
or
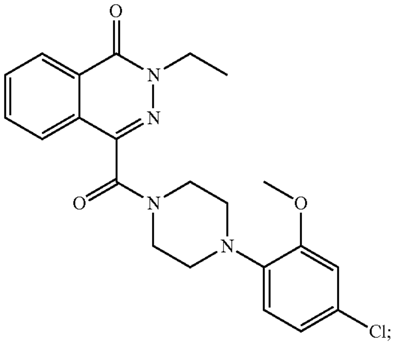 [SMILES: CCn1nc(C(=O)N2CCN(c3ccc(Cl)cc3OC)CC2)c2ccccc2c1=O]
or a salt of any one thereof.
In some embodiments, the compound of Formula (III) is
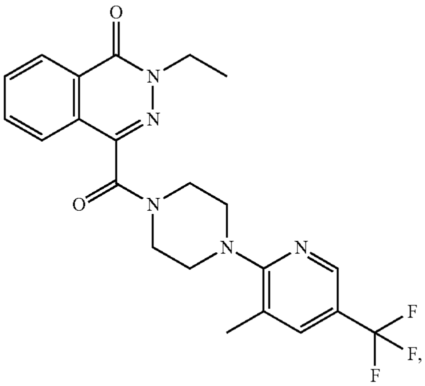
-continued
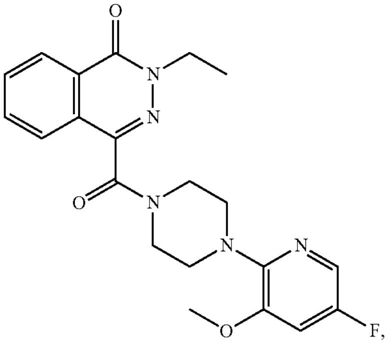
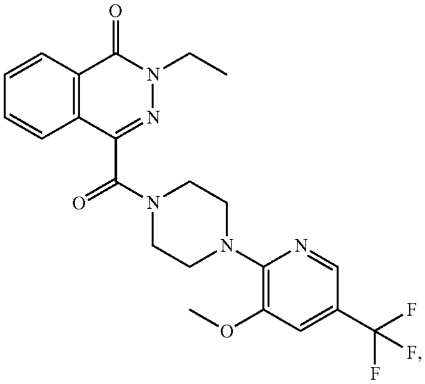
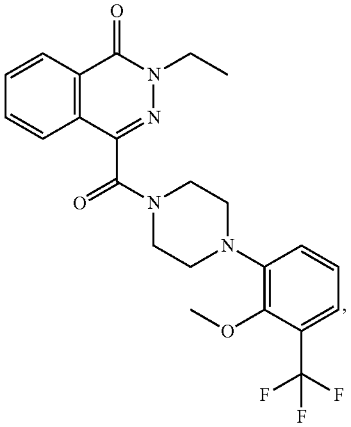
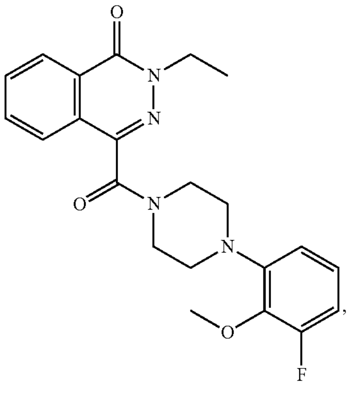

-continued
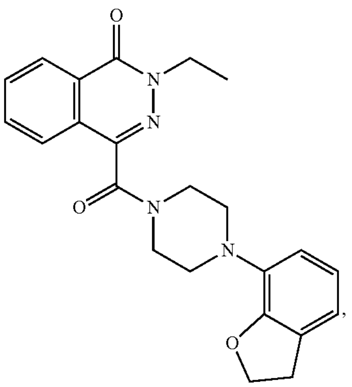
,
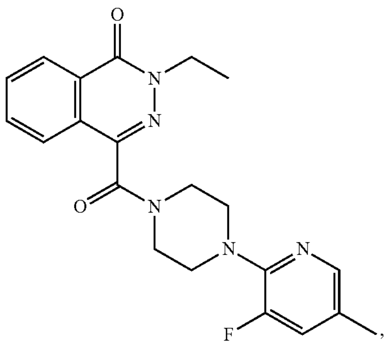
,
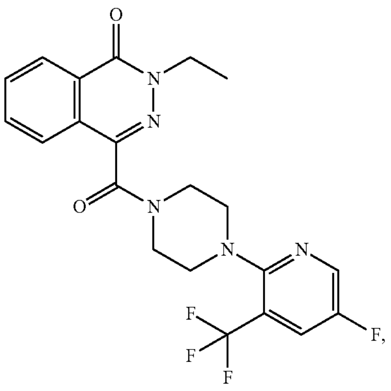
,
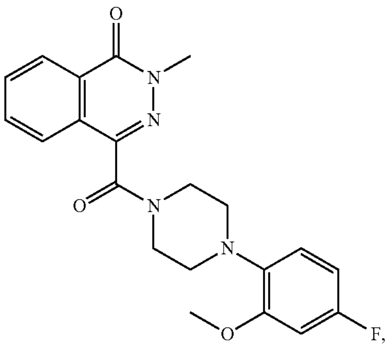
,
-continued
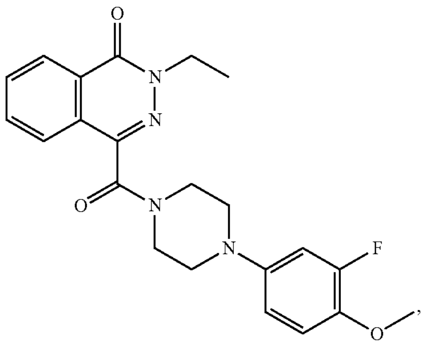
,
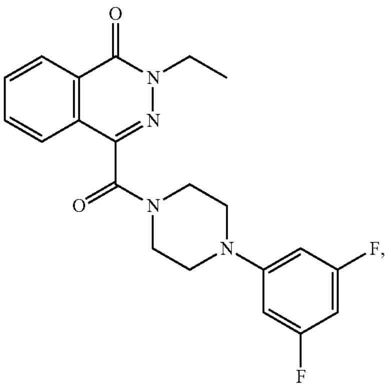
,
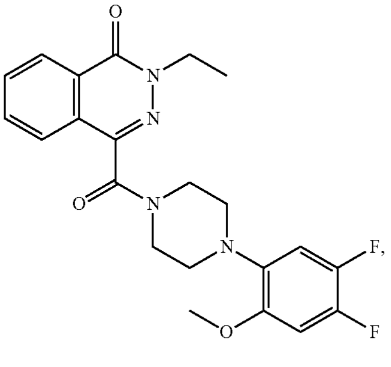
,
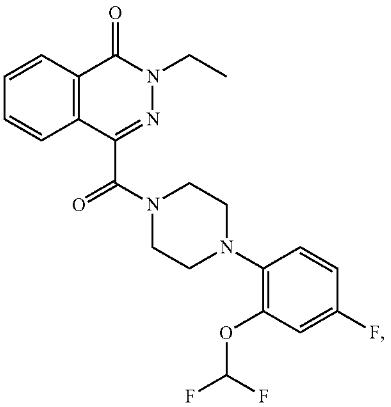
, -continued
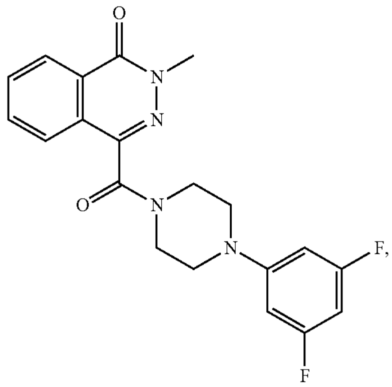
,
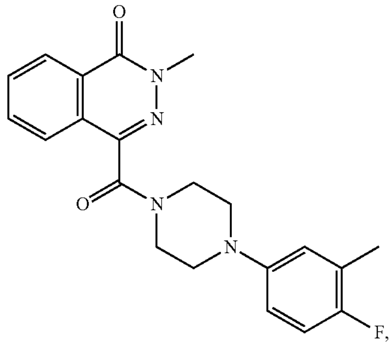
,
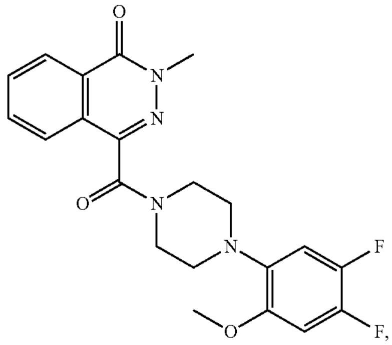
,
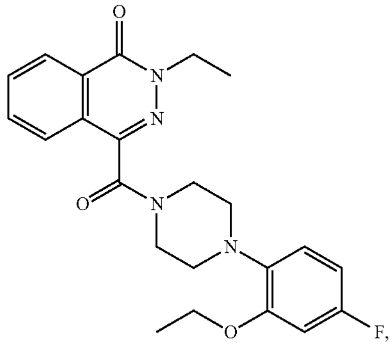
,
-continued
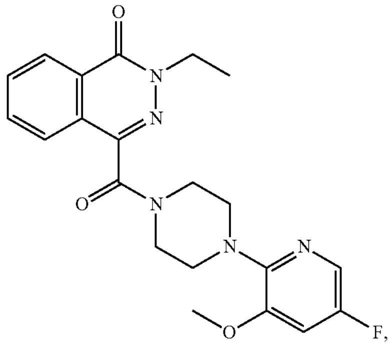
,
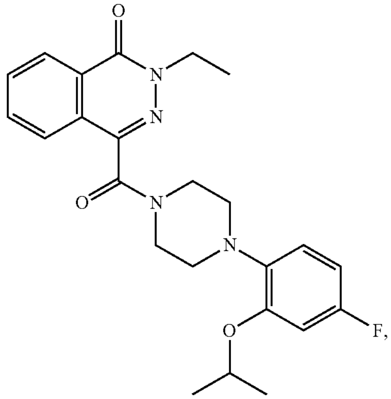
,
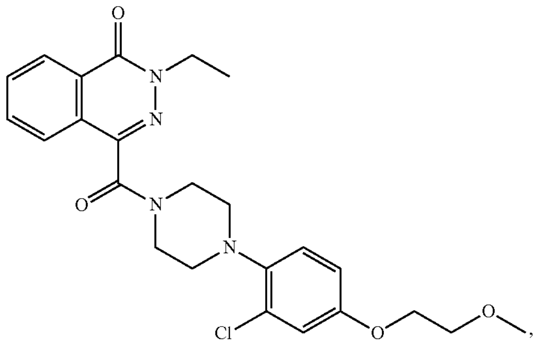
,
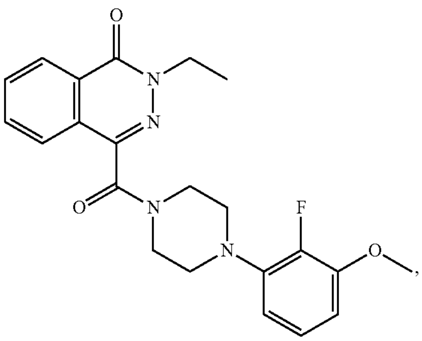
,

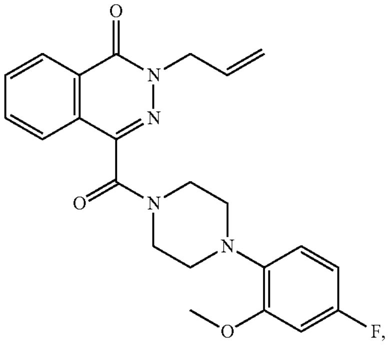
,
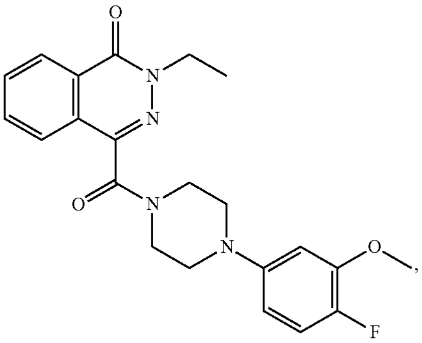
,
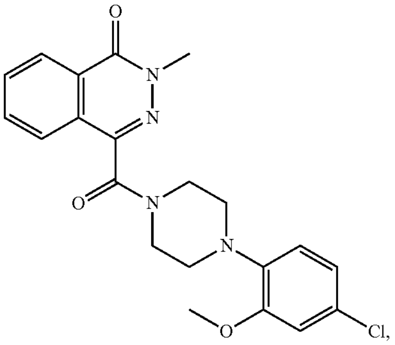
,
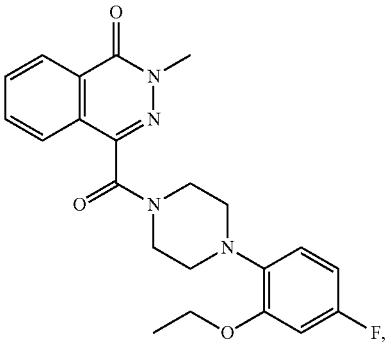
,
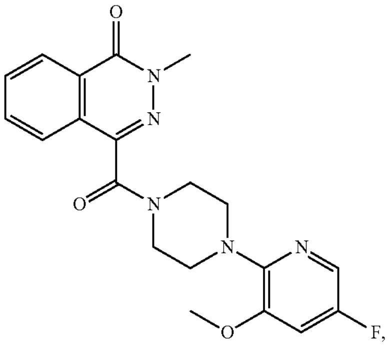
,
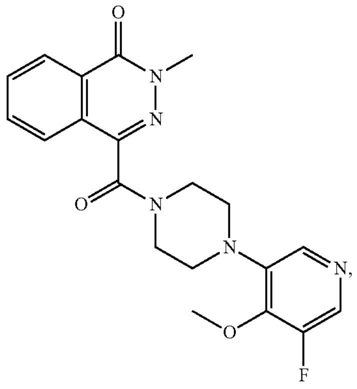
,
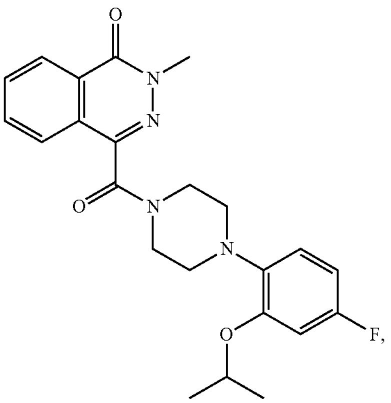
,
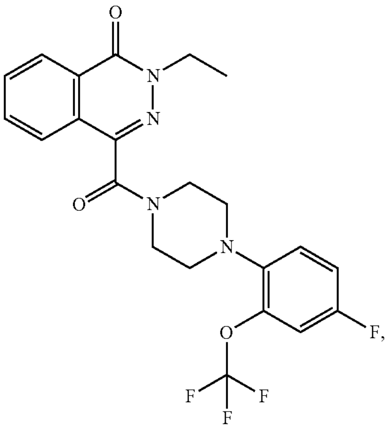
,
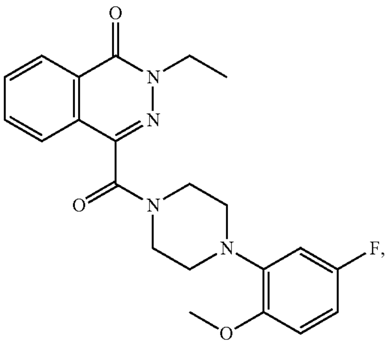
, -continued
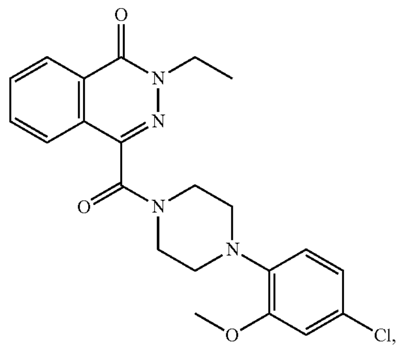
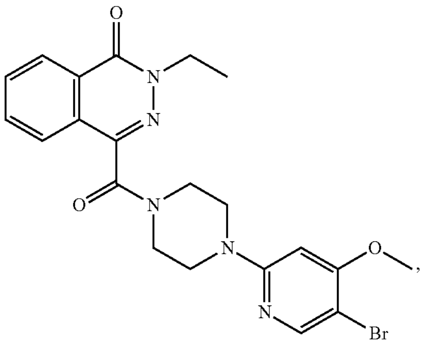
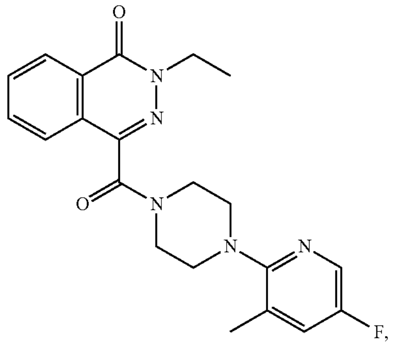
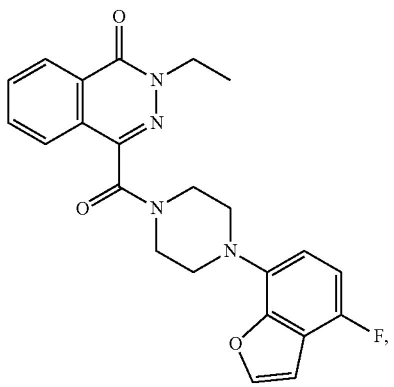
-continued
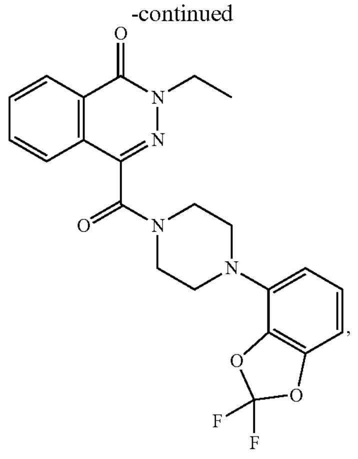
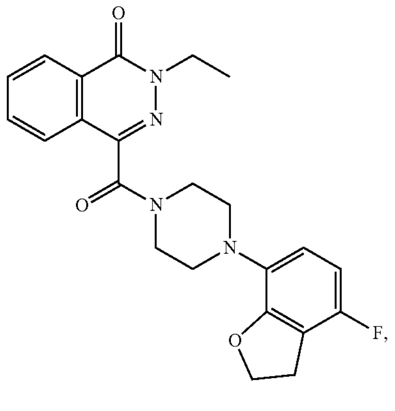
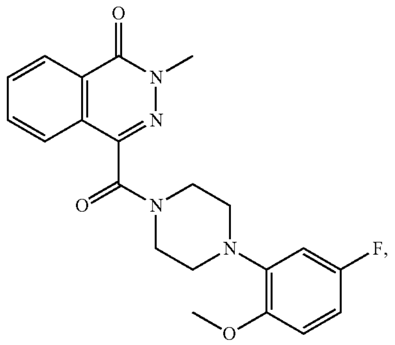
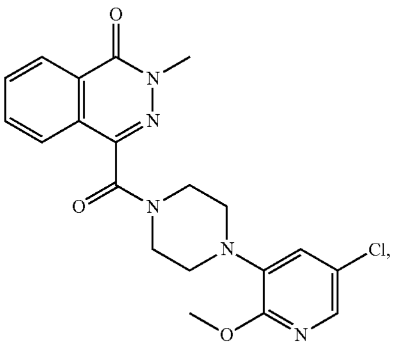

-continued
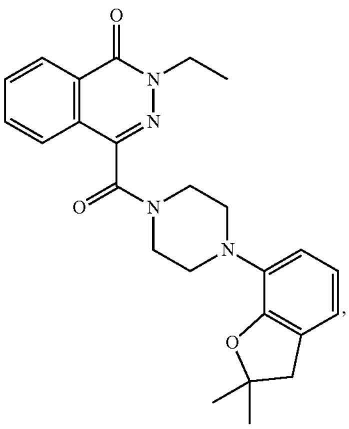
,
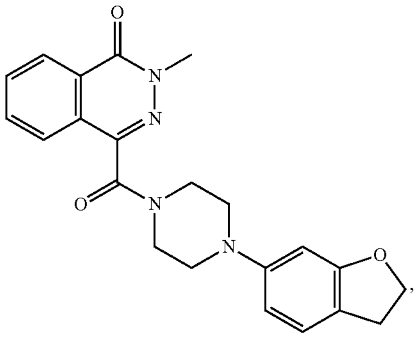
,
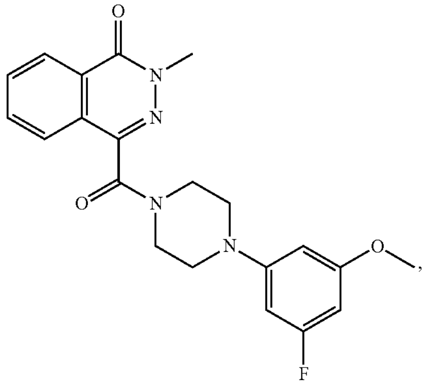
,
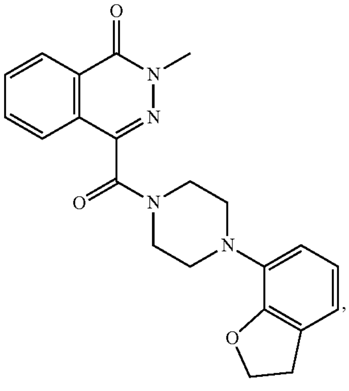
,
-continued
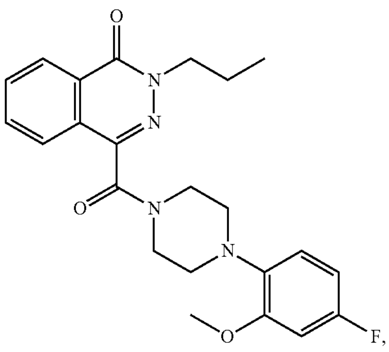
,
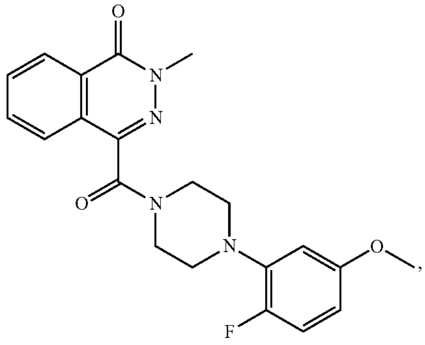
,
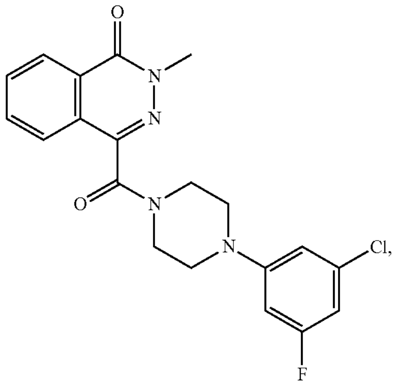
,
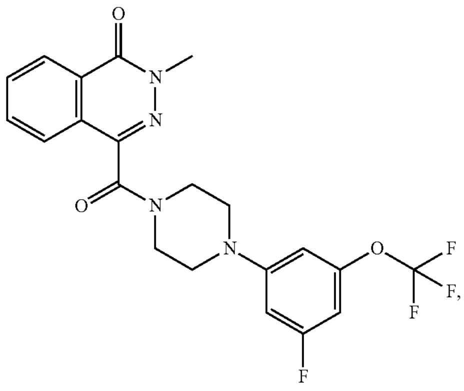
, -continued
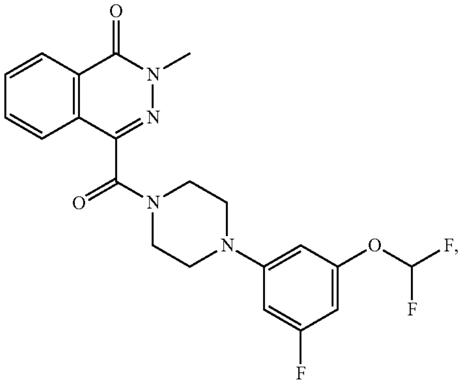
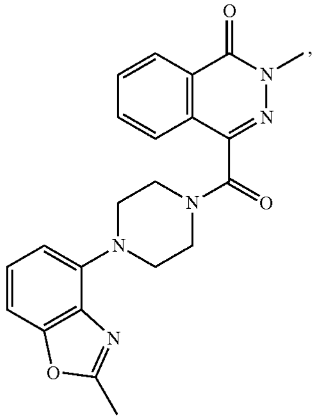
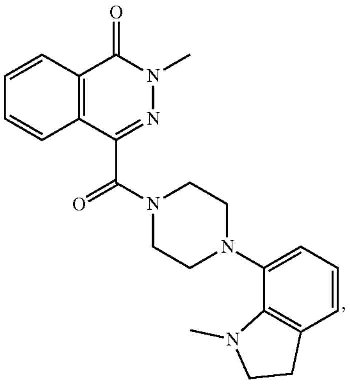
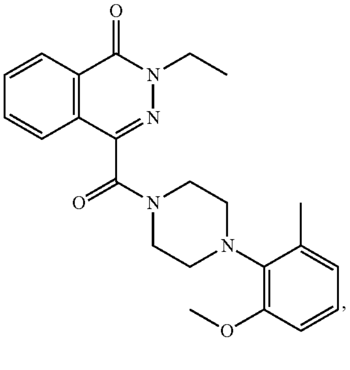
-continued
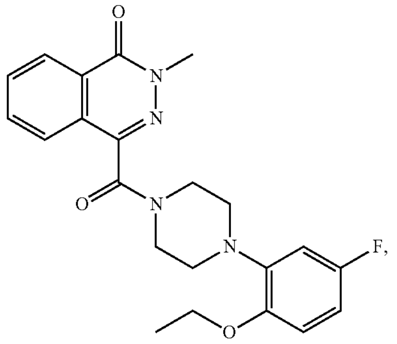
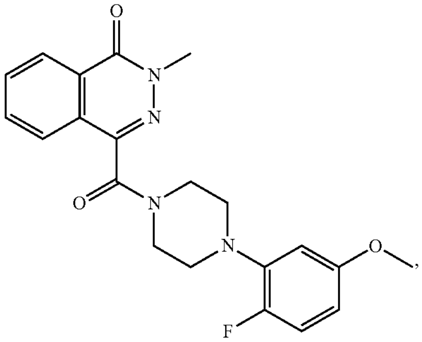
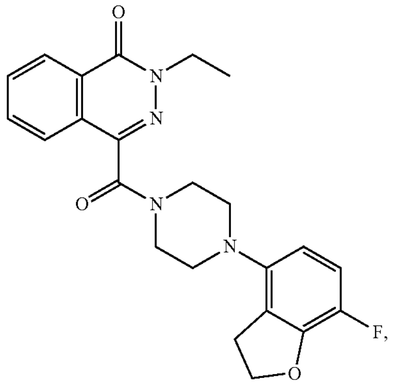
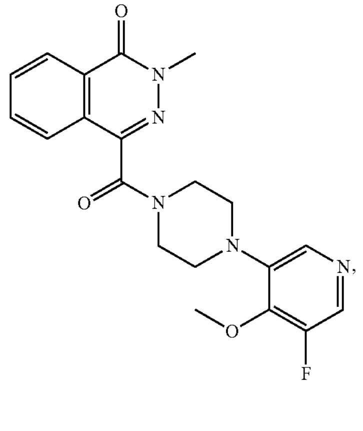

-continued
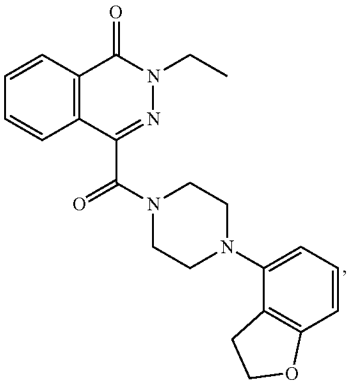
,
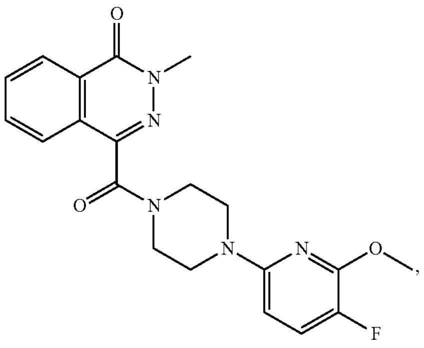
,
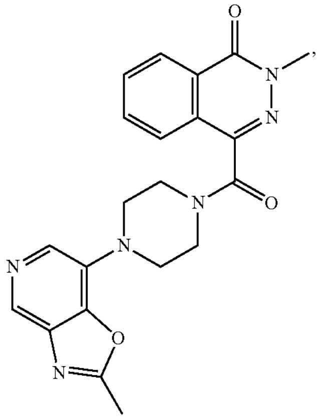
,
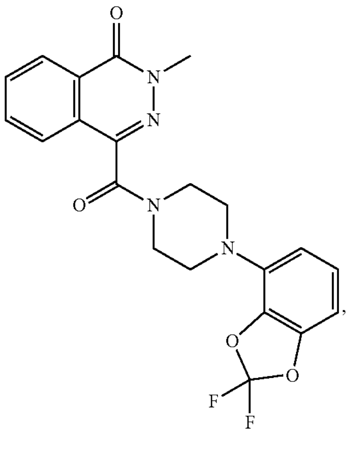
,
-continued
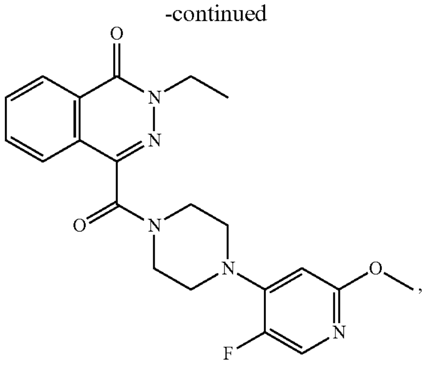
,
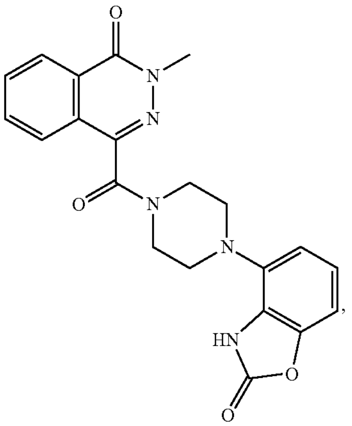
,
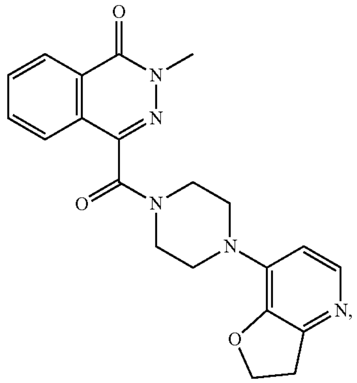
,
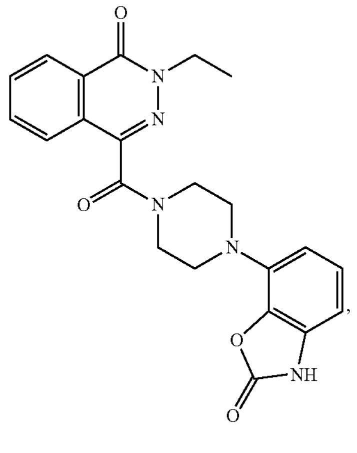
, -continued
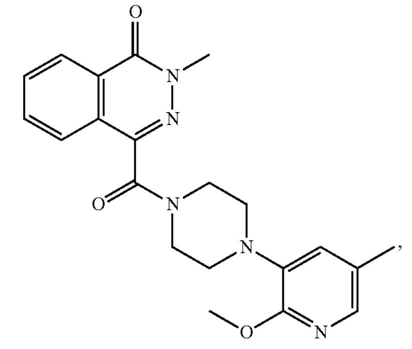
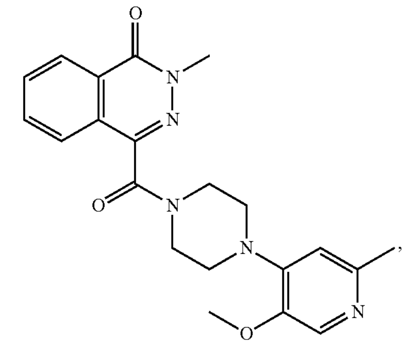
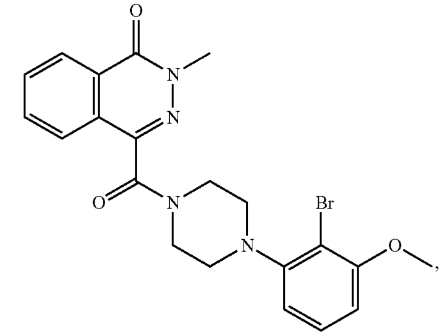
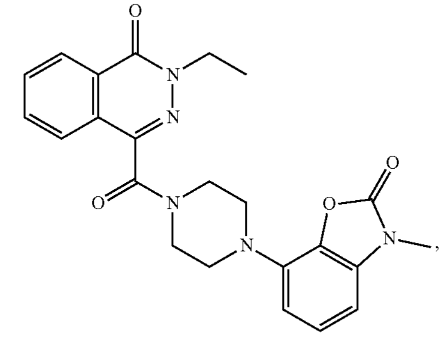
-continued
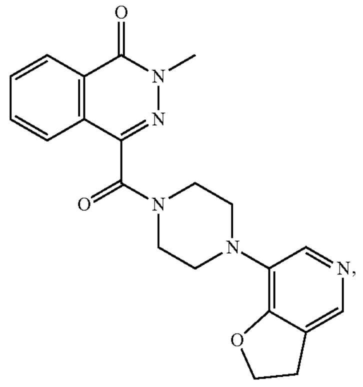
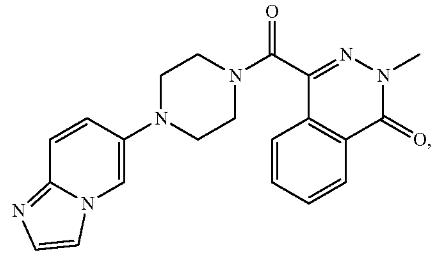
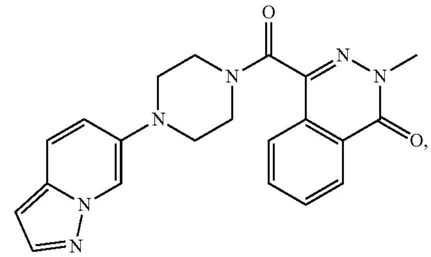
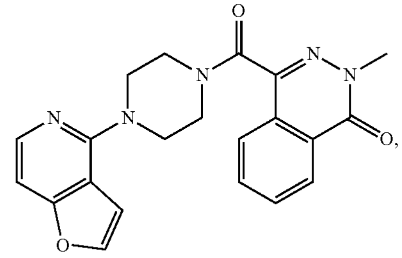
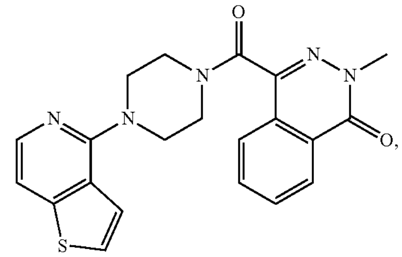
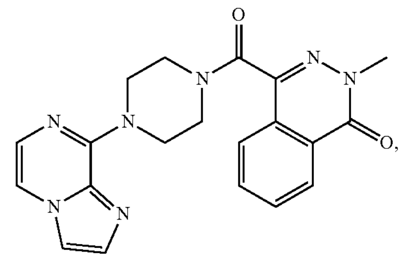

-continued
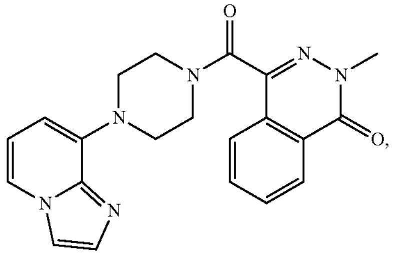
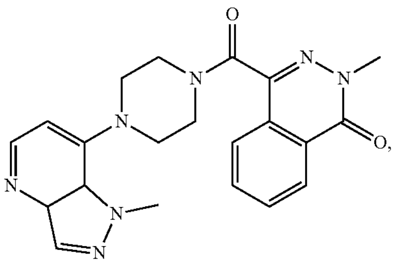
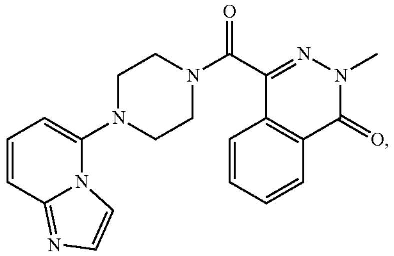
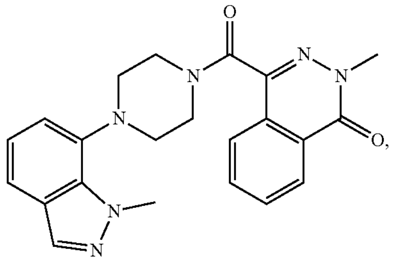
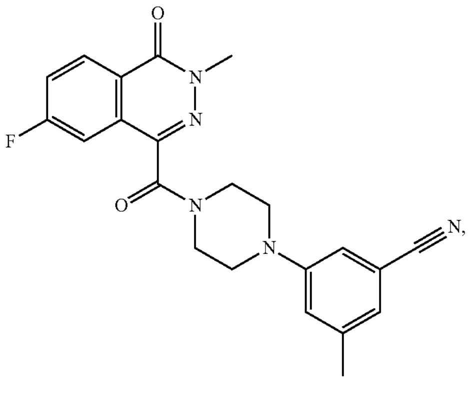
-continued
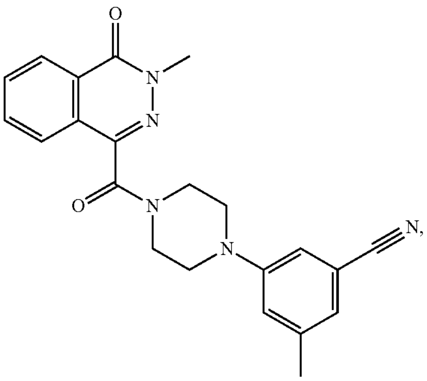
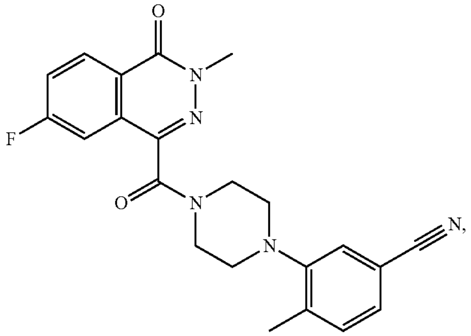
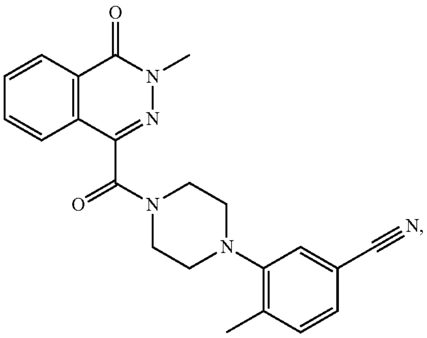
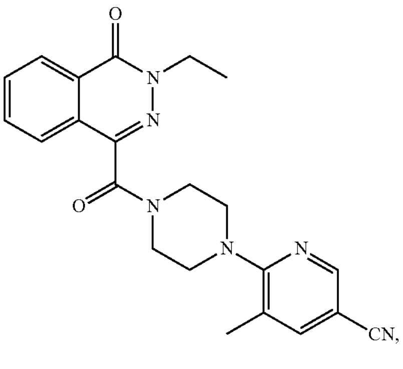
or -continued

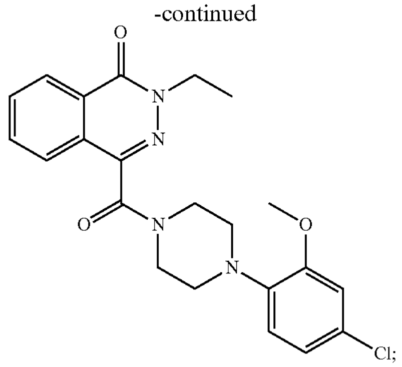

or a salt of any one thereof.

Compounds of Formula (IV).

In some aspects the present disclosure provides a compound represented by the structure of Formula (IV):

(IV)

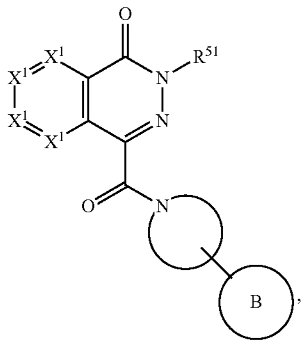

or a pharmaceutically acceptable salt wherein:

each $X^1$ is selected from $C(R^{50})$ and N, and at least one $X^1$ is N;

$R^{50}$ is independently selected at each occurrence from:

hydrogen, halogen, $-OR^{60}$, $-SR^{60}$, $-N(R^{60})_2$, $-C(O)R^{60}$, $-C(O)OR^{60}$, $-OC(O)R^{60}$, $-OC(O)N(R^{60})_2$, $-C(O)N(R^{60})_2$, $-N(R^{60})C(O)R^{60}$, $-N(R^{60})C(O)OR^{60}$, $-N(R^{60})C(O)N(R^{60})_2$, $-N(R^{60})S(O)_2(R^{60})$, $-S(O)R^{60}$, $-S(O)_2R^{60}$, $-S(O)_2N(R^{60})_2$, $-NO_2$, and $-CN$; and $C_{1-6}$ alkyl optionally substituted with one or more substituents independently selected from halogen, $-OR^{60}$, $-SR^{60}$, $-N(R^{60})_2$, $-C(O)R^{60}$, $-C(O)OR^{60}$, $-OC(O)R^{60}$, $-OC(O)N(R^{60})_2$, $-C(O)N(R^{60})_2$, $-N(R^{60})C(O)R^{60}$, $-N(R^{60})C(O)OR^{60}$, $-N(R^{60})C(O)N(R^{60})_2$, $-N(R^{60})S(O)_2(R^{60})$, $-S(O)R^{60}$, $-S(O)_2R^{60}$, $-S(O)_2N(R^{60})_2$, $-NO_2$, $=S$, $=O$, and $-CN$;

$R^{51}$ is independently selected from:

$C_{1-6}$ alkyl optionally substituted with one or more substituents independently selected from halogen, $-OR^{61}$, $-SR^{61}$, $-N(R^{61})_2$, $-C(O)R^{61}$, $-C(O)OR^{61}$, $-OC(O)R^{61}$, $-OC(O)N(R^{61})_2$, $-C(O)N(R^{61})_2$, $-N(R^{61})C(O)R^{61}$, $-N(R^{61})C(O)OR^{61}$, $-N(R^{61})C(O)N(R^{61})_2$, $-N(R^{61})S(O)_2(R^{61})$, $-S(O)R^{61}$, $-S(O)_2R^{61}$, $-S(O)_2N(R^{61})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{61}$, $-SR^{61}$, $-N(R^{61})_2$, $-C(O)R^{61}$, $-C(O)OR^{61}$, $-OC(O)R^{61}$, $-OC(O)N(R^{61})_2$, $-C(O)N(R^{61})_2$, $-N(R^{61})C(O)R^{61}$, $-N(R^{61})C(O)OR^{61}$, $-N(R^{61})C(O)N(R^{61})_2$, $-N(R^{61})S(O)_2(R^{61})$, $-S(O)R^{61}$, $-S(O)_2R^{61}$, $-S(O)_2N(R^{61})_2$, $-NO_2$, $=S$, $=O$, and $-CN$;

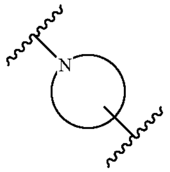

is 3- to 12-membered heterocyclene optionally substituted with one or more substituents independently selected from:

halogen, $-OR^{62}$, $-SR^{62}$, $-N(R^{62})_2$, $-C(O)R^{62}$, $-C(O)OR^{62}$, $-OC(O)R^{62}$, $-OC(O)N(R^{62})_2$, $-C(O)N(R^{62})_2$, $-N(R^{62})C(O)R^{62}$, $-N(R^{62})C(O)OR^{62}$, $-N(R^{62})C(O)N(R^{62})_2$, $-N(R^{62})S(O)_2(R^{62})$, $-S(O)R^{62}$, $-S(O)_2R^{62}$, $-S(O)_2N(R^{62})_2$, $-NO_2$, and $-CN$;

$C_{1-6}$ alkyl optionally substituted with one or more substituents independently selected from halogen, $-OR^{62}$, $-SR^{62}$, $-N(R^{62})_2$, $-C(O)R^{62}$, $-C(O)OR^{62}$, $-OC(O)R^{62}$, $-OC(O)N(R^{62})_2$, $-C(O)N(R^{62})_2$, $-N(R^{62})C(O)R^{62}$, $-N(R^{62})C(O)OR^{62}$, $-N(R^{62})C(O)N(R^{62})_2$, $-N(R^{62})S(O)_2(R^{62})$, $-S(O)R^{62}$, $-S(O)_2R^{62}$, $-S(O)_2N(R^{62})_2$, $-NO_2$, $=S$, $=O$, and $-CN$; and Ring B is selected from $C_{3-10}$ carbocycle and 3- to 10-membered heterocycle, any of which is optionally substituted with one or more substituents independently selected from:

halogen, $-OR^{63}$, $-SR^{63}$, $-N(R^{63})_2$, $-C(O)R^{63}$, $-C(O)OR^{63}$, $-OC(O)R^{63}$, $-OC(O)N(R^{63})_2$, $-C(O)N(R^{63})_2$, $-N(R^{63})C(O)R^{63}$, $-N(R^{63})C(O)OR^{63}$, $-N(R^{63})C(O)N(R^{63})_2$, $-N(R^{63})S(O)_2(R^{63})$, $-S(O)R^{63}$, $-S(O)_2R^{63}$, $-S(O)_2N(R^{63})_2$, $-NO_2$, and $-CN$; and $C_{1-6}$ alkyl optionally substituted with one or more substituents independently selected from halogen, $-OR^{63}$, $-SR^{63}$, $-N(R^{63})_2$, $-C(O)R^{63}$, $-C(O)OR^{63}$, $-OC(O)R^{63}$, $-OC(O)N(R^{63})_2$, $-C(O)N(R^{63})_2$, $-N(R^{63})C(O)R^{63}$, $-N(R^{63})C(O)OR^{63}$, $-N(R^{63})C(O)N(R^{63})_2$, $-N(R^{63})S(O)_2(R^{63})$, $-S(O)R^{63}$, $-S(O)_2R^{63}$, $-S(O)_2N(R^{63})_2$, $-NO_2$, $=S$, $=O$, and $-CN$;

$R^{60}$, $R^{61}$, $R^{62}$, and $R^{63}$ are independently selected at each occurrence from: hydrogen;

$C_{1-6}$ alkyl optionally substituted with one more substituents independently selected from halogen, $-O-C_{1-6}$ alkyl, $-O-C_{1-6}$ haloalkyl, $-NH_2$, $-NO_2$, $=O$, $-CN$, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, $-OH$, $-O-C_{1-6}$ alkyl, $-O-C_{1-6}$ haloalkyl, $-NH_2$, $-NO_2$, $=O$, and $-CN$; and $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound of Formula (IV), $X^1$ is $C(R^{50})$ and $R^{50}$ is selected from hydrogen, halogen, —$OR^{60}$, —$SR^{60}$, —$N(R^{60})_2$, —$C(O)R^{60}$, —$C(O)OR^{60}$, —$OC(O)R^{60}$, —$OC(O)N(R^{60})_2$, —$C(O)N(R^{60})_2$, —$N(R^{60})C(O)R^{60}$, —$N(R^{60})C(O)OR^{60}$, —$N(R^{60})C(O)N(R^{60})_2$, —$N(R^{60})S(O)_2(R^{60})$, —$S(O)R^{60}$, —$S(O)_2R^{60}$, —$S(O)_2N(R^{60})_2$, —$NO_2$, and —CN. In some embodiments, $X^1$ is $C(R^{50})$ and $R^{50}$ is selected from hydrogen, halogen, —$OR^{60}$, —$SR^{60}$, —$N(R^{60})_2$, —$C(O)R^{60}$, —$C(O)OR^{60}$, —$NO_2$, and —CN. In some embodiments, $X^1$ is $C(R^{50})$ and $R^{50}$ is hydrogen.

In some embodiments, Formula (IV) is represented by a structure selected from:

(IV-a)

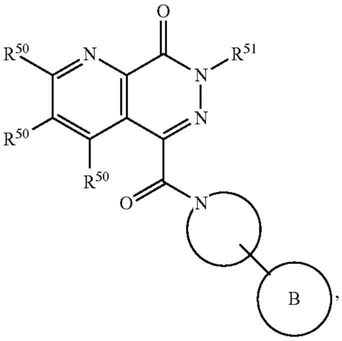

, (IV-b)

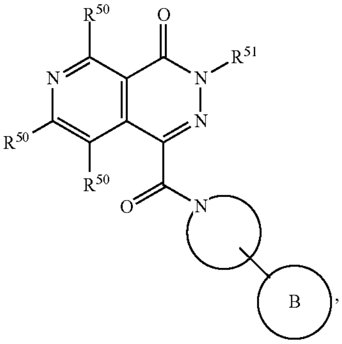

, (IV-c)

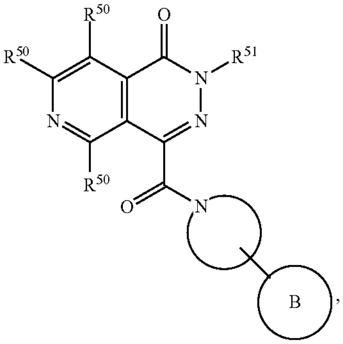

, and

-continued (IV-d)

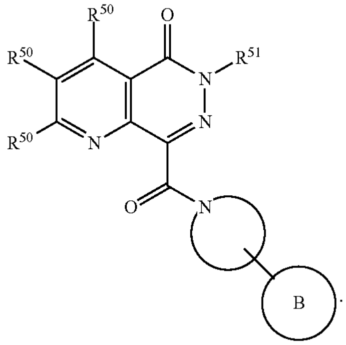

.

In some embodiments, a compound or salt of the disclosure is represented by Formula (IV-a):

(IV-a)

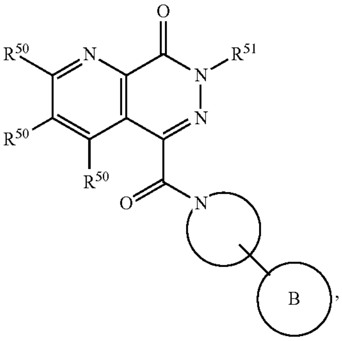

, or a pharmaceutically acceptable salt thereof, wherein $R^{50}$, $R^{51}$,

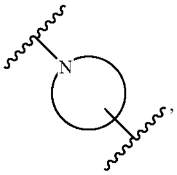

, and Ring B are as defined in Formula (IV).

In some embodiments, a compound or salt of the disclosure is represented by Formula (IV-b):

(IV-a)

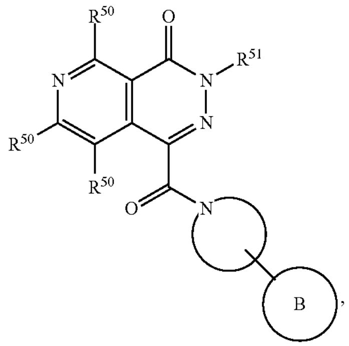

or a pharmaceutically acceptable salt thereof, wherein $R^{50}$, $R^{51}$,

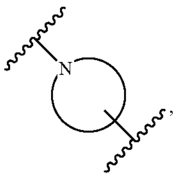

and Ring B are as defined in Formula (IV).

In some embodiments, a compound or salt of the disclosure is represented by Formula (IV-c):

(IV-c)

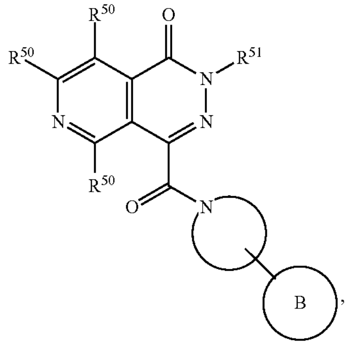

or a pharmaceutically acceptable salt thereof, wherein $R^{50}$, $R^{51}$,

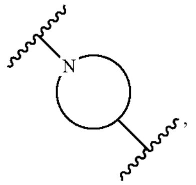

and Ring B are as defined in Formula (IV).

In some embodiments, a compound or salt of the disclosure is represented by Formula (IV-d):

(IV-d)

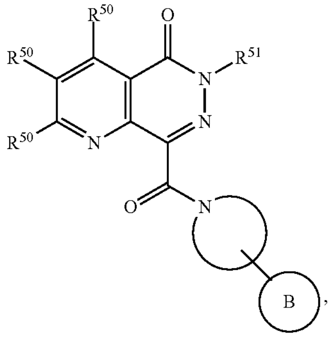

or a pharmaceutically acceptable salt thereof, wherein $R^{50}$, $R^{51}$,

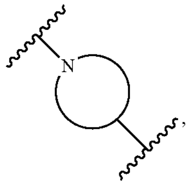

and Ring B are as defined in Formula (IV).

In some embodiments, for the compound or salt of Formula (IV), (IV-a), (IV-b), (IV-c), or (IV-d), $R^{51}$ is selected from $C_{1-6}$ alkyl optionally substituted with one or more substituents independently selected from halogen, —$OR^{61}$, —$SR^{61}$, —$N(R^{61})_2$, —$C(O)R^{61}$, —$C(O)OR^{61}$, —$OC(O)R^{61}$, —$OC(O)N(R^{61})_2$, —$C(O)N(R^{61})_2$, —$N(R^{61})C(O)R^{61}$, —$N(R^{61})C(O)OR^{61}$, —$N(R^{61})C(O)N(R^{61})_2$, —$N(R^{61})S(O)_2(R^{61})$, —$S(O)R^{61}$, —$S(O)_2R^{61}$, —$S(O)_2N(R^{61})_2$, —$NO_2$, =S, =O, and —CN; and $R^{61}$ is selected from hydrogen and $C_{1-3}$ alkyl. In some embodiments, $R^{51}$ is selected from $C_{1-6}$ alkyl optionally substituted with one or more substituents independently selected from halogen, —$OR^{61}$, —$SR^{61}$, —$N(R^{61})_2$, —$C(O)R^{61}$, —$C(O)OR^{61}$, —$NO_2$, =S, =O, and —CN; and $R^{61}$ is selected from hydrogen and $C_{1-3}$ alkyl. In some embodiments, $R^{51}$ is $C_{1-6}$ alkyl optionally substituted with one or more substituents independently selected from halogen, —$OR^{61}$, —$N(R^{61})_2$, —$C(O)R^{61}$, —$NO_2$, =S, =O, and —CN; and $R^{61}$ is selected from hydrogen and $C_{1-3}$ alkyl. In some embodiments, $R^{51}$ is unsubstituted $C_{1-3}$ alkyl.

In some embodiments, for the compound or salt of Formula (IV), (IV-a), (IV-b), (IV-c), or (IV-d), $R^{51}$ is selected from $C_{1-3}$ alkyl optionally substituted with one or more substituents independently selected from halogen, —$OR^{61}$, —$SR^{61}$, —$N(R^{61})_2$, —$C(O)R^{61}$, —$C(O)OR^{61}$, —$OC(O)R^{61}$, —$OC(O)N(R^{61})_2$, —$C(O)N(R^{61})_2$, —$N(R^{61})C(O)R^{61}$, —$N(R^{61})C(O)OR^{61}$, —$N(R^{61})C(O)N(R^{61})_2$, —$N(R^{61})S(O)_2(R^{61})$, —$S(O)R^{61}$, —$S(O)_2R^{61}$, —$S(O)_2N(R^{61})_2$, —$NO_2$, =S, =O, and —CN; and $R^{61}$ is selected from hydrogen and $C_{1-3}$ alkyl. In some embodiments, $R^{51}$ is selected from $C_{1-3}$ alkyl optionally substituted with one or more substituents independently selected from halogen, —$OR^{61}$, —$SR^{61}$, —$N(R^{61})_2$, —$C(O)R^{61}$, —$C(O)OR^{61}$, —$NO_2$, =S, =O, and —CN; and $R^{61}$ is selected from hydrogen and $C_{1-3}$ alkyl. In some embodiments, $R^{51}$ is $C_{1-3}$ alkyl optionally substituted with one or more substituents independently selected from halogen, —$OR^{61}$, —$N(R^{61})_2$, —$C(O)R^{61}$, —$NO_2$, =S, =O, and —CN; and $R^{61}$ is selected from hydrogen and $C_{1-3}$ alkyl.

In some embodiments, for the compound or salt of Formula (IV), (IV-a), (IV-b), (IV-c), or (IV-d), $R^{51}$ is selected from methyl, ethyl, propyl, and isopropyl, each of which is optionally substituted with one or more substituents independently selected from halogen, —$OR^{61}$, —$SR^{61}$, —$N(R^{61})_2$, —$C(O)R^{61}$, —$C(O)OR^{61}$, —$OC(O)R^{61}$, —$OC(O)N(R^{61})_2$, —$C(O)N(R^{61})_2$, —$N(R^{61})C(O)R^{61}$, —$N(R^{61})C(O)OR^{61}$, —$N(R^{61})C(O)N(R^{61})_2$, —$N(R^{61})S(O)_2(R^{61})$, —$S(O)R^{61}$, —$S(O)_2R^{61}$, —$S(O)_2N(R^{61})_2$, —$NO_2$, =S, =O, and —CN. In some embodiments, $R^{51}$ is selected from methyl, ethyl, propyl, and isopropyl, each of which is optionally substituted with one or more substituents independently selected from halogen, —$OR^{61}$, —$SR^{61}$, —$N(R^{61})_2$, —$C(O)R^{61}$, —$C(O)OR^{61}$, —$NO_2$, =S, =O, and —CN; and $R^{61}$ is selected from hydrogen and $C_{1-3}$ alkyl.

In some embodiments, for the compound or salt of Formula (IV), (IV-a), (IV-b), (IV-c), or (IV-d), the optionally substituted 3- to 12-membered heterocyclene of

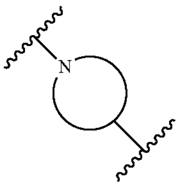

is selected from optionally substituted 3-membered heterocyclene, optionally substituted 4-membered heterocyclene, optionally substituted 5-membered heterocyclene, optionally substituted 6-membered heterocyclene, optionally substituted 7-membered heterocyclene, optionally substituted 8-membered heterocyclene, optionally substituted 9-membered heterocyclene, optionally substituted 10-membered heterocyclene, optionally substituted 11-membered heterocyclene, and optionally substituted 12-membered heterocyclene. In some embodiments, the optionally substituted 3- to 12-membered heterocyclene of

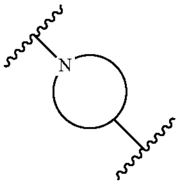

is selected from optionally substituted 3- to 4-membered heterocyclene, optionally substituted 3- to 5-membered heterocyclene, optionally substituted 3- to 6-membered heterocyclene, optionally substituted 3- to 7-membered heterocyclene, optionally substituted 3- to 8-membered heterocyclene, optionally substituted 3- to 9-membered heterocyclene, optionally substituted 3- to 10-membered heterocyclene, and optionally substituted 3- to 11-membered heterocyclene.

In some embodiments, for the compound or salt of Formula (IV), (IV-a), (IV-b), (IV-c), or (IV-d),

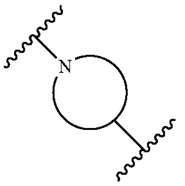

is 3- to 8-membered heterocyclene optionally substituted with one or more substituents independently selected from:

halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, and —CN;

$C_{1-6}$ alkyl optionally substituted with one or more substituents independently selected from halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, =S, =O, and —CN.

In some embodiments, for the compound or salt of Formula (IV), (IV-a), (IV-b), (IV-c), or (IV-d),

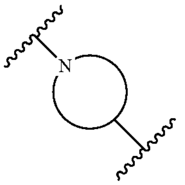

is 5- to 6-membered heterocyclene optionally substituted with one or more substituents independently selected from:

halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, and —CN;

$C_{1-6}$ alkyl optionally substituted with one or more substituents independently selected from halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, =S, =O, and —CN.

In some embodiments, for the compound or salt of Formula (IV), (IV-a), (IV-b), (IV-c), or (IV-d),

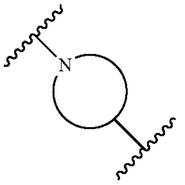

is 5- to 6-membered saturated heterocyclene optionally substituted with one or more substituents independently selected from:

halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, and —CN;

$C_{1-6}$ alkyl optionally substituted with one or more substituents independently selected from halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, =S, =O, and —CN.

In some embodiments, for the compound or salt of Formula (IV), (IV-a), (IV-b), (IV-c), or (IV-d),

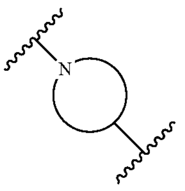

is selected from piperidinylene and piperazinylene, each of which is optionally substituted with one or more substituents independently selected from:

halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, and —CN;

$C_{1-6}$ alkyl optionally substituted with one or more substituents independently selected from halogen, —$OR^{62}$, —$SR^{62}$, —$N(R^{62})_2$, —$C(O)R^{62}$, —$C(O)OR^{62}$, —$OC(O)R^{62}$, —$OC(O)N(R^{62})_2$, —$C(O)N(R^{62})_2$, —$N(R^{62})C(O)R^{62}$, —$N(R^{62})C(O)OR^{62}$, —$N(R^{62})C(O)N(R^{62})_2$, —$N(R^{62})S(O)_2(R^{62})$, —$S(O)R^{62}$, —$S(O)_2R^{62}$, —$S(O)_2N(R^{62})_2$, —$NO_2$, =S, =O, and —CN.

In some embodiments, for the compound or salt of Formula (IV), (IV-a), (IV-b), (IV-c), or (IV-d),

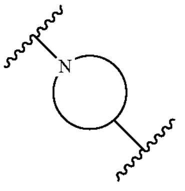

is selected from saturated 5- to 6-membered heterocyclene, each of which is optionally substituted with one or more substituents independently selected from halogen, —$OR^{62}$, —$N(R^{62})_2$, —$C(O)R^{62}$, —$C(O)OR^{62}$, —$C(O)N(R^{62})_2$, —$NO_2$, —CN; and $C_{1-6}$ alkyl optionally substituted with one or more substituents independently selected from halogen, —$OR^{62}$, —$N(R^{62})_2$, —$C(O)R^{62}$, —$C(O)OR^{62}$, —$C(O)N(R^{62})_2$, —$NO_2$, =S, =O, and —CN; and $R^{62}$ is selected from hydrogen and $C_{1-3}$ alkyl.

In some embodiments, for the compound or salt of Formula (IV), (IV-a), (IV-b), (IV-c), or (IV-d),

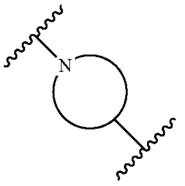

is selected from piperidinylene and piperazinylene, each of which is optionally substituted with one or more substituents independently selected from halogen, —$OR^{62}$, —$N(R^{62})_2$, —$C(O)R^{62}$, —$C(O)OR^{62}$, —$C(O)N(R^{62})_2$, —$NO_2$, —CN; and $C_{1-6}$ alkyl optionally substituted with one or more substituents independently selected from halogen, —$OR^{62}$, —$N(R^{62})_2$, —$C(O)R^{62}$, —$C(O)OR^{62}$, —$C(O)N(R^{62})_2$, —$NO_2$, =S, =O, and —CN; and $R^{62}$ is selected from hydrogen and $C_{1-3}$ alkyl.

In some embodiments, for the compound or salt of Formula (IV), (IV-a), (IV-b), (IV-c), or (IV-d),

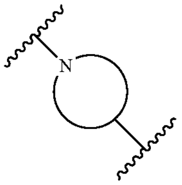 is 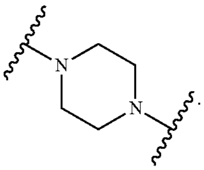.

In some embodiments,

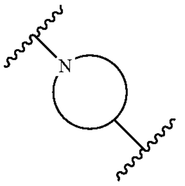

is unsubstituted piperazinylene.

In some embodiments, for the compound or salt of Formula (IV), (IV-a), (IV-b), (IV-c), or (IV-d), the optionally substituted $C_{3-10}$ carbocycle of Ring B is selected from optionally substituted $C_3$ carbocycle, optionally substituted $C_4$ carbocycle, optionally substituted $C_5$ carbocycle, optionally substituted $C_6$ carbocycle, optionally substituted $C_7$ carbocycle, optionally substituted $C_8$ carbocycle, optionally substituted $C_9$ carbocycle, and optionally substituted $C_{10}$ carbocycle. In some embodiments, the optionally substituted $C_{3-10}$ carbocycle of Ring B is selected from optionally substituted $C_{3-4}$ carbocycle, optionally substituted $C_{3-5}$ carbocycle, optionally substituted $C_{3-6}$ carbocycle, optionally substituted $C_{3-7}$ carbocycle, optionally substituted $C_{3-8}$ carbocycle, and optionally substituted $C_{3-9}$ carbocycle.

In some embodiments, for the compound or salt of Formula (IV), (IV-a), (IV-b), (IV-c), or (IV-d), the optionally substituted 3- to 10-membered heterocycle of Ring B is selected from optionally substituted 3-membered heterocycle, optionally substituted 4-membered heterocycle, optionally substituted 5-membered heterocycle, optionally substituted 6-membered heterocycle, optionally substituted 7-membered heterocycle, optionally substituted 8-membered heterocycle, optionally substituted 9-membered heterocycle, and optionally substituted 10-membered heterocycle. In some embodiments, the optionally substituted 3- to 10-membered heterocycle of Ring B is selected from optionally substituted 3- to 4-membered heterocycle, optionally substituted 3- to 5-membered heterocycle, optionally substituted 3- to 6-membered heterocycle, optionally substituted 3- to 7-membered heterocycle, optionally substituted 3- to 8-membered heterocycle, and optionally substituted 3- to 9-membered heterocycle.

In some embodiments, for the compound or salt of Formula (IV), (IV-a), (IV-b), (IV-c), or (IV-d), Ring B is selected from $C_{3-10}$ carbocycle optionally substituted with one or more substituents independently selected from:

halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN; and $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, =S, =O, and —CN.

In some embodiments, for the compound or salt of Formula (IV), (IV-a), (IV-b), (IV-c), or (IV-d), Ring B is selected from $C_{3-6}$ carbocycle optionally substituted with one or more substituents independently selected from:

halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN; and $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, =S, =O, and —CN.

In some embodiments, for the compound or salt of Formula (IV), (IV-a), (IV-b), (IV-c), or (IV-d), Ring B is phenyl optionally substituted with one or more substituents independently selected from:

halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN; and $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, =S, =O, and —CN.

In some embodiments, for the compound or salt of Formula (IV), (IV-a), (IV-b), (IV-c), or (IV-d), Ring B is phenyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN. In some embodiments, Ring B is phenyl optionally substituted with one or more substituents independently selected from: halogen, —$OR^{63}$, —$SR^{63}$, —$N(R^{63})_2$, —$C(O)R^{63}$, —$C(O)OR^{63}$, —$NO_2$, and —CN.

In some embodiments, for the compound or salt of Formula (IV), (IV-a), (IV-b), (IV-c), or (IV-d), Ring B is phenyl optionally substituted with one or more substituents independently selected from $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, =S, =O, and —CN. In some embodiments, Ring B is phenyl optionally substituted with one or more substituents independently selected from $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$NO_2$, =S, =O, and —CN. In some embodiments, Ring B is phenyl optionally substituted with one or more substituents independently selected from $C_{1-3}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$NO_2$, =S, =O, and —CN.

In some embodiments, for the compound or salt of Formula (IV), (IV-a), (IV-b), (IV-c), or (IV-d), Ring B is $C_{3-6}$ carbocycle optionally substituted with one or more substituents independently selected from halogen, —$OR^{63}$, —$N(R^{63})_2$, —$C(O)R^{63}$, —$NO_2$, —CN; and $C_{1-6}$ alkyl optionally substituted with one or more substituents independently selected from halogen, —$OR^{63}$, —$N(R^{63})_2$, —$C(O)R^{63}$, —$NO_2$, and —CN; and $R^{63}$ is selected from hydrogen and $C_{1-3}$ alkyl. In some embodiments, Ring B is phenyl optionally substituted with one or more substituents independently selected from halogen, —$OR^{63}$, —$N(R^{63})_2$, —$C(O)R^{63}$, —$NO_2$, —CN; and $C_{1-6}$ alkyl optionally substituted with one or more substituents independently selected from halogen, —$OR^{63}$, —$N(R^{63})_2$, —$C(O)R^{63}$, —$NO_2$, and —CN; and $R^{63}$ is selected from hydrogen and $C_{1-3}$ alkyl.

In some embodiments, for the compound or salt of Formula (IV), (IV-a), (IV-b), (IV-c), or (IV-d), Ring B is phenyl optionally substituted with one or more substituents independently selected from halogen and $C_{1-6}$ alkyl optionally substituted with one or more substituents independently selected from halogen and —$OR^{63}$; and $R^{63}$ is selected from hydrogen and $C_{1-3}$ alkyl. In some embodiments, wherein Ring B is phenyl optionally substituted with one or more substituents independently selected from halogen and $C_{1-3}$ alkyl optionally substituted with one or more substituents independently selected from halogen and —$OR^{63}$; and $R^{63}$ is selected from hydrogen and $C_{1-3}$ alkyl. In some embodiments, wherein Ring B is phenyl optionally substituted with one or more substituents independently selected from halogen, —O—$R^{63}$, and $C_{1-3}$ alkyl optionally substituted with one or more substituents independently selected from halogen and —$OR^{63}$; and each $R^{63}$ is independently selected from hydrogen and $C_{1-3}$ alkyl.

In some embodiments, for the compound or salt of Formula (IV), (IV-a), (IV-b), (IV-c), or (IV-d), Ring B is selected from 3- to 6-membered heterocycle optionally substituted with one or more substituents independently selected from:

halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN; and $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, ═S, ═O, and —CN.

In some embodiments, for the compound or salt of Formula (IV), (IV-a), (IV-b), (IV-c), or (IV-d), Ring B is pyridinyl optionally substituted with one or more substituents independently selected from:

halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN; and $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, ═S, ═O, and —CN.

In some embodiments, for the compound or salt of Formula (IV), (IV-a), (IV-b), (IV-c), or (IV-d), Ring B is pyridinyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, and —CN. In some embodiments, Ring B is pyridinyl optionally substituted with one or more substituents independently selected from: halogen, —$OR^{63}$, —$SR^{63}$, —$N(R^{63})_2$, —$C(O)R^{63}$, —$C(O)OR^{63}$, —$NO_2$, and —CN.

In some embodiments, for the compound or salt of Formula (IV), (IV-a), (IV-b), (IV-c), or (IV-d), Ring B is pyridinyl optionally substituted with one or more substituents independently selected from $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$OC(O)R^{63}$, —$OC(O)N(R^{63})_2$, —$C(O)N(R^{63})_2$, —$N(R^{63})C(O)R^{63}$, —$N(R^{63})C(O)OR^{63}$, —$N(R^{63})C(O)N(R^{63})_2$, —$N(R^{63})S(O)_2(R^{63})$, —$S(O)R^{63}$, —$S(O)_2R^{63}$, —$S(O)_2N(R^{63})_2$, —$NO_2$, ═S, ═O, and —CN. In some embodiments, Ring B is pyridinyl optionally substituted with one or more substituents independently selected from $C_{1-6}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$NO_2$, ═S, ═O, and —CN. In some embodiments, Ring B is pyridinyl optionally substituted with one or more substituents independently selected from $C_{1-3}$ alkyl optionally substituted with one or more substituents independently selected from halogen, —$OR^{63}$, —$SR^{63}$, —$N(R^{63})_2$, —$C(O)R^{63}$, —$C(O)OR^{63}$, —$NO_2$, ═S, ═O, and —CN.

In some embodiments, for the compound or salt of Formula (IV), (IV-a), (IV-b), (IV-c), or (IV-d), Ring B is 3- to 6-membered heterocycle optionally substituted with one or more substituents independently selected from halogen, —$OR^{63}$, —$N(R^{63})_2$, —$C(O)R^{63}$, —$NO_2$, —CN; and $C_{1-6}$ alkyl optionally substituted with one or more substituents independently selected from halogen, —$OR^{63}$, —$N(R^{63})_2$, —$C(O)R^{63}$, —$NO_2$, and —CN; and $R^{63}$ is selected from hydrogen and $C_{1-3}$ alkyl. In some embodiments, Ring B is pyridinyl optionally substituted with one or more substituents independently selected from halogen, —$OR^{63}$, —$N(R^{63})_2$, —$C(O)R^{63}$, —$NO_2$, —CN; and $C_{1-6}$ alkyl optionally substituted with one or more substituents independently selected from halogen, —$OR^{63}$, —$N(R^{63})_2$, —$C(O)R^{63}$, —$NO_2$, and —CN; and $R^{63}$ is selected from hydrogen and $C_{1-3}$ alkyl.

In some embodiments, for the compound or salt of Formula (IV), (IV-a), (IV-b), (IV-c), or (IV-d), Ring B is pyridinyl optionally substituted with one or more substituents independently selected from halogen and $C_{1-6}$ alkyl optionally substituted with one or more substituents independently selected from halogen and —$OR^{63}$; and $R^{63}$ is selected from hydrogen and $C_{1-3}$ alkyl. In some embodiments, wherein Ring B is pyridinyl optionally substituted with one or more substituents independently selected from halogen and $C_{1-3}$ alkyl optionally substituted with one or more substituents independently selected from halogen and —$OR^{63}$; and $R^{63}$ is selected from hydrogen and $C_{1-3}$ alkyl. In some embodiments, wherein Ring B is pyridinyl optionally substituted with one or more substituents independently selected from halogen, —O—$R^{63}$, and $C_{1-3}$ alkyl optionally substituted with one or more substituents independently selected from halogen and —$OR^{63}$; and each $R^{63}$ is independently selected from hydrogen and $C_{1-3}$ alkyl.

In some embodiments, for the compound or salt of Formula (IV), (IV-a), (IV-b), (IV-c), or (IV-d), Ring B is selected from

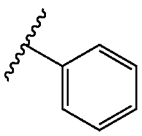

and

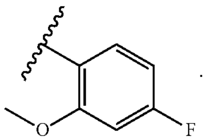

.

In some embodiments, for the compound or salt of Formula (IV), (IV-a), (IV-b), (IV-c), or (IV-d), Ring B is selected from

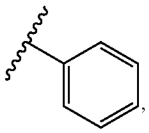

,

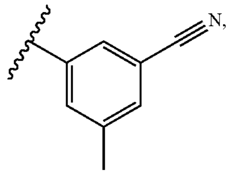

-continued

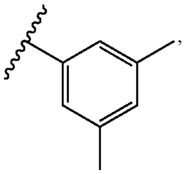,
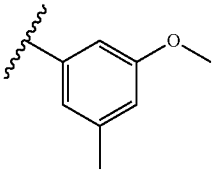,
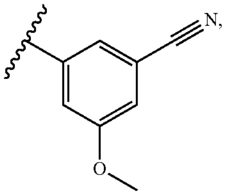
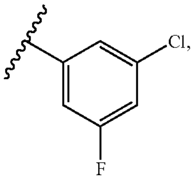
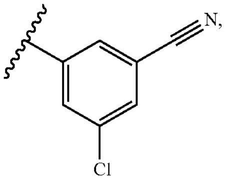
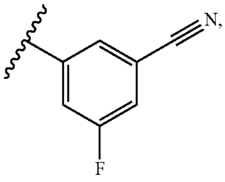
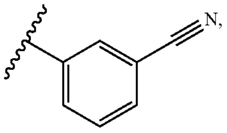
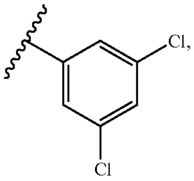
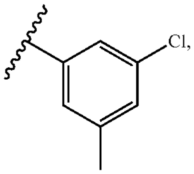
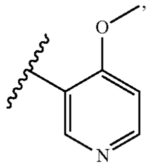
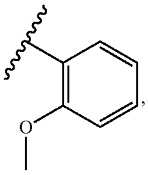,
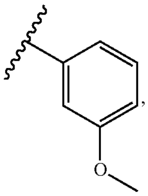,
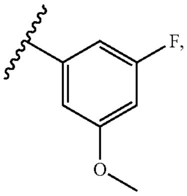 and
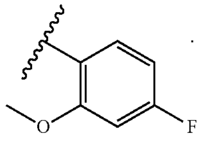.

In some embodiments, for the compound or salt of Formula (IV), (IV-a), (IV-b), (IV-c), or (IV-d), Ring B is selected from

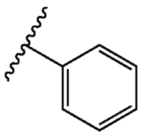,
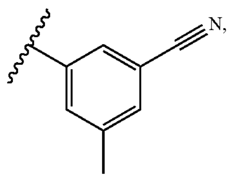
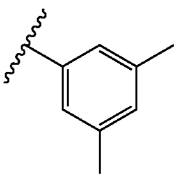,

-continued

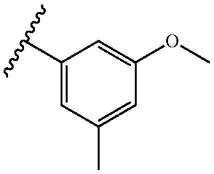,
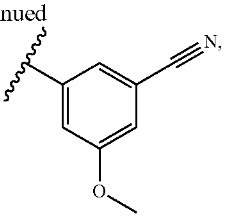
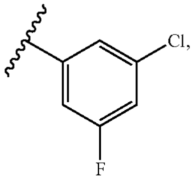
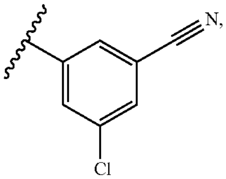
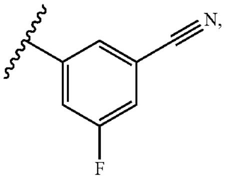
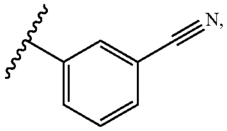
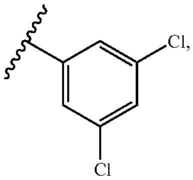
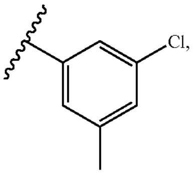
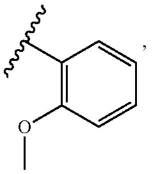,
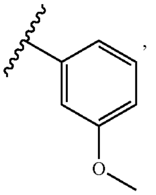,
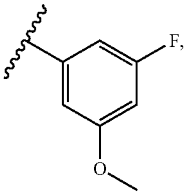 and
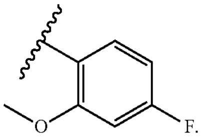

In some embodiments, for the compound or salt of Formula (IV), (IV-a), (IV-b), (IV-c), or (IV-d), Ring B is selected from

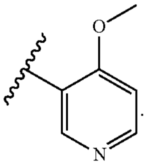 [SMILES: *c1cnccc1OC].

In some embodiments, for the compound or salt of Formula (IV), (IV-a), (IV-b), (IV-c), or (IV-d), $R^{60}$ is hydrogen. In some embodiments, $R^{60}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{60}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{60}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (IV), (IV-a), (IV-b), (IV-c), or (IV-d), $R^{61}$ is hydrogen. In some embodiments, $R^{61}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{61}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{61}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (IV), (IV-a), (IV-b), (IV-c), or (IV-d), $R^{62}$ is hydrogen. In some embodiments, $R^{62}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{62}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{62}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, for the compound or salt of Formula (IV), (IV-a), (IV-b), (IV-c), or (IV-d), $R^{63}$ is hydrogen. In some embodiments, $R^{63}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN. In some embodiments, $R^{63}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, and —CN. In some embodiments, $R^{63}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, =O, and —CN.

In some embodiments, the compound of Formula (IV) is:

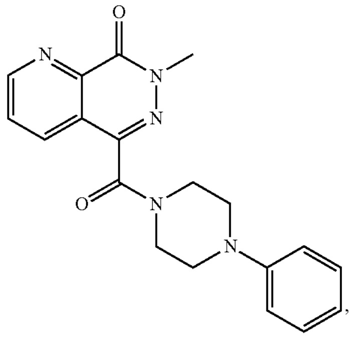
,

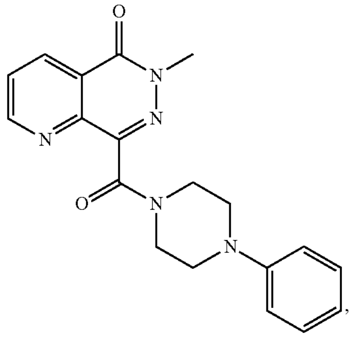
,

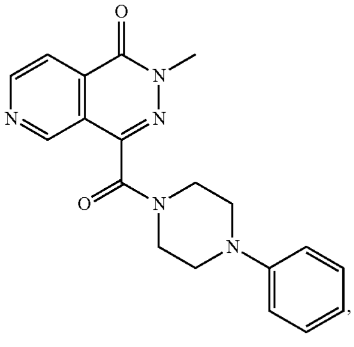
,

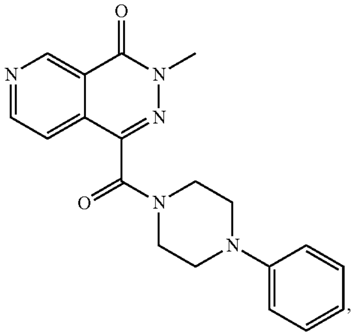
,

-continued
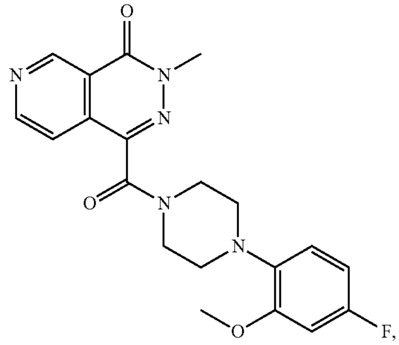
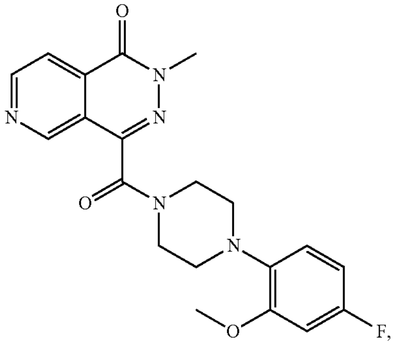
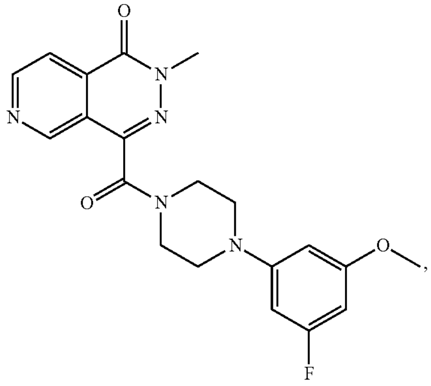
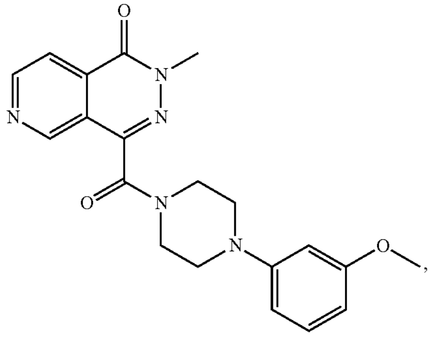
-continued
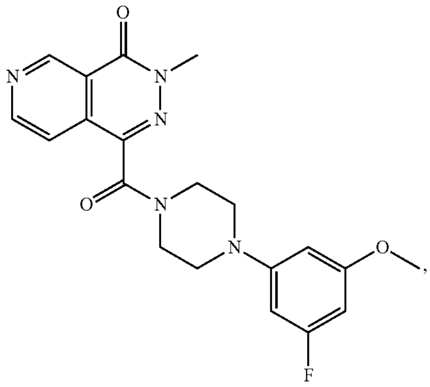
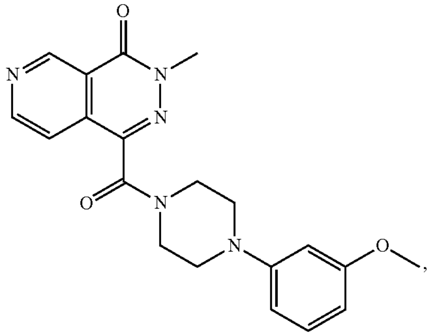
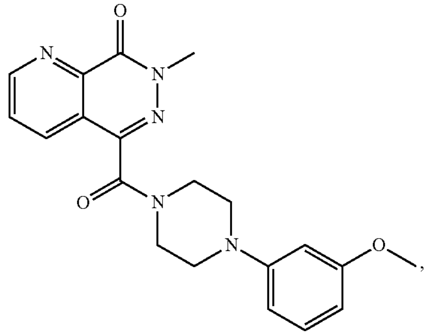
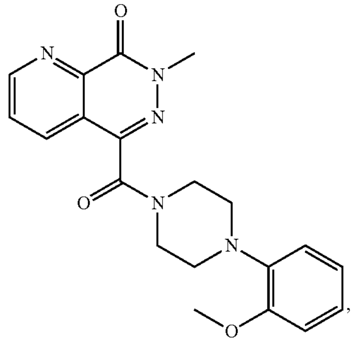

-continued
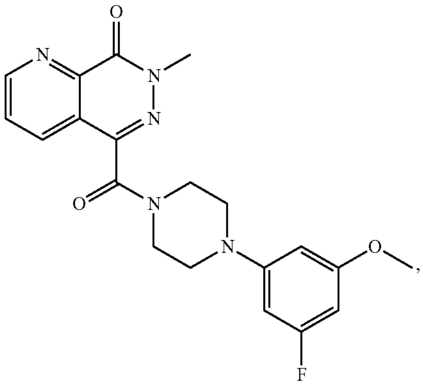
,
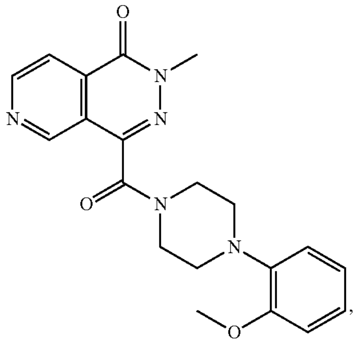
, or
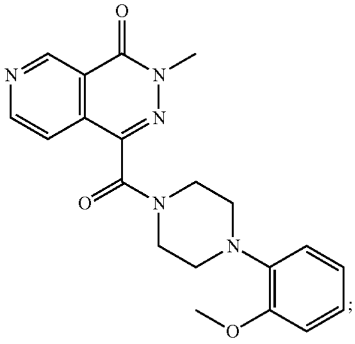
;
or a salt of any one thereof.
In some embodiments, the compound of Formula IV is:
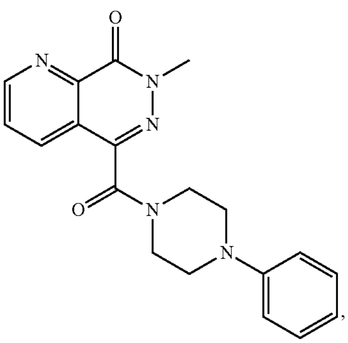
,
-continued
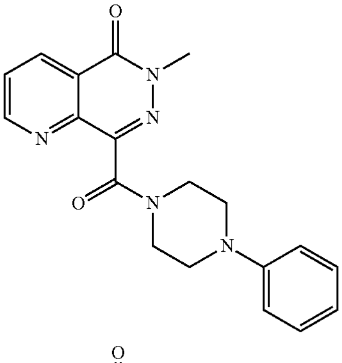
,
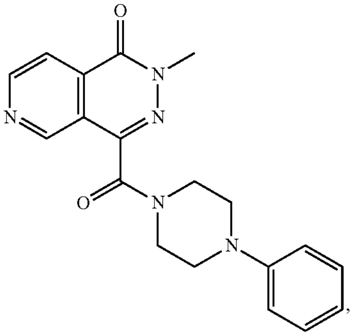
,
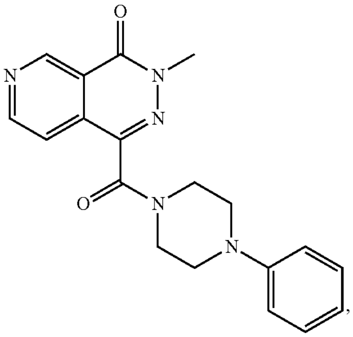
,
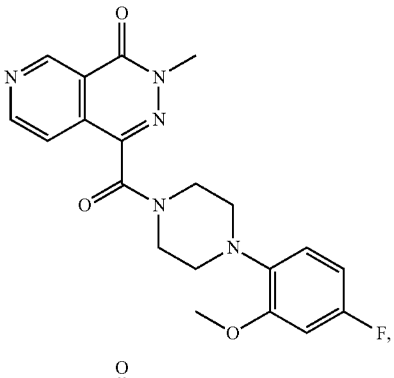
,
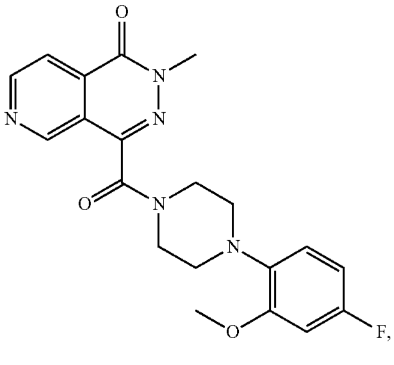
, -continued
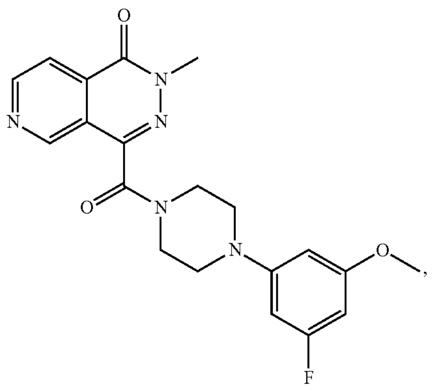
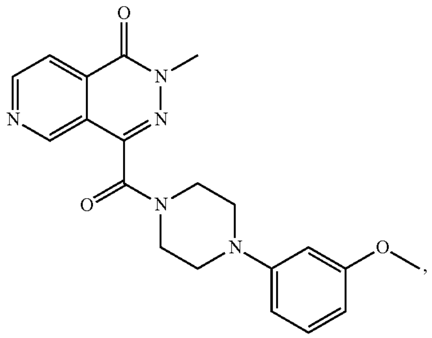
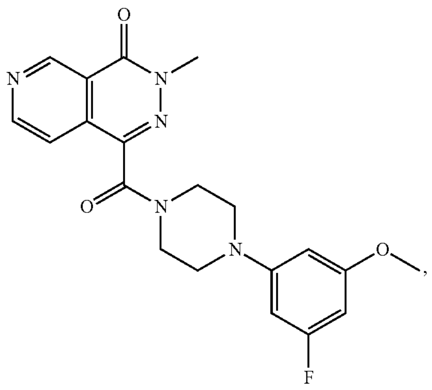
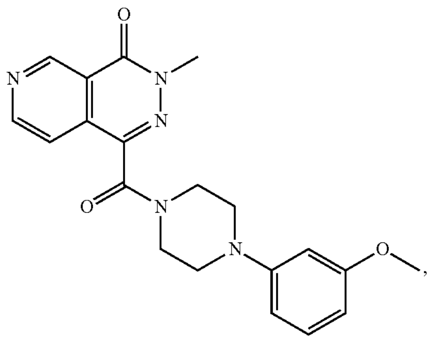
-continued
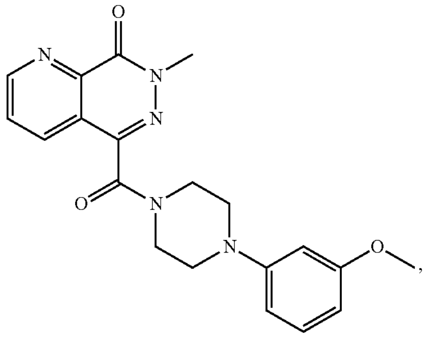
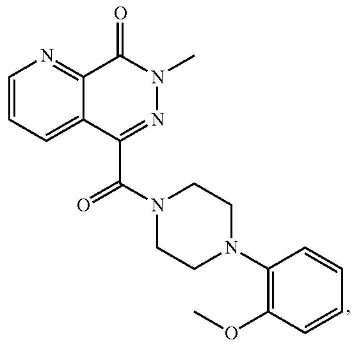
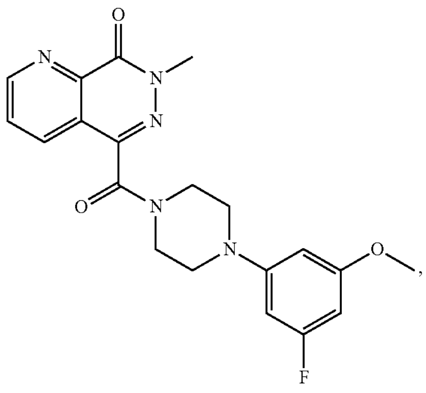
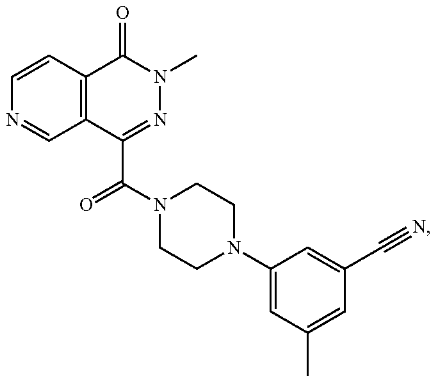

-continued
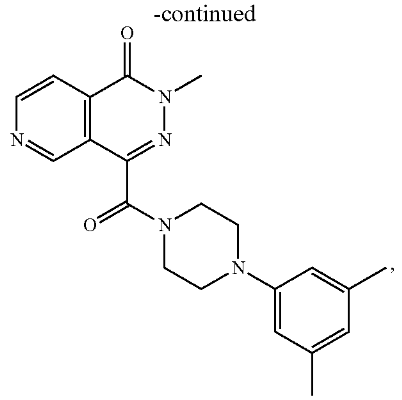
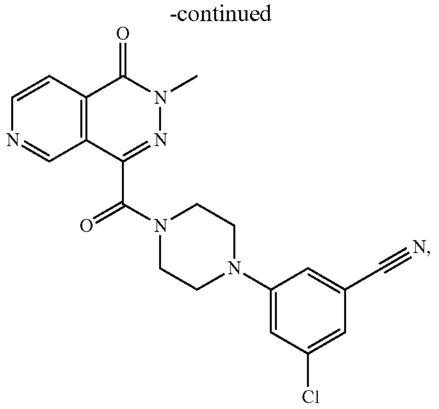
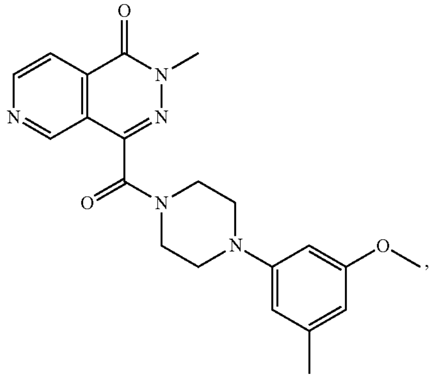
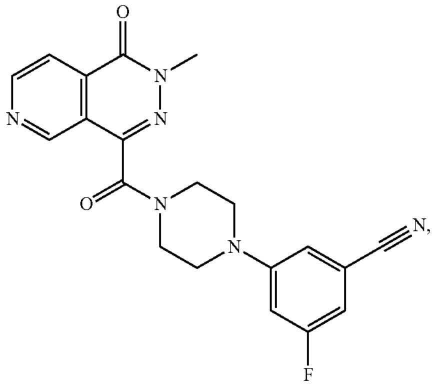
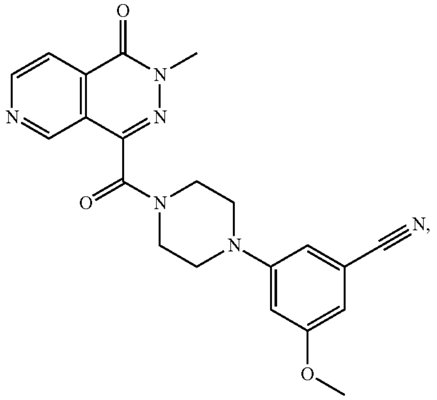
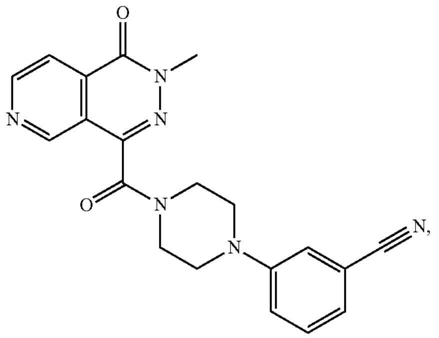
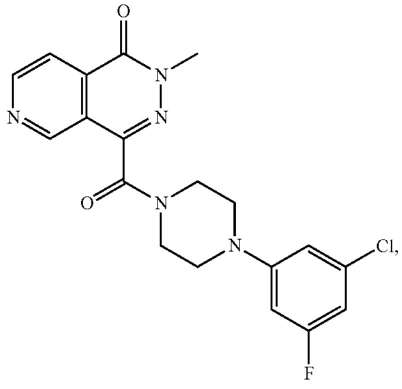
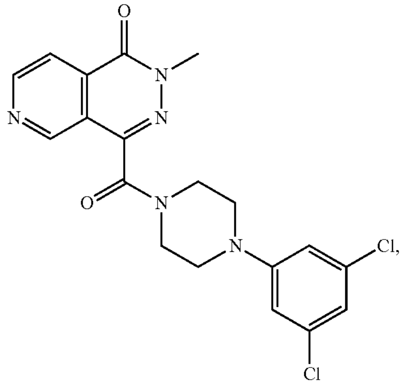

-continued
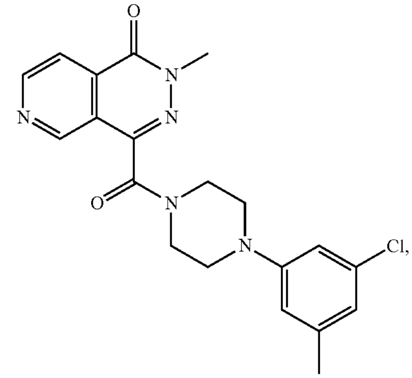
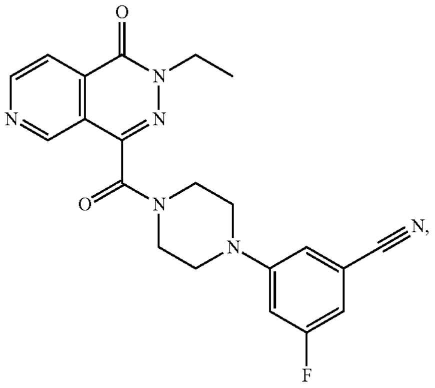
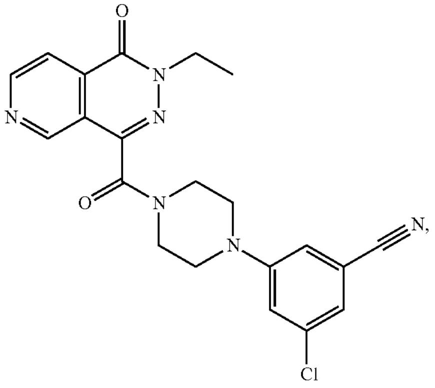
-continued
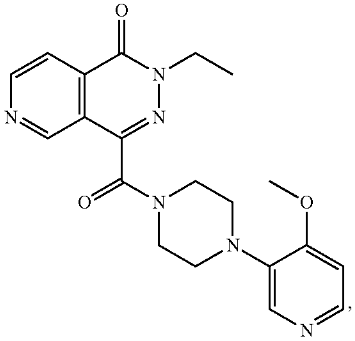
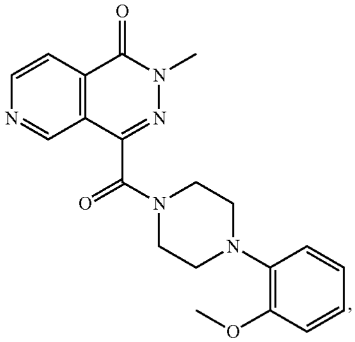
or
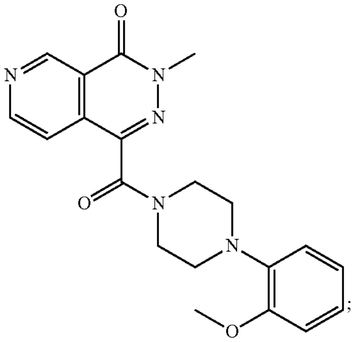
or a salt of any one thereof.
Compounds of Formula (VI).
In some aspects, the present disclosure provides a compound represented by Formula (VI):
(VI)
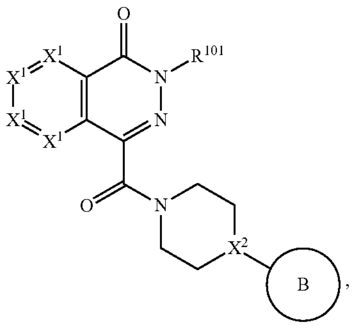
or a pharmaceutically acceptable salt wherein:
each $X^1$ is selected from $C(R^{100})$ and N;
$X^2$ is selected from $C(R^{104})$ and N;

$R^{100}$ is independently selected at each occurrence from: hydrogen, halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, and —CN;

$C_{1-6}$ alkyl optionally substituted with one or more substituents independently selected from halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, =S, =O, and —CN; and $C_{3-10}$ carbocycle and 3- to 10-membered heterocycle, any of which is optionally substituted with one or more substituents independently selected from halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, =S, =O, and —CN;

$R^{101}$ is independently selected from:

$C_{1-6}$ alkyl and $C_{2-6}$ alkenyl, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $C_{3-10}$ carbocycle and 3- to 10-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN;

Ring B is selected from phenyl, thiophenyl, imidazoyl, pyridyl, pyrazinyl, pyridazinyl, pyrimidinyl, quinolinyl, benzimidazolyl, benzisoxazolyl, benzodioxolyl, benzofuranyl, dihydrobenzofuranyl, dihydrofuropyridyl, furopyridyl, any of which is optionally substituted with one or more substituents independently selected from:

halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, and —CN;

$C_{1-6}$ alkyl optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, =S, =O, and —CN; and $C_{3-10}$ carbocycle and 3- to 10-membered heterocycle, any of which is optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, =S, =O, and —CN;

$R^{104}$ is selected from hydrogen and $C_{1-3}$ alkyl;

$R^{102}$, $R^{103}$, and $R^{105}$ are independently selected at each occurrence from: hydrogen;

$C_{1-6}$ alkyl optionally substituted with one more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN wherein the compound is not selected from:

2-methyl-4-[(4-phenyl-1-piperidinyl)carbonyl]-1(2H)-phthalazinone, 2-methyl-4-[(4-phenyl-1-piperazinyl)carbonyl]-1(2H)-phthalazinone, 2-(1-methylethyl)-4-[(4-phenyl-1-piperidinyl)carbonyl]-1(2H)-phthalazinone, 2-ethyl-4-[(4-phenyl-1-piperazinyl)carbonyl]-1(2H)-phthalazinone, 2-(1-methylethyl)-4-[[4-(2-thienyl)-1-piperazinyl]carbonyl]-1(2H)-phthalazinone, 2-(2-methylpropyl)-4-[(4-phenyl-1-piperidinyl)carbonyl]-1(2H)-phthalazinone, 2-methyl-4-[[4-(3-methylphenyl)-1-piperazinyl]carbonyl]-1(2H)-phthalazinone, 2-(1-methylethyl)-4-[(4-phenyl-1-piperazinyl)carbonyl]-1(2H)-phthalazinone, 4-[(4-phenyl-1-piperazinyl)carbonyl]-2-propyl-1(2H)-phthalazinone, 2-(1-methylethyl)-4-[[4-(4-pyridinyl)-1-piperidinyl]carbonyl]-1(2H)-phthalazinone, 2-(2-methylpropyl)-4-[(4-phenyl-1-piperazinyl)carbonyl]-1(2H)-phthalazinone, 2-methyl-4-[[4-(2-pyridinyl)-1-piperazinyl]carbonyl]-1(2H)-phthalazinone, 2-butyl-4-1(4-phenyl-1-piperazinyl)carbonyl]-1(2H)-phthalazinone, 2-(1-methylethyl)-4-[[4-(2-methylphenyl)-1-piperazinyl]carbonyl]-1(2H)-phthalazinone, 2-(1-methylethy])-4-[[4-(4-pyridinyl)-1-piperazinyl]carbonyl]-1(2H)-phthalazinone, 2-(1-methylethyl)-4-[[4-(3-methylphenyl)-1-piperazinyl]carbonyl]-1(2H)-phthalazinone, 4-[[4-(3-methylphenyl)-1-piperazinyl]carbonyl]-2-propyl-1(2H)-phthalazinone, 2-ethyl-4-[[4-(2-pyridinyl)-1-piperazinyl]carbonyl]-1(2H)-phthalazinone, 4-[[4-(4-hydroxyphenyl)-1-piperazinyl]carbonyl]-2-(1-methylethyl)-1(2H)-phthalazinone, 2-phenyl-4-[(4-phenyl-1-piperidinyl)carbonyl]-1(2H)-phthalazinone, 2-methyl-4-[[4-(2-pyrazinyl)-1-piperazinyl]carbonyl]-1(2H)-phthalazinone, 2-methyl-4-[[4-(2-pyrimidinyl)-1-piperazinyl]carbonyl]-1(2H)-phthalazinone.
4-[[4-(2,3-dimethylphenyl)-1-piperazinyl]carbonyl]-2-methyl-1(2H)-phthalazinone,
4-[[4-(4-methoxyphenyl)-1-piperazinyl]carbonyl]-2-methyl-1(2H)-phthalazinone.
4-[[4-(3-hydroxyphenyl)-1-piperazinyl]carbonyl]-2-(1-methylethyl)-1(2H)-phthalazinone,
2-(2-methylpropyl)-4-[[4-(4-pyridinyl)-1-piperazinyl]carbonyl]-1(2H)-phthalazinone,
4-[[4-(2-hydroxyphenyl)-1-piperazinyl]carbonyl]-2-(1-methylethyl)-1(2H)-phthalazinone,
2-ethyl-4-[[4-(2-pyrimidinyl)-1-piperazinyl]carbonyl]-1(2H)-phthalazinone,
2-pentyl-4-[(4-phenyl-1-piperazinyl)carbonyl]-1(2H)-phthalazinone.
4-[[4-(2,3-dimethylphenyl)-1-piperazinyl]carbonyl]-2-ethyl-1(2H)-phthalazinone,
2-ethyl-4-[[4-(4-methoxyphenyl)-1-piperazinyl]carbonyl]-1(2H)-phthalazinone,
4-[[4-(2-hydroxyphenyl)-1-piperazinyl]carbonyl]-2-propyl-1(2H)-phthalazinone,
4-[[4-(2-methylphenyl)-1-piperazinyl]carbonyl]-2-(2-methylpropyl)-1(2H)-phthalazinone,
4-[[4-(4-chlorophenyl)-1-piperazinyl]carbonyl]-2-methyl-1(2H)-phthalazinone,
2-(1-methylethyl)-4-[[4-(2-pyridinyl)-1-piperazinyl]carbonyl]-1(2H)-phthalazinone,
2-hexyl-4-[(4-phenyl-1-piperazinyl)carbonyl]-1(2H)-phthalazinone,
4-[[4-(2-methoxyphenyl)-1-piperazinyl]carbonyl]-2-methyl-1(2H)-phthalazinone,
4-[[4-(3-methoxyphenyl)-1-piperazinyl]carbonyl]-2-methyl-1(2H)-phthalazinone,
2-phenyl-4-[(4-phenyl-1-piperazinyl)carbonyl]-1(2H)-phthalazinone,
2-propyl-4-[[4-(2-pyridinyl)-1-piperazinyl]carbonyl]-1(2H)-phthalazinone,
4-[[4-(4-fluorophenyl)-1-piperazinyl]carbonyl]-2-methyl-1(2H)-phthalazinone,
2-(1-methylethyl)-4-[[4-(2-thiazolyl)-1-piperazinyl]carbonyl]-1(2H)-phthalazinone,
2-propyl-4-[[4-(2-thiazolyl)-1-piperazinyl]carbonyl]-1(2H)-phthalazinone.
2-(2-hydroxyethyl)-4-[[4-(2-pyridinyl)-1-piperazinyl]carbonyl]-1(2H)-phthalazinone.
2-(1-methylethy)-4-[[4-(3-pyridazinyl)-1-piperazinyl]carbonyl]-1(2H)-phthalazinone,
2-(1-methylethyl)-4-[[4-(4-methyl-3-pyridinyl)-1-piperazinyl]carbonyl]-1(2H)-phthalazinone,
4-[[4-(4-hydroxyphenyl)-1-piperazinyl]carbonyl]-2-(2-methylpropyl)-1(2H)-phthalazinone,
2-ethyl-4-[[4-(2-methoxyphenyl)-1-piperazinyl]carbonyl]-1(2H)-phthalazinone,
4-[[4-(4-acetylphenyl)-1-piperazinyl]carbonyl]-2-methyl-1(2H)-phthalazinone,
2-ethyl-4-[[4-(3-methoxyphenyl)-1-piperazinyl]carbonyl]-1(2H)-phthalazinone,
4-[[4-(3-chlorophenyl)-1-piperazinyl]carbonyl]-2-methyl-1(2H)-phthalazinone,
4-[[4-(2-chlorophenyl)-1-piperazinyl]carbonyl]-2-methyl-1(2H)-phthalazinone,
4-[[4-(2-fluorophenyl)-1-piperazinyl]carbonyl]-2-methyl-1(2H)-phthalazinone,
4-[[4-(4-hydroxyphenyl)-1-piperidinyl]carbonyl]-2-pentyl-1(2H)-phthalazinone,
4-[[4-(3-hydroxyphenyl)-1-piperazinyl]carbonyl]-2-(2-methylpropyl)-1(2H)-phthalazinone,
4-[[4-(2-hydroxyphenyl)-1-piperazinyl]carbonyl]-2-(2-methylpropyl)-1(2H)-phthalazinone,
2-ethyl-4-[[4-(4-fluorophenyl)-1-piperazinyl]carbonyl]-1(2H)-phthalazinone,
4-[[4-(4-methoxyphenyl)-1-piperazinyl]carbonyl]-2-(1-methylethyl)-1(2H)-phthalazinone,
2-(2-methylpropyl)-4-[[4-(2-pyridinyl)-1-piperazinyl]carbonyl]-1(2H)-phthalazinone,
4-[[4-(2-ethoxyphenyl)-1-piperazinyl]carbonyl]-2-methyl-1(2H)-phthalazinone,
4-[[4-(4-methoxyphenyl)-1-piperazinyl]carbonyl]-2-propyl-1(2H)-phthalazinone,
2-butyl-4-[[4-(2-pyridinyl)-1-piperazinyl]carbonyl]-1(2H)-phthalazinone,
4-[[4-(4-acetylphenyl)-1-piperazinyl]carbonyl]-2-ethyl-1(2H)-phthalazinone,
2-(1-methylethyl)-4-[[4-(2-pyrazinyl)-1-piperazinyl]carbonyl]-1(2H)-phthalazinone,
4-[(4-phenyl-1-piperazinyl)carbonyl]-2-(4-pyridinyl)-1(2H)-phthalazinone,
2-pentyl-4-[[4-(4-pyridinyl)-1-piperazinyl]carbonyl]-1(2H)-phthalazinone,
4-[[4-(1H-imidazol-5-yl)-1-piperidinyl]carbonyl]-2-(I-methylethyl)-1(2H)-phthalazinone,
4-[[4-(3-methylphenyl)-1-piperazinyl]carbonyl]-2-phenyl-1(2H)-phthalazinone,
2-ethyl-4-[[4-(2-fluorophenyl)-1-piperazinyl]carbonyl]-1(2H)-phthalazinone.
4-[[4-(2-chlorophenyl)-1-piperazinyl]carbonyl]-2-ethyl-1(2H)-phthalazinone,
2-(1-methylethyl)-4-[[4-(2-pyrimidinyl)-1-piperazinyl]carbonyl]-1(2H)-phthalazinone,
2-propyl-4-[[4-(2-pyrimidinyl)-1-piperazinyl]carbonyl]-1(2H)-phthalazinone,
4-[[4-(2,3-dimethylphenyl)-1-piperazinyl]carbonyl]-2-(1-methylethyl)-1(2H)-phthalazinone,
2-(1-methylethyl])-4-[[4-(4-methyl-2-pyridinyl)-1-piperazinyl]carbonyl]-1(2H)-phthalazinone,
4-[[4-(4-methoxyphenyl)-1-piperazinyl]carbonyl]-2-(2-methylpropyl)-1(2H)-phthalazinone,
4-[[4-(2-methylphenyl)-1-piperazinyl]carbonyl]-2-pentyl-1(2H)-phthalazinone,
4-[[4-(4-fluorophenyl)-1-piperazinyl]carbonyl]-2-(1-methylethyl)-1(2H)-phthalazinone,
4-[[4-(3-methoxyphenyl)-1-piperazinyl]carbonyl]-2-(1-methylethyl)-(2H)-phthalazinone,
4-[[4-(2-methoxyphenyl)-1-piperazinyl]carbonyl]-2-propyl-1(2H)-phthalazinone,
4-[[4-(2-methoxyphenyl)-1-piperazinyl]carbonyl]-2-(I-methylethyl)-1(2H)-phthalazinone,
4-[[4-(3-methoxyphenyl)-1-piperazinyl]carbonyl]-2-propyl-1(2H)-phthalazinone,
4-[[4-(2-ethoxyphenyl)-1-piperazinyl]carbonyl]-2-ethyl-1(2H)-phthalazinone,
1-|(3,4-dihydro-3-methyl-4-oxo-1-phthalazinyl)carbonyl]-4-phenyl-4-piperidinecarboxylic acid.
4-[[4-(4-acetylphenyl)-1-piperazinyl]carbonyl]-2-propyl-1(2H)-phthalazinone,
4-[[4-(2-fluorophenyl)-1-piperazinyl]carbonyl]-2-propyl-1(2H)-phthalazinone,
4-[[4-(3-chlorophenyl)-1-piperazinyl]carbonyl]-2-(1-methylethyl)-1(2H)-phthalazinone,
4-[[4-(3-hydroxyphenyl)-1-piperazinyl]carbonyl]-2-pentyl-1(2H)-phthalazinone, 4-[[4-(2-hydroxyphenyl)-1-piperazinyl]carbonyl]-2-pentyl-1(2H)-phthalazinone, 2-methyl-4-[[4-(2-nitrophenyl)-1-piperazinyl]carbonyl]-1(2H)-phthalazinone, 2-butyl-4-[[4-(4-methoxyphenyl)-1-piperazinyl]carbonyl]-1(2)-phthalazinone, 4-[[4-(2-fluorophenyl)-1-piperazinyl]carbonyl]-2-(1-methylethyl)-1(2H)-phthalazinone, 4-[[4-(4-acetylphenyl)-1-piperazinyl]carbonyl]-2-(1-methylethyl)-1(2H)-phthalazinone, 4-[[4-(3-chlorophenyl)-1-piperazinyl]carbonyl]-2-propyl-1(2H)-phthalazinone.

2-ethyl-4-[[4-(4-nitrophenyl)-1-piperazinyl]carbonyl]-(2H)-phthalazinone,

4-[[4-(2-hydroxyphenyl)-1-piperazinyl]carbonyl]-2-phenyl-1(2H)-phthalazinone, 2-phenyl-4-[[4-(2-pyridinyl)-1-piperazinyl]carbonyl]-1(2H)-phthalazinone, 4-[[4-(4-methoxy phenyl)-1-piperidinyl]carbonyl]-2-phenyl-1(2H)-phthalazinone.

2-hexyl-4-[[4-(2-pyridinyl)-1-piperazinyl]carbonyl]-1(2H)-phthalazinone,

4-[[4-(4-acetylphenyl)-1-piperazinyl]carbonyl]-2-(2-hydroxyethyl)-1(2H)-phthalazinone, 4-[[4-(2,3-dimethylphenyl)-1-piperazinyl]carbonyl]-2-(2-methylpropyl)-1(2H)-phthalazinone, 4-[[4-(3-methoxyphenyl)-1-piperazinyl]carbonyl]-2-(2-methylpropyl)-1(2H)-phthalazinone, 2-buty-4-[[4-(2-pyrazinyl)-1-piperazinyl]carbonyl]-1(2H)-phthalazinone, 4-[[4-(2-ethoxyphenyl)-1-piperazinyl]carbonyl]-2-propyl-1(2H)-phthalazinone, 1-1(3-ethyl-3,4-dihydro-4-oxo-1-phthalazinyl)carbonyl]-4-phenyl-4-piperidinecarboxylic acid, 2-butyl-4-[[4-(2,3-dimethylphenyl)-1-piperazinyl]carbonyl]-1(2H)-phthalazinone, 2-pentyl-4-[[4-(2-pyridinyl)-1-piperazinyl]carbonyl]-1(2H)-phthalazinone, 4-[[4-(2-methoxyphenyl)-1-piperazinyl]carbonyl]-2-(2-methylpropyl)-1(2H)-phthalazinone, 2-butyl-4-[[4-(2-pyrimidinyl)-1-piperazinyl]carbonyl]-1(2H)-phthalazinone, 2-(1-methylethyl)-4-[[4-(1-methyl-1H-imidazol-2-yl)-1-piperazinyl]carbonyl]-1(2H)-phthalazinone, 4-[[4-(5-chloro-2-methylphenyl)-1-piperazinyl]carbonyl]-2-methyl-1(2H)-phthalazinone, 4-[[4-(3-methylphenyl)-1-piperazinyl]carbonyl]-2-(4-pyridinyl)-1(2H)-phthalazinone, 2-ethyl-4-[[4-(2-nitrophenyl)-1-piperazinyl]carbonyl]-1(2H)-phthalazinone, 1-[[3,4-dihydro-3-(1-methylethyl)-4-oxo-1-phthalazinyl]carbonyl]-4-phenyl-4-piperidinecarboxylic acid, 1-[(3,4-dihydro-4-oxo-3-propyl-1-phthalazinyl)carbonyl]-4-phenyl-4-piperidinecarboxylic acid, 4-[[4-(4-nitrophenyl)-1-piperazinyl]carbonyl]-2-propyl-1(2H)-phthalazinone, 2-butyl-4-[[4-(2-methoxyphenyl)-1-piperazinyl]carbonyl]-1(2)-phthalazinone, 2-butyl-4-[[4-(3-methoxyphenyl)-1-piperazinyl]carbonyl]-1(2H)-phthalazinone, 4-[[4-(2,3-dimethylphenyl)-1-piperazinyl]carbonyl]-2-phenyl-1(2H)-phthalazinone, 4-[[4-(4-acetylphenyl)-1-piperazinyl]carbonyl]-2-(2-methylpropyl)-1(2H)-phthalazinone, 4-[[4-(4-acetylphenyl)-1-piperazinyl]carbonyl]-2-butyl-1(2H)-phthalazinone, 4-[[4-(4-methoxyphenyl)-1-piperazinyl]carbonyl]-2-pentyl-1(2H)-phthalazinone, 4-[[4-(2,3-dimethylphenyl)-1-piperazinyl]carbonyl]-2-pentyl-1(2H)-phthalazinone, 2-(1-methylethyl)-4-[[4-(4-nitrophenyl)-1-piperazinyl]carbonyl]-(2H)-phthalazinone, 2-butyl-4-[[4-(4-fluorophenyl)-1-piperazinyl]carbonyl]-1(2H)-phthalazinone, 4-[[4-(4-methoxyphenyl)-1-piperazinyl]carbonyl]-2-phenyl-1(2H)-phthalazinone, 2-(4-methoxyphenyl)-4-[(4-phenyl-1-piperazinyl)carbonyl]-1(2H)-phthalazinone, 4-[[4-(1H-indol-3-yl)-1-piperidinyl]carbonyl]-2-(2-methylpropyl)-1(2H)-phthalazinone, 4-[[4-(3,4-dichlorophenyl)-1-piperazinyl]carbonyl]-2-methyl-1(2H)-phthalazinone, 4-[[4-(1H-benzimidazol-2-yl)-1-piperidinyl]carbonyl]-2-methyl-1(2H)-phthalazinone, 4-[[4-(4-chlorophenyl)-4-hydroxy-1-piperidinyl]carbonyl]-2-methyl-1(2H)-phthalazinone, 4-[[4-(5-bromo-2-pyrimidinyl)-1-piperazinyl]carbonyl]-2-methyl-1(2H)-phthalazinone, 4-[[4-(2-benzoxazolyl)-1-piperidinyl]carbonyl]-2-methyl-1(2H)-phthalazinone.

4-[[4-(3-methoxyphenyl)-1-piperazinyl]carbonyl]-2-phenyl-1(2H)-phthalazinone,

4-[[4-(2-methoxyphenyl)-1-piperazinyl]carbonyl]-2-phenyl-1(2H)-phthalazinone, 2-hexyl-4-[[4-(2-pyrimidinyl)-1-piperazinyl]carbonyl]-1(2H)-phthalazinone, 2-pentyl-4-[[4-(2-pyrimidinyl)-1-piperazinyl]carbonyl]-1(2H)-phthalazinone, 2-(3-methoxyphenyl)-4-[(4-phenyl-1-piperazinyl)carbonyl]-1(2H)-phthalazinone, 4-[[4-(4-acetylphenyl)-1-piperazinyl]carbonyl]-2-hexyl-1(2H)-phthalazinone, 2-(4-pyridinyl)-4-[[4-(2-pyridinyl)-1-piperazinyl]carbonyl]-1(2H)-phthalazinone, 2-(2-methylpropyl)-4-[[4-(4-nitrophenyl)-1-piperazinyl]carbonyl]-1(2H)-phthalazinone, 1-[[3,4-dihydro-3-(2-methylpropyl)-4-oxo-1-phthalazinyl]carbonyl]-4-phenyl-4-piperidinecarboxylic acid, 2-(1-methylethy])-4-[[4-(2-nitrophenyl)-1-piperazinyl]carbonyl]-1(2H)-phthalazinone, 4-[[4-(4-chlorophenyl)-1-piperazinyl]carbonyl]-2-pentyl-1(2H)-phthalazinone, 4-[[4-(2-methoxyphenyl)-1-piperazinyl]carbonyl]-2-pentyl-1(2H)-phthalazinone, 4-[[4-(3-methoxyphenyl)-1-piperazinyl]carbonyl]-2-pentyl-1(2H)-phthalazinone, 4-[[4-(4-fluorophenyl)-1-piperazinyl]carbonyl]-2-pentyl-1(2H)-phthalazinone.

4-[[4-(4-acetylphenyl)-1-piperazinyl]carbonyl]-2-pentyl-1(2H)-phthalazinone, 2-phenyl-4-[[4-(2-pyrimidinyl)-1-piperazinyl]carbonyl]-1(2H)-phthalazinone, 2-(4-ethoxyphenyl)-4-[(4-phenyl-1-piperazinyl)carbonyl]-1(2H)-phthalazinone, 2-(2-methoxyphenyl)-4-[(4-phenyl-1-piperazinyl)carbonyl]-1(2H)-phthalazinone.

4-[[4-(1H-indol-3-yl)-1-piperidinyl]carbonyl]-2-pentyl-1(2H)-phthalazinone, 2-(4-chlorophenyl)-4-1(4-phenyl-1-piperazinyl)carbonyl]-1(2H)-phthalazinone, 2-(4-pyridinyl)-4-[[4-(2-pyrimidinyl)-1-piperazinyl]carbonyl]-1(2H)-phthalazinone, 4-[[4-(2,3-dimethylphenyl)-1-piperazinyl]carbonyl]-2-(4-pyridinyl)-1(2H)-phthalazinone,
4-[[4-(4-fluorophenyl)-1-piperazinyl]carbonyl]-2-phenyl-1(2H)-phthalazinone,
4-[[4-(2-fluorophenyl)-1-piperazinyl]carbonyl]-2-pentyl-1(2H)-phthalazinone,
4-[[4-(4-chlorophenyl)-1-piperazinyl]carbonyl]-2-phenyl-1(2H)-phthalazinone,
4-[[4-(3-chlorophenyl)-1-piperazinyl]carbonyl]-2-pentyl-1(2H)-phthalazinone.
4-[[4-(2-ethoxyphenyl)-1-piperazinyl]carbonyl]-2-phenyl-1(2H)-phthalazinone,
1-[(3-butyl-3,4-dihydro-4-oxo-1-phthalazinyl)carbonyl]-4-phenyl-4-piperidinecarboxylic acid.
4-[[4-(3-chlorophenyl)-1-piperazinyl]carbonyl]-2-phenyl-1(2H)-phthalazinone,
4-[[4-(2-fluorophenyl)-1-piperazinyl]carbonyl]-2-phenyl-1(2H)-phthalazinone,
2-butyl-4-[[4-(1H-indol-2-yl)-1-piperidinyl]carbonyl]-1(2H)-phthalazinone.
4-[[4-(4-methoxyphenyl)-1-piperazinyl]carbonyl]-2-(4-pyridinyl)-1(2H)-phthalazinone,
2-(2-methylpropyl)-4-[[4-(2-nitrophenyl)-1-piperazinyl]carbonyl]-1(2H)-phthalazinone,
2-[4-[(3-butyl-3,4-dihydro-4-oxo-1-phthalazinyl)carbonyl]-1-piperazinyl]-3-pyridinecarbonitrile,
4-[[4-(2-ethoxyphenyl)-1-piperazinyl]carbonyl]-2-pentyl-1(2H)-phthalazinone,
4-[[4-(4-nitrophenyl)-1-piperazinyl]carbonyl]-2-pentyl-1(2H)-phthalazinone,
4-[[4-(4-nitrophenyl)-1-piperazinyl]carbonyl]-2-phenyl-1(2H)-phthalazinone,
4-[[4-(4-acetylphenyl)-1-piperazinyl]carbonyl]-2-phenyl-1(2H)-phthalazinone, 4-[[4-(2-methoxyphenyl)-1-piperazinyl]carbonyl]-2-(4-pyridinyl)-1(2H)-phthalazinone.
4-[[4-(3-nitrophenyl)-1-piperazinyl]carbonyl]-2-phenyl-1(2H)-phthalazinone,
2-(4-chlorophenyl)-4-[[4-(4-methylphenyl)-1-piperazinyl]carbonyl]-1(2H)-phthalazinone,
4-[[4-(2-benzoxazolyl)-1-piperidinyl]carbonyl]-2-(2-hydroxyethyl)-1(2H)-phthalazinone,
4-[[4-(2-fluorophenyl)-1-piperazinyl]carbonyl]-2-(4-pyridinyl)-1(2H)-phthalazinone,
4-[[4-(4-fluorophenyl)-1-piperazinyl]carbonyl]-2-(4-pyridinyl)-1(2H)-phthalazinone,
4-[[4-(3-chlorophenyl)-1-piperazinyl]carbonyl]-2-(4-pyridinyl)-1(2H)-phthalazinone,
4-[[4-(5-chloro-2-methylphenyl)-1-piperazinyl]carbonyl]-2-(2-methylpropyl)-1(2H)-phthalazinone,
4-[[4-(2-nitrophenyl)-1-piperazinyl]carbonyl]-2-pentyl-1(2H)-phthalazinone,
4-[[4-(5-chloro-2-pyridinyl)-1-piperazinyl]carbonyl]-2-(2-methylpropyl)-1(2H)-phthalazinone,
2-[4-[[3,4-dihydro-3-(1-methylethyl)-4-oxo-1-phthalazinyl]carbonyl]-1-piperazinyl]-6-fluorobenzonitrile.
4-[[4-(1H-benzimidazol-2-yl)-1-piperidinyl]carbonyl]-2-(1-methylethyl)-1(2H)-phthalazinone,
2-[4-[(3,4-dihydro-4-oxo-3-phenyl-1-phthalazinyl)carbonyl]-1-piperazinyl]-4-pyridinecarbonitrile,
4-[[4-(2-benzoxazolyl)-1-piperidinyl]carbonyl]-2-(1-methylethyl)-1(2H)-phthalazinone,
6-[4-[(3,4-dihydro-4-oxo-3-phenyl-1-phthalazinyl)carbonyl]-1-piperazinyl]-3-pyridinecarbonitrile,
4-[[4-(2-benzothiazolyl)-1-piperidinyl]carbonyl]-2-propyl-1(2H)-phthalazinone,
2-(4-methoxyphenyl)-4-[[4-(4-methoxyphenyl)-1-piperazinyl]carbonyl]-1(2H)-phthalazinone,
2-(4-chlorophenyl)-4-[[4-(3-methylphenyl)-1-piperazinyl]carbonyl]-1(2H)-phthalazinone,
2-(4-chlorophenyl)-4-[[4-(2-methylphenyl)-1-piperazinyl]carbonyl]-1(2H)-phthalazinone,
4-[[4-(2-benzothiazolyl)-1-piperidinyl]carbonyl]-2-(1-methylethyl)-1(2H)-phthalazinone,
2-methyl-4-[[4-(8-nitro-5-isoquinolinyl)-1-piperazinyl]carbonyl]-1(2H)-phthalazinone,
1-[(3,4-dihydro-4-oxo-3-phenyl-1-phthalazinyl)carbonyl]-4-phenyl-4-piperidinecarboxylic acid,
2-(3,5-dimethoxy phenyl)-4-|(4-phenyl-1-piperazinyl)carbonyl]-1(2H)-phthalazinone,
1-[[4-[(3,4-dihydro-4-oxo-3-phenyl-1-phthalazinyl)carbonyl]-4-piperidinyl]-1H-pyrrole-2-carboxylic acid,
2-(2-methoxyphenyl)-4-[[4-(2-methoxyphenyl)-1-piperazinyl]carbonyl]-1(2H)-phthalazinone,
2-[4-[[3,4-dihydro-3-(2-methylpropyl)-4-oxo-1-phthalazinyl]carbonyl]-1-piperazinyl]-6-fluorobenzonitrile,
2-ethyl-4-[[4-(2-phenyl-4-pyrimidinyl)-1-piperazinyl]carbonyl]-1(2H)-phthalazinone,
4-[[4-(6-chloro-2-pyridinyl])-1-piperazinyl]carbonyl]-2-(1-methylethyl)-1(2H)-phthalazinone,
2-ethyl-4-[[4-(8-nitro-5-isoquinolinyl)-1-piperazinyl]carbonyl]-1(2H)-phthalazinone,
2-methyl-4-[[4-[3-(trifluoromethyl)phenyl-1-piperazinyl]carbonyl]-1(2H)-phthalazinone,
2-(4-methoxyphenyl)-4-[[4-(2-methoxyphenyl)-1-piperazinyl]carbonyl]-(2H)-phthalazinone,
2-(3-methoxyphenyl)-4-[[4-(4-methoxy phenyl)-1-piperazinyl]carbonyl]-1(2H)-phthalazinone,
2-(4-ethoxyphenyl)-4-[[4-(4-methoxyphenyl)-1-piperazinyl]carbonyl]-1(2H)-phthalazinone,
2-(4-chlorophenyl)-4-[[4-(4-chlorophenyl)-1-piperazinyl]carbonyl]-1(2H)-phthalazinone,
2-methyl-4-[[4-(1-methyl-1H-benzimidazol-2-yl)-1-piperazinyl]carbonyl]-1(2H)-phthalazinone,
4-[[4-(5-chloro-2-pyridinyl)-1-piperazinyl]carbonyl]-2-phenyl-1(2H)-phthalazinone,
4-[[4-(5-chloro-2-pyridinyl)-1-piperazinyl]carbonyl]-2-pentyl-1(2H)-phthalazinone,
2-(4-ethoxyphenyl)-4-[[4-(2-pyridinyl)-1-piperazinyl]carbonyl]-1(2H)-phthalazinone,
2-(2-methoxyphenyl)-4-[[4-(4-methoxyphenyl)-1-piperazinyl]carbonyl]-1(2H)-phthalazinone,
2-(3-methoxyphenyl)-4-[[4-(2-methoxyphenyl)-1-piperazinyl]carbonyl]-1(2H)-phthalazinone,
4-[[4-(5-chloro-1,6-dihydro-6-oxo-1-phenyl-4-pyridazinyl)-1-piperazinyl]carbonyl]-2-methyl-1(2H)-phthalazinone,
2-(4-chlorophenyl)-4-[[4-(3-chlorophenyl)-1-piperazinyl]carbonyl]-1(2H)-phthalazinone,
2-(4-chlorophenyl)-4-[[4-(2-chlorophenyl)-1-piperazinyl]carbonyl]-1(2H)-phthalazinone,
4-[[4-(2,6-dimethyl-4-pyrimidinyl)-1-piperazinyl]carbonyl]-2-(2-methylpropyl)-1(2H)-phthalazinone,
methyl 4-[4-[(3,4-dihydro-3-methyl-4-oxo-1-phthalazinyl)carbonyl]-3-methyl-1-piperazinyl]benzoate,
2-(4-chlorophenyl)-4-[[4-(2-fluorophenyl)-1-piperazinyl]carbonyl]-1(2H)-phthalazinone,
2-(4-ethoxyphenyl)-4-[[4-(2-methoxyphenyl)-1-piperazinyl]carbonyl]-1(2H)-phthalazinone,
4-[[4-(4-acetyl-2-fluorophenyl)-1-piperazinyl]carbonyl]-2-ethyl-1(2H)-phthalazinone,
4-[[4-(4-chloro-2-nitrophenyl)-1-piperazinyl]carbonyl]-2-methyl-1(2H)-phthalazinone,
2-propyl-4-[[4-[3-(trifluoromethyl)phenyl]-1-piperazinyl]carbonyl]-1(2H)-phthalazinone, 4-[[4-(4-fluorophenyl)-1-piperazinyl]carbonyl]-2-(4-methoxyphenyl)-1(2H)-phthalazinone, 2-(3,5-dimethoxyphenyl)-4-[[4-(4-methoxyphenyl)-1-piperazinyl]carbonyl]-1(2H)-phthalazinone, 2-(2,4-dimethoxyphenyl)-4-[(4-phenyl-1-piperazinyl)carbonyl]-1(2H)-phthalazinone, 4-[[4-(5-methoxy-1H-indol-3-yl)-1-piperidinyl]carbonyl]-2-(2-methylpropyl)-1(2H)-phthalazinone, 4-[[4-(5-chloro-1,6-dihydro-6-oxo-1-phenyl-4-pyridazinyl)-1-piperazinyl]carbonyl]-2-ethyl-1(2H)-phthalazinone, 4-[[4-(4-chloro-2-nitrophenyl)-1-piperazinyl]carbonyl]-2-ethyl-1(2H)-phthalazinone, 4-[[4-(2,6-dimethyl-4-pyrimidinyl)-1-piperazinyl]carbonyl]-2-pentyl-1(2H)-phthalazinone, 2-(1-methylethyl)-4-[[4-[6-methyl-2-(1-methylethyl)-4-pyrimidinyl]-1-piperazinyl]carbonyl]-1(2H)-phthalazinone, 4-[[4-[[6-methyl-2-(1-methylethyl)-4-pyrimidinyl]-1-piperazinyl]carbonyl]-2-propyl-1(2H)-phthalazinone, 4-[[4-(3-chlorophenyl)-1-piperazinyl]carbonyl]-2-(4-methoxyphenyl)-1(2H)-phthalazinone, 4-[[4-(2-fluorophenyl)-1-piperazinyl]carbonyl]-2-(4-methoxyphenyl)-1(2H)-phthalazinone, 2-(3,5-dimethoxyphenyl)-4-[[4-(2-methoxyphenyl)-1-piperazinyl]carbonyl]-1(2H)-phthalazinone, 4-[[4-(3-chlorophenyl)-1-piperazinyl]carbonyl]-2-(3-methoxyphenyl)-1(2H)-phthalazinone, 4-[[4-(6-fluoro-1,2-benzisoxazol-3-yl)-1-piperidinyl]carbonyl-2-methyl-1(2H)-phthalazinone, 4-[[4-(2,6-dimethyl-4-pyrimidinyl)-1-piperazinyl]carbonyl]-2-phenyl-1(2H)-phthalazinone, 4-[[4-(6-chloro-2-pyridinyl)-1-piperazinyl]carbonyl]-2-phenyl-1(2H)-phthalazinone, 2-methyl-4-[[4-[5-(trifluoromethyl)-2-pyridinyl]-1-piperazinyl]carbonyl-1(2H)-phthalazinone, 2-(4-chlorophenyl)-4-[[4-(2-methoxyphenyl)-1-piperazinyl]carbonyl-1(2H)-phthalazinone, 4-[[4-(2-fluorophenyl)-1-piperazinyl]carbonyl]-2-(2-methoxyphenyl)-1(2H)-phthalazinone, 4-[[4-(4-fluorophenyl)-1-piperazinyl]carbonyl]-2-(3-methoxyphenyl)-1(2H)-phthalazinone, 4-[[4-(2-fluorophenyl)-1-piperazinyl]carbonyl]-2-(3-methoxyphenyl)-1(2H)-phthalazinone, 2-(2-methylpropyl)-4-[[4-[3-(trifluoromethyl)phenyl]-1-piperazinyl]carbonyl]-1(2H)-phthalazinone, 4-[[4-(4-chloro-2-nitrophenyl)-1-piperazinyl]carbonyl]-2-(1-methylethyl)-1(2H)-phthalazinone, 2-butyl-4-[[4-[3-(trifluoromethyl)phenyl]-1-piperazinyl]carbonyl]-1(2H)-phthalazinone, 2-ethyl-4-[[4-[5-(trifluoromethyl)-2-pyridinyl]-1-piperazinyl]carbonyl]-1(2H)-phthalazinone, 4-[[4-(4-chloro-2-nitrophenyl)-1-piperazinyl]carbonyl]-2-propyl-1(2H)-phthalazinone, 4-[[4-(4-fluorophenyl)-1-piperazinyl]carbonyl]-2-(2-methoxy phenyl)-1(2H)-phthalazinone, 4-[[4-(3-chlorophenyl)-1-piperazinyl]carbonyl]-2-(2-methoxyphenyl)-1(2H)-phthalazinone, 2-(2,4-dimethoxyphenyl)-4-[[4-(4-methoxy)phenyl)-1-piperazinyl]carbonyl]-1(2H)-phthalazinone, 2-(2,4-dimethoxyphenyl)-4-[[4-(2-methoxyphenyl)-1-piperazinyl]carbonyl]-1(2H)-phthalazinone, 2-(4-ethoxyphenyl)-4-[[4-(4-fluorophenyl)-1-piperazinyl]carbonyl]-1(2H)-phthalazinone, 4-[[4-(3,5-dichloro-2-pyridinyl)-1-piperazinyl]carbonyl]-2-(2-methylpropyl)-1(2H)-phthalazinone, 2-(4-ethoxyphenyl)-4-[[4-(2-fluorophenyl)-1-piperazinyl]carbonyl]-1(2H)-phthalazinone, ethyl 6-[4-[(3-butyl-3,4-dihydro-4-oxo-1-phthalazinyl)carbonyl]-1-piperazinyl]-3-pyridinecarboxylate, 4-[[4-(4-acetyl-2-fluorophenyl)-1-piperazinyl]carbonyl]-2-butyl-1(2H)-phthalazinone, 2-propyl-4-[[4-[5-(trifluoromethyl)-2-pyridinyl]-1-piperazinyl]carbonyl]-1(2H)-phthalazinone, 2-(1-methylethyl)-4-[[4-[5-(trifluoromethyl)-2-pyridinyl]-1-piperazinyl]carbonyl]-1(2H)-phthalazinone.

2-pentyl-4-[[4-[3-(trifluoromethyl)phenyl]-1-piperazinyl]carbonyl]-1(2H)-phthalazinone, 4-[[4-(3-chlorophenyl)-1-piperazinyl]carbonyl]-2-(3,5-dimethoxyphenyl)-1(2H)-phthalazinone, 4-[[4-(4-chloro-2-nitrophenyl)-1-piperazinyl]carbonyl]-2-phenyl-1(2H)-phthalazinone, 2-phenyl-4-[[4-[3-(trifluoromethyl)phenyl]-1-piperazinyl]carbonyl]-1(2H)-phthalazinone, 2-(3,5-dimethoxyphenyl)-4-[[4-(4-fluorophenyl)-1-piperazinyl]carbonyl]-1(2H)-phthalazinone, 2-(3,5-dimethoxyphenyl)-4-[[4-(2-fluorophenyl)-1-piperazinyl]carbonyl]-1(2H)-phthalazinone, 2-(2,4-dimethoxyphenyl)-4-[[4-(2-pyridinyl)-1-piperazinyl]carbonyl]-1(2H)-phthalazinone, 4-[[4-(4-chloro-2-nitrophenyl)-1-piperazinyl]carbonyl]-2-pentyl-1(2H)-phthalazinone, 4-[[4-(4-acetyl-2-fluorophenyl)-1-piperazinyl]carbonyl]-2-phenyl-1(2H)-phthalazinone, 2-(2,4-dimethoxyphenyl)-4-[[4-(4-fluorophenyl)-1-piperazinyl]carbonyl]-1(2H)-phthalazinone, 2-pentyl-4-[[4-[5-(trifluoromethyl)-2-pyridinyl]-1-piperazinyl]carbonyl]-1(2H)-phthalazinone, 2-(2,4-dimethoxyphenyl)-4-[[4-(2-fluorophenyl)-1-piperazinyl]carbonyl]-1(2H)-phthalazinone, 2-phenyl-4-[[4-[5-(trifluoromethyl)-2-pyridinyl]-1-piperazinyl]carbonyl]-1(2H)-phthalazinone, 2-methyl-4-[[4-[2-nitro-4-(trifluoromethyl)phenyl]-1-piperazinyl]carbonyl]-1(2H)-phthalazinone, 4-[[4-[3-chloro-5-(trifluoromethyl)-2-pyridinyl]-1-piperazinyl]carbonyl]-2-ethyl-1(2H)-phthalazinone, 4-[[4-[2-nitro-4-(trifluoromethyl)phenyl]-1-piperazinyl]carbonyl]-2-propyl-1(2H)-phthalazinone, 4-[[4-[3-chloro-5-(trifluoromethyl)-2-pyridinyl]-1-piperazinyl]carbonyl]-2-(2-hydroxyethyl)-1(2H)-phthalazinone, 2-(1-methylethyl)-4-[[4-[2-nitro-4-(trifluoromethyl)phenyl]-1-piperazinyl]carbonyl]-1(2H)-phthalazinone, 4-[[4-[3-chloro-5-(trifluoromethyl)-2-pyridinyl]-1-piperazinyl]carbonyl]-2-(2-methylpropyl)-1(2H)-phthalazinone, and 2-hexyl-4-[[4-[2-nitro-4-(trifluoromethyl)phenyl]-1-piperazinyl]carbonyl]-1(2H)-phthalazinone.

In some aspects, the present disclosure provides a compound represented by the structure:

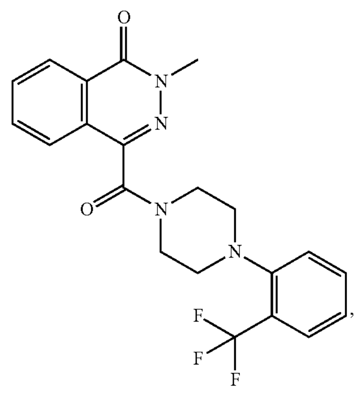
,

-continued
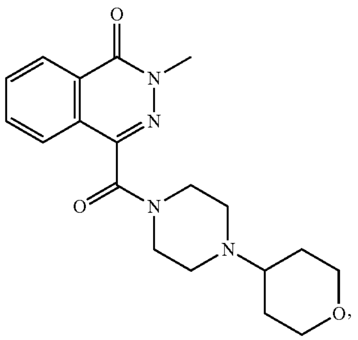
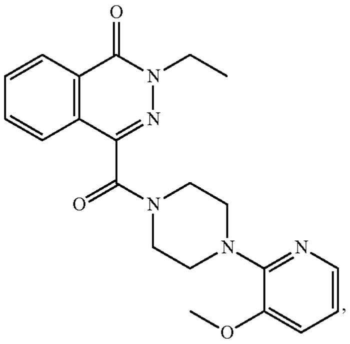
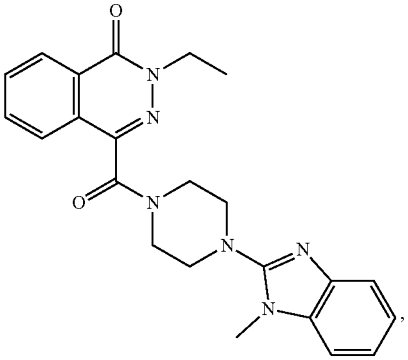
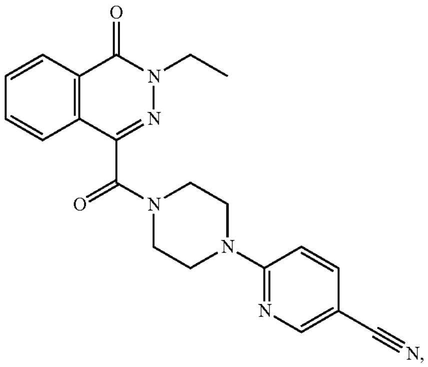
-continued
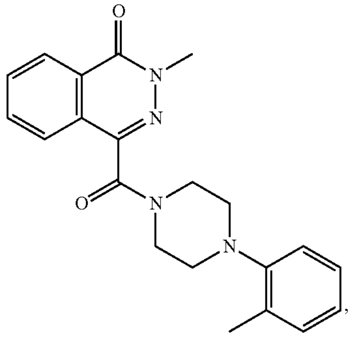
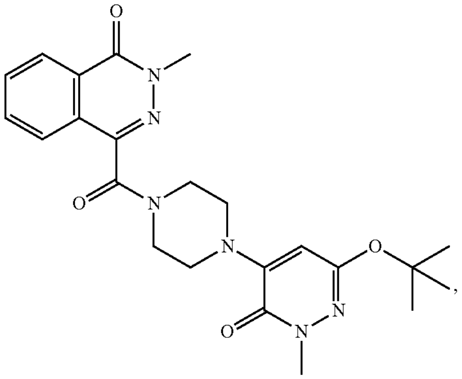
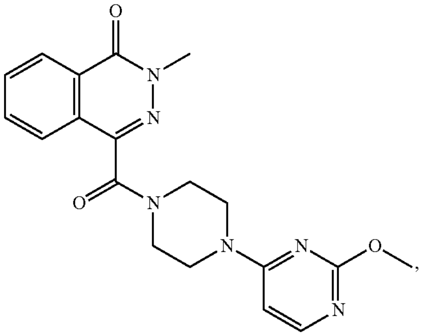
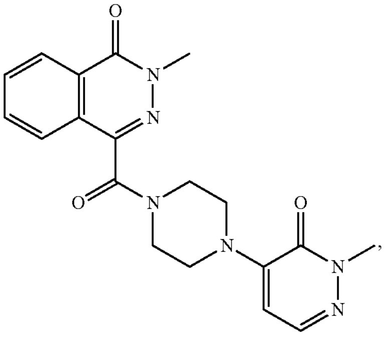
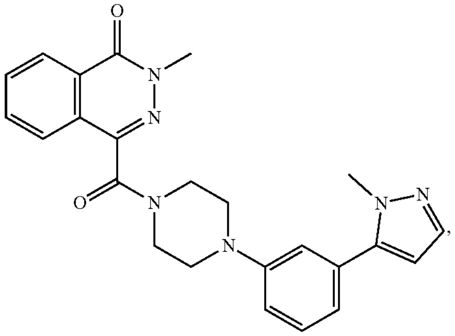

-continued
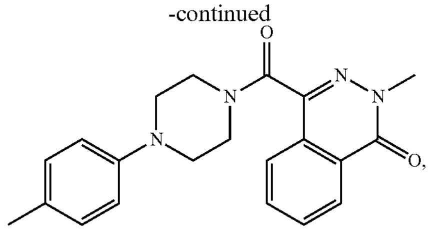
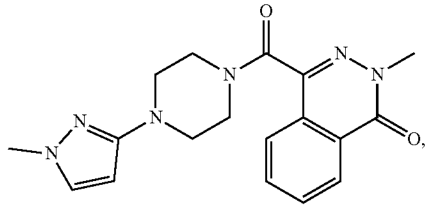
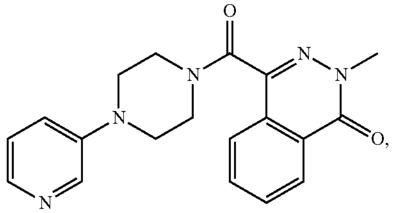
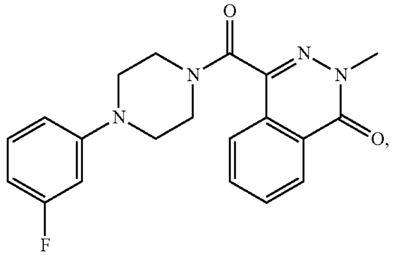
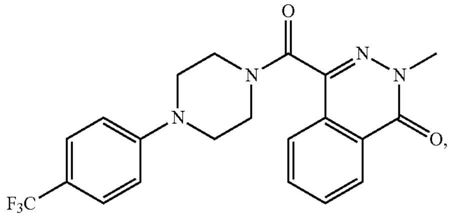
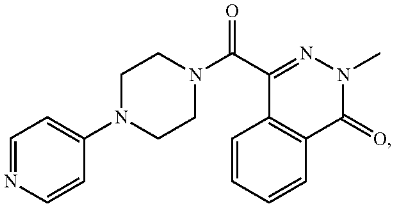
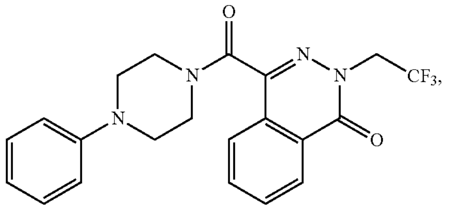
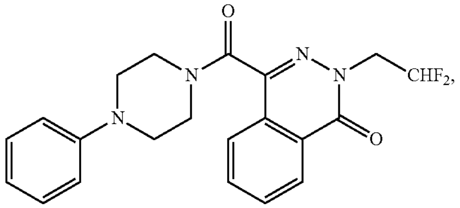
-continued
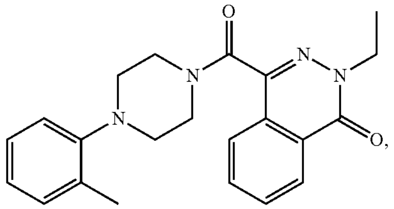
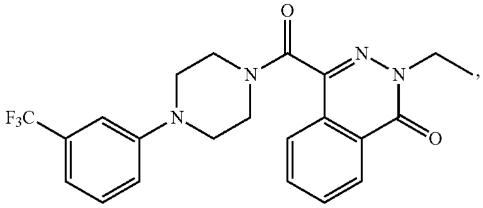
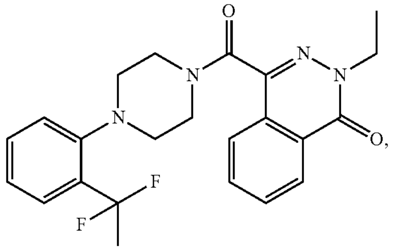
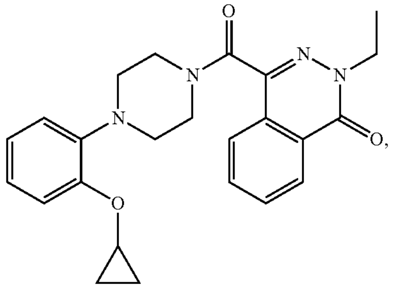
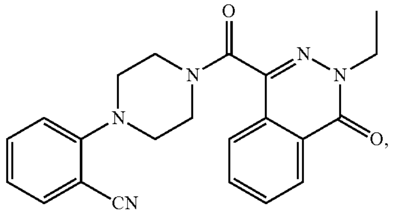
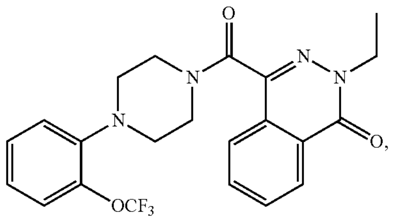
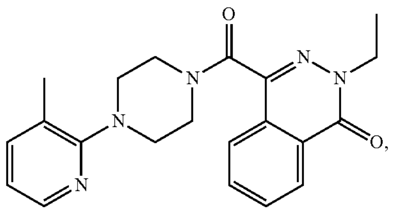

-continued
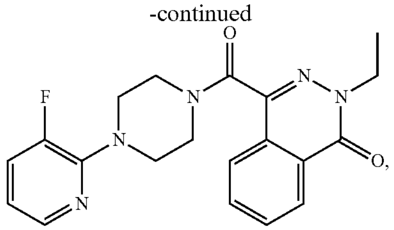
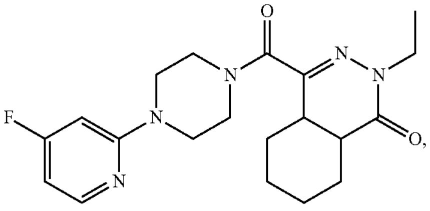
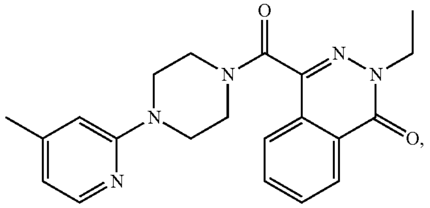
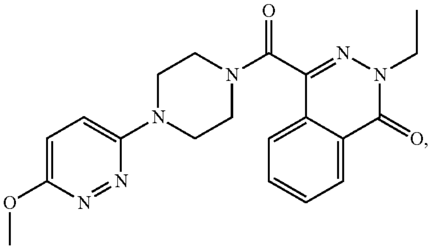
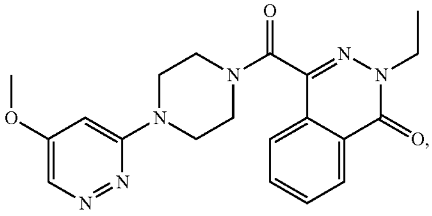
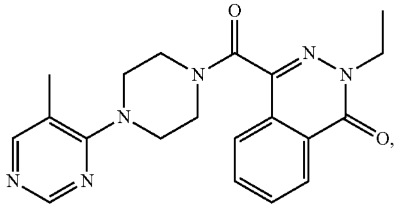
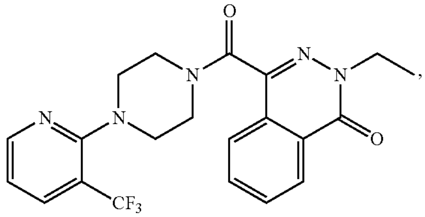
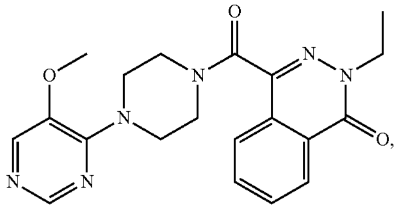
-continued
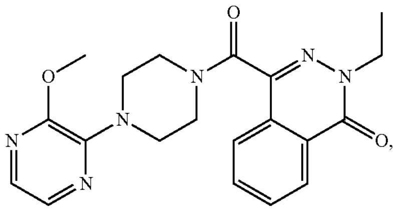
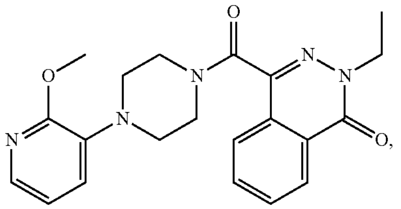
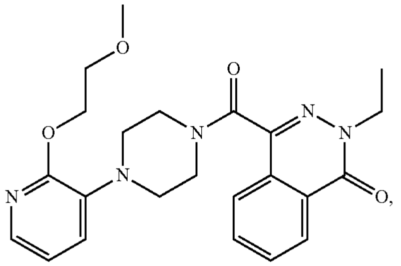
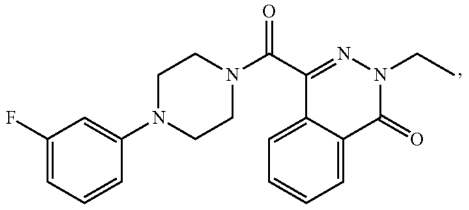
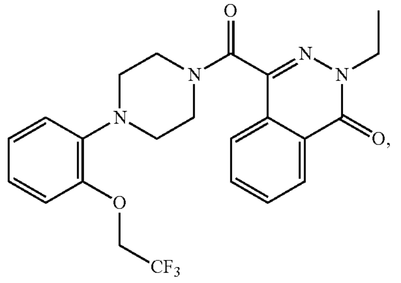
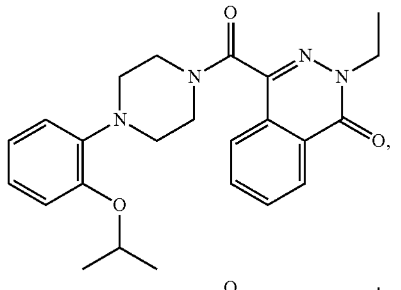
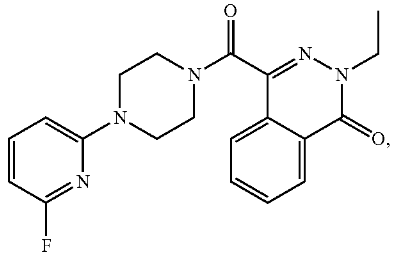

-continued
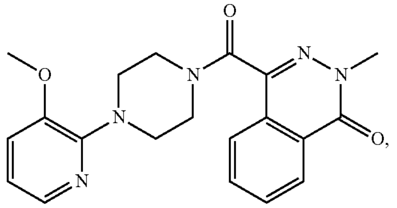
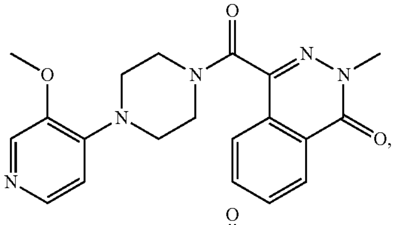
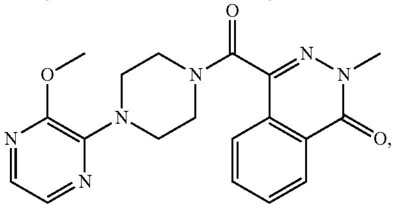
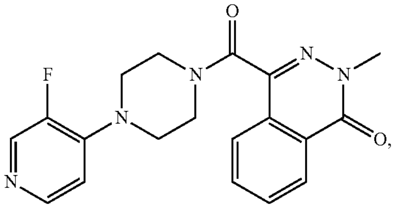
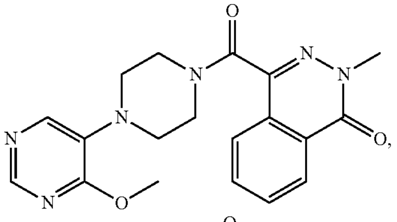
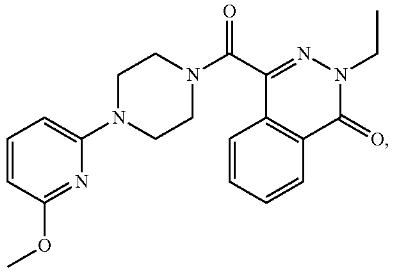
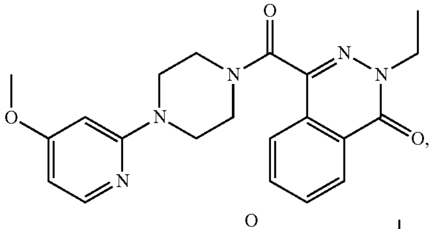
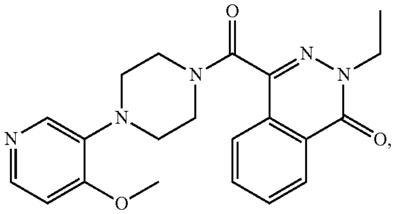
-continued
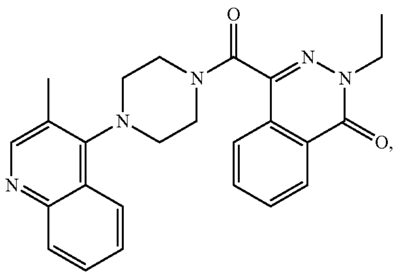
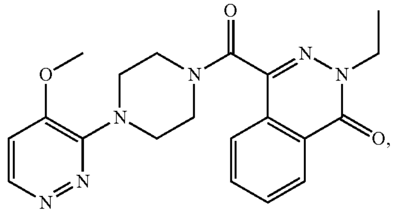
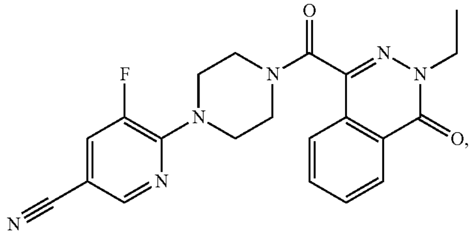
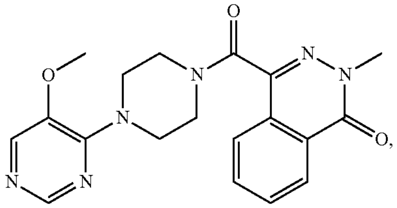
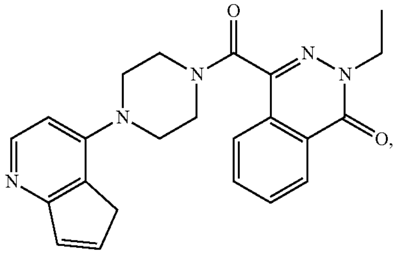
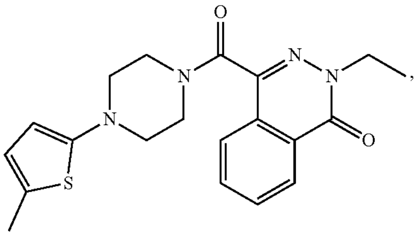
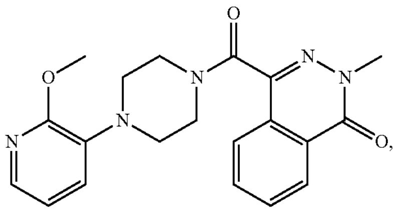

-continued
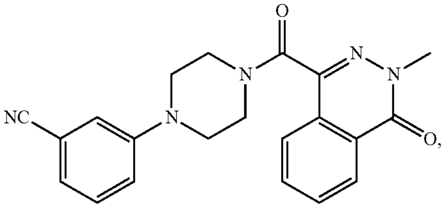
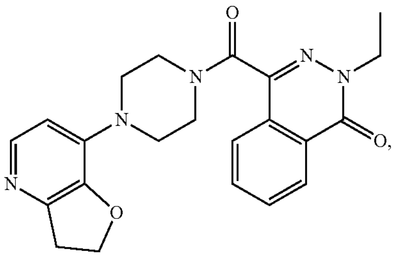
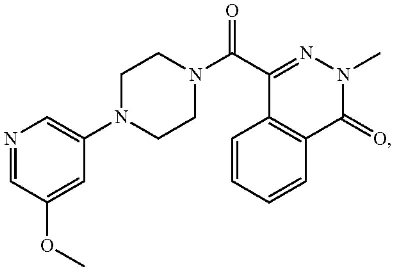
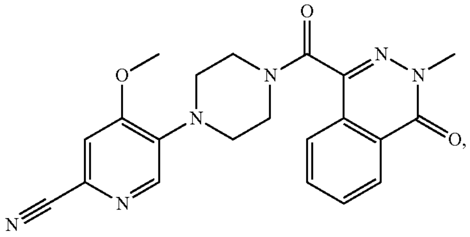
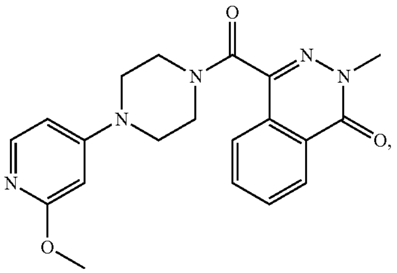
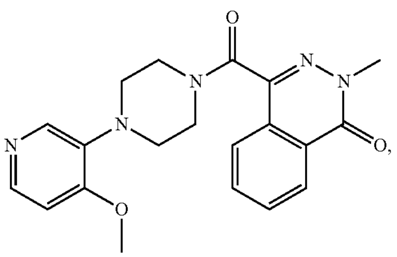
-continued
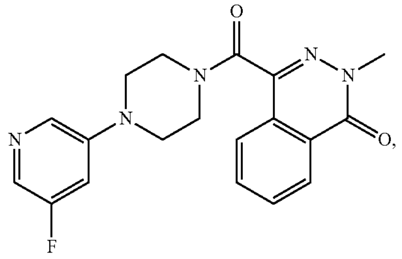
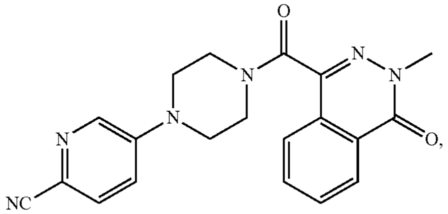
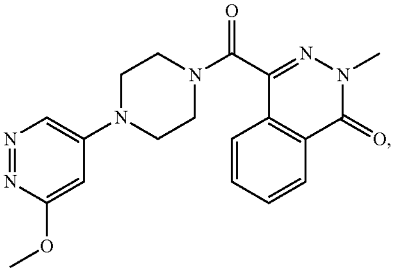
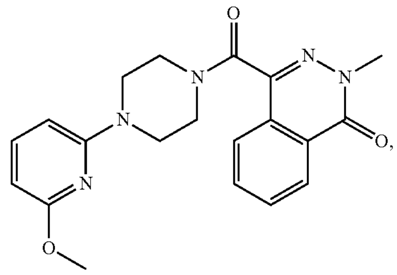
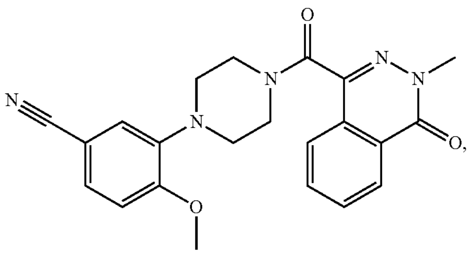
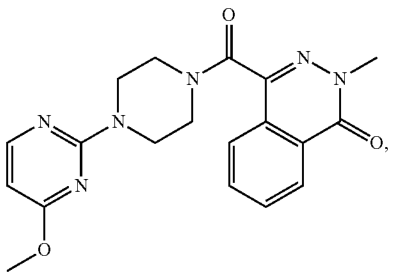

-continued
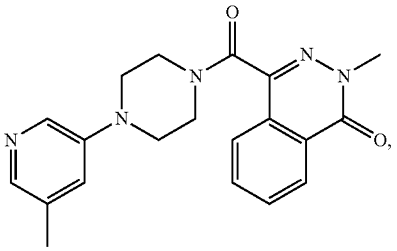
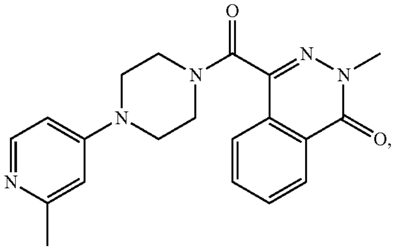
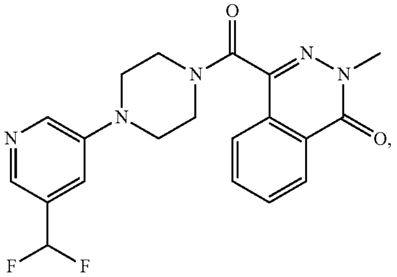
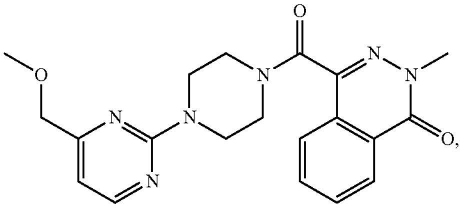
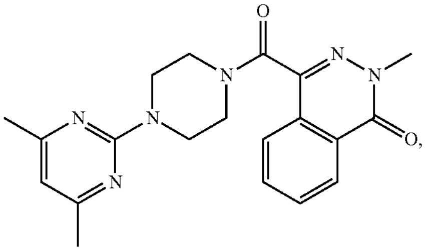
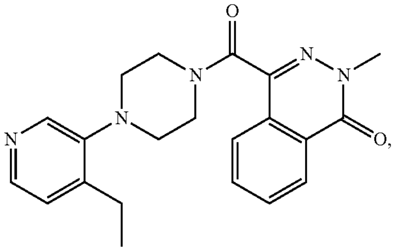
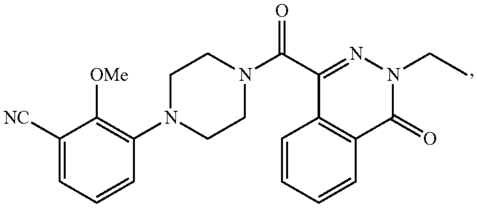
, or
-continued
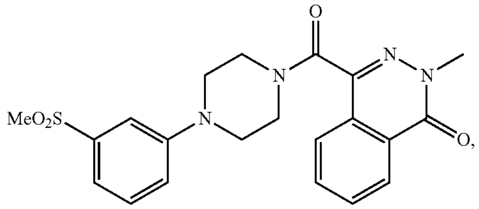
or a pharmaceutically acceptable salt of any one thereof.
In some aspects, the present disclosure provides a compound represented by the structure:
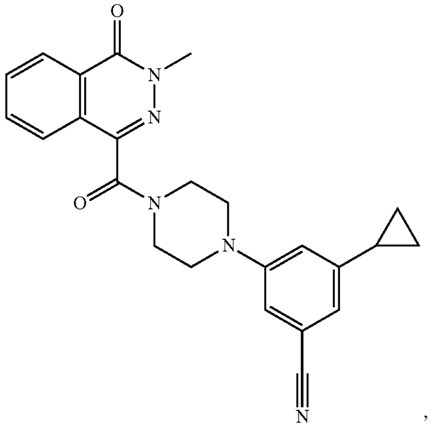
,
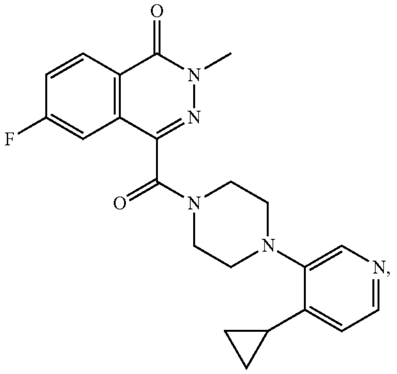
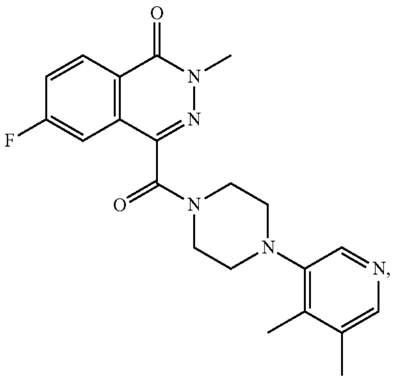

-continued
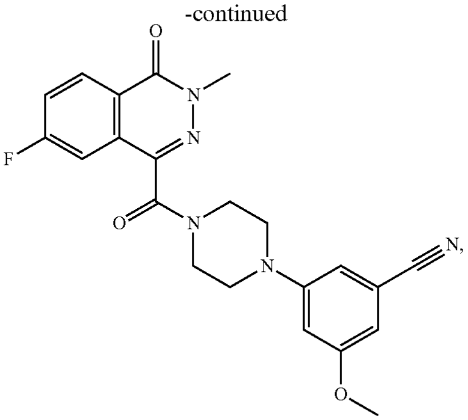
,
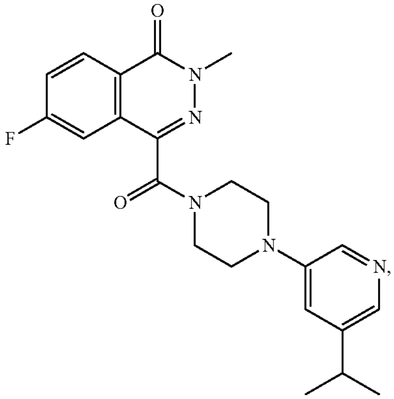
,
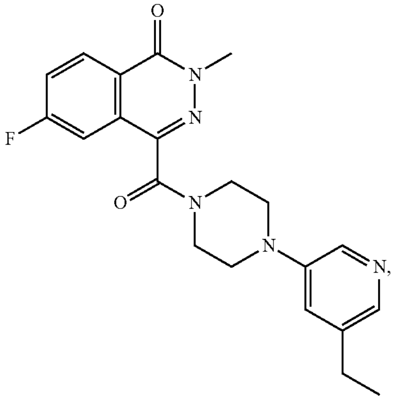
,
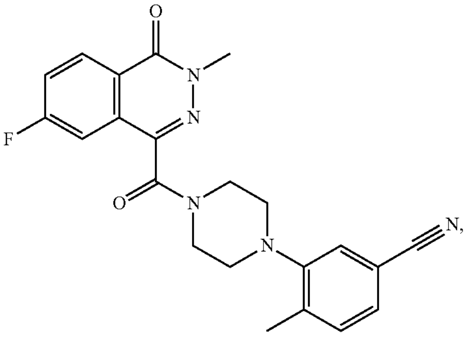
,
-continued
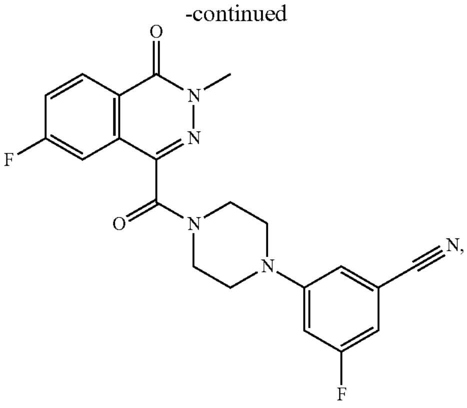
,
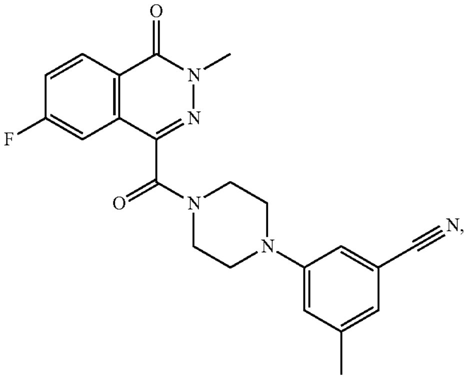
,
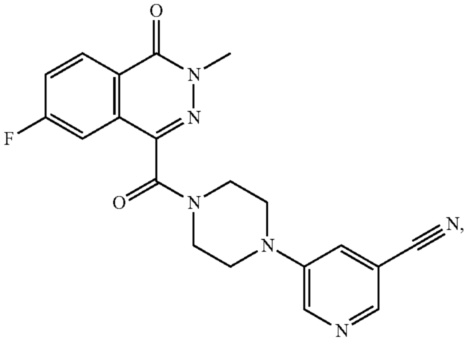
,
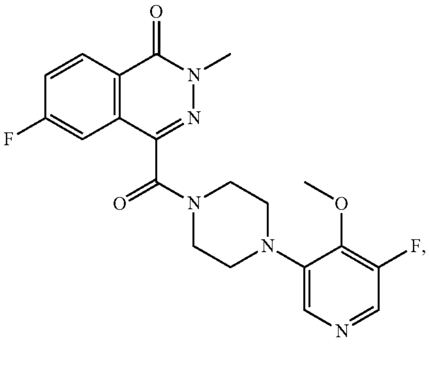
, -continued
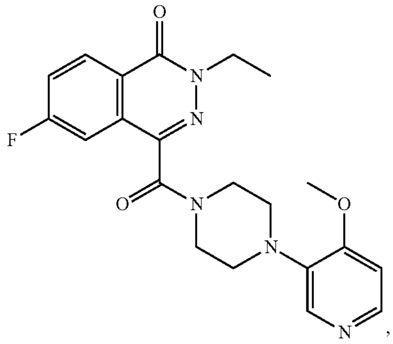
,
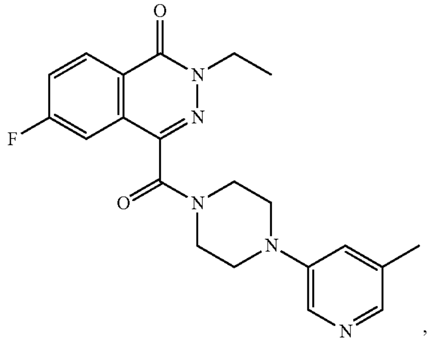
,
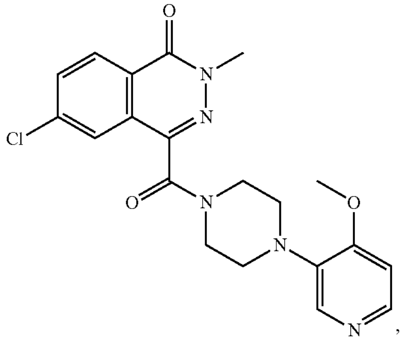
,
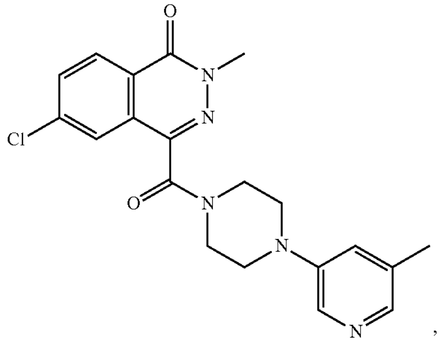
,
-continued
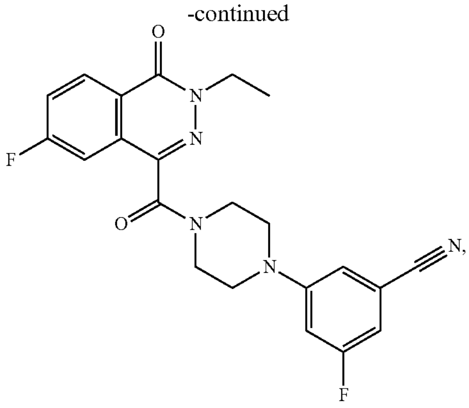
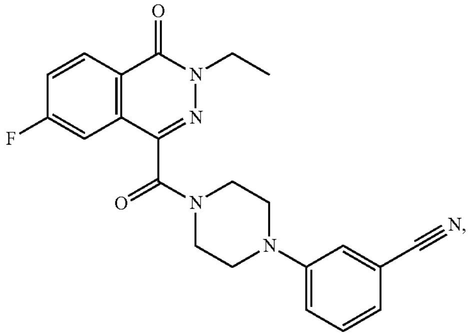
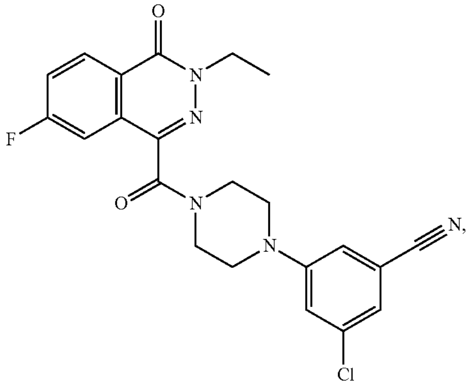
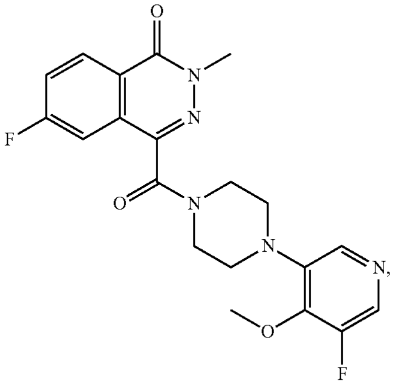

-continued
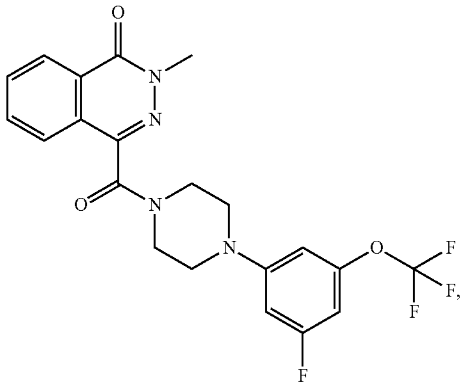
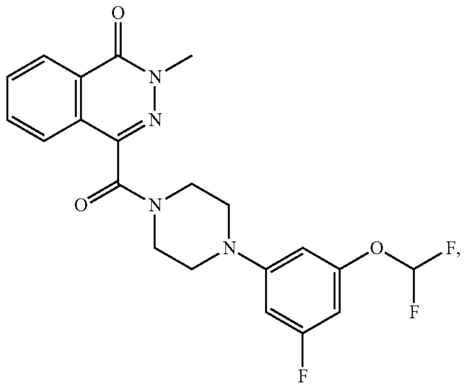
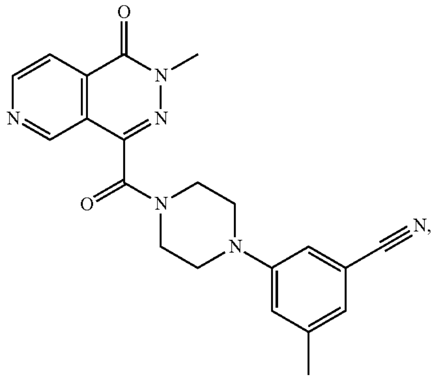
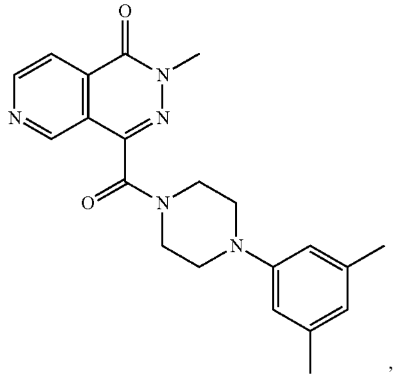
,
-continued
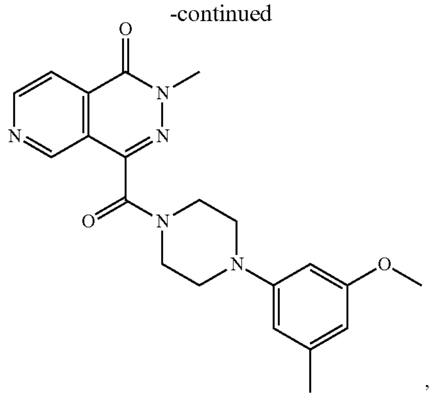
,
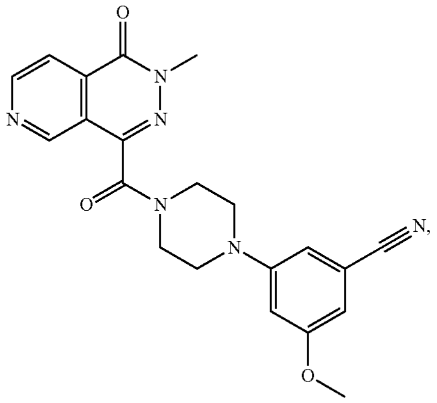
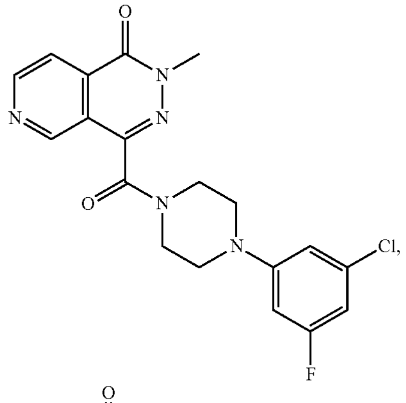
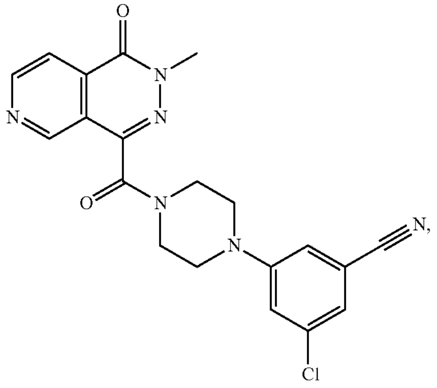

-continued
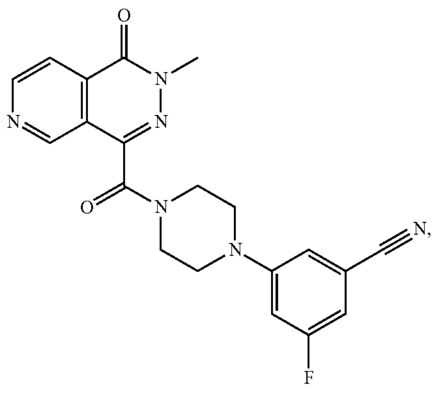
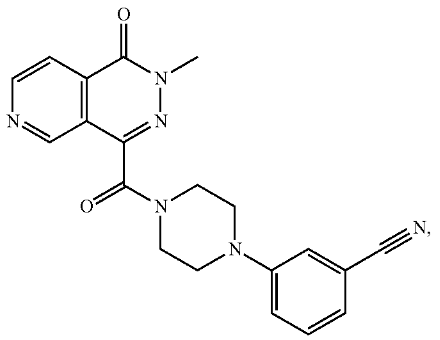
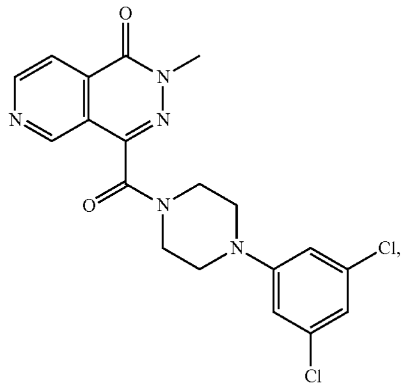
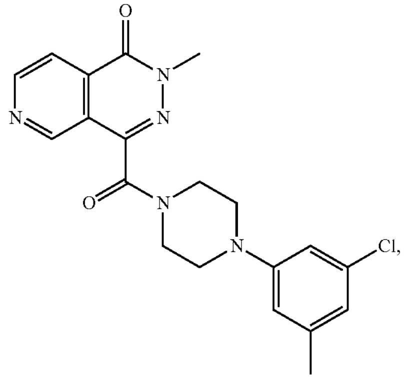
-continued
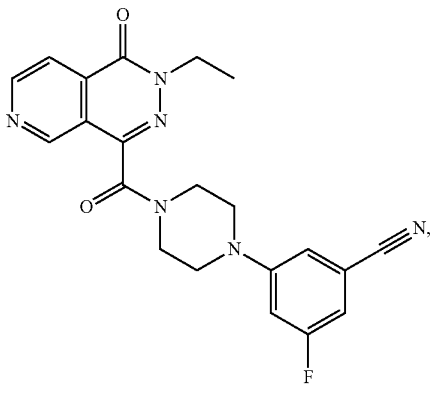
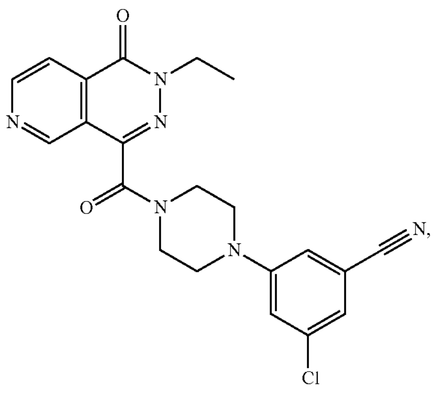
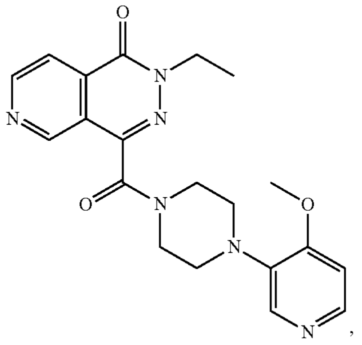
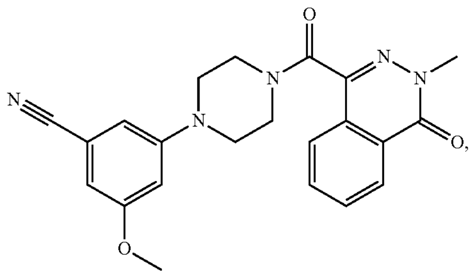
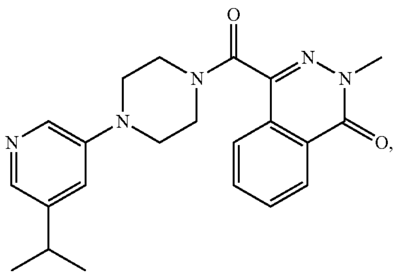

-continued
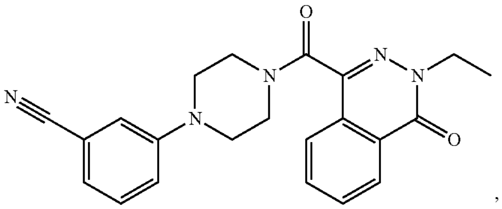
,
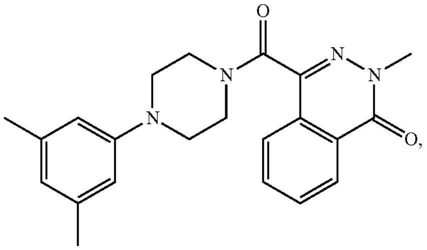
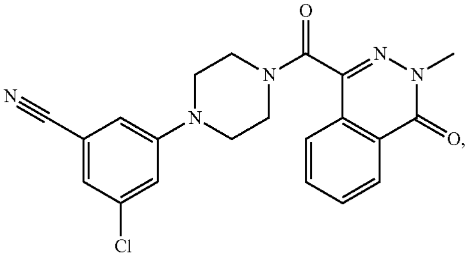
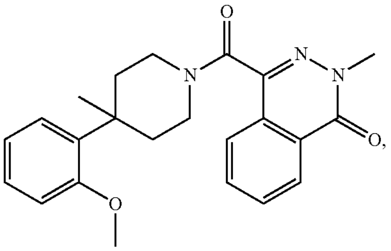
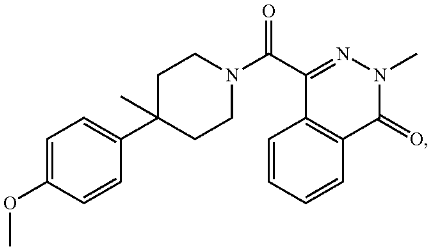
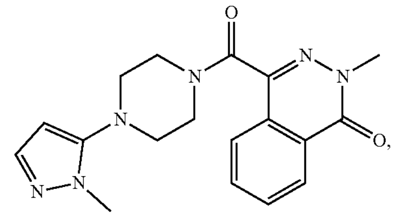
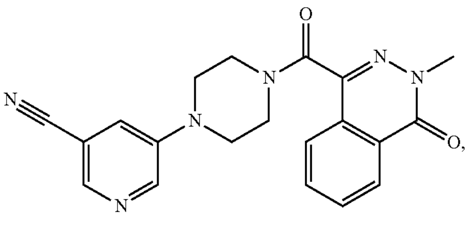
-continued
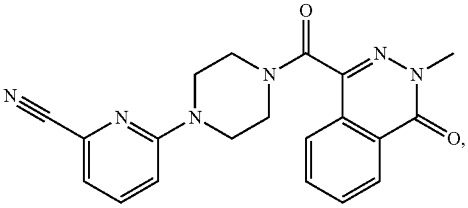
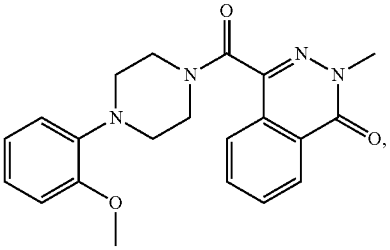
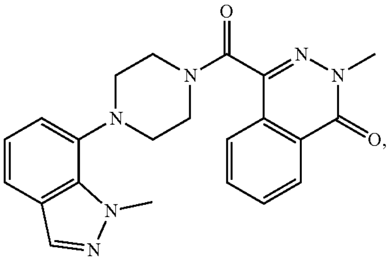
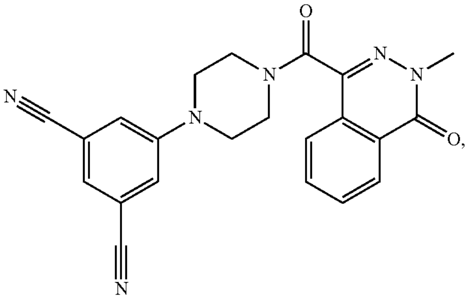
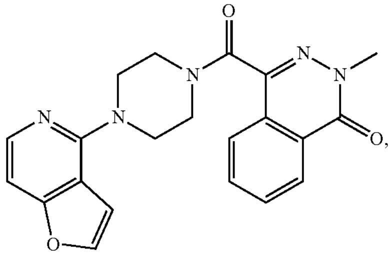
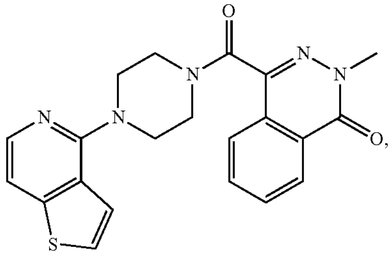

-continued

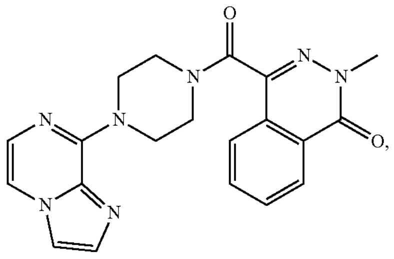

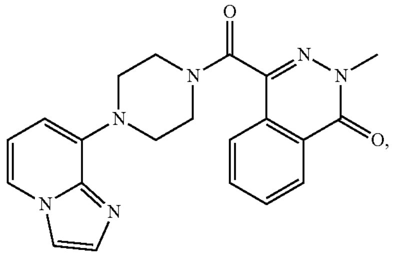

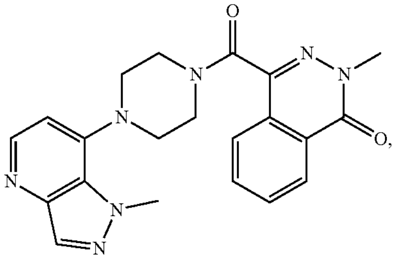

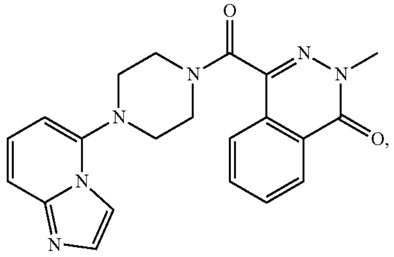

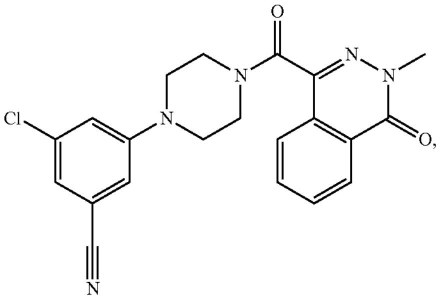

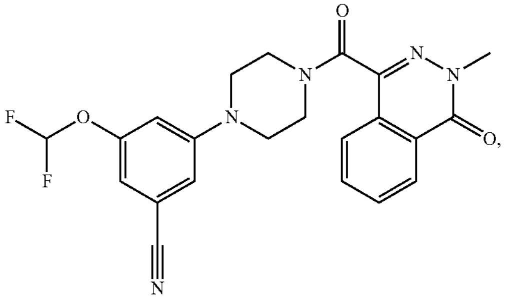

-continued

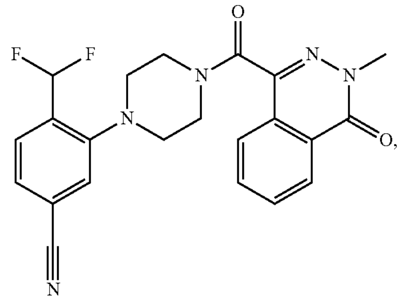

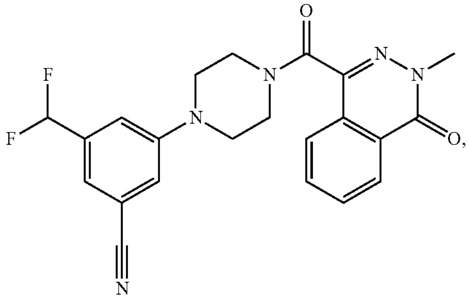

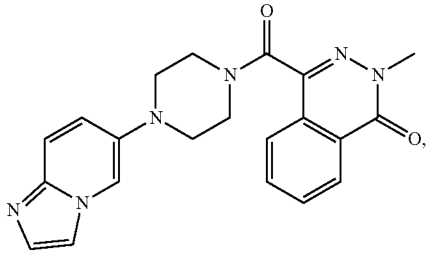

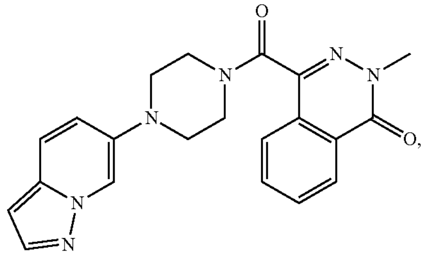

or

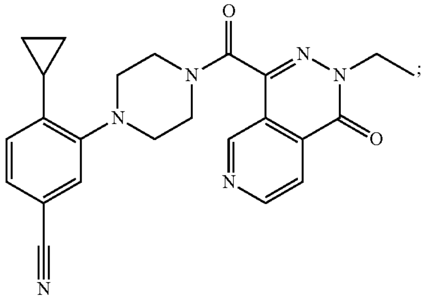

or a salt of any one thereof.

Methods of Treatment

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some aspects, the present disclosure provides methods of treating a cancer, comprising administering a compound or salt of the present disclosure to the cancer. In some embodiments, the cancer is a melanoma. In some embodiments, the cancer is ovarian cancer.

In some aspects, the present disclosure provides methods of inhibiting a A2058 cell, comprising administering a compound or salt of the present disclosure.

In some aspects, the present disclosure provides methods of inhibiting a PA1 cell, comprising administering a compound or salt of the present disclosure.

In some aspects, the present disclosure provides a method for killing a cancer cell or inhibiting cancer cell proliferation.

In some aspects, the present disclosure provides methods of inhibiting a A2058 cell, comprising administering a compound or salt of Formula (I), (II), (III), (IV), or (V), to the A2058 cell.

In some aspects, the present disclosure provides methods of inhibiting a PA1 cell, comprising administering a compound or salt of Formula (I), (II), (III), (IV), or (V), to the PAT cell.

In some aspects, the present disclosure provides methods of treating a cancer, comprising administering a compound or salt of Formula (I), (II), (III), (IV), or (V), to the cancer. In some embodiments, the cancer is a melanoma. In some embodiments, the cancer is ovarian cancer.

In some aspects, the present disclosure provides methods of inhibiting a melanoma cell, comprising administering a compound or salt of Formula (I), (II), (III), (IV), or (V), to the melanoma cell.

In some aspects, the present disclosure provides methods of inhibiting an ovarian cell, comprising administering a compound or salt of Formula (I), (II), (III), (IV), or (V), to the ovarian cell.

In some aspects, the present disclosure provides methods treating ovarian cancer, comprising administering to a subject in need thereof a compound or salt of Formula (I), (II), (III), (IV), or (V), or a pharmaceutical composition of any one thereof. In some embodiments, the method of treating ovarian cancer comprises administering to a subject in need thereof a compound or salt of Formula (I), or a pharmaceutical composition thereof. In some embodiments, the method of treating ovarian cancer comprises administering to a subject in need thereof a compound or salt of Formula (II), or a pharmaceutical composition thereof. In some embodiments, the method of treating ovarian cancer comprises administering to a subject in need thereof a compound or salt of Formula (III), or a pharmaceutical composition thereof. In some embodiments, the method of treating ovarian cancer comprises administering to a subject in need thereof a compound or salt of Formula (IV), or a pharmaceutical composition thereof. In some embodiments, the method of treating ovarian cancer comprises administering to a subject in need thereof a compound or salt of Formula (V), or a pharmaceutical composition thereof.

In some aspects, the present disclosure provides methods treating melanoma, comprising administering to a subject in need thereof a compound or salt of Formula (I), (II), (III), (IV), or (V), or a pharmaceutical composition of any one thereof. In some embodiments, the method of treating melanoma comprises administering to a subject in need thereof a compound or salt of Formula (I), or a pharmaceutical composition thereof. In some embodiments, the method of treating melanoma comprises administering to a subject in need thereof a compound or salt of Formula (II), or a pharmaceutical composition thereof. In some embodiments, the method of treating melanoma comprises administering to a subject in need thereof a compound or salt of Formula (III), or a pharmaceutical composition thereof. In some embodiments, the method of treating melanoma comprises administering to a subject in need thereof a compound or salt of Formula (IV), or a pharmaceutical composition thereof. In some embodiments, the method of treating melanoma comprises administering to a subject in need thereof a compound or salt of Formula (V), or a pharmaceutical composition thereof.

In some aspects, the present disclosure provides a method for killing a cancer cell or inhibiting cancer cell proliferation comprising contacting a cell with a compound represented by the structure of Formula (V):

(V)

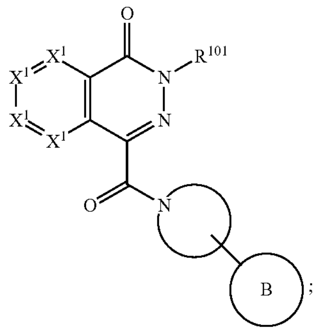

or a pharmaceutically acceptable salt wherein:

each $X^1$ is selected from $C(R^{100})$ and N;

$R^{100}$ is independently selected at each occurrence from: hydrogen, halogen, $—OR^{102}$, $—SR^{102}$, $—N(R^{102})_2$, $—C(O)R^{102}$, $—C(O)OR^{102}$, $—OC(O)R^{102}$, $—OC(O)N(R^{102})_2$, $—C(O)N(R^{102})_2$, $—N(R^{102})C(O)R^{102}$, $—N(R^{102})C(O)OR^{102}$, $—N(R^{102})C(O)N(R^{102})_2$, $—N(R^{102})S(O)_2(R^{102})$, $—S(O)R^{102}$, $—S(O)_2R^{102}$, $—S(O)_2N(R^{102})_2$, $—NO_2$, and —CN;

$C_{1-6}$ alkyl optionally substituted with one or more substituents independently selected from halogen, $—OR^{102}$, $—SR^{102}$, $—N(R^{102})_2$, $—C(O)R^{102}$, $—C(O)OR^{102}$, $—OC(O)R^{102}$, $—OC(O)N(R^{102})_2$, $—C(O)N(R^{102})_2$, $—N(R^{102})C(O)R^{102}$, $—N(R^{102})C(O)OR^{102}$, $-N(R^{102})C(O)N(R^{102})_2$, $-N(R^{102})S(O)_2(R^{102})$, $-S(O)R^{102}$, $-S(O)_2R^{102}$, $-S(O)_2N(R^{102})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{102}$, $-SR^{102}$, $-N(R^{102})_2$, $-C(O)R^{102}$, $-C(O)OR^{102}$, $-OC(O)R^{102}$, $-OC(O)N(R^{102})_2$, $-C(O)N(R^{102})_2$, $-N(R^{102})C(O)R^{102}$, $-N(R^{102})C(O)OR^{102}$, $-N(R^{102})C(O)N(R^{102})_2$, $-N(R^{102})S(O)_2(R^{102})$, $-S(O)R^{102}$, $-S(O)_2R^{102}$, $-S(O)_2N(R^{102})_2$, $-NO_2$, $=S$, $=O$, and $-CN$;

$R^{101}$ is independently selected from:

$C_{1-6}$ alkyl and $C_{2-6}$ alkenyl, any of which is optionally substituted with one or more substituents independently selected from halogen, $-OR^{103}$, $-SR^{103}$, $-N(R^{103})_2$, $-C(O)R^{103}$, $-C(O)OR^{103}$, $-OC(O)R^{103}$, $-OC(O)N(R^{103})_2$, $-C(O)N(R^{103})_2$, $-N(R^{103})C(O)R^{103}$, $-N(R^{103})C(O)OR^{103}$, $-N(R^{103})C(O)N(R^{103})_2$, $-N(R^{103})S(O)_2(R^{103})$, $-S(O)R^{103}$, $-S(O)_2R^{103}$, $-S(O)_2N(R^{103})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{103}$, $-SR^{103}$, $-N(R^{103})_2$, $-C(O)R^{103}$, $-C(O)OR^{103}$, $-OC(O)R^{103}$, $-OC(O)N(R^{103})_2$, $-C(O)N(R^{103})_2$, $-N(R^{103})C(O)R^{103}$, $-N(R^{103})C(O)OR^{103}$, $-N(R^{103})C(O)N(R^{103})_2$, $-N(R^{103})S(O)_2(R^{103})$, $-S(O)R^{103}$, $-S(O)_2R^{103}$, $-S(O)_2N(R^{103})_2$, $-NO_2$, $=S$, $=O$, and $-CN$;

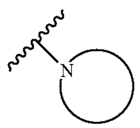

is 3- to 12-membered heterocyclene optionally substituted with one or more substituents independently selected from:

halogen, $-OR^{104}$, $-SR^{104}$, $-N(R^{104})_2$, $-C(O)R^{104}$, $-C(O)OR^{104}$, $-OC(O)R^{104}$, $-OC(O)N(R^{104})_2$, $-C(O)N(R^{104})_2$, $-N(R^{104})C(O)R^{104}$, $-N(R^{104})C(O)OR^{104}$, $-N(R^{104})C(O)N(R^{104})_2$, $-N(R^{104})S(O)_2(R^{104})$, $-S(O)R^{104}$, $-S(O)_2R^{104}$, $-S(O)_2N(R^{104})_2$, $-NO_2$, and $-CN$;

$C_{1-6}$ alkyl optionally substituted with one or more substituents independently selected from halogen, $-OR^{104}$, $-SR^{104}$, $-N(R^{104})_2$, $-C(O)R^{104}$, $-C(O)OR^{104}$, $-OC(O)R^{104}$, $-OC(O)N(R^{104})_2$, $-C(O)N(R^{104})_2$, $-N(R^{104})C(O)R^{104}$, $-N(R^{104})C(O)OR^{104}$, $-N(R^{104})C(O)N(R^{104})_2$, $-N(R^{104})S(O)_2(R^{104})$, $-S(O)R^{104}$, $-S(O)_2R^{104}$, $-S(O)_2N(R^{104})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{104}$, $-SR^{104}$, $-N(R^{104})_2$, $-C(O)R^{104}$, $-C(O)OR^{104}$, $-OC(O)R^{104}$, $-OC(O)N(R^{104})_2$, $-C(O)N(R^{104})_2$, $-N(R^{104})C(O)R^{104}$, $-N(R^{104})C(O)OR^{104}$, $-N(R^{104})C(O)N(R^{104})_2$, $-N(R^{104})S(O)_2(R^{104})$, $-S(O)R^{104}$, $-S(O)_2R^{104}$, $-S(O)_2N(R^{104})_2$, $-NO_2$, $=S$, $=O$, and $-CN$;

Ring B is selected from $C_{3-12}$ carbocycle and 3- to 12-membered heterocycle, any of which is optionally substituted with one or more substituents independently selected from:

halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, and $-CN$;

$C_{1-6}$ alkyl optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$;

$R^{102}$, $R^{103}$, $R^{104}$, and $R^{105}$ are independently selected at each occurrence from: hydrogen;

$C_{1-6}$ alkyl optionally substituted with one more substituents independently selected from halogen, $-O-C_{1-6}$ alkyl, $-O-C_{1-6}$ haloalkyl, $-NH_2$, $-NO_2$, $=O$, $-CN$, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, $-OH$, $-O-C_{1-6}$ alkyl, $-O-C_{1-6}$ haloalkyl, $-NH_2$, $-NO_2$, $=O$, and $-CN$; and $C_{3-10}$ carbocycle and 3- to 10-membered heterocycle optionally substituted with one or more substituents independently selected from: halogen, $-OH$, $-O-C_{1-6}$ alkyl, $-O-C_{1-6}$ haloalkyl, $-NH_2$, $-NO_2$, $=O$, and $-CN$.

In some embodiments, for the compound or salt of Formula (V), each $X^1$ is selected from $C(R^{100})$. In some embodiments, $R^{100}$ of $C(R^{100})$ is selected from hydrogen, halogen, $-OR^{102}$, $-SR^{102}$, $-N(R^{102})_2$, $-C(O)R^{102}$, $-C(O)OR^{102}$, $-OC(O)R^{102}$, $-OC(O)N(R^{102})_2$, $-C(O)N(R^{102})_2$, $-N(R^{102})C(O)R^{102}$, $-N(R^{102})C(O)OR^{102}$, $-N(R^{102})C(O)N(R^{102})_2$, $-N(R^{102})S(O)_2(R^{102})$, $-S(O)R^{102}$, $-S(O)_2R^{102}$, $-S(O)_2N(R^{102})_2$, $-NO_2$, and $-CN$. In some embodiments, $R^{100}$ of $C(R^{100})$ is selected from hydrogen, halogen, $-OR^{102}$, $-SR^{102}$, $-N(R^{102})_2$, $-C(O)R^{102}$, $-C(O)OR^{102}$, $-NO_2$, and $-CN$. In some embodiments, $R^{100}$ of $C(R^{100})$ is selected from hydrogen, halogen, $-OR^{102}$, and $-CN$. In some $R^{100}$ of $C(R^{100})$ is selected from hydrogen and halogen.

In some embodiments, for the compound or salt of Formula (V), $R^{100}$ of $C(R^{100})$ is selected from $C_{1-6}$ alkyl optionally substituted with one or more substituents independently selected from halogen, $-OR^{102}$, $-SR^{102}$, $-N(R^{102})_2$, $-C(O)R^{102}$, $-C(O)OR^{102}$, $-OC(O)R^{102}$, $-OC(O)N(R^{102})_2$, $-C(O)N(R^{102})_2$, $-N(R^{102})C(O)R^{102}$, $-N(R^{102})C(O)OR^{102}$, $-N(R^{102})C(O)N(R^{102})_2$, $-N(R^{102})S(O)_2(R^{102})$, $-S(O)R^{102}$, $-S(O)_2R^{102}$, $-S(O)_2N(R^{102})_2$, $-NO_2$, $=S$, $=O$, and $-CN$. In some embodiments, $R^{100}$ of $C(R^{100})$ is selected from $C_{1-6}$ alkyl optionally substituted with one or more substituents independently selected from halogen, $-OR^{102}$, $-SR^{102}$, $-N(R^{102})_2$, $-C(O)R^{102}$, $-C(O)OR^{102}$, $-NO_2$, $=S$, $=O$, and $-CN$. In some embodiments, $R^{100}$ of $C(R^{100})$ is selected from $C_{1-6}$ alkyl optionally substituted with one or more substituents independently selected from halogen, $-OR^{102}$, $-N(R^{102})_2$, $-NO_2$, $=S$, $=O$, and $-CN$. In some embodiments, $R^{100}$ of $C(R^{100})$ is selected from unsubstituted $C_{1-3}$ alkyl.

In some embodiments, for the compound or salt of Formula (V), $R^{100}$ of $C(R^{100})$ is selected from $C_{3-10}$ carbocycle and 3- to 10-membered heterocycle, any of which is optionally substituted with one or more substituents independently selected from halogen, $-OR^{102}$, $-SR^{102}$, $-N(R^{102})_2$, $-C(O)R^{102}$, $-C(O)OR^{102}$, $-OC(O)R^{102}$, $-OC(O)N(R^{102})_2$, $-C(O)N(R^{102})_2$, $-N(R^{102})C(O)R^{102}$, $-N(R^{102})C(O)OR^{102}$, $-N(R^{102})C(O)N(R^{102})_2$, $-N(R^{102})S(O)_2(R^{102})$, $-S(O)R^{102}$, $-S(O)_2R^{102}$, $-S(O)_2N(R^{102})_2$, $-NO_2$, $=S$, $=O$, and $-CN$. In some embodiments, $R^{100}$ of $C(R^{100})$ is selected from $C_{3-10}$ carbocycle and 3- to 10-membered heterocycle, any of which is optionally substituted with one or more substituents independently selected from halogen, $-OR^{102}$, $-SR^{102}$, $-N(R^{102})_2$, $-C(O)R^{102}$, $-C(O)OR^{102}$, $-NO_2$, $=S$, $=O$, and $-CN$. In some embodiments, $R^{100}$ of $C(R^{100})$ is selected from $C_{3-6}$ carbocycle and 3- to 6-membered heterocycle, any of which is optionally substituted with one or more substituents independently selected from halogen, $-OR^{102}$, $-SR^{102}$, $-N(R^{102})_2$, $-C(O)R^{102}$, $-C(O)OR^{102}$, $-NO_2$, $=S$, $=O$, and $-CN$. In some embodiments, $R^{100}$ of $C(R^{100})$ is selected from $C_{3-6}$ carbocycle and 3- to 6-membered heterocycle, any of which is optionally substituted with one or more substituents independently selected from halogen, $-OR^{102}$, $-N(R^{102})_2$, $-NO_2$, $=S$, $=O$, and $-CN$. In some embodiments, $R^{100}$ of $C(R^{100})$ is selected from unsubstituted $C_{3-6}$ carbocycle and unsubstituted 3- to 6-membered heterocycle.

In some embodiments, for the compound or salt of Formula (V), at least one of $X^1$ is selected from N.

In some embodiments, Formula (V) is represented by a structure selected from:

(V-a)

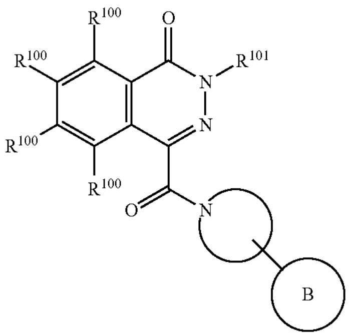

,

-continued (V-b)

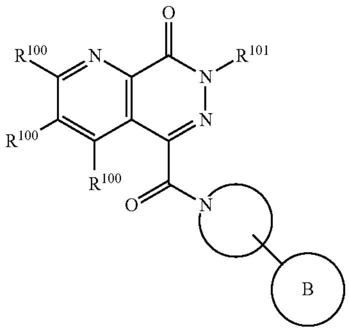

, (V-c)

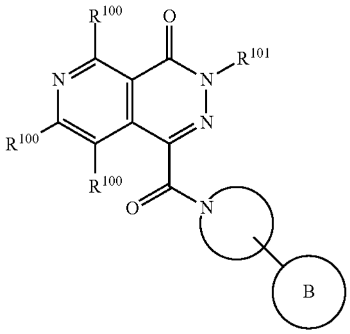

, (V-d)

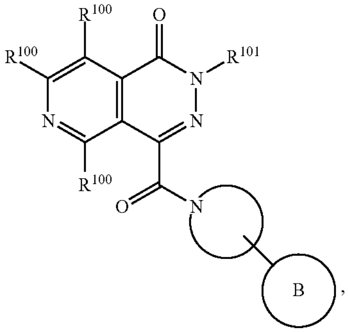

, and (V-e)

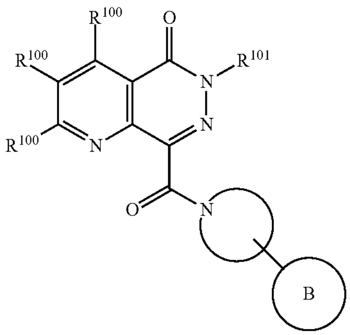

.

In some embodiments, a compound or salt of the disclosure is represented by Formula (V-a):

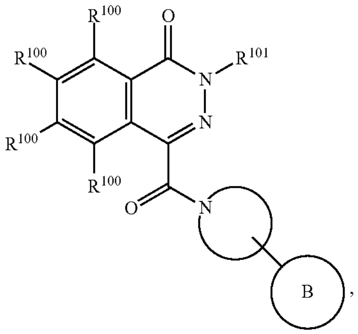

(V-a)

or a pharmaceutically acceptable salt thereof, wherein $R^{100}$, $R^{101}$,

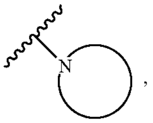 [SMILES: *N]

and Ring B, are as defined in Formula (V).

In some embodiments, a compound or salt of the disclosure is represented by Formula (V-b):

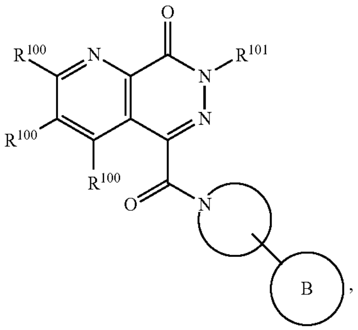

(V-b)

or a pharmaceutically acceptable salt thereof, wherein $R^{100}$, $R^{101}$,

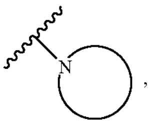 [SMILES: *N]

and Ring B, are as defined in Formula (V).

In some embodiments, a compound or salt of the disclosure is represented by Formula (V-c):

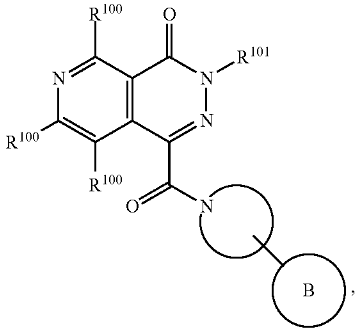

(V-c)

or a pharmaceutically acceptable salt thereof, wherein $R^{100}$, $R^{101}$,

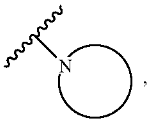 [SMILES: *N]

and Ring B, are as defined in Formula (V).

In some embodiments, a compound or salt of the disclosure is represented by Formula (V-c):

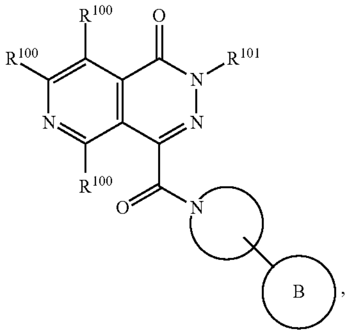

(V-d)

or a pharmaceutically acceptable salt thereof, wherein $R^{100}$, $R^{101}$,

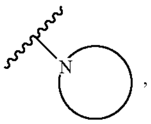 [SMILES: *N]

and Ring B, are as defined in Formula (V).

In some embodiments, a compound or salt of the disclosure is represented by Formula (V-e):

(V-e)

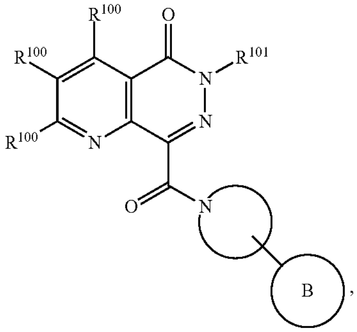

or a pharmaceutically acceptable salt thereof, wherein $R^{100}$, $R^{101}$,

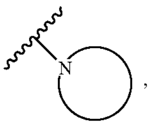 [SMILES: *N]

and Ring B, are as defined in Formula (V).

In some embodiments, Formula (V) is represented by a structure from Formula (V-b), Formula (V-c), Formula (V-d), and Formula (V-e). In some embodiments, the structure of Formula (V) is selected from (V-b)

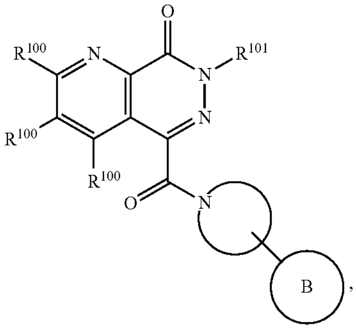

(V-c)

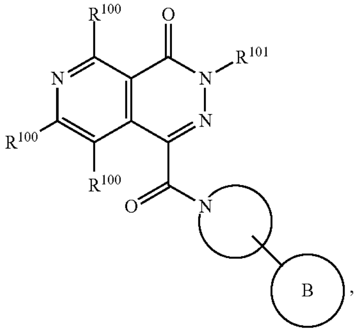

-continued (V-d)

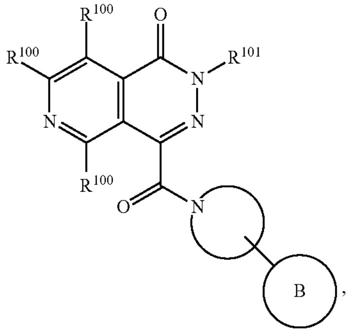

and (V-e)

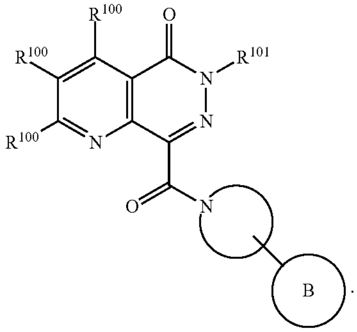

In some embodiments, for the compound or salt of Formula (V), (V-b), (V-c), (V-d), or (V-e), each $R^{100}$ is independently selected from: hydrogen, halogen, —$OR^{102}$, —$N(R^{102})_2$, —$C(O)R^{102}$, —$NO_2$, and —CN; $C_{1-6}$ alkyl optionally substituted with one or more substituents independently selected from halogen, —$OR^{102}$, —$N(R^{102})_2$, —$C(O)R^{102}$, —$NO_2$, and —CN; and $C_{3-10}$ carbocycle and 3- to 10-membered heterocycle, any of which is optionally substituted with one or more substituents independently selected halogen, —$OR^{102}$, —$N(R^{102})_2$, —$C(O)R^{102}$, —$NO_2$, and —CN. In some embodiments, each $R^{100}$ is independently selected from hydrogen, halogen, —$OR^{102}$, —$N(R^{102})_2$, —$C(O)R^{102}$, —$NO_2$, and —CN; and $R^{102}$ is selected from hydrogen and $C_{1-3}$ alkyl. In some embodiments, each $R^{100}$ is independently hydrogen. In some embodiments, each $R^{100}$ is independently selected from hydrogen and halogen. In some embodiments, each $R^{100}$ is hydrogen.

In some embodiments, for the compound or salt of Formula (V), (V-b), (V-c), (V-d), or (V-e), $R^{101}$ is $C_{1-6}$ alkyl optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, ═S, ═O, and —CN. In some embodiments, $R^{101}$ is $C_{1-6}$ alkyl optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, ═S, ═O, and —CN. In some embodiments, $R^{101}$ is $C_{1-3}$ alkyl optionally substituted with one or more substituents independently selected from halogen, —$OR^{103}$, —$N(R^{103})_2$, —$NO_2$, ═S, ═O, and —CN.

In some embodiments, for the compound or salt of Formula (V), (V-b), (V-c), (V-d), or (V-e), $R^{101}$ is $C_{1-6}$ alkyl optionally substituted with one or more substituents independently selected from halogen, —$OR^{103}$, —$N(R^{103})_2$, —$C(O)R^{103}$, —$NO_2$, ═S, ═O, and —CN; and $R^{103}$ is selected from hydrogen and $C_{1-3}$ alkyl. In some embodiments, $R^{101}$ is unsubstituted $C_{1-3}$ alkyl.

In some embodiments, for the compound or salt of Formula (V), (V-b), (V-c), (V-d), or (V-e), $R^{101}$ is $C_{3-10}$ carbocycle and 3- to 10-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, ═S, ═O, and —CN. In some embodiments, $R^{101}$ is $C_{3-10}$ carbocycle and 3- to 10-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, ═S, ═O, and —CN. In some embodiments, $R^{101}$ is $C_{3-6}$ carbocycle and 3- to 6-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, ═S, ═O, and —CN. In some embodiments, $R^{101}$ is unsubstituted $C_{3-6}$ carbocycle and unsubstituted 3- to 6-membered heterocycle.

In some embodiments, for the compound or salt of Formula (V), (V-b), (V-c), (V-d), or (V-e), the optionally substituted 3- to 12-membered heterocyclene of

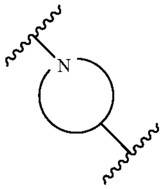

is selected from optionally substituted 3-membered heterocyclene, optionally substituted 4-membered heterocyclene, optionally substituted 5-membered heterocyclene, optionally substituted 6-membered heterocyclene, optionally substituted 7-membered heterocyclene, optionally substituted 8-membered heterocyclene, optionally substituted 9-membered heterocyclene, optionally substituted 10-membered heterocyclene, optionally substituted 11-membered heterocyclene, and optionally substituted 12-membered heterocyclene. In some embodiments, the optionally substituted 3- to 12-membered heterocyclene of

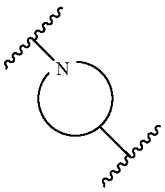

is selected from optionally substituted 3- to 4-membered heterocyclene, optionally substituted 3- to 5-membered heterocyclene, optionally substituted 3- to 6-membered heterocyclene, optionally substituted 3- to 7-membered heterocyclene, optionally substituted 3- to 8-membered heterocyclene, optionally substituted 3- to 9-membered heterocyclene, optionally substituted 3- to 10-membered heterocyclene, and optionally substituted 3- to 11-membered heterocyclene.

In some embodiments, for the compound or salt of Formula (V), (V-b), (V-c), (V-d), or (V-e),

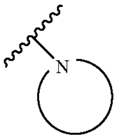 [SMILES: *N]

is 3- to 10-membered heterocyclene optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, ═S, ═O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, ═S, ═O, and —CN.

In some embodiments, for the compound or salt of Formula (V), (V-b), (V-c), (V-d), or (V-e),

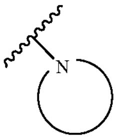 [SMILES: *N]

is 3- to 6-membered heterocyclene optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, ═S, ═O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN.

In some embodiments, for the compound or salt of Formula (V), (V-b), (V-c), (V-d), or (V-e),

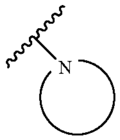 [SMILES: *N]

is 5- to 6-membered saturated heterocyclene optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN.

In some embodiments, for the compound or salt of Formula (V), (V-b), (V-c), (V-d), or (V-e),

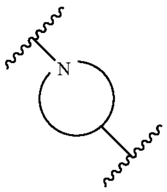

is selected from saturated 5- to 6-membered heterocyclene, each of which is optionally substituted with one or more substituents independently selected from halogen-$OR^{104}$, —$N(R^{104})_2$, —$C(O)R^{104}$, —$C(O)OR^{104}$, —$C(O)N(R^{104})_2$, —$NO_2$, —CN; and $C_{1-6}$ alkyl optionally substituted with one or more substituents independently selected from halogen, —$OR^{104}$, —$N(R^{104})_2$, —$C(O)R^{104}$, —$C(O)OR^{104}$, —$C(O)N(R^{104})_2$—$NO_2$, =S, =O, and —CN; and $R^{104}$ is selected from hydrogen and $C_{1-3}$ alkyl.

In some embodiments, for the compound or salt of Formula (V), (V-b), (V-c), (V-d), or (V-e),

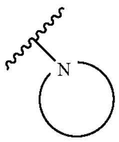 [SMILES: *N]

is piperidinylene and piperazinylene, each of which is optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN.

In some embodiments, for the compound or salt of Formula (V), (V-b), (V-c), (V-d), or (V-e),

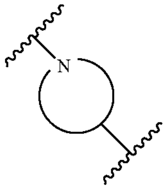

is selected from piperidinylene and piperazinylene, each of which is optionally substituted with one or more substituents independently selected from halogen, —$OR^{104}$, —$N(R^{104})_2$, —$C(O)R^{104}$, —$C(O)OR^{104}$, —$C(O)N(R^{104})_2$, —$NO_2$, —CN; and $C_{1-6}$ alkyl optionally substituted with one or more substituents independently selected from halogen, —$OR^{104}$, —$N(R^{104})_2$, —$C(O)R^{104}$, —$C(O)OR^{104}$, —$C(O)N(R^{104})_2$—$NO_2$, =S, =O, and —CN; and $R^{104}$ is selected from hydrogen and $C_{1-3}$ alkyl.

In some embodiments, for the compound or salt of Formula (V), (V-b), (V-c), (V-d), and (V-e),

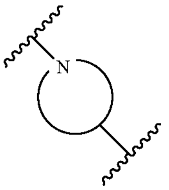

is

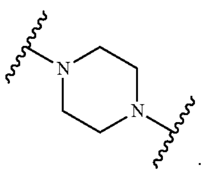

.

In some embodiments,

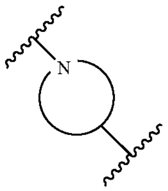

is unsubstituted piperazinylene.

In some embodiments, for the compound or salt of Formula (V), (V-b), (V-c), (V-d), or (V-e), the optionally substituted $C_{3-12}$ carbocycle of Ring B is selected from optionally substituted $C_3$ carbocycle, optionally substituted $C_4$ carbocycle, optionally substituted $C_5$ carbocycle, optionally substituted $C_6$ carbocycle, optionally substituted $C_7$ carbocycle, optionally substituted $C_8$ carbocycle, optionally substituted $C_9$ carbocycle, optionally substituted $C_{10}$ carbocycle, optionally substituted $C_{11}$ carbocycle, and optionally substituted $C_{12}$ carbocycle. In some embodiments, the optionally substituted $C_{3-12}$ carbocycle of Ring B is selected from optionally substituted $C_{3-4}$ carbocycle, optionally substituted $C_{3-5}$ carbocycle, optionally substituted $C_{3-6}$ carbocycle, optionally substituted $C_{3-7}$ carbocycle, optionally substituted $C_{3-8}$ carbocycle, optionally substituted $C_{3-9}$ carbocycle, optionally substituted $C_{3-10}$ carbocycle, and optionally substituted $C_{3-11}$ carbocycle.

In some embodiments, for the compound or salt of Formula (V), (V-b), (V-c), (V-d), or (V-e), the optionally substituted 3- to 12-membered heterocycle of Ring B is selected from optionally substituted 3-membered heterocycle, optionally substituted 4-membered heterocycle, optionally substituted 5-membered heterocycle, optionally substituted 6-membered heterocycle, optionally substituted 7-membered heterocycle, optionally substituted 8-membered heterocycle, optionally substituted 9-membered heterocycle, optionally substituted 10-membered heterocycle, optionally substituted 11-membered heterocycle, and optionally substituted 12-membered heterocycle. In some embodiments, the optionally substituted 3- to 12-membered heterocycle of Ring B is selected from optionally substituted 3- to 4-membered heterocycle, optionally substituted 3- to 5-membered heterocycle, optionally substituted 3- to 6-membered heterocycle, optionally substituted 3- to 7-membered heterocycle, optionally substituted 3- to 8-membered heterocycle, optionally substituted 3- to 9-membered heterocycle, optionally substituted 3- to 10-membered heterocycle, and optionally substituted 3- to 11-membered heterocycle.

In some embodiments, for the compound or salt of Formula (V), (V-b), (V-c), (V-d), or (V-e), Ring B is selected from $C_{3-12}$ carbocycle and 3- to 12-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, and —CN. In some embodiments, Ring B is selected from $C_{3-12}$ carbocycle and 3- to 12-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—NO_2$, and —CN.

In some embodiments, for the compound or salt of Formula (V), (V-b), (V-c), (V-d), or (V-e), Ring B is selected from $C_{3-12}$ carbocycle and 3- to 12-membered heterocycle, any of which is optionally substituted with one or more $C_{1-6}$ alkyl optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN. In some embodiments, Ring B is selected from $C_{3-12}$ carbocycle and 3- to 12-membered heterocycle, any of which is optionally substituted with one or more $C_{1-6}$ alkyl optionally substituted with one or more substituents independently selected from halogen, $—OR^{105}$, $—SR^{105}$, $—N(R^{105})_2$, $—C(O)R^{105}$, $—C(O)OR^{105}$, $—NO_2$, =S, =O, and —CN. In some embodiments, Ring B is selected from $C_{3-12}$ carbocycle and 3- to 12-membered heterocycle, any of which is optionally substituted with one or more $C_{1-3}$ alkyl optionally substituted with one or more substituents independently selected from halogen, $—OR^{105}$, $—SR^{105}$, $—N(R^{105})_2$, $—C(O)R^{105}$, $—C(O)OR^{105}$, $—NO_2$, =S, =O, and —CN. In some embodiments, Ring B is selected from $C_{3-12}$ carbocycle and 3- to 12-membered heterocycle, any of which is optionally substituted with one or more unsubstituted $C_{1-3}$ alkyl.

In some embodiments, for the compound or salt of Formula (V), (V-b), (V-c), (V-d), or (V-e), Ring B is selected from $C_{3-12}$ carbocycle and 3- to 12-membered heterocycle, any of which is optionally substituted with one or more $C_{3-10}$ carbocycle and 3- to 10-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN. In some embodiments, Ring B is selected from $C_{3-12}$ carbocycle and 3- to 12-membered heterocycle, any of which is optionally substituted with one or more $C_{3-10}$ carbocycle and 3- to 10-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—NO_2$, =S, =O, and —CN. In some embodiments, Ring B is selected from $C_{3-12}$ carbocycle and 3- to 12-membered heterocycle, any of which is optionally substituted with one or more unsubstituted $C_{3-10}$ carbocycle and unsubstituted 3- to 10-membered heterocycle.

In some embodiments, for the compound or salt of Formula (V), (V-b), (V-c), (V-d), or (V-e), Ring B is $C_{3-6}$ carbocycle optionally substituted with one or more substituents independently selected from halogen, $—OR^{105}$, $—N(R^{105})_2$, $—C(O)R^{105}$, $—NO_2$, —CN; and $C_{1-6}$ alkyl optionally substituted with one or more substituents independently selected from halogen, —$OR^{105}$, —$N(R^{105})_2$, —$C(O)R^{105}$, —$NO_2$, and —CN; and $R^{105}$ is selected from hydrogen and $C_{1-3}$ alkyl. In some embodiments, Ring B is phenyl optionally substituted with one or more substituents independently selected from halogen, —$OR^{105}$, —$N(R^{105})_2$, —$C(O)R^{105}$, —$NO_2$, —CN; and $C_{1-6}$ alkyl optionally substituted with one or more substituents independently selected from halogen, —$OR^{105}$, —$N(R^{105})_2$, —$C(O)R^{105}$, —$NO_2$, and —CN; and $R^{105}$ is selected from hydrogen and $C_{1-3}$ alkyl.

In some embodiments, for the compound or salt of Formula (V), (V-b), (V-c), (V-d), or (V-e), Ring B is phenyl optionally substituted with one or more substituents independently selected from halogen and $C_{1-6}$ alkyl optionally substituted with one or more substituents independently selected from halogen and —O—$C_{1-3}$ alkyl. In some embodiments, Ring B is selected from

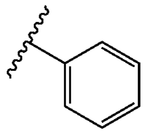 and 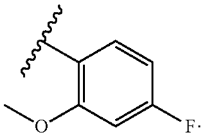

In some embodiments, Ring B is

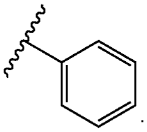

In some embodiments, Ring B is

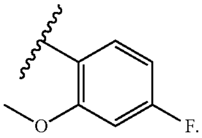 [SMILES: *c1ccc(F)cc1OC]

In some embodiments, Ring B is selected from

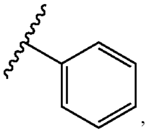, 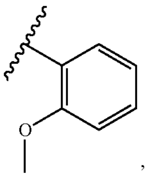, 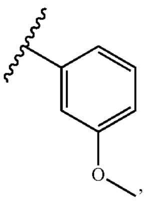, 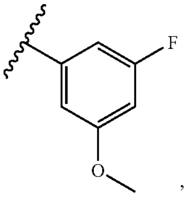, and 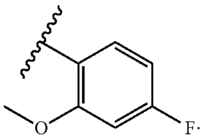

In some embodiments, Ring B is

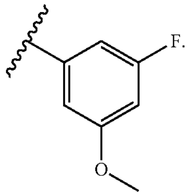 [SMILES: *c1cc(F)cc(OC)c1]

In some embodiments, Ring B is

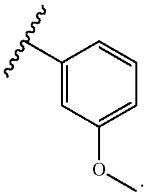 [SMILES: *c1cccc(OC)c1]

In some embodiments, Ring B is

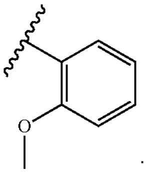 [SMILES: *c1ccccc1OC]

In some embodiments, the structure of Formula (V) is represented by the structure of Formula (V-a). In some embodiments, the structure of Formula (V) is represented by the structure of (V-a)

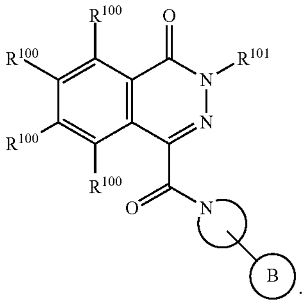

In some embodiments, for the compound or salt of Formula (V) or (V-a), each $R^{100}$ is independently selected from hydrogen, halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, and —CN. In some embodiments, each $R^{100}$ is independently selected from hydrogen, halogen, —$OR^{102}$, —$SR^{102}$, —$N(R^{102})_2$, —$C(O)R^{102}$, —$C(O)OR^{102}$, —$NO_2$, and —CN. In some embodiments, each $R^{100}$ is independently selected from hydrogen, halogen, —$OR^{102}$, —$N(R^{102})_2$, —$NO_2$, and —CN. In some embodiments, each $R^{100}$ is independently selected from hydrogen and halogen. In some embodiments, each $R^{100}$ is independently selected from hydrogen.

In some embodiments, for the compound or salt of Formula (V) or (V-a), each $R^{100}$ is independently selected from $C_{1-6}$ alkyl optionally substituted with one or more substituents independently selected from halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, =S, =O, and —CN. In some embodiments, each $R^{100}$ is independently selected from $C_{1-6}$ alkyl optionally substituted with one or more substituents independently selected from halogen, —$OR^{102}$, —$SR^{102}$, —$N(R^{102})_2$, —$C(O)R^{102}$, —$C(O)OR^{102}$, —$NO_2$, =S, =O, and —CN. In some embodiments, each $R^{100}$ is independently selected from $C_{1-6}$ alkyl optionally substituted with one or more substituents independently selected from halogen, —$OR^{102}$, —$N(R^{102})_2$, —$NO_2$, =S, =O, and —CN. In some embodiments, each $R^{100}$ is independently selected from $C_{1-3}$ alkyl optionally substituted with one or more substituents independently selected from halogen, —$OR^{102}$, —$N(R^{102})_2$, —$NO_2$, =S, =O, and —CN. In some embodiments, each $R^{100}$ is independently selected from unsubstituted $C_{1-3}$ alkyl.

In some embodiments, for the compound or salt of Formula (V) or (V-a), each $R^{100}$ is independently selected from $C_{3-10}$ carbocycle and 3- to 10-membered heterocycle, any of which is optionally substituted with one or more substituents independently selected from halogen, —$OR^{102}$, —$SR^{102}$, —$N(R^{102})_2$, —$C(O)R^{102}$, —$C(O)OR^{102}$, —$OC(O)R^{102}$, —$OC(O)N(R^{102})_2$, —$C(O)N(R^{102})_2$, —$N(R^{102})C(O)R^{102}$, —$N(R^{102})C(O)OR^{102}$, —$N(R^{102})C(O)N(R^{102})_2$, —$N(R^{102})S(O)_2(R^{102})$, —$S(O)R^{102}$, —$S(O)_2R^{102}$, —$S(O)_2N(R^{102})_2$, —$NO_2$, =S, =O, and —CN. In some embodiments, each $R^{100}$ is independently selected from $C_{3-10}$ carbocycle and 3- to 10-membered heterocycle, any of which is optionally substituted with one or more substituents independently selected from halogen, —$OR^{102}$, —$SR^{102}$, —$N(R^{102})_2$, —$C(O)R^{102}$, —$C(O)OR^{102}$, —$NO_2$, =S, =O, and —CN. In some embodiments, each $R^{100}$ is independently selected from $C_{3-6}$ carbocycle and 3- to 6-membered heterocycle, any of which is optionally substituted with one or more substituents independently selected from halogen, —$OR^{102}$, —$N(R^{102})_2$, —$C(O)R^{102}$, —$NO_2$, =S, =O, and —CN. In some embodiments, each $R^{100}$ is independently selected from unsubstituted $C_{3-6}$ carbocycle and unsubstituted 3- to 6-membered heterocycle.

In some embodiments, for the compound or salt of Formula (V) or (V-a), each $R^{100}$ is independently selected from:

hydrogen, halogen, —$OR^{102}$, —$SR^{102}$, —$N(R^{102})_2$, —$C(O)R^{102}$, —$C(O)OR^{102}$, —$NO_2$, and —CN;

$C_{1-6}$ alkyl optionally substituted with one or more substituents independently selected from halogen, —$OR^{102}$, —$SR^{102}$, —$N(R^{102})_2$, —$C(O)R^{102}$, —$C(O)OR^{102}$, —$NO_2$, =S, =O, and —CN; and $C_{3-10}$ carbocycle and 3- to 10-membered heterocycle, any of which is optionally substituted with one or more substituents independently selected from halogen, —$OR^{102}$, —$SR^{102}$, —$N(R^{102})_2$, —$C(O)R^{102}$, —$C(O)OR^{102}$, —$NO_2$, =S, =O, and —CN.

In some embodiments, for the compound or salt of Formula (V) or (V-a), each $R^{100}$ is independently selected from:

hydrogen, halogen, —$OR^{102}$, —$SR^{102}$, —$N(R^{102})_2$, —$C(O)R^{102}$, —$C(O)OR^{102}$, —$NO_2$, and —CN;

$C_{1-6}$ alkyl optionally substituted with one or more substituents independently selected from halogen, —$OR^{102}$, —$SR^{102}$, —$N(R^{102})_2$, —$C(O)R^{102}$, —$C(O)OR^{102}$, —$NO_2$, =S, =O, and —CN; and $C_{3-10}$ carbocycle and 3- to 10-membered heterocycle, any of which is optionally substituted with one or more substituents independently selected from halogen, —$OR^{102}$, —$SR^{102}$, —$N(R^{102})_2$, —$C(O)R^{102}$, —$C(O)OR^{102}$, —$NO_2$, =S, =O, and —CN; and $R^{102}$ is selected from hydrogen, $C_{1-3}$ alkyl, $C_{1-3}$ haloalkyl, —O—$C_{1-6}$ alkyl, —O—$C_{1-6}$ haloalkyl, $C_{3-6}$ carbocycle and 3- to 6-membered heterocycle.

In some embodiments, for the compound or salt of Formula (V) or (V-a), each $R^{100}$ is independently selected from:

hydrogen, halogen, —$OR^{102}$, —$N(R^{102})_2$, —$C(O)R^{102}$, —$NO_2$, and —CN; $C_{1-3}$ alkyl optionally substituted with one or more substituents independently selected from halogen, —$OR^{102}$, —$N(R^{102})_2$, —$C(O)R^{102}$, —$NO_2$, and —CN; and $C_{3-6}$ carbocycle and 3- to 6-membered heterocycle, any of which is optionally substituted with one or more substituents independently selected from halogen, —$OR^{102}$, —$N(R^{102})_2$, —$C(O)R^{102}$, —$NO_2$, and —CN.

In some embodiments, for the compound or salt of Formula (V) or (V-a), each $R^{100}$ is independently selected from:

hydrogen, halogen, —$OR^{102}$, —$N(R^{102})_2$, —$C(O)R^{102}$, —$NO_2$, and —CN; $C_{1-3}$ alkyl optionally substituted with one or more substituents independently selected from halogen, —$OR^{102}$, —$N(R^{102})_2$, —$C(O)R^{102}$, —$NO_2$, and —CN; and $C_{3-6}$ carbocycle and 3- to 6-membered heterocycle, any of which is optionally substituted with one or more substituents independently selected from halogen, —$OR^{102}$, —$N(R^{102})_2$, —$C(O)R^{102}$, —$NO_2$, and —CN; and $R^{102}$ is selected from hydrogen, $C_{1-3}$ alkyl, $C_{1-3}$ haloalkyl, —O—$C_{1-6}$ alkyl, —O—$C_{1-6}$ haloalkyl, $C_{3-6}$ carbocycle and 3- to 6-membered heterocycle.

In some embodiments, for the compound or salt of Formula (V) or (V-a), $R^{100}$ is selected from hydrogen, halogen, —$OR^{102}$, —$N(R^{102})_2$, —$C(O)R^{102}$, —$NO_2$, —CN, $C_{1-3}$ alkyl, and $C_{1-3}$ haloalkyl; and $R^{102}$ is selected from hydrogen and $C_{1-3}$ alkyl. In some embodiments, each $R^{100}$ is independently selected from hydrogen, fluoro, bromo, —O—$C_{1-3}$ alkyl, —$N(CH_3)_2$, —CN, —$CH_2CHF_2$, and —$CH_2CF_3$. In some embodiments, each $R^{100}$ is independently selected from hydrogen, fluoro, and bromo. In some embodiments, each $R^{100}$ is independently selected from hydrogen, —O—$C_{1-3}$ alkyl, —$N(CH_3)_2$, —CN, —$CH_2CHF_2$, and —$CH_2CF_3$.

In some embodiments, for the compound or salt of Formula (V) or (V-a), each $R^{100}$ is independently hydrogen.

In some embodiments, for the compound or salt of Formula (V) or (V-a), each $R^{100}$ is independently selected from: hydrogen; and $C_{3-6}$ carbocycle and 3- to 6-membered heterocycle, each of which is optionally substituted with one or more substituents independently selected from halogen, —$OR^{102}$, —$N(R^{102})_2$, —$C(O)R^{102}$, —$NO_2$, and —CN; and $R^{102}$ is selected from hydrogen and $C_{1-3}$ alkyl. In some embodiments, each $R^{100}$ is independently selected from: hydrogen; and $C_{3-5}$ saturated carbocycle and 3- to 5-membered saturated heterocycle, each of which is optionally substituted with one or more substituents independently selected from halogen, —$OR^{102}$, —$N(R^{102})_2$, —$C(O)R^{102}$, —$NO_2$, and —CN; and $R^{102}$ is selected from hydrogen and $C_{1-3}$ alkyl. In some embodiments, each $R^{100}$ is selected from: hydrogen; and cyclopropyl and pyrrolidinyl, each of which is optionally substituted with one or more substituents independently selected from halogen, —$OR^{102}$, —$N(R^{102})_2$, —$C(O)R^{102}$, —$NO_2$, and —CN; and $R^{102}$ is selected from hydrogen and $C_{1-3}$ alkyl. In some embodiments, each $R^{100}$ is selected from: hydrogen

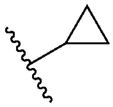
, and
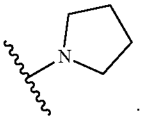
.

In some embodiments, each $R^{100}$ is selected from hydrogen

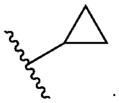
.

In some embodiments, each $R^{100}$ is selected from hydrogen and

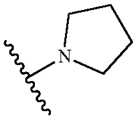
.

In some embodiments, for the compound or salt of Formula (V) or (V-a), $R^{101}$ is selected from $C_{1-6}$ alkyl and $C_{2-6}$ alkenyl, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN. In some embodiments, $R^{101}$ is selected from $C_{1-6}$ alkyl and $C_{2-6}$ alkenyl, any of which is optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, =S, =O, and —CN. In some embodiments, $R^{101}$ is selected from $C_{1-3}$ alkyl and $C_{24}$ alkenyl, any of which is optionally substituted with one or more substituents independently selected from halogen, —$OR^{103}$, —$N(R^{103})_2$, —$NO_2$, =S, =O, and —CN. In some embodiments, $R^{101}$ is selected from unsubstituted $C_{1-3}$ alkyl and unsubstituted $C_{24}$ alkenyl.

In some embodiments, for the compound or salt of Formula (V) or (V-a), $R^{101}$ is selected from $C_{3-10}$ carbocycle and 3- to 10-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN. In some embodiments, $R^{101}$ is selected from $C_{3-10}$ carbocycle and 3- to 10-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, =S, =O, and —CN. In some embodiments, $R^{101}$ is selected from $C_{3-6}$ carbocycle and 3- to 6-membered heterocycle, any of which is optionally substituted with one or more substituents independently selected from halogen, —$OR^{103}$, —$N(R^{103})_2$, —$NO_2$, =S, =O, and —CN. In some embodiments, $R^{101}$ is selected from $C_{3-6}$ saturated carbocycle and 3- to 6-membered saturated heterocycle, any of which is optionally substituted with one or more substituents independently selected from halogen, —$OR^{103}$, —$N(R^{103})_2$, —$NO_2$, =S, =O, and —CN. In some embodiments, $R^{101}$ is selected from unsubstituted $C_{3-6}$ saturated carbocycle and unsubstituted 3- to 6-membered saturated heterocycle.

In some embodiments, for the compound or salt of Formula (V) or (V-a), $R^{101}$ is selected from:

$C_{1-3}$ alkyl and $C_{24}$ alkenyl, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $C_{3-6}$ carbocycle and 3- to 6-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN.

In some embodiments, for the compound or salt of Formula (V) or (V-a), $R^{101}$ is selected from $C_{1-3}$ alkyl and $C_{2-6}$ alkenyl, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $R^{103}$ is selected from hydrogen and $C_{1-3}$ alkyl. In some embodiments, $R^{101}$ is selected from methyl, ethyl, propyl, isopropyl, and propenyl, each of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $R^{103}$ is selected from hydrogen and $C_{1-3}$ alkyl. In some embodiments, $R^{101}$ is selected from methyl, ethyl, propyl, isopropyl, and propenyl, each of which is optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, =S, =O, and —CN; and $R^{103}$ is selected from hydrogen and $C_{1-3}$ alkyl. In some embodiments, $R^{101}$ is selected from methyl, ethyl, propyl, isopropyl, and propenyl. In some embodiments, $R^{101}$ is selected from methyl and ethyl.

In some embodiments, for the compound or salt of Formula (V) or (V-a), $R^{101}$ is selected from $C_{3-6}$ carbocycle and 3- to 6-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $R^{103}$ is selected from hydrogen and $C_{1-3}$ alkyl. In some embodiments, $R^{101}$ is selected from $C_{3-6}$ carbocycle and 3- to 6-membered heterocycle, any of which is optionally substituted with one or more substituents independently selected from halogen, —$OR^{103}$, —$SR^{103}$, —$N(R^{103})_2$, —$C(O)R^{103}$, —$C(O)OR^{103}$, —$NO_2$, =S, =O, and —CN; and $R^{103}$ is selected from hydrogen and $C_{1-3}$ alkyl.

In some embodiments, for the compound or salt of Formula (V) or (V-a), $R^{101}$ is selected from saturated $C_{3-4}$ carbocycle and saturated 3- to 4-membered heterocycle, each of which is optionally substituted with one or more substituents independently selected from halogen, —$OR^{103}$, —$SR^{103}$, —$N(R^{103})_2$, —$C(O)R^{103}$, —$C(O)OR^{103}$, —$OC(O)R^{103}$, —$OC(O)N(R^{103})_2$, —$C(O)N(R^{103})_2$, —$N(R^{103})C(O)R^{103}$, —$N(R^{103})C(O)OR^{103}$, —$N(R^{103})C(O)N(R^{103})_2$, —$N(R^{103})S(O)_2(R^{103})$, —$S(O)R^{103}$, —$S(O)_2R^{103}$, —$S(O)_2N(R^{103})_2$, —$NO_2$, =S, =O, and —CN; and $R^{103}$ is selected from hydrogen and $C_{1-3}$ alkyl. In some embodiments, $R^{101}$ is selected from saturated $C_{3-4}$ carbocycle and saturated 3- to 4-membered heterocycle, each of which is optionally substituted with one or more substituents independently selected from halogen, —$OR^{103}$, —$N(R^{103})_2$, —$C(O)R^{103}$, —$NO_2$, =S, =O, and —CN; and $R^{103}$ is selected from hydrogen and $C_{1-3}$ alkyl. In some embodiments, $R^{101}$ is selected from cyclopropyl and oxetanyl, each of which is optionally substituted with one or more substituents independently selected from halogen, —$OR^{103}$, —$N(R^{103})_2$, —$C(O)R^{103}$, —$NO_2$, =S, =O, and —CN; and $R^{103}$ is selected from hydrogen and $C_{1-3}$ alkyl. In some embodiments, $R^{101}$ is selected from

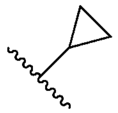
and
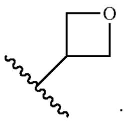
.

In some embodiments, $R^{101}$ is

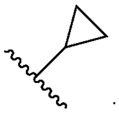
.

In some embodiments, $R^{101}$ is

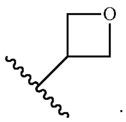 [SMILES: *C1COC1]
.

In some embodiments, the optionally substituted 3- to 12-membered heterocyclene of

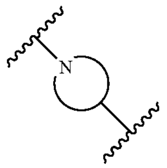

is selected from optionally substituted 3-membered heterocyclene, optionally substituted 4-membered heterocyclene, optionally substituted 5-membered heterocyclene, optionally substituted 6-membered heterocyclene, optionally substituted 7-membered heterocyclene, optionally substituted 8-membered heterocyclene, optionally substituted 9-membered heterocyclene, optionally substituted 10-membered heterocyclene, optionally substituted 11-membered heterocyclene, and optionally substituted 12-membered heterocyclene. In some embodiments, the optionally substituted 3- to 12-membered heterocyclene of

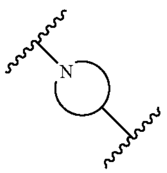

is selected from optionally substituted 3- to 4-membered heterocyclene, optionally substituted 3- to 5-membered heterocyclene, optionally substituted 3- to 6-membered heterocyclene, optionally substituted 3- to 7-membered heterocyclene, optionally substituted 3- to 8-membered heterocyclene, optionally substituted 3- to 9-membered heterocyclene, optionally substituted 3- to 10-membered heterocyclene, and optionally substituted 3- to 11-membered heterocyclene.

In some embodiments, for the compound or salt of Formula (V) or (V-a),

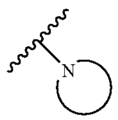

is 3- to 10-membered heterocyclene optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN; and $C_{3-10}$ carbocycle and 3- to 10-membered heterocycle, any of which is optionally substituted with one or more substituents independently selected from halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, =S, =O, and —CN.

In some embodiments, for the compound or salt of Formula (V), or (V-a),

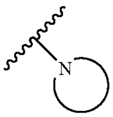 [SMILES: *N]

is 4- to 9-membered heterocyclene optionally substituted with one or more substituents independently selected from:

halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, and —CN;

$C_{1-6}$ alkyl optionally substituted with one or more substituents independently selected from halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, =S, =O, and —CN; and $C_{3-10}$ carbocycle and 3- to 10-membered heterocycle, any of which is optionally substituted with one or more substituents independently selected from halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, =S, =O, and —CN.

In some embodiments,

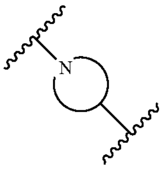

is selected from 4- to 9-heterocyclene, each of which is optionally substituted with one or more substituents independently selected from: halogen, —OR$^{104}$, —N(R$^{104}$)$_2$, —C(O)R$^{104}$, —C(O)OR$^{104}$, —C(O)N(R$^{104}$)$_2$—NO$_2$, —CN; and $C_{1-6}$ alkyl optionally substituted with one or more substituents independently selected from halogen, —OR$^{104}$, —N(R$^{104}$)$_2$, —C(O)R$^{104}$, —C(O)OR$^{104}$, —C(O)N(R$^{104}$)$_2$, —NO$_2$, =S, =O, and —CN.

In some embodiments, for the compound or salt of Formula (V), or (V-a),

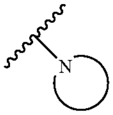

is 4- to 6-saturated membered heterocyclene optionally substituted with one or more substituents independently selected from:

halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, and —CN;

$C_{1-6}$ alkyl optionally substituted with one or more substituents independently selected from halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, =S, =O, and —CN; and $C_{3-10}$ carbocycle and 3- to 10-membered heterocycle, any of which is optionally substituted with one or more substituents independently selected from halogen, —OR$^{104}$, —SR$^{104}$, —N(R$^{104}$)$_2$, —C(O)R$^{104}$, —C(O)OR$^{104}$, —OC(O)R$^{104}$, —OC(O)N(R$^{104}$)$_2$, —C(O)N(R$^{104}$)$_2$, —N(R$^{104}$)C(O)R$^{104}$, —N(R$^{104}$)C(O)OR$^{104}$, —N(R$^{104}$)C(O)N(R$^{104}$)$_2$, —N(R$^{104}$)S(O)$_2$(R$^{104}$), —S(O)R$^{104}$, —S(O)$_2$R$^{104}$, —S(O)$_2$N(R$^{104}$)$_2$, —NO$_2$, =S, =O, and —CN.

In some embodiments,

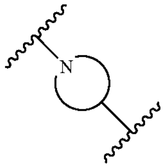

is selected from saturated 4- to 6-membered heterocyclene, each of which is optionally substituted with one or more substituents independently selected from: halogen, —OR$^{104}$, —N(R$^{104}$)$_2$, —C(O)R$^{104}$, —C(O)OR$^{104}$, —C(O)N(R$^{104}$)$_2$, —NO$_2$, —CN; and $C_{1-6}$ alkyl optionally substituted with one or more substituents independently selected from halogen, —OR$^{104}$, —N(R$^{104}$)$_2$, —C(O)R$^{104}$, —C(O)OR$^{104}$, —C(O)N(R$^{104}$)$_2$, —NO$_2$, =S, =O, and —CN; and R$^{104}$ is selected from hydrogen and $C_{1-3}$ alkyl.

In some embodiments, for the compound or salt of Formula (V) or (V-a),

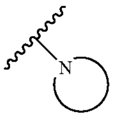 [SMILES: *N]

is selected from piperidinylene and piperazinylene, each of which is optionally substituted with one or more substituents independently selected from:

halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$OC(O)R^{104}$, —$OC(O)N(R^{104})_2$, —$C(O)N(R^{104})_2$, —$N(R^{104})C(O)R^{104}$, —$N(R^{104})C(O)OR^{104}$, —$N(R^{104})C(O)N(R^{104})_2$, —$N(R^{104})S(O)_2(R^{104})$, —$S(O)R^{104}$, —$S(O)_2R^{104}$, —$S(O)_2N(R^{104})_2$, —$NO_2$, =S, =O, and —CN.

In some embodiments, for the compound or salt of Formula (V) or (V-a),

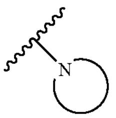 [SMILES: *N]

is selected from piperidinylene and piperazinylene, each of which is optionally substituted with one or more substituents independently selected from:

halogen, —$OR^{104}$, —$SR^{104}$, —$N(R^{104})_2$, —$C(O)R^{104}$, —$C(O)OR^{104}$—$NO_2$, and —CN;

$C_{1-6}$ alkyl optionally substituted with one or more substituents independently selected from halogen, —$OR^{104}$, —$SR^{104}$, —$N(R^{104})_2$, —$C(O)R^{104}$, —$C(O)OR^{104}$, —$NO_2$, =S, =O, and —CN; and $C_{3-10}$ carbocycle and 3- to 10-membered heterocycle, any of which is optionally substituted with one or more substituents independently selected from halogen, —$OR^{104}$, —$SR^{104}$, —$N(R^{104})_2$, —$C(O)R^{104}$, —$C(O)OR^{104}$, —$NO_2$, =S, =O, and —CN.

In some embodiments, for the compound or salt of Formula (V) or (V-a),

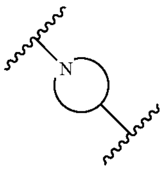

is selected from piperidinylene and piperazinylene, each of which is optionally substituted with one or more substituents independently selected from: halogen, —$OR^{104}$, —$N(R^{104})_2$, —$C(O)R^{104}$, —$C(O)OR^{104}$, —$C(O)N(R^{104})_2$—$NO_2$, —CN; and $C_{1-6}$ alkyl optionally substituted with one or more substituents independently selected from halogen, —$OR^{104}$, —$N(R^{104})_2$, —$C(O)R^{104}$, —$C(O)OR^{104}$, —$C(O)N(R^{104})_2$, —$NO_2$, =S, =O, and —CN; and $R^{104}$ is selected from hydrogen and $C_{1-3}$ alkyl. In some embodiments,

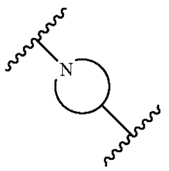

is selected from piperidinylene and piperazinylene, each of which is optionally substituted with one or more $C_{1-3}$ alkyl optionally substituted with one or more substituents independently selected from halogen, —$OR^{104}$, —$N(R^{104})_2$, —$C(O)R^{104}$, —$C(O)OR^{104}$, —$C(O)N(R^{104})_2$, —$NO_2$, =S, =O, and —CN; and $R^{104}$ is selected from hydrogen and $C_{1-3}$ alkyl. In some embodiments,

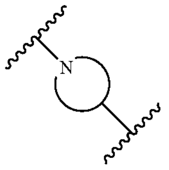

is selected from piperidinylene and piperazinylene, each of which is optionally substituted with one or more $C_{1-3}$ alkyl optionally substituted with one or more substituents independently selected from halogen, —$OR^{104}$, —$N(R^{104})_2$, —$NO_2$, =S, =O, and —CN; and $R^{104}$ is selected from hydrogen and $C_{1-3}$ alkyl. In some embodiments,

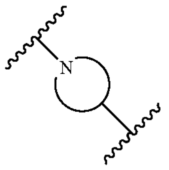

is selected from

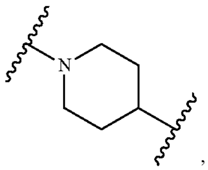
,
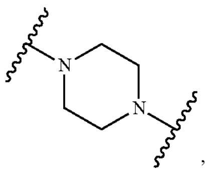
,
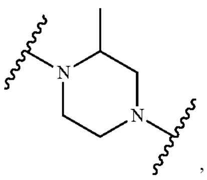
, and
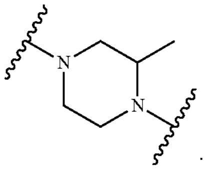
.

In some embodiments,

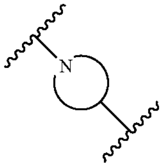

is selected from

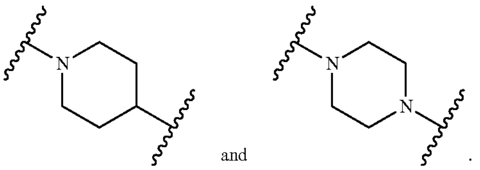 [SMILES: *C1CCN(*)CC1 ; *N1CCN(*)CC1]

In some embodiments,

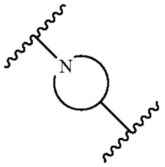

is selected from

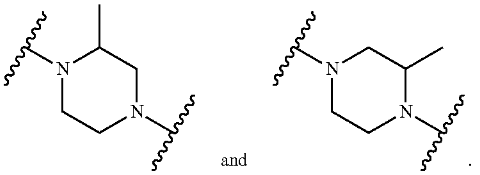

In some embodiments, for the compound or salt of Formula (V) or (V-a), for the compound or salt of Formula (V) or (V-a), the optionally substituted $C_{3-12}$ carbocycle of Ring B is selected from optionally substituted $C_3$ carbocycle, optionally substituted $C_4$ carbocycle, optionally substituted $C_5$ carbocycle, optionally substituted $C_6$ carbocycle, optionally substituted $C_7$ carbocycle, optionally substituted $C_8$ carbocycle, optionally substituted $C_9$ carbocycle, optionally substituted $C_{10}$ carbocycle, optionally substituted $C_{11}$ carbocycle, and optionally substituted $C_{12}$ carbocycle. In some embodiments, the optionally substituted $C_{3-12}$ carbocycle of Ring B is selected from optionally substituted $C_{3-4}$ carbocycle, optionally substituted $C_{3-5}$ carbocycle, optionally substituted $C_{3-6}$ carbocycle, optionally substituted $C_{3-7}$ carbocycle, optionally substituted $C_{3-8}$ carbocycle, optionally substituted $C_{3-9}$ carbocycle, optionally substituted $C_{3-10}$ carbocycle, and optionally substituted $C_{3-11}$ carbocycle.

In some embodiments, for the compound or salt of Formula (V) or (V-a), Ring B is $C_{3-10}$ carbocycle optionally substituted with one or more substituents independently selected from:

halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, and —CN;

$C_{1-6}$ alkyl optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN; and $C_{3-10}$ carbocycle and 3- to 10-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN.

In some embodiments, for the compound or salt of Formula (V) or (V-a), Ring B is $C_{3-6}$ carbocycle optionally substituted with one or more substituents independently selected from:

halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, and —CN;

$C_{1-6}$ alkyl optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN; and $C_{3-10}$ carbocycle and 3- to 10-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN.

In some embodiments, for the compound or salt of Formula (V) or (V-a), Ring B is phenyl optionally substituted with one or more substituents independently selected from:

halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, and —CN;

$C_{1-6}$ alkyl optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, =S, =O, and —CN; and $C_{3-10}$ carbocycle and 3- to 10-membered heterocycle, any of which is optionally substituted with one or more substituents independently selected from halogen, $—OR^{105}$, $—SR^{105}$, $—N(R^{105})_2$, $—C(O)R^{105}$, $—C(O)OR^{105}$, $—OC(O)R^{105}$, $—OC(O)N(R^{105})_2$, $—C(O)N(R^{105})_2$, $—N(R^{105})C(O)R^{105}$, $—N(R^{105})C(O)OR^{105}$, $—N(R^{105})C(O)N(R^{105})_2$, $—N(R^{105})S(O)_2(R^{105})$, $—S(O)R^{105}$, $—S(O)_2R^{105}$, $—S(O)_2N(R^{105})_2$, $—NO_2$, ═S, ═O, and —CN.

In some embodiments, for the compound or salt of Formula (V) or (V-a), Ring B is phenyl optionally substituted with one or more substituents independently selected from:

halogen, $—OR^{105}$, $—N(R^{105})_2$, $—C(O)R^{105}$, $—C(O)OR^{105}$, $—C(O)N(R^{105})_2$, $—N(R^{105})C(O)R^{105}$, $—NO_2$, and —CN;

$C_{1-6}$ alkyl optionally substituted with one or more substituents independently selected from halogen, $—OR^{105}$, $—N(R^{105})_2$, $—C(O)R^{105}$, $—C(O)OR^{105}$, $—C(O)N(R^{105})_2$, $—N(R^{105})C(O)R^{105}$, $—NO_2$, ═S, ═O, and —CN;

$C_{3-6}$ carbocycle and 3- to 6-membered heterocycle, any of which is optionally substituted with one or more substituents independently selected halogen, $—OR^{105}$, $—N(R^{105})_2$, $—C(O)R^{105}$, $—C(O)OR^{105}$, $—C(O)N(R^{105})_2$, $—N(R^{105})C(O)R^{105}$, $—NO_2$, ═S, ═O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle.

In some embodiments, for the compound or salt of Formula (V) or (V-a), Ring B is phenyl optionally substituted with one or more substituents independently selected from: halogen, $—OR^{105}$, $—N(R^{105})_2$, $—C(O)R^{105}$, $—C(O)OR^{105}$, $—C(O)N(R^{105})_2$, $—N(R^{105})C(O)R^{105}$, $—NO_2$, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

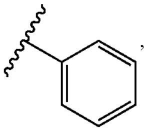,
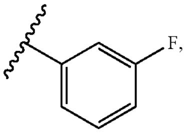,
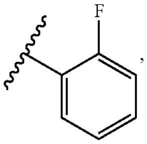,
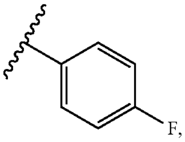
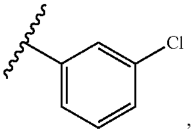,
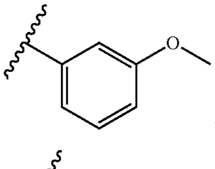,
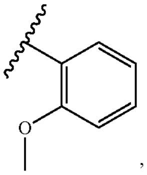,
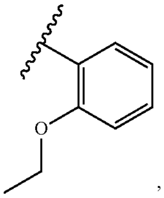,
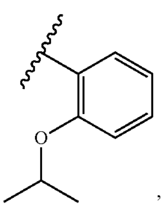,
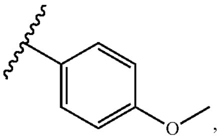,
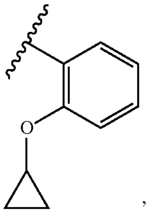, -continued

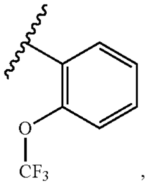,
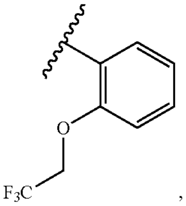,
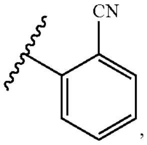,
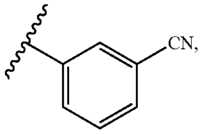
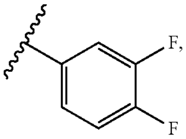
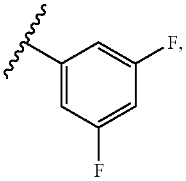
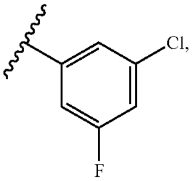
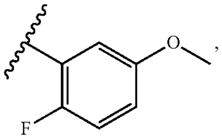,
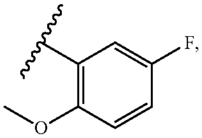
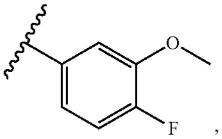,
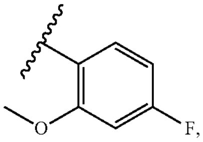
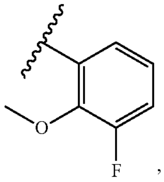,
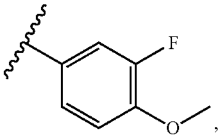,
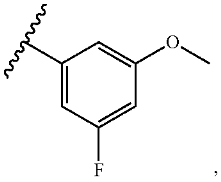,
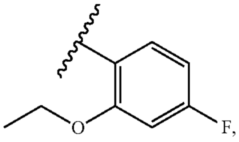
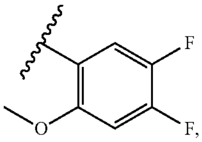
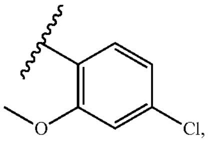
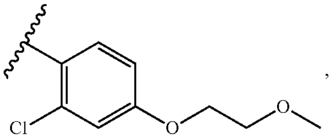,
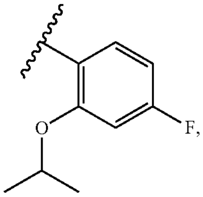

-continued
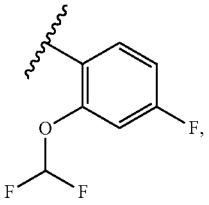 and 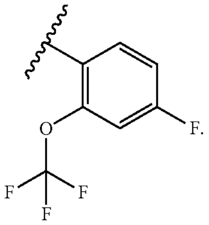
In some embodiments, Ring B is selected from:
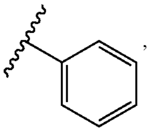, 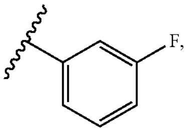 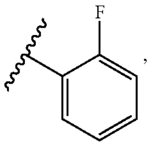,
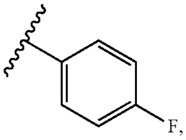 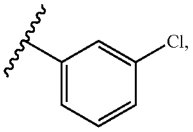
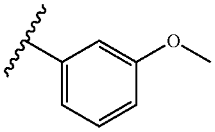, 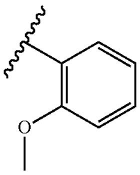, 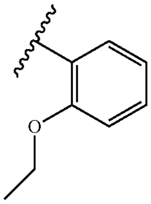,
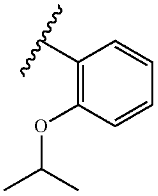, 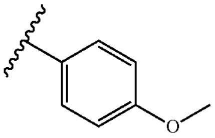, 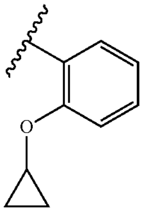,
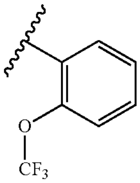, 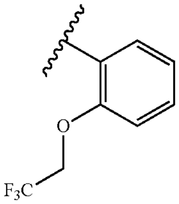, 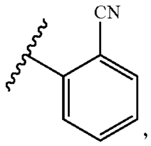,
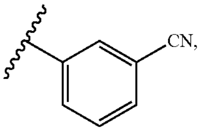 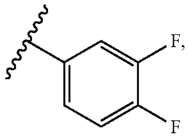
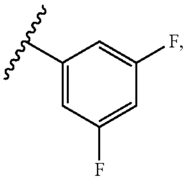 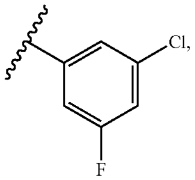
-continued
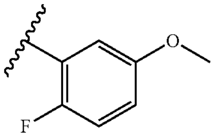, 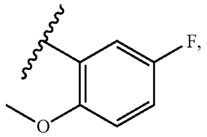
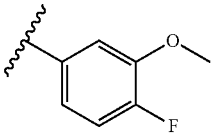, 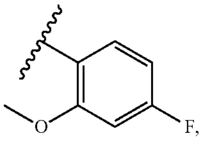
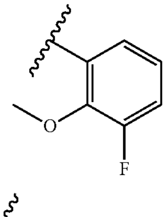, 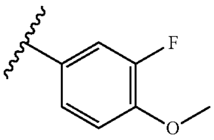,
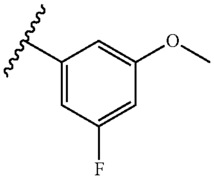, 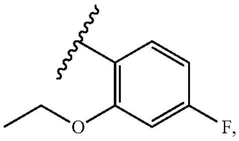
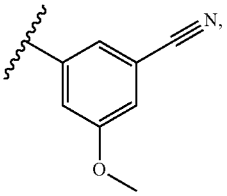 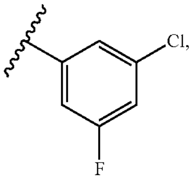
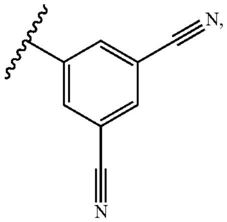 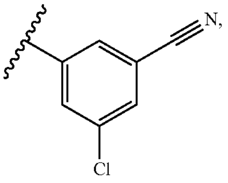
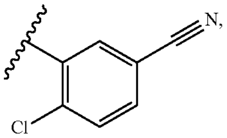 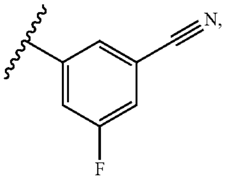
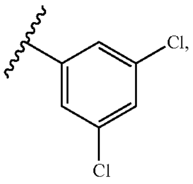 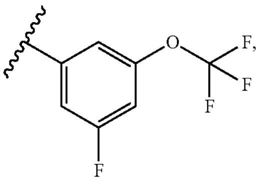
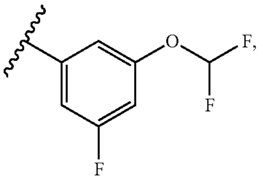 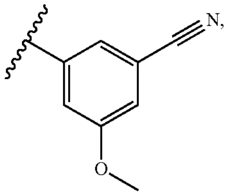

-continued

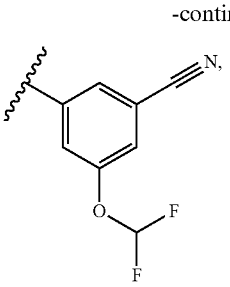
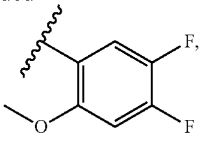
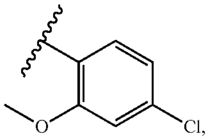
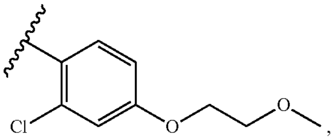
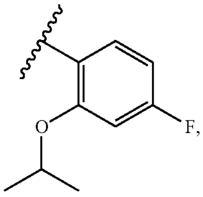
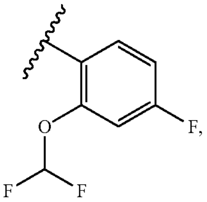
and
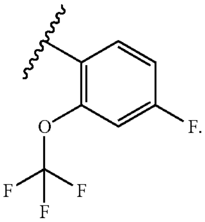

In some embodiments, for the compound or salt of Formula (V) or (V-a), Ring B is phenyl optionally substituted with one or more substituents independently selected from $C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

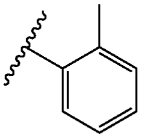
,
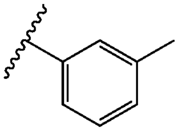
,
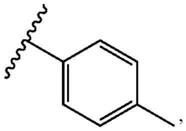
,
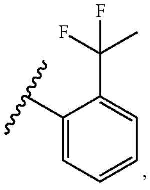
,
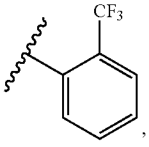
,
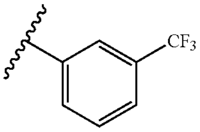
,
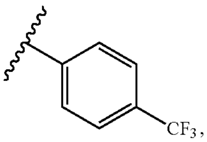
, and
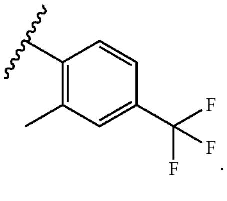
.

In some embodiments, Ring B is selected from:

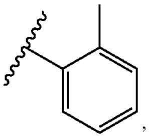
,
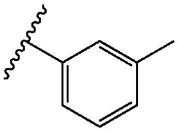
,
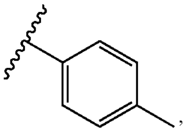
,
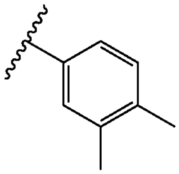
,
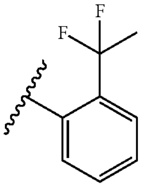
,
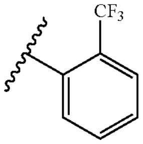
,
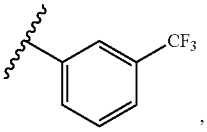
,
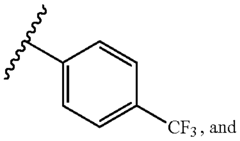
, and
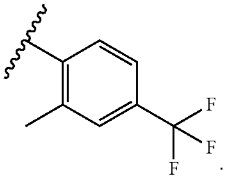
.

In some embodiments, for the compound or salt of Formula (V) or (V-a), Ring B is phenyl optionally substituted with one or more substituents independently selected from: $C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

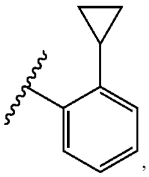
, and
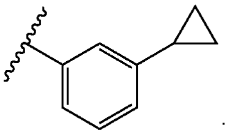
.

In some embodiments, for the compound or salt of Formula (V) or (V-a), Ring B is phenyl optionally substituted with one or more substituents independently selected from:

halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, and —CN; and $C_{1-6}$ alkyl optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

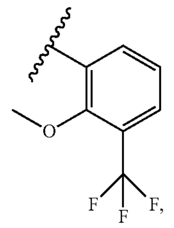
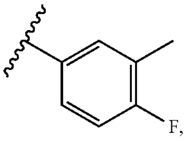
and
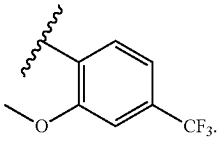

In some embodiments, Ring B is selected from:

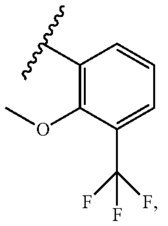
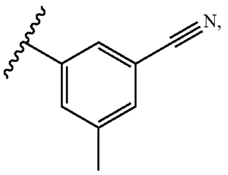
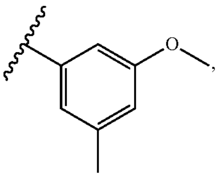
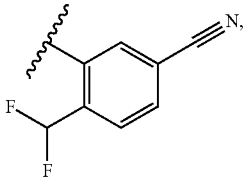
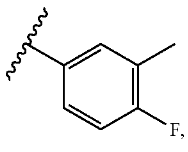
and
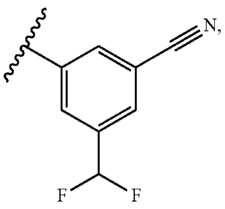
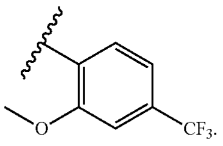

In some embodiments, for the compound or salt of Formula (V) or (V-a), Ring B is phenyl optionally substituted with one or more substituents independently selected from:

halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, and —CN; and $C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

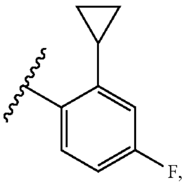
and
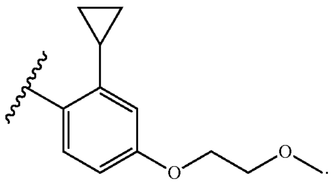

In some embodiments, Ring B is selected from:

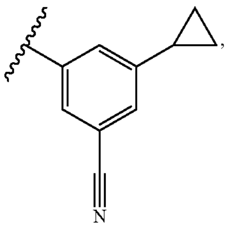
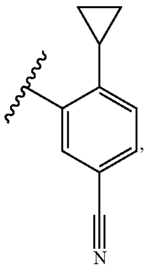
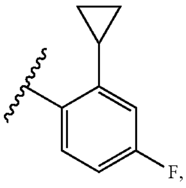
and
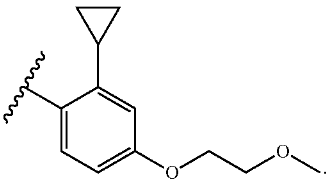

In some embodiments, for the compound or salt of Formula (V) or (V-a), Ring B is selected from:

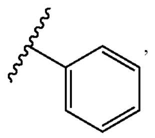
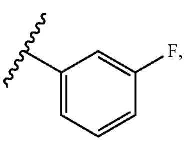
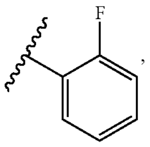

-continued
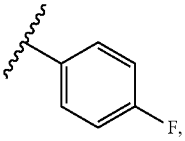 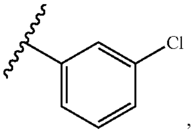 ,
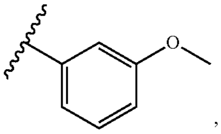 , 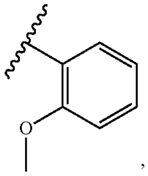 , 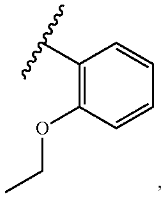 ,
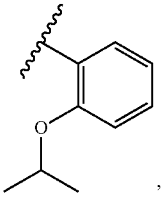 , 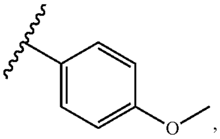 , 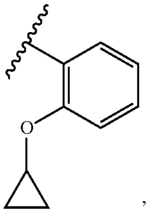 ,
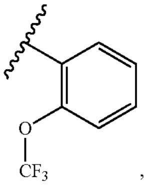 , 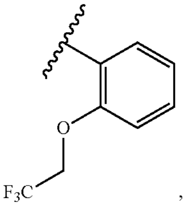 , 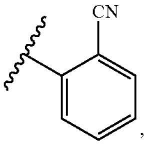 ,
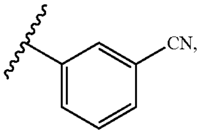 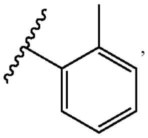 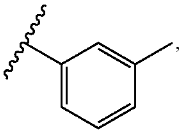
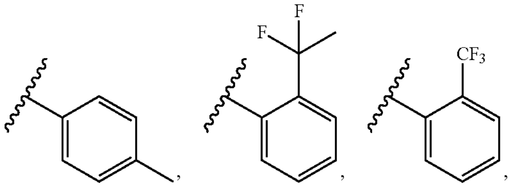
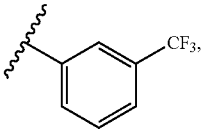 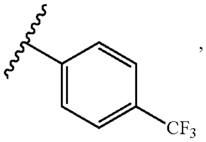 ,
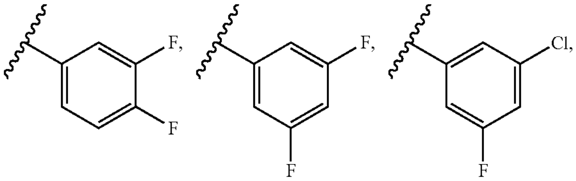
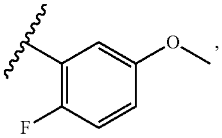 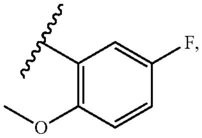
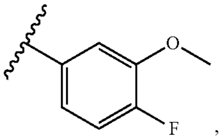 , 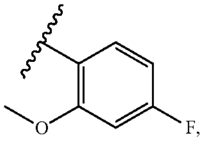
-continued
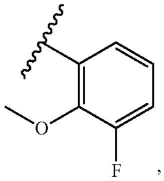 , 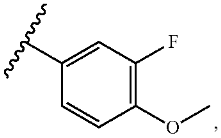
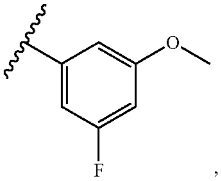 , 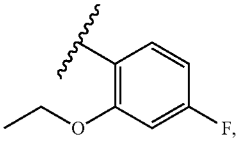
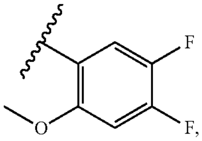 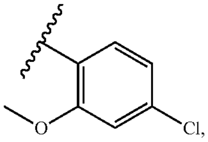
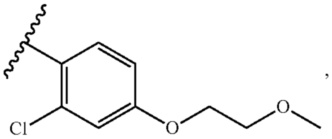 , 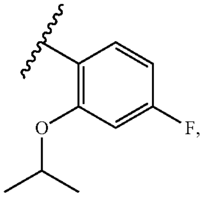
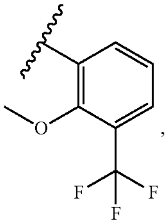 , 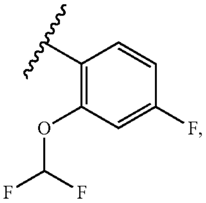
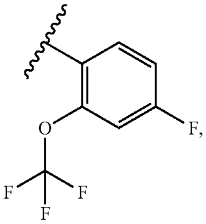 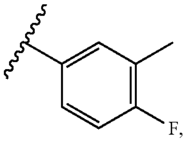
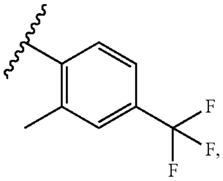 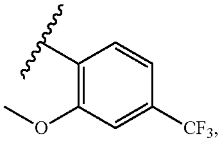
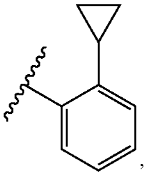 , 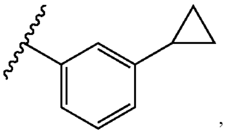 ,
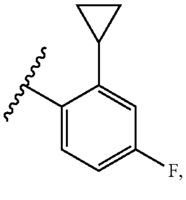 and 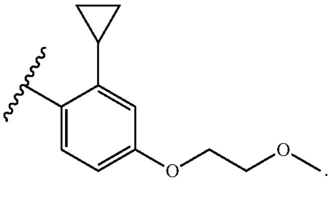

In some embodiments, for the compound or salt of Formula (V) or (V-a), Ring B is selected from:
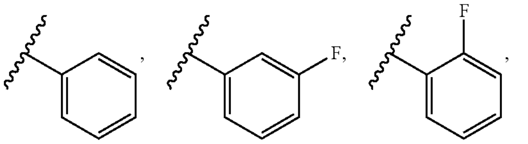
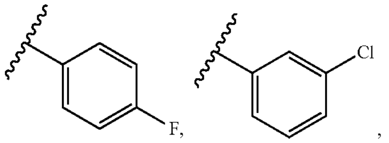
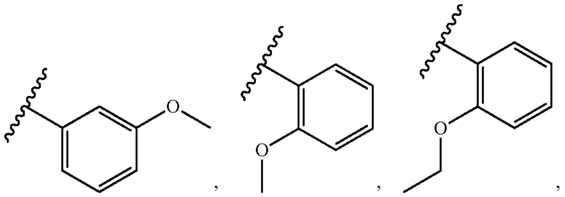
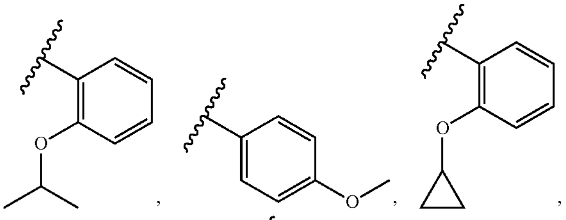
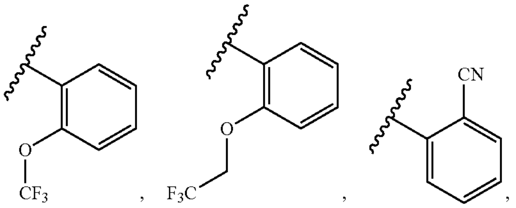
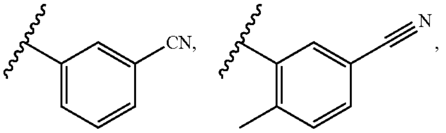
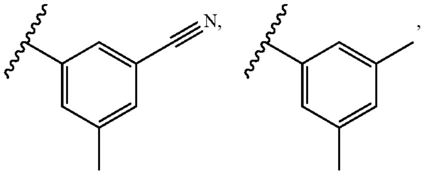
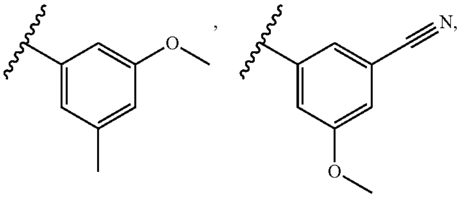
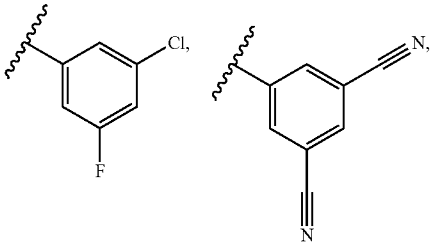
-continued
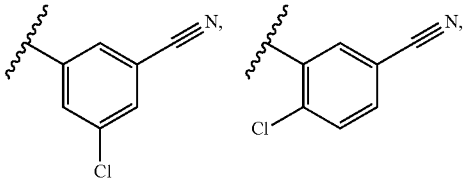
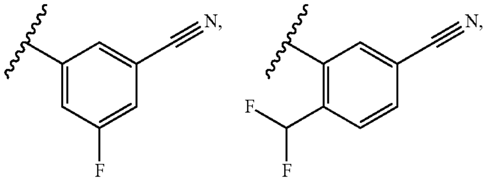
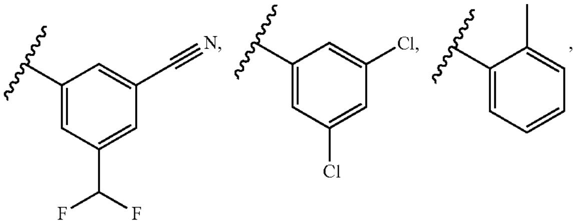
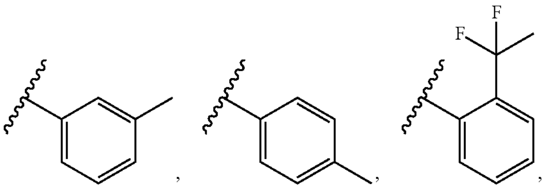
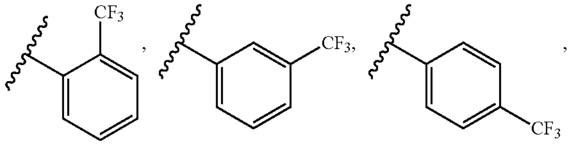
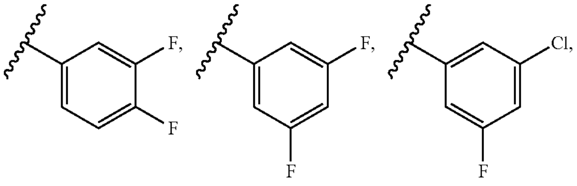
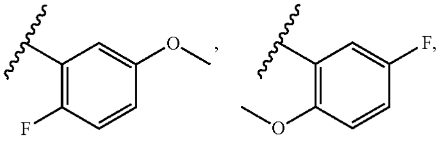
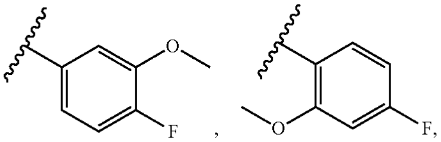
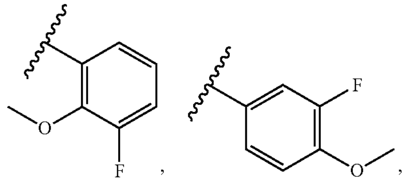

-continued

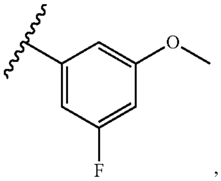,
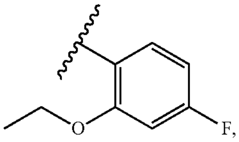
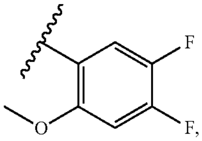
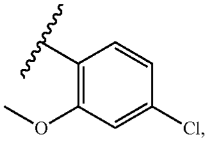
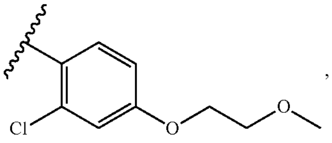,
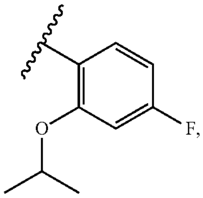
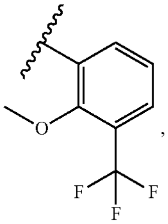,
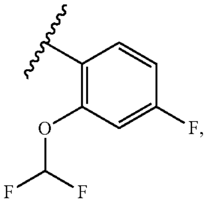
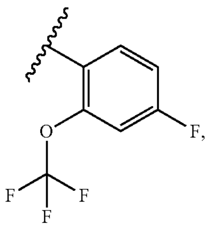
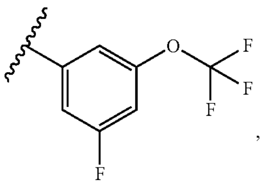,
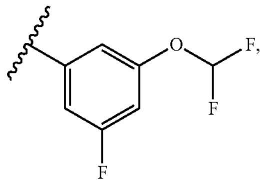
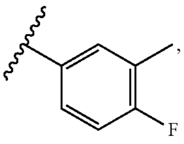
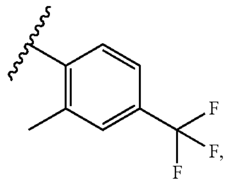
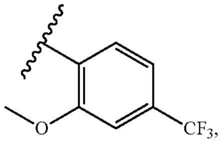
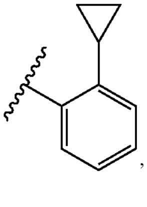,
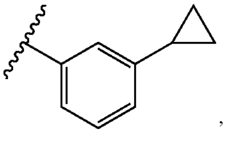, -continued

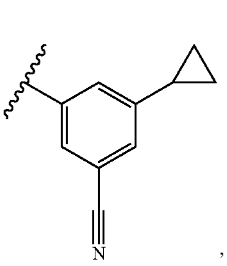,
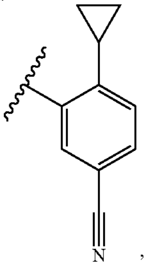,
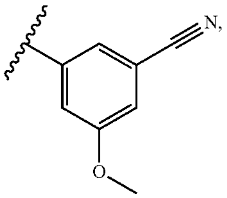
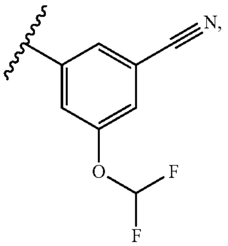
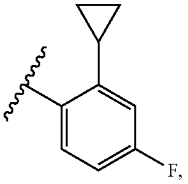 and
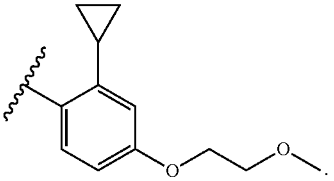

In some embodiments, for the compound or salt of Formula (V) or (V-a), the optionally substituted 3- to 12-membered heterocycle of Ring B is selected from optionally substituted 3-membered heterocycle, optionally substituted 4-membered heterocycle, optionally substituted 5-membered heterocycle, optionally substituted 6-membered heterocycle, optionally substituted 7-membered heterocycle, optionally substituted 8-membered heterocycle, optionally substituted 9-membered heterocycle, optionally substituted 10-membered heterocycle, optionally substituted 11-membered heterocycle, and optionally substituted 12-membered heterocycle. In some embodiments, the optionally substituted 3- to 12-membered heterocycle of Ring B is selected from optionally substituted 3- to 4-membered heterocycle, optionally substituted 3- to 5-membered heterocycle, optionally substituted 3- to 6-membered heterocycle, optionally substituted 3- to 7-membered heterocycle, optionally substituted 3- to 8-membered heterocycle, optionally substituted 3- to 9-membered heterocycle, optionally substituted 3- to 10-membered heterocycle, and optionally substituted 3- to 11-membered heterocycle.

In some embodiments, for the compound or salt of Formula (V) or (V-a), Ring B is 3- to 10-membered heterocycle optionally substituted with one or more substituents independently selected from.

halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, and —CN;

$C_{1-6}$ alkyl optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, =S, =O, and —CN; and $C_{3-10}$ carbocycle and 3- to 10-membered heterocycle, any of which is optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$ In some embodiments, for the compound or salt of Formula (V) or (V-a), Ring B is selected from 3- to 6-membered monocyclic heterocycle and 6- to 10-membered bicyclic heterocycle, each of which is optionally substituted with one or more substituents independently selected from:

halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, and $-CN$;

$C_{1-6}$ alkyl optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$.

In some embodiments, for the compound or salt of Formula (V) or (V-a), Ring B is selected from 3- to 6-membered monocyclic heterocycle and 6- to 10-membered bicyclic heterocycle, each of which is optionally substituted with one or more substituents independently selected from:

halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, and $-CN$;

$C_{1-6}$ alkyl optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $R^{105}$ is selected from hydrogen, $C_{1-4}$ alkyl, $C_{1-4}$haloalkyl, $C_{3-6}$ saturated carbocycle, and 3- to 6-membered saturated heterocycle.

In some embodiments, for the compound or salt of Formula (V) or (V-a), Ring B is selected from imidazoyl, thiophenyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, and quinolinyl, each of which is optionally substituted with one or more substituents independently selected from:

halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, and $-CN$;

$C_{1-6}$ alkyl optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$.

In some embodiments, for the compound or salt of Formula (V) or (V-a), Ring B is selected from imidazoyl, thiophenyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, and quinolinyl, each of which is optionally substituted with one or more substituents independently selected from:

halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, and $-CN$;

$C_{1-6}$ alkyl optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $C_{3-10}$ carbocycle and 3- to 10-membered heterocycle, any of which is optionally substituted with one or more substituents independently selected from halogen, $-OR^{105}$, $-SR^{105}$, $-N(R^{105})_2$, $-C(O)R^{105}$, $-C(O)OR^{105}$, $-OC(O)R^{105}$, $-OC(O)N(R^{105})_2$, $-C(O)N(R^{105})_2$, $-N(R^{105})C(O)R^{105}$, $-N(R^{105})C(O)OR^{105}$, $-N(R^{105})C(O)N(R^{105})_2$, $-N(R^{105})S(O)_2(R^{105})$, $-S(O)R^{105}$, $-S(O)_2R^{105}$, $-S(O)_2N(R^{105})_2$, $-NO_2$, $=S$, $=O$, and $-CN$; and $R^{105}$ is selected from hydrogen, $C_{1-4}$ alkyl, $C_{1-4}$haloalkyl, $C_{3-6}$ saturated carbocycle, and 3- to 6-membered saturated heterocycle In some embodiments, for the compound or salt of Formula (V) or (V-a), Ring B is selected from imidazolyl, thiophenyl, pyridazinonyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, and quinolinyl, each of which is optionally substituted with one or more substituents independently selected from:

halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, ═S, ═O, and —CN;

$C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, ═S, ═O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle.

In some embodiments, for the compound or salt of Formula (V) or (V-a), Ring B is selected from imidazolyl, thiophenyl, pyridazinonyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, and quinolinyl, each of which is optionally substituted with one or more substituents independently selected from:

halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, ═S, ═O, and —CN;

$C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, ═S, ═O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle.

In some embodiments, for the compound or salt of Formula (V) or (V-a), Ring B is selected from imidazoyl, thiophenyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, thienopyridinyl, indazolyl, pyrazolo[4,3-b]pyridinyl, imidazo[1,2-a]pyridinyl, imidazo[1,2-a]pyrazinyl, pyrazolo[1,5-a]pyridinyl, and quinolinyl, each of which is optionally substituted with one or more substituents independently selected from:

halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, and —CN;

$C_{1-6}$ alkyl optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, ═S, ═O, and —CN; and $C_{3-10}$ carbocycle and 3- to 10-membered heterocycle, any of which is optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, ═S, ═O, and —CN.

In some embodiments, for the compound or salt of Formula (V) or (V-a), Ring B is selected from imidazoyl, thiophenyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, thienopyridinyl, indazolyl, pyrazolo[4,3-b]pyridinyl, imidazo[1,2-a]pyridinyl, imidazo[1,2-a]pyrazinyl, pyrazolo[1,5-a]pyridinyl, and quinolinyl, each of which is optionally substituted with one or more substituents independently selected from:

halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, and —CN;

$C_{1-6}$ alkyl optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, ═S, ═O, and —CN; and $C_{3-10}$ carbocycle and 3- to 10-membered heterocycle, any of which is optionally substituted with one or more substituents independently selected from halogen, —$OR^{105}$, —$SR^{105}$, —$N(R^{105})_2$, —$C(O)R^{105}$, —$C(O)OR^{105}$, —$OC(O)R^{105}$, —$OC(O)N(R^{105})_2$, —$C(O)N(R^{105})_2$, —$N(R^{105})C(O)R^{105}$, —$N(R^{105})C(O)OR^{105}$, —$N(R^{105})C(O)N(R^{105})_2$, —$N(R^{105})S(O)_2(R^{105})$, —$S(O)R^{105}$, —$S(O)_2R^{105}$, —$S(O)_2N(R^{105})_2$, —$NO_2$, ═S, ═O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle In some embodiments, for the compound or salt of Formula (V) or (V-a), Ring B is selected from imidazolyl, thiophenyl, pyridazinonyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, thienopyridinyl, indazolyl, pyrazolo[4,3-b]pyridinyl, imidazo[1,2-a]pyridinyl, imidazo[1,2-a]pyrazinyl, pyrazolo[1,5-a]pyridinyl, and quinolinyl, each of which is optionally substituted with one or more substituents independently selected from:

halogen, —$OR^{105}$, —$N(R^{105})_2$, —$C(O)R^{105}$, —C(O)$OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, ═S, ═O, and —CN;

$C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —C(O)N$(R^{105})_2$, —$N(R^{105})C(O)R^{105}$, —$NO_2$, ═S, ═O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle.

In some embodiments, for the compound or salt of Formula (V) or (V-a), Ring B is selected from imidazolyl, thiophenyl, pyridazinonyl, pyridyl, pyrazinyl, pyridazinyl, pyrimidinyl, benzodioxolyl, dihydrobenzofuranyl, benzofuranyl, benzimidazolyl, benzisoxazolyl, dihydrofuropyridyl, furopyridyl, thienopyridinyl, indazolyl, pyrazolo[4,3-b]pyridinyl, imidazo[1,2-a]pyridinyl, imidazo[1,2-a]pyrazinyl, pyrazolo[1,5-a]pyridinyl, and quinolinyl, each of which is optionally substituted with one or more substituents independently selected from:

halogen, —$OR^{105}$, —$N(R^{105})_2$, —$C(O)R^{105}$, —C(O)$OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, ═S, ═O, and —CN;

$C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —C(O)N$(R^{105})_2$, —$N(R^{105})C(O)R^{105}$, —$NO_2$, ═S, ═O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle.

In some embodiments, for the compound or salt of Formula (V) or (V-a), Ring B is selected from imidazolyl, thiophenyl, pyridazinonyl, pyridyl, pyrazinyl, pyridazinyl, and pyrimidinyl, each of which is optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

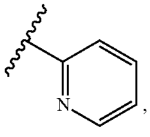 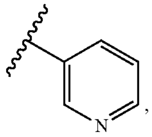 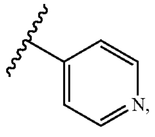

-continued

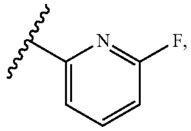 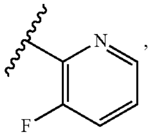 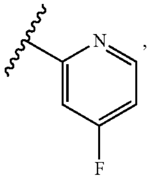

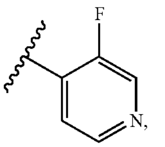 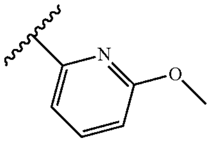 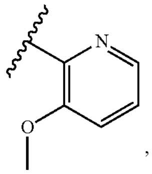

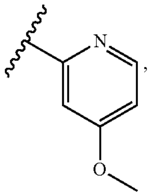 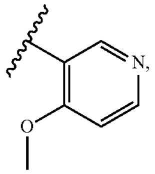 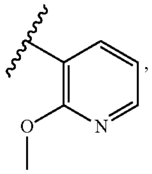

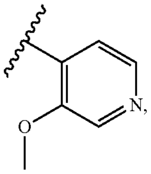 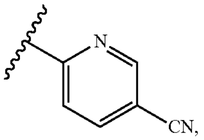 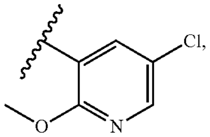

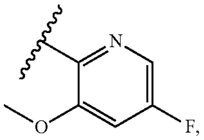 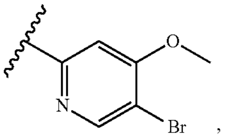

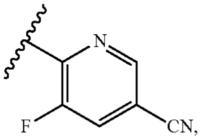 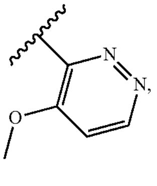 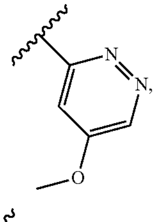

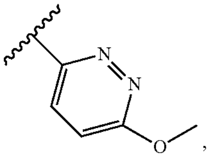 and 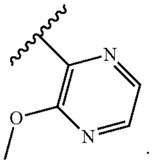

In some embodiments, Ring B is selected from:

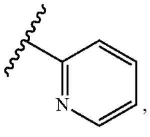 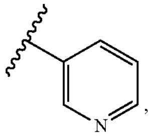 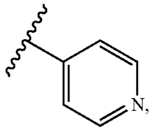

-continued
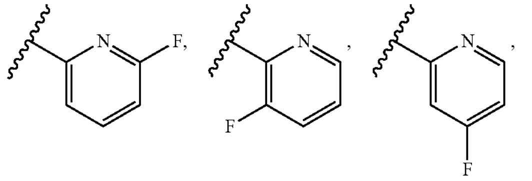
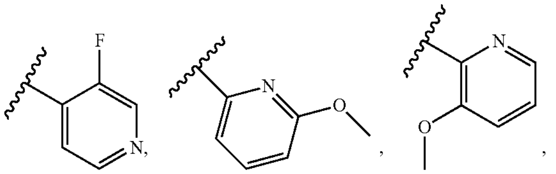
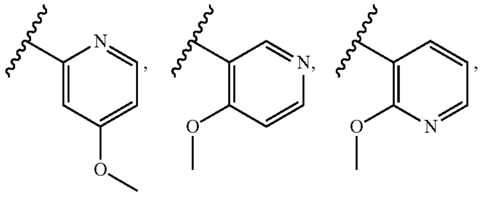
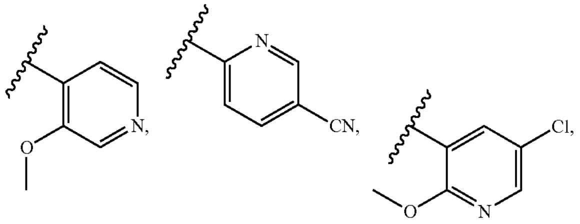
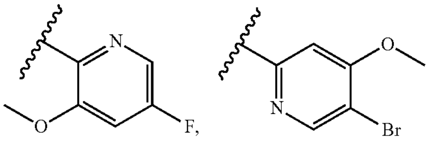
, and
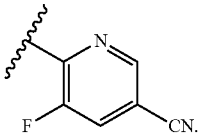
In some embodiments, Ring B is selected from:
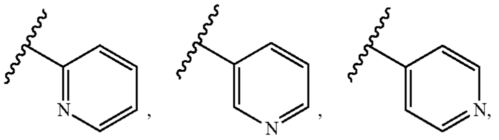
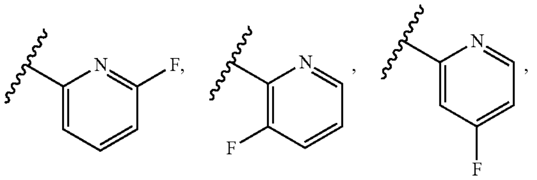
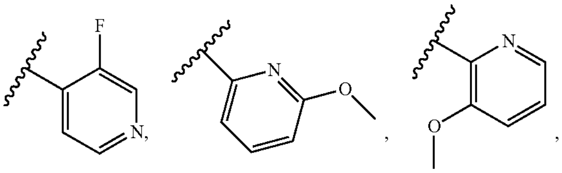
-continued
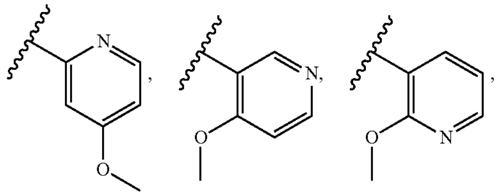
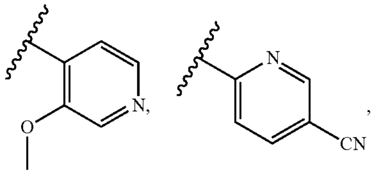
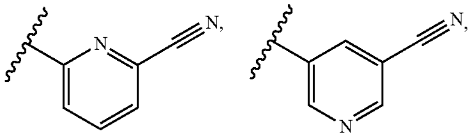
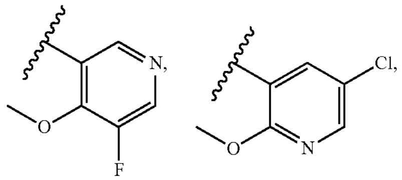
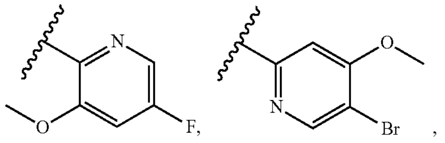
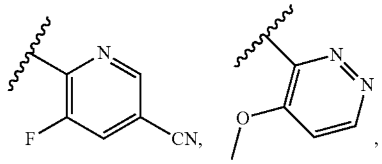
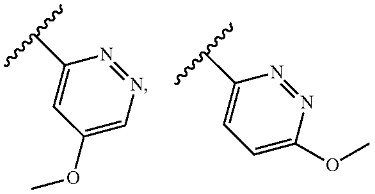
, and
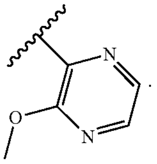
In some embodiments, Ring B is selected from:
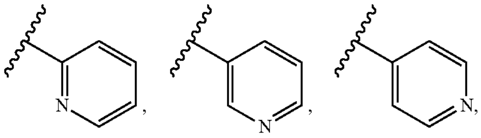

-continued

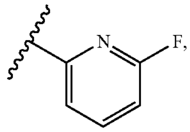 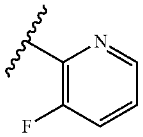, 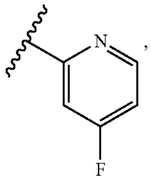,

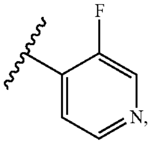 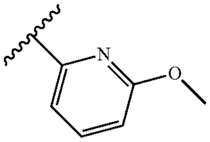, 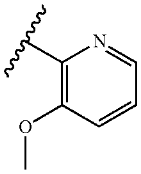,

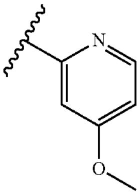, 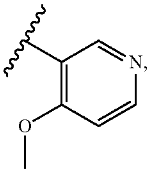 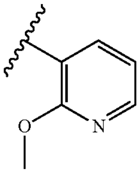,

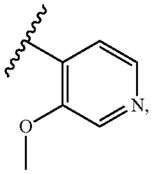 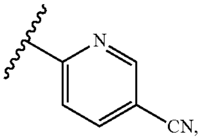

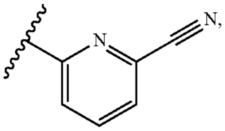 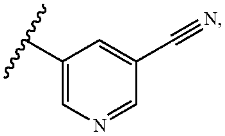

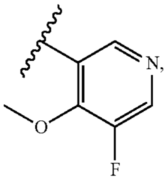 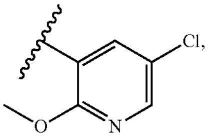

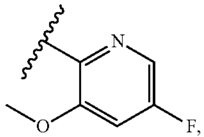 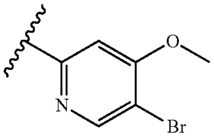, and

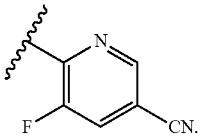

In some embodiments, Ring B is selected from

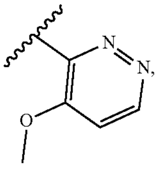 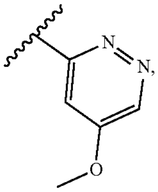

-continued

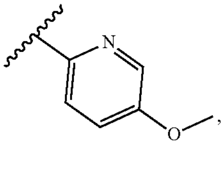, and 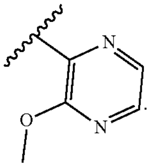

In some embodiments, for the compound or salt of Formula (V) or (V-a), Ring B is selected from imidazolyl, thiophenyl, pyridazinonyl, pyridyl, pyrazinyl, pyridazinyl, and pyrimidinyl, each of which is optionally substituted with one or more $C_{1-6}$ alkyl optionally substituted with one or more substituents independently selected from halogen, $—OR^{105}$, $—N(R^{105})_2$, $—C(O)R^{105}$, $—C(O)OR^{105}$, $—C(O)N(R^{105})_2$, $—N(R^{105})C(O)R^{105}$, $—NO_2$, $═S$, $═O$, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

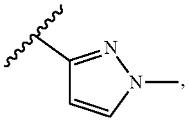, 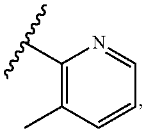,

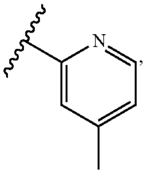, and 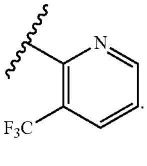.

In some embodiments, Ring B is selected from:

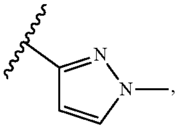, 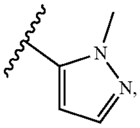, 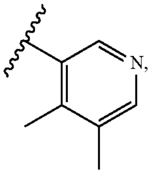

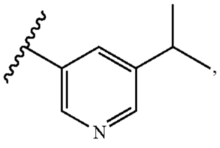, 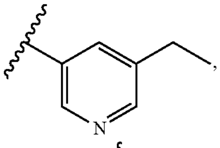,

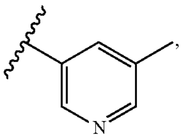, 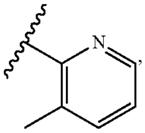, 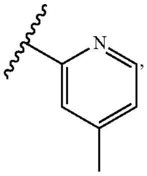, and

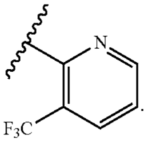.

In some embodiments, for the compound or salt of Formula (V) or (V-a), Ring B is selected from imidazolyl, thiophenyl, pyridazinonyl, pyridyl, pyrazinyl, pyridazinyl, and pyrimidinyl, each of which is optionally substituted with one or more substituents independently selected from:

halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN; and $C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

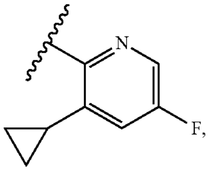
,
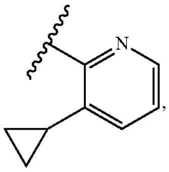
, and
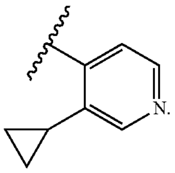
.

In some embodiments, Ring B is selected from:

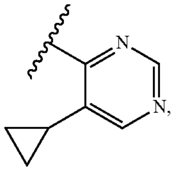
,
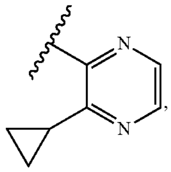
, and
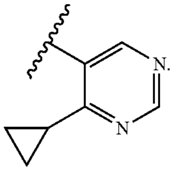
.

In some embodiments, Ring B is selected from:

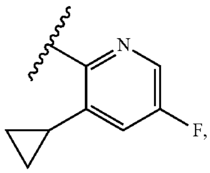
,
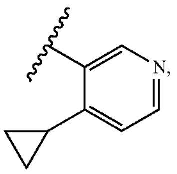
,

-continued

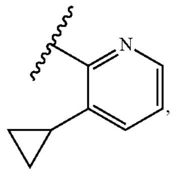
, and
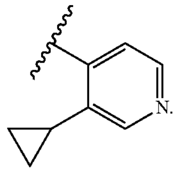
.

In some embodiments, for the compound or salt of Formula (V) or (V-a), Ring B is selected from imidazolyl, thiophenyl, pyridazinonyl, pyridyl, pyrazinyl, pyridazinyl, and pyrimidinyl, each of which is optionally substituted with one or more substituents independently selected from:

halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from:

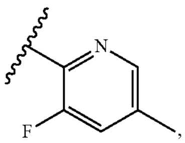
,
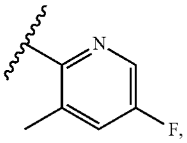
,
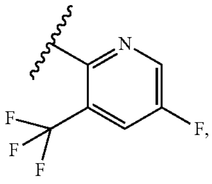
, and
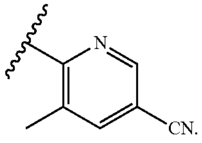
.

In some embodiments, for the compound or salt of Formula (V) or (V-a), Ring B is selected from:

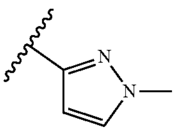
,
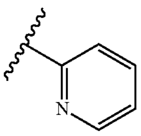
,
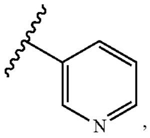
,
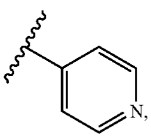
,
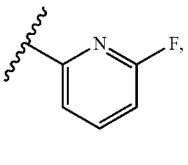
,
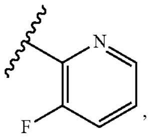
,
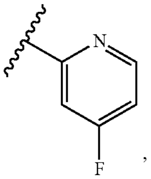
,
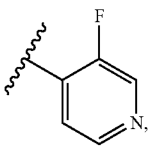
,
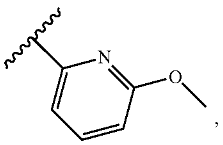
, -continued
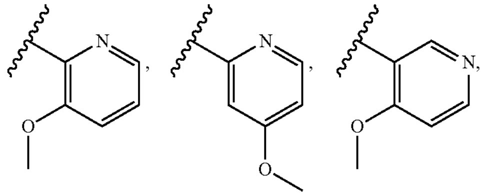
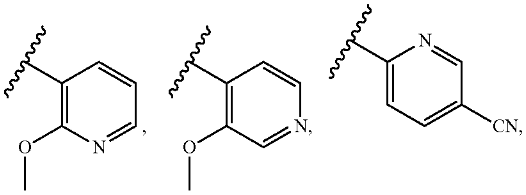
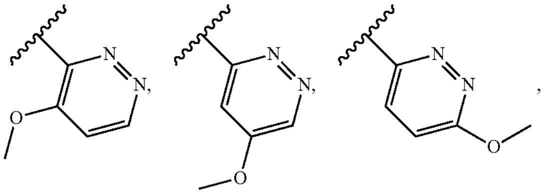
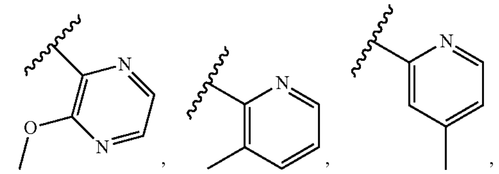
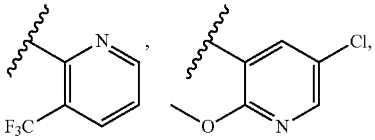
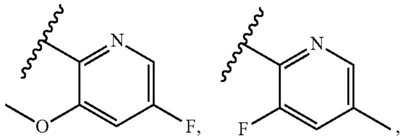
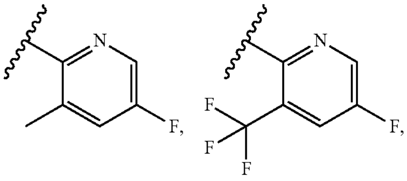
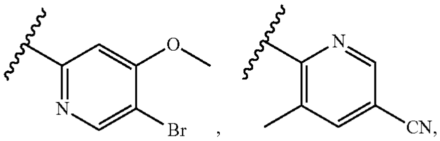
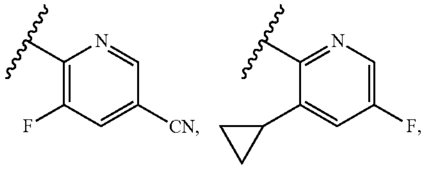
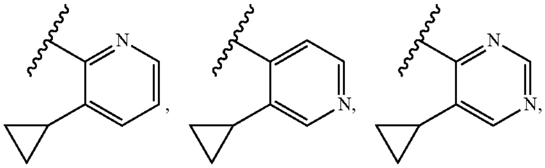
-continued
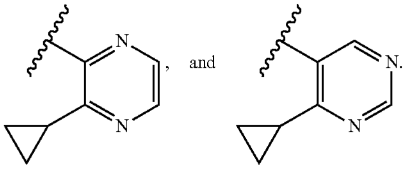
In some embodiments, for the compound or salt of Formula (V) or (V-a), Ring B is selected from:
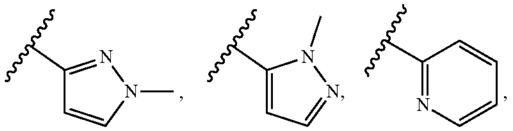
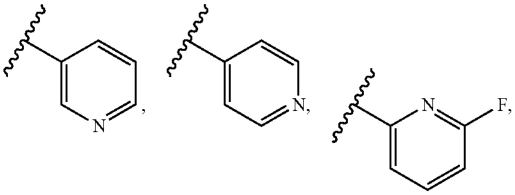
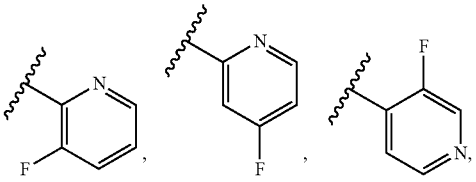
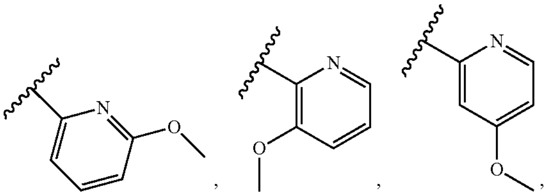
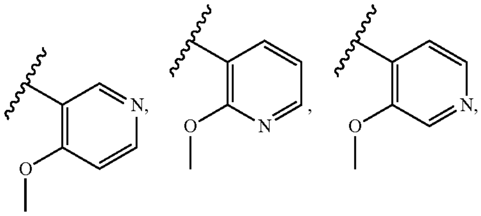
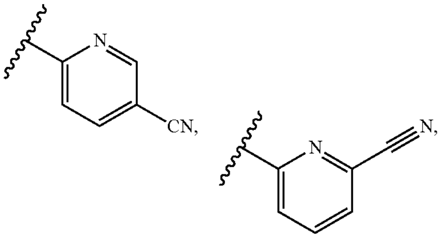
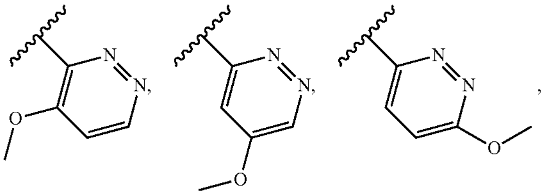

-continued

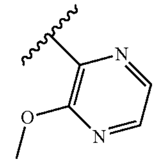, 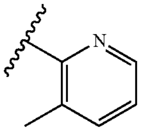, 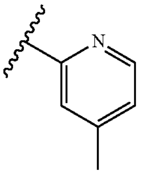,

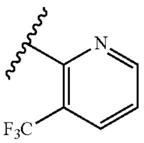, 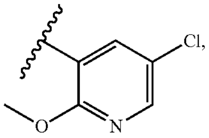 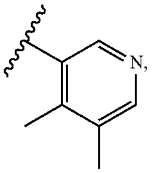

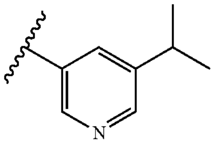, 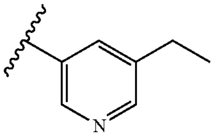,

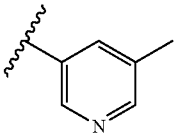, 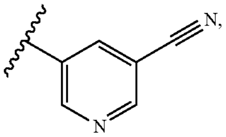

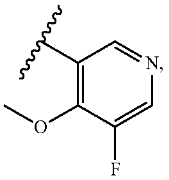 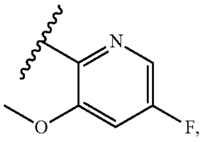 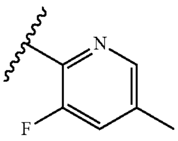,

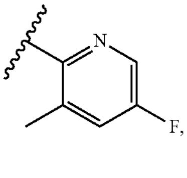 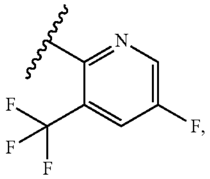

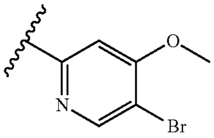, 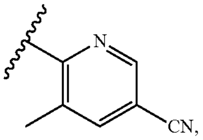

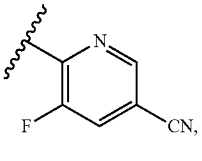 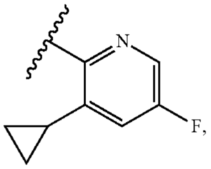

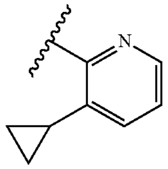, 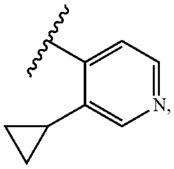, 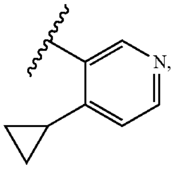

-continued

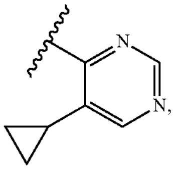 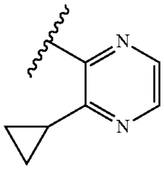, and

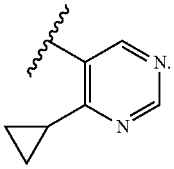

In some embodiments, for the compound or salt of Formula (V) or (V-a), Ring B is selected from benzodioxolyl, dihydrobenzofuranyl, benzofuranyl, benzimidazolyl, benzisoxazolyl, dihydrofuropyridyl, furopyridyl, and quinolinyl, each of which is optionally substituted with one or more substituents independently selected from:

halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN;

$C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from

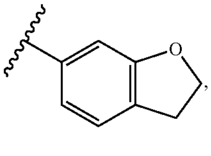, 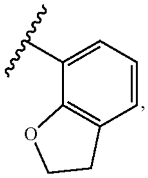, 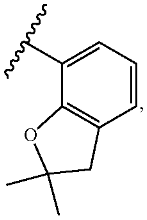,

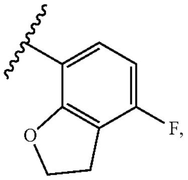 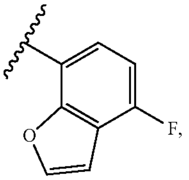 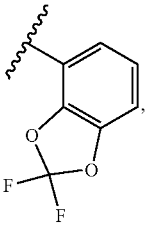,

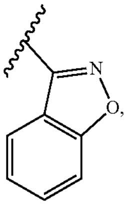 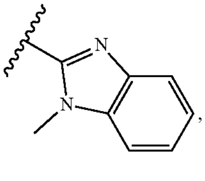, 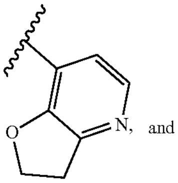 and

-continued

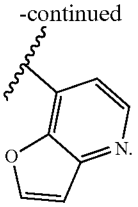

In some embodiments, Ring B is selected from

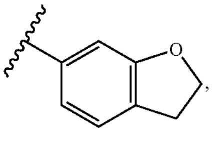, 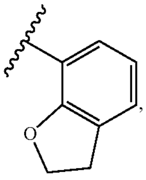, 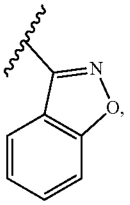

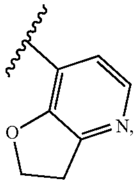 and 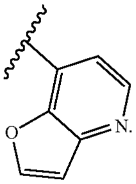

In some embodiments, Ring B is selected from

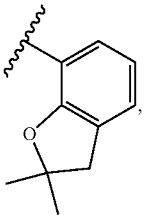, 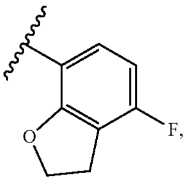 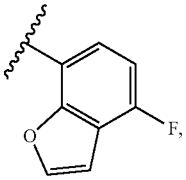

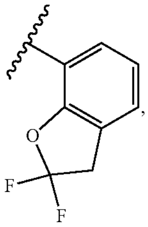 and 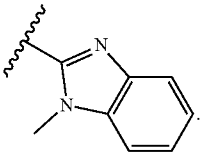

In some embodiments, for the compound or salt of Formula (V) or (V-a), Ring B is selected from benzodioxolyl, dihydrobenzofuranyl, benzofuranyl, benzimidazolyl, benzisoxazolyl, dihydrofuropyridyl, furopyridyl, thienopyridinyl, indazolyl, pyrazolo[4,3-b]pyridinyl, imidazo[1,2-a]pyridinyl, imidazo[1,2-a]pyrazinyl, pyrazolo[1,5-a]pyridinyl, and quinolinyl, each of which is optionally substituted with one or more substituents independently selected from:

halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, and —CN;

$C_{1-6}$ alkyl optionally substituted with one or more substituents independently selected from halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN;

$C_{3-6}$ carbocycle and 3- to 6-membered heterocycle, any of which is optionally substituted with one or more substituents independently selected halogen, —$OR^{105}$, —$N(R^{105})_2$, —$C(O)R^{105}$, —$C(O)OR^{105}$, —$C(O)N(R^{105})_2$, —$N(R^{105})C(O)R^{105}$, —$NO_2$, =S, =O, and —CN; and $R^{105}$ is selected from hydrogen, $C_{1-4}$ alkyl, $C_{1-4}$haloalkyl, $C_{3-6}$ saturated carbocycle, and 3- to 6-membered saturated heterocycle. In some embodiments, Ring B is selected from

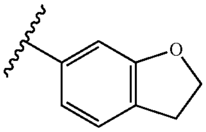, 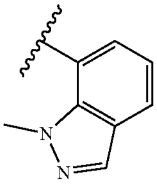, 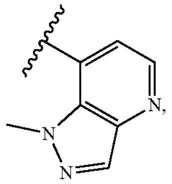

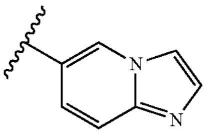, 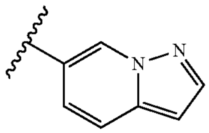,

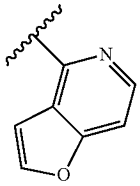, 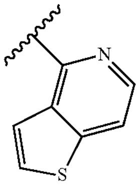, 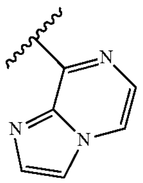,

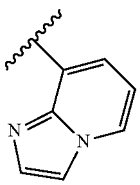, 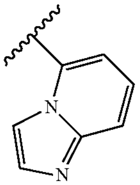, 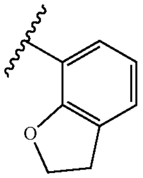,

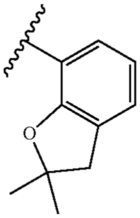, 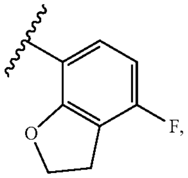 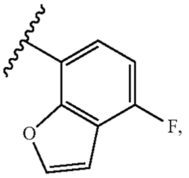

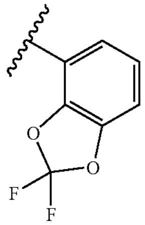, 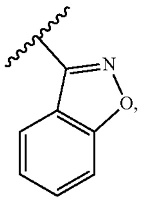 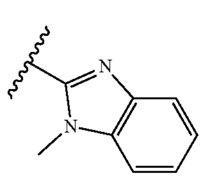,

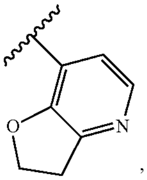, and 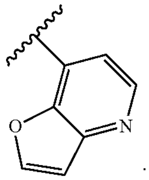.

In some embodiments, Ring B is selected from
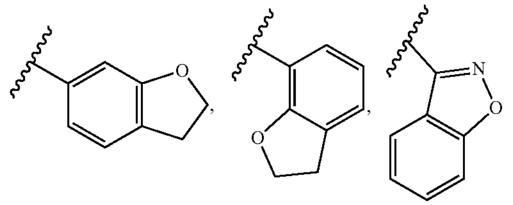
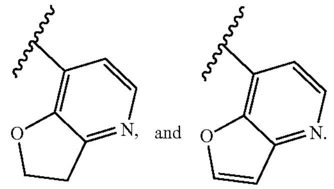
In some embodiments, Ring B is selected from
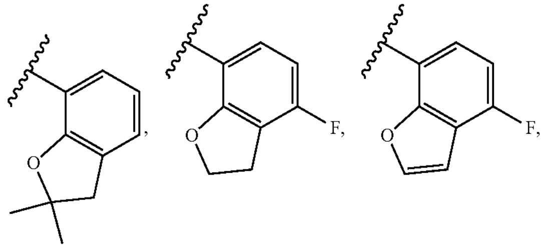
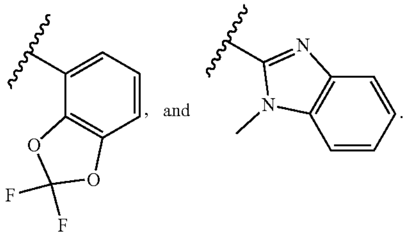
In some embodiments, Ring B is selected from
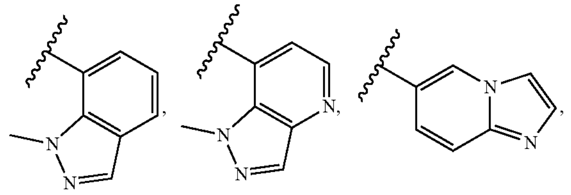
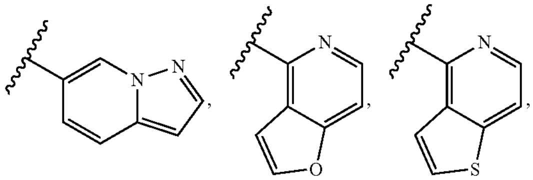
-continued
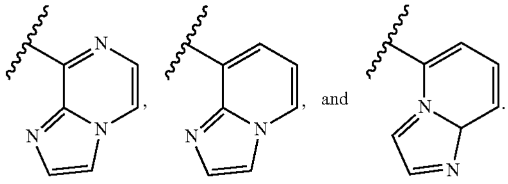
In some embodiments, for the compound or salt of Formula (V) or (V-a), Ring B is selected from:
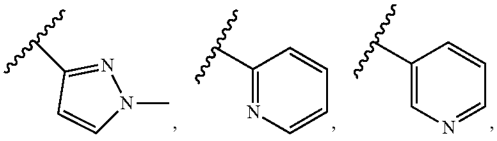
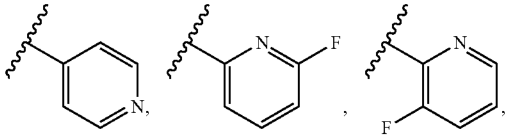
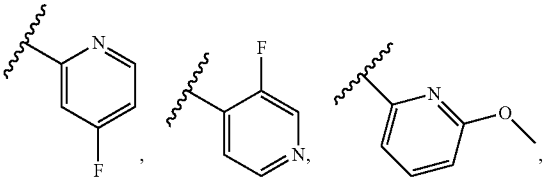
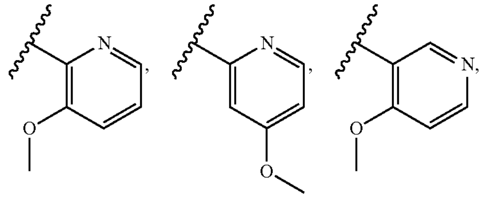
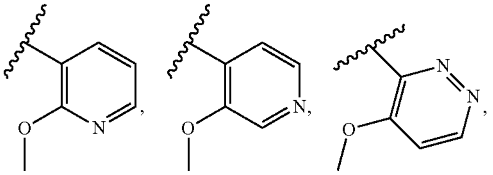
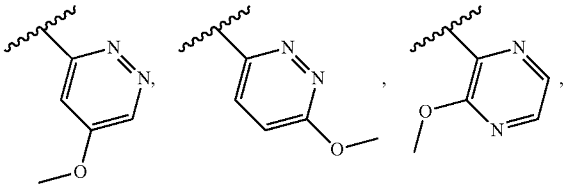
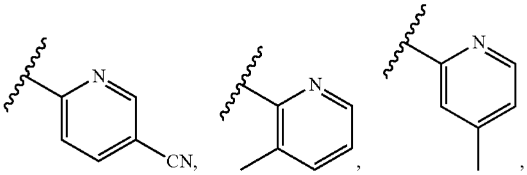
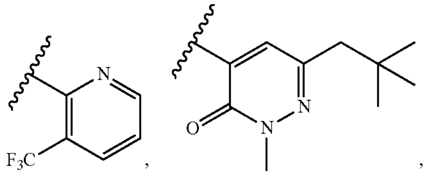

-continued
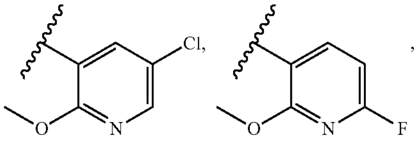
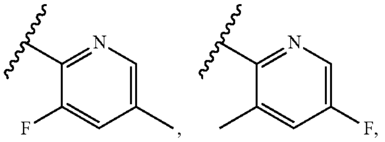
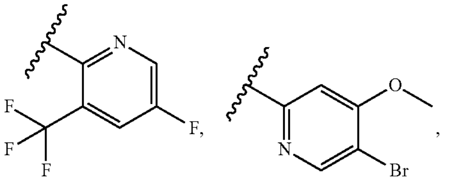
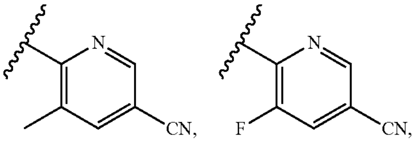
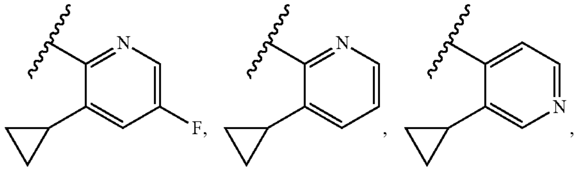
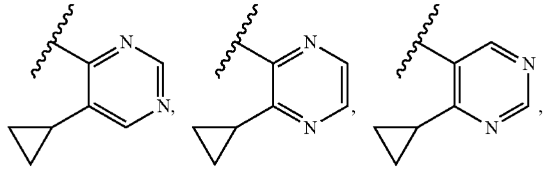
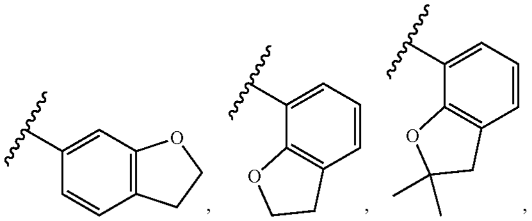
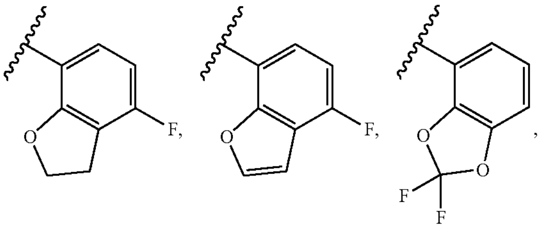
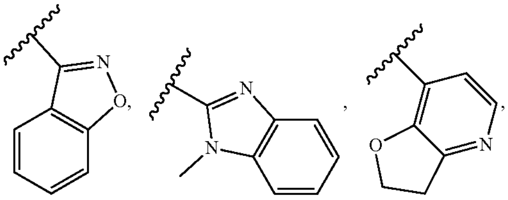
and
-continued
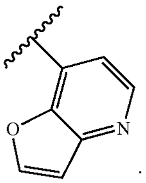
.
In some embodiments, for the compound or salt of Formula (V) or (V-a), Ring B is selected from:
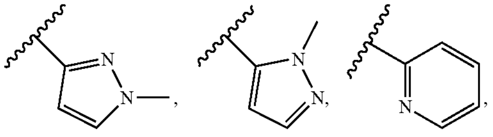
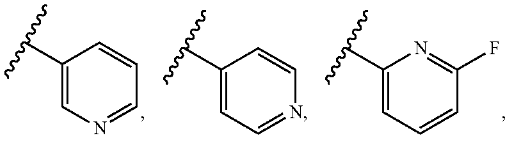
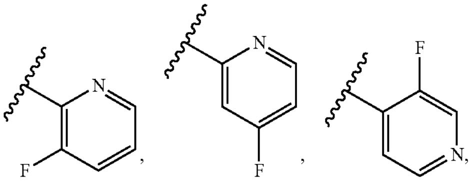
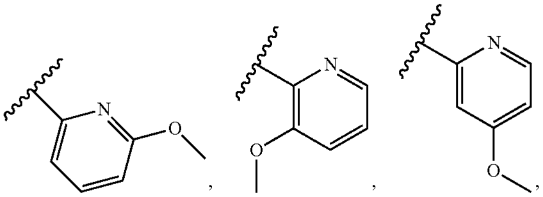
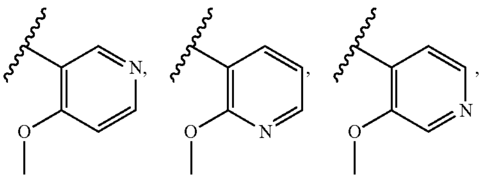
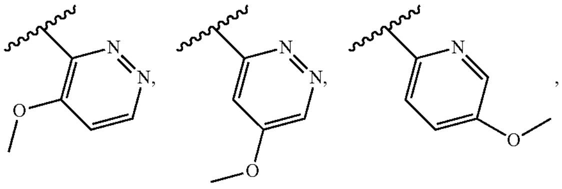
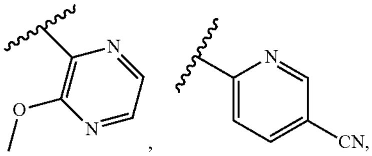
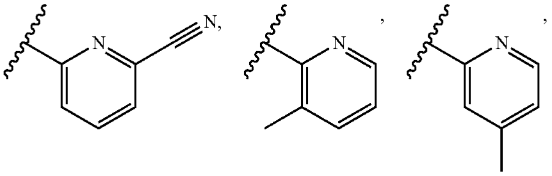

-continued

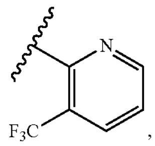, 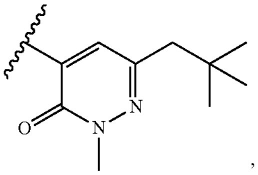,

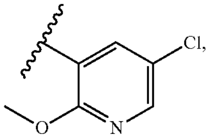 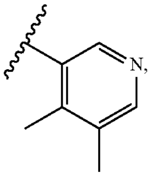

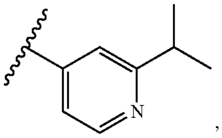, 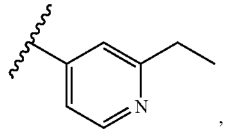,

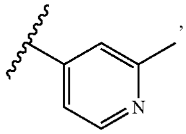, 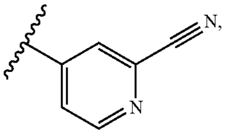

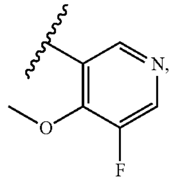 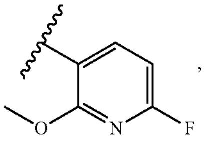,

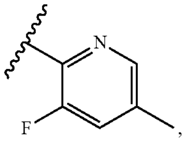, 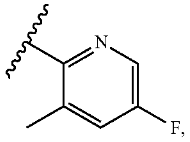

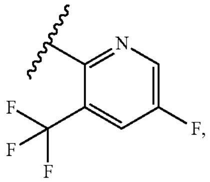 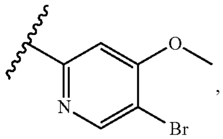,

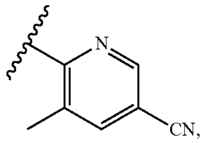 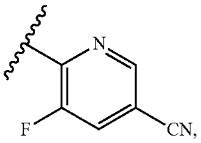

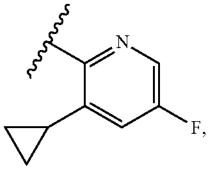 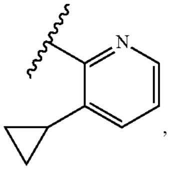, 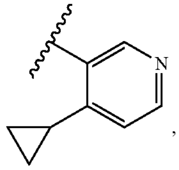,

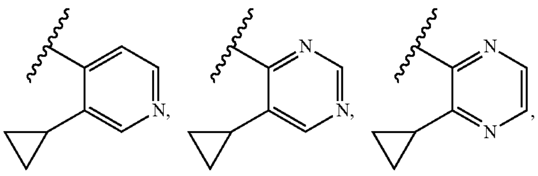

-continued

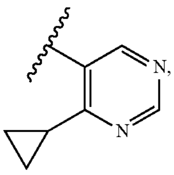 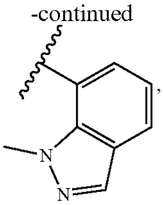, 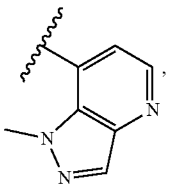,

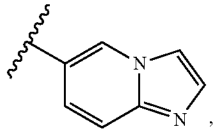, 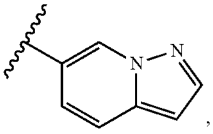,

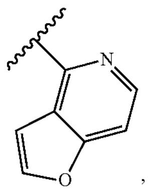, 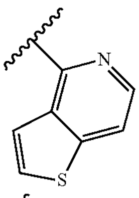, 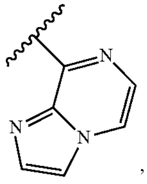,

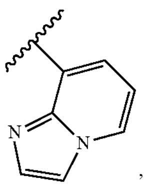, 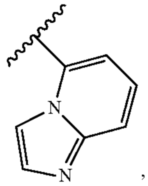, 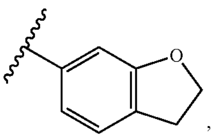,

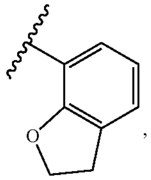, 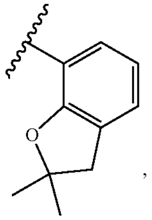, 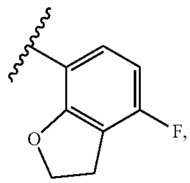

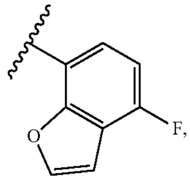 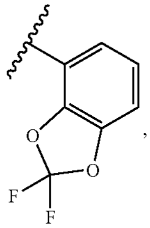, 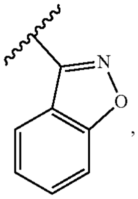,

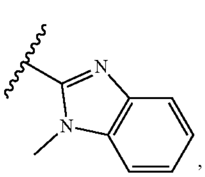, 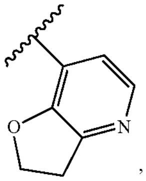, and 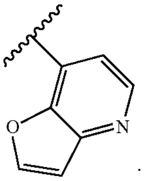.

In some embodiments, for the compound or salt of Formula (V), (V-a), (V-b), (V-c), (V-d), or (V-e), $R^{102}$ is hydrogen. In some embodiments, $R^{102}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN. In some embodiments, $R^{102}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, and —CN. In some embodiments, $R^{102}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN.

In some embodiments, for the compound or salt of Formula (V), (V-a), (V-b), (V-c), (V-d), or (V-e), $R^{103}$ is hydrogen. In some embodiments, $R^{103}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN. In some embodiments, $R^{103}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, and —CN. In some embodiments, $R^{103}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN.

In some embodiments, for the compound or salt of Formula (V), (V-a), (V-b), (V-c), (V-d), or (V-e), $R^{104}$ is hydrogen. In some embodiments, $R^{104}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN. In some embodiments, $R^{104}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, and —CN. In some embodiments, $R^{104}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN.

In some embodiments, for the compound or salt of Formula (V), (V-a), (V-b), (V-c), (V-d), or (V-e), $R^{105}$ is hydrogen. In some embodiments, $R^{105}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN. In some embodiments, $R^{105}$ is selected from $C_{1-6}$ alkyl optionally substituted with one more substituents independently selected from halogen, —O—$C_{1-6}$ alkyl, —O—$C_{1-6}$ haloalkyl, —$NH_2$, —$NO_2$, ═O, and —CN. In some embodiments, $R^{105}$ is selected from $C_{1-6}$ alkyl optionally substituted with one more substituents independently selected from $C_{3-10}$ carbocycle and 3- to 10-membered heterocycle, any of which are optionally substituted with one or more substituents independently selected from: halogen, —OH, —O—$C_{1-6}$ alkyl, —O—$C_{1-6}$ haloalkyl, —$NH_2$, —$NO_2$, ═O, and —CN.

In some embodiments, the compound of Formula (V) is:

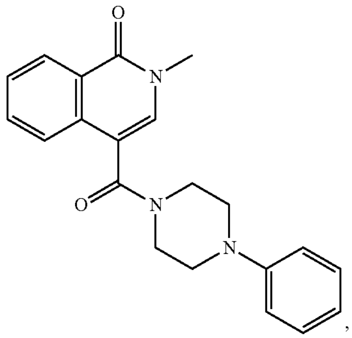
,

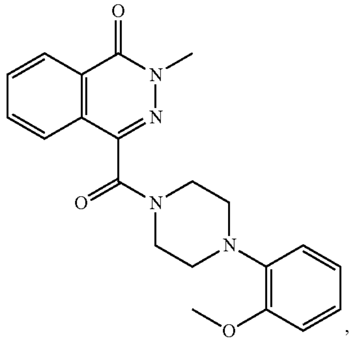
,

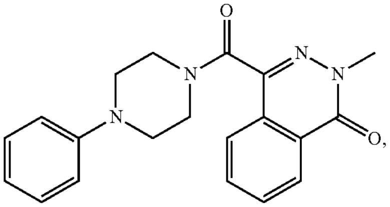

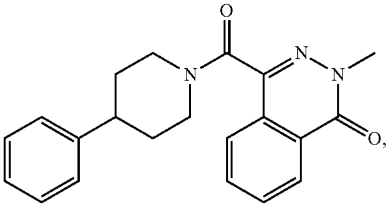

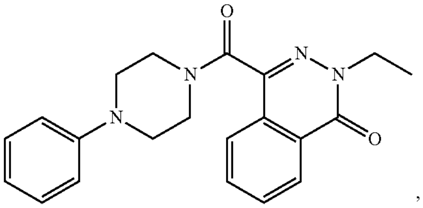
,

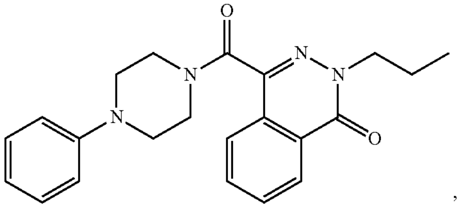
,

-continued
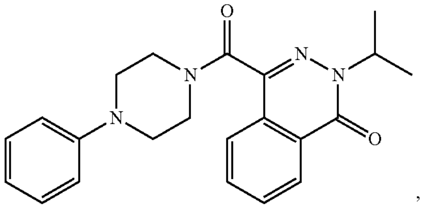
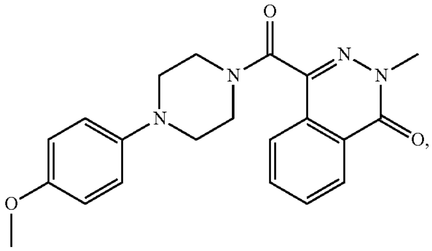
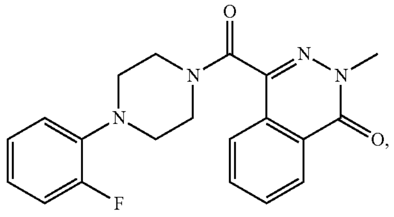
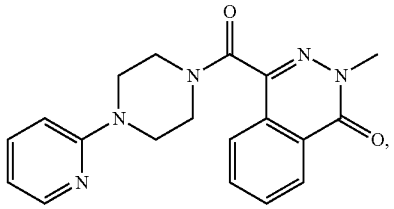
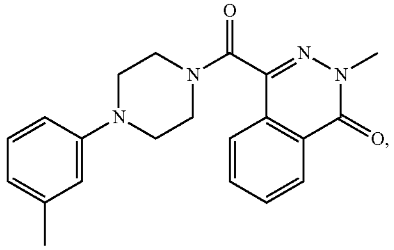
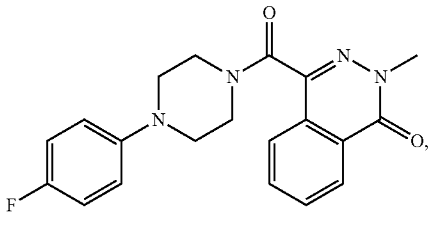
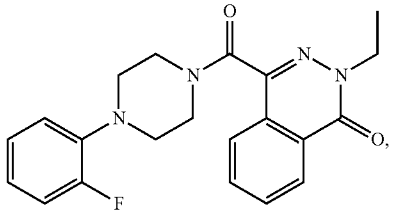
-continued
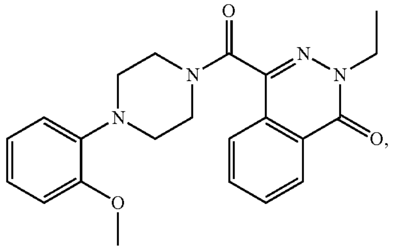
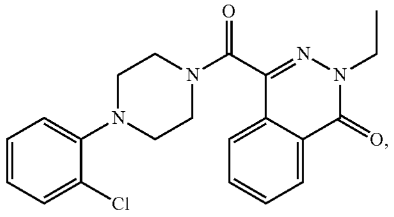
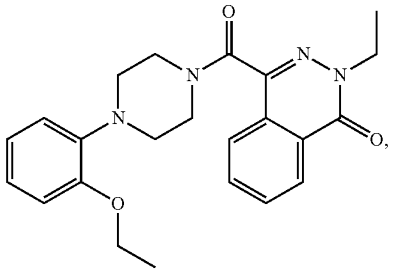
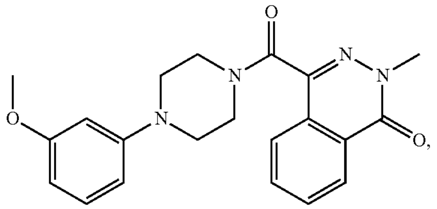
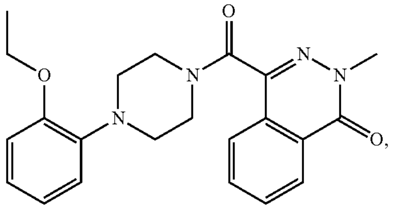
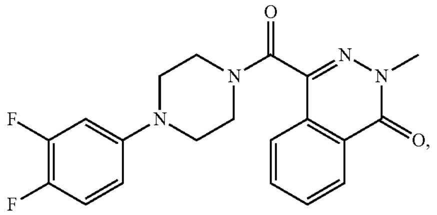
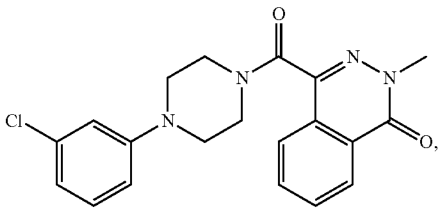
or a pharmaceutically acceptable salt of any one thereof.

In some embodiments, the compound of Formula (V) is:
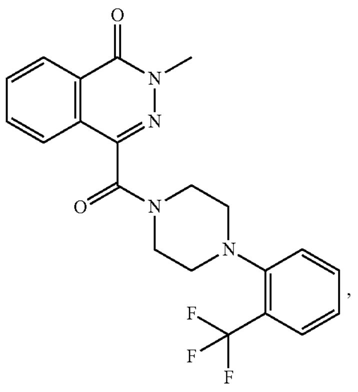
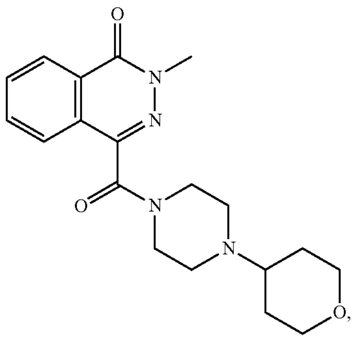
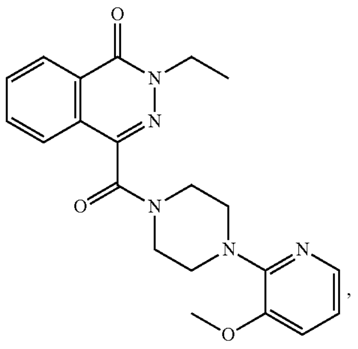
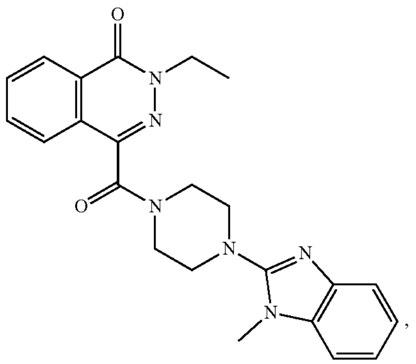
-continued
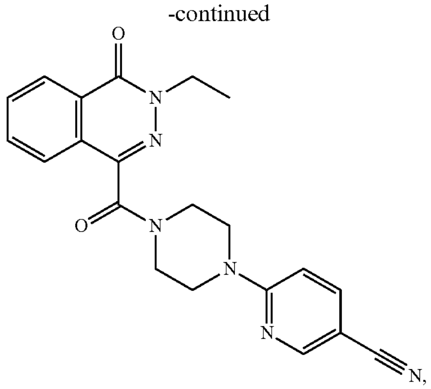
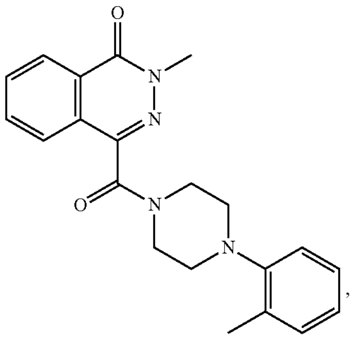
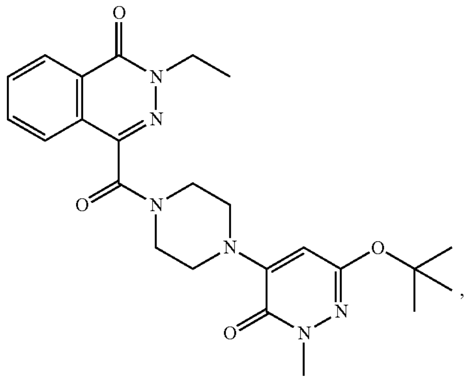
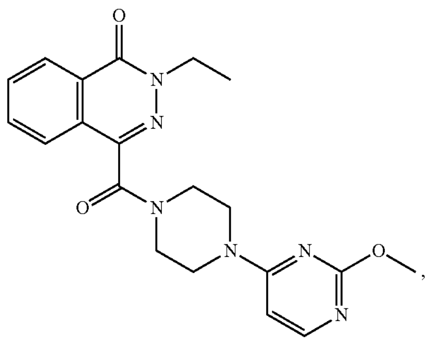

-continued
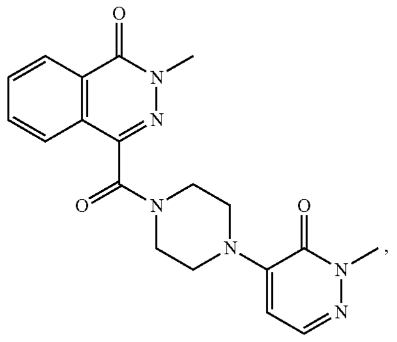
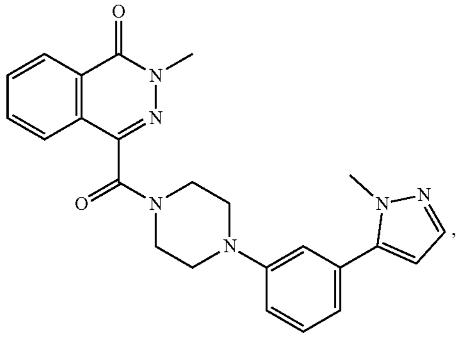
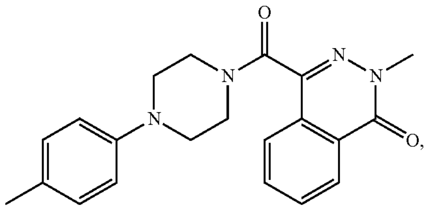
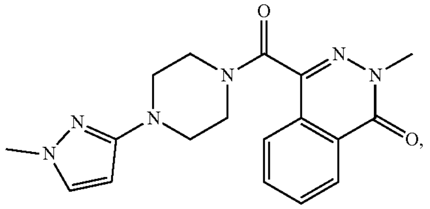
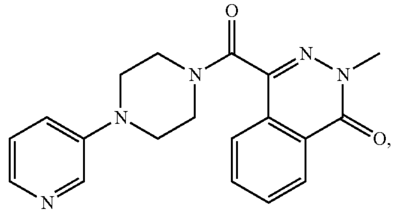
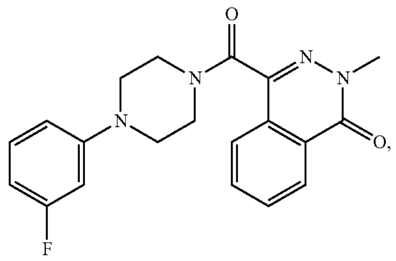
-continued
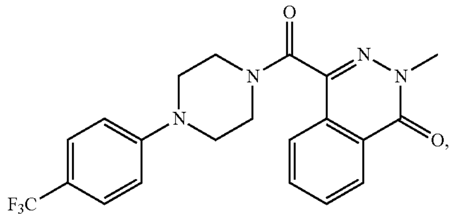
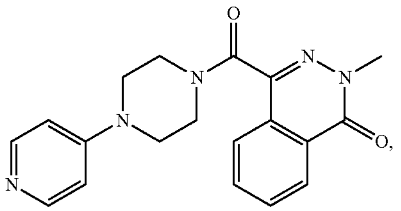
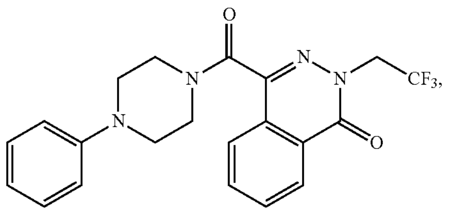
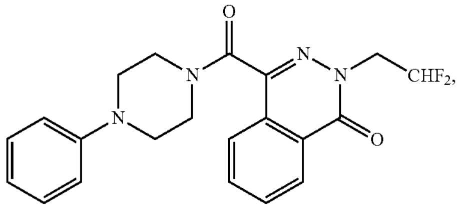
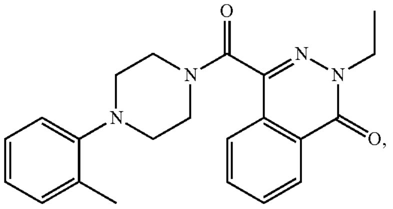
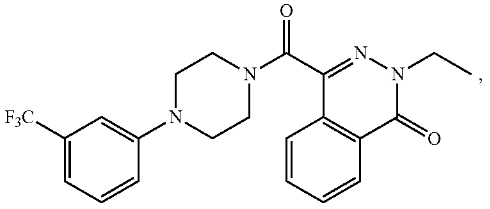
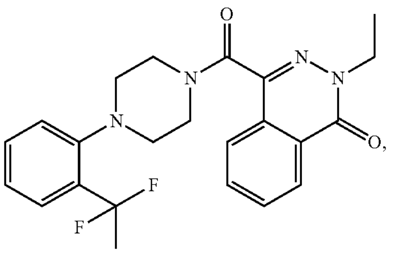

-continued
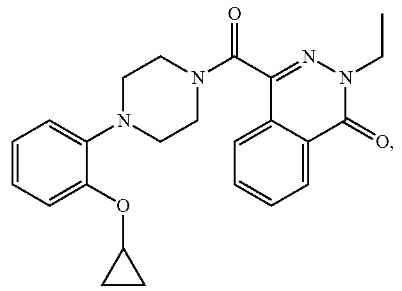
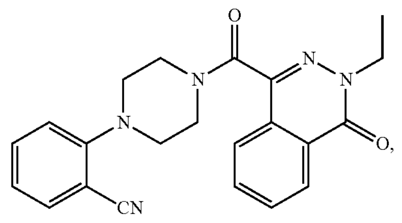
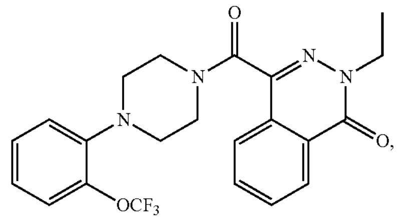
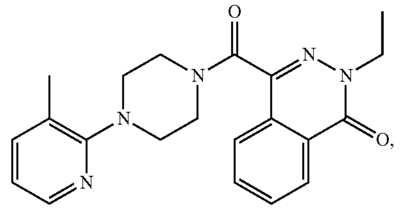
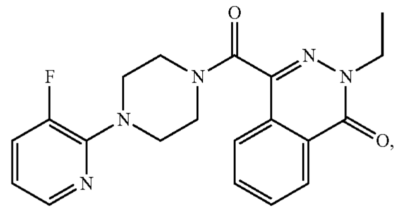
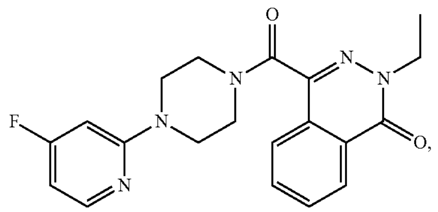
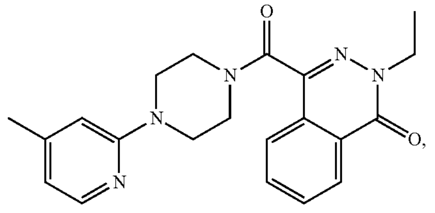
-continued
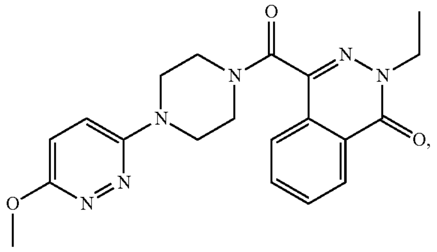
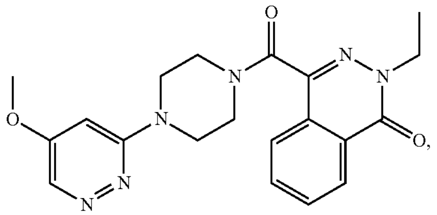
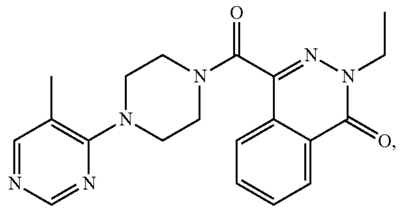
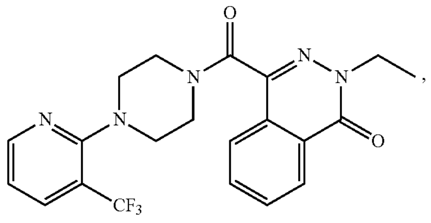
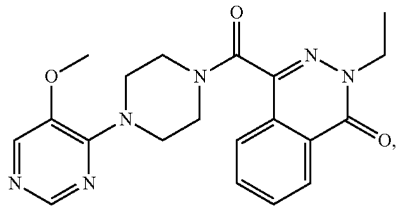
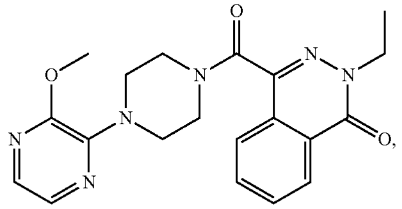
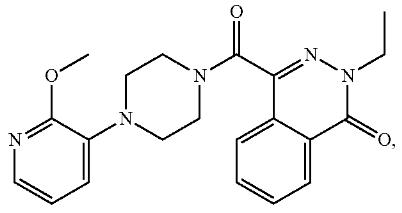

-continued
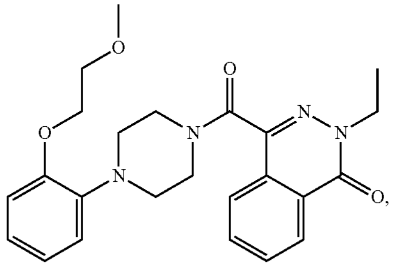
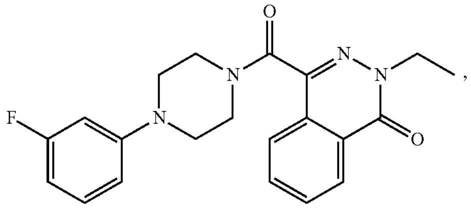
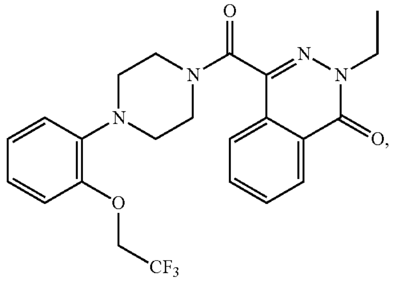
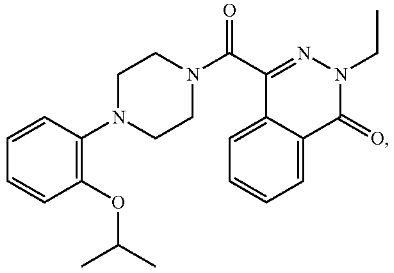
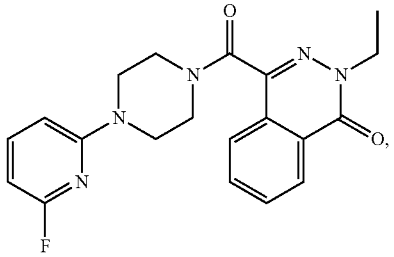
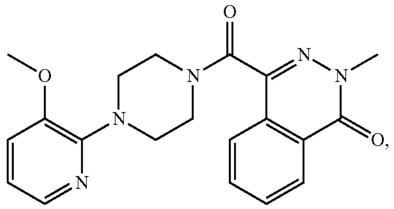
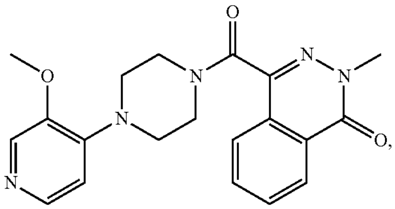
-continued
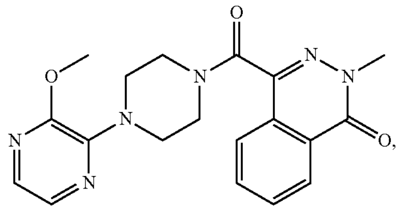
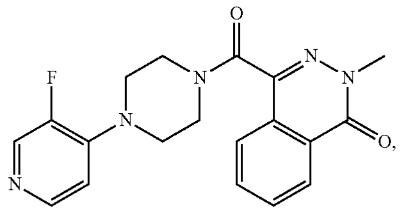
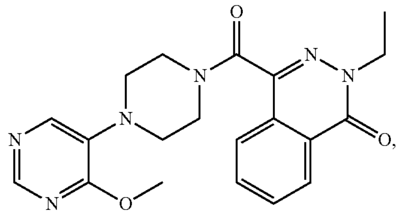
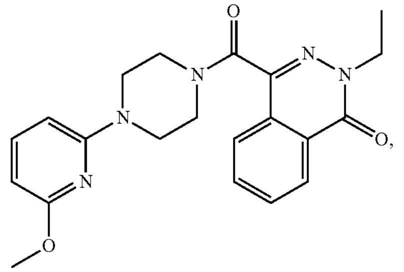
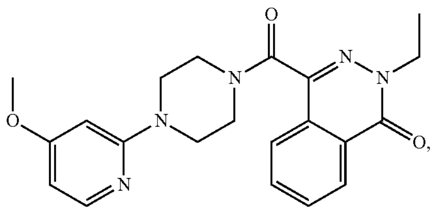
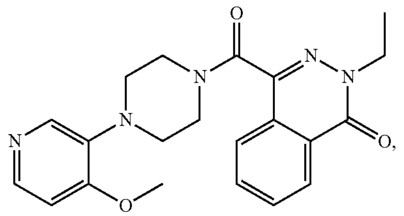
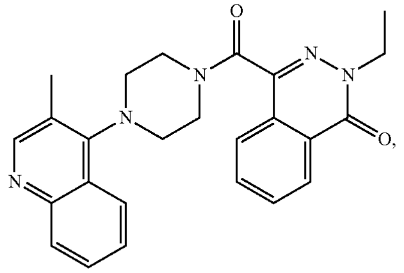

-continued
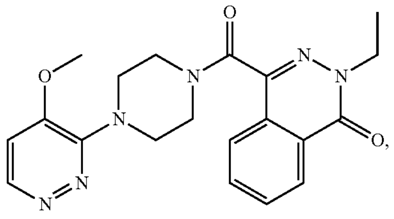
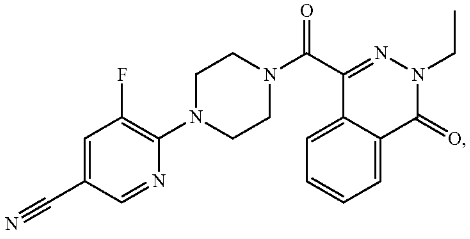
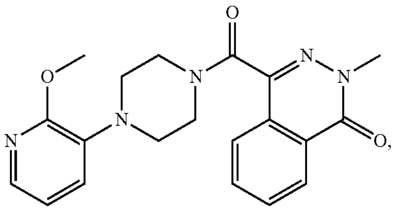
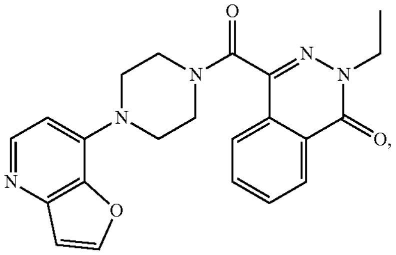
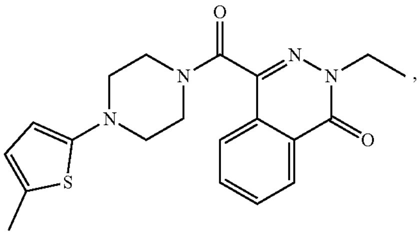
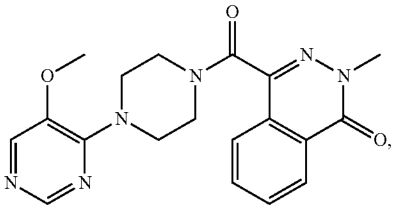
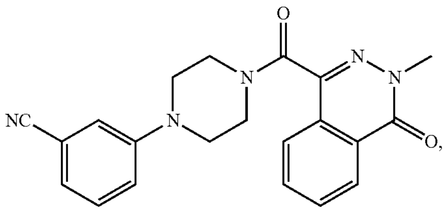
-continued
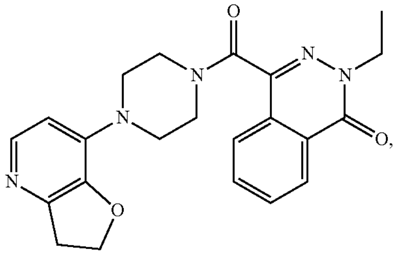
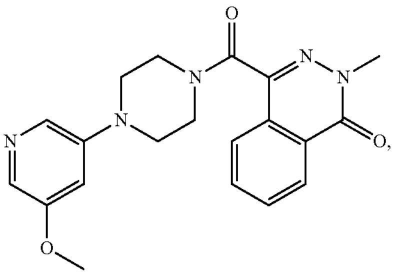
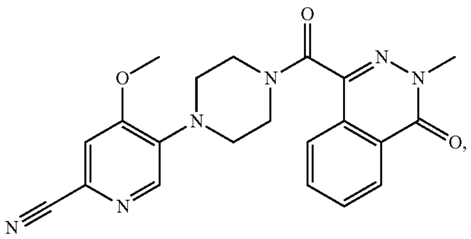
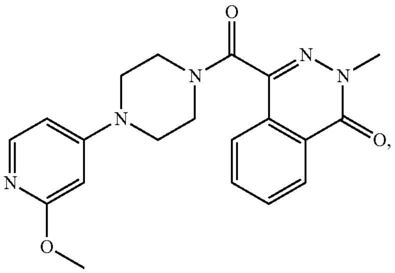
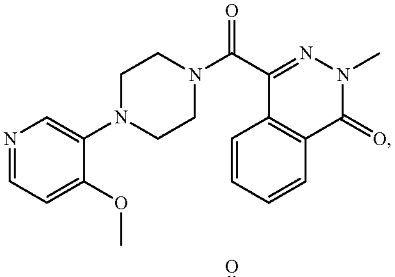
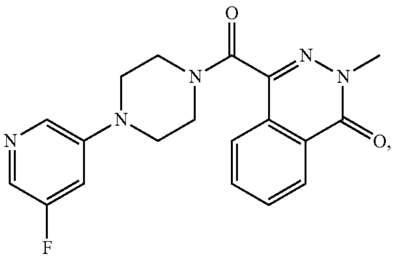

-continued
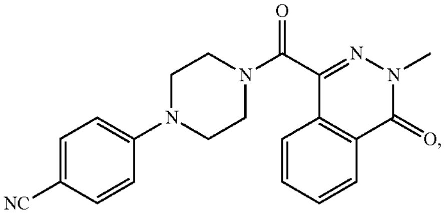
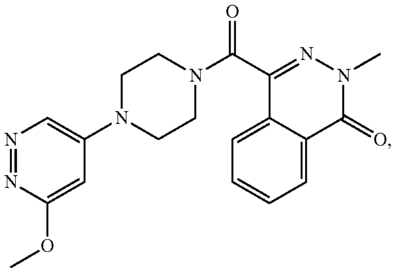
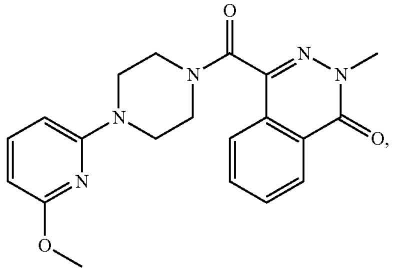
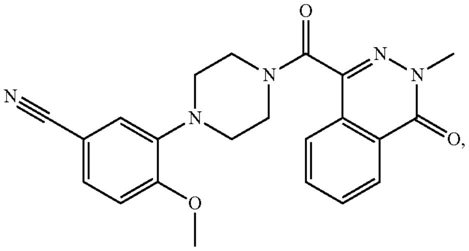
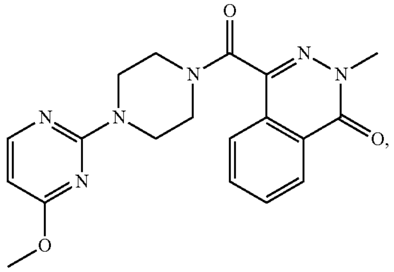
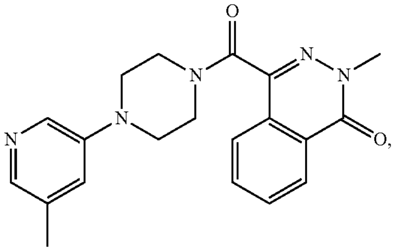
-continued
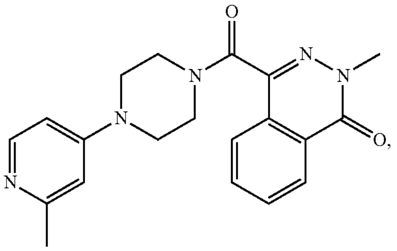
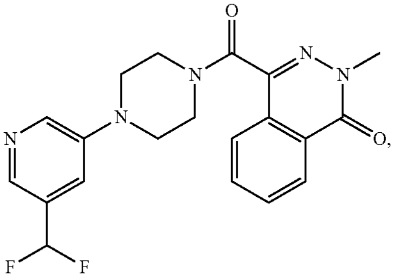
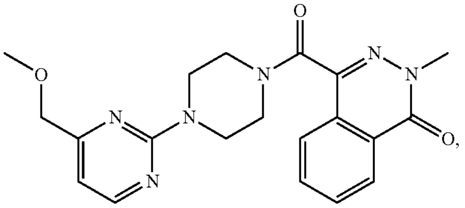
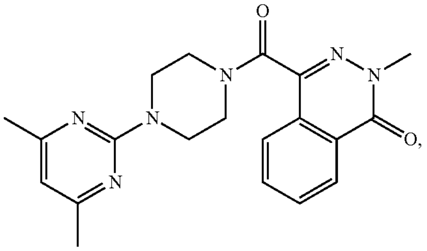
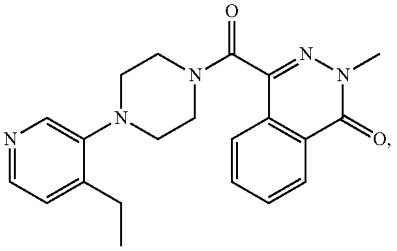
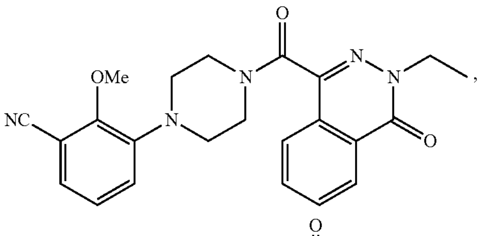
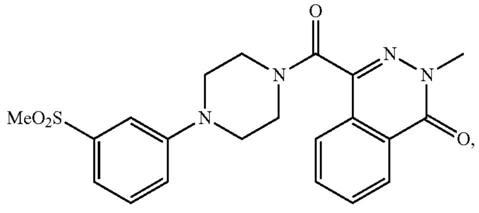
for a pharmaceutically acceptable salt of any one thereof.

In some embodiments, the compound of Formula (V) is:
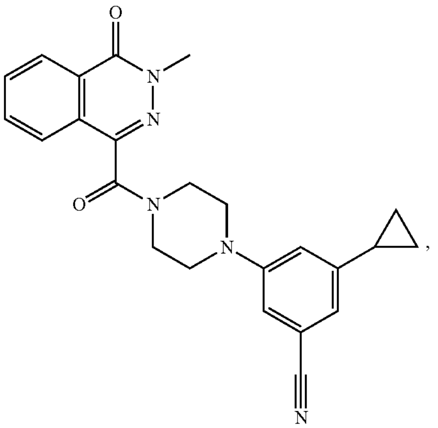
-continued
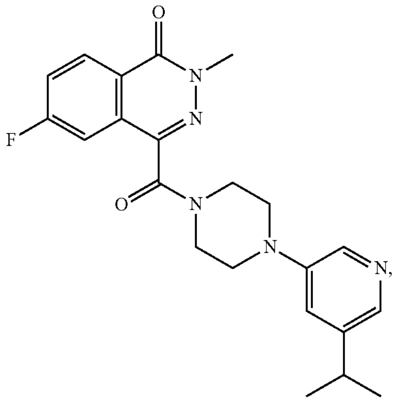
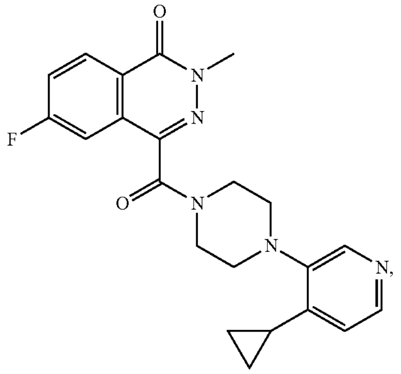
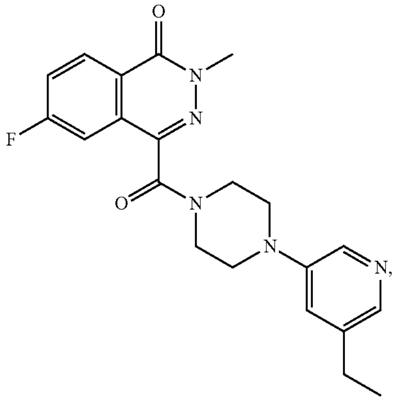
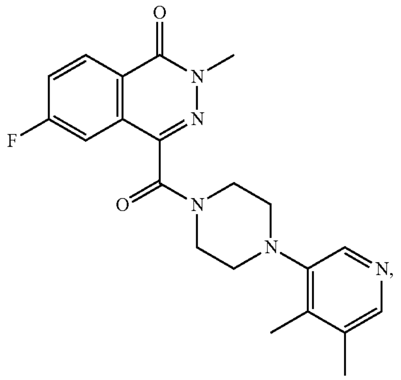
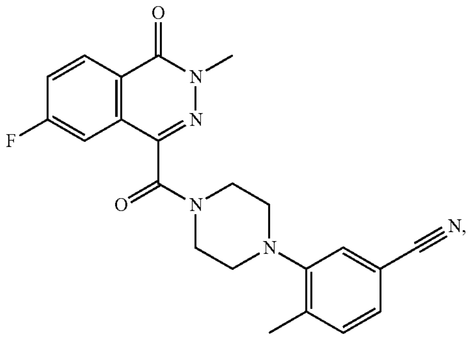
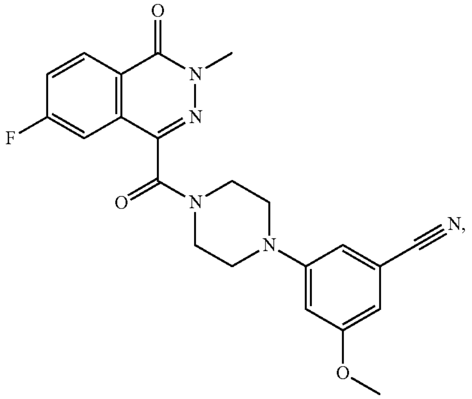
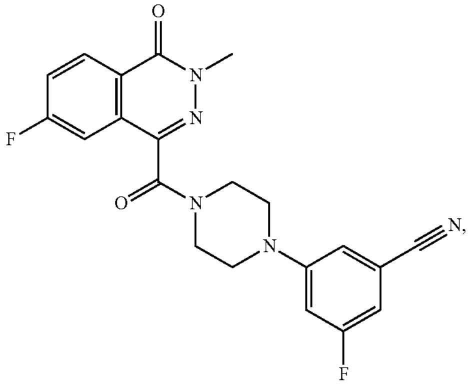

-continued
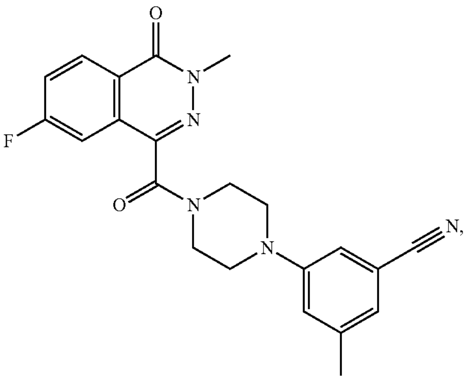
,
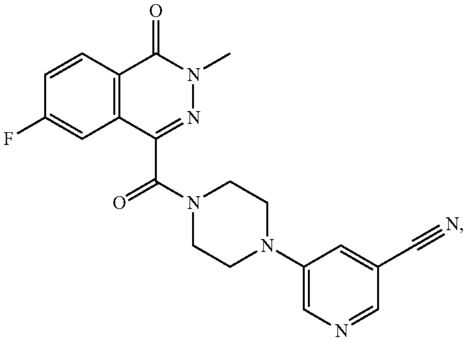
,
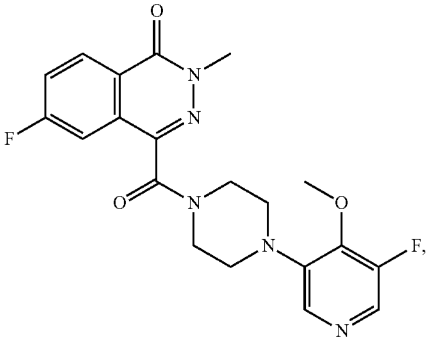
,
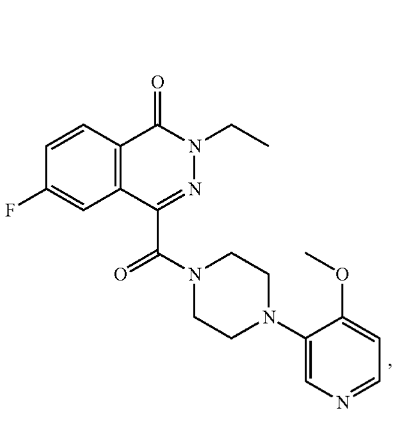
,
-continued
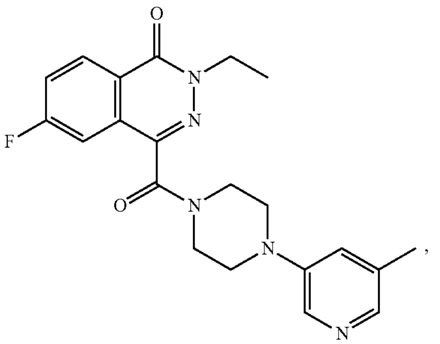
,
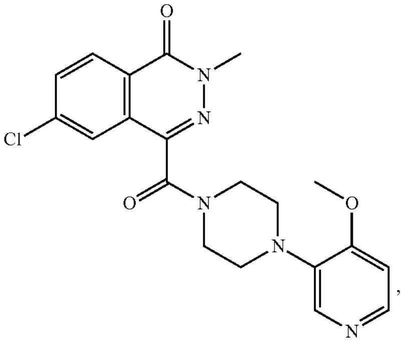
,
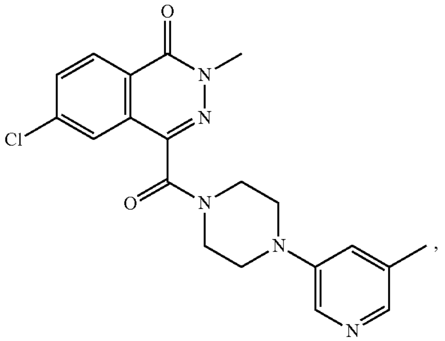
,
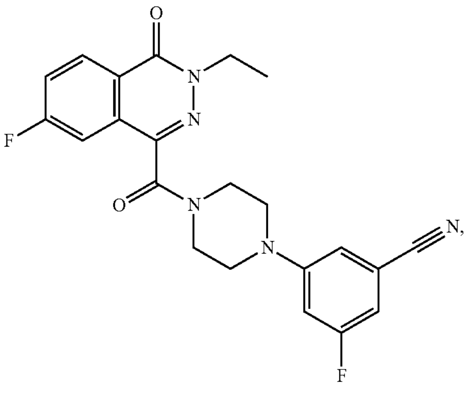
, -continued
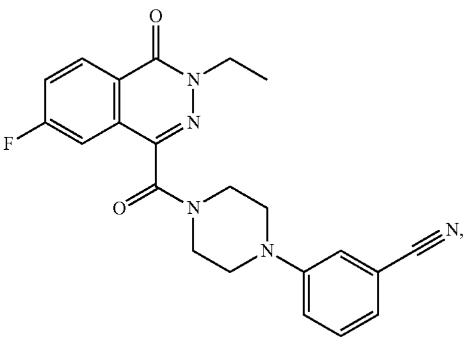
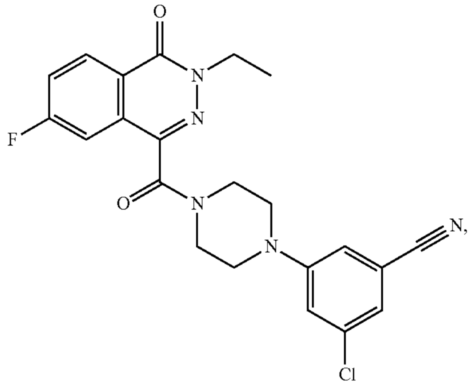
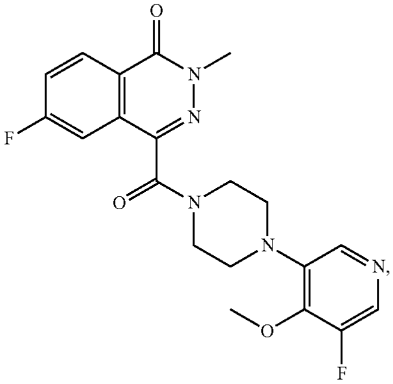
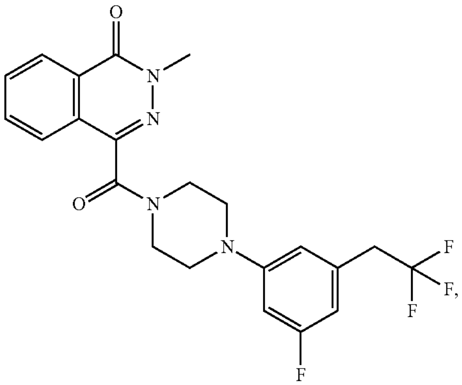
-continued
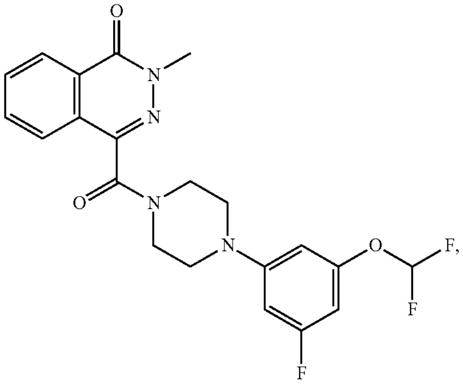
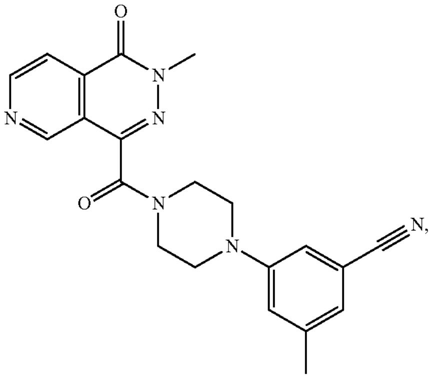
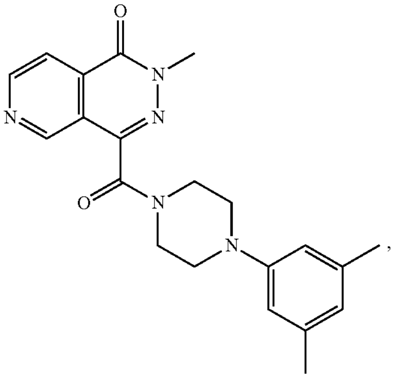
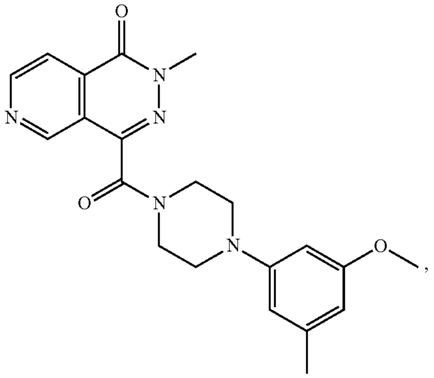

-continued
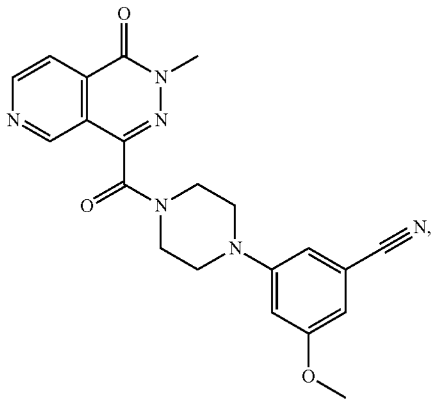
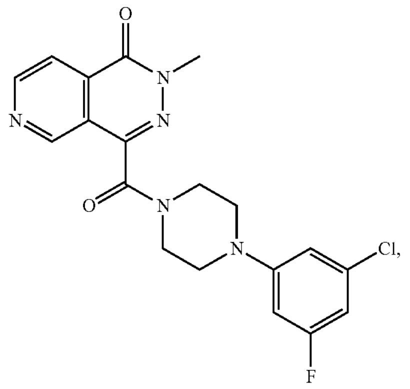
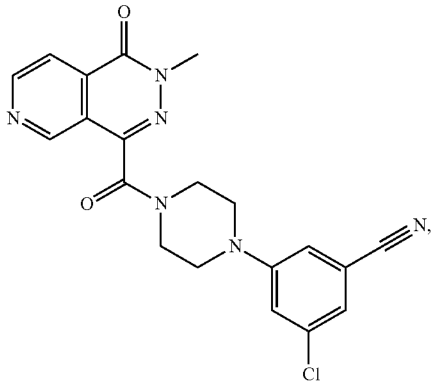
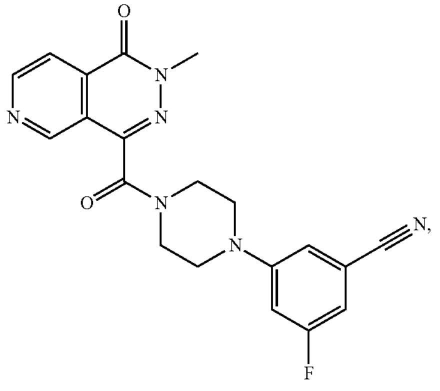
-continued
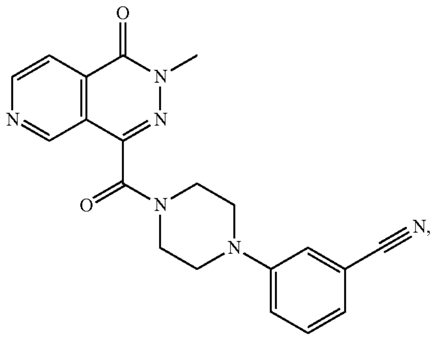
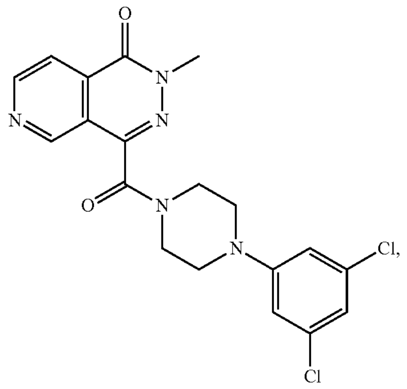
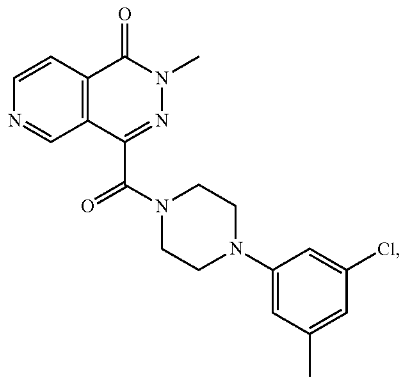
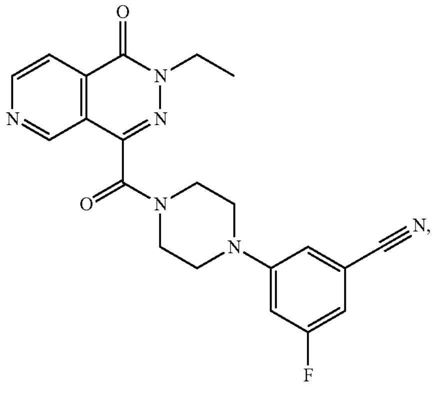

-continued
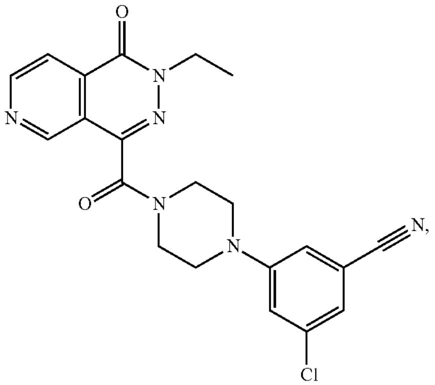
,
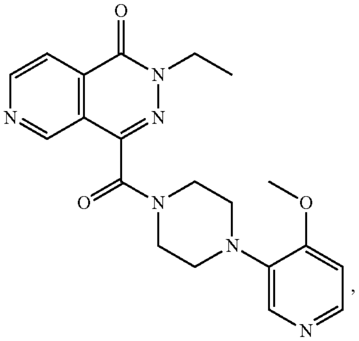
,
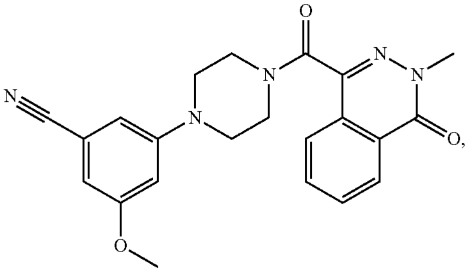
,
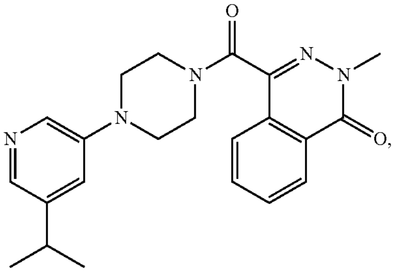
,
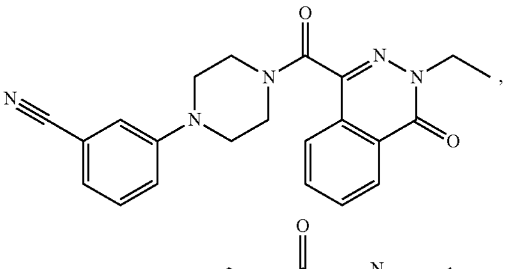
,
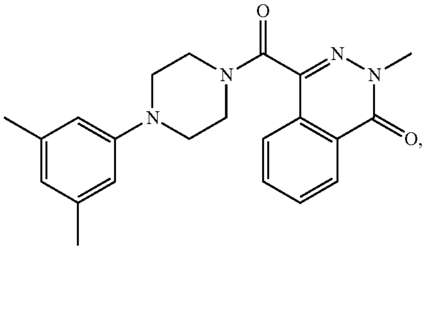
,
-continued
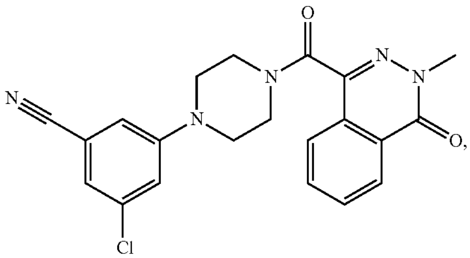
,
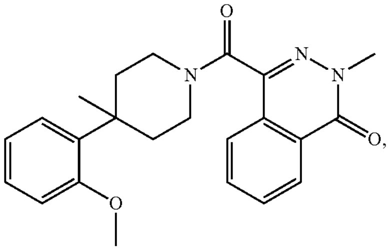
,
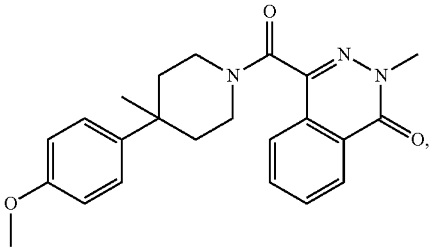
,
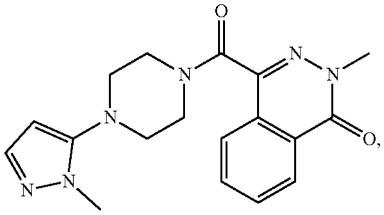
,
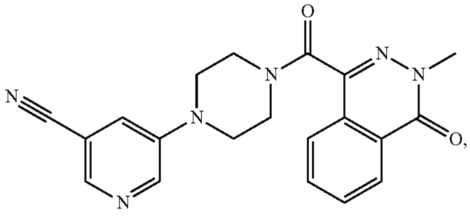
,
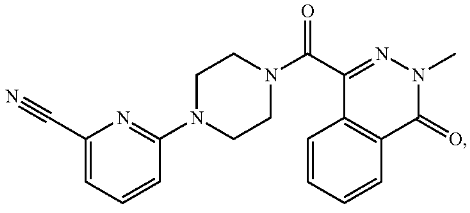
,
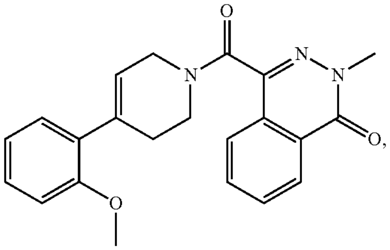
, -continued
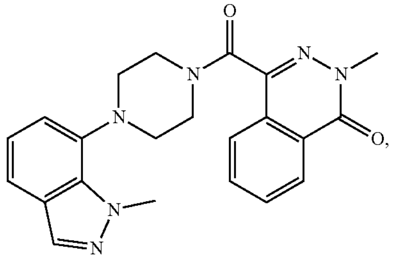
,
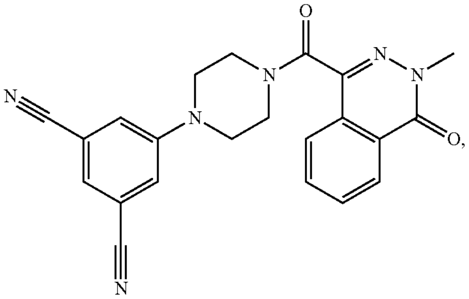
,
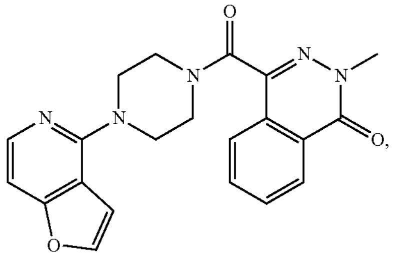
,
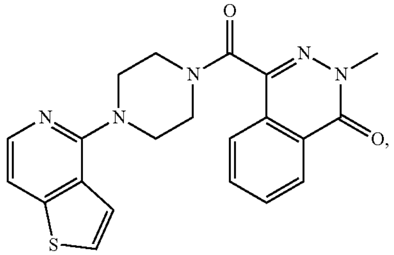
,
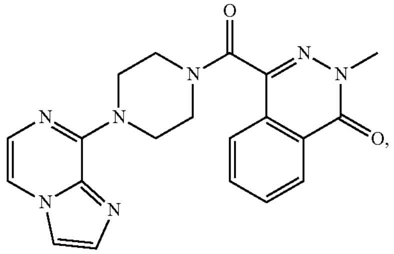
,
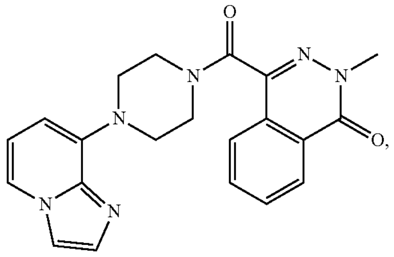
,
-continued
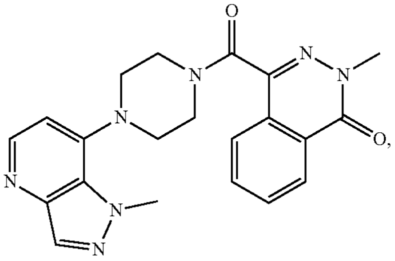
,
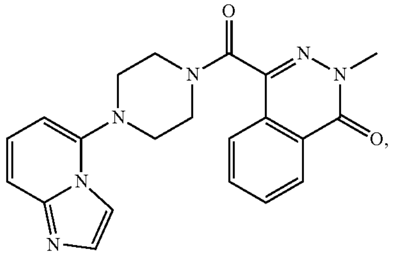
,
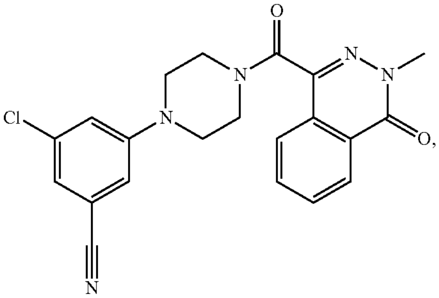
,
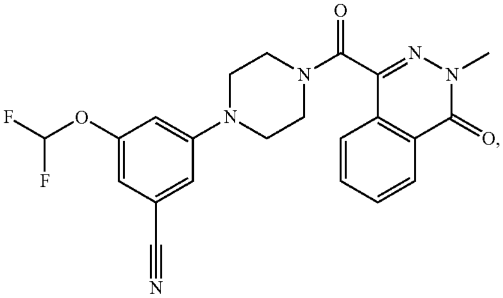
,
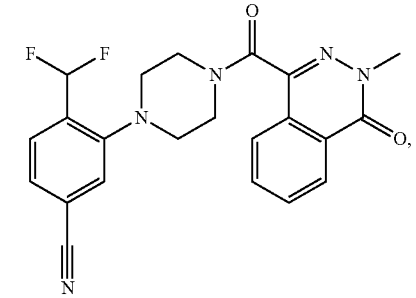
,
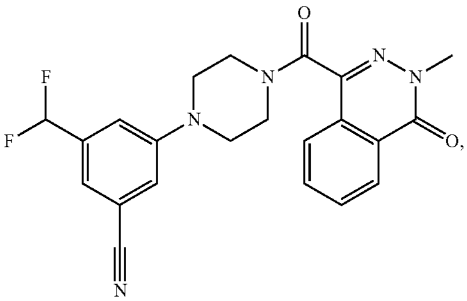
, -continued

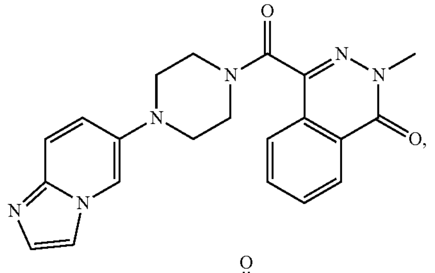

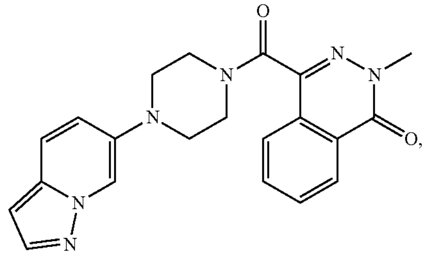

or

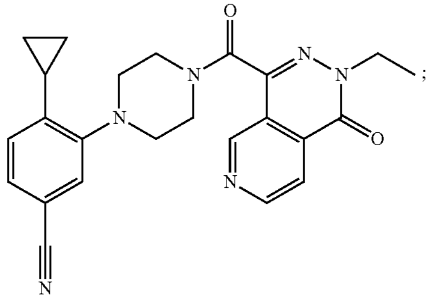

or a salt of any one thereof.

In some embodiments, In some embodiments, the compound of Formula (V) is a compound or salt of Formula (I), (II), (III), or (IV).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds or salts of the Formulas provided herein, are intended to include all Z-, E- and tautomeric forms as well.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R—S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The compounds or salts for the Formulas provided herein, herein may in some cases exist as diastereomers, enantiomers, or other stereoisomeric forms. The compounds presented herein include all diastereomeric, enantiomeric, and epimeric forms as well as the racemates, mixtures of diastereomers, and other mixtures thereof, to the extent they can be made by one of ordinary skill in the art by routine experimentation. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis. Furthermore, a mixture of two enantiomers enriched in one of the two can be purified to provide further optically enriched form of the major enantiomer by recrystallization and/or trituration.

In certain embodiments, compounds or salts for the Formulas provided herein, may comprise two or more enantiomers or diastereomers of a compound wherein a single enantiomer or diastereomer accounts for at least about 70% by weight, at least about 80% by weight, at least about 90% by weight, at least about 98% by weight, or at least about 99% by weight or more of the total weight of all stereoisomers. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) *J. Chromatogr.,* 113(3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

A "tautomer" refers to a molecule wherein a proton shift from one atom of a molecule to another atom of the same molecule is possible. In certain embodiments, the compounds or salts for the Formulas provided herein, exist as tautomers. In circumstances where tautomerization is possible, a chemical equilibrium of the tautomers may exist. The exact ratio of the tautomers depends on several factors, including physical state, temperature, solvent, and pH. Some non-limiting examples of tautomeric equilibrium include:

provide for the synthesis of deuterium-containing compounds. Large numbers of deuterium-containing reagents and building blocks are available commercially from chemical vendors, such as Aldrich Chemical Co.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

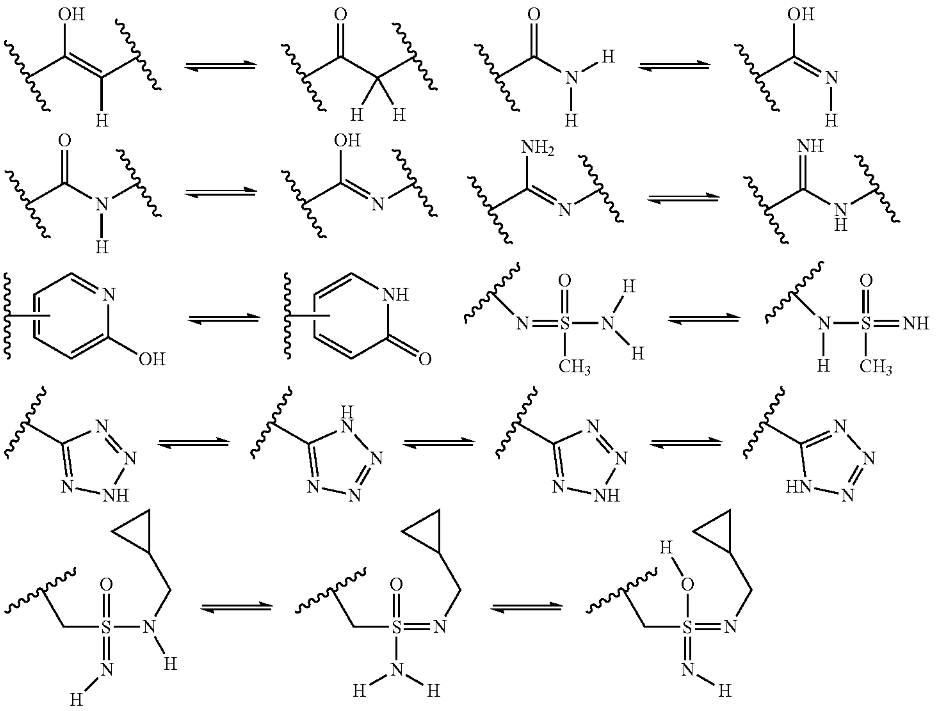

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$ $^{13}N$ $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

Included in the present disclosure are salts, particularly pharmaceutically acceptable salts, of the compounds of the Formulas provided herein. The compounds of the present disclosure may possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Synthetic chemistry transformations and methodologies useful in synthesizing the compounds described herein are known in the art and include, for example, those described in R. Larock, *Comprehensive Organic Transformations*

(1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Formulations

In some aspects, the present disclosure provides a pharmaceutical composition comprising a compound or salt of the Formulas provided herein and at least one pharmaceutically acceptable excipient.

Pharmaceutical compositions can be formulated using one or more physiologically-acceptable carriers comprising excipients and auxiliaries. Formulation can be modified depending upon the route of administration chosen. Pharmaceutical compositions comprising a compound, salt or conjugate can be manufactured, for example, by lyophilizing the compound, salt or conjugate, mixing, dissolving, emulsifying, encapsulating or entrapping the conjugate. The pharmaceutical compositions can also include the compounds, salts or conjugates in a free-base form or pharmaceutically-acceptable salt form.

Preparations for such pharmaceutical composition are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999).

EXAMPLES

The invention now being generally described, it will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Examples 1-30 show general and exemplary procedures for the preparation of the claimed phthalazinone based modulators. Example 31 provides cell viability data for selected phthalazinone based modulators.

General Experimental: All solvents and commercial reagents were used as received. Where products were purified by chromatography, silica refers to silica gel for chromatography, 0.035 to 0.070 mm (220 to 440 mesh) (e.g. Fluka silica gel 60), and an applied pressure of nitrogen up to 10 psi accelerated column elution or use of the CombiFlash® Companion purification system or use of the Biotage SP1 purification system. Where products were purified by preparative HPLC purification this was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. Specific columns, mobile phases, modifiers and gradients are listed with the data. Where products were purified by SFC purification this was performed using a Waters Thar Prep100 preparative SFC system (P200 $CO_2$ pump, 2545 modifier pump, 2998 UV/IS detector, 2767 liquid handler with Stacked Injection Module). Specific columns, mobile phases, modifiers, flow rates, pressures and temperatures are listed with the data. For both preparative HPLC and SFC a Waters 2767 liquid handler acted as both auto-sampler and fraction collector. The purification was controlled by Waters Fractionlynx software through monitoring at 210-400 nm and triggered a threshold collection value at 260 nm and, when using the Fractionlynx, the presence of target molecular ion as observed under API conditions. Collected fractions were analysed either by LCMS for preparative HPLC (Waters Acquity systems with Waters SQD) or by SFC (Waters/Thar SFC systems with Waters SQD).

The purity of the target compounds listed in the tables was assessed by UPLC. The methods used are listed below and the relevant method is listed with the data. All compounds showed ≥95% purity.

Analytical Method A: UPLC+Waters DAD+Waters SQD2, single quadrupole UPLC-MS instrument fitted with an Acquity UPLC HSS C18 1.8 μm 100×2.1 mm column plus guard cartridge maintained at 40° C. Mobile phase: MeCN (0.1% formic acid) in water (0.1% formic acid), from 5% to 95% within 5.6 min; Flow rate: 0.4 mL/min; Wavelength: 200-500 nm DAD.

Analytical Method B: UPLC+Waters DAD+Waters SQD2, single quadrupole UPLC-MS instrument fitted with an Acquity UPLC BEH C18 1.7 um 100×2.1 mm column plus guard cartridge maintained at 40° C. Mobile phase: MeCN in water+10 mM ammonium bicarbonate from 5% to 95% within 5.6 min. Flow rate: 0.4 mL/min. Wavelength: 210-400 nm DAD.

Analytical Method C: Acquity UPLC with PDA detector and ZQ Mass Spectrometer fitted with an Acquity UPLC BEH C18 column, 100×2.1 mm, 1.7 μm, maintained at 40° C. Mobile phase: MeCN (0.1% formic acid) in water (0.1% formic acid), from 5% to 95% within 5.6 min; Flow rate: 0.4 mL/min; Wavelength: 200-500 nm DAD.

Analytical Method D: UPLC+Waters DAD+Waters SQD2, single quadrupole UPLC-MS instrument fitted with an Acquity UPLC HSS C18 1.8 μm 100×2.1 mm column plus guard cartridge maintained at 40° C. Mobile phase: MeCN (0.1% formic acid) in water (0.1% formic acid), from 5% to 95% within 12.6 min; Flow rate: 0.4 mL/min; Wavelength: 200-500 nm DAD.

Analytical Method E: Acquity I-Class UPLC with PDA detector and QDa Mass Spectrometer fitted with an Acquity UPLC BEH C18 column, 50×2.1 mm, 1.7 μm, maintained at 50° C. Mobile phase: MeCN (0.1% formic acid) in 10 mM ammonium formate (0.1% formic acid), from 5% to 95% within 1.5 min; then isocratic for 0.50 min; Flow rate: 0.8 ml/min; ELS detection using Acquity UPLC ELS detector Analytical Method F: Acquity I-Class UPLC with PDA detector and QDa Mass Spectrometer fitted with an Acquity UPLC BEH C18 column, 50×2.1 mm, 1.7 μm, maintained at 50° C. Mobile phase: MeCN (0.1% ammonia) in water (0.1% ammonia), from 5% to 95% within 2.5 min; then isocratic for 0.50 min; Flow rate: 0.8 ml/min; ELS detection using Acquity UPLC ELS detector NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane (δ=0 ppm) or residual solvent ($CHCl_3$=7.27 ppm, DMSO=2.52 ppm). J values are given in Hz throughout. NMR spectra were assigned using DataChord Spectrum Analyst Version 4.0.b21 or SpinWorks version 3. All spectra were in accordance with the assigned structures. Where DMSO is listed as an NMR solvent, this refers to DMSO-$d_6$.

Abbreviations: aq.=aqueous; BINAP=2,2-Bis(diphenylphosphino)-1,1-binaphthalene; Boc=tert-butoxycarbonyl; br=broad; d=doublet; CPME=cyclopentyl methyl ether; dd=double doublet; ddd=doublet of doublet of doublet; DAD=diode array detector; DAST=(Diethylamino)sulfur trifluoride; DavePhos Pd G3=methanesulfonato 2-dicyclohexylphosphino-2-(N,N-dimethylamino)biphenyl(2-amino-1,1-biphenyl-2-yl) palladium(II); DCM=dichloromethane; DEA=diethylamine; DIPEA=N,N-Diisopropylethylamine; DMF=N,N'-dimethylformamide; DMSO=dimethyl sulfoxide; EtOAc=ethyl acetate; equiv=eqivalents; HATU=(1-[Bis(dimethylamino)methylene]-1H-1,2,3-triazolo[4,5-b]pyridinium 3-oxide hexafluorophosphate; HPLC=high pressure liquid chromatography; hr=hour; hrs=hours; IMS=Industrial methylated spirits; IPA=isopropyl alcohol; LCMS=liquid chromatography/mass spectrometry; MeCN=acetonitrile; MeOH=methanol; min=minutes; m/z=mass/charge; NMR=nuclear magnetic resonance; q=quartet; rt=room temperature; RT=retention time; RuPhos=2-Dicyclohexylphosphino-2,6-diisopropoxybiphenyl; RuPhos Pd G3=(2-dicyclohexylphosphino-2,6-diisopropoxy-1,1-biphenyl)[2-(2amino-1,1-biphenyl)]palladium(II) methanesulfonate; s=singlet; sat.=saturated; SCX-2=strong cation exchange chromatography; SFC=supercritical fluid chromatography; t=triplet; td=triplet of doublets; TFA=trifluoroacetic acid; THF=tetrahydrofuran; UPLC=ultra performance liquid chromatography.

Example 1: Synthesis of Intermediates 1-24

Synthesis of 4-(4-phenylpiperazine-1-carbonyl)-2H-phthalazin-1-one (Intermediate 1)

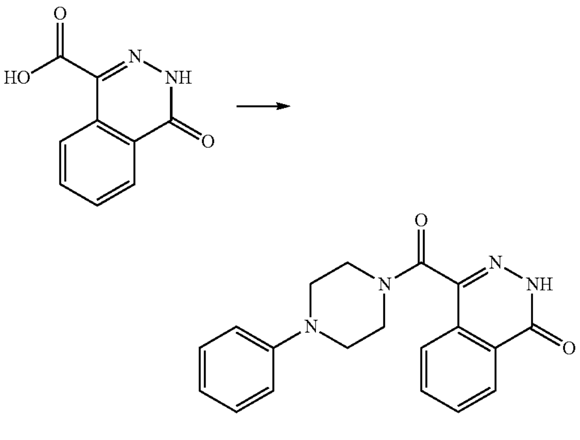

To a solution of 4-oxo-3H-phthalazine-1-carboxylic acid (1500 mg, 7.89 mmol, 1 equiv.) in DMF (25 mL) was added HATU (4499 mg, 11.8 mmol, 1.5 equiv.) and DIPEA (4.1 mL, 23.7 mmol, 3 equiv.) and the mixture stirred at room temp for 5 minutes. 1-Phenylpiperazine (1.4 mL, 9.47 mmol, 1.2 equiv.) was then added and the solution was stirred at rt for 2 hrs. The mixture was diluted with EtOAc and washed with water, then brine and dried over sodium sulfate, then filtered, the filtrate collected, and the solvent removed. The material was purified by column chromatography on silica (40 g cartridge, 15 μM silica, 10-50% [3:1 ethyl acetate:IMS]/cyclohexane) and the appropriate fractions were combined and the solvent removed to yield the title compound (550 mg, 21%) as a pale yellow solid. A 75 mg sample of this material was purified by reverse phase HPLC (Luna Phenyl-Hexyl 21.2×150 mm, 10 μm 40-100% MeOH/$H_2O$+0.1% formic acid, 20 mL/min, rt) to yield the title compound (19 mg, 25%) as an off white solid. LCMS: Method A, m/z=335.2 $(M+H)^+$, RT=3.81 min. $^1$H NMR (400 MHz, DMSO) δ 12.87 (s, 1H), 8.32 (dd, J=1.0, 7.9 Hz, 1H), 7.99-7.90 (m, 2H), 7.79 (d, J=7.4 Hz, 1H), 7.27-7.22 (m, 2H), 6.97 (d, J=8.0 Hz, 2H), 6.84 (dd, J=7.3, 7.3 Hz, 1H), 3.90 (dd, J=5.1, 5.1 Hz, 2H), 3.54 (dd, J=5.0, 5.0 Hz, 2H), 3.34-3.28 (m, 2H), 3.07 (dd, J=5.0, 5.0 Hz, 2H).

Synthesis of 2-methyl-4-(piperazine-1-carbonyl) phthalazin-1-one (Intermediate 2)

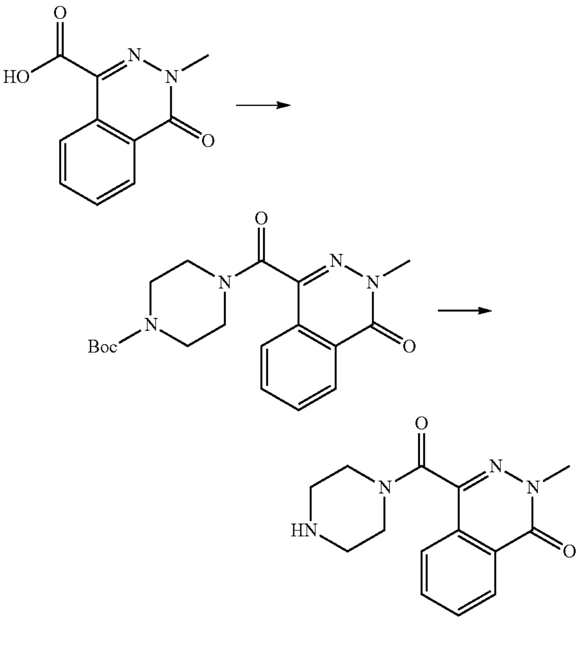

Step 1: Synthesis of tert-butyl 4-(3-methyl-4-oxo-phthalazine-1-carbonyl)piperazine-1-carboxylate: To a solution of 3-methyl-4-oxo-phthalazine-1-carboxylic acid (2500 mg, 12.2 mmol, 1.00 equiv.) in DMF (50 mL) was added HATU (6983 mg, 18.4 mmol, 1.5 equiv.) and DIPEA (6.4 mL, 36.7 mmol, 3 equiv.) and the mixture stirred at room temp for 5 min. 1-Boc-piperazine (2737 mg, 14.7 mmol, 1.20 equiv.) was then added and the solution was stirred at room temp for 2 hrs. The mixture was diluted with EtOAc and washed with water twice, then brine and dried over sodium sulfate. The mixture was filtered, the filtrate collected, and the solvent removed. The solid was triturated with diethyl ether, filtered and the solid collected and dried to yield the title compound (3.90 g, 81%) as a white solid. LCMS: Method A, m/z=373.4 $(M+H)^+$, RT=4.05 min. $^1H$ NMR (400 MHz, DMSO) δ 8.32 (dd, J=6.8 Hz and 2.8 Hz), 7.92 (ddd, J=7.4 Hz, 5.5 Hz, 2.2 Hz, 2H), 7.78 (dd, J=6.8 Hz and 2.8 Hz), 3.75-3.68 (m, 5H), 3.52-3.46 (m, 2H), 3.40-3.37 (m, 2H), 3.29-3.23 (m, 2H). 1.40 (s, 9H).

Step 2: Synthesis of 2-methyl-4-(piperazine-1-carbonyl) phthalazin-1-one: To a solution of tert-butyl 4-(3-methyl-4-oxo-phthalazine-1-carbonyl)piperazine-1-carboxylate (2000 mg, 5.37 mmol, 1 equiv.) in DCM (25 mL) was added trifluoroacetic acid (8.0 mL, 0.104 mol, 19.5 equiv.) and the mixture stirred at room temp for 2 hrs. The solvent was removed, and the residue was dissolved in DCM, loaded onto a 50 g SCX-2 cartridge (pre-washed with DCM). The cartridge was washed with DCM, followed by methanol, then eluted with 7M ammonia in methanol. The eluent was collected and the solvent removed to yield the title compound (1420 mg, 93%) as an off white solid. $^1H$ NMR (400 MHz, $CDCl_3$), 8.50-8.45 (m, 1H), 7.84-7.74 (m, 3H), 3.92-3.84 (m, 5H), 3.41 (app. t, J=5.0 Hz, 2H), 3.02 (app. t, J=5.0 Hz, 2H), 2.83 (app. t, J=5.0 Hz), 2.02 (s, 1H).

Synthesis of 2-ethyl-4-(piperazine-1-carbonyl) phthalazin-1(2H)-one (Intermediate 3)

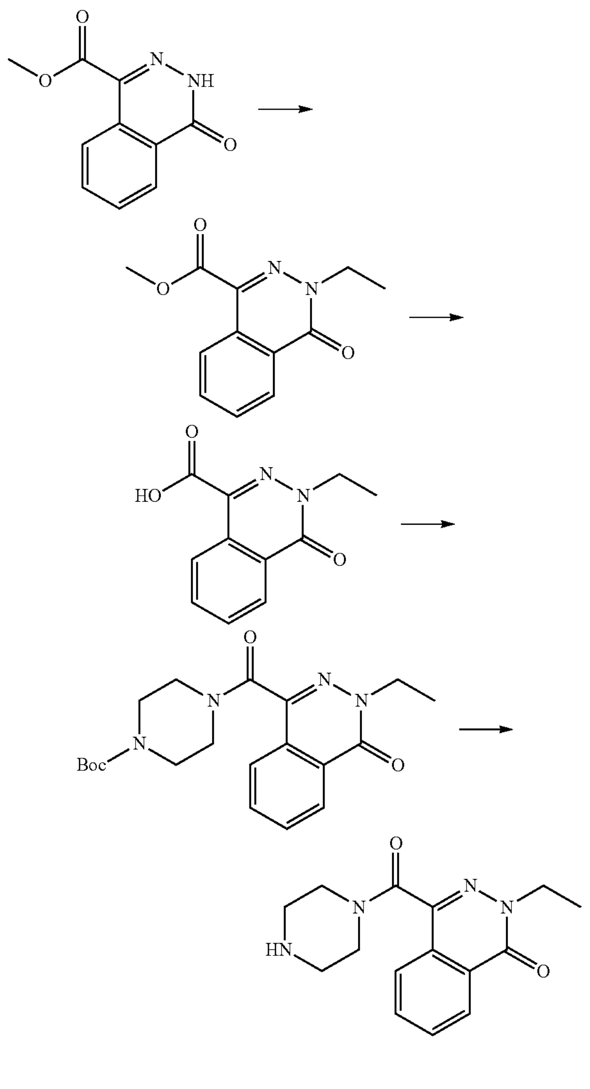

Step 1: Synthesis of Methyl 3-ethyl-4-oxo-phthalazine-1-carboxylate: To a solution of methyl 4-oxo-3H-phthalazine-1-carboxylate (1.00 g, 4.90 mmol, 1 eq) in DMF (15 mL) was added potassium carbonate (1692 mg, 12.2 mmol, 2.5 equiv.) followed by iodoethane (0.98 mL, 12.2 mmol, 2.5 equiv.) and the solution was stirred at 50° C. for 3 hrs then allowed to rt. The mixture was diluted with EtOAc and washed with water twice, then brine and dried over sodium sulfate. The mixture was filtered, the filtrate collected, and the solvent removed to yield the title compound (1000 mg, 86%) as a white solid. $^1H$ NMR (400 MHz, $CDCl_3$) δ 8.55 (d, J=8.0 Hz, 1H), 8.47 (dd, J=8.2 Hz, 1.3 Hz, 1H), 7.85 (td, J=7.1 Hz, 1.3 Hz, 1H), 7.79 (td, J=7.1 Hz, 1.3 Hz, 1H), 4.38 (q, J=7.2 Hz, 2H), 1.46 (t, J=7.2 Hz, 1H).

Step 2: Synthesis of 3-ethyl-4-oxo-phthalazine-1-carboxylic acid: To a solution of methyl 3-ethyl-4-oxo-phthalazine-1-carboxylate (1000 mg, 4.31 mmol, 1 equiv.) in THF (10 mL) and water (5 mL) was added lithium hydroxide monohydrate (199 mg, 4.74 mmol, 1.1 equiv.) and the solution was stirred at rt for 4 hrs. The solvent was reduced to low volume in vacuo and the residual aqueous solution acidified with 1 M HCl. A white precipitate formed and this was filtered, washed well with water and dried in vacuo at 45° C. to yield the title compound (855 mg, 89%) as a white solid. $^1H$ NMR (400 MHz, DMSO) δ 8.62 (d, J=8.2 Hz, 1H), 8.32 (dd, J=8.2 Hz, 1.3 Hz, 1H), 7.97 (td, J=7.3 Hz, 1.5 Hz, 1H), 7.79 (td, J=7.3 Hz, 1.5 Hz, 1H), 4.22 (q, J=7.3 Hz, 2H), 1.33 (t, J=7.3 Hz, 1H).

Step 3: Synthesis of tert-butyl 4-(3-ethyl-4-oxo-phthalazine-1-carbonyl)piperazine-1-carboxylate: To a solution of 3-ethyl-4-oxo-phthalazine-1-carboxylic acid (1000 mg, 4.58 mmol, 1 equiv.) in DMF (20 mL) was added HATU (2614 mg, 6.87 mmol, 1.5 equiv.) and DIPEA (2.4 mL, 13.7 mmol, 3 equiv.) and the mixture stirred at rt for 5 min. 1-Boc-piperazine (1024 mg, 5.50 mmol, 1.2 equiv.) was then added and the solution was stirred at rt for 4 hrs. The mixture was diluted with EtOAc and washed with water twice, then brine and dried over sodium sulfate. The mixture was filtered, the filtrate collected, and the solvent removed. The material was purified by column chromatography on silica (25 g cartridge, 15 μM silica, 00-50% ethyl acetate/cyclohexane) and the appropriate fractions were combined and the solvent removed to yield the title compound (1430 mg, 81%) as a colourless foam. $^1H$ NMR (400 MHz, $CDCl_3$) δ 8.51-8.45 (m, 1H), 7.83-7.77 (m, 3H), 4.29 (q, J=7.1 Hz, 2H), 3.87 (t, J=5.0 Hz, 2H), 3.60 (t, J=5.0 Hz, 2H), 3.46 (s, 4H), 1.48 (s, 9H), 1.41 (t, J=7.1 Hz, 3H).

Step 4: Synthesis of 2-ethyl-4-(piperazine-1-carbonyl) phthalazin-1-one: To a solution of tert-butyl 4-(3-ethyl-4-oxo-phthalazine-1-carbonyl)piperazine-1-carboxylate (1430 mg, 3.70 mmol, 1 equiv.) in DCM (12 mL) was added trifluoroacetic acid (6.0 mL, 78.4 mmol, 21.2 equiv.) and the solution was stirred at rt for 2 hrs. The solvent was removed, and the residue was dissolved in DCM, loaded onto a 20 g SCX-2 cartridge (pre-washed with DCM). The cartridge was washed with DCM, followed by methanol, then eluted with 7M ammonia in methanol. The eluent was collected, and the solvent removed to yield the title compound (930 mg, 86%) as an off white foam. $^1H$ NMR (400 MHz, $CDCl_3$) δ 8.51-8.45 (m, 1H), 7.84-7.76 (m, 3H), 4.29 (q, J=7.2 Hz, 2H), 3.88 (t, J=4.9 Hz, 2H), 3.43 (t, J=4.9 Hz, 2H), 3.04 (t, J=4.9 Hz, 2H), 2.86 (t, J=4.9 Hz, 2H), 1.41 (t, J=7.2 Hz, 3H).

Synthesis of 4-chloro-6-fluoro-2-methylphthalazin-1 (2H)-one (Intermediate 4) and 4-chloro-7-fluoro-2-methylphthalazin-1(2H)-one (Intermediate 5)

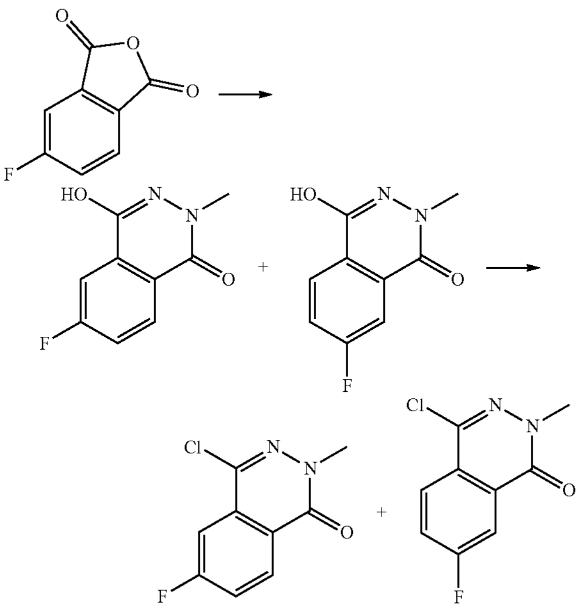

Intermediate 4 Intermediate 5

Step 1: Synthesis of 6-fluoro-3-methyl-2H-phthalazine-1,4-dione and 7-fluoro-3-methyl-2H-phthalazine-1,4-dione: To a solution of 4-fluorophthalic anhydride (2.00 g, 12.0 mmol, 1 equiv.) in ethanol (20 mL) was added methylhydrazine (0.63 mL, 12.0 mmol, 1 equiv.). The mixture was heated at 80° C. for 18 hrs, during which time the reagents initially went into solution, then slowly precipitated out as a white solid, forming a thick slurry. The mixture was allowed to rt and filtered. The solid was collected and washed with ethanol and diethyl ether and dried to yield the title compounds (2000 mg, 86%, ca. 1:1 mixture) as a white solid. $^1H$ NMR (400 MHz, DMSO) Regioisomer 1-δ 11.78 (br. s, 1H), 8.28 (dd, J=9.1 Hz, 5.4 Hz, 1H), 7.72 (td, J=9.1 Hz, 2.6 Hz, 1H), 7.64 (dd, J=9.1 Hz, 2.6 Hz, 1H), 3.56 (s, 3H). Regioisomer 2-δ 11.78 (br. s, 1H), 8.05 (dd, J=9.1 Hz, 5.4 Hz, 1H), 7.88 (dd, J=9.1 Hz, 2.7 Hz, 1H), 7.77 (td, J=8.8 Hz, 2.7 Hz, 1H), 3.57 (s, 3H). Regioisomer ratio 1:1.3 (R1:R2).

Step 2: Synthesis of 4-chloro-6-fluoro-2-methylphthalazin-1(2H)-one and 4-chloro-7-fluoro-2-methylphthalazin-1(2H)-one: A mixture of 7-fluoro-3-methyl-2H-phthalazine-1,4-dione (1000 mg, 5.15 mmol, 1 equiv.) and 6-fluoro-3-methyl-2H-phthalazine-1,4-dione (1000 mg, 5.15 mmol, 1 equiv.) was heated with phosphorus(V) oxychloride (9.1 mL, 97.9 mmol, 19. equiv.) at 110° C. for 18 hrs and then allowed to rt. The excess phosphorus(V) oxychloride was removed in vacuo and the residue was quenched with sat. aq. sodium bicarbonate solution. The product was extracted with EtOAc twice and the combined organic phases were washed with water, then with brine and dried over sodium sulfate. The mixture was filtered, the filtrate collected, and the solvent removed. The material was purified by column chromatography on silica (40 g cartridge, 15 μM silica, 0-50% ethyl acetate/cyclohexane) and the appropriate fractions were combined, and the solvent removed to yield 4-chloro-6-fluoro-2-methyl-phthalazin-1-one (679 mg, 59%) and 4-chloro-7-fluoro-2-methyl-phthalazin-1-one (434 mg, 38%) as white solids. 4-chloro-6-fluoro-2-methyl-phthalazin-1-one: $^1H$ NMR (400 MHz, $CDCl_3$)$^1H$ NMR (400 MHz, DMSO) δ 8.10 (dd, J=8.5 Hz, 2.5 Hz, 1H), 8.04 (dd, J=8.5 Hz, 4.9 Hz, 1H), 7.58 (td, J=8.5 Hz, 2.5 Hz), 3.8 (s, 3H). 4-chloro-7-fluoro-2-methyl-phthalazin-1-one: $^1H$ NMR (400 MHz, $CDCl_3$)$^1H$ NMR (400 MHz, $CDCl_3$) δ 8.48 (dd, J=8.8 Hz, 5.3 Hz, 1H), 7.62 (dd, J=8.8 Hz, 2.5 Hz, 1H), 7.53 (td, J=8.8 Hz, 2.5 Hz, 1H), 3.82 (s, 3H).

Synthesis of 7-fluoro-3-methyl-4-oxo-phthalazine-1-carboxylic acid (Intermediate 6)

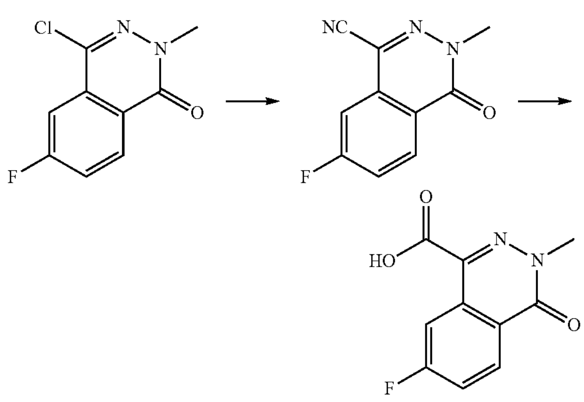

Step 1: Synthesis of 7-fluoro-3-methyl-4-oxo-phthalazine-1-carbonitrile: To a solution of 4-chloro-7-fluoro-2-methyl-phthalazin-1-one (Intermediate 3) (1.29 g, 6.07 mmol, 1 equiv.) in DMF (15 mL) was added zinc cyanide (0.93 g, 7.89 mmol, 1.30 equiv.), bis(diphenylphosphino) ferrocene (0.27 g, 0.485 mmol, 0.08 equiv.) and tris(dibenzylideneacetone)dipalladium(O) (0.28 g, 0.303 mmol, 0.05 equiv.) and the suspension degassed with argon. The vessel was sealed and heated at 110° C. for 18 hrs. The mixture was allowed to rt, diluted with EtOAc and washed with sat. aq. ammonium chloride solution. The aqueous layer was extracted with EtOAc and the combined organic layers were washed with water, then with brine and dried over sodium sulfate. The mixture was filtered, the filtrate collected, and the solvent removed. The material was purified by column chromatography on silica (12 g cartridge, 15 μM silica, 0-100% ethyl acetate/cyclohexane) and the appropriate fractions were combined, and the solvent removed to yield the title compound (590 mg, 47%) as an off white solid. $^1H$ NMR (400 MHz, $CDCl_3$) δ 8.49 (dd, J=8.8 Hz, 5.3 Hz, 1H), 7.63-7.55 (m, 2H), 3.91 (s, 3H).

Step 2: Synthesis of 7-fluoro-3-methyl-4-oxo-phthalazine-1-carboxylic acid: 7-fluoro-3-methyl-4-oxo-phthalazine-1-carbonitrile (490 mg, 2.41 mmol, 1 equiv.) was suspended in Conc. hydrochloric acid (5 ml) and the mixture was heated at 80° C. for 2 hrs, then allowed to rt and the solvent removed. The mixture was re-suspended in Conc. hydrochloric acid (10 ml) and heated at 80° C. for a further 4 hrs, then allowed to rt and the solvent removed to yield the title compound (690 mg, 116%) as an off white solid. $^1H$ NMR (400 MHz, DMSO) δ 8.42-8.32 (m, 2H), 7.77 (td, J=9.0 Hz, 2.6 Hz, 1H), 3.79 (s, 3H).

Synthesis of 6-fluoro-2-methyl-4-(piperazine-1-carbonyl)phthalazin-1(2H)-one (Intermediate 7)

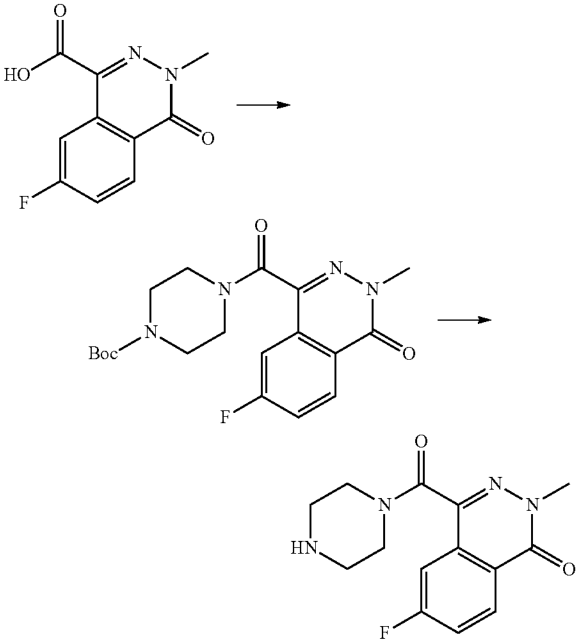

Step 1: Synthesis of tert-butyl 4-(7-fluoro-3-methyl-4-oxo-3,4-dihydrophthalazine-1-carbonyl)piperazine-1-carboxylate: To a solution of 7-fluoro-3-methyl-4-oxo-phthalazine-1-carboxylic acid (650 mg, 2.93 mmol, 1 equiv.) and 1-Boc-piperazine (654 mg, 3.51 mmol, 1.2 equiv.) in DMF (10 mL) was added triethylamine (0.61 mL, 1.5 equiv.) followed by HATU (1446 mg, 3.80 mmol, 1.3 equiv.) and the mixture was stirred at rt for 24 hrs. The mixture was partitioned between ethyl acetate and 5% aq. lithium chloride and the phases separated. The organics were washed with brine, dried with sodium sulfate, filtered, the filtrate collected, and the solvent removed. The material was purified by column chromatography on silica (40 g cartridge, 0-60% ethyl acetate/cyclohexane) to yield the title compound (729 mg, 64%) as a white solid. $^1$H NMR (400 MHz, $CDCl_3$) δ 8.50 (t, J=7.0 Hz, 1H), 7.53-7.44 (m, 2H), 3.92-3.81 (m, 5H), 3.60 (t, J=4.6 Hz, 2H), 3.47 (s, 4H), 1.48 (s, 9H).

Step 2: Synthesis of 6-fluoro-2-methyl-4-(piperazine-1-carbonyl)phthalazin-1(2H)-one: To a solution of tert-butyl 4-(7-fluoro-3-methyl-4-oxo-phthalazine-1-carbonyl)piperazine-1-carboxylate (1390 mg, 3.56 mmol, 1 equiv.) in DCM (18 mL) was added trifluoroacetic acid (8.2 mL, 0.107 mol, 30 equiv.) and the mixture was stirred at rt for 2 hrs. The mixture was loaded onto an SCX-2 cartridge (25 g, pre-washed with DCM), washed with DCM, followed by methanol then eluted with 7M ammonia in methanol. The eluent was collected, and the solvent removed, azeotroping with diethyl ether to yield the title compound (1015 mg, 98%) as a white solid. $^1$H NMR (400 MHz, DMSO) δ 8.38 (dd, J=9.2 Hz, 5.6 Hz, 1H), 7.77 (td, J=9.2 Hz, 2.5 Hz, 1H), 7.48 (dd, J=9.2 Hz, 2.5 Hz, 1H), 3.71 (s, 3H), 3.64 (t, J=4.8 Hz, 2H), 3.20 (t, J=4.8 Hz, 2H), 2.80 (t, J=4.8 Hz, 2H), 2.60 (t, J=4.8 Hz, 2H).

Synthesis of 2-methyl-1-oxo-pyrido[3,4-d]pyridazine-4-carboxylic acid (Intermediate 8) and 3-methyl-4-oxo-pyrido[3,4-d]pyridazine-1-carboxylic acid (Intermediate 9)

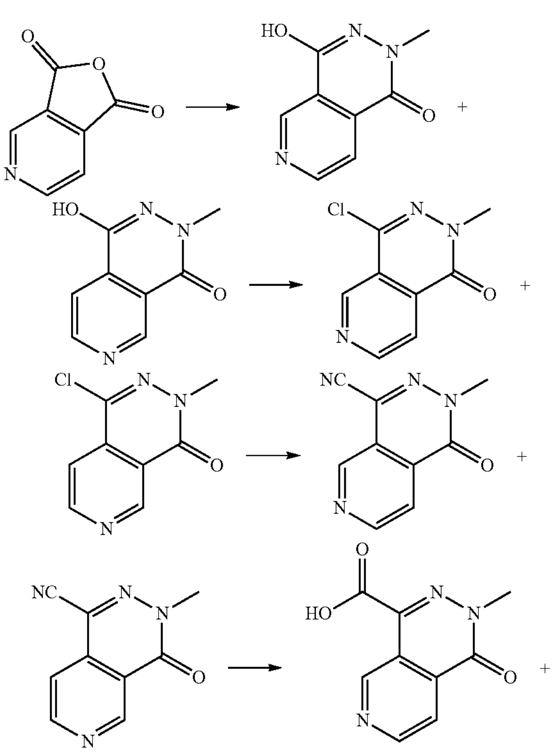

Intermediate 8

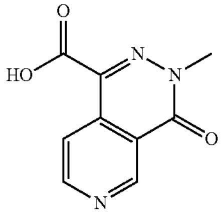

Intermediate 9

Step 1: Synthesis of 2-methyl-3H-pyrido[3,4-d]pyridazine-1,4-dione and 3-methyl-2H-pyrido[3,4-d]pyridazine-1,4-dione: A mixture of 3,4-pyridinedicarboxylic anhydride (2.93 g, 19.7 mmol, 1 equiv.) and methylhydrazine (1.0 mL, 19.7 mmol, 1 equiv.) was heated neat at 135'C for 1 hr. The mixture melted, then resolidified to a pale yellow solid. The cooled mixture was triturated with ether and the solid filtered off, washed with diethyl ether and dried to give a mixture the title compounds of 2-methyl-3H-pyrido[3,4-d]pyridazine-1,4-dione (3.84 g, >100%) as a light brown solid. The mixture was used directly in the next step without further purification. $^1$H NMR (400 MHz, DMSO) Regioisomer 1-δ 9.41 (s, 1H), 9.00 (d, J=5.3 Hz, 1H), 7.81 (d, J=5.3 Hz, 1H), 3.56 (s, 3H). Regioisomer 2-δ 9.28 (s, 1H), 8.73 (d, J=5.1 Hz, 1H), 7.98 (d, J=5.1 Hz, 1H), 3.57 (s, 3H). Regioisomer ratio 1:2.0 (R1:R2).

Step 2: Synthesis of 4-chloro-2-methylpyrido[3,4-d]pyridazin-1(2H)-one and 1-chloro-3-methylpyrido[3,4-d]pyridazin-4(3H)-one: A mixture of 2-methyl-3H-pyrido[3,4-d]pyridazine-1,4-dione and 3-methyl-2H-pyrido[3,4-d]

pyridazine-1,4-dione (2000 mg, 11.28 mmol, 1 equiv.) was suspended in phosphorus(V) oxychloride (10 mL, 0.107 mol, 9.5 equiv.) at stirred at 110° C. for 18 hrs. The mixture was allowed to rt. The excess phosphorus(V) oxychloride was removed in vacuo and the residue was quenched with sat. aq. sodium bicarbonate solution. The product was extracted with EtOAc twice and the combined organic phases were washed with water, then with brine and dried over sodium sulfate. The mixture was filtered, the filtrate collected, and the solvent removed. The material was purified by column chromatography on silica (25 g cartridge, 15 μM silica, 0-50% ethyl acetate/cyclohexane) and the appropriate fractions were combined, and the solvent removed to yield a mixture of the title compounds (250 mg, 22%) as a colourless oil which solidified on standing. $^1H$ NMR (400 MHz, DMSO) Regioisomer 1-δ 9.48 (d, J=0.6 Hz, 1H), 9.13 (d, J=5.5 Hz, 1H), 7.86 (dd, J=5.5 Hz, 1H), 3.71 (s, 3H). Regioisomer 2-δ 9.33 (d, J=0.6 Hz, 1H), 9.09 (d, J=5.2 Hz), 8.14 (dd, J=5.2 Hz, 0.6 Hz, 1H), 3.71 (s, 3H). Regioisomer ratio 1:0.6 (R1:R2).

Step 3: Synthesis of 2-methyl-1-oxo-pyrido[3,4-d]pyridazine-4-carbonitrile and 3-methyl-4-oxo-pyrido[3,4-d]pyridazine-1-carbonitrile: To a mixture of 4-chloro-2-methyl-pyrido[3,4-d]pyridazin-1-one and 1-chloro-3-methyl-pyrido[3,4-d]pyridazin-4-one (3.84 g, 8.74 mmol, 1 equiv.) in DMF (15 mL) was added zinc cyanide (1334 mg, 11.4 mmol, 1.3 equiv.), bis(diphenyl phosphanyl) ferrocene (388 mg, 0.699 mmol, 0.08 equiv.) and tris(dibenzylideneacetone) dipalladium(O) (400 mg, 0.437 mmol, 0.05 equiv.) and the suspension degassed with argon. The mixture was heated at 110° C. for 3 hrs then allowed to rt and stood overnight. The mixture was re-heated to 110° C. for 2 hrs then allowed to rt. The mixture was partitioned between EtOAc and water, then filtered through a Celite™ pad. The filtrate was collected, and the phases were separated. The aqueous layer was extracted with EtOAc and the combined organic layers were washed with brine and dried over sodium sulfate. The mixture was filtered, the filtrate collected and evaporated. The material was purified by column chromatography on silica (25 g cartridge, 15 μM silica, 0-100% ethyl acetate]/cyclohexane) to yield a mixture of the title compounds (560 mg, 35%) as a beige solid. $^1H$ NMR (400 MHz, $CDCl_3$) Regioisomer 1-δ 9.73 (s, 1H), 9.14 (d, J=5.3 Hz, 1H), 7.76 (d, J=5.4 Hz, 1H), 3.95 (s, 3H). Regioisomer 2-δ 9.41 (s, 1H), 9.10 (d, J=5.4 Hz, 1H), 8.22 (J=5.4 Hz, 1H), 3.94 (s, 3H). Regioisomer ratio 1:0.6 (R1:R2).

Step 4: Synthesis of 2-methyl-1-oxo-pyrido[3,4-d]pyridazine-4-carboxylic acid hydrochloride and 3-methyl-4-oxo-pyrido[3,4-d]pyridazine-1-carboxylic acid hydrochloride: A mixture of 2-methyl-1-oxo-pyrido[3,4-d]pyridazine-4-carbonitrile and 3-methyl-4-oxo-pyrido[3,4-d]pyridazine-1-carbonitrile (593 mg, 3.19 mmol, 1 equiv.) was suspended in Conc. hydrochloric acid (10 mL), and the solution was heated at 90° C. for 3 hrs, then allowed to rt. The mixture was filtered, the filtrate collected, and the solvent removed to yield the title compounds (740 mg, 96%) as a pale yellow solid. The material was used without purification. $^1H$ NMR (400 MHz, DMSO) Regioisomer 1-δ 9.93 (s, 1H), 9.01 (d, J=5.4 Hz, 1H), 8.15 (d, J=5.4 Hz, 1H), 3.80 (s, 3H). Regioisomer 2-δ 9.50 (s, 1H), 9.06 (d, J=5.6 Hz, 1H), 8.48 (d, J=5.6 Hz, 1H), 3.80 (s, 3H). Regioisomer ratio 1:1.1 (R1:R2).

Synthesis of 2-methyl-4-(piperazine-1-carbonyl) pyrido[3,4-d]pyridazin-1-one (Intermediate 10) and 3-methyl-1-(piperazine-1-carbonyl)pyrido[3,4-d] pyridazin-4-one (Intermediate 11)

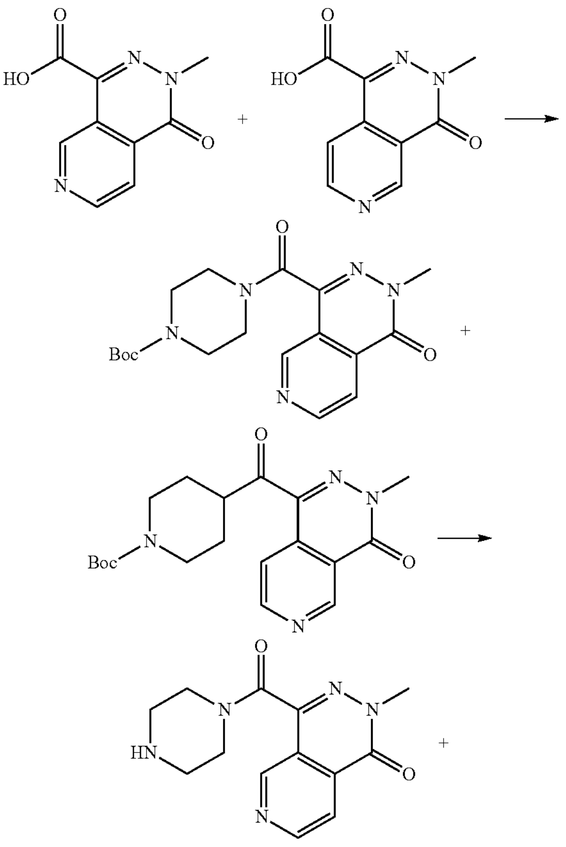

Intermediate 10

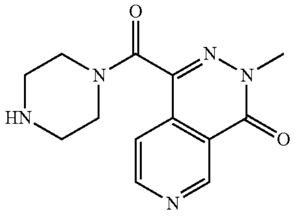

Intermediate 11

Step 1: Synthesis of tert-butyl 4-(2-methyl-1-oxo-pyrido[3,4-d]pyridazine-4-carbonyl)piperazine-1-carboxylate and tert-butyl 4-(3-methyl-4-oxo-pyrido[3,4-d]pyridazine-1-carbonyl)piperazine-1-carboxylate: To a solution of 3-methyl-4-oxo-pyrido[3,4-d]pyridazin-6-ium-1-carboxylic acid chloride and 2-methyl-1-oxo-pyrido[3,4-d]pyridazin-6-ium-4-carboxylic acid chloride (800 mg, 3.22 mmol, 1 equiv.) in DMF (20 mL) was added 1-Boc-piperazine (740 mg, 3.97 mmol, 1.2 equiv.) and HATU (1.89 g, 4.97 mmol, 1.5 equiv.). The mixture was stirred at rt for 2.5 hrs. and then partitioned between EtOAc and water and the phases separated. The aqueous layer was extracted with EtOAc and the combined organic layers were washed with brine and dried over sodium sulfate. The mixture was filtered, the filtrate collected and evaporated. The material was purified by column chromatography on silica (25 g cartridge, 15 μM silica, 0-100% ethyl acetate]/cyclohexane) to yield the title compounds (834 mg, 66%, 1:1 mixture) as a beige solid. $^1$H NMR (400 MHz, DMSO) Regioisomer 1-δ 9.52 (s, 1H), 7.95 (s, 1H), 7.70 (d, J=5.9 Hz, 1H), 3.75-3.68 (m, 5H), 3.52-3.42 (m, 4H), 3.31-3.24 (2H), 1.41 (s, 9H). Regioisomer 2-δ 9.17 (s, 1H), 9.02 (d, J=5.7 Hz, 1H), 8.16 (d, J=5.7 Hz, 1H), 3.75-3.68 (m, 5H), 3.52-3.42 (m, 4H), 3.31-3.24 (2H), 1.41 (s, 9H). Regioisomer ratio 1:2.0 (R1:R2).

Step 2: Synthesis of 2-methyl-4-(piperazine-1-carbonyl) pyrido[3,4-d]pyridazin-1-one and 3-methyl-1-(piperazine-1-carbonyl)pyrido[3,4-d]pyridazin-4-one: To a solution tert-butyl 4-(2-methyl-1-oxo-pyrido[3,4-d]pyridazine-4-carbonyl)piperazine-1-carboxylate and tert-butyl 4-(3-methyl-4-oxo-pyrido[3,4-d]pyridazine-1-carbonyl) piperazine-1-carboxylate (834 mg, 2.24 mmol, 1 equiv.) in DCM (10 mL) was added trifluoroacetic acid (5 mL, 65.3 mmol, 30 equiv.). The mixture was stirred at rt for 2.5 hrs. The solvent was removed in vacuo and the residue was dissolved in methanol and the mixture was loaded onto an SCX-2 cartridge (10 g, pre-washed with DCM). The cartridge was washed with DCM, followed by methanol then eluted with 7M ammonia in methanol. The eluent was collected, and the solvent removed, azeotroping with diethyl ether to yield the title compounds (500 mg, 82%) as an off-white solid. $^1$H NMR (400 MHz, DMSO) Regioisomer 1-δ 9.52 (s, 1H), 9.03 (d, J=5.4 Hz, 1H) 7.64 (d, J=5.4 Hz, 1H), 3.73 (s, 3H), 3.69-3.60 (m, 2H), 2.86-2.68 (m, 2H), 2.64-2.56 (m, 2H). 2H obscured by water peak at 3.33 ppm. Regioisomer 2-δ 9.11 (s, 1H), 9.02 (d, J=5.5 Hz, 1H), 8.16 (d, J=5.5 Hz, 1H), 3.73 (s, 3H), 3.69-3.60 (m, 2H), 2.86-2.68 (m, 2H), 2.64-2.56 (m, 2H). 2H obscured by water peak at 3.33 ppm. Regioisomer ratio 1:2.1 (R1:R2).

Synthesis of 3-bromo-5-(difluoromethyl)benzonitrile (Intermediate 12)

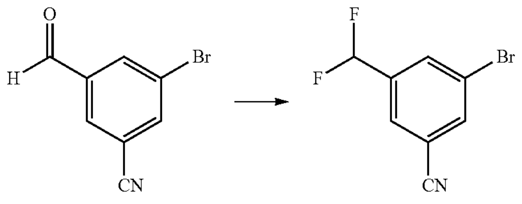 [SMILES: N#Cc1cc(Br)cc(C=O)c1 ; N#Cc1cc(Br)cc(C(F)F)c1]

To a solution of 3-bromo-5-formyl-benzonitrile (497 mg, 2.37 mmol, 1.0 equiv.) in DCM (5 mL) at 0° C. was added DAST (0.86 mL, 4.73 mmol, 2.0 equiv.) dropwise and the mixture was stirred at 0° C. and allowed to gradually warm to rt over 17 hrs. Sat. aq. $NaHCO_3$ was added dropwise until gas evolution ceased. The resulting biphasic mixture was diluted with DCM and stirred for a further 30 min then the aqueous layer was separated and extracted with further DCM. The combined organics were dried with sodium sulfate, filtered, the filtrate collected, and the solvent was removed to yield the title compound (496 mg, 90%) as a beige solid. $^1$H NMR (400 MHz, $CDCl_3$) δ 7.92 (s, 1H), 7.76 (dd, J=8.1, 21.0 Hz, 2H), 6.91 (t, J=53.7 Hz, 1H). $^{19}$F NMR (376 MHz, $CDCl_3$) −116.25 (s, 2F).

Synthesis of 3-bromo-5-(difluoromethoxy)benzonitrile (Intermediate 13)

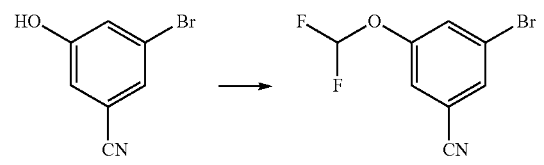 [SMILES: N#Cc1cc(O)cc(Br)c1 ; N#Cc1cc(Br)cc(OC(F)F)c1]

3-Bromo-5-hydroxy-benzonitrile (2.0 g, 10.1 mmol, 1.0 equiv.), potassium carbonate (3472 mg, 25.1 mmol, 2.5 equiv.) and (2-bromo-2,2-difluoro-acetyl)oxysodium (2982 mg, 15.1 mmol, 1.5 equiv.) were suspended in a mixture of DMF (18 mL) and water (2 mL). The mixture was stirred at 100° C. for 2 hr, then cooled to rt. The mixture was diluted with water and then extracted with diethyl ether. The organics were washed with water and brine, then driedl with sodium sulfate, filtered, the filtrate collected, and the solvent was removed. The material was purified by column chromatography on silica (25 g cartridge, 50 μm, 0-25% EtOAc/cyclohexane). The appropriate fractions were combined, and the solvent was removed to yield the title compound (1.62 g, 65%) as an off-white solid. $^1$H NMR (400 MHz, $CDCl_3$) δ 7.66 (s, 1H), 7.56 (s, 1H), 7.39 (s, 1H), 6.55 (t, J=71.8 Hz, 1H). $^{19}$F NMR (376 MHz, $CDCl_3$) −82.2 (s, 2F).

Synthesis of 1-bromo-3-(difluoromethoxy)-5-fluorobenzene (Intermediate 14)

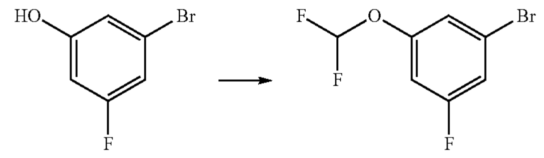 [SMILES: Oc1cc(F)cc(Br)c1 ; Fc1cc(Br)cc(OC(F)F)c1]

3-Bromo-5-fluorophenol (2.0 g, 10.5 mmol, 1.0 equiv.), potassium carbonate (3.6 g, 26.0 mmol, 2.5 equiv.) and (2-bromo-2,2-difluoro-acetyl)oxysodium (3.1 g, 15.7 mmol, 1.5 equiv.) were suspended in a mixture of DMF (18 mL) and water (2 mL). The mixture was stirred at 100° C. for 2 hr. The mixture was diluted with water and then extracted with diethyl ether. The organics were washed with water and brine, then dried with sodium sulfate, filtered, the filtrate collected, and the solvent was removed. The material was purified by column chromatography on silica (25 g cartridge, 15 μm, 0-25% EtOAc/cyclohexane). The appropriate fractions were combined, and the solvent was removed to yield the title compound (2.33 g, 92%) as a colourless oil. $^1$H NMR (400 MHz, $CDCl_3$) δ 7.15-7.10 (m, 2H), 6.84 (d, J=9.9 Hz, 1H), 6.50 (t, J=73.2 Hz, 1H). $^{19}$F NMR (376 MHz, $CDCl_3$) δ −81.92 (s, 2F), −108.33 (s, 1F).

Synthesis of 3-bromo-4-(difluoromethyl)benzonitrile (Intermediate 15)

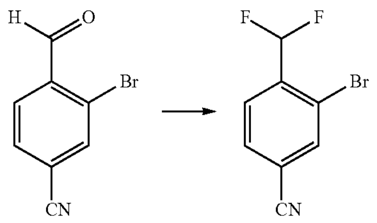 [SMILES: N#Cc1ccc(C=O)c(Br)c1 ; N#Cc1ccc(C(F)F)c(Br)c1]

To a solution of 3-bromo-4-formyl-benzonitrile (500 mg, 2.38 mmol, 1.0 equiv.) in DCM (5 mL) at 0° C. was added DAST (0.86 mL, 4.76 mmol, 2.0 equiv.). The mixture was stirred at 0° C. and allowed slowly to rt over 16 hrs. Sat. aq. $NaHCO_3$ was added dropwise to the reaction until the evolution of gas ceased and then stirred vigorously for a further 15 min. The biphasic solution was diluted with water and extracted with DCM (3x25 mL). The organics were collected, dried with sodium sulfate, filtered, the filtrate was collected, and the solvent was removed to yield the title compound (548 mg, 99%) as a yellow/brown solid. $^1H$ NMR (400 MHz, $CDCl_3$) δ 7.92 (s, 1H), 7.78 (d, J=8.5, 1H), 7.73 (d, J=8.5, 1H), 6.90 (t, J=54.5 Hz, 1H). $^{19}F$ NMR (376 MHz, $CDCl_3$) δ −116.25 (s, 2F).

Synthesis of 3-ethyl-7-fluoro-4-oxo-phthalazine-1-carboxylic acid (Intermediate 16)

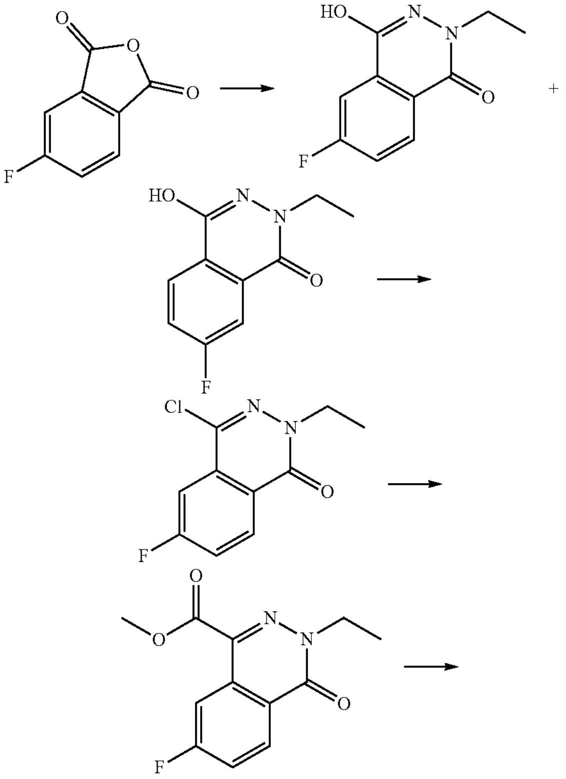

-continued

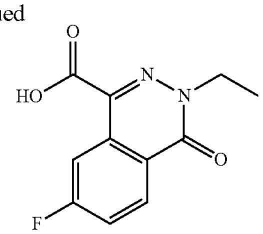

Step 1: Synthesis of 3-ethyl-6-fluoro-2H-phthalazine-1,4-dione and 3-ethyl-7-fluoro-2H-phthalazine-1,4-dione: To a solution of ethyl hydrazine oxalate (25 g, 0.167 mol, 1.1 equiv.) in IMS (250 mL) was added DIPEA (39 mL, 0.226 mol, 1.5 equiv.) and the mixture was stirred at rt for 30 mins. 4-fluorophthalic anhydride (25 g, 0.151 mol, 1.0 equiv.) was then added and the mixture was heated at 75° C. for 3 hrs. The mixture was allowed to rt and then filtered. The filtrate was collected, and the solvent reduced to low volume, then water was added to give a white precipitate. The mixture was filtered, the solid was collected and washed with water, then dried at 45° C. in a vacuum desiccator to yield the title compounds (3-ethyl-6-fluoro-2H-phthalazine-1,4-dione (10.60 g, 34%) and 3-ethyl-7-fluoro-2H-phthalazine-1,4-dione (12.70 g, 41%) as a white solid. $^1H$ NMR (400 MHz, DMSO) Regioisomer 1-δ 8.29 (dd, J=8.8 Hz, 5.4 Hz 1H), 7.73 (td, J=8.8 Hz, 2.7 Hz, 1H), 7.65 (dd, J=8.8 Hz, 2.7 Hz, 1H), 4.00 (q, J=7.0 Hz, 2H), 1.26 (t, J=7.0 Hz, 3H), 1.18 (s, 1H). Regioisomer 2-δ 8.05 (dd, J=9.0 Hz, 5.2 Hz, 1H), 7.89 (dd, J=9.0 Hz, 2.7 Hz, 1H), 7.78 (td, J=9.0 Hz, 2.7 Hz, 1H), 4.00 (q, J=7.2 Hz, 2H), 1.27 (t, J=7.2 Hz, 3H), 1.20 (s, 1H). Regioisomer ratio 1:1.4 (R1:R2).

Step 2: Synthesis of 4-chloro-2-ethyl-6-fluoro-phthalazin-1-one: A suspension of 3-ethyl-6-fluoro-2H-phthalazine-1,4-dione (12.20 g, 58.6 mmol, 1.0 equiv.) and 3-ethyl-7-fluoro-2H-phthalazine-1,4-dione (12.20 g, 58.6 mmol, 1.0 equiv.) in phosphorus(V) oxychloride (100 mL, 1.07 mol, 18.3 equiv.) was heated at 110° C. for 5 hrs, then allowed to rt. The solvent was reduced to low volume then treated with sat. aq. $NaHCO_3$ solution and extracted with EtOAc. The aqueous phase was re-extracted with EtOAc and the combined organics were washed with water, then brine, dried with sodium sulfate, filtered. The filtrate was collected, and the solvent was removed. The material was purified by column chromatography on silica (330 g cartridge, 0-40% EtOAc/cyclohexane) and the appropriate fractions were combined, and the solvent was removed to yield the title compound (7.30 g, 54%) as a colourless crystalline solid. $^1H$ NMR (400 MHz, $CDCl_3$) δ 8.48 (dd, J=9.0 Hz, 5.4 Hz, 1H), 7.62 (dd, J=9.0 Hz, 2.2 Hz, 1H), 7.52 (t, J=9.0 Hz, 2.2 Hz), 4.26 (q, J=7.1 Hz, 2H), 1.42 (t, J=7.1 Hz, 1H).

Step 3: Synthesis of methyl 3-ethyl-7-fluoro-4-oxo-phthalazine-1-carboxylate: To a solution of 4-chloro-2-ethyl-6-fluoro-phthalazin-1-one (7300 mg, 32.2 mmol, 1.0 equiv.) in MeOH (75 mL) in a 100 mL pressure vessel was added triethylamine (5.4 mL, 38.7 mmol, 1.2 equiv.), bis(diphenylphosphino)ferrocene (1071 mg, 1.93 mmol, 0.06 equiv.) and palladium (II) acetate (362 mg, 1.61 mmol, 0.05 equiv.). The vessel was sealed, flushed with carbon monoxide at stirred at 120° C. and 10 bar pressure for 3 hrs. The mixture was allowed to rt and filtered through a Celite™ pad. The filtrate was collected and the solvent was removed. The material was purified by column chromatography on silica (220 g cartridge, 0-40% EtOAc/cyclohexane). The appropriate fractions were combined and the solvent was removed to yield the title compound (6.3 g, 78%) as a colourless solid.

$^1H$ NMR (400 MHz, $CDCl_3$) δ 8.49 (dd, J=9.0 Hz, 5.6 Hz, 1H), 8.39 (dd, J=10.1 Hz, 2.1 Hz, 1H), 7.48 (td, J=9.0 Hz, 2.1 Hz, 1H), 4.37 (q, J=7.2 Hz, 2H), 4.02 (s, 3H), 1.45 (t, J=7.2 Hz, 1H).

Step 4: Synthesis of 3-ethyl-7-fluoro-4-oxo-phthalazine-1-carboxylic acid: To a solution of methyl 3-ethyl-7-fluoro-4-oxo-phthalazine-1-carboxylate (6300 mg, 25.2 mmol, 1.0 equiv.) in THF (100 mL) and water (40 mL) was added lithium hydroxide monohydrate (1336 mg, 31.8 mmol, 1.25 equiv.) and the mixture was stirred at rt for 1.5 hrs. The organics were removed, and the aqueous solution acidified to pH 1 with HCl. A precipitate formed and the mixture was filtered, the solid was collected and washed with water, then dried at 45° C. in a vacuum desiccator to yield the title compound (3750 mg, 62%) as a white solid. $^1H$ NMR (400 MHz, DMSO) δ 8.29 (dd, J=9.0 Hz, 6.0 Hz, 1H), 8.19 (dd, J=10.4 Hz, 2.2 Hz, 1H), 7.63 (td, J=9.0 Hz, 2.2 Hz), 4.11 (q, J=7.1 Hz, 2H), 1.27 (t, J=7.1 Hz, 3H).

Synthesis of 3-chloro-5-(piperazin-1-yl)benzonitrile (Intermediate 17)

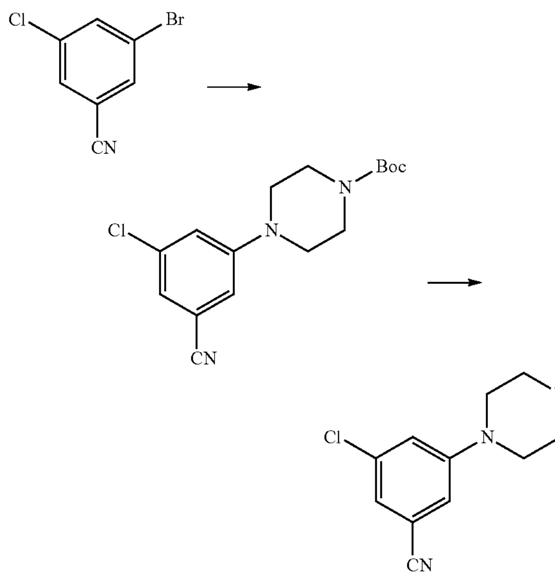

Step 1: Synthesis of tert-butyl 4-(3-chloro-5-cyanophenyl)piperazine-1-carboxylate: To a solution of 1-Boc-piperazine (850 mg, 4.56 mmol, 1.0 equiv.) in CPME (15 mL) in a vial was added 3-bromo-5-chloro-benzonitrile (1185 mg, 5.48 mmol, 1.2 equiv.), sodium tert-butoxide (789 mg, 8.21 mmol, 1.8 equiv.) and RuPhos Pd G3 (286 mg, 0.342 mmol, 0.075 equiv.) and the vial was sealed. The mixture in each was thoroughly degassed with nitrogen after repeated evacuation and refill with nitrogen. This method was repeated to give 4 vials of the same reaction scale. These vials were then stirred at 100° C. for 5 hr, then allowed to cool to rt and stood for 16 hrs. The four vials were combined and diluted with EtOAc. The organics were washed with water, then brine and dried with sodium sulfate. The mixture was filtered, the filtrate collected, and the solvent was removed. The material was purified by column chromatography on silica (40 g cartridge, 50 μm, 0-40% EtOAc/cyclohexane). The appropriate fractions were combined, and the solvent was removed to yield a pale-yellow oil which crystallised on cooling. The material was triturated with hexane, filtered, and dried to yield the title compound (3.17 g, 54%) as an off-white solid. $^1H$ NMR (400 MHz, $CDCl_3$) δ 7.06 (s, 1H), 7.04 (s, 1H), 6.99 (s, 1H), 3.58 (t, J=4.5 Hz, 4H), 3.20 (t, J=4.5 Hz, 4H), 1.49 (s, 9H).

Step 2: Synthesis of 3-chloro-5-(piperazin-1-yl)benzonitrile: To a solution of tert-butyl 4-(3-chloro-5-cyano-phenyl)piperazine-1-carboxylate (2200 mg, 6.84 mmol, 1.0 equiv.) in dichloromethane (30 mL) was added TFA (15 mL, 0.196 mol, 29 equiv.) and the mixture was stirred for 1.5 hr. The solvent was removed, and the material was re-dissolved in DCM and washed with sat. aq. $NaHCO_3$, then water and brine. The solution was dried with sodium sulfate, filtered, the filtrate collected, and the solvent was removed. The material was purified by column chromatography on silica (40 g cartridge, 15 μm, 0-5% (5% 2 M $NH_3$ in MeOH/DCM)/DCM). The appropriate fractions were combined, and the solvent was removed to yield the title compound (1343 mg, 89%) a yellow oil. $^1H$ NMR (400 MHz, $CDCl_3$) δ 7.03 (s, 2H), 6.99 (s, 1H), 3.19 (t, J=5.3 Hz, 4H), 3.02 (t, J=5.3 Hz, 4H). NH not observed.

Synthesis of 3-fluoro-5-(piperazin-1-yl)benzonitrile (Intermediate 18)

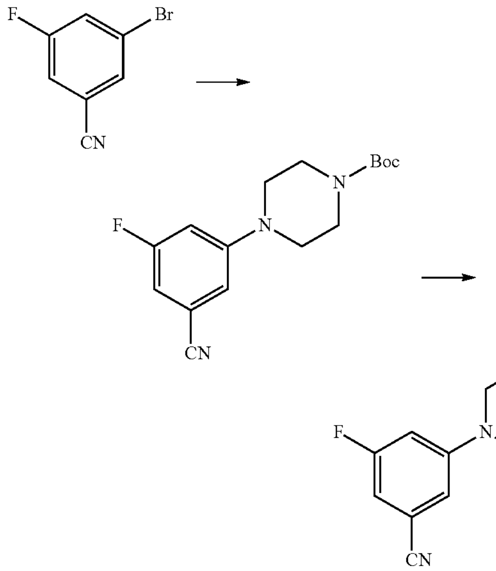

Step 1: Synthesis of tert-butyl 4-(3-cyano-5-fluorophenyl)piperazine-1-carboxylate: To a solution of 1-Boc-piperazine (1.00 g, 5.37 mmol, 1.0 equiv.) in toluene (15 mL) in a vial was added 3-bromo-5-fluoro-benzonitrile (1.07 g, 5.37 mmol, 1.0 equiv.), sodium tert-butoxide (0.77 g, 8.05 mmol, 1.5 equiv.), BINAP (0.33 g, 0.537 mmol, 0.1 equiv.) and tris(dibenzylideneacetone)dipalladium(O) (0.49 g, 0.537 mmol, 0.1 equiv.) and the vial was sealed. The mixture was thoroughly degassed with nitrogen after repeated evacuation and refill with nitrogen. This method was repeated to give 4 vials of the same reaction scale. These vials were then stirred at 100° C. for 4 hr, then allowed to cool to rt and stood for 16 hrs. The four vials were combined and diluted with EtOAc. The organics were washed with water, then brine and dried with sodium sulfate. The mixture was filtered, the filtrate collected, and the solvent was removed. The material was purified by column chromatography on silica (40 g cartridge, 15 μm, 0-50% EtOAc/cyclohexane). The appropriate fractions were combined, and the solvent was removed to yield the title compound (5.15 g, 78%) as a pale-yellow solid. $^1$H NMR (400 MHz, $CDCl_3$) δ 6.89 (s, 1H), 6.82-6.72 (m, 2H), 3.58 (t, J=5.1 Hz, 4H), 3.20 (t, J=5.1 Hz, 4H), 1.49 (s, 9H).

Step 2: Synthesis of 3-fluoro-5-(piperazin-1-yl)benzonitrile: To a solution of tert-butyl 4-(3-cyano-5-fluoro-phenyl) piperazine-1-carboxylate (5.30 g, 17.4 mmol, 1.0 equiv.) in DCM (60 mL) was added TFA (30 mL, 0.392 mol, 22.6 equiv.) and the mixture was stirred at rt for 2 hr. The solvent was removed, the material re-dissolved in DCM then loaded onto an SCX-2 cartridge (50 g, pre-washed with DCM). The cartridge was washed with DCM, then methanol and eluted with 2 M $NH_3$ in methanol. The appropriate fractions were combined, and the solvent was removed to yield the title compound (3.19 g, 89%) as an orange oil which crystallised on standing to a yellow solid. $^1$H NMR (400 MHz, $CDCl_3$) δ 6.89 (s, 1H), 6.93-6.72 (m, 2H), 3.19 (t, J=5.1 Hz, 4H), 3.02 (t, J=5.1 Hz, 4H), 1.66 (s, 1H). $^{19}$F NMR (376 MHz, $CDCl_3$) −109.3 (s, 1F).

Synthesis of 1-(5-methylpyridin-3-yl)piperazine (Intermediate 19)

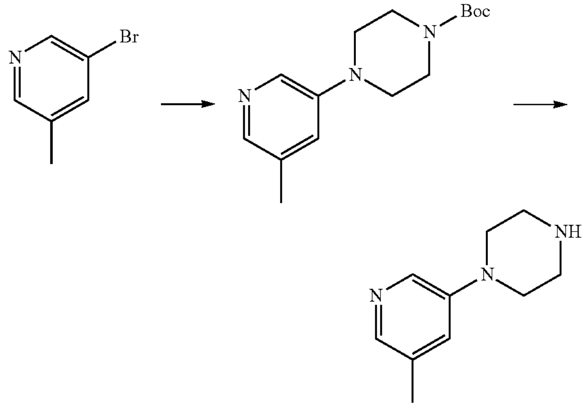

Step 1: Synthesis of tert-butyl 4-(5-methyl-3-pyridyl) piperazine-1-carboxylate: 2-methyl-4-(piperazine-1-carbonyl)phthalazin-1-one (70 mg, 0.257 mmol, 1.0 equiv.), 3-bromo-5-methylpyridine (0.37 mL, 3.22 mmol, 1.0 equiv.), DavePhos Pd G3 (123 mg, 0.161 mmol, 0.05 equiv.) and sodium tert-butoxide (464 mg, 4.83 mmol, 1.5 equiv.) were suspended in CPME (12 mL) in a vial. The vial was sealed, evacuated and flushed with nitrogen twice. The solution was stirred at 110° C. for 2 hrs, then allowed to rt. The mixture was partitioned between EtOAc and water and the phases separated. The organics were washed with brine, dried with sodium sulfate, filtered, the filtrate collected, and the solvent removed. The material was purified by column chromatography on silica (40 g cartridge, 50-100% EtOAc/cyclohexane) and the appropriate fractions were combined and the solvent removed to yield the title compound (630 mg, 70%) as a white solid. $^1$H NMR (400 MHz, $CDCl_3$) δ 8.12 (d, J=2.6 Hz, 1H), 7.97 (s, 1H), 7.00 (s, 1H), 3.59 (t, J=5.6 Hz, 4H), 3.15 (t, J=5.6 Hz, 4H), 2.30 (s, 3H), 1.49 (s, 9H).

Step 2: Synthesis of 1-(5-methylpyridin-3-yl)piperazine: To a solution of tert-butyl 4-(5-methyl-3-pyridyl)piperazine-1-carboxylate (625 mg, 2.25 mmol, 1.0 equiv.) in DCM (7 mL) was added TFA (3.5 mL, 45.1 mmol, 20 equiv.) and the mixture was stirred at rt for 1.5 hrs. The mixture was loaded onto an SCX-2 cartridge (25 g, pre-washed with DCM), washed with DCM, then methanol and eluted with 7 M ammonia in methanol. The eluent was collected, and the solvent removed to yield the title compound (400 mg, 100%) as a pale-yellow oil. $^1$H NMR (400 MHz, $CDCl_3$) δ 8.12 (d, J=2.6 Hz, 1H), 7.95 (s, 1H), 6.99 (s, 1H), 3.17 (t, J=4.7 Hz, 4H), 3.05 (t, J=4.7 Hz, 4H), 2.29 (s, 3H).

Synthesis of 1-(4-methoxypyridin-3-yl)piperazine (Intermediate 20)

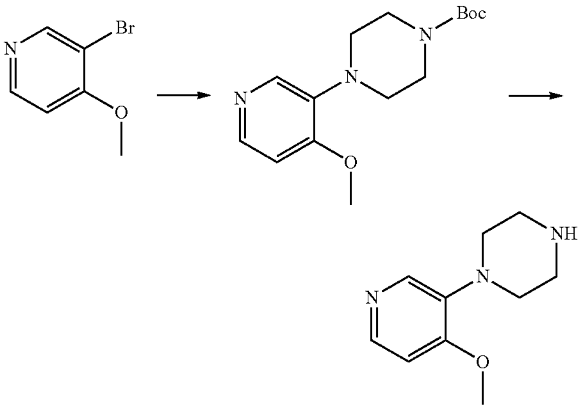

Step 1: Synthesis of tert-butyl 4-(4-methoxypyridin-3-yl) piperazine-1-carboxylate: 3-Bromo-4-methoxy-pyridine (5.0 g, 26.6 mmol, 1.0 equiv.), 1-Boc-piperazine (7.4 g, 39.9 mmol, 1.5 equiv.) and RuPhos Pd G2 (2066 mg, 2.66 mmol, 0.1 equiv.) were suspended in CPME (250 mL) and 2 M sodium tert-butoxide in THF (40 mL, 79.8 mmol, 3.0 equiv.) was then added and the mixture was purged with nitrogen for 10 min then stirred at 100° C. for 3 hr. The mixture was cooled to rt, diluted with DCM, and passed through a Celite™ pad, washing with DCM. The filtrate was collected, and the solvent removed. The material was purified by column chromatography on silica in two batches (220 g cartridge, 50 μm, 30-100% EtOAc/cyclohexane then 0-25% EtOAc/methanol). The appropriate fractions were combined, and the solvent was removed to yield the title compound (7.5 g, 76%) as a pale-yellow solid. $^1$H NMR (400 MHz, $CDCl_3$) δ 8.24 (d, J=5.7 Hz, 1H), 8.11 (s, 1H), 6.78 (d, J=5.7 Hz, 1H), 3.92 (s, 3H), 3.60 (t, J=5.3 Hz, 4H), 3.05 (t, J=5.3 Hz, 4H), 1.48 (s, 9H).

Step 2: Synthesis of 1-(4-methoxypyridin-3-yl)piperazine: To a solution of tert-butyl 4-(4-methoxy-3-pyridyl) piperazine-1-carboxylate (2.50 g, 8.52 mmol, 1.0 equiv.) in DCM (100 mL) was added TFA (10 mL, 0.128 mol, 15 equiv.) and the mixture was stirred at rt for 2 hr. The solvent was removed, re-dissolved in DCM then loaded onto an SCX-2 cartridge (50 g, pre-washed with methanol) and the cartridge was washed with 1:1 methanol/DCM, then methanol and eluted with 1 M $NH_3$ in MeOH. The appropriate fractions were combined, and the solvent was removed to yield the title compound (1.81 g, >100%) as a pale-brown oil. $^1$H NMR (400 MHz, DMSO) δ 8.11 (d, J=5.9 Hz, 1H), 7.99 (s, 1H), 6.95 (d, J=5.4 Hz, 1H), 3.84 (s, 3H), 2.92 (t, J=5.59 Hz, 4H), 2.81 (t, J=5.59 Hz, 4H).

Synthesis of 2-ethyl-1-oxo-pyrido[3,4-d]pyridazine-4-carboxylic acid (Intermediate 21) and 3-ethyl-4-oxo-pyrido[3,4-d]pyridazine-1-carboxylic acid (Intermediate 22)

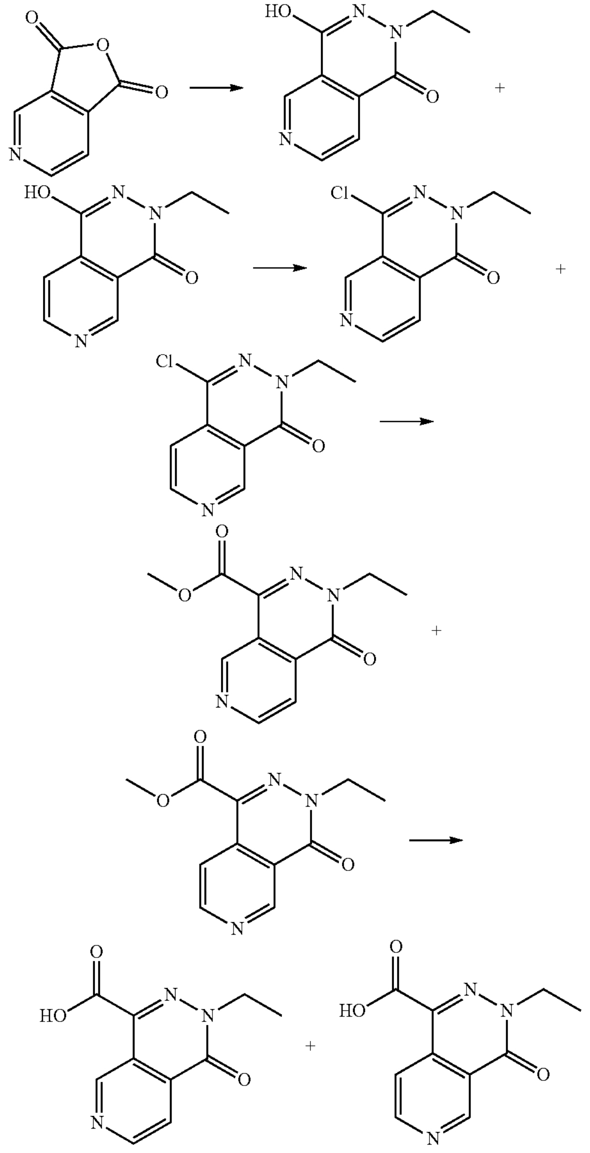

Intermediate 21 Intermediate 22

Step 1: Synthesis of 2-ethyl-3H-pyrido[3,4-d]pyridazine-1,4-dione and 3-ethyl-2H-pyrido[3,4-d]pyridazine-1,4-dione: To a suspension of ethyl hydrazine oxalate (25 g, 0.167 mol, 1.18 equiv.) in IMS (200 mL) was added DIPEA (37 mL, 0.211 mol, 1.5 equiv.) and the mixture was stirred at rt for 30 mins. 3,4-pyridinedicarboxylic anhydride (21 g, 0.141 mol, 1.0 equiv.) was then added and the mixture was heated at 70° C. for 3 hrs. The mixture was allowed to rt, then filtered and the solid was washed with IMS, then collected. The solid was triturated with water twice, then filtered, collected and dried at 45° C. in a vacuum desiccator to yield the title compounds in a 3:1 ratio (12.75 g, 46%) as a brown solid. $^{1}$H NMR (400 MHz, DMSO) Regioisomer 1-δ 9.26 (s, 1H), 9.02 (d, J=5.0 Hz, 1H), 8.06 (d, J=5.00 Hz), 4.02 (q, J=7.0 Hz, 2H), 1.28 (t, J=7.0 Hz, 3H). Regioisomer 2-δ 9.42 (s, 1H), 9.03 (d, J=5.2 Hz, 1H), 7.81 (d, J=5.2 Hz, 1H), 4.02 (q, J=7.0 Hz, 2H), 1.28 (t, J=7.0 Hz, 3H). Regioisomer ratio 1:0.25 (R1:R2)

Step 2: Synthesis of 4-chloro-2-ethyl-pyrido[3,4-d]pyridazin-1-one and 1-chloro-3-ethyl-pyrido[3,4-d]pyridazin-4-one: A solution of 2-ethyl-3H-pyrido[3,4-d]pyridazine-1,4-dione (14.20 g, 74.3 mmol, 1.0 equiv.) and 3-ethyl-2H-pyrido[3,4-d]pyridazine-1,4-dione (3.55 g, 18.6 mmol, 0.25 equiv.) in phosphorus(V) oxychloride (75 mL, 0.805 mol, 10.8 equiv.) was heated at 100° C. for 20 hrs, then allowed to rt. The solvent was reduced to low volume then treated with sat. aq. $NaHCO_3$ solution and extracted with DCM. The aqueous phase was re-extracted with DCM and the combined organics were washed with water, then brine, dried with sodium sulfate, filtered. The filtrate was collected, and the solvent was removed. The material was purified by column chromatography on silica (220 g cartridge, 0-50% EtOAc/cyclohexane) and the appropriate fractions were combined, and the solvent was removed to yield the title compounds (8.58 g, 54% as a 3.1:1 ratio) as a pale yellow crystalline solid. $^{1}$H NMR (400 MHz, $CDCl_3$) Regioisomer 1-δ 9.37 (s, 1H), 9.05 (d, J=5.3 Hz, 1H), 8.22 (d, J=5.3 Hz, 1H), 4.27 (q, J=7.6 Hz, 2H), 1.43 (t, J=7.6 Hz, 3H). Regioisomer 2-δ 9.71 (s, 1H), 9.08 (d, J=5.5 Hz, 1H), 7.75 (d, J=5.5 Hz, 1H), (q, J=7.6 Hz, 2H), 1.43 (t, J=7.6 Hz, 3H). Regioisomer ratio 1:0.3 (R1:R2).

Step 3: Synthesis of methyl 2-ethyl-1-oxo-pyrido[3,4-d]pyridazine-4-carboxylate and methyl 3-ethyl-4-oxo-pyrido[3,4-d]pyridazine-1-carboxylate: To a solution of 4-chloro-2-ethyl-pyrido[3,4-d]pyridazin-1-one and 1-chloro-3-ethyl-pyrido[3,4-d]pyridazin-4-one (8580 mg, 40.9 mmol, 1.0 equiv., 3.1:1 ratio) in MeOH (70 mL) in a 100 ml pressure vessel was added triethylamine (6.8 mL, 49.1 mmol, 1.2 equiv.), bis(diphenylphosphino)ferrocene (1361 mg, 2.46 mmol, 0.06 equiv.) and palladium diacetate (459 mg, 2.05 mmol, 0.05 equiv.). The vessel was sealed, evacuated and flushed with carbon monoxide, then heated at 120° C. and 15 bar pressure for 3 hrs. The mixture was allowed to rt, the carbon monoxide was evacuated and the vessel flushed with air. The mixture was filtered through Celite™, the filtrate was collected and the solvent was removed. The material was purified by column chromatography on silica (120 g cartridge, 0-40% EtOAc/cyclohexane). The appropriate fractions were combined and the solvent was removed to yield the title compounds (8.1 g, 84%, 3.1:1 ratio of isomers) as a pale-yellow solid. $^{1}$H NMR (400 MHz, DMSO) Regioisomer 1-δ 10.07 (d, J=1.0 Hz, 1H), 9.00 (d, J=5.6, 1H), 8.23 (dd, J=5.6 Hz, 1.0 Hz, 1H), 4.39 (q, J=7.6 Hz, 2H), 4.07 (s, 3H), 1.47 (t, J=7.6 Hz, 1H). Regioisomer 2-δ 9.73 (d, J=0.9 Hz, 1H), 9.02 (d, J=5.8 Hz, 1H), 8.50 (dd, J=5.8 Hz, 0.9 Hz, 1H), 4.39 (q, J=7.2 Hz, 1H), 4.04 (s, 3H), 1.47 (t, J=7.2 Hz, 1H). Regioisomer ratio 1:0.3 (R1:R2).

Step 4: Synthesis of 2-ethyl-1-oxo-pyrido[3,4-d]pyridazine-4-carboxylic acid and 3-ethyl-4-oxo-pyrido[3,4-d]pyridazine-1-carboxylic acid: To a solution of methyl 2-ethyl-1-oxo-pyrido[3,4-d]pyridazine-4-carboxylate (6.22 g, 26.7 mmol, 1.0 equiv.) and methyl 3-ethyl-4-oxo-pyrido[3,4-d]pyridazine-1-carboxylate (2.08 g, 8.92 mmol, 0.33 equiv.) in THF (75 mL) and water (25 mL) was added lithium hydroxide monohydrate (1943 mg, 46.3 mmol, 1.74 equiv.). The mixture was stirred at rt for 1.5 hrs. The solvent was reduced to low volume to remove the organics. The remaining aqueous layer was acidified with 1 M aq. HCl (46.3 mL, 1.1 equiv.) and the resulting precipitate was filtered and the solid collected and then dried at 45° C. in a vacuum desiccator to yield the title compounds (7.8 g, 98%, 3.2:1 mixture of isomers) as a pale-yellow solid. $^1$H NMR (400 MHz, DMSO) Regioisomer 1-δ 9.92 (d, J=0.9 Hz, 1H), 9.00 (d, J=5.14 Hz, 1H), 8.14 (dd, J=5.1 Hz, 0.9 Hz, 1H), 4.23 (q, J=7.6 Hz, 2H), 1.34 (t, J=7.6 Hz, 3H). Regioisomer 2-δ 9.51 (d, J=1.0 Hz, 1H), 9.05 (d, J=5.6 Hz, 1H), 8.45 (dd, J=5.6 Hz, J=1.0 Hz, 1H), 4.23 (q, J=7.2 Hz, 2H), 1.34 (t, J=7.2 Hz, 3H). Regioisomer ratio 1:0.3 (R1:R2).

Synthesis of 4-cyclopropyl-3-(piperazin-1-yl)benzonitrile (Intermediate 23)

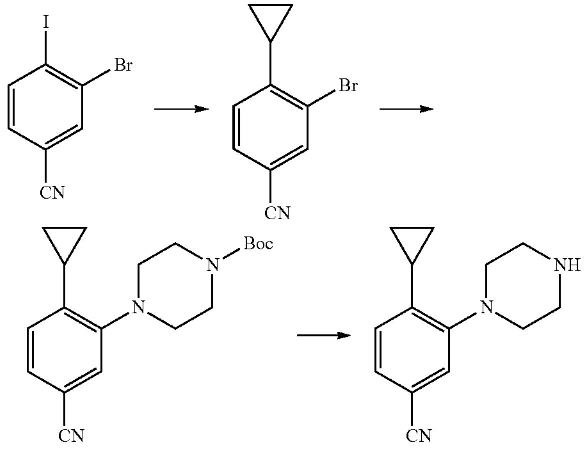

Step 1: Synthesis of 3-bromo-4-cyclopropyl-benzonitrile: 3-Bromo-4-iodo-benzonitrile (1.0 g, 3.25 mmol, 1.0 equiv.), cyclopropylboronic acid (418 mg, 4.87 mmol, 1.5 equiv.), cesium carbonate (3174 mg, 9.74 mmol, 3.0 equiv.) and Pd(dppf)$Cl_2$ (119 mg, 0.162 mmol, 0.05 equiv.) were placed in a vial and the vial was sealed. The vial was evacuated and flushed with nitrogen three times. 2-Methyltetrahydrofuran (10 mL) was added and the mixture was stirred at 60° C. for 18 hrs. Further cyclopropylboronic acid (139 mg, 1.62 mmol, 0.5 equiv.) and Pd(dppf)$Cl_2$ (119 mg, 0.162 mmol, 0.05 equiv.) and stirred at 60° C. for 1 hr. The mixture was diluted with DCM and filtered through a small silica pad. The filtrate was collected and the solvent was removed. The material was purified by column chromatography on silica (0-5% EtOAc/cyclohexane). The appropriate fractions were combined, and the solvent was removed to yield the title compound (594 mg, 82%) as a white solid. $^1$H NMR (400 MHz, $CDCl_3$) δ 7.82 (d, J=1.7 Hz, 1H), 7.49 (dd, J=8.0 Hz and 1.7 Hz, 1H), 6.96 (d, J=8.0 Hz, 1H), 2.27-2.21 (m, 1H), 1.17-1.11 (m, 2H), 0.78-0.72 (m, 2H).

Step 2: Synthesis of tert-butyl 4-(5-cyano-2-cyclopropyl-phenyl)piperazine-1-carboxylate: 1-Boc-piperazine (747 mg, 4.01 mmol, 1.5 equiv.), DavePhos Pd G3 (204 mg, 0.267 mmol, 0.1 equiv.), and sodium tert-butoxide (386 mg, 4.01 mmol, 1.5 equiv.) were added to a vial. The vial was sealed, evacuated and flushed with nitrogen, three times. A solution of 3-bromo-4-cyclopropyl-benzonitrile (594 mg, 2.67 mmol, 1.0 equiv.) in CPME (6 mL) was added and the mixture was stirred at 110° C. for 1.5 hrs and allowed to rt. The solvent was removed and the material was suspended in DCM and filtered through Celite™, the filtrate was collected and the solvent was removed. The material was purified by column chromatography on silica (0-40% EtOAc in cyclohexane) to yield the title compound (556 mg, 64%) as an off white solid. $^1$H NMR (400 MHz, $CDCl_3$) δ 7.27 (dd, J=8.1 and 1.7, 1H), 7.20 (d, J=1.7 Hz, 1H), 6.80 (d, J=8.1 Hz, 1H), 3.60 (t, J=4.9 Hz, 4H), 2.96 (t, J=4.9 Hz, 4H), 2.36-2.27 (m, 1H), 1.49 (s, 9H) 1.14-1.07 (m, 2H), 0.81-0.75 (m, 2H).

Step 3: Synthesis of 4-cyclopropyl-3-(piperazin-1-yl)benzonitrile: To a solution of tert-butyl 4-(5-cyano-2-cyclopropyl-phenyl)piperazine-1-carboxylate (556 mg, 1.70 mmol, 1.0 equiv.) in DCM (2 mL) was added TFA (3.9 mL, 50.9 mmol, 30 equiv.) and the flask was equipped with a bubbler. The mixture was stirred at rt until gas evolution ceased, then the solvent was removed. The material was dissolved in MeOH and loaded onto an SCX-2 cartridge (10 g), washed with methanol and eluted with 2 M $NH_3$ in MeOH. The eluent was collected, and the solvent removed to yield the title compound (403 mg, 99%) as a yellow oil. $^1$H NMR (400 MHz, $CDCl_3$) δ 7.26-7.23 (m, 1H), 7.22 (d, J=1.6 Hz, 1H), 6.78 (d, J=8 Hz, 1H), 3.10-2.97 (m, 8H), 2.37-2.28 (m, 1H), 1.12-1.07 (m, 2H), 0.80-0.74 (m, 2H).

Synthesis of 6-chloro-2-methyl-4-(piperazine-1-carbonyl)phthalazin-1(2H)-one (Intermediate 24)

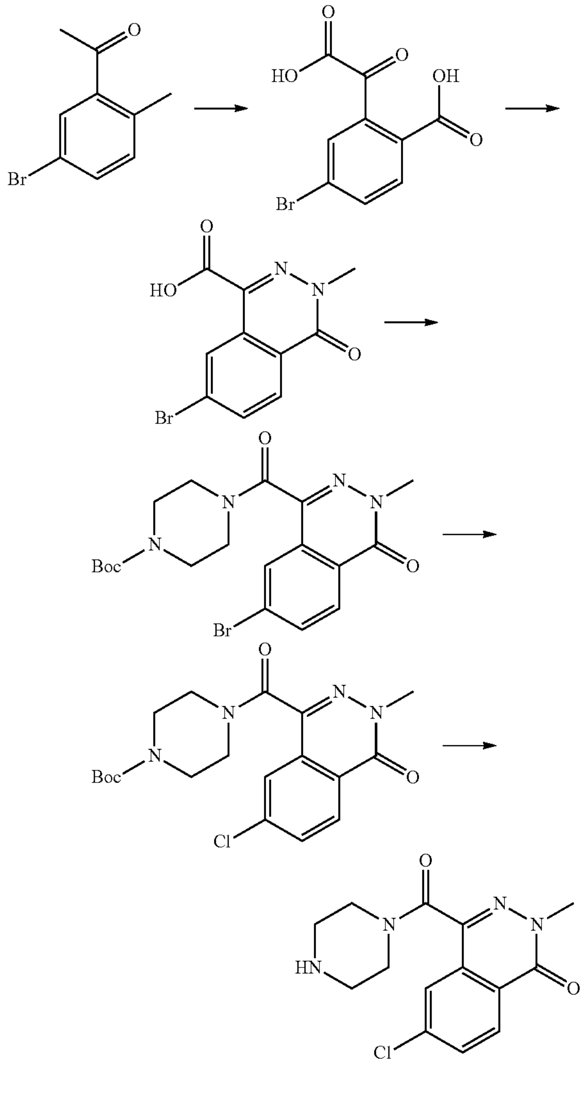

Step 1: Synthesis of 4-bromo-2-oxalo-benzoic acid: To a mixture of 1-(5-bromo-2-methyl-phenyl)ethanone (10 g, 46.9 mmol, 1.0 equiv.) and potassium carbonate (9.73 g, 70.4 mmol, 1.5 equiv.) in water (50 mL) was added potassium permanganate (44.50 g, 0.282 mol, 6.0 equiv.) and the mixture was heated at 50° C. for 6 hrs then allowed to rt. The solution was added portion-wise to ethanol (50 mL) at 50° C. The mixture was stirred at 50° C. for 30 min, then allowed to rt. The resultant suspension was filtered through Celite™, and the filtrate was collected. The filtrate was acidified with 37%. aq. HCl to pH 1-2, then reduced in volume to remove the majority of the EtOH. A white precipitate formed, which was washed with EtOAc (20 mL), then filtered. The solid was collected and re-crystallised from DCM (50 mL), filtered and the solid collected and dried to yield the title compound (4.98 g, 38%) as a white solid. $^1$H NMR (400 MHz, DMSO) δ 7.96-7.86 (m, 2H), 7.82 (d, J=7.8 Hz, 1H).

Step 2: Synthesis of 7-bromo-3-methyl-4-oxo-3,4-dihydrophthalazine-1-carboxylic acid: To a stirred solution of 4-bromo-2-oxalo-benzoic acid (2.48 g, 9.08 mmol, 1.0 equiv.) in IMS (37.5 mL) was added methylhydrazine (0.60 mL, 11.4 mmol, 1.25 equiv.) dropwise and the mixture was stirred at 75° C. for 3 hrs, then cooled to rt. The mixture was filtered and the solid was collected, washed with diethyl ether (30 mL), then dried in a vacuum desiccator at 45° C. for 1 hr to yield the title compound (2520 mg, 97%) as an off-white solid. This was used directly in the next step without further purification.

Step 3: Synthesis of tert-butyl 4-(7-bromo-3-methyl-4-oxo-phthalazine-1-carbonyl)piperazine-1-carboxylate: To a solution of 7-bromo-3-methyl-4-oxo-phthalazine-1-carboxylic acid (840 mg, 2.97 mmol, 1.0 equiv.) in DMF (10 mL) was added HATU (2257 mg, 5.93 mmol, 2.0 equiv.) and 1-Boc-piperazine (1105 mg, 5.93 mmol, 2.0 equiv.) and the mixture stirred at rt for 5 min, then DIPEA (1.6 mL, 8.90 mmol, 3.0 equiv.) was added and the mixture was stirred at rt for 6 hrs. The mixture was partitioned between EtOAc and water and the phases were separated. The organics were washed with water then 5% aq. LiCl solution, dried with sodium sulfate, filtered and the filtrate was collected and the solvent removed. The material was purified by column chromatography on silica. This was purified by silica gel chromatography (40 g cartridge, 15 μm, 0-50% EtOAc/cyclohexane) and the appropriate fractions were combined and the solvent removed to yield the title compound (740 mg, 55%) as a colourless solid. $^1$H NMR (400 MHz, $CDCl_3$) δ 8.31 (d, J=8.7 Hz, 1H), 7.98 (d, J=2.0 Hz, 1H), 7.89 (dd, J=8.7 Hz, 2.0 Hz, 1H), 3.87-3.82 (m, 5H), 3.60 (t, J=5.6 Hz, 2H), 3.48 (s, 4H), 1.48 (s, 9H).

Step 4: Synthesis of tert-butyl 4-(7-chloro-3-methyl-4-oxo-phthalazine-1-carbonyl)piperazine-1-carboxylate: tert-Butyl 4-(7-bromo-3-methyl-4-oxo-phthalazine-1-carbonyl) piperazine-1-carboxylate (340 mg, 0.753 mmol, 1.0 equiv.) and copper(I) chloride (246 mg, 2.49 mmol, 3.3 equiv.) were suspended in DMSO (3 mL) and the mixture was stirred at 110° C. for 22 hrs, then allowed to rt. The mixture was filtered, the filtrate was collected and partitioned between EtOAc and water. The phases were separated, and the organics were washed with brine, dried with sodium sulfate, filtered and the filtrate was collected, and the solvent removed to yield the title compound (260 mg, 84%) as an off white solid. $^1$H NMR (400 MHz, $CDCl_3$) δ 8.40 (d, J=8.6 Hz, 1H), 7.81 (d, J=1.9 Hz, 1H), 7.73 (dd, J=8.6 Hz, 1.9 Hz, 1H), 3.85 (t, J=5.1 Hz, 4H), 3.84 (s, 3H), 3.60 (t, J=5.1 Hz, 4H).

Step 5: Synthesis of 6-chloro-2-methyl-4-(piperazine-1-carbonyl)phthalazin-1(2H)-one: To a solution of tert-butyl 4-(7-chloro-3-methyl-4-oxo-phthalazine-1-carbonyl)piperazine-1-carboxylate (255 mg, 0.627 mmol, 1.0 equiv.) in DCM (3 mL) was added trifluoroacetic acid (0.96 mL, 12.5 mmol, 20 equiv.) and the mixture was stirred at rt for 3 hrs. The mixture was loaded onto an SCX-2 cartridge (10 g, pre-washed with DCM), the cartridge washed with DCM then methanol before eluting with 7 M ammonia in methanol. The eluent was collected and the was solvent removed and the solid was triturated with diethyl ether to yield the title compound (180 mg, 94%) as an off white solid. $^1$H NMR (400 MHz, DMSO) δ 8.31 (d, J=8.6 Hz, 1H), 7.94 (dd, J=8.6 Hz, 2.0 Hz, 1H), 7.74 (d, J=2.0 Hz, 1H), 3.71 (s, 3H), 3.65 (t, J=5.1 Hz, 2H), 3.36 (t, 5.1 Hz, 1H), 2.82 (t, 5.1 Hz, 2H), 2.63 (t, 5.1 Hz, 2H).

Example 2: Synthesis of 2-methyl-4-(4-phenylpiperazine-1-carbonyl)isoquinolin-1-one (Compound 1)

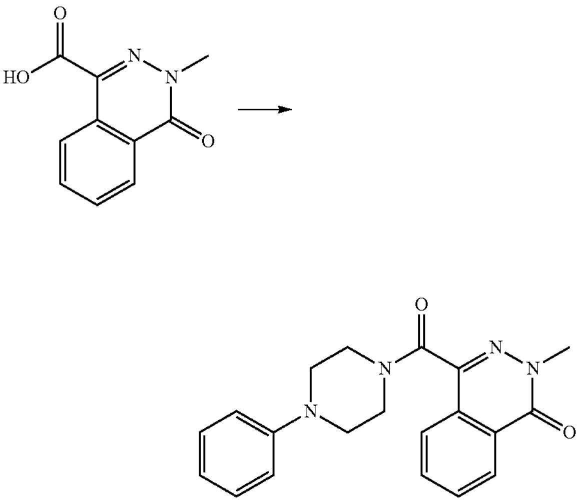

To a solution of 2-methyl-1-oxo-isoquinoline-4-carboxylic acid (100 mg, 0.492 mmol, 1 equiv.) in DMF (3 mL) was added HATU (281 mg, 0.738 mmol, 1.5 equiv.) and DIPEA (0.26 mL, 1.48 mmol, 3 equiv.) and the mixture stirred at rt for 5 min. 1-phenylpiperazine (0.090 mL, 0.591 mmol, 1.2 equiv.) was then added and the solution was stirred at rt for 20 hrs. The mixture was diluted with EtOAc and washed with water, then brine and dried over sodium sulphate. The mixture was filtered, the filtrate collected and evaporated. The residue was purified by reverse phase HPLC (Sunfire C18 19×150 mm, 10 μm 20-80% MeCN/$H_2O$+0.1% formic acid, 20 mL/min, rt) to yield the title compound (150 mg, 88%) as a white solid. LCMS: Method A, m/z=348.2 $(M+H)^+$, RT=4.05 min. $^1$H NMR (400 MHz, DMSO) δ 8.32-8.29 (m, 1H), 7.77 (ddd, J=1.4, 7.1, 8.3 Hz, 1H), 7.72 (s, 1H), 7.62-7.56 (m, 2H), 7.24 (dd, J=7.5, 8.6 Hz, 2H), 6.97 (d, J=8.0 Hz, 2H), 6.83 (dd, J=7.3, 7.3 Hz, 1H), 3.88-3.62 (m, 4H), 3.55 (s, 3H), 3.26-3.11 (m, 4H).

The compound in Table 1 was synthesized according to the method described in Example

TABLE 1

| Compound No. | Structure | LCMS data | NMR data |
|---|---|---|---|
| Structure and Spectroscopic Data for Compound 2. | | | |
| 2 | 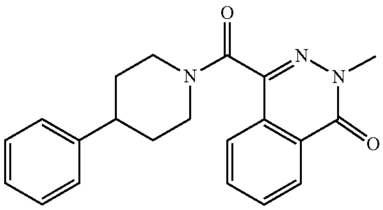 [SMILES: Cn1nc(C(=O)N2CCC(c3ccccc3)CC2)c2ccccc2c1=O] | Method A m/z 348.5 $(M + H)^+$ RT 4.55 min | $^1$H NMR (400 MHz, DMSO) δ 8.36-8.33 (m, 1H), 8.02-7.91 (m, 2H), 7.82-7.79 (m, 1H), 7.35-7.27 (m, 4H), 7.25-7.19 (m, 1H), 4.78-4.71 (m, 1H), 3.81-3.75 (m, 4H), 3.21 (dt, J = 2.4, 13.0 Hz, 1H), 3.00 (dt, J = 2.8, 12.8 Hz, 1H), 2.87 (tt, J = 3.4, 12.0 Hz, 1H), 2.00-1.93 (m, 1H), 1.74 (ddt, J = 4.1, 12.7, 12.7 Hz, 2H), 1.50 (ddt, J = 4.1, 12.5, 12.6 Hz, 1H). |

Example 3: Synthesis of 2-ethyl-4-(4-phenylpiperazine-1-carbonyl)phthalazin-1-one (Compound 3)

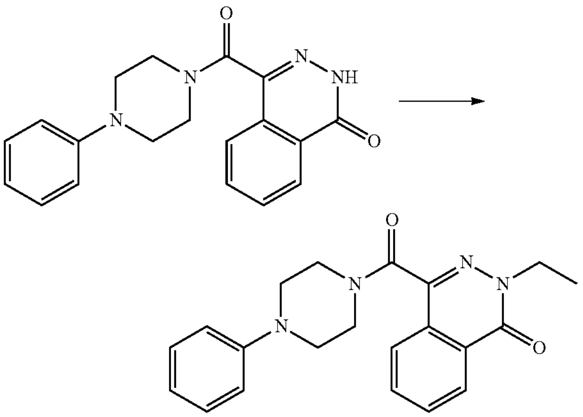

To a solution of 4-(4-phenylpiperazine-1-carbonyl)-2H-phthalazin-1-one (100 mg, 0.299 mmol, 1 equiv.) in DMF (1.5 mL) was added potassium carbonate (103 mg, 0.748 mmol, 2.5 equiv.). Iodoethane (0.060 mL, 0.748 mmol, 2.5 equiv.) was then added and the solution was stirred at 50° C. overnight. The mixture was diluted with EtOAc and washed with water, then brine and dried over sodium sulfate. The mixture was filtered, the filtrate collected, and the solvent removed. The material was purified by reverse phase HPLC (Sunfire C18 19×150 mm, 10 μm 20-80% $MeCN/H_2O$ (10 mM $NH_4CO_3$), 20 mL/min, rt) to yield the title compound (12 mg, 11%) as an off white solid. LCMS: Method A, m/z=363.2 $(M+H)^+$, RT=4.60 min. $^1$H NMR (400 MHz, DMSO) δ 8.37-8.35 (m, 1H), 7.99-7.91 (m, 2H), 7.83-7.80 (m, 1H), 7.25 (dd, J=7.5, 8.6 Hz, 2H), 6.98 (d, J=8.0 Hz, 2H), 6.84 (dd, J=7.3, 7.3 Hz, 1H), 4.20 (q, J=7.2 Hz, 2H), 3.91 (dd, J=5.2, 5.2 Hz, 2H), 3.57 (dd, J=5.1, 5.1 Hz, 2H), 3.33-3.29 (m, 2H), 3.10 (dd, J=5.1, 5.1 Hz, 2H), 1.33 (dd, J=7.2, 7.2 Hz, 3H).

The compounds in Table 2 were made according to the method described in Example 3, using Intermediate 1 and the appropriate haloalkyl reagent.

TABLE 2

| Compound No. | Structure | LCMS data | NMR data |
|---|---|---|---|
| Structure and Spectroscopic Data for Compounds 4 to 8. | | | |
| 4 | 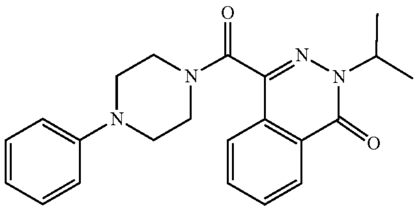 [SMILES: CC(C)n1nc(C(=O)N2CCN(c3ccccc3)CC2)c2ccccc2c1=O] | Method B m/z 377.2 $(M + H)^+$ RT 4.82 min | $^1$H NMR (400 MHz, DMSO) δ 8.38-8.34 (m, 1H), 7.99-7.90 (m, 2H), 7.85-7.82 (m, 1H), 7.28-7.23 (m, 2H), 7.01-6.97 (m, 2H), 6.84 (t, J = 7.3 Hz, 1H), 5.37-5.27 (m, 1H), 3.94-3.89 (m, 2H), 3.62-3.57 (m, 2H), 3.33-3.30 (m, 2H), 3.15 3.10 (m, 2H), 1.35 (d, J = 6.7 Hz, 6H). |

TABLE 2-continued

| Structure and Spectroscopic Data for Compounds 4 to 8. | | | |
|---|---|---|---|
| Compound No. | Structure | LCMS data | NMR data |
| 5 | 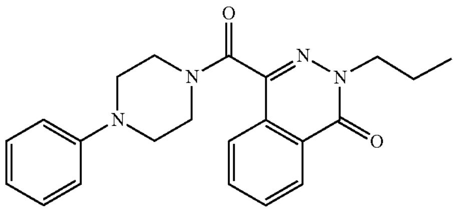 [SMILES: CCCn1nc(C(=O)N2CCN(c3ccccc3)CC2)c2ccccc2c1=O] | Method A m/z 377.2 $(M + H)^+$ RT 4.91 min | $^1H$ NMR (400 MHz, DMSO) δ 8.38-8.34 (m, 1H), 8.00-7.91 (m, 2H), 7.83-7.80 (m, 1H), 7.27-7.22 (m, 2H), 7.00-6.95 (m, 2H), 6.84 (t, J = 7.3 Hz, 1H), 4.13 (t, J = 7.2 Hz, 2H), 3.93-3.88 (m, 2H), 3.58-3.53 (m, 2H), 3.12-3.07 (m, 2H), 1.79 (tq, J = 7.3, 7.3 Hz, 2H), 0.93 (t, J = 7.5 Hz, 3H). 2H obscured by solvent signal. |
| 6 | 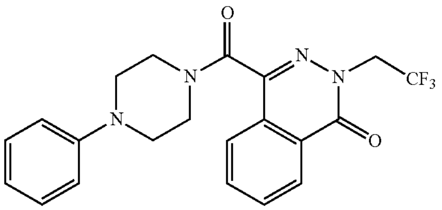 [SMILES: O=C(c1nn(CC(F)(F)F)c(=O)c2ccccc12)N1CCN(c2ccccc2)CC1] | Method B m/z 417.4 $(M + H)^+$ RT 4.80 min | $^1H$ NMR (400 MHz, DMSO) δ 8.41-8.38 (m, 1H), 8.06-7.97 (m, 2H), 7.87-7.83 (m, 1H), 7.28-7.23 (m, 2H), 7.00-6.96 (m, 2H), 6.84 (t, J = 7.2 Hz, 1H), 5.05 (q, J = 9.1 Hz, 2H), 3.93-3.88 (m, 2H), 3.59-3.54 (m, 2H), 3.13-3.08 (m, 2H). 2H obscured by solvent signal. |
| 7 | 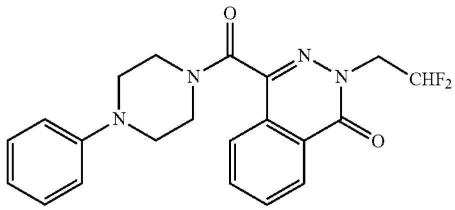 [SMILES: O=C(c1nn(CC(F)F)c(=O)c2ccccc12)N1CCN(c2ccccc2)CC1] | Method A m/z 399.2 $(M + H)^+$ RT 4.60 min | $^1H$ NMR (400 MHz, DMSO) δ 8.40-8.36 (m, 1H), 8.04-7.95 (m, 2H), 7.86-7.83 (m, 1H), 7.28-7.22 (m, 2H), 6.98 (d, J = 7.9 Hz, 2H), 6.84 (t, J = 7.2 Hz, 1H), 6.43 (tt, J = 3.9, 55.1 Hz, 1H), 4.61 (dt, J = 4.0, 14.6 Hz, 2H), 3.93-3.88 (m, 2H), 3.59-3.55 (m, 2H), 3.12-3.08 (m, 2H). 2H obscured by solvent signal. |
| 8 | 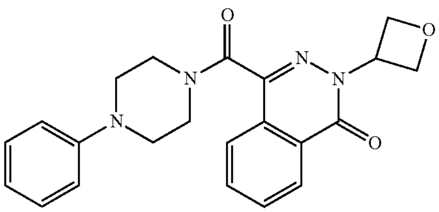 [SMILES: O=C(c1nn(C2COC2)c(=O)c2ccccc12)N1CCN(c2ccccc2)CC1] | Method A m/z 391.6 $(M + H)^+$ RT 4.16 min | $^1H$ NMR (400 MHz, DMSO) δ 8.35-8.33 (m, 1H), 8.01-7.92 (m, 2H), 7.87-7.84 (m, 1H), 7.28-7.22 (m, 2H), 7.01-6.97 (m, 2H), 6.87-6.82 (m, 1H), 6.06-5.98 (m, 1H), 4.93-4.87 (m, 4H), 3.96-3.92 (m, 2H), 3.69-3.65 (m, 2H), 3.15-3.11 (m, 2H). 2H obscured by solvent signal. |

Example 4: Synthesis of 2-cyclopropyl-4-(4-phenylpiperazine-1-carbonyl)phthalazin-1-one (Compound 9)

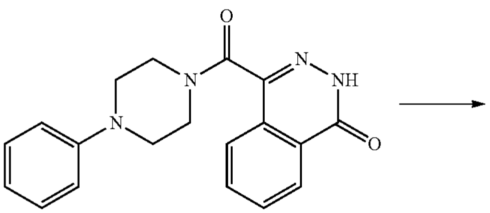

-continued

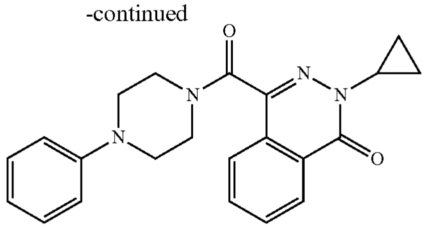

To a solution of 4-(4-phenylpiperazine-1-carbonyl)-2H-phthalazin-1-one (200 mg, 0.598 mmol, 1 equiv.) in 1,2-dichloroethane (4 mL) was added cyclopropyl boronic acid (103 mg, 1.20 mmol, 2 equiv.), triethylamine (0.33 mL, 2.39 mmol, 4 equiv.), pyridine (0.24 mL, 2.99 mmol, 5 equiv.)

and copper (II) acetate (217 mg, 1.20 mmol, 2 equiv.) and the mixture was stirred at 80° C. for 4 hrs. The mixture was allowed to rt and quenched with Satd. ammonium chloride. The mixture was extracted with DCM three times. The organic extracts were combined and dried over sodium sulphate, filtered, the filtrate collected, and the solvent removed. The material was purified by column chromatography on silica (12 g cartridge, 15 μM silica, 10-50% [3:1 ethyl acetate:IMS]/cyclohexane) and the appropriate fractions were combined and the solvent removed to yield the title compound (72 mg, 32%) as a white solid. LCMS: Method C, m/z=374.9 $(M+H)^+$, RT=4.40 min. $^1H$ NMR (400 MHz, DMSO) δ 8.34 (dd, J=2.5, 6.6 Hz, 1H), 7.97-7.89 (m, 2H), 7.79 (dd, J=2.4, 6.6 Hz, 1H), 7.26-7.21 (m, 2H), 6.96 (d, J=8.1 Hz, 2H), 6.82 (dd, J=7.3, 7.3 Hz, 1H), 4.04-3.97 (m, 1H), 3.88 (dd, J=5.1, 5.1 Hz, 2H), 3.54 (dd, J=5.0, 5.0 Hz, 2H), 3.32-3.27 (m, 2H), 3.07 (dd, J=5.0, 5.0 Hz, 2H), 1.01-0.98 (m, 4H).

Example 5: Synthesis of 2-methyl-4-[4-(p-tolyl)piperazine-1-carbonyl]phthalazin-1-one (Compound 10)

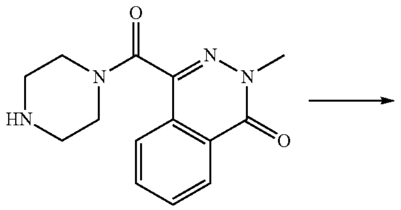

-continued

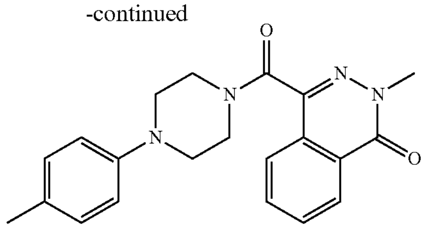

To a solution of 2-methyl-4-(piperazine-1-carbonyl)phthalazin-1-one (100 mg, 0.367 mmol, 1 equiv.) in 1,4-dioxane (3 mL) was added 4-bromotoluene (0.054 mL, 0.441 mmol, 1.2 equiv.), RuPhos PdG3 (31 mg, 0.0367 mmol, 0.1 equiv.), RuPhos (26 mg, 0.0551 mmol, 0.15 equiv.), and caesium carbonate (359 mg, 1.10 mmol, 3 equiv.) and the mixture was degassed with argon for 5 min. The tube was sealed and heated at 80° C. for 72 hrs, then allowed to rt. The mixture was partitioned between EtOAc and water and the phases separated. The organics were collected and washed with brine, dried over sodium sulfate, filtered and the solvent was removed. The material was purified by column chromatography on silica (4 g cartridge, 15 μM silica, 0-50% [3:1 ethyl acetate:IMS]/cyclohexane) and the appropriate fractions were combined and the solvent removed to yield the title compound (50 mg, 38%) as a white solid. LCMS: Method C, m/z=363.1 $(M+H)^+$, RT=4.32 min. $^1H$ NMR (400 MHz, $CDCl_3$) δ 8.50-8.47 (m, 1H), 7.81-7.79 (m, 3H), 7.10 (d, J=8.3 Hz, 2H), 6.85 (d, J=8.6 Hz, 2H), 4.07-4.03 (m, 2H), 3.86 (s, 3H), 3.63-3.59 (m, 2H), 3.30-3.26 (m, 2H), 3.12-3.08 (m, 2H), 2.28 (s, 3H).

The compounds in Table 3 were made according to the method described in Example 5, using Intermediate 2 and the appropriate aryl halide reagent.

TABLE 3

Structure and Spectroscopic Data for Compounds 11 to 33.

| Compound No. | Structure | LCMS data | NMR data |
|---|---|---|---|
| 11 | 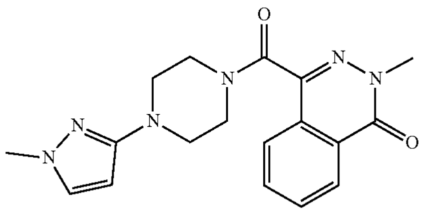 | Method A m/z 353.2 $(M + H)^+$ RT 3.02 min | $^1H$ NMR (400 MHz, DMSO) δ 8.36-8.33 (m, 1H), 7.99-7.90 (m, 2H), 7.79-7.76 (m, 1H), 7.46 (d, J = 2.1 Hz, 1H), 5.72 (d, J = 2.3 Hz, 1H), 3.87-3.82 (m, 2H), 3.75 (s, 3H), 3.66 (s, 3H), 3.52-3.47 (m, 2H), 3.27-3.22 (m, 2H), 3.04-2.99 (m, 2H). |
| 12 | 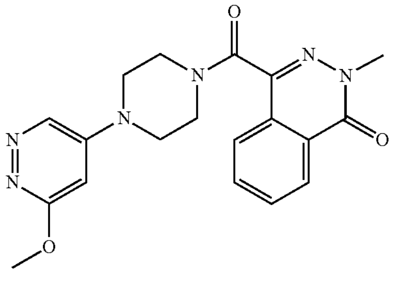 [SMILES: COc1cc(N2CCN(C(=O)c3nn(C)c(=O)c4ccccc34)CC2)cnn1] | Method B m/z 381.2 $(M + H)^+$ RT 3.04 min | $^1H$ NMR (400 MHz, DMSO) δ 8.75 (d, J = 2.5 Hz, 1H), 8.35-8.32 (m, 1H), 7.96-7.89 (m, 2H), 7.82-7.79 (m, 1H), 6.35 (d, J = 2.5 Hz, 1H), 3.93 (s, 3H), 3.87-3.82 (m, 2H), 3.73 (s, 3H), 3.64-3.59 (m, 2H), 3.57-3.52 (m, 2H), 3.37 (d, J = 14.1 Hz, 2H). |

TABLE 3-continued

| Structure and Spectroscopic Data for Compounds 11 to 33. | | | |
|---|---|---|---|
| Compound No. | Structure | LCMS data | NMR data |
| 13 | 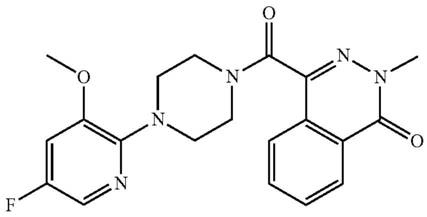 [SMILES: COc1cc(F)cnc1N1CCN(C(=O)c2nn(C)c(=O)c3ccccc23)CC1] | Method E m/z 398.3 $(M + H)^+$ RT 1.51 min | $^1H$ NMR (400 MHz, DMSO) δ 8.29 (dd, J = 7.7, 1.6 Hz, 1H), 7.96-7.83 (m, 2H), 7.77-7.71 (m, 2H), 7.33 (dd, J = 10.3, 2.5 Hz, 1H), 3.85-3.78 (m, 2H), 3.79 (s, 2H), 3.69 (s, 3H), 3.47 (dd, J = 6.4, 3.6 Hz, 2H), 3.32 (dd, J = 6.7, 3.9 Hz, 2H), 3.13-3.06 (m, 2H). 19F NMR (376 MHz, DMSO) δ −135.53 ppm |
| 14 | 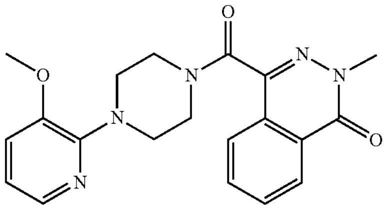 [SMILES: COc1cccnc1N1CCN(C(=O)c2nn(C)c(=O)c3ccccc23)CC1] | Method F m/z 380.3 $(M + H)^+$ RT 1.31 min | $^1H$ NMR (400 MHz, DMSO) δ 8.33-8.26 (m, 1H), 7.96-7.83 (m, 2H), 7.80-7.71 (m, 2H), 7.23 (dd, J = 8.0, 1.4 Hz, 1H), 6.89 (dd, J = 7.9, 4.8 Hz, 1H), 3.86-3.78 (m, 2H), 3.76 (s, 3H), 3.70 (s, 3H), 3.51-3.43 (m, 2H), 3.43-3.35 (m, 2H), 3.21-3.14 (m, 2H). |
| 15 | 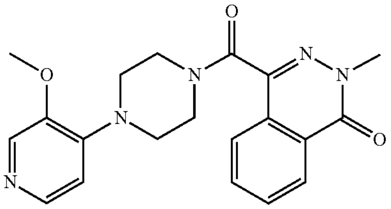 [SMILES: COc1cnccc1N1CCN(C(=O)c2nn(C)c(=O)c3ccccc23)CC1] | Method E m/z 380.3 $(M + H)^+$ RT 0.91 min | $^1H$ NMR (400 MHz, DMSO) δ 8.33-8.26 (m, 1H), 7.96-7.83 (m, 2H), 7.80-7.71 (m, 2H), 7.23 (dd, J = 8.0, 1.4 Hz, 1H), 6.89 (dd, J = 7.9, 4.8 Hz, 1H), 3.86-3.78 (m, 2H), 3.76 (s, 3H), 3.70 (s, 3H), 3.51-3.43 (m, 2H), 3.43-3.35 (m, 2H), 3.21-3.14 (m, 2H). |
| 16 | 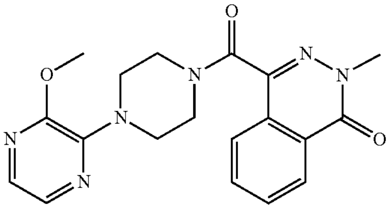 [SMILES: COc1nccnc1N1CCN(C(=O)c2nn(C)c(=O)c3ccccc23)CC1] | Method F m/z 381.3 $(M + H)^+$ RT 1.31 min | $^1H$ NMR (400 MHz, DMSO) δ 8.37-8.30 (m, 1H), 7.98-7.88 (m, 2H), 7.81-7.78 (m, 1H), 7.77 (d, J = 2.9 Hz, 1H), 7.65 (d, J = 2.9 Hz, 1H), 3.90 (s, 3H), 3.89-3.84 (m, 2H), 3.73 (s, 3H), 3.64-3.57 (m, 2H), 3.55-3.50 (m, 2H), 3.40-3.35 (m, 2H). |
| 17 | 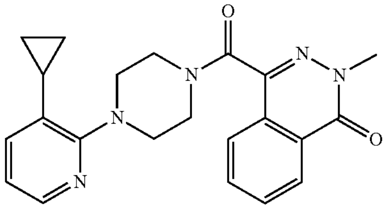 [SMILES: Cn1nc(C(=O)N2CCN(c3ncccc3C3CC3)CC2)c2ccccc2c1=O] | Method F m/z 390.3 $(M + H)^+$ RT 1.53 min | $^1H$ NMR (400 MHz, DMSO) δ 8.33-8.26 (m, 1H), 8.02 (dd, J = 4.8, 1.7 Hz, 1H), 7.97-7.84 (m, 2H), 7.78-7.71 (m, 1H), 7.17 (dd, J = 7.6, 1.8 Hz, 1H), 6.89 (dd, J = 7.6, 4.8 Hz, 1H), 3.92-3.83 (m, 2H), 3.70 (s, 3H), 3.56-3.49 (m, 2H), 3.32-3.25 (m, 1H), 3.11-3.04 (m, 2H), 2.06-1.93 (m, 1H), 1.01-0.90 (m, 2H), 0.73-0.64 (m, 2H). |

TABLE 3-continued

| Structure and Spectroscopic Data for Compounds 11 to 33. | | | |
|---|---|---|---|
| Compound No. | Structure | LCMS data | NMR data |
| 18 | 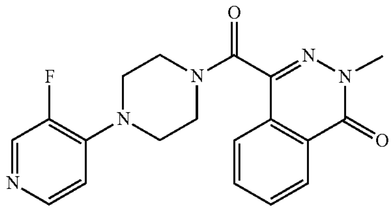 [SMILES: Cn1nc(C(=O)N2CCN(c3ccncc3F)CC2)c2ccccc2c1=O] | Method E m/z 368.4 $(M + H)^+$ RT 0.86 min | $^1H$ NMR (400 MHz, DMSO) δ 8.34-8.22 (m, 2H), 8.13 (d, J = 5.5 Hz, 1H), 7.95-7.83 (m, 2H), 7.82-7.72 (m, 1H), 6.97 (dd, J = 8.3, 5.5 Hz, 1H), 3.89-3.82 (m, 2H), 3.70 (s, 2H), 3.70 (s, 1H), 3.54 (t, J = 5.1 Hz, 2H), 3.43-3.36 (m, 2H), 3.16 (dd, J = 6.3, 2.8 Hz, 2H). 19F NMR (376 MHz, DMSO) δ −138.42 (dd, J = 8.3, 5.6 Hz) |
| 19 | 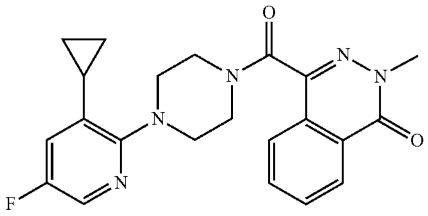 | Method E m/z 408.3 $(M + H)^+$ RT 1.79 min | $^1H$ NMR (400 MHz, DMSO) δ 8.33-8.26 (m, 1H), 8.00 (d, J = 2.8 Hz, 1H), 7.95-7.84 (m, 2H), 7.78-7.71 (m, 1H), 7.15 (dd, J = 9.8, 2.9 Hz, 1H), 3.91-3.79 (m, 2H), 3.70 (s, 3H), 3.56-3.49 (m, 2H), 3.22 (dd, J = 6.1, 3.9 Hz, 2H), 3.04-2.97 (m, 2H), 2.09-1.97 (m, 1H), 1.06-0.94 (m, 2H), 0.84-0.72 (m, 2H). |
| 20 | 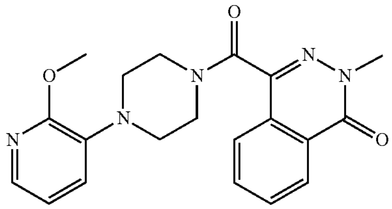 [SMILES: COc1ncccc1N1CCN(C(=O)c2nn(C)c(=O)c3ccccc23)CC1] | Method F m/z 380.3 $(M + H)^+$ RT 1.41 min | $^1H$ NMR (400 MHz, DMSO) δ 8.36-8.30 (m, 1H), 7.99-7.88 (m, 2H), 7.81-7.75 (m, 2H), 7.21 (dd, J = 7.7, 1.6 Hz, 1H), 6.92 (dd, J = 7.6, 4.9 Hz, 1H), 3.87 (s, 5H), 3.73 (s, 3H), 3.54 (q, J = 3.8 Hz, 2H), 3.14 (t, J = 5.1 Hz, 2H), 2.92 (t, J = 5.0 Hz, 2H). |
| 21 | 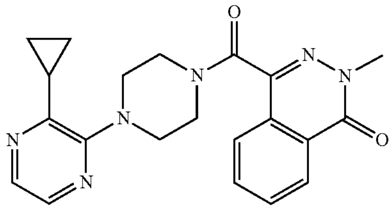 [SMILES: Cn1nc(C(=O)N2CCN(c3nccnc3C3CC3)CC2)c2ccccc2c1=O] | Method E m/z 391.3 $(M + H)^+$ RT 1.58 min | $^1H$ NMR (400 MHz, DMSO) δ 8.33 (ddd, J = 7.5, 1.9, 0.8 Hz, 1H), 8.04 (ddd, J = 12.3, 2.6, 0.7 Hz, 2H), 8.00-7.87 (m, 2H), 7.83-7.74 (m, 1H), 3.98-3.91 (m, 2H), 3.74 (s, 3H), 3.64-3.57 (m, 2H), 3.42-3.34 (m, 2H), 3.20-3.13 (m, 2H), 2.22 (tt, J = 7.7, 5.0 Hz, 1H), 1.09-0.96 (m, 4H). |
| 22 | 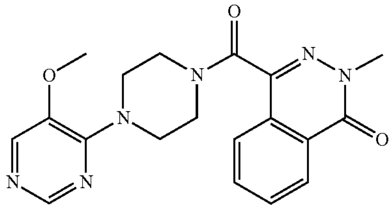 [SMILES: COc1cncnc1N1CCN(C(=O)c2nn(C)c(=O)c3ccccc23)CC1] | Method F m/z 381.3 $(M + H)^+$ RT 1.21 min | $^1H$ NMR (400 MHz, DMSO) δ 8.35-8.31 (m, 1H), 8.28 (s, 1H), 8.09 (s, 1H), 7.98-7.88 (m, 2H), 7.82-7.78 (m, 1H), 3.84 (d, J = 1.2 Hz, 7H), 3.73 (s, 3H), 3.61 (dd, J = 6.8, 3.4 Hz, 2H), 3.51 (dd, J = 6.4, 3.7 Hz, 2H). |

TABLE 3-continued

Structure and Spectroscopic Data for Compounds 11 to 33.

| Compound No. | Structure | LCMS data | NMR data |
|---|---|---|---|
| 23 | 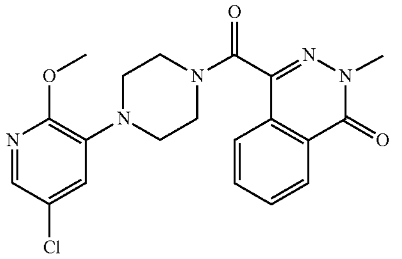 [SMILES: COc1ncc(Cl)cc1N1CCN(C(=O)c2nn(C)c(=O)c3ccccc23)CC1] | Method E m/z 414.3 $(M + H)^+$ RT 1.73 min | $^1H$ NMR (400 MHz, DMSO) δ 8.37-8.30 (m, 1H), 8.00-7.87 (m, 2H), 7.79 (m, 2H), 7.26 (d, J = 2.3 Hz, 1H), 3.87 (m, 5H), 3.74 (s, 3H), 3.57-3.45 (m, 2H), 3.20 (t, J = 5.1 Hz, 2H), 2.98 (t, J = 5.0 Hz, 2H). |
| 24 | 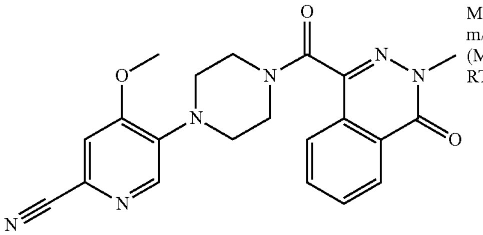 | Method F m/z 405.3 $(M + H)^+$ RT 1.34 min | $^1H$ NMR (400 MHz, CDCl3 and CD3OD) δ 8.38 (ddt, J = 6.4, 2.2, 1.1 Hz, 1H), 8.03-7.99 (m, 1H), 7.84-7.68 (m, 3H), 7.17-7.12 (m, 1H), 4.04-3.93 (m, 2H), 3.93-3.88 (m, 3H), 3.79 (q, J = 1.8 Hz, 3H), 3.57 (d, J = 4.6 Hz, 2H), 3.29 (dq, J = 5.4, 2.0 Hz, 2H), 3.18-3.08 (m, 2H). |
| 25 | 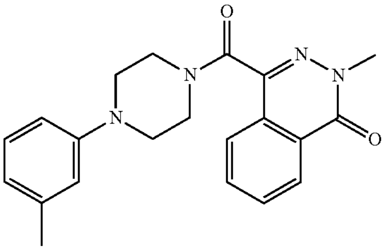 [SMILES: Cc1cccc(N2CCN(C(=O)c3nn(C)c(=O)c4ccccc34)CC2)c1] | Method A m/z 363.2 $(M + H)^+$ RT 4.57 min | $^1H$ NMR (400 MHz, DMSO) δ 8.37-8.34 (m, 1H), 7.99-7.91 (m, 2H), 7.82-7.78 (m, 1H), 7.12 (t, J = 7.8 Hz, 1H), 6.81-6.75 (m, 2H), 6.66 (d, J = 7.4 Hz, 1H), 3.91-3.87 (m, 2H), 3.76 (s, 3H), 3.57-3.52 (m, 2H), 3.32-3.27 (m, 2H), 3.09-3.04 (m, 2H), 2.26 (s, 3H). |
| 26 | 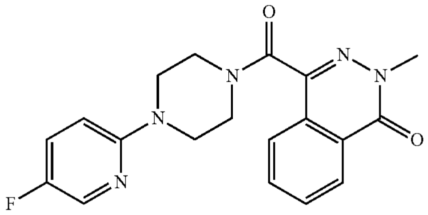 [SMILES: Cn1nc(C(=O)N2CCN(c3ccc(F)cn3)CC2)c2ccccc2c1=O] | Method C m/z 367.0 $(M + H)^+$ RT 4.08 min | $^1H$ NMR (400 MHz, DMSO) δ 8.35-8.32 (m, 1H), 7.97-7.89 (m, 2H), 7.79-7.77 (m, 1H), 7.10-7.04 (m, 2H), 7.01-6.96 (m, 2H), 3.91-3.86 (m, 2H), 3.74 (s, 3H), 3.56-3.52 (m, 2H), 3.27-3.22 (m, 2H), 3.03-2.98 (m, 2H). |
| 27 | 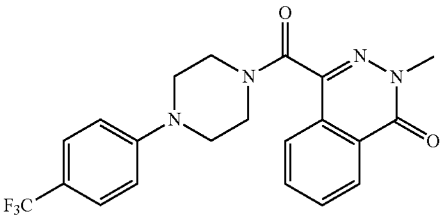 [SMILES: Cn1nc(C(=O)N2CCN(c3ccc(C(F)(F)F)cc3)CC2)c2ccccc2c1=O] | Method C m/z 417.0 $(M + H)^+$ RT 4.68 min | $^1H$ NMR (400 MHz, DMSO) δ 8.35-8.32 (m, 1H), 7.97-7.89 (m, 2H), 7.82-7.79 (m, 1H), 7.53 (d, J = 8.7 Hz, 2H), 7.09 (d, J = 8.7 Hz, 2H), 3.91-3.86 (m, 2H), 3.74 (s, 3H), 3.59-3.54 (m, 2H), 3.51-3.46 (m, 2H), 3.27-3.22 (m, 2H). |
| 28 | 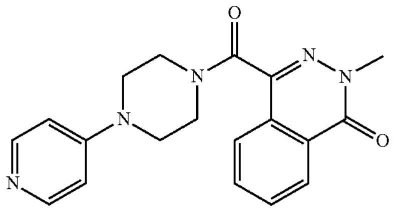 [SMILES: Cn1nc(C(=O)N2CCN(c3ccncc3)CC2)c2ccccc2c1=O] | Method A m/z 350.2 $(M + H)^+$ RT 2.12 min | $^1H$ NMR (400 MHz, DMSO) δ 8.37-8.34 (m, 1H), 8.21-8.19 (m, 2H), 7.98-7.91 (m, 2H), 7.84-7.81 (m, 1H), 6.87-6.84 (m, 2H), 3.89-3.85 (m, 2H), 3.75 (s, 3H), 3.58-3.53 (m, 4H), 3.32-3.29 (m, 2H). |

TABLE 3-continued

| Structure and Spectroscopic Data for Compounds 11 to 33. | | | |
|---|---|---|---|
| Compound No. | Structure | LCMS data | NMR data |
| 29 | 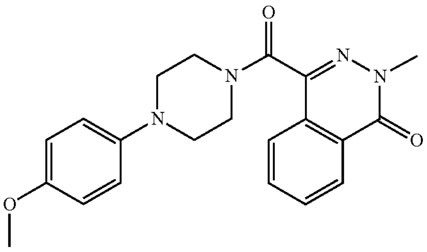 [SMILES: COc1ccc(N2CCN(C(=O)c3nn(C)c(=O)c4ccccc34)CC2)cc1] | Method C m/z 379.0 $(M + H)^+$ RT 3.72 min | $^1H$ NMR (400 MHz, DMSO) δ 8.35-8.32 (m, 1H), 7.98-7.89 (m, 2H), 7.79-7.76 (m, 1H), 6.94-6.91 (m, 2H), 6.85-6.81 (m, 2H), 3.90-3.86 (m, 2H), 3.74 (s, 3H), 3.68 (s, 3H), 3.55-3.51 (m, 2H), 3.19-3.14 (m, 2H), 2.95-2.90 (m, 2H). |
| 30 | 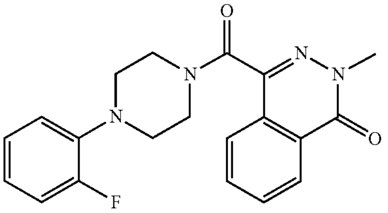 [SMILES: Cn1nc(C(=O)N2CCN(c3ccccc3F)CC2)c2ccccc2c1=O] | Method m/z 367.2 $(M + H)^+$ RT 4.21 min | $^1H$ NMR (400 MHz, DMSO) δ 8.35-8.32 (m, 1H), 7.99-7.90 (m, 2H), 7.81-7.78 (m, 1H), 7.18-6.99 (m, 4H), 3.93-3.88 (m, 2H), 3.74 (s, 3H), 3.59-3.54 (m, 2H), 3.19-3.14 (m, 2H), 2.96-2.92 (m, 2H). |
| 31 | 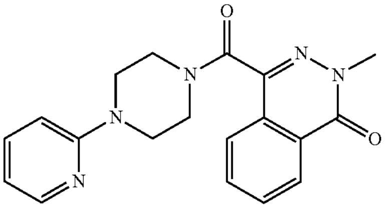 [SMILES: Cn1nc(C(=O)N2CCN(c3ccccn3)CC2)c2ccccc2c1=O] | Method A m/z 350.2 $(M + H)^+$ RT 2.27 min | $^1H$ NMR (400 MHz, DMSO) δ 8.37-8.34 (m, 1H), 8.14 (ddd, J = 0.7, 2.0, 4.9 Hz, 1H), 7.98-7.91 (m, 2H), 7.83-7.80 (m, 1H), 7.58 (ddd, J = 1.8, 7.0, 8.7 Hz, 1H), 6.87 (d, J = 8.7 Hz, 1H), 6.70 (ddd, J = 0.5, 5.0, 7.1 Hz, 1H), 3.88-3.83 (m, 2H), 3.76 (s, 3H), 3.72-3.67 (m, 2H), 3.55-3.50 (m, 2H), 3.48-3.44 (m, 2H). |
| 32 | 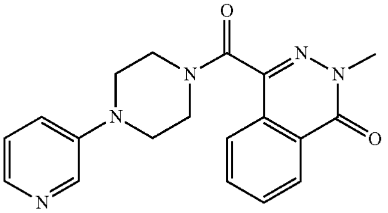 [SMILES: Cn1nc(C(=O)N2CCN(c3cccnc3)CC2)c2ccccc2c1=O] | Method A m/z 350.2 $(M + H)^+$ RT 2.15 min | $^1H$ NMR (400 MHz, DMSO) δ 8.37-8.33 (m, 2H), 8.05 (dd, J = 1.4, 4.5 Hz, 1H), 7.99-7.91 (m, 2H), 7.83-7.80 (m, 1H), 7.37 (ddd, J = 1.3, 3.0, 8.5 Hz, 1H), 7.25 (ddd, J = 0.5, 4.6, 8.5 Hz, 1H), 3.94-3.89 (m, 2H), 3.76 (s, 3H), 3.61-3.56 (m, 2H), 3.43-3.38 (m, 2H), 3.18-3.13 (m, 2H). |
| 33 | 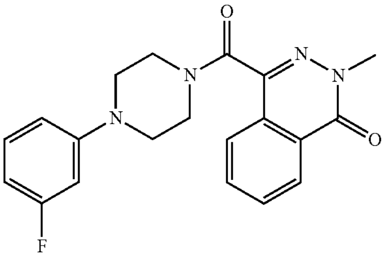 [SMILES: Cn1nc(C(=O)N2CCN(c3cccc(F)c3)CC2)c2ccccc2c1=O] | Method B m/z 367.2 $(M + H)^+$ RT 4.31 min | $^1H$ NMR (400 MHz, DMSO) δ 8.37-8.34 (m, 1H), 7.99-7.91 (m, 2H), 7.83-7.79 (m, 1H), 7.25 (dd, J = 8.1, 15.7 Hz, 1H), 6.82-6.76 (m, 2H), 6.63-6.58 (m, 1H), 3.91-3.86 (m, 2H), 3.76 (s, 3H), 3.55 (t, J = 5.1 Hz, 2H), 3.41-3.36 (m, 2H), 3.17-3.12 (m, 2H). |

Example 6: Synthesis of 4-(4-(3-fluoro-5-methoxy-phenyl)piperazine-1-carbonyl)-2-methylphthalazin-1(2H)-one (Compound 34)

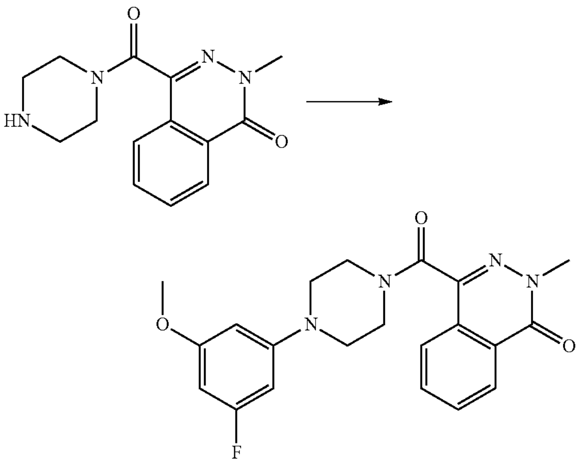

2-methyl-4-(piperazine-1-carbonyl)phthalazin-1-one (70 mg, 0.257 mmol, 1 equiv.), 1-bromo-3-fluoro-5-methoxy-benzene (79 mg, 0.386 mmol, 1.5 equiv.), DavePhos PdG3 (20 mg, 0.0257 mmol, 0.1 equiv.) and Sodium tert-butoxide (37 mg, 0.386 mmol, 1.5 equiv) were suspended in 1,4-dioxane (2 mL) in a vial. The vial was sealed, evacuated, and flushed with nitrogen twice. The mixture was stirred at 110° C. for 4 hrs, then allowed to rt. The mixture was partitioned between dichloromethane and water and the phases separated. The organics were collected, and the solvent removed. The material was purified by reverse phase HPLC (Sunfire C18 19×150 mm, 10 µm 20-80% $MeCN/H_2O$ (10 mM $NH_4CO_3$), 20 m/min, rt) and the appropriate fractions were combined and lyophilized to yield the title compound (59 mg, 58%) as an off white solid. LCMS: Method A, m/z 397.4 $(M+H)^+$, RT 4.58 min. $^1H$ NMR (400 MHz, DMSO) δ 8.35-8.31 (m, 1H), 7.93 (tdd, J=3.7, 11.0, 11.0 Hz, 2H), 7.80-7.77 (m, 1H), 6.38 (td, J=2.1, 12.4 Hz, 1H), 6.30 (s, 1H), 6.24 (td, J=2.0, 10.8 Hz, 1H), 3.85 (dd, J=5.1, 5.1 Hz, 2H), 3.73 (s, 3H), 3.72 (s, 3H), 3.51 (dd, J=5.1, 5.1 Hz, 2H), 3.35 (dd, J=5.2, 5.2 Hz, 2H), 3.11 (dd, J=5.1, 5.1 Hz, 2H).

The compounds in Table 4 were made according to the method described in Example 6, using Intermediate 2 and the appropriate aryl halide reagent.

TABLE 4

Structure and Spectroscopic Data for Compounds 35 to 60.

| Compound No. | Structure | LCMS data | NMR data |
|---|---|---|---|
| 35 | 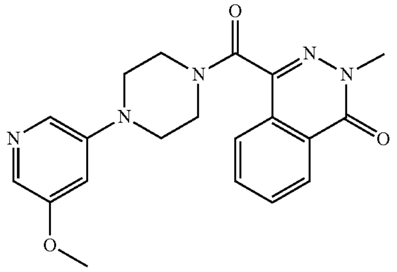 [SMILES: COc1cncc(N2CCN(C(=O)c3nn(C)c(=O)c4ccccc34)CC2)c1] | Method B m/z 380.2 $(M + H)^+$ RT 3.42 min | $^1H$ NMR (400 MHz, DMSO) δ 8.35-8.32 (m, 1H), 7.97-7.89 (m, 3H), 7.81-7.76 (m, 2H), 6.90 (t, J = 2.4 Hz, 1H), 3.91-3.86 (m, 2H), 3.79 (s, 3H), 3.74 (s, 3H), 3.58-3.53 (m, 2H), 3.42-3.38 (m, 2H), 3.19-3.14 (m, 2H). |
| 36 | 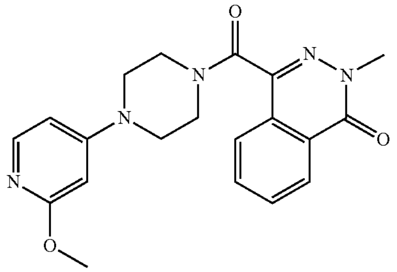 [SMILES: COc1cc(N2CCN(C(=O)c3nn(C)c(=O)c4ccccc34)CC2)ccn1] | Method A m/z 380.2 $(M + H)^+$ RT 2.33 min | $^1H$ NMR (400 MHz, DMSO) δ 8.35-8.32 (m, 1H), 7.97-7.89 (m, 2H), 7.83-7.78 (m, 2H), 6.57 (dd, J = 2.3, 6.1 Hz, 1H), 6.14 (d, J = 2.0 Hz, 1H), 3.86-3.81 (m, 2H), 3.77 (s, 3H), 3.73 (s, 3H), 3.54-3.47 (m, 4H), 3.28-3.23 (m, 2H). |
| 37 | 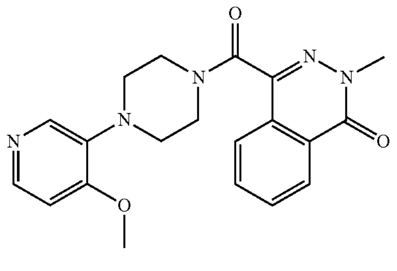 [SMILES: COc1ccncc1N1CCN(C(=O)c2nn(C)c(=O)c3ccccc23)CC1] | Method A m/z 380.2 $(M + H)^+$ RT 2.32 min | $^1H$ NMR (400 MHz, DMSO) δ 8.39-8.36 (m, 1H), 8.19 (d, J = 5.6 Hz, 1H), 8.09 (s, 1H), 8.02-7.93 (m, 2H), 7.85-7.82 (m, 1H), 7.04 (d, J = 5.6 Hz, 1H), 3.94-3.90 (m, 2H), 3.89 (s, 3H), 3.78 (s, 3H), 3.60-3.55 (m, 2H), 3.23-3.19 (m, 2H), 3.02-2.97 (m, 2H). |

TABLE 4-continued

| Compound No. | Structure | LCMS data | NMR data |
|---|---|---|---|
| Structure and Spectroscopic Data for Compounds 35 to 60. | | | |
| 38 | 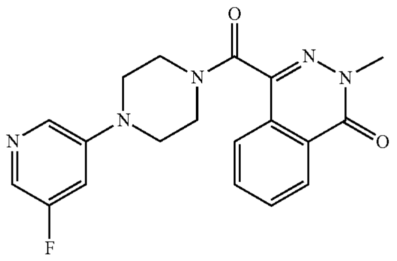 [SMILES: Cn1nc(C(=O)N2CCN(c3cncc(F)c3)CC2)c2ccccc2c1=O] | Method B m/z 368.2 (M + H)$^+$ RT 3.49 min | $^1$H NMR (400 MHz, DMSO) δ 8.35-8.32 (m, 1H), 8.22-8.19 (m, 1H), 7.97 (d, J = 2.2 Hz, 1H), 7.95-7.89 (m, 2H), 7.82-7.78 (m, 1H), 7.29 (td, J = 2.4, 12.6 Hz, 1H), 3.90-3.86 (m, 2H), 3.74 (s, 3H), 3.59-3.54 (m, 2H), 3.49-3.44 (m, 2H), 3.26-3.20 (m, 2H). |
| 39 | 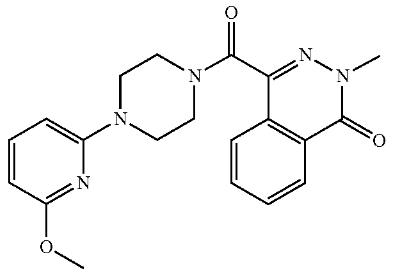 [SMILES: COc1cccc(N2CCN(C(=O)c3nn(C)c(=O)c4ccccc34)CC2)n1] | Method B m/z 380.2 (M + H)$^+$ RT 4.31 min | $^1$H NMR (400 MHz, DMSO) δ 8.35-8.32 (m, 1H), 7.97-7.89 (m, 2H), 7.82-7.78 (m, 1H), 7.47 (t, J = 8.0 Hz, 1H), 6.35 (d, J = 7.8 Hz, 1H), 6.08 (d, J = 7.8 Hz, 1H), 3.87-3.82 (m, 2H), 3.76 (s, 3H), 3.74 (s, 3H), 3.70-3.65 (m, 2H), 3.54-3.48 (m, 2H), 3.46-3.41 (m, 2H). |
| 40 | 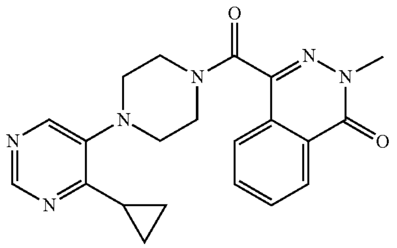 [SMILES: Cn1nc(C(=O)N2CCN(c3cncnc3C3CC3)CC2)c2ccccc2c1=O] | Method A m/z 391.3 (M + H)$^+$ RT 3.64 min | $^1$H NMR (400 MHz, DMSO) δ 8.67 (s, 1H), 8.36-8.32 (m, 2H), 7.99-7.89 (m, 2H), 7.82-7.79 (m, 1H), 3.97-3.92 (m, 2H), 3.74 (s, 3H), 3.63-3.58 (m, 2H), 3.23-3.17 (m, 2H), 3.00-2.95 (m, 2H), 2.45-2.38 (m, 1H), 1.12-1.04 (m, 4H). |
| 41 | 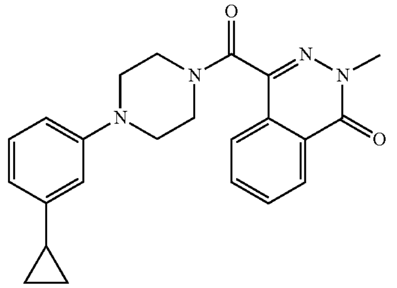 [SMILES: Cn1nc(C(=O)N2CCN(c3cccc(C4CC4)c3)CC2)c2ccccc2c1=O] | Method A m/z 389.3 (M + H)$^+$ RT .497 min | $^1$H NMR (400 MHz, DMSO) δ 8.35-8.32 (m, 1H), 7.97-7.89 (m, 2H), 7.80-7.76 (m, 1H), 7.09 (t, J = 7.8 Hz, 1H), 6.74-6.66 (m, 2H), 6.1 (d, J = 7.8 Hz, 1H), 3.90-3.85 (m, 2H), 3.74 (s, 3H), 3.52 (t, J = 4.9 Hz, 2H), 3.30-3.25 (m, 2H), 3.07-3.02 (m, 2H), 1.88-1.80 (m, 1H), 0.92-0.86 (m, 2H), 0.66-0.61 (m, 2H). |
| 42 | 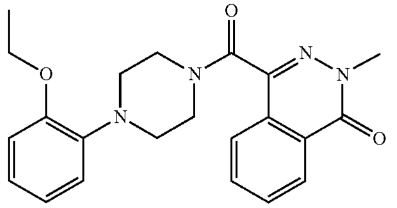 [SMILES: CCOc1ccccc1N1CCN(C(=O)c2nn(C)c(=O)c3ccccc23)CC1] | Method B m/z 4.57 (M + H)$^+$ RT 393.2 min | $^1$H NMR (400 MHz, DMSO) δ 8.35-8.31 (m, 1H), 7.99-7.89 (m, 2H), 7.80-7.76 (m, 1H), 6.96-6.86 (m, 4H), 4.02 (q, J = 7.0 Hz, 2H), 3.90-3.86 (m, 2H), 3.74 (s, 3H), 3.54-3.50 (m, 2H), 3.15-3.10 (m, 2H), 2.93-2.89 (m, 2H), 1.33 (t, J = 6.9 Hz, 3H). |

TABLE 4-continued

Structure and Spectroscopic Data for Compounds 35 to 60.

| Compound No. | Structure | LCMS data | NMR data |
|---|---|---|---|
| 43 | 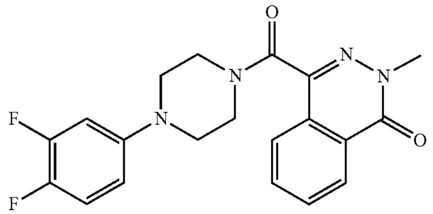 [SMILES: Cn1nc(C(=O)N2CCN(c3ccc(F)c(F)c3)CC2)c2ccccc2c1=O] | Method A m/z 385.2 $(M + H)^+$ RT 4.60 min | $^1H$ NMR (400 MHz, DMSO) δ 8.35-8.32 (m, 1H), 7.97-7.89 (m, 2H), 7.80-7.77 (m, 1H), 7.27 (dd, J = 9.3, 20.0 Hz, 1H), 7.04 (ddd, J = 2.9, 6.9, 14.1 Hz, 1H), 6.79-6.75 (m, 1H), 3.89-3.84 (m, 2H), 3.74 (s, 3H), 3.56-3.51 (m, 2H), 3.30-3.27 (m, 2H), 3.08-3.04 (m, 2H). |
| 44 | 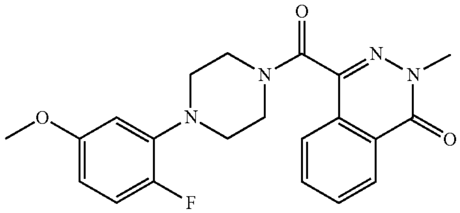 | Method B m/z 397.2 $(M + H)^+$ RT 4.42 min | $^1H$ NMR (400 MHz, DMSO) δ 8.35-8.32 (m, 1H), 7.98-7.89 (m, 2H), 7.81-7.77 (m, 1H), 7.06 (dd, J = 8.6, 12.4 Hz, 1H), 6.57-6.50 (m, 2H), 3.92-3.87 (m, 2H), 3.74 (s, 3H), 3.71 (s, 3H), 3.57-3.53 (m, 2H), 3.18-3.14 (m, 2H), 2.96-2.91 (m, 2H). |
| 45 | 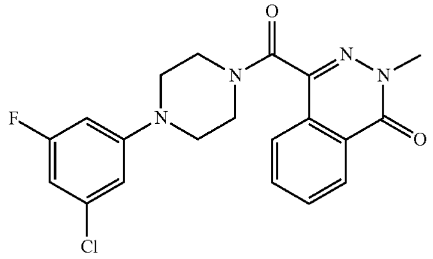 [SMILES: Cn1nc(C(=O)N2CCN(c3cc(F)cc(Cl)c3)CC2)c2ccccc2c1=O] | Method B m/z 401.2 $(M + H)^+$ RT 4.86 min | $^1H$ NMR (400 MHz, DMSO) δ 8.35-8.32 (m, 1H), 7.97-7.89 (m, 2H), 7.81-7.78 (m, 1H), 6.85-6.70 (m, 3H), 3.87-3.82 (m, 2H), 3.74 (s, 3H), 3.55-3.50 (m, 2H), 3.45-3.40 (m, 2H), 3.21-3.16 (m, 2H). |
| 46 | 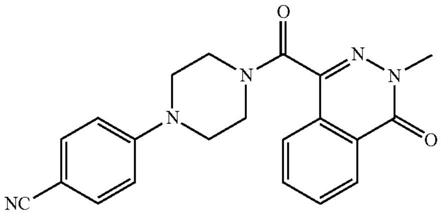 [SMILES: Cn1nc(C(=O)N2CCN(c3ccc(C#N)cc3)CC2)c2ccccc2c1=O] | Method A m/z 374.4 $(M + H)^+$ RT 4.05 min | $^1H$ NMR (400 MHz, DMSO) δ 8.35-8.32 (m, 1H), 7.97-7.89 (m, 2H), 7.83-7.79 (m, 1H), 7.63-7.59 (m, 2H), 7.07-7.01 (m, 2H), 3.89-3.84 (m, 2H), 3.74 (s, 3H), 3.58-3.53 (m, 4H). 2H obscured by solvent signal. |
| 47 | 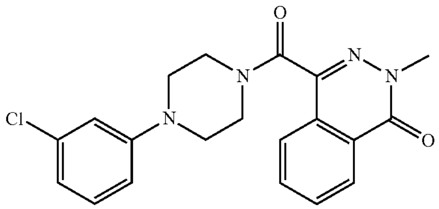 [SMILES: Cn1nc(C(=O)N2CCN(c3cccc(Cl)c3)CC2)c2ccccc2c1=O] | Method A m/z 383.5 $(M + H)^+$ RT 4.88 min | $^1H$ NMR (400 MHz, DMSO) δ 8.35-8.31 (m, 1H), 7.97-7.89 (m, 2H), 7.81-7.77 (m, 1H), 7.23 (t, J = 8.1 Hz, 1H), 6.99-6.96 (m, 1H), 6.92 (dd, J = 2.4, 8.5 Hz, 1H), 6.82 (dd, J = 1.3, 7.8 Hz, 1H), 3.89-3.84 (m, 2H), 3.74 (s, 3H), 3.56-3.51 (m, 2H), 3.39-3.34 (m, 2H), 3.15-3.10 (m, 2H). |

TABLE 4-continued

| Structure and Spectroscopic Data for Compounds 35 to 60. | | | |
|---|---|---|---|
| Compound No. | Structure | LCMS data | NMR data |
| 48 | 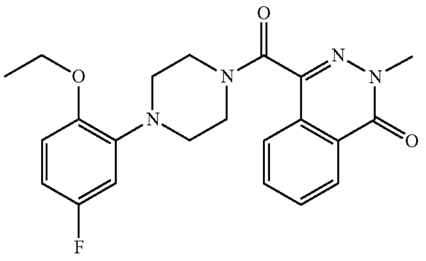 [SMILES: CCOc1ccc(F)cc1N1CCN(C(=O)c2nn(C)c(=O)c3ccccc23)CC1] | Method B m/z 411.2 (M + H)+ RT 4.68 min | 1H NMR (400 MHz, DMSO) δ 8.35-8.31 (m, 1H), 7.98-7.89 (m, 2H), 7.80-7.76 (m, 1H), 6.91 (dd, J = 5.6, 9.6 Hz, 1H), 6.75-6.70 (m, 2H), 3.99 (q, J = 6.9 Hz, 2H), 3.90-3.85 (m, 2H), 3.74 (s, 3H), 3.55-3.50 (m, 2H), 3.18-3.13 (m, 2H), 2.97-2.92 (m, 2H), 1.31 (t, J = 6.9 Hz, 3H). |
| 49 | 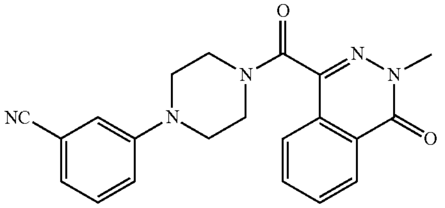 [SMILES: Cn1nc(C(=O)N2CCN(c3cccc(C#N)c3)CC2)c2ccccc2c1=O] | Method A m/z 374.5 (M + H)+ RT 4.17 min | 1H NMR (400 MHz, DMSO) δ 8.35-8.32 (m, 1H), 7.97-7.89 (m, 2H), 7.81-7.78 (m, 1H), 7.43-7.36 (m, 2H), 7.30 (dd, J = 2.1, 8.5 Hz, 1H), 7.20 (d, J = 7.6 Hz, 1H), 3.90-3.85 (m, 2H), 3.74 (s, 3H), 3.57-3.52 (m, 2H), 3.45-3.40 (m, 2H), 3.21-3.16 (m, 2H). |
| 50 | 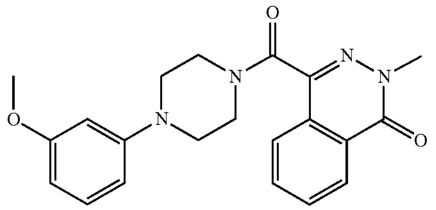 [SMILES: COc1cccc(N2CCN(C(=O)c3nn(C)c(=O)c4ccccc34)CC2)c1] | Method A m/z 379.6 (M + H)+ RT 4.30 min | 1H NMR (400 MHz, DMSO) δ 8.35-8.32 (m, 1H), 7.97-7.89 (m, 2H), 7.80-7.77 (m, 1H), 7.13 (t, J = 8.1 Hz, 1H), 6.54 (dd, J = 1.9, 8.0 Hz, 1H), 6.48 (t, J = 2.2 Hz, 1H), 6.43-6.39 (m, 1H), 3.89-3.85 (m, 2H), 3.74 (s, 3H), 3.71 (s, 3H), 3.55-3.50 (m, 2H), 3.09-3.04 (m, 2H). 2H obscured by solvent signal. |
| 51 | 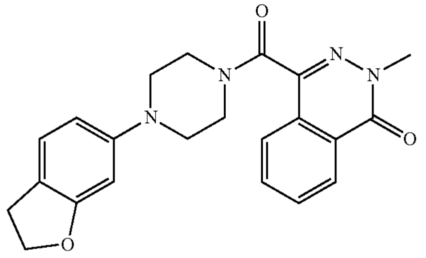 [SMILES: Cn1nc(C(=O)N2CCN(c3ccc4c(c3)OCC4)CC2)c2ccccc2c1=O] | Method A m/z 391.4 (M + H)+ RT 4.23 min | 1H NMR (400 MHz, DMSO) δ 8.35-8.31 (m, 1H), 7.97-7.89 (m, 2H), 7.79-7.76 (m, 1H), 7.06-7.03 (m, 1H), 6.43-6.39 (m, 2H), 4.47 (t, J = 8.6 Hz, 1H), 3.88-3.83 (m, 2H), 3.73 (s, 3H), 3.54-3.49 (m, 2H), 3.26-3.21 (m, 2H), 3.06 (t, J = 8.8 Hz, 2H), 3.02-2.97 (m, 2H). |
| 52 | 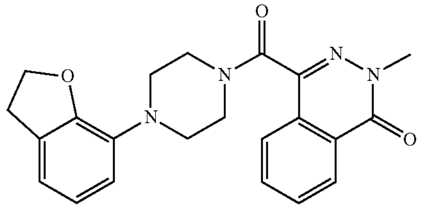 [SMILES: Cn1nc(C(=O)N2CCN(c3cccc4c3OCC4)CC2)c2ccccc2c1=O] | Method A m/z 391.2 (M + H)+ RT 4.40 min | 1H NMR (400 MHz, DMSO) δ 8.33 (dd, J = 1.3, 7.6 Hz, 1H), 7.98-7.89 (m, 2H), 7.80-7.76 (m, 1H), 6.86 (d, J = 6.6 Hz, 1H), 6.75 (t, J = 7.6 Hz, 1H), 6.66 (d, J = 7.6 Hz, 1H), 4.51 (t, J = 8.7 Hz, 2H), 3.89-3.85 (m, 2H), 3.74 (s, 3H), 3.55-3.50 (m, 2H), 3.20-3.11 (m, 4H), 2.98-2.93 (m, 2H). |

TABLE 4-continued

| Structure and Spectroscopic Data for Compounds 35 to 60. | | | |
|---|---|---|---|
| Compound No. | Structure | LCMS data | NMR data |
| 53 | 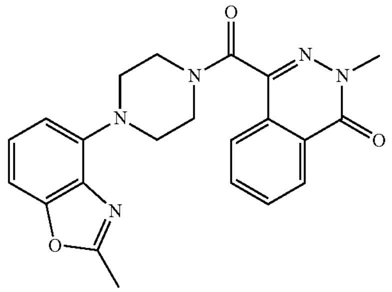 [SMILES: Cc1nc2c(N3CCN(C(=O)c4nn(C)c(=O)c5ccccc45)CC3)cccc2o1] | Method A m/z 404.2 (M + H)+ RT 3.88 min | $^1$H NMR (400 MHz, DMSO) δ 8.36-8.32 (m, 1H), 7.98-7.90 (m, 2H), 7.83-7.80 (m, 1H), 7.21-7.18 (m, 2H), 6.85-6.80 (m, 1H), 3.98-3.94 (m, 2H), 3.75 (s, 3H), 3.65-3.60 (m, 2H), 3.47-3.43 (m, 2H), 3.24-3.19 (m, 2H), 2.59 (s, 3H). |
| 54 | 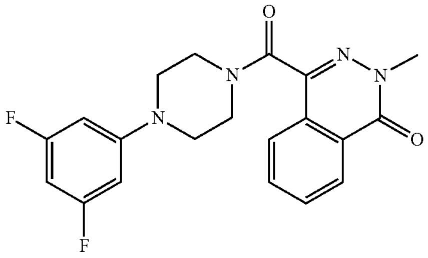 | Method F m/z F (M + H)+ RT 1.75 min | $^1$H NMR (400 MHz, DMSO) δ 8.36-8.30 (m, 1H), 7.97-7.88 (m, 2H), 7.84-7.76 (m, 1H), 6.71-6.60 (m, 2H), 6.56-6.47 (m, 1H), 3.88-3.82 (m, 2H), 3.74 (s, 3H), 3.52 (t, J = 5.2 Hz, 2H), 3.42 (dd, J = 6.4, 4.2 Hz, 2H), 3.18 (t, J = 5.2 Hz, 2H). 19F NMR (376 MHz, DMSO) |
| 55 | 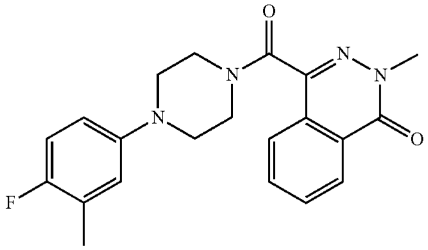 [SMILES: Cc1cc(N2CCN(C(=O)c3nn(C)c(=O)c4ccccc34)CC2)ccc1F] | Method F m/z 381.3 (M + H)+ RT 1.77 min | $^1$H NMR (400 MHz, DMSO) δ 8.37-8.29 (m, 1H), 7.93 (pd, J = 7.2, 1.6 Hz, 2H), 7.80-7.75 (m, 1H), 6.99 (t, J = 9.2 Hz, 1H), 6.88 (dd, J = 6.8, 3.0 Hz, 1H), 6.78 (dt, J = 8.9, 3.7 Hz, 1H), 3.90-3.84 (m, 2H), 3.74 (s, 3H), 3.53 (dd, J = 6.2, 4.0 Hz, 2H), 3.22 (dd, J = 6.2, 4.2 Hz, 2H), 3.02-2.94 (m, 2H), 2.18 (d, J = 2.0 Hz, 3H). 19F NMR (376 MHz, DMSO) δ −128.84 (dddd, J = 9.3, 6.5, 4.2 2.1 Hz). |
| 56 | 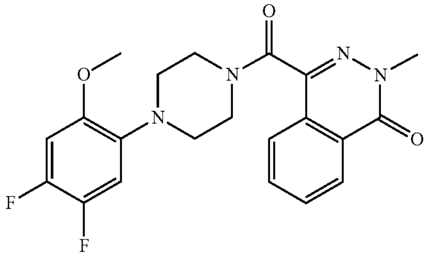 [SMILES: COc1cc(F)c(F)cc1N1CCN(C(=O)c2nn(C)c(=O)c3ccccc23)CC1] | Method F m/z 415.3 (M + H)+ RT 1.71 min | $^1$H NMR (400 MHz, DMSO) δ 8.36-8.30 (m, 1H), 7.99-7.89 (m, 2H), 7.80-7.75 (m, 1H), 7.10 (dd, J = 12.8, 7.9 Hz, 1H), 6.98 (dd, J = 12.6, 8.6 Hz, 1H), 3.86 (dd, J = 6.3, 3.9 Hz, 2H), 3.78 (s, 3H), 3.74 (s, 3H), 3.55-3.48 (m, 2H), 3.07 (t, J = 5.1 Hz, 2H), 2.85 (t, J = 5.0 Hz, 2H). 19F NMR (376 MHz, DMSO) δ −144.68 (ddd, J = 24.0, 12.7, 8.6 Hz), −147.99 (ddd, J = 24.1, 12.6, 7.8 Hz). |

TABLE 4-continued

| Structure and Spectroscopic Data for Compounds 35 to 60. | | | |
|---|---|---|---|
| Compound No. | Structure | LCMS data | NMR data |
| 57 | 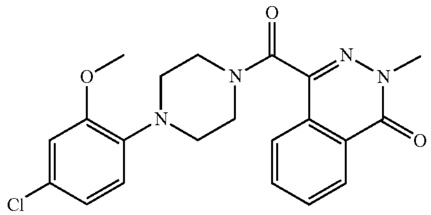 [SMILES: COc1cc(Cl)ccc1N1CCN(C(=O)c2nn(C)c(=O)c3ccccc23)CC1] | Method F m/z 413.3 $(M + H)^+$ RT 1.79 min | $^1H$ NMR (400 MHz, DMSO) δ 8.35-8.30 (m, 1H), 7.99-7.88 (m, 2H), 7.81-7.76 (m, 1H), 7.00 (d, J = 2.1 Hz, 1H), 6.95-6.86 (m, 2H), 3.90-3.83 (m, 2H), 3.80 (s, 3H), 3.73 (s, 3H), 3.55-3.49 (m, 2H), 3.08 (t, J = 5.1 Hz, 2H), 2.86 (t, J = 5.0 Hz, 2H). |
| 58 | 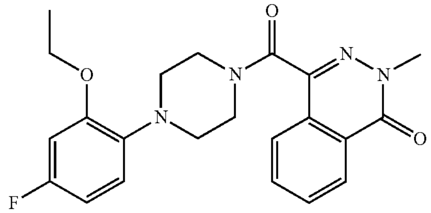 [SMILES: CCOc1cc(F)ccc1N1CCN(C(=O)c2nn(C)c(=O)c3ccccc23)CC1] | Method F m/z 411.3 $(M + H)^+$ RT 1.78 min | $^1H$ NMR (400 MHz, DMSO) δ 8.35-8.31 (m, 1H), 7.99-7.89 (m, 2H), 7.80-7.75 (m, 1H), 6.86 (ddd, J = 16.7, 9.9, 4.5 Hz, 2H), 6.66 (td, J = 8.5, 2.8 Hz, 1H), 4.02 (q, J = 6.9 Hz, 2H), 3.87 (t, J = 5.0 Hz, 2H), 3.73 (s, 3H), 3.54-3.47 (m, 2H), 3.07 (t, J = 5.0 Hz, 2H), 2.85 (t, J = 4.9 Hz, 2H), 1.33 (t, J = 7.0 Hz, 3H). 19F NMR (376 MHz, DMSO) δ −118.66 (ddd, J = 10.9, 8.2, 6.2 Hz). |
| 59 | 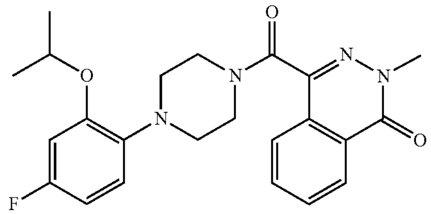 [SMILES: CC(C)Oc1cc(F)ccc1N1CCN(C(=O)c2nn(C)c(=O)c3ccccc23)CC1] | Method F m/z 425.4 $(M + H)^+$ RT 1.93 min | $^1H$ NMR (400 MHz, DMSO) δ 8.36-8.30 (m, 1H), 7.99-7.89 (m, 2H), 7.80-7.74 (m, 1H), 6.87 (ddd, J = 16.1, 9.9, 4.6 Hz, 2H), 6.66 (td, J = 8.5, 2.8 Hz, 1H), 4.63 (hept, J = 6.1 Hz, 1H), 3.87 (t, J = 5.0 Hz, 2H), 3.73 (s, 3H), 3.50 (t, J = 4.9 Hz, 2H), 3.06 (t, J = 5.1 Hz, 2H), 2.85 (t, J = 4.9 Hz, 2H), 1.26 (d, J = 6.0 Hz, 6H). 19F NMR (376 MHz, DMSO) δ −118.78 (ddd, J = 10.9, 8.1, 6.2 Hz). |
| 60 | 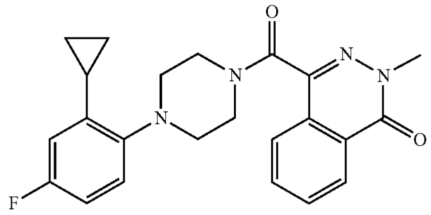 [SMILES: Cn1nc(C(=O)N2CCN(c3ccc(F)cc3C3CC3)CC2)c2ccccc2c1=O] | Method F m/z 407.4 $(M + H)^+$ RT 2.01 min | $^1H$ NMR (400 MHz, DMSO) δ 8.29 (ddd, J = 7.7, 1.6, 0.6 Hz, 1H), 7.97-7.85 (m, 2H), 7.75 (ddd, J = 7.8, 1.5, 0.6 Hz, 1H), 7.02 (dd, J = 8.8, 5.5 Hz, 1H), 6.86 (td, J = 8.5, 3.0 Hz, 1H), 6.56 (dd, J = 10.5, 3.0 Hz, 1H), 3.87 (s, 2H), 3.70 (s, 3H), 3.51 (t, J = 4.9 Hz, 2H), 3.00 (t, J = 5.0 Hz, 2H), 2.78 (t, J = 4.8 Hz, 2H), 2.27 (ddt, J = 12.3, 8.7, 3.8 Hz, 1H), 0.98-0.90 (m, 2H), 0.70-0.62 (m, 2H). 19F NMR (376 MHz, DMSO) δ −119.15 (dddd, J = 10.1, 8.1, 5.4, 1.6 Hz) |

Example 7: Synthesis of 3-fluoro-5-(4-(3-methyl-4-oxo-3,4-dihydrophthalazine-1-carbonyl)piperazin-1-yl)benzonitrile (Compound 61)

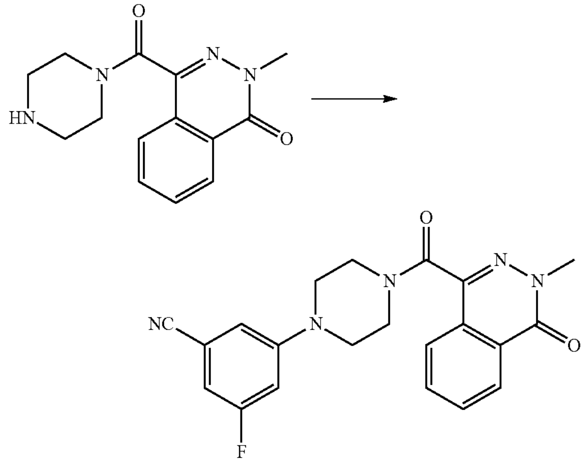

2-methyl-4-(piperazine-1-carbonyl)phthalazin-1-one (70 mg, 0.257 mmol, 1 equiv.), 3-bromo-5-fluoro-benzonitrile (77 mg, 0.386 mmol, 1.5 equiv.), DavePhos PdG3 (20 mg, 0.0257 mmol, 0.1 equiv.) and sodium tert-butoxide (37 mg, 0.386 mmol, 1.5 equiv.) were suspended in CPME (2 mL) in a vial. The vial was sealed, evacuated and flushed with nitrogen twice. The solution was stirred at 110° C. for 3 hrs, then allowed to rt. The mixture was partitioned between dichloromethane and water and the phases separated. The organics were collected, and the solvent removed. The material was purified by reverse phase HPLC (Xbridge C18 19×150 mm, 10 μm 20-80% $MeCN/H_2O$+10 mM $NH_4CO_3$, 20 mL/min, rt) and the appropriate fractions were combined and lyophilized to yield the title compound (17 mg, 17%) as an off white solid. LCMS: Method A, m/z 392.3 $(M+H)^+$, RT 4.33 min. $^1$H NMR (400 MHz, DMSO) δ 8.35-8.32 (m, 1H), 7.96-7.89 (m, 2H), 7.81-7.78 (m, 1H), 7.26 (s, 1H), 7.18-7.09 (m, 2H), 3.85 (dd, J=5.2, 5.2 Hz, 2H), 3.74 (s, 3H), 3.54 (t, J=5.1 Hz, 2H), 3.49 (t, J=5.2 Hz, 2H), 3.24 (t, J=5.2 Hz, 2H).

The compounds in Table 5 were made according to the method described in Example 7, using Intermediate 1 and the appropriate aryl halide reagent:

TABLE 5

Structure and Spectroscopic Data for Compounds 62 to 80 and 191 to 206.

| Compound No. | Structure | LCMS data | NMR data |
|---|---|---|---|
| 62 | 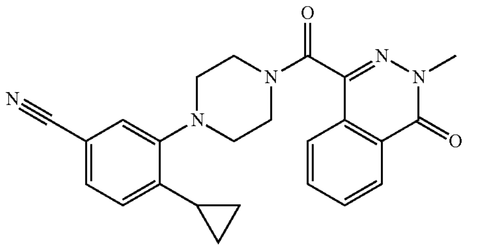 [SMILES: Cn1nc(C(=O)N2CCN(c3cc(C#N)ccc3C3CC3)CC2)c2ccccc2c1=O] | Method A m/z 414.2 $(M + H)^+$ RT 4.91 min | $^1$H NMR (400 MHz, DMSO) δ 8.35-8.32 (m, 1H), 8.00-7.90 (m, 2H), 7.82-7.79 (m, 1H), 7.44-7.39 (m, 2H), 6.95 (d, J = 8.1 Hz, 1H), 3.96-3.90 (m, 2H), 3.74 (s, 3H), 3.60-3.55 (m, 2H), 3.16-3.11 (m, 2H), 2.94-2.89 (m, 2H), 2.35-2.26 (m, 1H), 1.12-1.05 (m, 2H), 0.82-0.76 (m, 2H). |
| 63 | 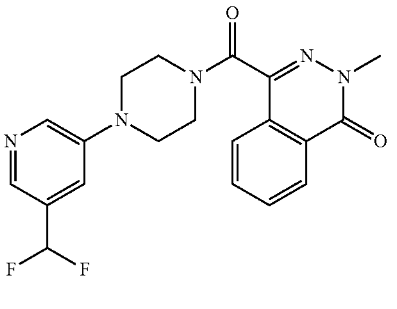 [SMILES: Cn1nc(C(=O)N2CCN(c3cncc(C(F)F)c3)CC2)c2ccccc2c1=O] | Method A m/z 400.2 $(M + H)^+$ RT 3.24 min | $^1$H NMR (400 MHz, DMSO) δ 8.49 (d, J = 2.8 Hz, 1H), 8.35-8.32 (m, 1H), 8.20 (d, J = 1.3 Hz, 1H), 7.95-7.90 (m, 2H), 7.82-7.79 (m, 1H), 7.49 (s, 1H), 7.05 (t, J = 55.2 Hz, 1H), 3.92-3.88 (m, 2H), 3.74 (s, 3H), 3.60-3.55 (m, 2H), 3.50-3.45 (m, 2H), 3.26-3.21 (m, 2H). |
| 64 | 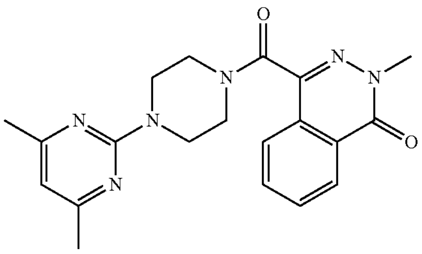 | Method B m/z 379.2 $(M + H)^+$ RT 4.30 min | $^1$H NMR (400 MHz, DMSO) δ 8.41-8.38 (m, 1H), 8.03-7.95 (m, 2H), 7.87-7.84 (m, 1H), 6.51 (s, 1H), 3.98-3.94 (m, 2H), 3.88-3.83 (m, 2H), 3.80 (s, 3H), 3.76-3.71 (m, 2H), 3.55-3.50 (m, 2H), 2.29 (s, 6H). |

TABLE 5-continued

Structure and Spectroscopic Data for Compounds 62 to 80 and 191 to 206.

| Compound No. | Structure | LCMS data | NMR data |
|---|---|---|---|
| 65 | 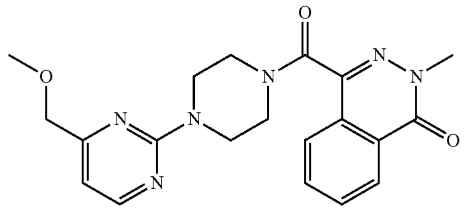 | Method A m/z 395.2 $(M + H)^+$ RT 3.71 min | $^1H$ NMR (400 MHz, DMSO) δ 8.44 (d, J = 4.2 Hz, 1H), 8.41-8.38 (m, 1H), 8.03-7.95 (m, 2H), 7.87-7.84 (m, 1H), 6.75 (d, J = 4.8 Hz, 1H), 4.37 (s, 2H), 3.99-3.95 (m, 2H), 3.89-3.85 (m, 2H), 3.80 (s, 3H), 3.76-3.72 (m, 2H), 3.57-3.52 (m, 2H), 3.41 (s, 3H). |
| 66 | 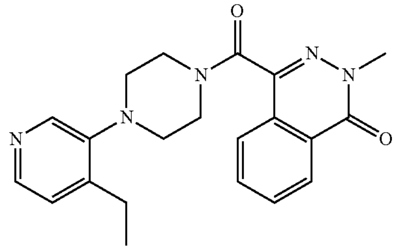 [SMILES: CCc1ccncc1N1CCN(C(=O)c2nn(C)c(=O)c3ccccc23)CC1] | Method B m/z 378.2 $(M + H)^+$ RT 3.86 min | $^1H$ NMR (400 MHz, DMSO) δ 8.35-8.32 (m, 1H), 8.30 (s, 1H), 8.24 (d, J = 5.1 Hz, 1H), 8.00-7.90 (m, 2H), 7.83-7.80 (m, 1H), 7.24 (d, J = 5.1 Hz, 1H), 3.92-3.87 (m, 2H), 3.74 (s, 3H), 3.57-3.52 (m, 2H), 3.10-3.05 (m, 2H), 2.87-2.83 (m, 2H), 2.68 (q, J = 7.6 Hz, 2H), 1.20 (t, J = 7.6 Hz, 3H). |
| 67 | 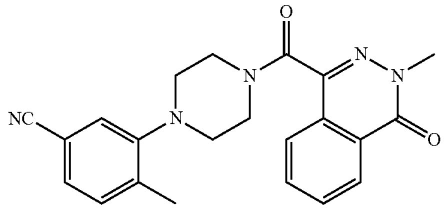 [SMILES: Cc1ccc(C#N)cc1N1CCN(C(=O)c2nn(C)c(=O)c3ccccc23)CC1] | Method A m/z 388.2 $(M + H)^+$ RT 4.46 min | $^1H$ NMR (400 MHz, DMSO) δ 8.36-8.32 (m, 1H), 8.00-7.90 (m, 2H), 7.82-7.80 (m, 1H), 7.46-7.37 (m, 3H), 3.93-3.88 (m, 2H), 3.75 (s, 3H), 3.57-3.52 (m, 2H), 3.06-3.01 (m, 2H), 2.84-2.80 (m, 2H), 2.35 (s, 3H). |
| 68 | 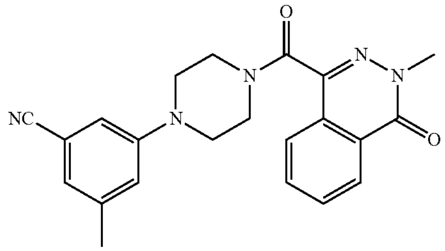 [SMILES: Cc1cc(C#N)cc(N2CCN(C(=O)c3nn(C)c(=O)c4ccccc34)CC2)c1] | Method A m/z 388.2 $(M + H)^+$ RT 4.41 min | $^1H$ NMR (400 MHz, DMSO) δ 8.35-8.32 (m, 1H), 7.97-7.89 (m, 2H), 7.81-7.77 (m, 1H), 7.18 (s, 1H), 7.13 (s, 1H), 7.03 (s, 1H), 3.89-3.84 (m, 2H), 3.74 (s, 3H), 3.56-3.51 (m, 2H), 3.43-3.38 (m, 2H), 3.19-3.14 (m, 2H), 2.29 (s, 3H). |
| 69 | 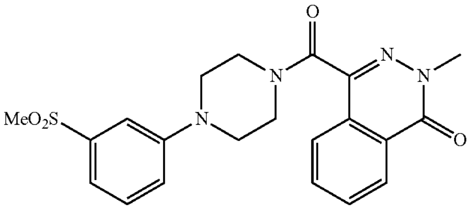 [SMILES: Cn1nc(C(=O)N2CCN(c3cccc(S(C)(=O)=O)c3)CC2)c2ccccc2c1=O] | Method B m/z 427.3 $(M + H)^+$ RT 3.56 min | $^1H$ NMR (400 MHz, DMSO) δ 8.36-8.32 (m, 1H), 7.97-7.90 (m, 2H), 7.82-7.79 (m, 1H), 7.48 (t, J = 8.0 Hz, 1H), 7.40-7.38 (m, 1H), 7.33-7.28 (m, 2H), 3.93-3.88 (m, 2H), 3.74 (s, 3H), 3.60-3.55 (m, 2H), 3.48-3.43 (m, 2H), 3.23-3.20 (m, 2H), 3.19 (s, 3H). |
| 70 | 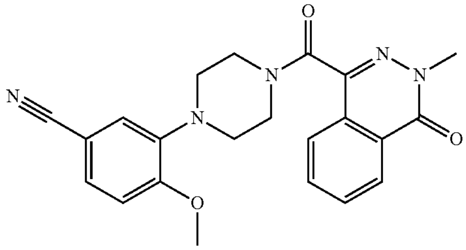 [SMILES: COc1ccc(C#N)cc1N1CCN(C(=O)c2nn(C)c(=O)c3ccccc23)CC1] | Method C m/z404.2 $(M + H)^+$ RT 3.80 min | $^1H$ NMR (400 MHz, DMSO) δ 8.35-8.32 (m, 1H), 7.99-7.90 (m, 2H), 7.81-7.77 (m, 1H), 7.49 (dd, J = 2.0, 8.4 Hz, 1H), 7.28 (d, J = 2.0 Hz, 1H), 7.12 (d, J = 8.5 Hz, 1H), 3.91-3.85 (m, 5H), 3.74 (s, 3H), 3.56-3.51 (m, 2H), 3.17-3.12 (m, 2H), 2.96-2.91 (m, 2H). |

TABLE 5-continued

| Structure and Spectroscopic Data for Compounds 62 to 80 and 191 to 206. | | | |
|---|---|---|---|
| Compound No. | Structure | LCMS data | NMR data |
| 71 | 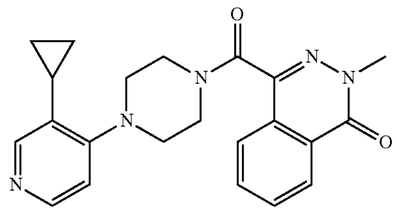 [SMILES: Cn1nc(C(=O)N2CCN(c3ccncc3C3CC3)CC2)c2ccccc2c1=O] | Method B m/z 390.2 $(M + H)^+$ RT 3.70 min | $^1$H NMR (400 MHz, DMSO) δ 8.35-8.32 (m, 1H), 8.22 (d, J = 5.3 Hz, 1H), 8.02 (s, 1H), 7.99-7.90 (m, 2H), 7.82-7.79 (m, 1H), 6.89 (d, J = 5.6 Hz, 1H), 3.96-3.91 (m, 2H), 3.74 (s, 3H), 3.61-3.56 (m, 2H), 3.29-3.24 (m, 2H), 3.07-3.02 (m, 2H), 2.01-1.93 (m, 1H), 1.03-0.97 (m, 2H), 0.82-0.76 (m, 2H). |
| 72 | 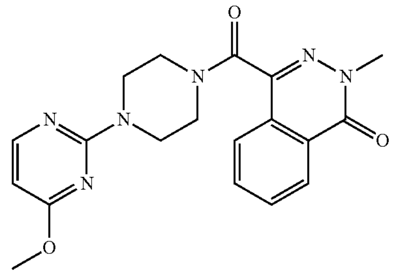 [SMILES: COc1ccnc(N2CCN(C(=O)c3nn(C)c(=O)c4ccccc34)CC2)n1] | Method A m/z 381.2 $(M + H)^+$ RT 3.13 min | $^1$H NMR (400 MHz, DMSO) δ 8.35-8.32 (m, 1H), 8.11 (d, J = 5.6 Hz, 1H), 7.97-7.89 (m, 2H), 7.82-7.79 (m, 1H), 6.12 (d, J = 5.6 Hz, 1H), 3.94-3.90 (m, 2H), 3.84-3.79 (m, 5H), 3.74 (s, 3H), 3.71-3.66 (m, 2H), 3.51-3.46 (m, 2H). |
| 73 | 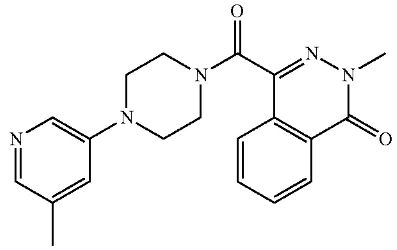 [SMILES: Cc1cncc(N2CCN(C(=O)c3nn(C)c(=O)c4ccccc34)CC2)c1] | Method A m/z 364.5 $(M + H)^+$ RT 2.42 min | $^1$H NMR (400 MHz, DMSO) δ 8.35-8.32 (m, 1H), 8.12 (d, J = 2.8 Hz, 1H), 7.97-7.89 (m, 2H), 7.89-7.87 (m, 1H), 7.81-7.77 (m, 1H), 7.18 (s, 1H), 3.91-3.86 (m, 2H), 3.74 (s, 3H), 3.57-3.53 (m, 2H), 3.39-3.35 (m, 2H), 3.15-3.10 (m, 2H), 2.24 (s, 3H). |
| 74 | 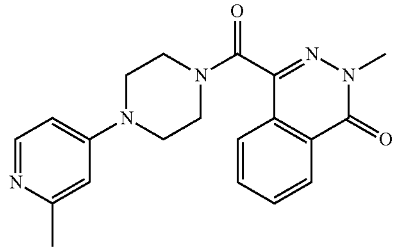 [SMILES: Cc1cc(N2CCN(C(=O)c3nn(C)c(=O)c4ccccc34)CC2)ccn1] | Method A m/z 364.2 $(M + H)^+$ RT 2.31 min | $^1$H NMR (400 MHz, DMSO) δ 8.35-8.32 (m, 1H), 8.06 (d, J = 5.8 Hz, 1H), 7.97-7.89 (m, 2H), 7.82-7.79 (m, 1H), 6.72 (d, J = 2.3 Hz, 1H), 6.66 (dd, J = 2.7, 5.8 Hz, 1H), 3.87-3.82 (m, 2H), 3.74 (s, 3H), 3.55-3.50 (m, 4H), 2.33 (s, 3H). 2H obscured by solvent signal |
| 75 | 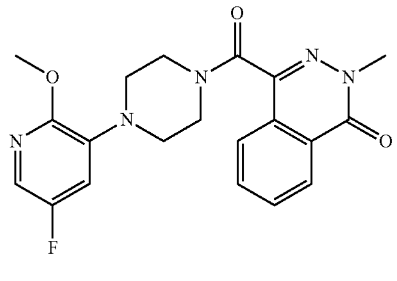 [SMILES: COc1ncc(F)cc1N1CCN(C(=O)c2nn(C)c(=O)c3ccccc23)CC1] | Method C m/z 398.3 $(M + H)^+$ RT 3.99 min | $^1$H NMR (400 MHz, CDCl3) δ 8.51-8.47 (m, 1H), 7.86-7.78 (m, 3H), 7.68 (d, J = 2.6 Hz, 1H), 6.88 (dd, J = 2.6, 9.4 Hz, 1H), 4.10-4.06 (m, 2H), 3.98 (s, 3H), 3.87 (s, 3H), 3.66-3.62 (m, 2H), 3.26-3.22 (m, 2H), 3.10-3.06 (m, 2H). |

TABLE 5-continued

| Structure and Spectroscopic Data for Compounds 62 to 80 and 191 to 206. | | | |
|---|---|---|---|
| Compound No. | Structure | LCMS data | NMR data |
| 76 | 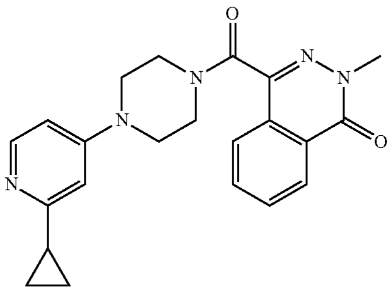 [SMILES: Cn1nc(C(=O)N2CCN(c3ccnc(C4CC4)c3)CC2)c2ccccc2c1=O] | Method A m/z 390.2 $(M + H)^+$ RT 2.60 min | $^1H$ NMR (400 MHz, DMSO) δ 8.35-8.32 (m, 1H), 8.01 (d, J = 5.8 Hz, 1H), 7.97-7.89 (m, 2H), 7.82-7.79 (m, 1H), 6.77 (d, J = 2.5 Hz, 1H), 6.60 (dd, J = 2.7, 5.9 Hz, 1H), 3.87-3.82 (m, 2H), 3.74 (s, 3H), 3.55-3.50 (m, 4H), 1.96-1.89 (m, 1H), 0.87-0.79 (m, 4H). 2H obscured by solvent signal |
| 77 | 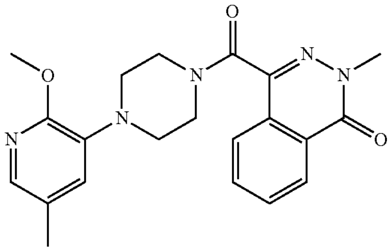 [SMILES: COc1ncc(C)cc1N1CCN(C(=O)c2nn(C)c(=O)c3ccccc23)CC1] | Method A m/z 394.2 $(M + H)^+$ RT 3.94 min | $^1H$ NMR (400 MHz, DMSO) δ 8.35-8.32 (m, 1H), 7.99-7.89 (m, 2H), 7.80-7.77 (m, 1H), 7.60-7.57 (m, 1H), 7.06 (d, J = 1.8 Hz, 1H), 3.91-3.85 (m, 2H), 3.84 (s, 3H), 3.74 (s, 3H), 3.56-3.51 (m, 2H), 3.17-3.11 (m, 2H), 2.94-2.89 (m, 2H), 2.18 (s, 3H). |
| 78 | 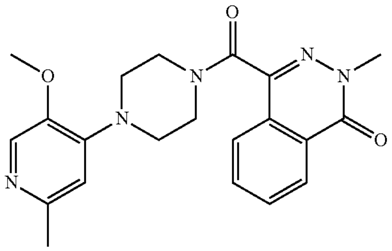 [SMILES: COc1cnc(C)cc1N1CCN(C(=O)c2nn(C)c(=O)c3ccccc23)CC1] | Method B m/z 394.2 $(M + H)^+$ RT 3.40 min | $^1H$ NMR (400 MHz, DMSO) δ 8.35-8.32 (m, 1H), 7.98-7.90 (m, 3H), 7.81-7.77 (m, 1H), 6.70 (s, 1H), 3.89-3.85 (m, 2H), 3.82 (s, 3H), 3.74 (s, 3H), 3.55-3.51 (m, 2H), 3.30-3.26 (m, 2H), 3.08-3.04 (m, 2H), 2.33 (s, 3H). |
| 79 | 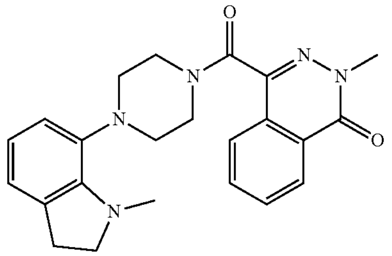 [SMILES: CN1CCc2cccc(N3CCN(C(=O)c4nn(C)c(=O)c5ccccc45)CC3)c21] | Method A m/z 404.2 $(M + H)^+$ RT 3.23 min | $^1H$ NMR (400 MHz, DMSO) δ 8.35-8.32 (m, 1H), 7.99-7.89 (m, 2H), 7.80-7.77 (m, 1H), 6.80 (d, J = 7.1 Hz, 1H), 6.74 (d, J = 7.3 Hz, 1H), 6.65 (t, J = 7.5 Hz, 1H), 3.94-3.88 (m, 2H), 3.74 (s, 3H), 3.58-3.53 (m, 2H), 3.25 (t, J = 7.9 Hz, 2H), 3.01-2.96 (m, 2H), 2.91 (s, 3H), 2.85 (t, J = 7.9 Hz, 2H), 2.81-2.76 (m, 2H). |
| 80 | 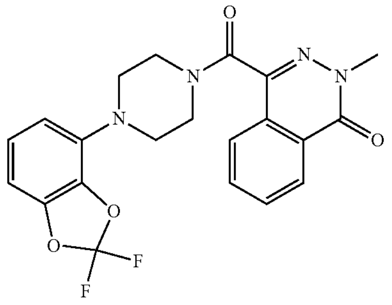 [SMILES: Cn1nc(C(=O)N2CCN(c3cccc4c3OC(F)(F)O4)CC2)c2ccccc2c1=O] | Method C m/z 429.3 $(M + H)^+$ RT 4.88 min | $^1H$ NMR (400 MHz, DMSO) δ 8.35-8.32 (m, 1H), 7.98-7.89 (m, 2H), 7.82-7.79 (m, 1H), 7.11 (t, J = 8.3 Hz, 1H), 6.94 (dd, J = 0.8, 8.1 Hz, 1H), 6.81 (dd, J = 0.8, 8.5 Hz, 1H), 3.93-3.89 (m, 2H), 3.74 (s, 3H), 3.61-3.56 (m, 2H), 3.15-3.10 (m, 2H). 2H obscured by solvent signal. |

TABLE 5-continued

Structure and Spectroscopic Data for Compounds 62 to 80 and 191 to 206.

| Compound No. | Structure | LCMS data | NMR data |
|---|---|---|---|
| 191 | 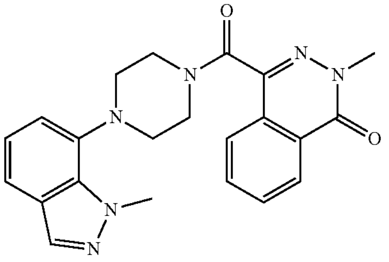 [SMILES: Cn1nc(C(=O)N2CCN(c3cccc4cnn(C)c34)CC2)c2ccccc2c1=O] | Method A m/z = 403.5 $(M + H)^+$ RT = 4.13 min | $^1H$ NMR (400 MHz, DMSO) δ 8.34 (d, J = 8.2 Hz, 1H), 8.02-7.93 (m, 3H), 7.84-7.82 (m, 1H), 7.47 (d, J = 7.6 Hz, 1H), 7.09-7.02 (m, 2H), 4.69 (bs, 1H), 4.32 (s, 3H), 3.76-3.75 (m, 4H), 3.50 (bs, 2H), 3.12 (bs, 2H), 2.94 (bs, 1H), 2.74 (bs, 1H). |
| 192 | 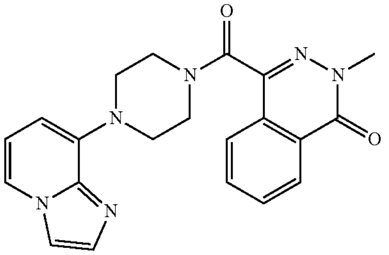 [SMILES: Cn1nc(C(=O)N2CCN(c3cccn4ccnc34)CC2)c2ccccc2c1=O] | Method A m/z = 389.5 $(M + H)^+$ RT = 2.30 min | $^1H$ NMR (400 MHz, DMSO) δ 8.36-8.33 (m, 1H), 8.15 (d, J = 6.5 Hz, 1H), 7.97-7.88 (m, 3H), 7.83-7.81 (m, 1H), 7.48 (s, 1H), 6.76 (dd, J = 7.1, 7.1 Hz, 1H), 6.48 (d, J = 7.5 Hz, 1H), 3.96 (t, J = 5.0 Hz, 2H), 3.75 (s, 3H), 3.70 (t, J = 4.9 Hz, 2H), 3.63 (t, J = 5.3 Hz, 2H), 3.42 (t, J = 4.9 Hz, 2H). |
| 193 | 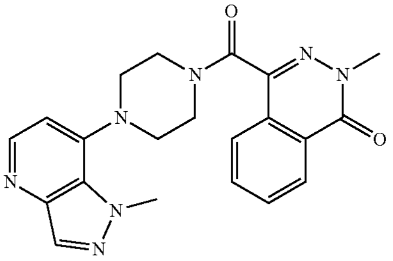 [SMILES: Cn1nc(C(=O)N2CCN(c3ccnc4cnn(C)c34)CC2)c2ccccc2c1=O] | Method A m/z = 404.5 $(M + H)^+$ RT = 2.35 min | $^1H$ NMR (400 MHz, DMSO) δ 8.36-8.33 (m, 2H), 8.20-8.20 (m, 1H), 8.00-7.91 (m, 2H), 7.85-7.82 (m, 1H), 6.94 (d, J = 5.0 Hz, 1H), 4.24 (s, 3H), 4.06-4.02 (m, 2H), 3.75 (s, 3H), 3.69 (t, J = 4.8 Hz, 2H), 3.30-3.26 (m, 2H), 3.05 (t, J = 4.8 Hz, 2H). |
| 194 | 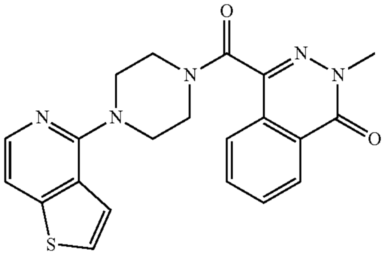 [SMILES: Cn1nc(C(=O)N2CCN(c3nccc4sccc34)CC2)c2ccccc2c1=O] | Method A m/z = 406.6 $(M + H)^+$ RT = 2.75 min | $^1H$ NMR (400 MHz, DMSO) δ 8.36-8.33 (m, 1H), 8.05-7.92 (m, 3H), 7.84-7.78 (m, 2H), 7.59 (d, J = 5.5 Hz, 2H), 3.98 (t, J = 5.1 Hz, 2H), 3.75 (s, 3H), 3.65-3.59 (m, 4H), 3.39 (d, J = 5.9 Hz, 2H). |
| 195 | 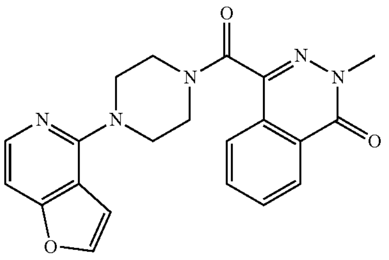 [SMILES: Cn1nc(C(=O)N2CCN(c3nccc4occc34)CC2)c2ccccc2c1=O] | Method A m/z = 390.5 $(M + H)^+$ RT = 2.45 min | $^1H$ NMR (400 MHz, DMSO) □ 8.35 (dd, J = 2.3, 6.9 Hz, 1H), 8.01-7.92 (m, 4H), 7.82 (dd, J = 2.1, 6.9 Hz, 1H), 7.19 (d, J = 1.5 Hz, 1H), 7.10 (d, J = 5.8 Hz, 1H), 3.95-3.90 (m, 2H), 3.85-3.80 (m, 2H), 3.75 (s, 3H), 3.61-3.56 (m, 4H). |

TABLE 5-continued

| Structure and Spectroscopic Data for Compounds 62 to 80 and 191 to 206. | | | |
|---|---|---|---|
| Compound No. | Structure | LCMS data | NMR data |
| 196 | 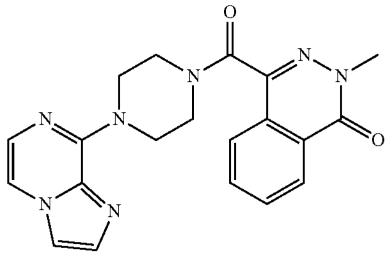 [SMILES: Cn1nc(C(=O)N2CCN(c3nccn4ccnc34)CC2)c2ccccc2c1=O] | Method A m/z = 390.7 $(M + H)^+$ RT = 2.76 min | $^1H$ NMR (400 MHz, DMSO) δ 8.36-8.33 (m, 1H), 7.98-7.93 (m, 4H), 7.84-7.80 (m, 1H), 7.57 (d, J = 0.9 Hz, 1H), 7.36 (d, J = 4.4 Hz, 1H), 4.42-4.37 (m, 2H), 4.14 (t, J = 4.7 Hz, 2H), 3.90 (t, J = 5.2 Hz, 2H), 3.75 (s, 3H), 3.57 (t, J = 5.1 Hz, 2H). |
| 197 | 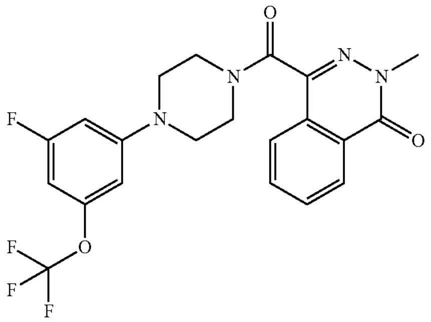 [SMILES: Cn1nc(C(=O)N2CCN(c3cc(F)cc(OC(F)(F)F)c3)CC2)c2ccccc2c1=O] | Method A m/z = 451.5 $(M + H)^+$ RT = 5.22 min | $^1H$ NMR (400 MHz, DMSO) δ 8.35-8.32 (m, 1H), 7.97-7.89 (m, 2H), 7.82-7.79 (m, 1H), 6.88-6.83 (m, 1H), 6.76 (s, 1H), 6.68-6.64 (m, 1H), 3.86 (t, J = 5.2 Hz, 2H), 3.74 (s, 3H), 3.53 (t, J = 5.0 Hz, 2H), 3.45 (t, J = 5.0 Hz, 2H), 3.20 (t, J = 5.1 Hz, 2H). |
| 198 | 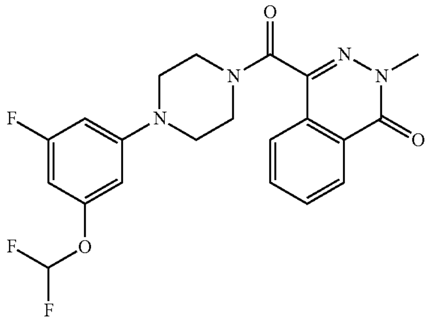 [SMILES: Cn1nc(C(=O)N2CCN(c3cc(F)cc(OC(F)F)c3)CC2)c2ccccc2c1=O] | Method A m/z = 433.3 $(M + H)^+$ RT = 4.74 min | $^1H$ NMR (400 MHz, DMSO) δ 8.35-8.32 (m, 1H), 7.96-7.90 (m, 2H), 7.81-7.79 (m, 1H), 7.26 (t, J = 74.1 Hz, 1H), 6.71-6.44 (m, 3H), 3.85 (t, J = 4.3 Hz, 2H), 3.74 (s, 3H), 3.53 (t, J = 5.0 Hz, 2H) 3.42 (t, J = 5.0 Hz, 2H) 3.17 (t, J = 5.0 Hz, 2H). |
| 199 | 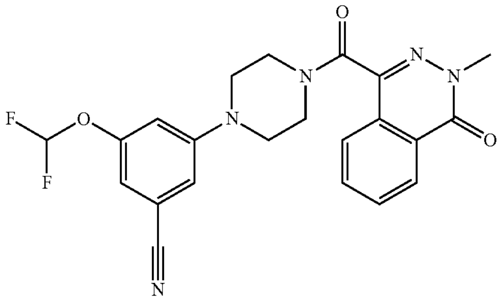 [SMILES: Cn1nc(C(=O)N2CCN(c3cc(C#N)cc(OC(F)F)c3)CC2)c2ccccc2c1=O] | Method A m/z = 440.4 $(M + H)^+$ RT = 4.51 min | $^1H$ NMR (400 MHz, DMSO) δ 8.35-8.32 (m, 1H), 7.95-7.78 (m, 3H), 7.31 (t, J = 74.0 Hz, 1H), 7.30 (s, 1H), 7.04 (s, 2H), 3.86 (t, J = 4.5 Hz, 2H), 3.74 (s, 3H), 3.55 (t, J = 4.7 Hz, 2H), 3.49 (t, J = 5.5 Hz, 2H), 3.27 (t, J = 5.4 Hz, 2H). |
| 200 | 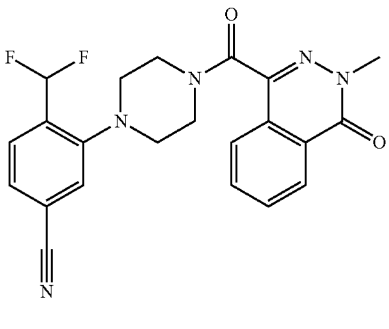 [SMILES: Cn1nc(C(=O)N2CCN(c3cc(C#N)ccc3C(F)F)CC2)c2ccccc2c1=O] | Method A m/z = 424.4 $(M + H)^+$ RT = 4.57 min | $^1H$ NMR (400 MHz, DMSO) δ 8.50-8.32 (m, 1H), 7.99-7.73 (m, 6H), 7.30 (t, J = 54.3 Hz, 1H), 3.92 (t, J = 4.6 Hz, 2H), 3.74 (s, 3H), 3.59 (t, J = 4.5 Hz, 2H), 3.07 (t, J = 5.4 Hz, 2H), 2.85 (t, J = 4.8 Hz, 2H). |

TABLE 5-continued

| Structure and Spectroscopic Data for Compounds 62 to 80 and 191 to 206. | | | |
|---|---|---|---|
| Compound No. | Structure | LCMS data | NMR data |
| 201 | 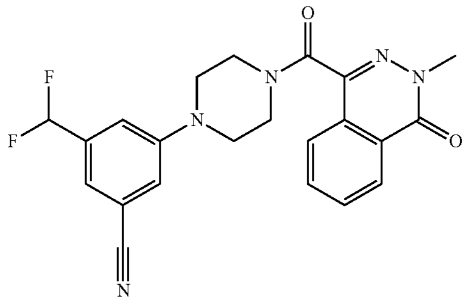 [SMILES: Cn1nc(C(=O)N2CCN(c3cc(C#N)cc(C(F)F)c3)CC2)c2ccccc2c1=O] | Method A m/z = 424.4 $(M + H)^+$ RT = 4.41 min | $^1H$ NMR (400 MHz, DMSO) δ 8.36-8.32 (m, 1H), 7.96-7.79 (m, 3H), 7.56-7.37 (m, 3H), 6.98 (t, J = 55.5 Hz, 1H), 3.88 (t, J = 4.6 Hz, 2H), 3.74 (s, 3H), 3.56 (t, J = 4.2 Hz, 2H), 3.51 (t, J = 5.2 Hz, 2H). One signal of two piperazine protons is obscured by water peak. |
| 202 | 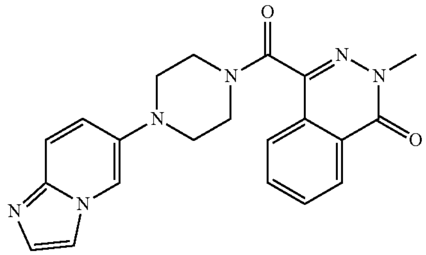 [SMILES: Cn1nc(C(=O)N2CCN(c3ccc4nccn4c3)CC2)c2ccccc2c1=O] | Method A m/z = 389.3 $(M + H)^+$ RT = 2.33 min | $^1H$ NMR (400 MHz, DMSO) δ 8.40 (s, 1H), 8.35-8.35 (m, 1H), 8.04 (d, J = 1.5 Hz, 1H), 7.93 (pd, J = 7.2, 1.5 Hz, 1H), 7.81-7.79 (m, 1H), 7.47-7.43 (m, 1H), 7.23 (dd, J = 2.3, 9.8 Hz, 1H), 6.83 (s, 2H), 3.92 (t, J = 5.1 Hz, 1H), 3.74 (s, 2H), 3.58 (t, J = 4.9 Hz, 1H), 3.20 (t, J = 5.2 Hz, 2H), 2.97 (t, J = 4.9 Hz, 1H). |
| 203 | 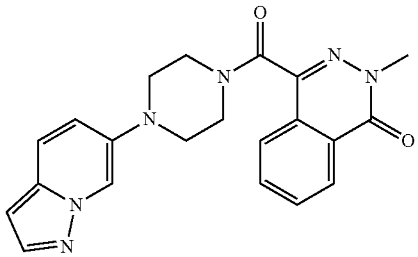 [SMILES: Cn1nc(C(=O)N2CCN(c3ccc4ccnn4c3)CC2)c2ccccc2c1=O] | Method A m/z = 389.4 $(M + H)^+$ RT = 3.65 min | $^1H$ NMR (400 MHz, DMSO) δ 8.34 (dd, J = 2.0, 7.0 Hz, 1H), 8.12 (s, 1H), 7.97-7.90 (m, 2H), 7.84-7.78 (m, 2H), 7.59 (d, J = 9.6 Hz, 1H), 7.23 (dd, J = 1.9, 9.6 Hz, 1H), 6.48 (d, J = 2.1 Hz, 1H), 3.92 (t, J = 4.8 Hz, 2H), 3.74 (s, 3H), 3.58 (t, J = 4.9 Hz, 2H), 3.32 (s, 2H), 3.24 (t, J = 5.2 Hz, 2H), 3.02 (t, J = 4.8 Hz, 2H). |
| 204 | 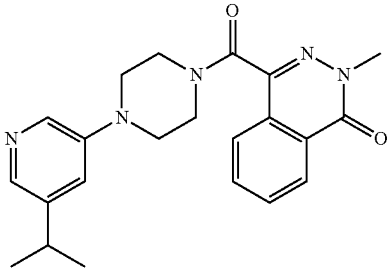 [SMILES: CC(C)c1cncc(N2CCN(C(=O)c3nn(C)c(=O)c4ccccc34)CC2)c1] | Method B m/z = 392.5 $(M + H)^+$ RT = 4.08 min | $^1H$ NMR (400 MHz, DMSO) δ 8.35-8.32 (m, 1H), 8.13 (d, J = 2.8 Hz, 1H), 7.97-7.89 (m, 3H), 7.81-7.78 (m, 1H), 7.21 (dd, J = 2.1, 2.1 Hz, 1H), 3.89 (dd, J = 5.2, 5.2 Hz, 2H), 3.74 (s, 3H), 3.58-3.53 (m, 2H), 3.38 (dd, J = 5.9, 5.9 Hz, 2H), 3.14 (dd, J = 5.1, 5.1 Hz, 2H), 2.91-2.83 (m, 1H), 1.21 (d, J = 6.8 Hz, 6H). |
| 205 | 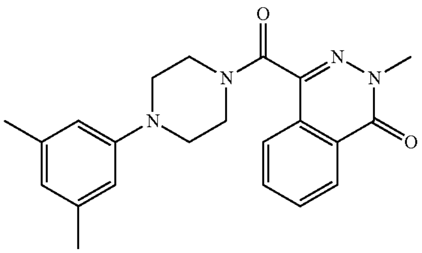 | Method C m/z = 377.7 $(M + H)^+$ RT = 4.76 min | $^1H$ NMR (400 MHz, DMSO) δ 8.35-8.32 (m, 1H), 7.93 (pd, J = 7.2, 2.0 Hz, 2H), 7.79-7.76 (m, 1H), 6.57 (s, 2H), 6.47 (s, 1H), 3.86 (t, J = 4.9 Hz, 2H), 3.74 (s, 3H), 3.51 (t, J = 4.7 Hz, 2H), 3.27 (t, J = 5.2 Hz, 2H), 3.02 (t, J = 4.9 Hz, 2H), 2.20 (s, 6H). |

TABLE 5-continued

| Structure and Spectroscopic Data for Compounds 62 to 80 and 191 to 206. | | | |
|---|---|---|---|
| Compound No. | Structure | LCMS data | NMR data |
| 206 | 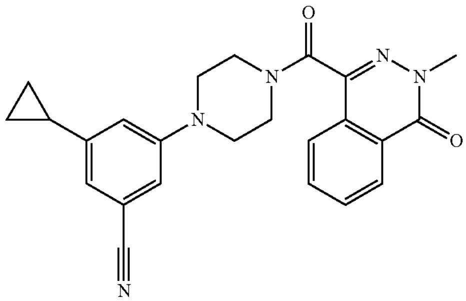 [SMILES: Cn1nc(C(=O)N2CCN(c3cc(C#N)cc(C4CC4)c3)CC2)c2ccccc2c1=O] | Method A m/z = 414.3 (M + H)$^+$ RT = 4.75 min | $^1$H NMR (400 MHz, DMSO) δ 8.35-8.32 (m, 1H), 7.97-7.89 (m, 2H), 7.81-7.77 (m, 1H), 7.13-7.11 (m, 1H), 7.02-6.99 (m, 1H), 6.91-6.88 (m, 1H), 3.89-3.83 (m, 2H), 3.74 (s, 3H), 3.19-3.13 (m, 2H), 1.96-1.88 (m, 1H), 0.98-0.91 (m, 2H), 0.76-0.71 (m, 2H). 4H obscured by water peak. |

Example 8: Synthesis of 2-ethyl-4-(4-(3-(trifluoromethyl)phenyl)piperazine-1-carbonyl)phthalazin-1(2H)-one (Compound 81)

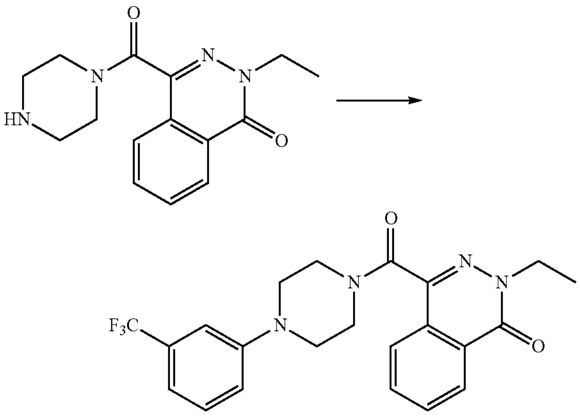

To a solution of 2-ethyl-4-(piperazine-1-carbonyl)phthalazin-1-one, Intermediate 3, (80 mg, 0.279 mmol, 1 equiv.) in 1,4-dioxane (3 mL) was added 3-bromobenzotrifluoride (0.047 mL, 0.335 mmol, 1.2 equiv.), RuPhos (20 mg, 0.0419 mmol, 0.15 eq), RuPhos PdG3 (23 mg, 0.0279 mmol, 0.1 eq) and cesium carbonate (273 mg, 0.838 mmol, 3 equiv.) The tube was sealed and heated at 80° C. for 20 hrs, then allowed to rt. The mixture was partitioned between EtOAc and water and the phases separated. The organics were collected and washed with brine, dried over sodium sulfate, filtered and the solvent was removed. The material was purified by reverse phase HPLC (Sunfire C18 19×150 mm, 10 μm 20-80% MeCN/$H_2O$+10 mM $NH_4CO_3$, 20 mL/min, rt) and then further purified (Luna Phenyl-Hexyl 21.2×150 mm, 10 μm 40-100% MeOH/$H_2O$+0.10% formic acid, 20 mL/min, rt) and the appropriate fractions were combined and lyophilized to yield the title compound (38 mg, 31%) as an off white solid. LCMS: Method A, m/z=431.2 (M+H)$^+$, RT=5.07 min. $^1$H NMR (400 MHz, DMSO) δ 8.36 (dd, J=2.2, 6.7 Hz, 1H), 7.99-7.92 (m, 2H), 7.83 (dd, J=2.1, 6.7 Hz, 1H), 7.46 (dd, J=8.0, 8.0 Hz, 1H), 7.27 (dd, J=2.4, 8.2 Hz, 1H), 7.23 (s, 1H), 7.13 (d, J=7.5 Hz, 1H), 4.21 (q, J=7.2 Hz, 2H), 3.91 (dd, J=5.1, 5.1 Hz, 2H), 3.58 (dd, J=5.0, 5.0 Hz, 2H), 3.44 (dd, J=5.2, 5.2 Hz, 2H), 3.22 (dd, J=5.0, 5.0 Hz, 2H), 1.33 (dd, J=7.2, 7.2 Hz, 3H).

The compounds in Table 6 were made according to the method described in Example 8, using Intermediate 3 and the appropriate aryl halide reagent.

TABLE 6

| Structure and Spectroscopic Data for Compounds 82 to 115. | | | |
|---|---|---|---|
| Compound No. | Structure | LCMS data | NMR data |
| 82 | 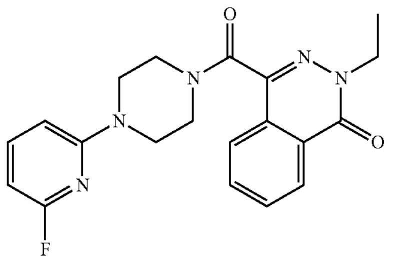 [SMILES: CCn1nc(C(=O)N2CCN(c3cccc(F)n3)CC2)c2ccccc2c1=O] | Method B m/z 382.2 (M + H)$^+$ RT 4.49 min | $^1$H NMR (400 MHz, DMSO) δ 8.36-8.33 (m, 1H), 7.97-7.89 (m, 2H), 7.83-7.80 (m, 1H), 7.70 (dd, J = 8.1, 16.9 Hz, 1H), 6.72 (dd, J = 2.7, 8.2 Hz, 1H), 6.32 (dd, J = 2.8, 7.6 Hz, 1H), 4.18 (q, J = 7.2 Hz, 2H), 3.86-3.82 (m, 2H), 3.73-3.66 (m, 2H), 3.55-3.50 (m, 2H), 3.49-3.44 (m, 2H), 1.32 (t, J = 7.1 Hz, 3H). |

TABLE 6-continued

| Structure and Spectroscopic Data for Compounds 82 to 115. | | | |
|---|---|---|---|
| Compound No. | Structure | LCMS data | NMR data |
| 83 | 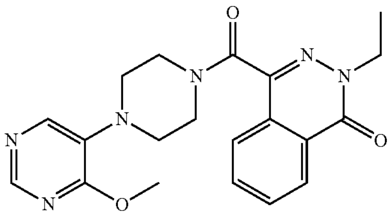 | Method B m/z 395.2 (M + H)+ RT 3.54 min | $^1$H NMR (400 MHz, DMSO) δ 8.43 (s, 1H), 8.36-8.32 (m, 1H), 8.11 (s, 1H), 7.98-7.90 (m, 2H), 7.82-7.79 (m, 1H), 4.18 (q, J = 7.1 Hz, 2H), 3.96 (s, 3H), 3.89 (t, J = 5.1 Hz, 2H), 3.55 (t, J = 4.8 Hz, 2H), 3.23 (t, J = 5.1 Hz, 2H), 3.02 (t, J = 4.7 Hz, 2H), 1.31 (t, J = 7.2 Hz, 3H). |
| 84 | 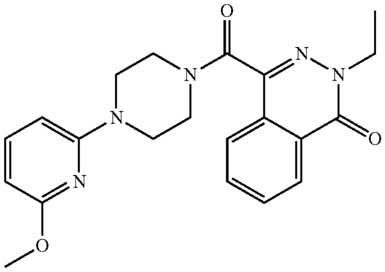 [SMILES: CCn1nc(C(=O)N2CCN(c3cccc(OC)n3)CC2)c2ccccc2c1=O] | Method A m/z 394.2 (M + H)+ RT 4.74 min | $^1$H NMR (400 MHz, DMSO) δ 8.36-8.32 (m, 1H), 7.96-7.91 (m, 2H), 7.83-7.79 (m, 1H), 7.47 (dd, J = 8.0, 8.0 Hz, 1H), 6.35 (d, J = 8.1 Hz, 1H), 6.08 (d, J = 7.8 Hz, 1H), 4.19 (q, J = 7.2 Hz, 2H), 3.87-3.82 (m, 2H), 3.76 (s, 3H), 3.70-3.65 (m, 2H), 3.54-3.42 (m, 4H), 1.32 (dd, J = 7.1, 7.1 Hz, 3H). |
| 85 | 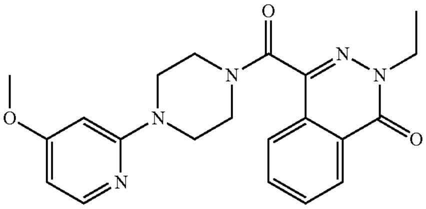 [SMILES: CCn1nc(C(=O)N2CCN(c3cc(OC)ccn3)CC2)c2ccccc2c1=O] | Method B m/z 394.2 (M + H)+ RT 4.04 min | $^1$H NMR (400 MHz, DMSO) δ 8.39-8.33 (m, 1H), 7.96-7.91 (m, 3H), 7.82-7.79 (m, 1H), 6.34-6.32 (m, 2H), 4.19 (q, J = 7.1 Hz, 2H), 3.86-3.81 (m, 2H), 3.77 (s, 3H), 3.70-3.65 (m, 2H), 3.48 (q, J = 5.7 Hz, 4H), 1.32 (dd, J = 7.1, 7.1 Hz, 3H). |
| 86 | 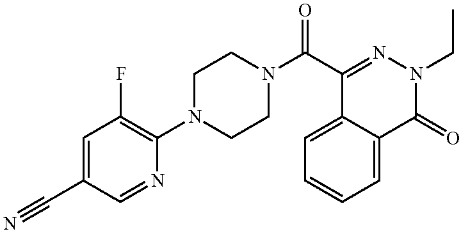 [SMILES: CCn1nc(C(=O)N2CCN(c3ncc(C#N)cc3F)CC2)c2ccccc2c1=O] | Method B m/z 407.2 (M + H)+ RT 4.27 min | $^1$H NMR (400 MHz, DMSO) δ 8.44 (t, J = 1.5 Hz, 1H), 8.36-8.32 (m, 1H), 8.05 (dd, J = 1.8, 14.1 Hz, 1H), 7.97-7.89 (m, 2H), 7.84-7.81 (m, 1H), 4.18 (q, J = 7.1 Hz, 2H), 3.88-3.86 (m, 4H), 3.66-3.54 (m, 4H), 1.31 (t, J = 7.2 Hz, 3H). |
| 87 | 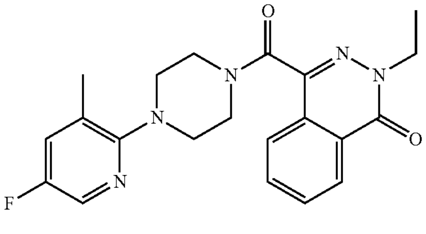 [SMILES: CCn1nc(C(=O)N2CCN(c3ncc(F)cc3C)CC2)c2ccccc2c1=O] | Method B m/z 396.2 (M + H)+ RT 4.59 min | $^1$H NMR (400 MHz, DMSO) δ 8.34 (dd, J = 1.1, 7.7 Hz, 1H), 8.10 (d, J = 2.8 Hz, 1H), 7.99-7.90 (m, 2H), 7.81-7.78 (m, 1H), 7.55 (dd, J = 2.9, 9.2 Hz, 1H), 4.18 (q, J = 7.2 Hz, 2H), 3.90 (t, J = 5.1 Hz, 2H), 3.53 (t, J = 4.8 Hz, 2H), 3.14 (t, J = 5.1 Hz, 2H), 2.95 (t, J = 4.9 Hz, 2H), 2.29 (s, 3H), 1.31 (t, J = 7.1 Hz, 3H). |
| 88 | 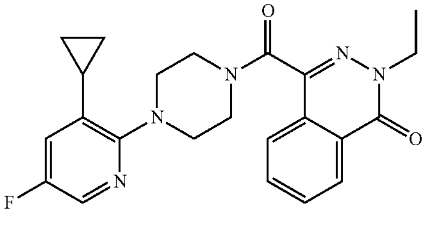 [SMILES: CCn1nc(C(=O)N2CCN(c3ncc(F)cc3C3CC3)CC2)c2ccccc2c1=O] | Method B m/z 422.2 (M + H)+ RT 4.88 min | $^1$H NMR (400 MHz, DMSO) δ 8.34 (dd, J = 1.0, 7.6 Hz, 1H), 8.04 (d, J = 2.9 Hz, 1H), 7.99-7.89 (m, 2H), 7.81-7.77 (m, 1H), 7.18 (dd, J = 2.9, 9.7 Hz, 1H), 4.18 (q, J = 7.2 Hz, 2H), 3.92 (t, J = 5.1 Hz, 2H), 3.56 (t, J = 4.8 Hz, 2H), 3.28-3.24 (m, 2H), 3.08-3.03 (m, 2H), 2.11-2.04 (m, 1H), 1.31 (t, J = 7.1 Hz, 3H), 1.07-1.02 (m, 2H), 0.82-0.77 (m, 2H). |

TABLE 6-continued

| Structure and Spectroscopic Data for Compounds 82 to 115. | | | |
|---|---|---|---|
| Compound No. | Structure | LCMS data | NMR data |
| 89 | 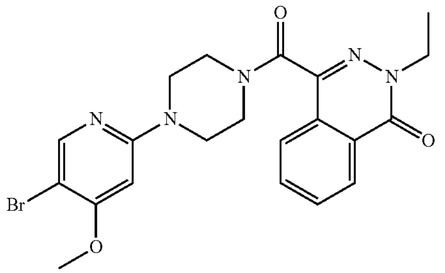 [SMILES: CCn1nc(C(=O)N2CCN(c3cc(OC)c(Br)cn3)CC2)c2ccccc2c1=O] | Method B m/z 472.3 (M + H)+ RT 4.66 min | $^1$H NMR (400 MHz, DMSO) δ 8.36-8.33 (m, 1H), 8.06 (s, 1H), 7.96-7.91 (m, 2H), 7.83-7.80 (m, 1H), 6.50 (s, 1H), 4.18 (q, J = 7.2 Hz, 2H), 3.89 (s, 3H), 3.86-3.83 (m, 2H), 3.74-3.70 (m, 2H), 3.51 (s, 4H), 1.32 (t, J = 7.2 Hz, 3H). |
| 90 | 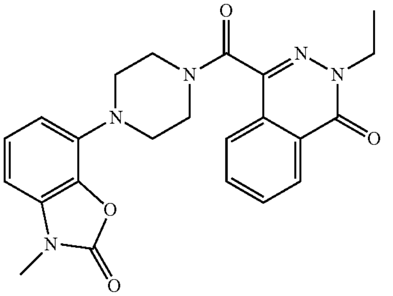 [SMILES: CCn1nc(C(=O)N2CCN(c3cccc4c3oc(=O)n4C)CC2)c2ccccc2c1=O] | Method B m/z 434.2 (M + H)+ RT 4.11 min | $^1$H NMR (400 MHz, DMSO) δ 8.36-8.33 (m, 1H), 7.97-7.90 (m, 2H), 7.83-7.80 (m, 1H), 7.13 (t, J = 8.1 Hz, 1H), 6.84 (dd, J = 1.0, 8.0 Hz, 1H), 6.72 (dd, J = 0.9, 8.4 Hz, 1H), 4.19 (q, J = 7.2 Hz, 2H), 3.95-3.91 (m, 2H), 3.62-3.58 (m, 2H), 3.37-3.35 (m, 2H), 3.17-3.12 (m, 2H), 1.32 (t, J = 7.1 Hz, 3H). 3H obscured by solvent signal |
| 91 | 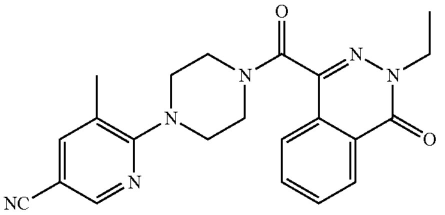 [SMILES: CCn1nc(C(=O)N2CCN(c3ncc(C#N)cc3C)CC2)c2ccccc2c1=O] | Method B m/z 403.3 (M + H)+ RT 4.28 min | $^1$H NMR (400 MHz, DMSO) δ 8.51 (d, J = 2.0 Hz, 1H), 8.34 (dd, J = 1.4, 7.7 Hz, 1H), 7.96-7.91 (m, 3H), 7.81 (dd, J = 1.8, 7.1 Hz, 1H), 4.18 (q, J = 7.2 Hz, 2H), 3.91-3.86 (m, 2H), 3.57-3.52 (m, 2H), 3.50-3.45 (m, 2H), 3.29-3.24 (m, 2H), 2.27 (s, 3H), 1.31 (t, J = 7.2 Hz, 3H). |
| 92 | 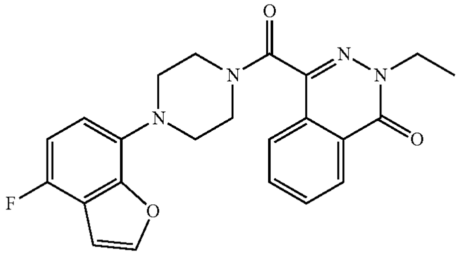 [SMILES: CCn1nc(C(=O)N2CCN(c3ccc(F)c4ccoc34)CC2)c2ccccc2c1=O] | Method B m/z 421.2 (M + H)+ RT 4.87 min | $^1$H NMR (400 MHz, DMSO) δ 8.36-8.33 (m, 1H), 8.04 (d, J = 2.0 Hz, 1H), 7.99-7.90 (m, 2H), 7.84-7.80 (m, 1H), 7.05 (d, J = 2.0 Hz, 1H), 6.98 (t, J = 9.0 Hz, 1H), 6.79 (dd, J = 4.5, 8.6 Hz, 1H), 4.19 (q, J = 7.1 Hz, 2H), 3.99-3.95 (m, 2H), 3.66-3.61 (m, 2H), 3.16-3.11 (m, 2H), 1.32 (t, J = 7.1 Hz, 3H). 2H obscured by solvent signal |
| 93 | 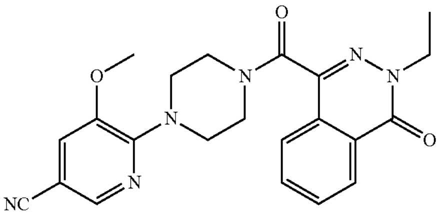 [SMILES: CCn1nc(C(=O)N2CCN(c3ncc(C#N)cc3OC)CC2)c2ccccc2c1=O] | Method B m/z 419.2 (M + H)+ RT 4.25 min | $^1$H NMR (400 MHz, DMSO) δ 8.36-8.32 (m, 1H), 8.22 (d, J = 1.5 Hz, 1H), 7.97-7.89 (m, 2H), 7.81 (dd, J = 1.9, 6.9 Hz, 1H), 7.61 (d, J = 1.8 Hz, 1H), 4.18 (q, J = 7.2 Hz, 2H), 3.88-3.84 (m, 5H), 3.78-3.73 (m, 2H), 3.54-3.51 (m, 4H), 1.31 (t, J = 7.1 Hz, 3H). |
| 94 | 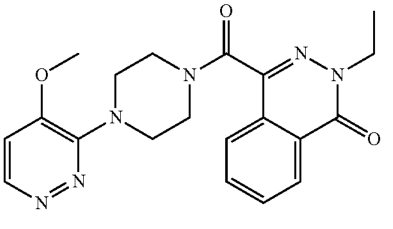 [SMILES: CCn1nc(C(=O)N2CCN(c3nnccc3OC)CC2)c2ccccc2c1=O] | Method B m/z 395.2 (M + H)+ RT 3.23 min | $^1$H NMR (400 MHz, DMSO) δ 8.65 (d, J = 5.6 Hz, 1H), 8.36-8.33 (m, 1H), 7.98-7.89 (m, 2H), 7.83-7.80 (m, 1H), 7.10 (d, J = 5.6 Hz, 1H), 4.19 (q, J = 7.2 Hz, 2H), 3.92-3.88 (m, 5H), 3.57-3.52 (m, 4H), 3.32 (s, 2H), 1.32 (dd, J = 7.2, 7.2 Hz, 3H). |

TABLE 6-continued

Structure and Spectroscopic Data for Compounds 82 to 115.

| Compound No. | Structure | LCMS data | NMR data |
|---|---|---|---|
| 95 | 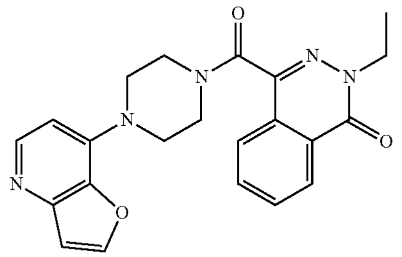 [SMILES: CCn1nc(C(=O)N2CCN(c3ccnc4ccoc34)CC2)c2ccccc2c1=O] | Method B m/z 404.2 (M + H)+ RT 3.68 min | $^1$H NMR (400 MHz, DMSO) δ 8.36-8.33 (m, 1H), 8.19 (d, J = 5.8 Hz, 1H), 8.15 (d, J = 2.0 Hz, 1H), 7.98-7.90 (m, 2H), 7.85-7.82 (m, 1H), 7.00 (d, J = 2.3 Hz, 1H), 6.73 (d, J = 5.6 Hz, 1H), 4.19 (q, J = 7.2 Hz, 2H), 3.97-3.92 (m, 2H), 3.79-3.74 (m, 2H), 3.65-3.61 (m, 2H), 3.56-3.51 (m, 2H), 1.32 (t, J = 7.1 Hz, 3H). |
| 96 | 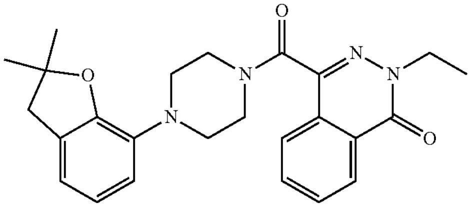 [SMILES: CCn1nc(C(=O)N2CCN(c3cccc4c3OC(C)(C)C4)CC2)c2ccccc2c1=O] | Method A m/z 433.2 (M + H)+ RT 5.29 min | $^1$H NMR (400 MHz, DMSO) δ 8.34 (dd, J = 1.3, 7.6 Hz, 1H), 7.98-7.90 (m, 2H), 7.80-7.77 (m, 1H), 6.81 (d, J = 7.1 Hz, 1H), 6.74 (t, J = 7.6 Hz, 1H), 6.67 (d, J = 7.3 Hz, 1H), 4.19 (q, J = 7.2 Hz, 2H), 3.91-3.86 (m, 2H), 3.55-3.52 (m, 2H), 3.17 (dd, J = 5.1, 5.1 Hz, 2H), 2.99-2.94 (m, 4H), 1.41 (s, 6H), 1.32 (t, J = 7.2 Hz, 3H). |
| 97 | 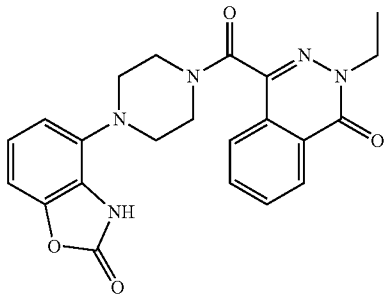 [SMILES: CCn1nc(C(=O)N2CCN(c3cccc4oc(=O)[nH]c34)CC2)c2ccccc2c1=O] | Method A m/z 420.2 (M + H)+ RT 4.05 min | $^1$H NMR (400 MHz, DMSO) δ 11.71 (s, 1H), 8.36-8.33 (m, 1H), 7.99-7.90 (m, 2H), 7.83-7.80 (m, 1H), 7.02-6.93 (m, 2H), 6.75 (d, J = 7.8 Hz, 1H), 4.19 (q, J = 7.2 Hz, 2H), 3.96-3.91 (m, 2H), 3.61-3.57 (m, 2H), 3.15-3.10 (m, 2H), 2.93-2.89 (m, 2H), 1.32 (t, J = 7.1 Hz, 3H). |
| 98 | 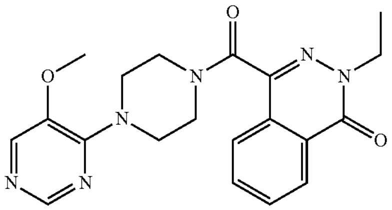 [SMILES: CCn1nc(C(=O)N2CCN(c3ncncc3OC)CC2)c2ccccc2c1=O] | Method A m/z 395.5 (M + H)+ RT 2.58 min | $^1$H NMR (400 MHz, DMSO) δ 8.36-8.32 (m, 1H), 8.28 (s, 1H), 8.09 (s, 1H), 7.97-7.89 (m, 2H), 7.83-7.79 (m, 1H), 4.18 (q, J = 7.2 Hz, 2H), 3.86-3.83 (m, 7H), 3.65-3.61 (m, 2H), 3.53-3.49 (m, 2H), 1.31 (t, J = 7.1 Hz, 3H). |
| 99 | 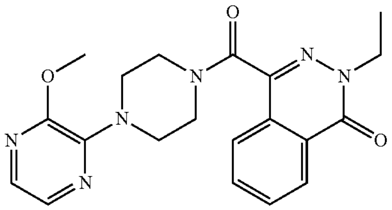 [SMILES: CCn1nc(C(=O)N2CCN(c3nccnc3OC)CC2)c2ccccc2c1=O] | Method A m/z 395.2 (M + H)+ RT 4.19 min | $^1$H NMR (400 MHz, DMSO) δ 8.36-8.32 (m, 1H), 7.98-7.89 (m, 2H), 7.82-7.79 (m, 1H), 7.78 (d, J = 3.0 Hz, 1H), 7.65 (d, J = 2.8 Hz, 1H), 4.18 (q, J = 7.2 Hz, 2H), 3.91 (s, 3H), 3.89-3.86 (m, 2H), 3.63-3.58 (m, 2H), 3.56-3.51 (m, 2H), 3.42-3.37 (m, 2H), 1.31 (t, J = 7.2 Hz, 3H). |
| 100 | 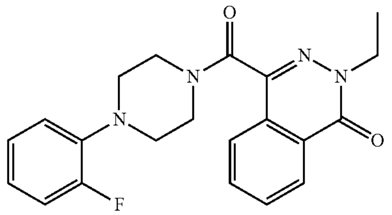 [SMILES: CCn1nc(C(=O)N2CCN(c3ccccc3F)CC2)c2ccccc2c1=O] | Method B m/z 381.2 (M + H)+ RT 4.65 min | $^1$H NMR (400 MHz, DMSO) δ 8.38-8.34 (m, 1H), 8.00-7.91 (m, 2H), 7.84-7.81 (m, 1H), 7.20-7.01 (m, 4H), 4.20 (q, J = 7.1 Hz, 2H), 3.95-3.90 (m, 2H), 3.61-3.56 (m, 2H), 3.21-3.16 (m, 2H), 2.99-2.94 (m, 2H), 1.33 (t, J = 7.2 Hz, 3H). |

TABLE 6-continued

| Structure and Spectroscopic Data for Compounds 82 to 115. | | | |
|---|---|---|---|
| Compound No. | Structure | LCMS data | NMR data |
| 101 | 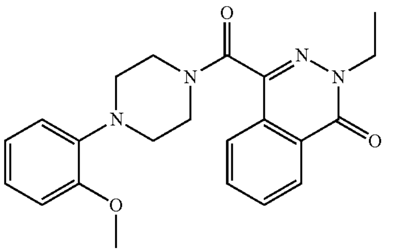 [SMILES: CCn1nc(C(=O)N2CCN(c3ccccc3OC)CC2)c2ccccc2c1=O] | Method B m/z 393.2 (M + H)+ RT 4.33 min | $^1$H NMR (400 MHz, DMSO) δ 8.37-8.34 (m, 1H), 8.01-7.91 (m, 2H), 7.83-7.79 (m, 1H), 7.03-6.87 (m, 4H), 4.20 (q, J = 7.2 Hz, 2H), 3.93-3.88 (m, 2H), 3.80 (s, 3H), 3.57-3.52 (m, 2H), 3.14-3.10 (m, 2H), 2.93-2.89 (m, 2H), 1.33 (t, J = 7.2 Hz, 3H). |
| 102 | 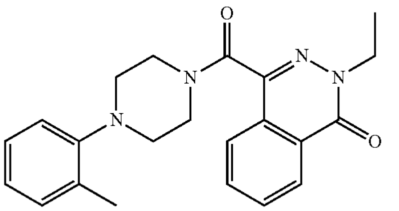 [SMILES: CCn1nc(C(=O)N2CCN(c3ccccc3C)CC2)c2ccccc2c1=O] | Method D m/z 377.2 (M + H)+ RT 8.70 min | $^1$H NMR (400 MHz, DMSO) δ 8.38-8.34 (m, 1H), 8.02-7.92 (m, 2H), 7.85-7.81 (m, 1H), 7.18 (dd, J = 7.4, 12.9 Hz, 2H), 7.06-6.97 (m, 2H), 4.20 (q, J = 7.2 Hz, 2H), 3.94-3.89 (m, 2H), 3.58-3.53 (m, 2H), 3.02-2.97 (m, 2H), 2.81-2.76 (m, 2H), 2.29 (s, 3H), 1.33 (t, J = 7.2 Hz, 3H). |
| 103 | 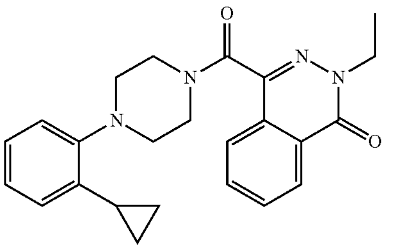 [SMILES: CCn1nc(C(=O)N2CCN(c3ccccc3C3CC3)CC2)c2ccccc2c1=O] | Method A m/z 403.2 (M + H)+ RT 5.47 min | $^1$H NMR (400 MHz, DMSO) δ 8.36-8.33 (m, 1H), 8.00-7.90 (m, 2H), 7.82-7.79 (m, 1H), 7.13-7.08 (m, 1H), 7.03-6.94 (m, 2H), 6.78 (dd, J = 1.4, 7.7 Hz, 1H), 4.19 (q, J = 7.2 Hz, 2H), 3.96-3.90 (m, 2H), 3.59-3.54 (m, 2H), 3.11-3.06 (m, 2H), 2.90-2.85 (m, 2H), 2.31-2.22 (m, 1H), 1.32 (t, J = 7.1 Hz, 3H), 0.99-0.93 (m, 2H), 0.69-0.63 (m, 2H). |
| 104 | 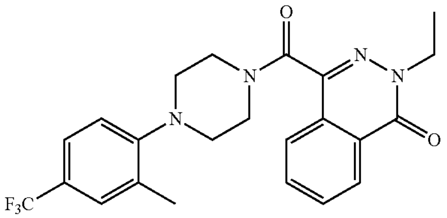 [SMILES: CCn1nc(C(=O)N2CCN(c3ccc(C(F)(F)F)cc3C)CC2)c2ccccc2c1=O] | Method A m/z 445.2 (M + H)+ RT 5.61 min | $^1$H NMR (400 MHz, DMSO) δ 8.36-8.33 (m, 1H), 8.00-7.90 (m, 2H), 7.83-7.80 (m, 1H), 7.53-7.48 (m, 2H), 7.18 (d, J = 8.3 Hz, 1H), 4.19 (q, J = 7.2 Hz, 2H), 3.95-3.90 (m, 2H), 3.59-3.54 (m, 2H), 3.09-3.05 (m, 2H), 2.88-2.83 (m, 2H), 2.34 (s, 3H), 1.32 (t, J = 7.1 Hz, 3H). |
| 105 | 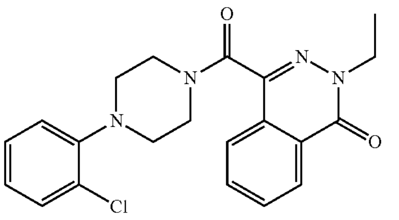 [SMILES: CCn1nc(C(=O)N2CCN(c3ccccc3Cl)CC2)c2ccccc2c1=O] | Method A m/z 397.3 (M + H)+ RT 5.14 min | $^1$H NMR (400 MHz, DMSO) δ 8.36-8.32 (m, 1H), 7.99-7.90 (m, 2H), 7.83-7.79 (m, 1H), 7.43 (dd, J = 1.5, 7.9 Hz, 1H), 7.31 (dt, J = 1.3, 7.7 Hz, 1H), 7.18 (dd, J = 1.4, 8.1 Hz, 1H), 7.07 (dt, J = 1.4, 7.6 Hz, 1H), 4.19 (q, J = 7.2 Hz, 2H), 3.94-3.89 (m, 2H), 3.59-3.53 (m, 2H), 3.15-3.11 (m, 2H), 2.94-2.89 (m, 2H), 1.31 (t, J = 7.2 Hz, 3H). |
| 106 | 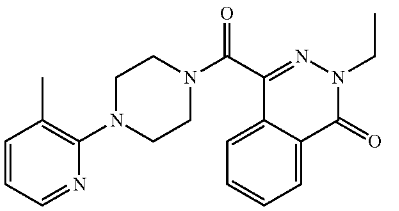 [SMILES: CCn1nc(C(=O)N2CCN(c3ncccc3C)CC2)c2ccccc2c1=O] | Method A m/z 378.2 (M + H)+ RT 3.10 min | $^1$H NMR (400 MHz, DMSO) δ 8.36-8.33 (m, 1H), 8.11 (dd, J = 1.4, 4.8 Hz, 1H), 8.00-7.90 (m, 2H), 7.82-7.78 (m, 1H), 7.53 (ddd, J = 0.7, 1.7, 7.3 Hz, 1H), 6.96 (dd, J = 4.8, 7.3 Hz, 1H), 4.19 (q, J = 7.2 Hz, 2H), 3.93-3.88 (m, 2H), 3.56-3.51 (m, 2H), 3.22-3.17 (m, 2H), 3.03-2.98 (m, 2H), 2.26 (s, 3H), 1.32 (t, J = 7.2 Hz, 3H). |

TABLE 6-continued

| Structure and Spectroscopic Data for Compounds 82 to 115. | | | |
|---|---|---|---|
| Compound No. | Structure | LCMS data | NMR data |
| 107 | 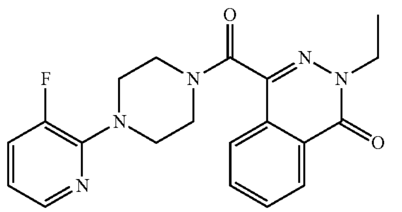 [SMILES: CCn1nc(C(=O)N2CCN(c3ncccc3F)CC2)c2ccccc2c1=O] | Method B m/z 382.2 (M + H)+ RT 4.14 min | $^1$H NMR (400 MHz, DMSO) δ 8.36-8.32 (m, 1H), 8.03 (td, J = 1.5, 4.8 Hz, 1H), 7.96-7.90 (m, 2H), 7.83-7.79 (m, 1H), 7.55 (ddd, J = 1.4, 7.9, 13.6 Hz, 1H), 6.96-6.91 (m, 1H), 4.18 (q, J = 7.2 Hz, 2H), 3.91-3.86 (m, 2H), 3.57-3.53 (m, 4H), 3.38-3.34 (m, 2H), 1.31 (t, J = 7.2 Hz, 3H). |
| 108 | 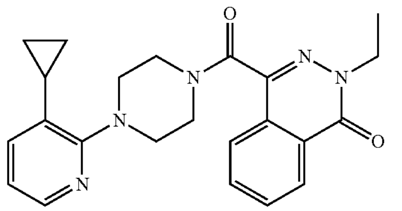 [SMILES: CCn1nc(C(=O)N2CCN(c3ncccc3C3CC3)CC2)c2ccccc2c1=O] | Method A m/z 404.2 (M + H)+ RT 3.62 min | $^1$H NMR (400 MHz, DMSO) δ 8.36-8.33 (m, 1H), 8.06 (dd, J = 1.8, 4.8 Hz, 1H), 7.99-7.90 (m, 2H), 7.81-7.78 (m, 1H), 7.21 (dd, J = 1.8, 7.5 Hz, 1H), 6.93 (dd, J = 4.8, 7.5 Hz, 1H), 4.19 (q, J = 7.1 Hz, 2H), 3.95-3.90 (m, 2H), 3.59-3.54 (m, 2H), 3.38-3.30 (m, 2H), 3.15-3.10 (m, 2H), 2.08-1.99 (m, 1H), 1.32 (t, J = 7.2 Hz, 3H), 1.04-0.98 (m, 2H), 0.75-0.70 (m, 2H). |
| 109 | 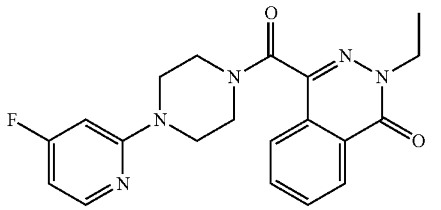 [SMILES: CCn1nc(C(=O)N2CCN(c3cc(F)ccn3)CC2)c2ccccc2c1=O] | Method A m/z 382.2 (M + H)+ RT 3.66 min | $^1$H NMR (400 MHz, DMSO) δ 8.36-8.33 (m, 1H), 8.13 (dd, J = 5.6, 9.9 Hz, 1H), 7.96-7.91 (m, 2H), 7.83-7.80 (m, 1H), 6.73 (dd, J = 2.1, 13.3 Hz, 1H), 6.57 (ddd, J = 2.3, 5.9, 8.3 Hz, 1H), 4.19 (q, J = 7.2 Hz, 2H), 3.86-3.81 (m, 2H), 3.75-3.70 (m, 2H), 3.51 (s, 4H), 1.32 (t, J = 7.1 Hz, 3H). |
| 110 | 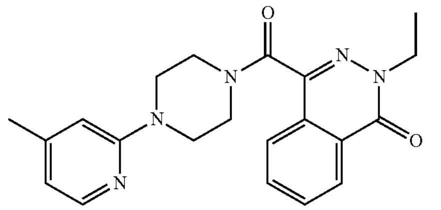 [SMILES: CCn1nc(C(=O)N2CCN(c3cc(C)ccn3)CC2)c2ccccc2c1=O] | Method B m/z 378.2 (M + H)+ RT 4.12 min | $^1$H NMR (400 MHz, DMSO) δ 8.42-8.38 (m, 1H), 8.04 (d, J = 5.2 Hz, 1H), 8.03-7.95 (m, 2H), 7.88-7.84 (m, 1H), 6.75 (s, 1H), 6.59 (d, J = 4.8 Hz, 1H), 4.24 (q, J = 7.1 Hz, 2H), 3.91-3.87 (m, 2H), 3.74-3.70 (m, 2H), 3.57-3.47 (m, 4H), 2.28 (s, 3H), 1.37 (t, J = 7.2 Hz, 3H). |
| 111 | 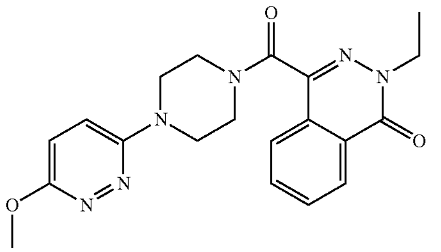 [SMILES: CCn1nc(C(=O)N2CCN(c3ccc(OC)nn3)CC2)c2ccccc2c1=O] | Method A m/z 395.3 (M + H)+ RT 2.82 min | $^1$H NMR (400 MHz, DMSO) δ 8.36-8.33 (m, 1H), 7.97-7.89 (m, 2H), 7.83-7.79 (m, 1H), 7.43 (d, J = 9.6 Hz, 1H), 7.07 (d, J = 9.6 Hz, 1H), 4.19 (q, J = 7.1 Hz, 2H), 3.90 (s, 3H), 3.89-3.85 (m, 2H), 3.66-3.61 (m, 2H), 3.57-3.52 (m, 2H), 3.45-3.40 (m, 2H), 1.32 (t, J = 7.1 Hz, 3H). |
| 112 | 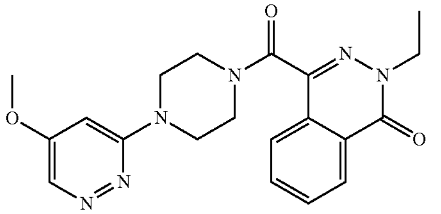 [SMILES: CCn1nc(C(=O)N2CCN(c3cc(OC)cnn3)CC2)c2ccccc2c1=O] | Method B m/z 395.2 (M + H)+ RT 3.17 min | $^1$H NMR (400 MHz, DMSO) δ 8.37-8.33 (m, 2H), 7.97-7.91 (m, 2H), 7.85-7.81 (m, 1H), 6.73 (d, J = 2.3 Hz, 1H), 4.19 (q, J = 7.2 Hz, 2H), 3.90-3.85 (m, 5H), 3.83-3.79 (m, 2H), 3.63-3.58 (m, 2H), 3.58-3.53 (m, 2H), 1.32 (t, J = 7.1 Hz, 3H). |

TABLE 6-continued

| Structure and Spectroscopic Data for Compounds 82 to 115. | | | |
|---|---|---|---|
| Compound No. | Structure | LCMS data | NMR data |
| 113 | 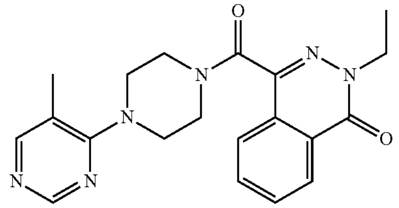 [SMILES: CCn1nc(C(=O)N2CCN(c3ncncc3C)CC2)c2ccccc2c1=O] | Method A m/z 379.2 (M + H)+ RT 2.48 min | $^1$H NMR (400 MHz, DMSO) δ 8.53 (s, 1H), 8.36-8.32 (m, 1H), 8.21 (s, 1H), 7.98-7.89 (m, 2H), 7.82 (dd, J = 1.8, 7.1 Hz, 1H), 4.18 (q, J = 7.2 Hz, 2H), 3.89-3.85 (m, 2H), 3.62-3.57 (m, 2H), 3.56-3.51 (m, 2H), 3.40-3.35 (m, 2H), 2.21 (s, 3H), 1.31 (t, J = 7.1 Hz, 3H). |
| 114 | 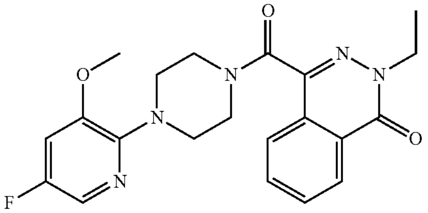 [SMILES: CCn1nc(C(=O)N2CCN(c3ncc(F)cc3OC)CC2)c2ccccc2c1=O] | Method A m/z 412.6 (M + H)+ RT 4.35 min | $^1$H NMR (400 MHz, DMSO) δ 8.35-8.32 (m, 1H), 7.98-7.89 (m, 2H), 7.81-7.77 (m, 2H), 7.37 (dd, J = 2.3, 10.4 Hz, 1H), 4.22-4.14 (m, 2H), 3.89-3.83 (m, 5H), 3.54-3.49 (m, 2H), 3.39-3.34 (m, 2H), 3.18-3.13 (m, 2H), 1.31 (t, J = 7.1 Hz, 3H). |
| 115 | 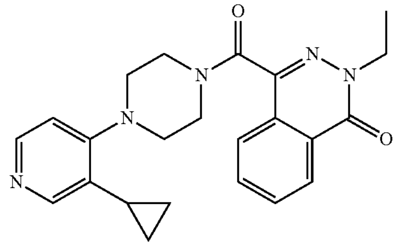 [SMILES: CCn1nc(C(=O)N2CCN(c3ccncc3C3CC3)CC2)c2ccccc2c1=O] | Method A m/z 404.2 (M + H)+ RT 2.74 min | $^1$H NMR (400 MHz, DMSO) δ 8.36-8.33 (m, 1H), 8.22 (d, J = 5.3 Hz, 1H), 8.02 (s, 1H), 7.99-7.90 (m, 2H), 7.82-7.80 (m, 1H), 6.89 (d, J = 5.6 Hz, 1H), 4.19 (q, J = 7.2 Hz, 2H), 3.96-3.91 (m, 2H), 3.61-3.56 (m, 2H), 3.29-3.24 (m, 2H), 3.08-3.03 (m, 2H), 2.01-1.93 (m, 1H), 1.32 (t, J = 7.2 Hz, 3H), 1.03-0.97 (m, 2H), 0.81-0.76 (m, 2H). |

Example 9: Synthesis of 4-(4-(3-cyclopropylphenyl) piperazine-1-carbonyl)-2-ethylphthalazin-1(2H)-one (Compound 116)

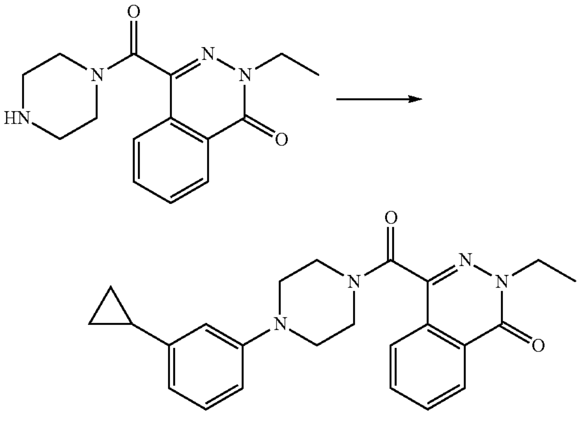

To an argon-purged suspension of sodium t-butoxide (50 mg, 0.524 mmol, 3 equiv.), 1-bromo-3-cyclopropylbenzene (38 mg, 0.192 mmol, 1.1 equiv.) and 2-ethyl-4-(piperazine-1-carbonyl)phthalazin-1-one (50 mg, 0.175 mmol, 1 equiv.) in 1,4-dioxane (2.4 mL) was added DavePhos Pd G3 (6.7 mg, 8.73 mmol, 0.05 equiv.) under an argon atmosphere in a vial. The vial was sealed and heated to 100° C. for 16 hours. The reaction mixture was cooled, then water (5 mL) and DCM (50 mL) were added. The resulting biphasic solution was passed through a phase separator containing silica. The organic phase was collected, and the solvent removed. The material was purified by reverse phase HPLC (Sunfire C18 19×150 mm, 10 μm 40-100% MeCN/$H_2O$+ 0.1% formic acid, 20 mL/min, rt) and then further purified (Sunfire C18 19×150 mm, 10 μm 40-100% MeCN/$H_2O$+ 0.100 formic acid, 20 mL/min, rt) and the appropriate fractions were combined and lyophilized to yield the title compound (15 mg, 21%) as an off white solid. LCMS: Method A, m/z=403.2 $(M+H)^+$, RT=5.27 mi. $^1$H NMR (400 MHz, DMSO) δ 8.36-8.32 (t, 1H), 7.98-7.89 (t, 2H), 7.79 (dd, J=2.0, 7.1 Hz, 1H), 7.09 (dd, J=7.8, 7.8 Hz, 1H), 6.73-6.67 (m, 2H), 6.52 (d, J=7.6 Hz, 1H), 4.18 (q, J=7.2 Hz, 2H), 3.90-3.85 (m, 2H), 3.53 (dd, J=4.9, 4.9 Hz, 2H), 3.30-3.25 (m, 2H), 3.06 (dd, J=5.1, 5.1 Hz, 2H), 1.88-1.80 (m, 1H), 1.31 (t, J=7.1 Hz, 3H), 0.89 (ddd, J=4.2, 6.4, 8.4 Hz, 2H), 0.66-0.61 (m, 2H).

The compounds in Table 7 were made according to the method described in Example 9, using Intermediate 2 and the appropriate aryl halide reagent.

TABLE 7

| Structure and Spectroscopic Data for Compounds 117 to 150. | | | |
|---|---|---|---|
| Compound No. | Structure | LCMS data | NMR data |
| 117 | 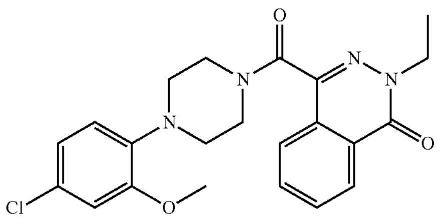 [SMILES: CCn1nc(C(=O)N2CCN(c3ccc(Cl)cc3OC)CC2)c2ccccc2c1=O] | Method A m/z 427.2 $(M + H)^+$ RT 5.03 min | $^1H$ NMR (400 MHz, DMSO) δ 8.35-8.32 (m, 1H), 7.99-7.89 (m, 2H), 7.81-7.78 (m, 1H), 7.00 (d, J = 2.0 Hz, 1H), 6.95-6.88 (m, 2H), 4.18 (q, J = 7.2 Hz, 2H), 3.90-3.85 (m, 2H), 3.81 (s, 3H), 3.55-3.50 (m, 2H), 3.11-3.06 (m, 2H), 2.90-2.86 (m, 2H), 1.31 (t, J = 7.2 Hz, 3H). |
| 118 | 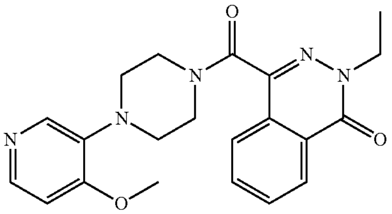 [SMILES: CCn1nc(C(=O)N2CCN(c3cnccc3OC)CC2)c2ccccc2c1=O] | Method A m/z 394.2 $(M + H)^+$ RT 2.46 min | $^1H$ NMR (400 MHz, DMSO) δ 8.36-8.32 (m, 1H), 8.16 (d, J = 5.3 Hz, 1H), 8.05 (s, 1H), 7.99-7.89 (m, 2H), 7.82-7.79 (m, 1H), 7.00 (d, J = 5.6 Hz, 1H), 4.19 (q, J = 7.2 Hz, 2H), 3.91-3.86 (m, 2H), 3.85 (s, 3H), 3.56-3.51 (m, 2H), 3.20-3.15 (m, 2H), 2.99-2.94 (m, 2H), 1.31 (t, J = 7.1 Hz, 3H). |
| 119 | 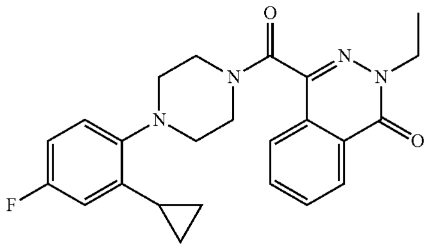 [SMILES: CCn1nc(C(=O)N2CCN(c3ccc(F)cc3C3CC3)CC2)c2ccccc2c1=O] | Method B m/z 421.2 $(M + H)^+$ RT 5.30 min | $^1H$ NMR (400 MHz, DMSO) δ 8.36-8.32 (m, 1H), 8.00-7.90 (m, 2H), 7.82-7.79 (m, 1H), 7.06 (dd, J = 5.6, 8.8 Hz, 1H), 6.90 (dt, J = 3.0, 8.6 Hz, 1H), 6.60 (dd, J = 2.9, 10.5 Hz, 1H), 4.19 (q, J = 7.2 Hz, 2H), 3.95-3.89 (m, 2H), 3.58-3.53 (m, 2H), 3.07-3.02 (m, 2H), 2.86-2.81 (m, 2H), 2.35-2.28 (m, 1H), 1.31 (t, J = 7.2 Hz, 3H), 1.02-0.96 (m, 2H), 0.73-0.67 (m, 2H). |
| 120 | 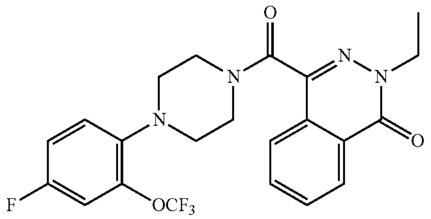 [SMILES: CCn1nc(C(=O)N2CCN(c3ccc(F)cc3OC(F)(F)F)CC2)c2ccccc2c1=O] | Method B m/z 465.2 $(M + H)^+$ RT 5.33 min | $^1H$ NMR (400 MHz, DMSO) δ 8.39-8.36 (m, 1H), 8.03-7.93 (m, 2H), 7.86-7.83 (m, 1H), 7.36 (d, J = 8.9 Hz, 1H), 7.33-7.26 (m, 2H), 4.22 (q, J = 7.2 Hz, 2H), 3.93-3.89 (m, 2H), 3.58-3.54 (m, 2H), 3.16-3.12 (m, 2H), 2.95-2.91 (m, 2H), 1.35 (t, J = 7.2 Hz, 3H). |

TABLE 7-continued

| Structure and Spectroscopic Data for Compounds 117 to 150. | | | |
|---|---|---|---|
| Compound No. | Structure | LCMS data | NMR data |
| 121 | 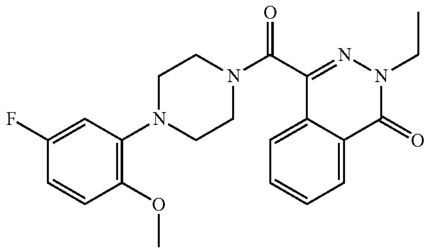 [SMILES: CCn1nc(C(=O)N2CCN(c3cc(F)ccc3OC)CC2)c2ccccc2c1=O] | Method B m/z 411.2 $(M + H)^+$ RT 4.59 min | $^1H$ NMR (400 MHz, DMSO) δ 8.35-8.32 (m, 1H), 7.99-7.89 (m, 2H), 7.81-7.78 (m, 1H), 6.93 (dd, J = 5.4, 8.7 Hz, 1H), 6.79-6.72 (m, 2H), 4.18 (q, J = 7.2 Hz, 2H), 3.90-3.86 (m, 2H), 3.77 (s, 3H), 3.55-3.51 (m, 2H), 3.16-3.11 (m, 2H), 2.95-2.90 (m, 2H), 1.31 (t, J = 7.2 Hz, 3H). |
| 122 | 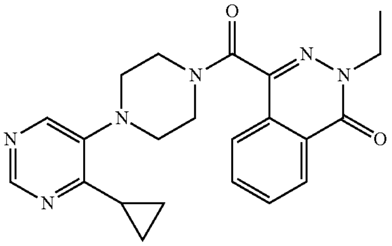 [SMILES: CCn1nc(C(=O)N2CCN(c3cncnc3C3CC3)CC2)c2ccccc2c1=O] | Method A m/z 405.7 $(M + H)^+$ RT 3.94 min | $^1H$ NMR (400 MHz, DMSO) δ 8.67 (s, 1H), 8.36-8.33 (m, 2H), 7.99-7.90 (m, 2H), 7.83-7.80 (m, 1H), 4.19 (q, J = 7.1 Hz, 2H), 3.98-3.92 (m, 2H), 3.63-3.58 (m, 2H), 3.23-3.18 (m, 2H), 3.01-2.96 (m, 2H), 2.45-2.37 (m, 1H), 1.32 (t, J = 7.1 Hz, 3H), 1.12-1.04 (m, 4H). |
| 123 | 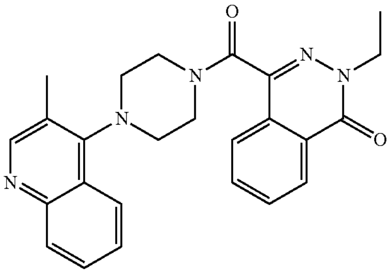 [SMILES: CCn1nc(C(=O)N2CCN(c3c(C)cnc4ccccc34)CC2)c2ccccc2c1=O] | Method A m/z 428.3 $(M + H)^+$ RT 2.90 min | $^1H$ NMR (400 MHz, DMSO) δ 8.69 (s, 1H), 8.41 (dd, J = 1.1, 7.8 Hz, 1H), 8.30 (dd, J = 1.0, 8.5 Hz, 1H), 8.07-7.93 (m, 4H), 7.74-7.69 (m, 1H), 7.65-7.60 (m, 1H), 4.26 (q, J = 7.2 Hz, 2H), 3.74-3.68 (m, 2H), 3.52-3.46 (m, 2H), 3.30-3.25 (m, 2H), 2.53 (s, 3H), 1.39 (t, J = 7.1 Hz, 3H). 2H obscured by solvent signal. |
| 124 | 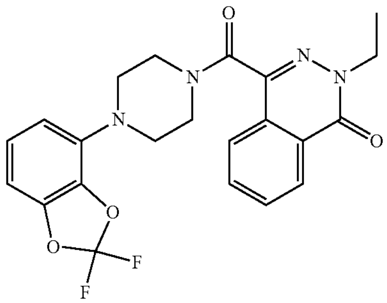 [SMILES: CCn1nc(C(=O)N2CCN(c3cccc4c3OC(F)(F)O4)CC2)c2ccccc2c1=O] | Method C m/z 443.3 $(M + H)^+$ RT 5.14 min | $^1H$ NMR (400 MHz, DMSO) δ 8.36-8.33 (m, 1H), 7.98-7.90 (m, 2H), 7.83-7.80 (m, 1H), 7.11 (t, J = 8.3 Hz, 1H), 6.94 (d, J = 7.8 Hz, 1H), 6.81 (d, J = 8.4 Hz, 1H), 4.19 (q, J = 7.2 Hz, 2H), 3.93-3.89 (m, 2H), 3.61-3.56 (m, 2H), 3.37-3.33 (m, 2H), 3.14-3.12 (m, 2H), 1.32 (t, J = 7.2 Hz, 3H). |
| 125 | 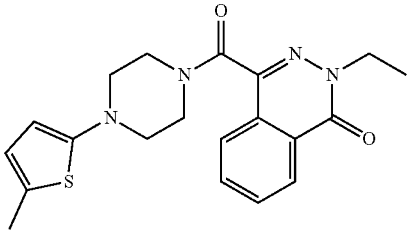 [SMILES: CCn1nc(C(=O)N2CCN(c3ccc(C)s3)CC2)c2ccccc2c1=O] | Method A m/z 383.4 $(M + H)^+$ RT 5.02 min | $^1H$ NMR (400 MHz, DMSO) δ 8.35-8.32 (m, 1H), 7.97-7.89 (m, 2H), 7.80-7.77 (m, 1H), 6.44-6.42 (m, 1H), 6.00 (d, J = 3.5 Hz, 1H), 4.18 (q, J = 7.2 Hz, 2H), 3.90-3.85 (m, 2H), 3.56-3.52 (m, 2H), 3.17-3.13 (m, 2H), 2.95-2.91 (m, 2H), 2.29 (d, J = 1.1 Hz, 3H), 1.31 (t, J = 7.2 Hz, 3H). |

TABLE 7-continued

| Structure and Spectroscopic Data for Compounds 117 to 150. | | | |
|---|---|---|---|
| Compound No. | Structure | LCMS data | NMR data |
| 126 | 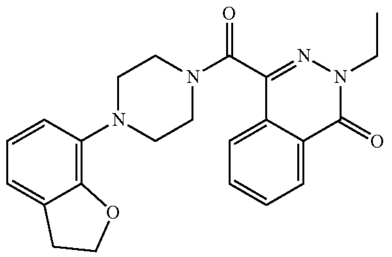 [SMILES: CCn1nc(C(=O)N2CCN(c3cccc4c3OCC4)CC2)c2ccccc2c1=O] | Method A m/z 405.7 (M + H)+ RT 4.69 min | $^1$H NMR (400 MHz, DMSO) δ 8.36-8.32 (m, 1H), 7.98-7.89 (m, 2H), 7.81-7.77 (m, 1H), 6.86 (d, J = 7.2 Hz, 1H), 6.75 (t, J = 7.7 Hz, 1H), 6.66 (d, J = 7.9 Hz, 1H), 4.51 (t, J = 8.7 Hz, 2H), 4.18 (q, J = 7.2 Hz, 2H), 3.90-3.85 (m, 2H), 3.56-3.51 (m, 2H), 3.20 3.17 (m, 2H), 3.14 (t, J = 8.8 Hz, 2H), 2.99-2.94 (m, 2H), 1.31 (t, J = 7.1 Hz, 3H). |
| 127 | 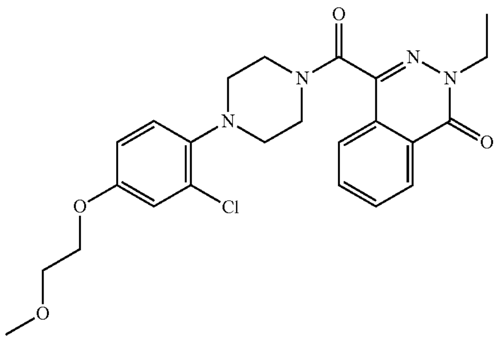 [SMILES: CCn1nc(C(=O)N2CCN(c3ccc(OCCOC)cc3Cl)CC2)c2ccccc2c1=O] | Method B m/z 471.2 (M + H)+ RT 4.86 min | $^1$H NMR (400 MHz, DMSO) δ 8.35-8.32 (m, 1H), 7.99-7.90 (m, 2H), 7.82-7.79 (m, 1H), 7.13 (d, J = 8.8 Hz, 1H), 7.05 (d, J = 2.8 Hz, 1H), 6.90 (dd, J = 2.8, 8.8 Hz, 1H), 4.19 (q, J = 7.2 Hz, 2H), 4.08-4.05 (m, 2H), 3.92-3.86 (m, 2H), 3.64-3.60 (m, 2H), 3.56-3.51 (m, 2H), 3.29 (s, 3H), 3.06-3.01 (m, 2H), 2.85-2.80 (m, 2H), 1.31 (t, J = 7.2 Hz, 3H). |
| 128 | 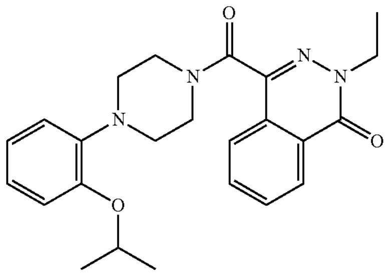 [SMILES: CCn1nc(C(=O)N2CCN(c3ccccc3OC(C)C)CC2)c2ccccc2c1=O] | Method A m/z 421.7 (M + H)+ RT 5.22 min | $^1$H NMR (400 MHz, DMSO) δ 8.36-8.33 (m, 1H), 7.99 - 7.90 (m, 2H), 7.81-7.78 (m, 1H), 6.98-6.85 (m, 4H), 4.65-4.56 (m, 1H), 4.19 (q, J = 7.2 Hz, 2H), 3.92-3.86 (m, 2H), 3.55-3.50 (m, 2H), 3.16-3.11 (m, 2H), 2.95-2.90 (m, 2H), 1.32 (t, J = 7.2 Hz, 3H), 1.26 (d, J = 6.0 Hz, 6H). |
| 129 | 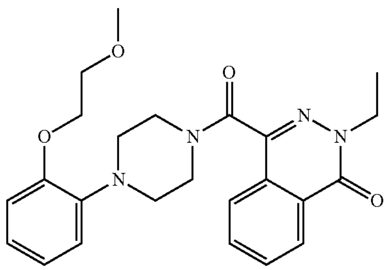 [SMILES: CCn1nc(C(=O)N2CCN(c3ccccc3OCCOC)CC2)c2ccccc2c1=O] | Method A m/z 437.2 (M + H)+ RT 4.39 min | $^1$H NMR (400 MHz, DMSO) δ 8.36-8.32 (m, 1H), 7.99-7.89 (m, 2H), 7.81-7.78 (m, 1H), 6.96-6.87 (m, 4H), 4.18 (q, J = 7.2 Hz, 2H), 4.10-4.07 (m, 2H), 3.91-3.86 (m, 2H), 3.69-3.65 (m, 2H), 3.55-3.50 (m, 2H), 3.17-3.12 (m, 2H), 2.96-2.92 (m, 2H), 1.31 (t, J = 7.2 Hz, 3H). 3H obscured by solvent signal. |

TABLE 7-continued

| Structure and Spectroscopic Data for Compounds 117 to 150. | | | |
|---|---|---|---|
| Compound No. | Structure | LCMS data | NMR data |
| 130 | 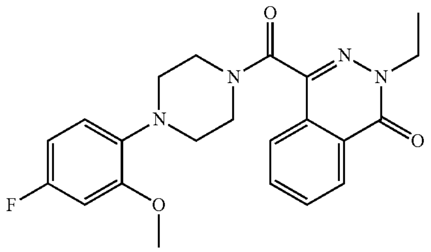 [SMILES: CCn1nc(C(=O)N2CCN(c3ccc(F)cc3OC)CC2)c2ccccc2c1=O] | Method B m/z 411.2 $(M + H)^+$ RT 4.41 min | $^1H$ NMR (400 MHz, DMSO) δ 8.35-8.32 (m, 1H), 7.99-7.89 (m, 2H), 7.81-7.77 (m, 1H), 6.93-6.85 (m, 2H), 6.68 (dt, J = 2.8, 8.5 Hz, 1H), 4.18 (q, J = 7.2 Hz, 2H), 3.89-3.85 (m, 2H), 3.79 (s, 3H), 3.54-3.50 (m, 2H), 3.08-3.03 (m, 2H), 2.87-2.82 (m, 2H), 1.31 (t, J = 7.1 Hz, 3H). |
| 131 | 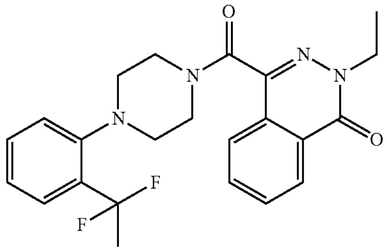 [SMILES: CCn1nc(C(=O)N2CCN(c3ccccc3C(C)(F)F)CC2)c2ccccc2c1=O] | Method A m/z 427.2 $(M + H)^+$ RT 5.28 min | $^1H$ NMR (400 MHz, DMSO) δ 8.35-8.32 (m, 1H), 8.01-7.90 (m, 2H), 7.84 (d, J = 8.0 Hz, 1H), 7.56-7.48 (m, 3H), 7.33-7.28 (m, 1H), 4.18 (q, J = 7.2 Hz, 2H), 3.93-3.80 (m, 2H), 3.55-3.50 (m, 2H), 3.02-2.97 (m, 2H), 2.80-2.75 (m, 2H), 2.10 (t, J = 19.1 Hz, 3H), 1.31 (t, J = 7.1 Hz, 3H). |
| 132 | 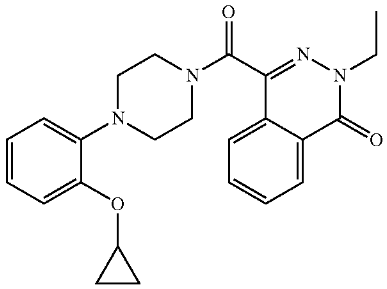 [SMILES: CCn1nc(C(=O)N2CCN(c3ccccc3OC3CC3)CC2)c2ccccc2c1=O] | Method A m/z 419.2 $(M + H)^+$ RT 4.95 min | $^1H$ NMR (400 MHz, DMSO) δ 8.35-8.32 (m, 1H), 7.99-7.89 (m, 2H), 7.80-7.76 (m, 1H), 7.23 (d, J = 7.8 Hz, 1H), 7.02-6.96 (m, 1H), 6.91-6.88 (m, 2H), 4.18 (q, J = 7.2 Hz, 2H), 3.89-3.81 (m, 3H), 3.52-3.47 (m, 2H), 3.09-3.04 (m, 2H), 2.88-2.83 (m, 2H), 1.31 (t, J = 7.1 Hz, 3H), 0.80-0.74 (m, 2H), 0.68-0.63 (m, 2H). |
| 133 | 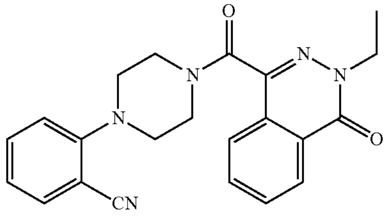 | Method m/z $(M + H)^+$ RT min | $^1H$ NMR (400 MHz, DMSO) δ 8.36-8.33 (m, 1H), 7.99-7.90 (m, 2H), 7.84-7.81 (m, 1H), 7.74 (dd, J = 1.6, 7.7 Hz, 1H), 7.65-7.60 (m, 1H), 7.21 (d, J = 8.2 Hz, 1H), 7.14 (dd, J = 7.2, 7.2 Hz, 1H), 4.19 (q, J = 7.2 Hz, 2H), 3.96-3.91 (m, 2H), 3.63-3.58 (m, 2H), 3.31-3.28 (m, 2H), 3.12-3.08 (m, 2H), 1.32 (t, J = 7.2 Hz, 3H). |

TABLE 7-continued

| Structure and Spectroscopic Data for Compounds 117 to 150. | | | |
|---|---|---|---|
| Compound No. | Structure | LCMS data | NMR data |
| 134 | 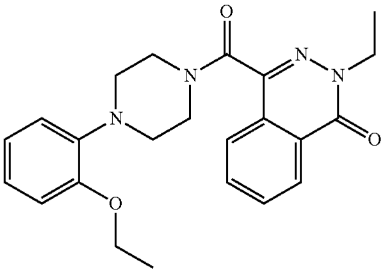 [SMILES: CCOc1ccccc1N1CCN(C(=O)c2nn(CC)c(=O)c3ccccc23)CC1] | Method B m/z 407.2 $(M + H)^+$ RT 4.70 min | $^1H$ NMR (400 MHz, DMSO) δ 8.36-8.32 (m, 1H), 7.99-7.89 (m, 2H), 7.81-7.77 (m, 1H), 6.96-6.85 (m, 4H), 4.18 (q, J = 7.2 Hz, 2H), 4.02 (q, J = 7.0 Hz, 2H), 3.91-3.86 (m, 2H), 3.55-3.50 (m, 2H), 3.15-3.10 (m, 2H), 2.95-2.90 (m, 2H), 1.36-1.29 (m, 6H). |
| 135 | 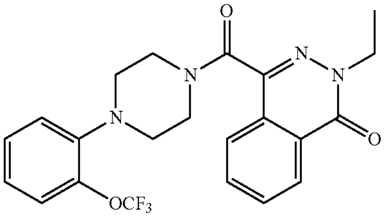 [SMILES: CCn1nc(C(=O)N2CCN(c3ccccc3OC(F)(F)F)CC2)c2ccccc2c1=O] | Method A m/z 447.2 $(M + H)^+$ RT 5.43 min | $^1H$ NMR (400 MHz, DMSO) δ 8.36-8.32 (m, 1H), 7.99-7.89 (m, 2H), 7.83-7.80 (m, 1H), 7.36-7.29 (m, 2H), 7.19 (dd, J = 1.4, 8.0 Hz, 1H), 7.14-7.09 (m, 1H), 4.18 (q, J = 7.2 Hz, 2H), 3.91-3.86 (m, 2H), 3.56-3.51 (m, 2H), 3.18-3.13 (m, 2H), 2.97-2.92 (m, 2H), 1.31 (t, J = 7.2 Hz, 3H). |
| 136 | 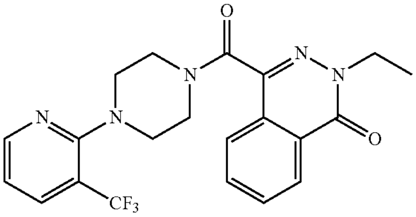 [SMILES: CCn1nc(C(=O)N2CCN(c3ncccc3C(F)(F)F)CC2)c2ccccc2c1=O] | Method A m/z 432.2 $(M + H)^+$ RT 4.84 min | $^1H$ NMR (400 MHz, DMSO) δ 8.57-8.54 (m, 1H), 8.36-8.32 (m, 1H), 8.11 (dd, J = 1.8, 7.9 Hz, 1H), 7.99 - 7.90 (m, 2H), 7.83-7.79 (m, 1H), 7.28-7.24 (m, 1H), 4.18 (q, J = 7.2 Hz, 2H), 3.91-3.86 (m, 2H), 3.57-3.52 (m, 2H), 3.14-3.09 (m, 2H), 1.31 (t, J = 7.2 Hz, 3H). 2H obscured by solvent signal. |
| 137 | 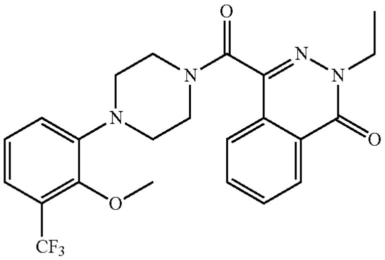 [SMILES: CCn1nc(C(=O)N2CCN(c3cccc(C(F)(F)F)c3OC)CC2)c2ccccc2c1=O] | Method B m/z 461.2 $(M + H)^+$ RT 5.26 min | $^1H$ NMR (400 MHz, DMSO) δ 8.35 (d, J = 7.1 Hz, 1H), 8.01 (ddd, J = 7.6, 7.6, 1.2 Hz, 1H), 7.93 (ddd, J = 7.6, 7.6, 0.9 Hz, 1H), 7.80 (d, J = 7.8 Hz, 1H), 7.42-7.34 (m, 2H), 7.24 (dd, J = 1.8, 7.3 Hz, 1H), 4.58 (d, J = 12.1 Hz, 1H), 4.19 (q, J = 7.1 Hz, 2H), 3.89 (s, 3H), 3.66 (d, J = 10.1 Hz, 1H), 3.41 (dt, J = 2.3, 11.4 Hz, 1H), 3.29-3.20 (m, 2H), 3.04 (dt, J = 3.2, 12.3 Hz, 1H), 2.89-2.83 (m, 1H), 2.61 (d, J = 8.6 Hz, 1H), 1.32 (t, J = 7.2 Hz, 3H). |

TABLE 7-continued

| Compound No. | Structure | LCMS data | NMR data |
|---|---|---|---|
| | Structure and Spectroscopic Data for Compounds 117 to 150. | | |
| 138 | 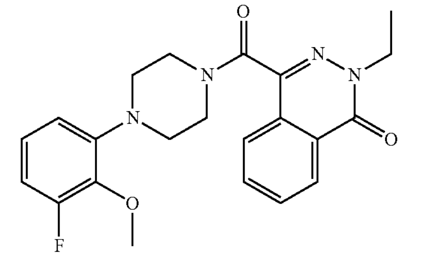 [SMILES: CCn1nc(C(=O)N2CCN(c3cccc(F)c3OC)CC2)c2ccccc2c1=O] | Method A m/z 411.2 $(M + H)^+$ RT 4.84 min | $^1H$ NMR (400 MHz, DMSO) δ 8.36-8.32 (m, 1H), 8.01-7.90 (m, 2H), 7.81-7.77 (m, 1H), 7.07 (ddd, J = 8.3, 8.3, 6.3 Hz, 1H), 6.83 (d, J = 8.4 Hz, 1H), 6.77 (ddd, J = 1.2, 8.3, 11.2 Hz, 1H), 4.18 (q, J = 7.2 Hz, 2H), 3.85-3.82 (m, 2H), 3.80 (s, 3H), 3.49-3.44 (m, 2H), 3.20-3.16 (m, 2H), 3.02-2.97 (m, 2H), 1.31 (t, J = 7.2 Hz, 3H). |
| 139 | 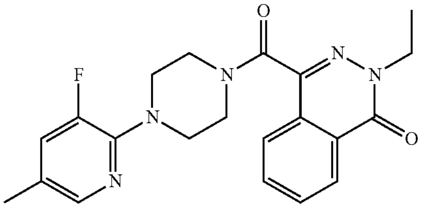 [SMILES: CCn1nc(C(=O)N2CCN(c3ncc(C)cc3F)CC2)c2ccccc2c1=O] | Method B m/z 396.2 $(M + H)^+$ RT 4.46 min | $^1H$ NMR (400 MHz, DMSO) δ 8.36-8.32 (m, 1H), 7.98-7.89 (m, 2H), 7.88 (s, 1H), 7.82-7.78 (m, 1H), 7.43 (dd, J = 1.3, 13.9 Hz, 1H), 4.18 (q, J = 7.2 Hz, 2H), 3.90-3.86 (m, 2H), 3.56-3.52 (m, 2H), 3.49-3.44 (m, 2H), 3.28-3.23 (m, 2H), 2.21 (s, 3H), 1.31 (t, J = 7.2 Hz, 3H). |
| 140 | 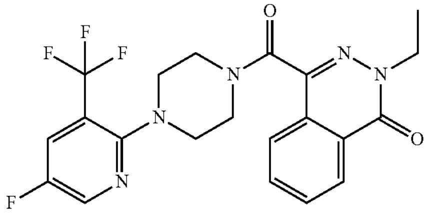 [SMILES: CCn1nc(C(=O)N2CCN(c3ncc(F)cc3C(F)(F)F)CC2)c2ccccc2c1=O] | Method B m/z 450.2 $(M + H)^+$ RT 4.85 min | $^1H$ NMR (400 MHz, DMSO) δ 8.65 (d, J = 2.5 Hz, 1H), 8.35-8.32 (m, 1H), 8.20 (dd, J = 3.0, 8.6 Hz, 1H), 7.99-7.89 (m, 2H), 7.82- 7.79 (m, 1H), 4.18 (q, J = 7.2 Hz, 2H), 3.91-3.86 (m, 2H), 3.56-3.52 (m, 2H), 3.24-3.20 (m, 2H), 3.04-3.00 (m, 2H), 1.31 (t, J = 7.1 Hz, 3H). |
| 141 | 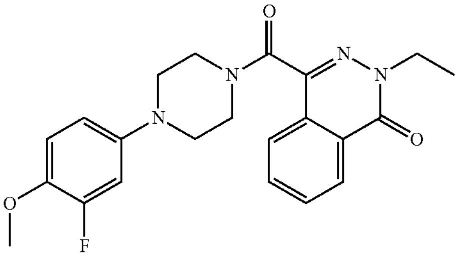 [SMILES: CCn1nc(C(=O)N2CCN(c3ccc(OC)c(F)c3)CC2)c2ccccc2c1=O] | Method A m/z 411.2 $(M + H)^+$ RT 4.53 min | $^1H$ NMR (400 MHz, DMSO) δ 8.36-8.32 (m, 1H), 7.97-7.89 (m, 2H), 7.81-7.77 (m, 1H), 7.03 (t, J = 9.5 Hz, 1H), 6.90 (dd, J = 2.8, 14.4 Hz, 1H), 6.71 (ddd, J = 1.1, 2.7, 9.0 Hz, 1H), 4.18 (q, J = 7.2 Hz, 2H), 3.89-3.85 (m, 2H), 3.76 (s, 3H), 3.56-3.51 (m, 2H), 3.24-3.19 (m, 2H), 3.02-2.97 (m, 2H), 1.31 (t, J = 7.1 Hz, 3H). |

TABLE 7-continued

Structure and Spectroscopic Data for Compounds 117 to 150.

| Compound No. | Structure | LCMS data | NMR data |
| --- | --- | --- | --- |
| 142 | 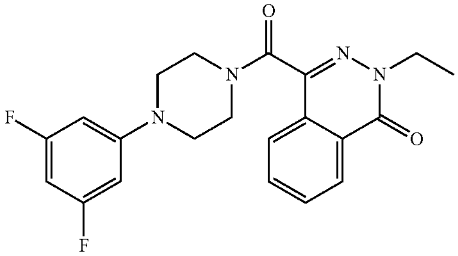 [SMILES: CCn1nc(C(=O)N2CCN(c3cc(F)cc(F)c3)CC2)c2ccccc2c1=O] | Method B m/z 399.2 $(M + H)^+$ RT 4.95 min | $^1H$ NMR (400 MHz, DMSO) δ 8.36-8.32 (m, 1H), 7.97-7.89 (m, 2H), 7.83-7.79 (m, 1H), 6.68-6.62 (m, 2H), 6.52 (tdd, J = 2.1, 9.2, 9.2 Hz, 1H), 4.18 (q, J = 7.2 Hz, 2H), 3.88-3.83 (m, 2H), 3.56-3.51 (m, 2H), 3.44-3.39 (m, 2H), 3.22-3.17 (m, 2H), 1.31 (t, J = 7.1 Hz, 3H). |
| 143 | 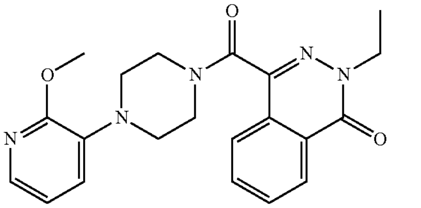 [SMILES: CCn1nc(C(=O)N2CCN(c3cccnc3OC)CC2)c2ccccc2c1=O] | Method A m/z 394.2 $(M + H)^+$ RT 4.04 min | $^1H$ NMR (400 MHz, DMSO) δ 8.36-8.32 (m, 1H), 7.98-7.89 (m, 2H), 7.81-7.77 (m, 2H), 7.22 (dd, J = 1.6, 7.7 Hz, 1H), 6.92 (dd, J = 4.8, 7.6 Hz, 1H), 4.18 (q, J = 7.2 Hz, 2H), 3.92-3.87 (m, 5H), 3.57-3.53 (m, 2H), 3.18-3.13 (m, 2H), 2.97-2.92 (m, 2H), 1.31 (t, J = 7.2 Hz, 3H). |
| 144 | 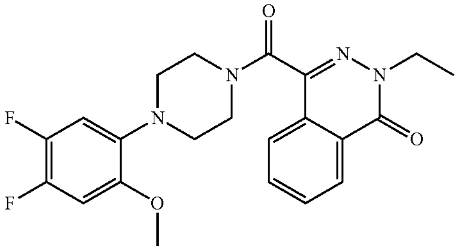 [SMILES: CCn1nc(C(=O)N2CCN(c3cc(F)c(F)cc3OC)CC2)c2ccccc2c1=O] | Method A m/z 429.2 $(M + H)^+$ RT 4.80 min | $^1H$ NMR (400 MHz, DMSO) δ 8.34 (d, J = 7.8 Hz, 1H), 7.98-7.89 (m, 2H), 7.79 (d, J = 7.6 Hz, 1H), 7.10 (dd, J = 7.8, 12.6 Hz, 1H), 6.98 (dd, J = 8.6, 12.6 Hz, 1H), 4.18 (q, J = 7.2 Hz, 2H), 3.89-3.84 (m, 2H), 3.78 (s, 3H), 3.55-3.50 (m, 2H), 3.10-3.05 (m, 2H), 2.89-2.84 (m, 2H), 1.31 (t, J = 7.2 Hz, 3H). |
| 145 | 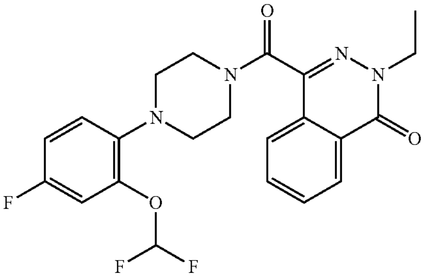 [SMILES: CCn1nc(C(=O)N2CCN(c3ccc(F)cc3OC(F)F)CC2)c2ccccc2c1=O] | Method B m/z 447.2 $(M + H)^+$ RT 5.05 min | $^1H$ NMR (400 MHz, DMSO) δ 8.36-8.32 (m, 1H), 7.99-7.89 (m, 2H), 7.82-7.79 (m, 1H), 7.23 (t, J = 74.3 Hz, 1H), 7.17 (dd, J = 6.0, 8.5 Hz, 1H), 7.13-7.06 (m, 2H), 4.18 (q, J = 7.2 Hz, 2H), 3.91-3.86 (m, 2H), 3.56-3.52 (m, 2H), 3.11-3.06 (m, 2H), 2.89-2.85 (m, 2H), 1.31 (t, J = 7.1 Hz, 3H). |
| 146 | 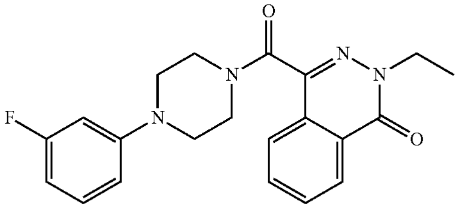 [SMILES: CCn1nc(C(=O)N2CCN(c3cccc(F)c3)CC2)c2ccccc2c1=O] | Method B m/z 381.0 $(M + H)^+$ RT 4.83 min | $^1H$ NMR (400 MHz, DMSO) δ 8.36-8.33 (m, 1H), 7.97-7.89 (m, 2H), 7.82-7.79 (m, 1H), 7.23 (q, J = 7.9 Hz, 1H), 6.80-6.75 (m, 2H), 6.61-6.55 (m, 1H), 4.18 (q, J = 7.2 Hz, 2H), 3.90-3.85 (m, 2H), 3.57-3.52 (m, 2H), 3.39-3.34 (m, 2H), 3.17-3.12 (m, 2H), 1.31 (t, J = 7.1 Hz, 3H). |

TABLE 7-continued

Structure and Spectroscopic Data for Compounds 117 to 150.

| Compound No. | Structure | LCMS data | NMR data |
| --- | --- | --- | --- |
| 147 | 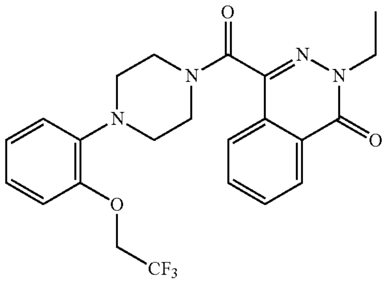 [SMILES: CCn1nc(C(=O)N2CCN(c3ccccc3OCC(F)(F)F)CC2)c2ccccc2c1=O] | Method B m/z 461.2 (M + H)$^+$ RT 5.04 min | $^1$H NMR (400 MHz, DMSO) δ 8.35-8.32 (m, 1H), 7.98-7.89 (m, 2H), 7.81-7.78 (m, 1H), 7.05-6.98 (m, 4H), 4.73 (q, J = 8.9 Hz, 2H), 4.18 (q, J = 7.1 Hz, 2H), 3.91-3.86 (m, 2H), 3.56-3.51 (m, 2H), 3.15-3.10 (m, 2H), 2.95-2.90 (m, 2H), 1.31 (t, J = 7.1 Hz, 3H). |
| 148 | 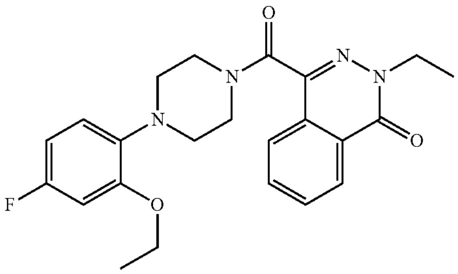 [SMILES: CCOc1cc(F)ccc1N1CCN(C(=O)c2nn(CC)c(=O)c3ccccc23)CC1] | Method A m/z 425.7 (M + H)$^+$ RT 4.97 min | $^1$H NMR (400 MHz, DMSO) δ 8.35-8.32 (m, 1H), 7.99-7.89 (m, 2H), 7.80-7.77 (m, 1H), 6.91-6.82 (m, 2H), 6.67 (dt, J = 2.9, 8.5 Hz, 1H), 4.18 (q, J = 7.2 Hz, 2H), 4.03 (q, J = 7.0 Hz, 2H), 3.90-3.85 (m, 2H), 3.53-3.49 (m, 2H), 3.10-3.05 (m, 2H), 2.89-2.85 (m, 2H), 1.36-1.29 (m, 6H). |
| 149 | 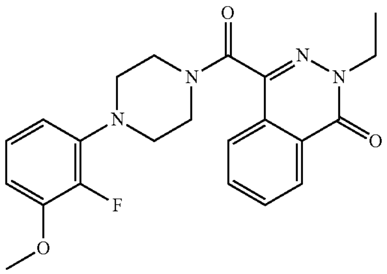 [SMILES: CCn1nc(C(=O)N2CCN(c3cccc(OC)c3F)CC2)c2ccccc2c1=O] | Method B m/z 411.2 (M + H)$^+$ RT 4.65 min | $^1$H NMR (400 MHz, DMSO) δ 8.36-8.32 (m, 1H), 7.99-7.89 (m, 2H), 7.82-7.78 (m, 1H), 7.03 (dt, J = 1.7, 8.3 Hz, 1H), 6.82 (t, J = 7.6 Hz, 1H), 6.68-6.63 (m, 1H), 4.18 (q, J = 7.2 Hz, 2H), 3.93-3.87 (m, 2H), 3.80 (s, 3H), 3.58-3.53 (m, 2H), 3.17-3.12 (m, 2H), 2.96-2.91 (m, 2H), 1.31 (t, J = 7.2 Hz, 3H). |
| 150 | 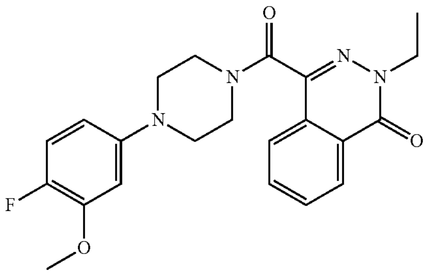 [SMILES: CCn1nc(C(=O)N2CCN(c3ccc(F)c(OC)c3)CC2)c2ccccc2c1=O] | Method A m/z 411.2 (M + H)$^+$ RT 4.80 min | $^1$H NMR (400 MHz, DMSO) δ 8.36-8.32 (m, 1H), 7.99-7.90 (m, 2H), 7.82-7.79 (m, 1H), 7.06 (dd, J = 8.7, 12.5 Hz, 1H), 6.57-6.50 (m, 2H), 4.19 (q, J = 7.2 Hz, 2H), 3.92-3.88 (m, 2H), 3.71 (s, 3H), 3.58-3.53 (m, 2H), 3.19-3.14 (m, 2H), 2.97-2.93 (m, 2H), 1.31 (t, J = 7.1 Hz, 3H). |

Example 10: Synthesis of 3-(4-(3-ethyl-4-oxo-3,4-dihydrophthalazine-1-carbonyl)piperazin-1-yl)-2-methoxybenzonitrile (Compound 151)

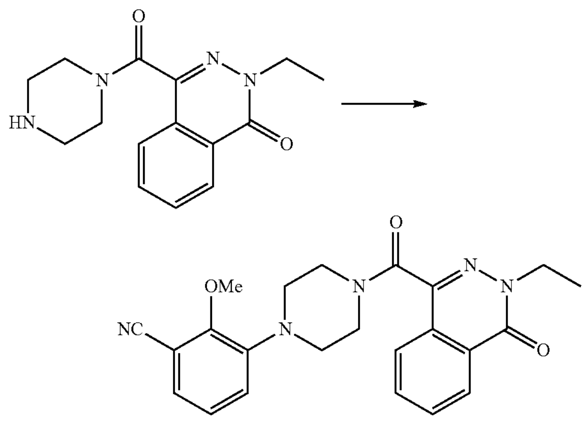

To an argon-purged suspension of sodium t-butoxide (25 mg, 0.262 mmol, 1.5 equiv.), 3-bromo-2-methoxybenzonitrile (41 mg, 0.192 mmol, 1.1 equiv.) and 2-ethyl-4-(piperazine-1-carbonyl)phthalazin-1-one (50 mg, 0.175 mmol, 1 equiv.) in CPME (2.4 mL) was added DavePhos PdG3 (13 mg, 0.0175 mmol, 0.1 equiv.) under an argon atmosphere in a vial. The vial was sealed and stirred at 100° C. for 16 hours. The reaction mixture was cooled, then water (5 mL) and DCM (50 mL) were added. The resulting biphasic solution was passed through a phase separator containing silica. The organic phase was collected, and the solvent removed. The material was purified by reverse phase HPLC (Xbridge C18 19×150 mm, 10 μm 20-80% $MeCN/H_2O$+10 mM $NH_4CO_3$), 20 mL/min, rt) and the appropriate fractions were combined and lyophilized to yield the title compound (30 mg, 40%) as an off white solid. LCMS: Method B, m/z=418.2 $(M+H)^+$, RT=4.52 min. $^1H$ NMR (400 MHz, DMSO) δ 8.34 (dd, J=1.8, 7.1 Hz, 1H), 7.98-7.89 (m, 2H), 7.81 (dd, J=1.8, 7.1 Hz, 1H), 7.37 (dd, J=1.5, 7.6 Hz, 1H), 7.32 (dd, J=1.5, 8.1 Hz, 1H), 7.22 (dd, J=8.0, 8.0 Hz, 1H), 4.18 (q, J=7.2 Hz, 2H), 3.95 (s, 3H), 3.95-3.92 (m, 2H), 3.62-3.58 (m, 2H), 3.21 (dd, J=5.2, 5.2 Hz, 2H), 3.00 (dd, J=4.8, 4.8 Hz, 2H), 1.31 (dd, J=7.2, 7.2 Hz, 3H).

The compounds in Table 8 were made according to the method described in Example 10, using Intermediate 2 and the appropriate aryl halide reagent.

TABLE 8

Structure and Spectroscopic Data for Compounds 152 to 155 and 207.

| Compound No. | Structure | LCMS data | NMR data |
|---|---|---|---|
| 152 | 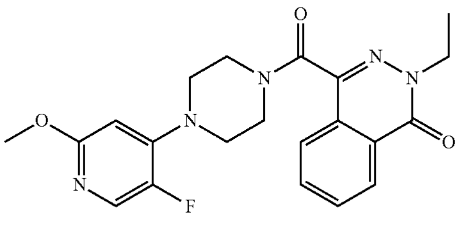 [SMILES: CCn1nc(C(=O)N2CCN(c3cc(OC)ncc3F)CC2)c2ccccc2c1=O] | Method B m/z 412.2 $(M + H)^+$ RT 4.34 min | $^1H$ NMR (400 MHz, DMSO) δ 8.36-8.32 (m, 1H), 7.98-7.90 (m, 3H), 7.83-7.79 (m, 1H), 6.31 (d, J = 6.6 Hz, 1H), 4.18 (q, J = 7.2 Hz, 2H), 3.91-3.86 (m, 2H), 3.77 (s, 3H), 3.59-3.54 (m, 2H), 3.40-3.36 (m, 2H), 3.19-3.14 (m, 2H), 1.31 (t, J = 7.1 Hz, 3H). |
| 153 | 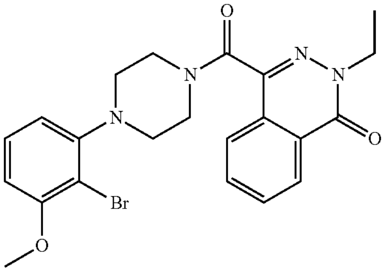 [SMILES: CCn1nc(C(=O)N2CCN(c3cccc(OC)c3Br)CC2)c2ccccc2c1=O] | Method B m/z 471.2 $(M + H)^+$ RT 4.86 min | $^1H$ NMR (400 MHz, DMSO) δ 8.36-8.32 (m, 1H), 7.99-7.90 (m, 2H), 7.83-7.80 (m, 1H), 7.30 (t, J = 8.1 Hz, 1H), 6.86 (dd, J = 1.0, 8.3 Hz, 1H), 6.80 (dd, J = 1.3, 8.1 Hz, 1H), 4.19 (q, J = 7.2 Hz, 2H), 3.93-3.89 (m, 2H), 3.82 (s, 3H), 3.58-3.53 (m, 2H), 3.13-3.08 (m, 2H), 2.91-2.86 (m, 2H), 1.31 (t, J = 7.1 Hz, 3H). |
| 154 | 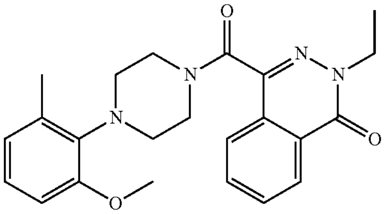 [SMILES: CCn1nc(C(=O)N2CCN(c3c(C)cccc3OC)CC2)c2ccccc2c1=O] | Method A m/z 407.7 $(M + H)^+$ RT 5.54 min | $^1H$ NMR (400 MHz, DMSO) δ 8.42-8.38 (m, 1H), 8.09-8.04 (m, 1H), 8.01-7.96 (m, 1H), 7.84 (d, J = 7.8 Hz, 1H), 7.08 (t, J = 8.0 Hz, 1H), 6.86 (dd, J = 7.8, 11.4 Hz, 2H), 4.62-4.54 (m, 1H), 4.24 (q, J = 7.2 Hz, 2H), 3.83 (s, 3H), 3.70-3.63 (m, 1H), 3.26-3.10 (m, 2H), 2.97-2.90 (m, 1H), |

TABLE 8-continued

| Structure and Spectroscopic Data for Compounds 152 to 155 and 207. | | | |
|---|---|---|---|
| Compound No. | Structure | LCMS data | NMR data |
| | | | 2.70-2.65 (m, 1H), 2.34 (s, 3H), 1.38 (t, J = 7.2 Hz, 3H). 2H obscured by solvent signal |
| 155 | 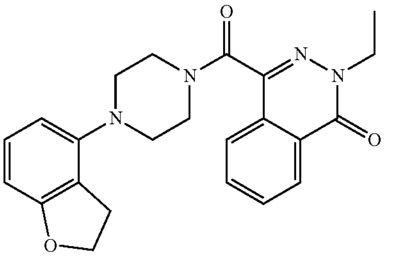 [SMILES: CCn1nc(C(=O)N2CCN(c3cccc4c3CCO4)CC2)c2ccccc2c1=O] | Method B m/z 405.2 $(M + H)^+$ RT 4.54 min | $^1H$ NMR (400 MHz, DMSO) δ 8.36-8.32 (m, 1H), 7.99-7.91 (m, 2H), 7.82-7.79 (m, 1H), 7.02 (t, J = 8.1 Hz, 1H), 6.43 (dd, J = 1.0, 8.1 Hz, 2H), 4.47 (t, J = 8.6 Hz, 2H), 4.19 (q, J = 7.2 Hz, 2H), 3.90-3.85 (m, 2H), 3.55-3.50 (m, 2H), 3.15-3.07 (m, 4H), 2.94-2.89 (m, 2H), 1.31 (t, J = 7.1 Hz, 3H). |
| 207 | 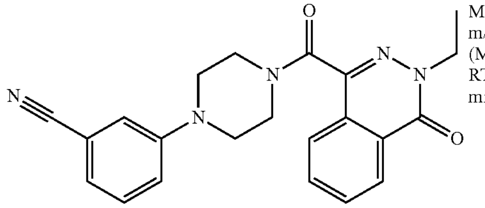 | Method B m/z = 388.3 $(M + H)^+$, RT = 4.38 min | $^1H$ NMR (400 MHz, DMSO) δ 8.36-8.32 (m, 1H), 7.97-7.90 (m, 2H), 7.81 (dd, J = 2.0, 6.6 Hz, 1H), 7.43-7.36 (m, 2H), 7.30 (dd, J = 2.0, 8.6 Hz, 1H), 7.20 (d, J = 7.3 Hz, 1H), 4.18 (q, J = 7.2 Hz, 2H), 3.88 (dd, J = 5.2, 5.2 Hz, 2H), 3.55 (dd, J = 5.1, 5.1 Hz, 2H), 3.42 (dd, J = 5.1, 5.1 Hz, 2H), 3.20 (dd, J = 5.1, 5.1 Hz, 2H), 1.32 (t, J = 7.2 Hz, 3H). |

Example 11: Synthesis of 6-fluoro-2-methyl-4-(4-phenylpiperazine-1-carbonyl)phthalazin-1-one (Compound 156)

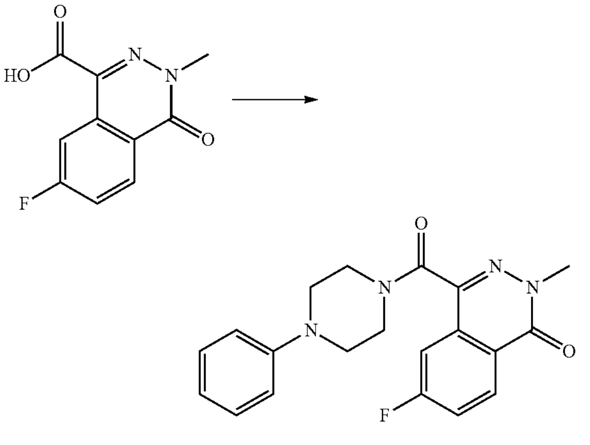

To a solution of 7-fluoro-3-methyl-4-oxo-phthalazine-1-carboxylic acid (Intermediate 6) (120 mg, 0.54 mmol, 1 equiv.) in DMF (4 mL) was added DIPEA (0.094 mL, 0.540 mmol, 1 equiv.) and HATU (205 mg, 0.54 mmol, 1 equiv.). The mixture was stirred at rt for 10 min, then 1-phenylpiperazine (0.083 mL, 0.54 mmol, 1 equiv.) was added and the mixture was stirred at rt for 4 hrs. The mixture was diluted with EtOAc and washed with water, then brine and dried over sodium sulfate, then filtered, the filtrate collected, and the solvent removed. The material was purified by reverse phase HPLC (Sunfire C18 19×150 mm, 10 μm 20-80% $MeCN/H_2O$+0.10% formic acid, 20 mL/min, rt) and the appropriate fractions were combined and lyophilized to yield the title compound (25 mg, 12%) as an off white solid. LCMS: Method B, m/z 367.2 $(M+H)^+$, RT 4.30 min. $^1H$ NMR (400 MHz, DMSO) δ 8.42 (dd, J=5.5, 8.8 Hz, 1H), 7.83-7.76 (m, 1H), 7.58 (dd, J=2.4, 9.2 Hz, 1H), 7.28-7.22 (m, 2H), 6.98 (d, J=7.9 Hz, 2H), 6.84 (dd, J=7.3, 7.3 Hz, 1H), 3.89 (dd, J=5.1, 5.1 Hz, 2H), 3.75 (s, 3H), 3.61 (dd, J=5.0, 5.0 Hz, 2H), 3.34-3.31 (m, 2H), 3.11 (dd, J=5.1, 5.1 Hz, 2H).

Example 12: Synthesis of 3-(4-(7-fluoro-3-methyl-4-oxo-3,4-dihydrophthalazine-1-carbonyl)piperazin-1-yl)benzonitrile (Compound 157)

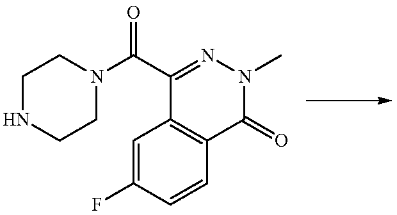

-continued

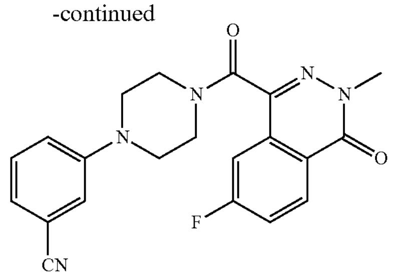

6-fluoro-2-methyl-4-(piperazine-1-carbonyl)phthalazin-1-one (70 mg, 0.241 mmol, 1 equiv.), 3-bromobenzonitrile (66 mg, 0.362 mmol, 1.5 equiv.), DavePhos Pd G3 (18 mg, 0.0241 mmol, 0.1 equiv.) and sodium tert-butoxide (35 mg, 0.362 mmol, 1.5 equiv.) were suspended in CPME (2 mL) in a vial. The vial was sealed, evacuated and flushed with nitrogen twice. The mixture was stirred at 110° C. for 1 hr then allowed to rt. The mixture was partitioned between dichloromethane and water and the phases separated. The organics were collected, and the solvent removed. The material was purified by column chromatography (12 g cartridge, 30-100% ethyl acetate/cyclohexane) and the appropriate fractions were combined, and solvent removed to yield the title compound (56 mg, 59%) as a pale yellow solid. LCMS: Method C, m/z 392.2 $(M+H)^+$, RT 4.21 min. $^1$H NMR (400 MHz, DMSO) δ 8.40 (dd, J=5.5, 8.9 Hz, 1H), 7.81-7.75 (m, 1H), 7.58 (dd, J=2.5, 9.2 Hz, 1H), 7.43-7.37 (m, 2H), 7.30 (dd, J=2.3, 8.4 Hz, 1H), 7.20 (d, J=7.5 Hz, 1H), 3.86 (dd, J=5.2, 5.2 Hz, 2H), 3.73 (s, 3H), 3.60 (dd, J=5.1, 5.1 Hz, 2H), 3.46-3.40 (m, 2H), 3.21 (dd, J=5.1, 5.1 Hz, 2H).

The compounds in Table 9 were made according to the method described in Example 12, using Intermediate 7 and the appropriate aryl halide reagent.

Table 9

Structure and Spectroscopic Data for Compounds 158 to 169 and 208 to 213.

| Compound No. | Structure | LCMS data | NMR data |
|---|---|---|---|
| 158 | 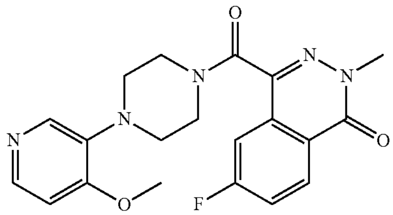 [SMILES: COc1ccncc1N1CCN(C(=O)c2nn(C)c(=O)c3ccc(F)cc23)CC1] | Method B m/z 398.2 $(M + H)^+$ RT 4.82 min | $^1$H NMR (400 MHz, DMSO) δ 8.40 (dd, J = 5.6, 8.8 Hz, 1H), 8.16 (d, J = 5.3 Hz, 1H), 8.06 (s, 1H), 7.78 (dt, J = 2.5, 8.8 Hz, 1H), 7.56 (dd, J = 2.5, 9.1 Hz, 1H), 7.00 (d, J = 5.6 Hz, 1H), 3.89-3.86 (m, 5H), 3.73 (s, 3H), 3.61-3.56 (m, 2H), 3.20-3.15 (m, 2H), 3.01-2.96 (m, 2H). |
| 159 | 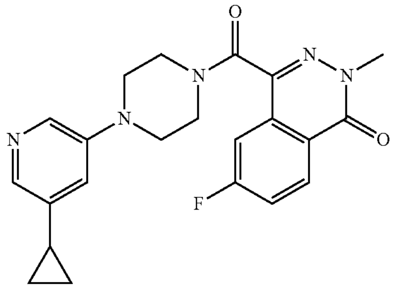 [SMILES: Cn1nc(C(=O)N2CCN(c3cncc(C4CC4)c3)CC2)c2cc(F)ccc2c1=O] | Method A m/z 408.4 $(M + H)^+$ RT 2.88 min | $^1$H NMR (400 MHz, DMSO) δ 8.40 (dd, J = 5.6, 8.8 Hz, 1H), 8.09 (d, J = 2.8 Hz, 1H), 7.86 (d, J = 1.5 Hz, 1H), 7.78 (dt, J = 2.5, 8.7 Hz, 1H), 7.57 (dd, J = 2.5, 9.1 Hz, 1H), 6.96-6.94 (m, 1H), 3.89-3.84 (m, 2H), 3.73 (s, 3H), 3.62-3.57 (m, 2H), 3.39-3.35 (m, 2H), 3.18-3.13 (m, 2H), 1.92-1.85 (m, 1H), 0.98-0.92 (m, 2H), 0.76-0.71 (m, 2H). |
| 160 | 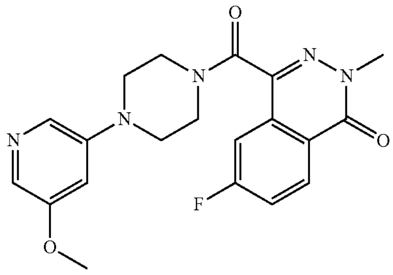 [SMILES: COc1cncc(N2CCN(C(=O)c3nn(C)c(=O)c4ccc(F)cc34)CC2)c1] | Method C m/z 398.7 $(M + H)^+$ RT 2.51 min | $^1$H NMR (400 MHz, DMSO) δ 8.40 (dd, J = 5.5, 8.9 Hz, 1H), 7.94 (d, J = 2.3 Hz, 1H), 7.81-7.75 (m, 2H), 7.58 (dd, J = 2.5, 9.2 Hz, 1H), 6.91 (t, J = 2.4 Hz, 1H), 3.90-3.84 (m, 2H), 3.80 (s, 3H), 3.73 (s, 3H), 3.63-3.58 (m, 2H), 3.42-3.38 (m, 2H), 3.22-3.17 (m, 2H). |

Table 9-continued

Structure and Spectroscopic Data for Compounds 158 to 169 and 208 to 213.

| Compound No. | Structure | LCMS data | NMR data |
| --- | --- | --- | --- |
| 161 | 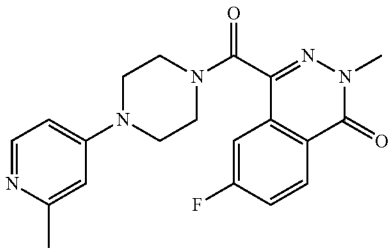 [SMILES: Cc1cc(N2CCN(C(=O)c3nn(C)c(=O)c4ccc(F)cc34)CC2)ccn1] | Method A m/z 382.5 (M + H)+ RT 2.50 min | $^1$H NMR (400 MHz, DMSO) δ 8.40 (dd, J = 5.6, 8.8 Hz, 1H), 8.06 (d, J = 6.1 Hz, 1H), 7.78 (dt, J = 2.4, 8.8 Hz, 1H), 7.59 (dd, J = 2.5, 9.3 Hz, 1H), 6.73 (d, J = 2.5 Hz, 1H), 6.67 (dd, J = 2.5, 6.1 Hz, 1H), 3.85-3.80 (m, 2H), 3.73 (s, 3H), 3.61-3.56 (m, 2H), 3.55-3.50 (m, 2H), 2.33 (s, 3H). 2H obscured by solvent signal |
| 162 | 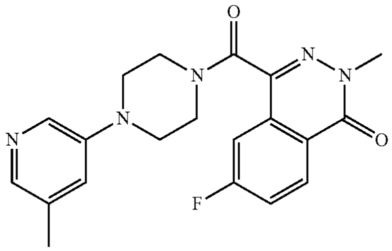 [SMILES: Cc1cncc(N2CCN(C(=O)c3nn(C)c(=O)c4ccc(F)cc34)CC2)c1] | Method B m/z 382.2 (M + H)+ RT 3.68 min | $^1$H NMR (400 MHz, DMSO) δ 8.40 (dd, J = 5.6, 8.8 Hz, 1H), 8.13 (d, J = 2.8 Hz, 1H), 7.88 (d, J = 1.0 Hz, 1H), 7.78 (dt, J = 2.5, 8.8 Hz, 1H), 7.57 (dd, J = 2.5, 9.3 Hz, 1H), 7.19 (s, 1H), 3.89-3.85 (m, 2H), 3.73 (s, 3H), 3.63-3.58 (m, 2H), 3.39-3.34 (m, 2H), 3.18-3.13 (m, 2H), 2.24 (s, 3H). |
| 163 | 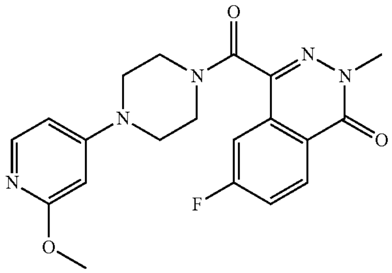 [SMILES: COc1cc(N2CCN(C(=O)c3nn(C)c(=O)c4ccc(F)cc34)CC2)ccn1] | Method A m/z 398.2 (M + H)+ RT 2.55 min | $^1$H NMR (400 MHz, DMSO) δ 8.40 (dd, J = 5.4, 9.0 Hz, 1H), 7.82 (d, J = 6.1 Hz, 1H), 7.78 (dt, J = 2.5, 8.8 Hz, 1H), 7.59 (dd, J = 2.5, 9.3 Hz, 1H), 6.58 (dd, J = 2.3, 6.1 Hz, 1H), 6.14 (d, J = 2.0 Hz, 1H), 3.84-3.79 (m, 2H), 3.77 (s, 3H), 3.73 (s, 3H), 3.59-3.54 (m, 2H), 3.53-3.48 (m, 2H), 3.29-3.26 (m, 2H). |
| 164 | 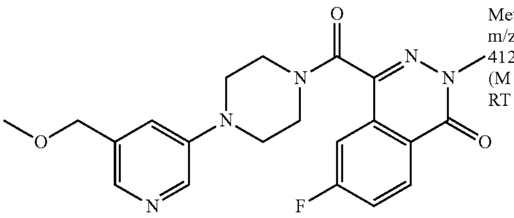 | Method A m/z 412.2 (M + H)+ RT 2.51 min | $^1$H NMR (400 MHz, DMSO) δ 8.40 (dd, J = 5.6, 8.8 Hz, 1H), 8.26 (d, J = 3.0 Hz, 1H), 7.99 (d, J = 1.5 Hz, 1H), 7.78 (dt, J = 2.5, 8.8 Hz, 1H), 7.58 (dd, J = 2.5, 9.1 Hz, 1H), 7.29-7.27 (m, 1H), 4.39 (s, 2H), 3.90-3.85 (m, 2H), 3.73 (s, 3H), 3.64-3.59 (m, 2H), 3.43-3.37 (m, 2H), 3.29 (s, 3H), 3.22-3.16 (m, 2H). |

Table 9-continued

| Structure and Spectroscopic Data for Compounds 158 to 169 and 208 to 213. | | | |
|---|---|---|---|
| Compound No. | Structure | LCMS data | NMR data |
| 165 | 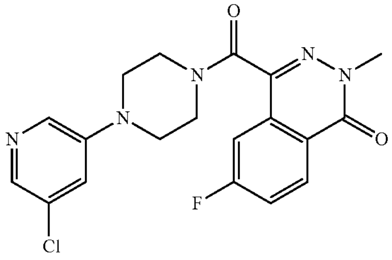 [SMILES: Cn1nc(C(=O)N2CCN(c3cncc(Cl)c3)CC2)c2cc(F)ccc2c1=O] | Method C m/z 402.0 $(M + H)^+$ RT 3.74 min | $^1H$ NMR (400 MHz, DMSO) δ 8.40 (dd, J = 5.5, 8.9 Hz, 1H), 8.29 (d, J = 2.6 Hz, 1H), 8.01 (d, J = 2.0 Hz, 1H), 7.78 (dt, J = 2.5, 8.8 Hz, 1H), 7.58 (dd, J = 2.5, 9.2 Hz, 1H), 7.47 (t, J = 2.3 Hz, 1H), 3.89-3.84 (m, 2H), 3.73 (s, 3H), 3.63-3.59 (m, 2H), 3.50-3.46 (m, 2H), 3.26 (t, J = 5.1 Hz, 2H). |
| 166 | 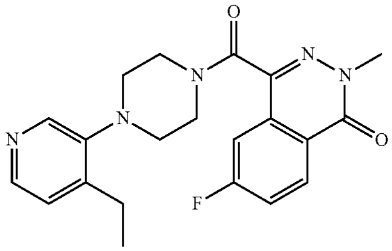 [SMILES: CCc1ccncc1N1CCN(C(=O)c2nn(C)c(=O)c3ccc(F)cc23)CC1] | Method A m/z 396.2 $(M + H)^+$ RT 2.72 min | $^1H$ NMR (400 MHz, DMSO) δ 8.46 (dd, J = 5.6, 8.8 Hz, 1H), 8.37 (s, 1H), 8.30 (d, J = 5.1 Hz, 1H), 7.84 (dt, J = 2.6, 8.8 Hz, 1H), 7.64 (dd, J = 2.5, 9.1 Hz, 1H), 7.30 (d, J = 5.1 Hz, 1H), 3.97-3.92 (m, 2H), 3.79 (s, 3H), 3.68-3.63 (m, 2H), 3.15-3.11 (m, 2H), 2.96-2.91 (m, 2H), 2.74 (q, J = 7.5 Hz, 2H), 1.26 (t, J = 7.5 Hz, 3H). |
| 167 | 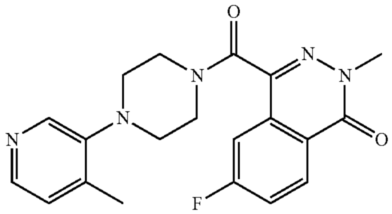 [SMILES: Cc1ccncc1N1CCN(C(=O)c2nn(C)c(=O)c3ccc(F)cc23)CC1] | Method B m/z 382.2 $(M + H)^+$ RT 3.75 min | $^1H$ NMR (400 MHz, DMSO) δ 8.46 (dd, J = 5.6, 8.8 Hz, 1H), 8.31 (s, 1H), 8.22 (d, J = 4.5 Hz, 1H), 7.84 (ddd, J = 8.8, 8.8, 2.5 Hz, 1H), 7.64 (dd, J = 2.4, 9.2 Hz, 1H), 7.25 (d, J = 4.8 Hz, 1H), 3.97-3.92 (m, 2H), 3.79 (s, 3H), 3.68-3.63 (m, 2H), 3.17-3.12 (m, 2H), 2.98-2.93 (m, 2H), 2.35 (s, 3H). |
| 168 | 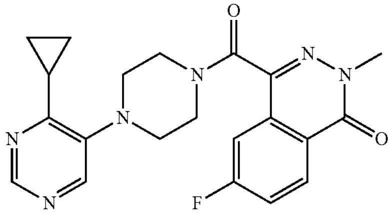 [SMILES: Cn1nc(C(=O)N2CCN(c3cncnc3C3CC3)CC2)c2cc(F)ccc2c1=O] | Method C m/z 409.7 $(M + H)^+$ RT 3.74 min | $^1H$ NMR (400 MHz, DMSO) δ 8.67 (s, 1H), 8.40 (dd, J = 5.5, 8.9 Hz, 1H), 8.35 (s, 1H), 7.79 (dt, J = 2.5, 8.8 Hz, 1H), 7.57 (dd, J = 2.5, 9.2 Hz, 1H), 3.96-3.91 (m, 2H), 3.74 (s, 3H), 3.68-3.63 (m, 2H), 3.23-3.18 (m, 2H), 3.03-2.98 (m, 2H), 2.45-2.38 (m, 1H), 1.12-1.04 (m, 4H). |

Table 9-continued

Structure and Spectroscopic Data for Compounds 158 to 169 and 208 to 213.

| Compound No. | Structure | LCMS data | NMR data |
|---|---|---|---|
| 169 | 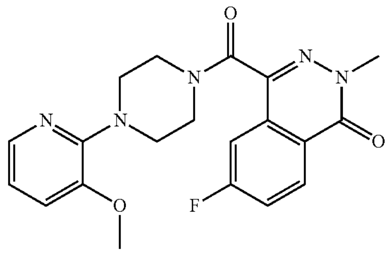 [SMILES: COc1cccnc1N1CCN(C(=O)c2nn(C)c(=O)c3ccc(F)cc23)CC1] | Method A m/z 398.2 (M + H)$^+$ RT 3.12 min | $^1$H NMR (400 MHz, DMSO) δ 8.40 (dd, J = 5.4, 9.0 Hz, 1H), 7.81-7.75 (m, 2H), 7.56 (dd, J = 2.5, 9.1 Hz, 1H), 7.27 (dd, J = 1.3, 8.1 Hz, 1H), 6.92 (dd, J = 4.9, 8.0 Hz, 1H), 3.87-3.82 (m, 2H), 3.80 (s, 3H), 3.73 (s, 3H), 3.59-3.54 (m, 2H), 3.47-3.42 (m, 2H), 3.26-3.23 (m, 2H). |
| 208 | 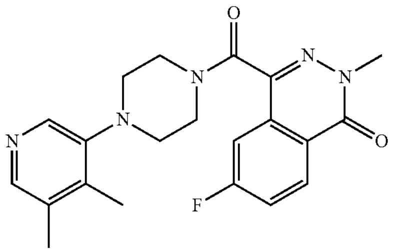 [SMILES: Cc1cncc(N2CCN(C(=O)c3nn(C)c(=O)c4ccc(F)cc34)CC2)c1C] | Method A m/z = 396.3 (M + H)$^+$ RT = 2.63 min | $^1$H NMR (400 MHz, DMSO) δ 8.40 (dd, J = 5.6, 8.8 Hz, 1H), 8.13 (s, 1H), 8.09 (s, 1H), 7.81-7.75 (m, 1H), 7.58 (dd, J = 2.4, 9.2 Hz, 1H), 3.92-3.89 (m, 2H), 3.74 (s, 3H), 3.61 (dd, J = 4.8, 4.8 Hz, 2H), 3.05 (dd, J = 4.9, 4.9 Hz, 2H), 2.85 (dd, J = 4.8, 4.8 Hz, 2H), 2.20 (d, J = 1.5 Hz, 6H). |
| 209 | 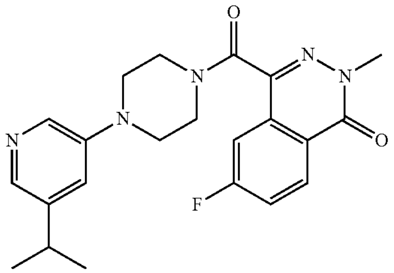 [SMILES: CC(C)c1cncc(N2CCN(C(=O)c3nn(C)c(=O)c4ccc(F)cc34)CC2)c1] | Method B m/z = 410.5 (M + H)$^+$ RT = 4.30 min | $^1$H NMR (400 MHz, DMSO) δ 8.40 (dd, J = 8.4 Hz, 1H), 7.77 (td, J = 8.8, 2.5 Hz, 1H), 7.56 (dd, J = 9.2, 2.6 Hz, 1H), 7.00 (bs, 1H), 6.82-6.77 (m, 2H), 3.84 (t, J = 4.5, 2H), 3.77 (s, 3H), 3.73 (s, 3H), 3.58 (t, J = 4.7 Hz, 2H), 3.42 (t, J = 5.4 Hz, 2H), 3.21 (t, J = 5.53 Hz, 2H). |
| 210 | 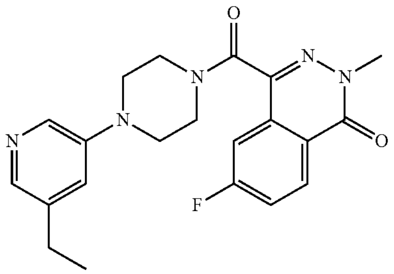 [SMILES: CCc1cncc(N2CCN(C(=O)c3nn(C)c(=O)c4ccc(F)cc34)CC2)c1] | Method A m/z = 396.4 (M + H)$^+$ RT = 2.69 min | $^1$H NMR (400 MHz, DMSO) δ 8.40 (dd, J = 5.6, 8.8 Hz, 1H), 8.14 (d, J = 2.5 Hz, 1H), 7.91 (d, J = 1.5 Hz, 1H), 7.81-7.75 (m, 1H), 7.57 (dd, J = 2.5, 9.1 Hz, 1H), 7.20 (d, J = 2.0 Hz, 1H), 3.87 (dd, J = 5.2, 5.2 Hz, 2H), 3.73 (s, 3H), 3.61 (dd, J = 4.9, 4.9 Hz, 2H), 3.37 (dd, J = 4.9, 4.9 Hz, 2H), 3.17 (dd, J = 5.1, 5.1 Hz, 2H), 2.56 (q, J = 7.2 Hz, 2H), 1.18 (t, J = 7.7 Hz, 3H). |
| 211 | 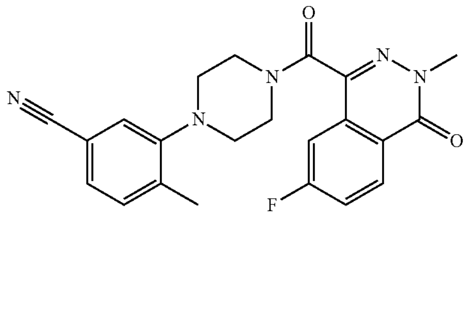 [SMILES: Cc1ccc(C#N)cc1N1CCN(C(=O)c2nn(C)c(=O)c3ccc(F)cc23)CC1] | Method C m/z = 406.2 (M + H)$^+$ RT = 4.59 min | $^1$H NMR (400 MHz, DMSO) δ 8.40 (dd, J = 5.5, 8.9 Hz, 1H), 7.79 (td, J = 2.6, 8.8 Hz, 1H), 7.57 (dd, J = 2.5, 9.2 Hz, 1H), 7.47-7.37 (m, 3H), 3.89 (t, J = 4.6 Hz, 2H), 3.74 (s, 3H), 3.60 (t, J = 4.8 Hz, 2H), 3.03 (t, J = 4.9 Hz, 2H), 2.84 (t, J = 4.8 Hz, 2H), 2.36 (s, 3H). |

Table 9-continued

Structure and Spectroscopic Data for Compounds 158 to 169 and 208 to 213.

| Compound No. | Structure | LCMS data | NMR data |
|---|---|---|---|
| 212 | 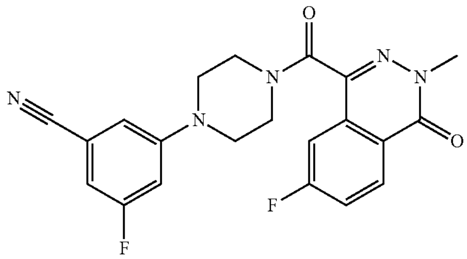 [SMILES: Cn1nc(C(=O)N2CCN(c3cc(F)cc(C#N)c3)CC2)c2cc(F)ccc2c1=O] | Method C m/z = 410 $(M + H)^+$ RT = 4.36 min | $^1H$ NMR (400 MHz, DMSO) δ 8.40 (dd, J = 5.5, 8.9 Hz, 1H), 7.78 (td, J = 2.56, 8.82 Hz, 1H), 7.58 (dd, J = 2.4, 9.3 Hz, 1H), 7.27-7.26 (m, 1H), 7.19-7.10 (m, 2H), 3.84 (t, J = 5.2 Hz, 2H), 3.59 (t, J = 5.1 Hz, 2H), 3.50 (t, J = 5.3 Hz, 2H), 3.28 (t, J = 5.3 Hz, 5H). |
| 213 | 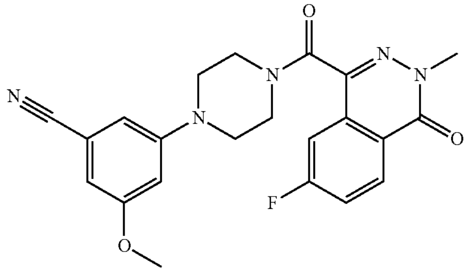 [SMILES: COc1cc(C#N)cc(N2CCN(C(=O)c3nn(C)c(=O)c4ccc(F)cc34)CC2)c1] | Method C m/z = 422.2 $(M + H)^+$ RT = 4.30 min | $^1H$ NMR (400 MHz, DMSO) δ 8.40 (dd, J = 5.5, 8.9 Hz, 1H), 7.78 (td, J = 2.6, 8.8 Hz, 1H), 7.58 (dd, J = 2.5, 9.2 Hz, 1H), 7.00 (d, J = 1.4 Hz, 1H), 6.82-6.77 (m, 2H), 3.87-3.82 (t, J = 4.8 Hz, 2H), 3.78 (s, 3H), 3.73 (s, 3H), 3.58 (t, J = 5.0 Hz, 2H), 3.33 (s, 2H),3.43 (t, J = 35.6 Hz, 1H), 3.21 (t, J = 5.0 Hz, 2H). |

Example 13: Synthesis of 2-methyl-4-(4-phenylpiperazine-1-carbonyl)pyrido[3,4-d]pyridazin-1-one (Compound 170) and 3-methyl-1-(4-phenylpiperazine-1-carbonyl)pyrido[3,4-d]pyridazin-4-one (Compound 171)

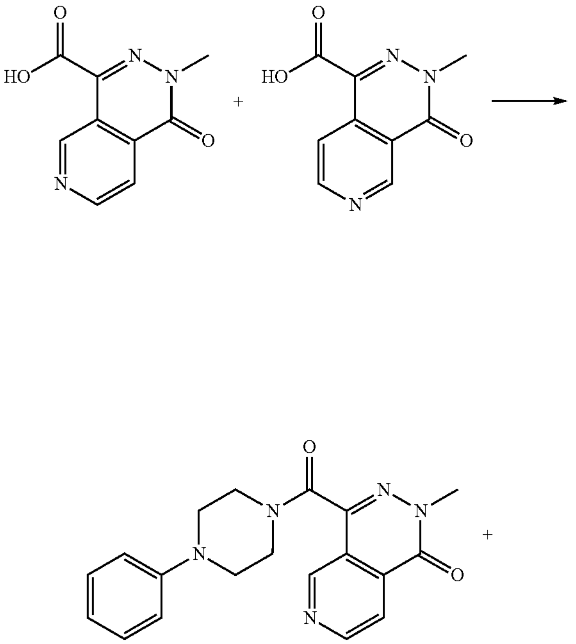

Compound 170

-continued

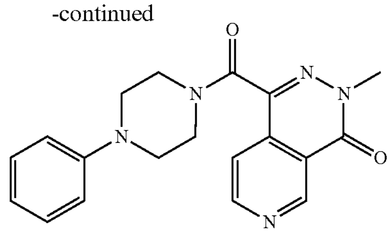

Compound 171

To mixture of 2-methyl-1-oxo-pyrido[3,4-d]pyridazine-4-carboxylic acid hydrochloride and 3-methyl-1-oxo-pyrido[3,4-d]pyridazine-4-carboxylic acid hydrochloride (330 mg, 0.682 mmol, 1 equiv.) (Intermediates 8 and 9), 1-phenylpiperazine (0.16 mL, 1.02 mmol, 1.5 equiv.) and DIPEA (0.24 mL, 1.37 mmol, 2 equiv.) in DMF (2 mL) was added HATU (389 mg, 1.02 mmol, 1.5 equiv.) and the mixture stirred at rt for 3 hr. The reaction mixture was partitioned between water and EtOAc, the phases separated, and the organic phases were washed with water, then with brine and dried over sodium sulfate. The mixture was filtered, the filtrate collected, and the solvent removed. The material was purified by reverse phase HPLC (Luna Phenyl-Hexyl 21.2×150 mm, 10 μm, 40-100% $MeOH/H_2O$+0.1% formic acid, 20 mL/min, rt) and then further by SFC (YMC Amylose-C 20×250 mm, 5 μm 40/60 MeOH+0.1% $NH_4OH/CO_2$, 100 mL/min, 120 bar, 40° C., DAD 250 nm) and the appropriate fractions were combined and lyophilized to yield the title compounds Example 13 (21 mg, 17%) and Example 14 (20 mg, 16%) as off white solids.

Compound 170: LCMS: Method A, m/z 350.2 $[M+H]^+$, RT 3.90 min. $^1H$ NMR (DMSO-d6, 400 MHz) δ: 9.18 (s, 1H), 9.02 (d, J=5.3 Hz, 1H), 8.17 (d, J=5.3 Hz, 1H), 7.24

(dd, J=7.5, 8.5 Hz, 2H), 6.99-6.95 (m, 2H), 6.82 (t, J=7.3 Hz, 1H), 3.92-3.87 (m, 2H), 3.75 (s, 3H), 3.66 (t, J=5.1 Hz, 2H), 3.3 (m, 2H obscured by water), 3.13-3.08 (m, 2H).

Compound 171: LCMS: Method A, m/z 350.2 $[M+H]^+$, RT 3.88 min. $^1H$ NMR (DMSO-d6, 400 MHz) δ: 9.53 (s, 1H), 9.03 (d, J=5.6 Hz, 1H), 7.71 (d, J=5.6 Hz, 1H), 7.26-7.21 (m, 2H), 6.99-6.95 (m, 2H), 6.82 (t, J=7.2 Hz, 1H), 3.88 (t, J=5.2 Hz, 2H), 3.76-3.75 (m, 3H), 3.63 (t, J=5.1 Hz, 2H), 3.3 (m, 2H obscured by water), 3.09 (t, J=4.9 Hz, 2H).

Example 14: Synthesis of 1-(4-(3-methoxyphenyl)piperazine-1-carbonyl)-3-methylpyrido[3,4-d]pyridazin-4(3H)-one (Compound 172) and 4-(4-(3-methoxyphenyl)piperazine-1-carbonyl)-2-methylpyrido[3,4-d]pyridazin-1(2H)-one (Compound 173)

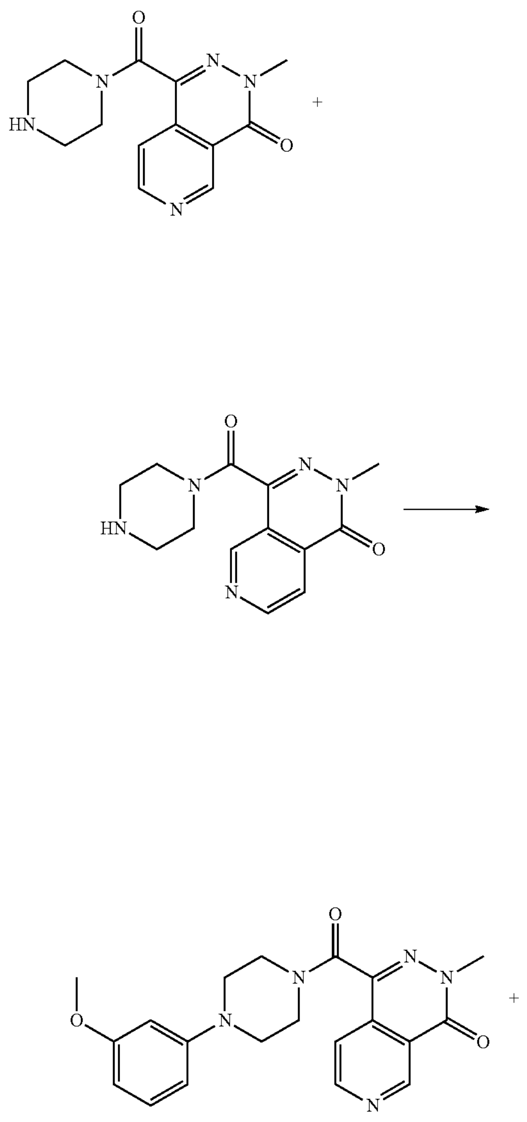

Compound 172

-continued

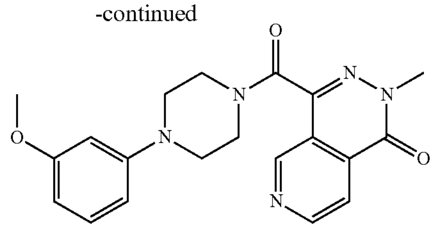

Compound 173

To a suspension of 2-methyl-4-(piperazine-1-carbonyl)pyrido[3,4-d]pyridazin-1-one and 3-methyl-1-(piperazine-1-carbonyl)pyrido[3,4-d]pyridazin-4-one (70 mg, 0.256 mmol, 1 equiv.) (Intermediates 10 and 11), 3-bromoanisole (0.049 mL, 0.384 mmol, 1.5 equiv.) in CPME (2.5 mL) was added sodium tert-butoxide (49 mg, 0.512 mmol, 2.0 equiv.) and DavePhos PdG3 (20 mg, 0.0256 mmol, 0.1 equiv.). The suspension was degassed with nitrogen, then stirred at 90° C. for 1.5 hrs and allowed to rt. The mixture was diluted with dichloromethane, filtered, the filtrate collected, and the solvent removed. The material was purified by column chromatography (12 g cartridge, 15 μM silica, 0-50% % [3:1 ethyl acetate:IMS]/cyclohexane) and the appropriate fractions were combined, and the solvent removed. The isomers were separated by SFC (LUX Amylose-1 10×250 mm, 5 μm column, 55/45 MeOH+0.1% $NH_4OH/CO_2$, 15 mL/min, 120 bar, 40° C., DAD 250 nm) to yield 1-[4-(3-methoxyphenyl)piperazine-1-carbonyl]-3-methyl-pyrido[3,4-d]pyridazin-4-one (8.2 mg, 17%) and 4-[4-(3-methoxyphenyl)piperazine-1-carbonyl]-2-methyl-pyrido[3,4-d]pyridazin-1-one (19 mg, 38%) as off-white solids.

Compound 172: LCMS: Method A, m/z 380.5 $(M+H)^+$, RT 3.85 min. $^1H$ NMR (400 MHz, DMSO) δ 9.53 (s, 1H), 9.03 (d, J=5.6 Hz, 1H), 7.71 (dd, J=1.0, 5.6 Hz, 1H), 7.13 (dd, J=8.2, 8.2 Hz, 1H), 6.55 (dd, J=2.0, 8.1 Hz, 1H), 6.49 (dd, J=2.3, 2.3 Hz, 1H), 6.41 (dd, J=2.0, 8.1 Hz, 1H), 3.86 (dd, J=5.1, 5.1 Hz, 2H), 3.75 (s, 3H), 3.71 (s, 3H), 3.61 (dd, J=5.1, 5.1 Hz, 2H), 3.33-3.28 (m, 2H), 3.09 (dd, J=5.1, 5.1 Hz, 2H).

Compound 173: LCMS: Method A, m/z 380.5 $(M+H)^+$, RT 3.87 min. $^1H$ NMR (400 MHz, DMSO) δ 9.18 (s, 1H), 9.02 (d, J=5.3 Hz, 1H), 8.17 (dd, J=1.0, 5.3 Hz, 1H), 7.13 (dd, J=8.1, 8.1 Hz, 1H), 6.56 (dd, J=1.8, 8.1 Hz, 1H), 6.49 (dd, J=2.3, 2.3 Hz, 1H), 6.41 (dd, J=1.8, 8.1 Hz, 1H), 3.88 (dd, J=5.2, 5.2H, 2 Hz), 3.75 (s, 3H), 3.71 (s, 3H), 3.64 (dd, J=5.1, 5.1 Hz, 2H), 3.33-3.29 (m, 2H), 3.10 (dd, J=5.1, 5.1 Hz, 2H)

The compounds in Table 10 were made according to the method described in Example 14, using Intermediates 9 and 10 and the appropriate aryl halide reagent.

TABLE 10

| Structure and Spectroscopic Data for Compounds 174 to 181 and 214 to 223. | | | |
|---|---|---|---|
| Compound No. | Structure | LCMS data | NMR data |
| 174 | 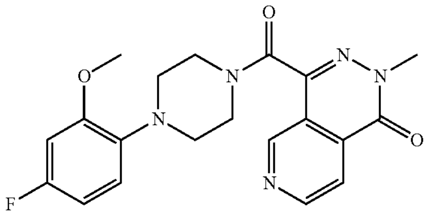 [SMILES: COc1cc(F)ccc1N1CCN(C(=O)c2nn(C)c(=O)c3ccncc23)CC1] | Method A m/z 398.2 $(M + H)^+$ RT 3.92 min | $^1H$ NMR (400 MHz, DMSO) δ 9.17 (d, J = 0.8 Hz, 1H), 9.02 (d, J = 5.3 Hz, 1H), 8.16 (dd, J = 0.8, 5.3 Hz, 1H), 6.94-6.85 (m, 2H), 6.68 (dt, J = 2.8, 8.5 Hz, 1H), 3.90-3.85 (m, 2H), 3.80 (s, 3H), 3.75 (s, 3H), 3.65-3.60 (m, 2H), 3.09-3.04 (m, 2H), 2.89-2.84 (m, 2H). |
| 175 | 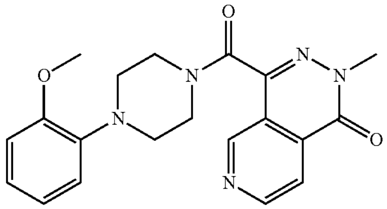 [SMILES: COc1ccccc1N1CCN(C(=O)c2nn(C)c(=O)c3ccncc23)CC1] | Method A m/z 380.2 $(M + H)^+$ RT 3.77 min | $^1H$ NMR (400 MHz, DMSO) δ 9.22 (d, J = 0.7 Hz, 1H), 9.07 (d, J = 5.3 Hz, 1H), 8.21 (dd, J = 0.8, 5.4 Hz, 1H), 7.05-6.89 (m, 4H), 3.95-3.91 (m, 2H), 3.83 (s, 3H), 3.79 (s, 3H), 3.70-3.65 (m, 2H), 3.18-3.13 (m, 2H), 2.98-2.93 (m, 2H). |
| 176 | 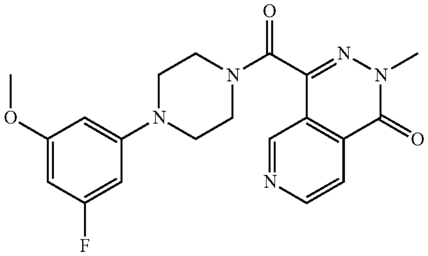 [SMILES: COc1cc(F)cc(N2CCN(C(=O)c3nn(C)c(=O)c4ccncc34)CC2)c1] | Method A m/z 398.2 $(M + H)^+$ RT 4.15 min | $^1H$ NMR (400 MHz, DMSO) δ 9.19 (d, J = 0.8 Hz, 1H), 9.02 (d, J = 5.3 Hz, 1H), 8.16 (dd, J = 1.0, 5.3 Hz, 1H), 6.40 (td, J = 2.1, 12.5 Hz, 1H), 6.32-6.30 (m, 1H), 6.24 (td, J = 2.0, 10.9 Hz, 1H), 3.88-3.84 (m, 2H), 3.75 (s, 3H), 3.72 (s, 3H), 3.66-3.61 (m, 2H), 3.39-3.34 (m, 2H), 3.18-3.13 (m, 2H). |
| 177 | 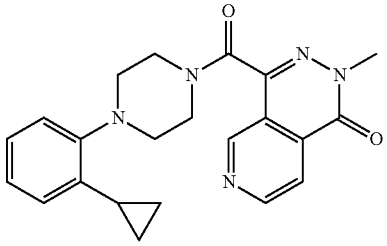 [SMILES: Cn1nc(C(=O)N2CCN(c3ccccc3C3CC3)CC2)c2cnccc2c1=O] | Method A m/z 390.2 $(M + H)^+$ RT 4.78 min | $^1H$ NMR (400 MHz, DMSO) δ 9.19 (d, J = 1.0 Hz, 1H), 9.03 (d, J = 5.3 Hz, 1H), 8.17 (dd, J = 0.8, 5.3 Hz, 1H), 7.13-7.08 (m, 1H), 7.03 (dd, J = 1.4, 8.0 Hz, 1H), 6.97 (dt, J = 1.1, 7.4 Hz, 1H), 6.79 (dd, J = 1.4, 7.7 Hz, 1H), 3.96-3.91 (m, 2H), 3.75 (s, 3H), 3.70-3.65 (m, 2H), 3.13-3.08 (m, 2H), 2.92-2.88 (m, 2H), 2.32-2.24 (m, 1H), 1.00-0.94 (m, 2H), 0.70-0.65 (m, 2H). |
| 178 | 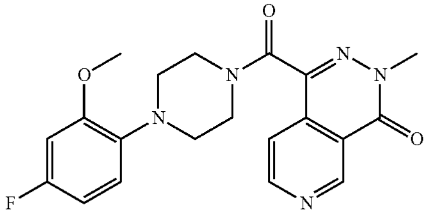 [SMILES: COc1cc(F)ccc1N1CCN(C(=O)c2nn(C)c(=O)c3cnccc23)CC1] | Method A m/z 398.2 $(M + H)^+$ RT 3.90 min | $^1H$ NMR (400 MHz, DMSO) δ 9.53 (s, 1H), 9.04 (d, J = 5.3 Hz, 1H), 7.70 (dd, J = 0.7, 5.5 Hz, 1H), 6.93-6.85 (m, 2H), 6.68 (dt, J = 2.8, 8.5 Hz, 1H), 3.89-3.83 (m, 2H), 3.80 (s, 3H), 3.75 (s, 3H), 3.62-3.57 (m, 2H), 3.07-3.02 (m, 2H), 2.87-2.82 (m, 2H). |
| 179 | 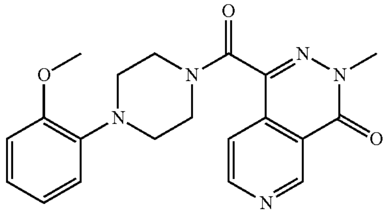 [SMILES: COc1ccccc1N1CCN(C(=O)c2nn(C)c(=O)c3cnccc23)CC1] | Method A m/z 380.2 $(M + H)^+$ RT 3.76 min | $^1H$ NMR (400 MHz, DMSO) δ 9.57 (d, J = 0.7 Hz, 1H), 9.08 (d, J = 5.3 Hz, 1H), 7.74 (dd, J = 0.9, 5.4 Hz, 1H), 7.05-6.89 (m, 4H), 3.94-3.89 (m, 2H), 3.82 (s, 3H), 3.79 (s, 3H), 3.67-3.62 (m, 2H), 3.17-3.11 (m, 2H), 2.96-2.91 (m, 2H). |

TABLE 10-continued

Structure and Spectroscopic Data for Compounds 174 to 181 and 214 to 223.

| Compound No. | Structure | LCMS data | NMR data |
| --- | --- | --- | --- |
| 180 | 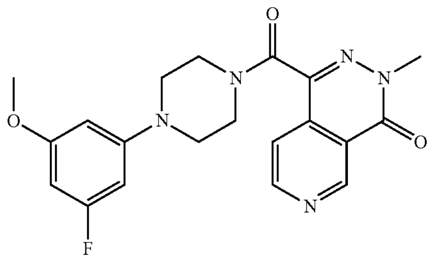 [SMILES: COc1cc(F)cc(N2CCN(C(=O)c3nn(C)c(=O)c4cnccc34)CC2)c1] | Method A m/z 398.2 (M + H)$^+$ RT 4.13 min | $^1$H NMR (400 MHz, DMSO) δ 9.53 (d, J = 0.8 Hz, 1H), 9.02 (d, J = 5.3 Hz, 1H), 7.71 (dd, J = 1.0, 5.6 Hz, 1H), 6.40 (td, J = 2.2, 12.5 Hz, 1H), 6.32-6.29 (m, 1H), 6.24 (td, J = 2.1, 10.7 Hz, 1H), 3.87-3.82 (m, 2H), 3.75 (s, 3H), 3.72 (s, 3H), 3.62-3.58 (m, 2H), 3.37-3.33 (m, 2H), 3.16-3.11 (m, 2H). |
| 181 | 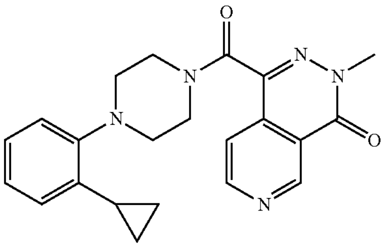 [SMILES: Cn1nc(C(=O)N2CCN(c3ccccc3C3CC3)CC2)c2ccncc2c1=O] | Method A m/z 390.2 (M + H)$^+$ RT 4.75 min | $^1$H NMR (400 MHz, DMSO) δ 9.53 (d, J = 1.0 Hz, 1H), 9.05 (d, J = 5.6 Hz, 1H), 7.71 (dd, J = 0.9, 5.4 Hz, 1H), 7.13-7.08 (m, 1H), 7.05-6.95 (m, 2H), 6.79 (dd, J = 1.5, 7.8 Hz, 1H), 3.94-3.90 (m, 2H), 3.75 (s, 3H), 3.66-3.62 (m, 2H), 3.11-3.07 (m, 2H), 2.90-2.87 (m, 2H), 2.29-2.22 (m, 1H), 0.99-0.94 (m, 2H), 0.69-0.64 (m, 2H). |
| 214 | 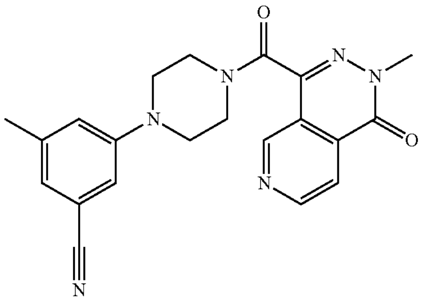 | Method C m/z = 389.3 (M + H)$^+$ RT = 4.04 min | $^1$H NMR (400 MHz, DMSO) δ 9.19 (d, J = 0.9 Hz, 1H), 9.02 (d, J = 5.3 Hz, 1H), 8.17 (dd, J = 0.9, 5.3 Hz, 1H), 7.19 (s, 1H), 7.15 (s, 1H), 7.04 (s, 1H), 3.87 (t, J = 5.2 Hz, 2H), 3.75 (s, 3H), 3.65 (t, J = 5.0 Hz, 2H), 3.42 (t, J = 5.3 Hz, 2H), 3.21 (t, J = 5.3 Hz, 2H), 2.29 (s, 3H). |
| 215 | 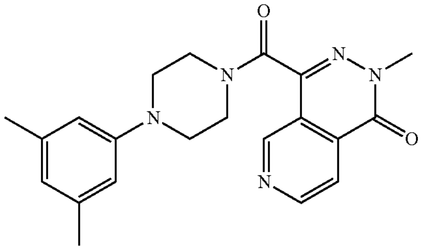 | Method C m/z = 378.7 (M + H)$^+$ RT = 4.40 min | $^1$H NMR (400 MHz, DMSO) δ 9.18 (d, J = 0.9 Hz, 1H), 9.02 (d, J = 5.3 Hz, 1H), 8.17 (dd, J = 1.0, 5.3 Hz, 1H), 6.58 (s, 2H), 6.47 (s, 1H), 3.87 (t, J = 5.2 Hz, 2H), 3.75 (s, 3H), 3.63 (t, J = 5.0 Hz, 2H), 3.28 (t, J = 5.4 Hz, 2H), 3.06 (t, J = 5.1 Hz, 2H), 2.20 (s, 6H). |
| 216 | 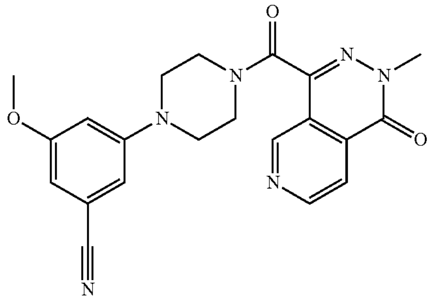 [SMILES: COc1cc(C#N)cc(N2CCN(C(=O)c3nn(C)c(=O)c4ccncc34)CC2)c1] | Method A m/z = 405.4 (M + H)$^+$ RT = 3.90 min | $^1$H NMR (400 MHz, DMSO) δ 9.19 (d, J = 0.8 Hz, 1H), 9.02 (d, J = 5.3 Hz, 1H), 8.17 (dd, J = 1.0, 5.3 Hz, 1H), 7.02-7.00 (m, 1H), 6.82-6.78 (m, 2H), 3.89-3.84 (m, 2H), 3.78 (s, 3H), 3.75 (m, 3H), 3.65 (t, J = 4.9 Hz, 2H), 3.46-3.41 (t, J = 5.5 Hz, 2H), 3.22 (t, J = 5.5 Hz, 2H). |

TABLE 10-continued

| Compound No. | Structure | LCMS data | NMR data |
| --- | --- | --- | --- |
| Structure and Spectroscopic Data for Compounds 174 to 181 and 214 to 223. | | | |
| 217 | 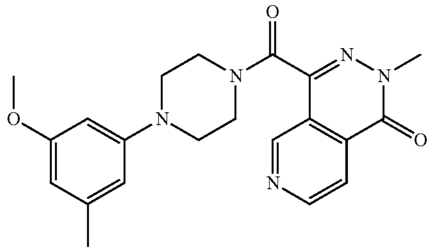 [SMILES: COc1cc(C)cc(N2CCN(C(=O)c3nn(C)c(=O)c4ccncc34)CC2)c1] | Method A m/z = 394.5 (M + H)+ RT = 4.15 min | $^{1}H$ NMR (400 MHz, DMSO) δ 9.18 (d, J = 0.8 Hz, 1H), 9.02 (d, J = 5.3 Hz, 1H), 8.17 (dd, J = 1.0, 5.3 Hz, 1H), 6.38 (s, 1H), 6.30 (dd, J = 2.1, 2.1 Hz, 1H), 6.24 (s, 1H), 3.87 (t, J = 5.2 Hz, 2H), 3.75 (s, 3H), 3.69 (s, 3H), 3.63 (t, J = 5.1 Hz, 2H), 3.32 (s, 2H), 3.08 (t, J = 5.1 Hz, 2H), 2.22 (s, 3H). A signal of two piperazine protons is obscured by water peak. |
| 218 | 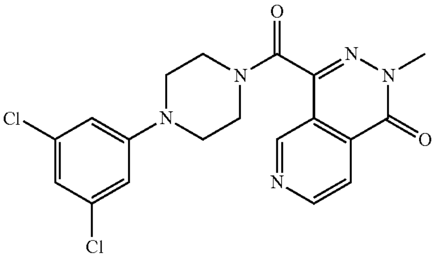 [SMILES: Cn1nc(C(=O)N2CCN(c3cc(Cl)cc(Cl)c3)CC2)c2cnccc2c1=O] | Method A m/z = 420 (M + H)+ RT = 5.00 mir | $^{1}H$ NMR (400 MHz, DMSO) δ 9.20 (d, J = 0.9 Hz, 1H), 9.03 (d, J = 5.3 Hz, 1H), 8.17 (dd, J = 1.0, 5.3 Hz, 1H), 6.99 (d, J = 1.8 Hz, 2H), 6.91 (t, J = 1.7 Hz, 1H), 3.86 (t, J = 5.2 Hz, 2H), 3.76 (s, 3H), 3.64 (t, J = 5.1 Hz, 2H), 3.46 (t, J = 5.2 Hz, 2H), 3.24 (s, J = 5.2 Hz, 2H). |
| 219 | 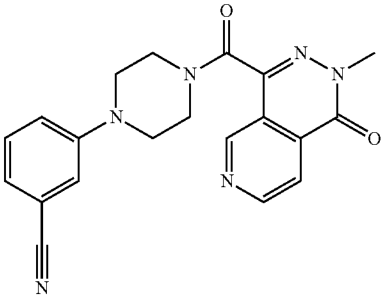 [SMILES: Cn1nc(C(=O)N2CCN(c3cccc(C#N)c3)CC2)c2cnccc2c1=O] | Method A m/z = 375.1 (M + H)+ RT = 3.79 min | $^{1}H$ NMR (400 MHz, DMSO) δ 9.19 (d, J = 1.0 Hz, 1H), 9.02 (d, J = 5.3 Hz, 1H), 8.16 (dd, J = 1.0, 5.3 Hz, 1H), 7.44-7.37 (m, 2H), 7.31 (dd, J = 2.1, 8.3 Hz, 1H), 7.20 (d, J = 7.5 Hz, 1H), 3.88 (t, J = 5.2 Hz, 2H), 3.75 (s, 3H), 3.66 (t, J = 5.1 Hz, 2H), 3.43 (t, J = 5.8 Hz, 2H), 3.23 (t, J = 5.2 Hz, 2H). |
| 220 | 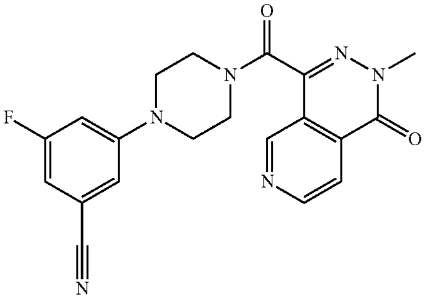 [SMILES: Cn1nc(C(=O)N2CCN(c3cc(F)cc(C#N)c3)CC2)c2cnccc2c1=O] | Method A m/z = 393.3 (M + H)+ RT = 4.04 min | $^{1}H$ NMR (400 MHz, DMSO) δ 9.20 (d, J = 1.0 Hz, 1H), 9.02 (d, J = 5.3 Hz, 1H), 8.16 (dd, J = 1.0, 5.3 Hz, 1H), 7.27 (t, J = 1.1 Hz, 1H), 7.17 (td, J = 2.3, 12.7 Hz, 1H), 7.11 (td, J = 1.0, 8.2 Hz, 1H), 3.86 (t, J = 5.3 Hz, 2H), 3.75 (s, 3H), 3.65 (t, J = 5.3 Hz, 2H), 3.50 (t, J = 5.3 Hz, 2H), 3.27 (t, J = 4.3 Hz, 2H). |
| 221 | 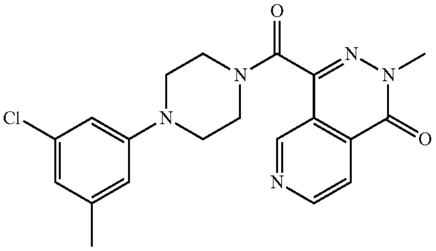 [SMILES: Cc1cc(Cl)cc(N2CCN(C(=O)c3nn(C)c(=O)c4ccncc34)CC2)c1] | Method A m/z = 398.4 (M + H)+ RT = 4.77 min | $^{1}H$ NMR (400 MHz, DMSO) δ 9.19 (d, J = 0.9 Hz, 1H), 9.03 (d, J = 5.3 Hz, 1H), 8.17 (dd, J = 1.0, 5.3 Hz, 1H), 6.80 (dd, J = 1.9, 1.9 Hz, 1H), 6.76 (s, 1H), 6.68 (s, 1H), 3.87 (t, J = 5.1 Hz, 2H), 3.76 (s, 3H), 3.64 (t, J = 5.1 Hz, 2H), 3.33 (s, 2H), 3.15 (t, J = 5.1 Hz, 2H), 2.25 (s, 3H). A signal of two piperazine protons is obscured by water peak. |

TABLE 10-continued

Structure and Spectroscopic Data for Compounds 174 to 181 and 214 to 223.

| Compound No. | Structure | LCMS data | NMR data |
|---|---|---|---|
| 222 | 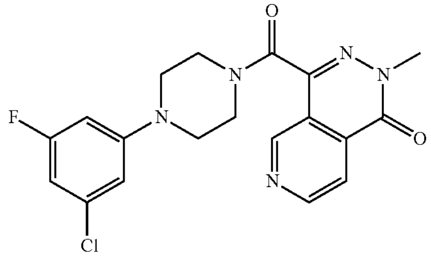 | Method A m/z = 402.5 (M + H)$^+$ RT = 4.66 min | $^1$H NMR (400 MHz, DMSO) δ 9.19 (s, 1H), 9.02 (d, J = 5.3 Hz, 1H), 8.16 (d, J = 5.3 Hz, 1H), 6.86-6.77 (m, 2H), 6.72 (d, J = 8.3 Hz, 1H), 3.85 (t, J = 5.1 Hz, 2H), 3.75 (s, 3H), 3.64 (t, J = 4.9 Hz, 2H), 3.44 (t, J = 5.2 Hz, 2H), 3.26-3.20 (m, 2H). |
| 223 | 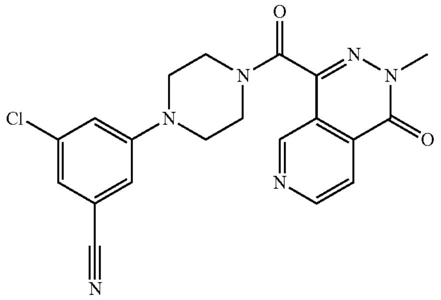 [SMILES: Cn1nc(C(=O)N2CCN(c3cc(Cl)cc(C#N)c3)CC2)c2cnccc2c1=O] | Method A m/z = 409.1 (M + H)$^+$ RT = 4.33 min | $^1$H NMR (400 MHz, DMSO) δ 9.19 (s, 1H), 9.02 (d, J = 5.3 Hz, 1H), 8.16 (d, J = 5.4 Hz, 1H), 7.40 (s, 1H), 7.34 (s, 1H), 7.30 (s, 1H), 3.86 (t, J = 4.9 Hz, 2H), 3.75 (s, 3H), 3.65 (t, J = 4.9 Hz, 2H), 3.50 (t, J = 4.6 Hz, 2H), 3.32 (s, 2H). A signal of two piperazine protons is obscured by water peak. |

Example 15: Synthesis of 5-(4-(3-methoxyphenyl) piperazine-1-carbonyl)-7-methylpyrido[2,3-d] pyridazin-8(7H)-one (Compound 182)

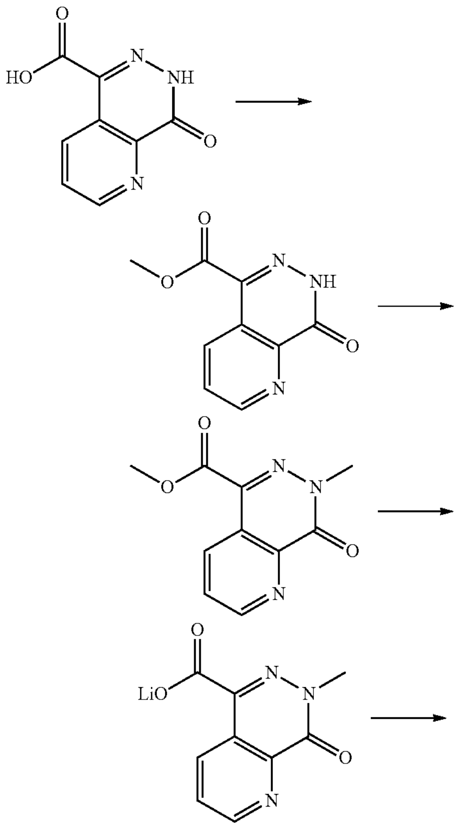

-continued

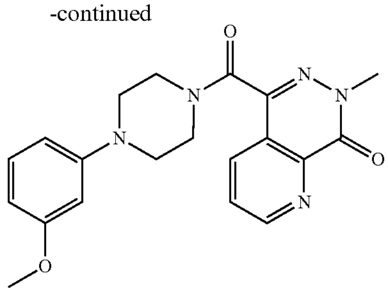

Step 1: Synthesis of Methyl 8-oxo-7,8-dihydropyrido[2, 3-d]pyridazine-5-carboxylate: To a suspension of 8-oxo-7H-pyrido[2,3-d]pyridazine-5-carboxylic acid (975 mg, 5.10 mmol, 1 equiv.) in methyl alcohol (35 mL) was added sulfuric acid (2.2 mL, 40.8 mmol, 8 equiv.) and the mixture was stirred at 50° C. for 6 hrs until all the solid had dissolved and the mixture was allowed to rt. The mixture was diluted with dichloromethane, basified with 2M sodium carbonate and the phases were separated. The aqueous was further extracted with dichloromethane twice. The organics were combined, washed with brine, dried with sodium sulfate and filtered. The organics collected and the solvent was removed to yield the title compound (667 mg, 64%) as a light beige solid.

Step 2: Synthesis of Methyl 7-methyl-8-oxo-7,8-dihydro-pyrido[2,3-d]pyridazine-5-carboxylate: To a solution of methyl 8-oxo-7H-pyrido[2,3-d]pyridazine-5-carboxylate (970 mg, 4.73 mmol, 1 equiv.) in acetonitrile (35 mL) was added cesium carbonate (2003 mg, 6.15 mmol, 1.3 equiv.) followed by iodomethane (0.32 mL, 5.20 mmol, 1.1 equiv.) and the mixture was stirred at 80° C. for 1.5 hrs then allowed to rt. The mixture was partitioned between dichloromethane and brine. The phases were separated, and the organics were collected and the solvent removed. The material was triturated with ca. 40:1 diethyl ether:methanol, filtered and the solid collected and dried to yield the title compound (881 mg, 85%) as a beige solid.

Step 3: Synthesis of Lithium 7-methyl-8-oxo-7,8-dihydropyrido[2,3-d]pyridazine-5-carboxylate: To a suspension of methyl 7-methyl-8-oxo-pyrido[2,3-d]pyridazine-5-carboxylate (878 mg, 4.01 mmol, 1 equiv.) in tetrahydrofuran (16 mL) and methyl alcohol (16 mL) was added 2 M lithium hydroxide (2.2 mL, 4.41 mmol, 1.1 equiv.) and the mixture was stirred at rt for 2 hrs. The mixture was filtered and the solid collected and dried to yield the title compound (699 mg, 82%) as a white solid.

Step 4: Synthesis of 5-(4-(3-methoxyphenyl)piperazine-1-carbonyl)-7-methylpyrido[2,3-d]pyridazin-8(7H)-one: To a suspension of lithium;7-methyl-8-oxo-pyrido[2,3-d]pyridazine-5-carboxylate (74 mg, 0.351 mmol, 1 equiv.) in DMF (3 mL) was added triethylamine (0.15 mL, 1.05 mmol, 3 equiv.) followed by HATU (240 mg, 0.631 mmol, 1.8 equiv.) and the mixture stirred at rt for 10 min, then 1-(3-methoxyphenyl)piperazine (0.059 mL, 0.344 mmol, 0.98 equiv.) was added and the mixture was stirred at rt for 3 hrs. The mixture was partitioned between dichloromethane and 5% aq. lithium chloride and the phases separated. The organics were collected, and the solvent removed. The material was purified by reverse phase HPLC (Xbridge Phenyl 19×150 mm, 10 μm 40-100% MeOH/$H_2O$ (10 mM $NH_4CO_3$), 20 mL/min, rt) and the appropriate fractions were combined and lyophilized to yield the title compound (42 mg, 32%) as an off white solid. LCMS: Method B, m/z=380.2 $(M+H)^+$, RT=3.71 min. $^1H$ NMR (400 MHz, DMSO) δ 9.14 (dd, J=1.5, 4.3 Hz, 1H), 8.26 (dd, J=1.5, 8.3 Hz, 1H), 7.93 (dd, J=4.3, 8.3 Hz, 1H), 7.15 (t, J=8.0 Hz, 1H), 6.57 (dd, J=1.9, 8.1 Hz, 1H), 6.50 (t, J=2.4 Hz, 1H), 6.43 (dd, J=1.9, 8.1 Hz, 1H), 3.91-3.85 (m, 2H), 3.78 (s, 3H), 3.73 (s, 3H), 3.66-3.60 (m, 2H), 3.34-3.28 (m, 2H), 3.13-3.07 (m, 2H).

The compounds in Table 11 were made according to the method described in Example 15, using the appropriate aryl piperazine reagent.

Example 16: Synthesis of 5-(4-(3-fluoro-5-methoxyphenyl)piperazine-1-carbonyl)-7-methylpyrido[2,3-d]pyridazin-8(7H)-one (Compound 184)

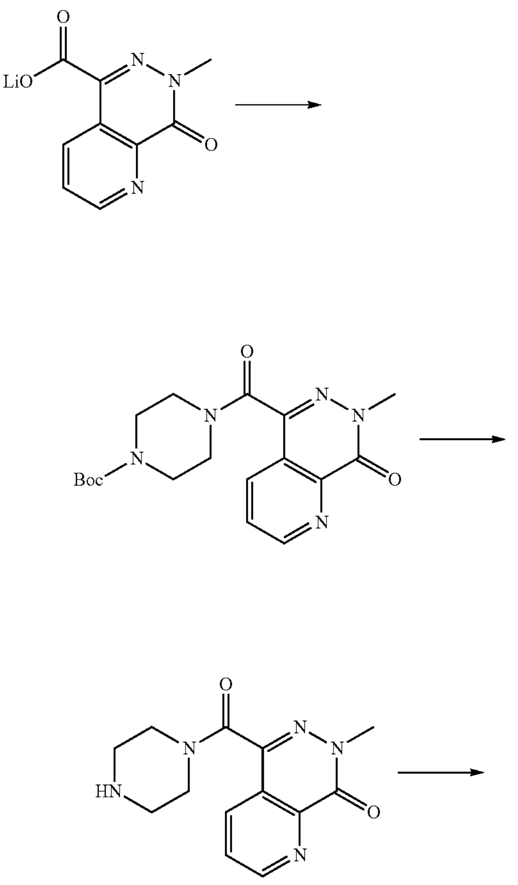

TABLE 11

| Structure and Spectroscopic Data for Compound 183. | | | |
|---|---|---|---|
| Compound No. | Structure | LCMS data | NMR data |
| 183 | 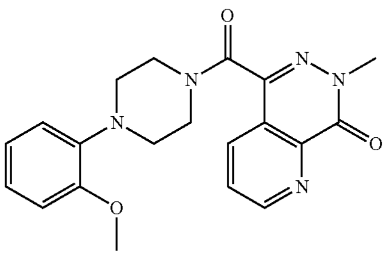 [SMILES: COc1ccccc1N1CCN(C(=O)c2nn(C)c(=O)c3ncccc23)CC1] | Method B m/z 380.4 $(M + H)^+$ RT 3.62 min | $^1H$ NMR (400 MHz, DMSO) δ 9.12 (dd, J = 1.6, 4.4 Hz, 1H), 8.24 (dd, J = 1.5, 8.3 Hz, 1H), 7.92 (dd, J = 4.4, 8.2 Hz, 1H), 7.01-6.93 (m, 2H), 6.92-6.85 (m, 2H), 3.89-3.85 (m, 2H), 3.78 (s, 3H), 3.76 (s, 3H), 3.63-3.58 (m, 2H), 3.12-3.07 (m, 2H), 2.91-2.87 (m, 2H). |

-continued

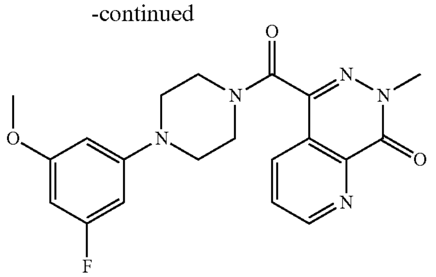

Step 1: Synthesis of tert-butyl 4-(7-methyl-8-oxo-7,8-dihydropyrido[2,3-d]pyridazine-5-carbonyl)piperazine-1-carboxylate: To a suspension of lithium 7-methyl-8-oxo-pyrido[2,3-d]pyridazine-5-carboxylate (230 mg, 1.09 mmol, 1 equiv.) in DMF (5 mL) was added triethylamine (0.46 mL, 3.27 mmol, 3 equiv.) followed by HATU (746 mg, 1.96 mmol, 1.8 equiv.) and the mixture stirred at rt for 10 min, then 1-Boc-piperazine (264 mg, 1.42 mmol, 1.3 equiv.) was added and stirring was continued for 18 hrs. The mixture was partitioned between ethyl acetate and 5% aq. lithium chloride and the phases separated. The aqueous was further extracted with ethyl acetate and the organics combined. The organics were washed with brine, dried with sodium sulfate, filtered, the filtrate collected, and the solvent removed. The material was purified by column chromatography on silica (25 g cartridge, 15 μM silica, 10-100% [3:1 ethyl acetate: IMS]/cyclohexane) to yield the title compound (180 mg, 44%) as a yellow foam.

Step 2: Synthesis of 7-methyl-5-(piperazine-1-carbonyl)pyrido[2,3-d]pyridazin-8(7H)-one: To a solution of tert-butyl 4-(7-methyl-8-oxo-pyrido[2,3-d]pyridazine-5-carbonyl)piperazine-1-carboxylate (515 mg, 1.38 mmol, 1 equiv.) in DCM (10 mL) was added trifluoroacetic acid (2.1 mL, 27.6 mmol, 20 equiv.) and the mixture was stirred at rt for 2 hrs. The mixture was loaded onto an SCX-2 cartridge (10 g, pre-washed with DCM), washed with DCM, followed by methanol then eluted with 7M ammonia in methanol. The eluent was collected, and the solvent removed, azeotroping with diethyl ether to yield the title compound (356 mg, 94%) as a reddish solid.

Step 3: 7-methyl-5-(piperazine-1-carbonyl)pyrido[2,3-d]pyridazin-8-one (80 mg, 0.293 mmol, 1 equiv.), 1-bromo-3-fluoro-5-methoxy-benzene (90 mg, 0.439 mmol, 1.5 equiv.), DavePhos Pd G3 (22 mg, 0.0293 mmol, 0.1 equiv.) and sodium tert-butoxide (42 mg, 0.439 mmol, 1.50 equiv.) were suspended in CPME (2 mL) in a vial. The vial was sealed, evacuated and flushed with nitrogen, twice. The solution was stirred at 110° C. for 2 hrs, then allowed to cool to rt. The mixture was partitioned between DCM and water and the phases separated. The organics were collected, and the solvent removed. The material was purified by reverse phase HPLC (Xbridge C18 19×150 mm, 10 μm, 20-80% $MeCN/H_2O$ (10 mM $NH_4CO_3$), 20 mL/min, rt) and the appropriate fractions were combined and lyophilized to yield the title compound (10 mg, 9%) as an off white solid. LCMS: Method B, m/z 398.2 (M+H), RT 3.93 min. $^1H$ NMR (400 MHz, DMSO) δ 9.12 (dd, J=1.5, 4.5 Hz, 1H), 8.24 (dd, J=1.8, 8.3 Hz, 1H), 7.91 (dd, J=4.5, 8.3 Hz, 1H), 6.42-6.36 (m, 1H), 6.30 (dd, J=2.1, 2.1 Hz, 1H), 6.26-6.21 (m, 1H), 3.84 (dd, J=5.2, 5.2 Hz, 2H), 3.76 (s, 3H), 3.72 (s, 3H), 3.62-3.58 (m, 2H), 3.35 (dd, J=4.8, 5.7 Hz, 2H), 3.13 (dd, J=5.1, 5.1 Hz, 2H).

Example 17: Synthesis of 4-[4-(4-cyclopropylpyridazin-3-yl)piperazine-1-carbonyl]-2-methyl-phthalazin-1-one (Compound 185)

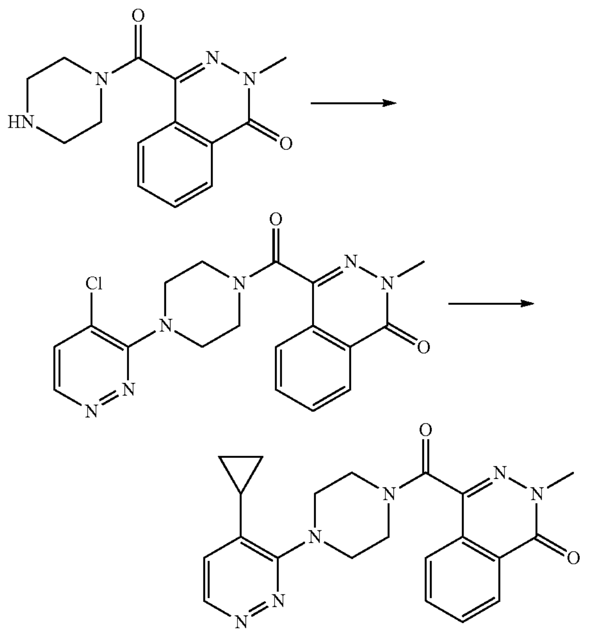

Step 1: A solution of 2-methyl-4-(piperazine-1-carbonyl)phthalazin-1-one (75 mg, 0.275 mmol, 1 equiv.), 3,4-dichloropyridazine (62 mg, 0.413 mmol, 1.5 equiv.), RuPhos PdG3 (23 mg, 0.0275 mmol, 0.1 equiv.) and caesium carbonate (269 mg, 0.826 mmol, 3 equiv.) in 1,4-dioxane (1 mL) was degassed with argon for 5 min. The tube was sealed and heated at 100° C. for 16 hrs, then allowed to cool to rt. The mixture was diluted with DCM and washed with water. The aqueous phase was separated and further extracted with DCM twice. The combined organic fractions were filtered through a phase separator and the solvent evaporated. The material was purified by column chromatography on silica (12 g cartridge, 0-50% [3:1 ethyl acetate:IMS]/isohexane) and the appropriate fractions were combined and the solvent removed to yield the title compound (32 mg, 30%) as a yellow solid. LCMS: Method F, m/z 385.2 $(M+H)^+$, RT=1.27 min.

Step 2: A solution of 4-[4-(4-chloropyridazin-3-yl)piperazine-1-carbonyl]-2-methyl-phthalazin-1-one (105 mg, 0.273 mmol, 1 equiv.) cyclopropyl boronic acid (29 mg, 0.341 mmol, 1.25 equiv.) and sodium hydrogen carbonate (92 mg, 1.09 mmol, 4 equiv.) in 1,4-dioxane (2 mL) and water (0.9 mL) was degassed with nitrogen for 5 min. [1,1'-bis(diphenylphosphino) ferrocene]dichloropalladium (II) (40 mg, 0.0546 mmol, 0.2 equiv.) was added. The vial was sealed and heated at 100° C. for 16 hrs, then allowed to cool to rt. The mixture was diluted with DCM and washed with water. The aqueous phase was separated and further extracted with DCM twice. The combined organic fractions were filtered through a phase separator and the solvent was evaporated. The material was purified by column chromatography on C18 (24 g cartridge, 20-90% MeCN in water+0.10% ammonia) and the appropriate fractions were combined and lyophilized to yield the title compound (19 mg, 17%) as a brown oil. LCMS: Method E, m/z 391.4 $(M+H)^+$, RT=1.31 min. $^1H$ NMR (400 MHz, CDCl3) δ 8.72 (dd, J=5.0, 0.5 Hz, 1H), 8.51-8.44 (m, 1H), 7.86-7.76 (m, 3H), 6.78 (dd, J=5.0, 0.6 Hz, 1H), 4.13-4.04 (m, 2H), 3.86 (s, 3H), 3.68-3.63 (m, 2H), 3.61-3.54 (m, 2H), 3.48-3.41 (m, 2H), 2.07-1.98 (m, 1H), 1.23-1.16 (m, 2H), 0.89-0.82 (m, 2H).

Example 18: Synthesis of 2-ethyl-4-(4-(4-fluoro-2,3-dihydrobenzofuran-7-yl)piperazine-1-carbonyl)phthalazin-1(2H)-one (Compound 186)

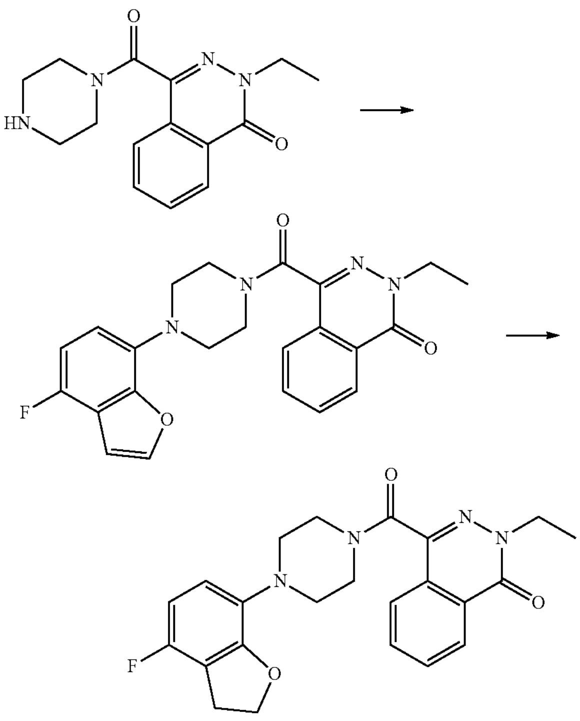

Step 1: 2-ethyl-4-(4-(4-fluorobenzofuran-7-yl)piperazine-1-carbonyl)phthalazin-1(2H)-one was synthesized according to the method described in Example 10, using Intermediate 2 and the appropriate aryl halide reagent.

Step 2: To a solution of 2-ethyl-4-[4-(4-fluorobenzofuran-7-yl)piperazine-1-carbonyl]phthalazin-1-one (74 mg, 0.176 mmol, 1 equiv.) in EtOH (2 mL) was added 5% rhodium on carbon (5.0%, 36 mg, 17.8 mmol, 0.1 equiv.). The mixture was purged with argon, then stirred under a hydrogen atmosphere for 5 days at rt. Next, an additional amount of 5% rhodium on carbon (5.0%, 36 mg, 8.68 mmol, 0.05 equiv.) was added to the reaction mixture and the reaction was stirred under a hydrogen atmosphere for another 18 hrs. The mixture was filtered through celite and the filtrate was concentrated. The residue was purified by reversed phase HPLC (Sunfire C18 19×150 mm, 10 um 5-60% ACN/H2O (0.1% FA), 20 ml/min, rt) to yield the title compound (23.7 mg, 31) as off-white amorphous solid. LCMS: Method A, m/z=423.7 $(M+H)^+$, RT=4.86 min. $^1H$ NMR (400 MHz, DMSO) δ 8.35-8.32 (m, 1H), 7.98-7.89 (m, 2H), 7.80-7.78 (m, 1H), 6.70 (dd, J=5.2, 8.7 Hz, 1H), 6.59 (t, J=8.5 Hz, 1H), 4.62 (t, J=8.7 Hz, 2H), 4.18 (q, J=7.2 Hz, 2H), 3.88-3.86 (i, 2H), 3.55-3.50 (m, 2H), 3.20 (t, J=8.8 Hz, 2H), 3.13-3.11 (m, 2H), 2.92-2.90 (m, 2H), 1.31 (t, J=7.2 Hz, 3H).

The compounds in Table 12 were made according to the method described in Example 18, using the appropriate benzofuran reagent.

TABLE 12

Structure and Spectroscopic Data for Compounds 187 to 190.

| Compound No. | Structure | LCMS data | NMR data |
|---|---|---|---|
| 187 | 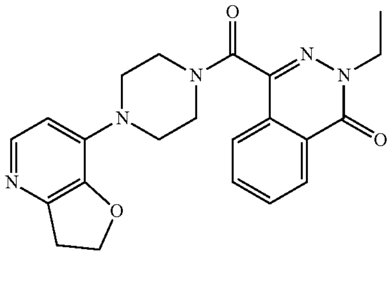 [SMILES: CCn1nc(C(=O)N2CCN(c3ccnc4c3OCC4)CC2)c2ccccc2c1=O] | Method A m/z 406.6 $(M + H)^+$ RT 2.64 min | $^1H$ NMR (400 MHz, DMSO) δ 8.35-8.32 (m, 1H), 7.97-7.89 (m, 2H), 7.82-7.78 (m, 2H), 6.61 (d, J = 5.8 Hz, 1H), 4.57 (t, J = 9.0 Hz, 2H), 4.18 (q, J = 7.2 Hz, 2H), 3.88-3.83 (m, 2H), 3.56-3.51 (m, 2H), 3.46-3.41 (m, 2H), 3.24-3.20 (m, 2H), 3.17 (t, J = 9.0 Hz, 2H), 1.31 (t, J = 7.1 Hz, 3H). |
| 188 | 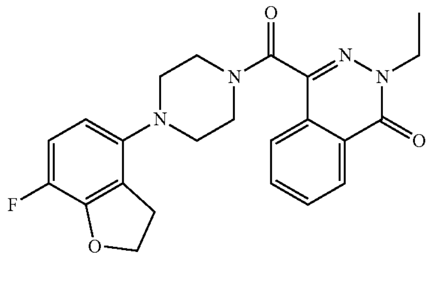 [SMILES: CCn1nc(C(=O)N2CCN(c3ccc(F)c4c3CCO4)CC2)c2ccccc2c1=O] | Method A m/z 423.2 $(M + H)^+$ RT 4.82 min | $^1H$ NMR (400 MHz, DMSO) δ 8.36-8.33 (m, 1H), 7.99-7.90 (m, 2H), 7.82-7.79 (m, 1H), 6.96 (dd, J = 9.0, 10.5 Hz, 1H), 6.41 (dd, J = 3.5, 8.8 Hz, 1H), 4.61 (t, J = 8.7 Hz, 2H), 4.18 (q, J = 7.2 Hz, 2H), 3.90-3.85 (m, 2H), 3.54-3.49 (m, 2H), 3.18 (t, J = 8.5 Hz, 2H), 3.10-3.05 (m, 2H), 2.89-2.84 (m, 2H), 1.31 (t, J = 7.2 Hz, 3H). |

TABLE 12-continued

Structure and Spectroscopic Data for Compounds 187 to 190.

| Compound No. | Structure | LCMS data | NMR data |
|---|---|---|---|
| 189 | 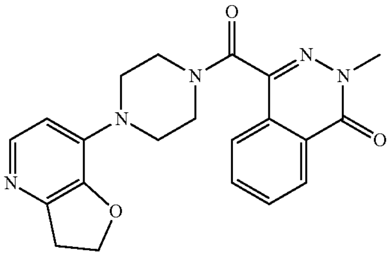 [SMILES: Cn1nc(C(=O)N2CCN(c3ccnc4c3OCC4)CC2)c2ccccc2c1=O] | Method A m/z 392.2 $(M + H)^+$ RT 2.51 min | $^1H$ NMR (400 MHz, DMSO) δ 8.35-8.31 (m, 1H), 7.97-7.89 (m, 2H), 7.80-7.78 (m, 2H), 6.61 (d, J = 5.6 Hz, 1H), 4.57 (t, J = 9.0 Hz, 2H), 3.88-3.83 (m, 2H), 3.73 (s, 3H), 3.55-3.50 (m, 2H), 3.46-3.41 (m, 2H), 3.23-3.14 (m, 4H). |
| 190 | 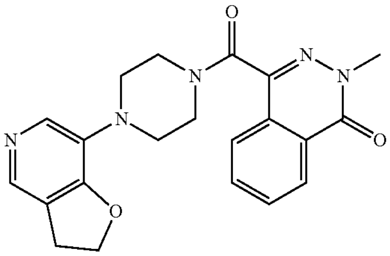 [SMILES: Cn1nc(C(=O)N2CCN(c3cncc4c3OCC4)CC2)c2ccccc2c1=O] | Method B m/z 392.2 $(M + H)^+$ RT 3.36 min | $^1H$ NMR (400 MHz, DMSO) δ 8.35-8.32 (m, 1H), 8.03 (s, 1H), 7.98-7.90 (m, 3H), 7.81-7.77 (m, 1H), 4.64 (t, J = 8.8 Hz, 2H), 3.90-3.85 (m, 2H), 3.74 (s, 3H), 3.56-3.52 (m, 2H), 3.27-3.23 (m, 2H), 3.20 (t, J = 8.8 Hz, 2H), 3.06-3.02 (m, 2H). |

Example 19: Synthesis of 3-methoxy-5-(4-(3-methyl-4-oxo-3,4-dihydrophthalazine-1-carbonyl)piperazin-1-yl)benzonitrile (Compound 224)

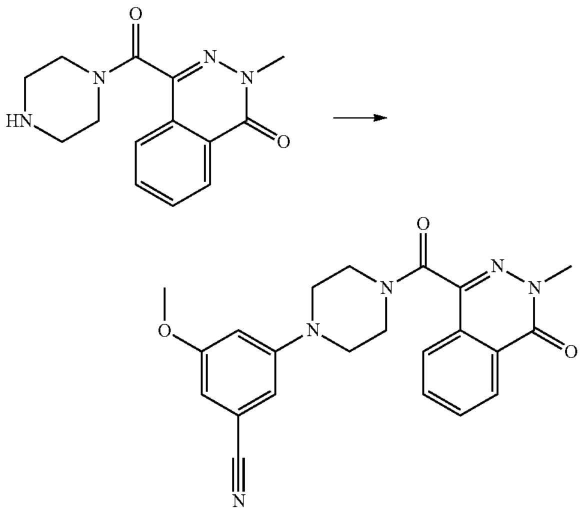

To an argon-purged suspension of 2-methyl-4-(piperazine-1-carbonyl)phthalazin-1-one (80 mg, 0.294 mmol, 1.0 equiv.), 3-bromo-5-methoxy-benzonitrile (69 mg, 0.323 mmol, 1.1 equiv.) and sodium tert-butoxide (42 mg, 0.441 mmol, 1.5 equiv.) in CPME (2.4 mL) was added RuPhos Pd G3 (25 mg, 0.0294 mmol, 0.1 equiv.) under an argon atmosphere (5 mL). The resulting suspension was stirred at 110° C. for 72 hrs. The mixture was cooled to rt, then water (5 mL) and DCM (50 mL) were added. The resulting biphasic solution was passed through a phase separator containing silica. The organic phase was collected, and the solvent removed. The material was purified by reverse phase HPLC (Xbridge C18 19×150 mm, 10 μm, 20-80% MeCN/water (10 mM $NH_4CO_3$), 20 mL/min, rt) and the appropriate fractions were combined and lyophilized to yield the title compound (8 mg, 7%) as an off white solid. LCMS: Method A, m/z=404.32 $(M+H)^+$, RT=4.25 min. $^1H$ NMR (400 MHz, DMSO) δ 8.35-8.32 (m, 1H), 7.96-7.91 (m, 2H), 7.81-7.78 (m, 1H), 7.00-6.99 (m, 1H), 6.83-6.81 (m, 1H), 6.78 (dd, J=2.3, 2.3 Hz, 1H), 3.86 (t, J=5.3 Hz, 2H), 3.78-3.73 (m, 6H), 3.53 (t, J=5.1 Hz, 2H), 3.42 (t, J=5.3 Hz, 2H), 3.18 (t, J=5.1 Hz, 2H).

The compounds in Table 13 were made according to the method described in Example 19, using appropriate aryl halide reagent.

TABLE 13

Structure and Data for Compounds 225 to 228.

| Compound No. | Structure | LCMS data | NMR data |
|---|---|---|---|
| 225 | 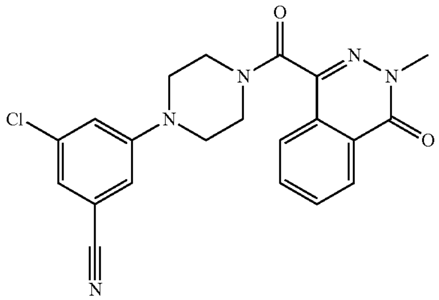 [SMILES: Cn1nc(C(=O)N2CCN(c3cc(Cl)cc(C#N)c3)CC2)c2ccccc2c1=O] | Method B m/z = 408.2 $(M + H)^+$ RT = 4.56 min | $^1H$ NMR (400 MHz, DMSO) δ 8.36-8.33 (m, 1H), 7.96-7.91 (m, 2H), 7.82-7.79 (m, 1H), 7.40-7.38 (m, 1H), 7.35-7.30 (m, 2H), 3.88-3.83 (m, 2H), 3.75 (s, 3H), 3.56-3.47 (m, 4H), 3.33 (s, 2H). |
| 226 | 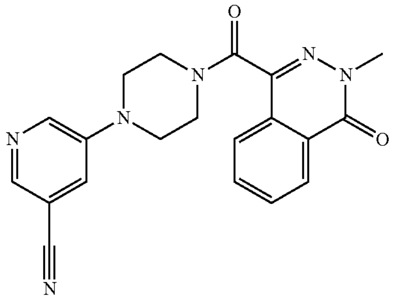 [SMILES: Cn1nc(C(=O)N2CCN(c3cncc(C#N)c3)CC2)c2ccccc2c1=O] | Method A m/z = 375.3 $(M + H)^+$ RT = 3.37 min | $^1H$ NMR (400 MHz, DMSO) δ 8.60 (d, J = 3.0 Hz, 1H), 8.37 (d, J = 1.6 Hz, 1H), 8.35-8.32 (m, 1H), 7.95-7.91 (m, 2H), 7.83-7.78 (m, 2H), 3.88 (dd, J = 5.2, 5.2 Hz, 2H), 3.74 (s, 3H), 3.59-3.49 (m, 4H), 3.29-3.25 (m, 2H). |
| 227 | 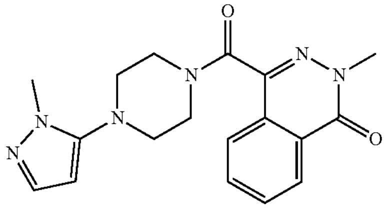 [SMILES: Cn1nccc1N1CCN(C(=O)c2nn(C)c(=O)c3ccccc23)CC1] | Method A m/z = 353.4 $(M + H)^+$ RT = 3.07 min | $^1H$ NMR (400 MHz, DMSO) δ 8.33 (dd, J = 1.1, 7.7 Hz, 1H), 7.99-7.90 (m, 2H), 7.80 (dd, J = 1.1, 6.9 Hz, 1H), 7.27 (d, J = 2.0 Hz, 1H), 5.89 (d, J = 1.8 Hz, 1H), 3.89 (dd, J = 5.1, 5.1 Hz, 2H), 3.74 (s, 3H), 3.65 (s, 3H), 3.55 (dd, J = 4.9, 4.9 Hz, 2H), 3.00 (dd, J = 5.1, 5.1 Hz, 2H), 2.78 (dd, J = 4.9, 4.9 Hz, 2H). |
| 228 | 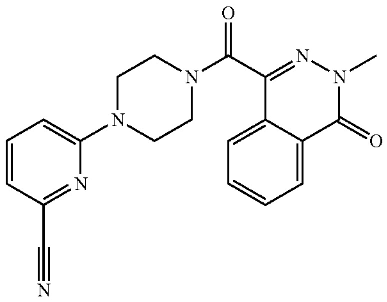 [SMILES: Cn1nc(C(=O)N2CCN(c3cccc(C#N)n3)CC2)c2ccccc2c1=O] | Method A m/z = 375.2 $(M + H)^+$ RT = 3.98 min | $^1H$ NMR (400 MHz, DMSO) δ 8.36-8.33 (m, 1H), 7.97-7.90 (m, 2H), 7.84-7.79 (m, 1H), 7.75 (dd, J = 7.1, 9.1 Hz, 1H), 7.24 (dd, J = 7.4, 11.5 Hz, 2H), 3.87-3.82 (m, 2H), 3.79-3.76 (m, 2H), 3.75 (s, 3H), 3.53 (tt, J = 6.7, 7.2 Hz, 4H). |

Example 20: Synthesis of 4-chloro-3-(4-(3-methyl-4-oxo-3,4-dihydrophthalazine-1-carbonyl)piperazin-1-yl)benzonitrile (Compound 229)

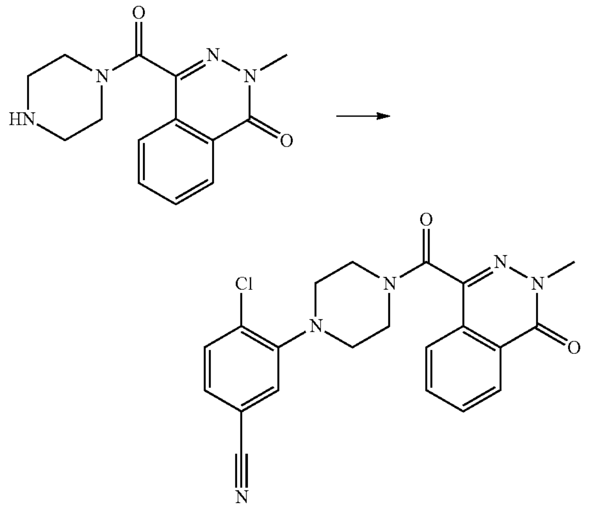

2-methyl-4-(piperazine-1-carbonyl)phthalazin-1-one (70 mg, 0.257 mmol, 1.0 equiv.), 3-bromo-4-chloro-benzonitrile (83 mg, 0.386 mmol, 1.5 equiv.), tris(dibenzylideneacetone) dipalladium(O) (12 mg, 0.0129 mmol, 0.05 equiv.), rac-BINAP (11 mg, 0.018 mmol, 0.07 equiv.) and cesium carbonate (168 mg, 0.514 mmol, 2.0 equiv.) were placed in a vial. The vial was sealed, evacuated then flushed with argon three times, then toluene (1 mL) (degassed prior to addition by sonicating and sparging with argon for 15 min) was added. The mixture was stirred at 100° C. for 2 hrs, then allowed to rt. The mixture was diluted with DCM and filtered through Celite™. The filtrate was collected, and the solvent was removed. The solid was suspended in 10% aq. DMSO and sonicated until a uniform suspension was formed. The suspension was filtered, the solid collected and washed twice with 10% aq. DMSO, then twice with water. The solid was dried under vacuum at 40° C. overnight to yield the title compound (25 mg, 23%) as a white solid. LCMS: Method C, m/z=408.1 $(M+H)^+$, RT=4.44 min. $^1H$ NMR (400 MHz, DMSO) δ 8.36-8.32 (m, 1H), 8.00-7.90 (m, 2H), 7.82-7.79 (m, 1H), 7.68-7.64 (m, 2H), 7.56-7.52 (m, 1H), 3.93-3.89 (m, 2H), 3.75 (s, 3H), 3.59-3.55 (m, 2H), 3.21-3.17 (m, 2H), 3.00-2.95 (m, 2H).

Example 21: Synthesis of 5-(4-(3-methyl-4-oxo-3,4-dihydrophthalazine-1-carbonyl)piperazin-1-yl) isophthalonitrile (Compound 230)

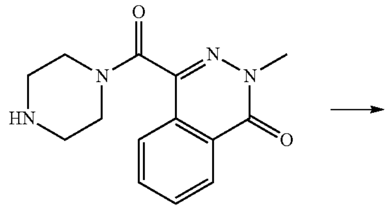

-continued

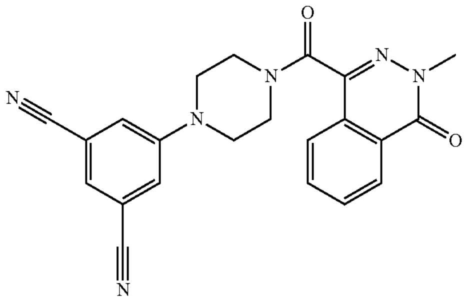

2-Methyl-4-(piperazine-1-carbonyl)phthalazin-1-one (50 mg, 0.184 mmol, 1.0 equiv.), 5-bromobenzene-1,3-dicarbonitrile (42 mg, 0.202 mmol, 1.1 equiv.), DavePhos Pd G3 (14 mg, 0.0184 mmol, 0.1 equiv.), and caesium carbonate (90 mg, 0.275 mmol, 1.5 equiv.) were suspended in CPME (2 mL) in a vial. The vial was sealed, evacuated and then flushed with nitrogen three times. The mixture was heated to 110° C. for 16 hrs, then allowed to rt. The mixture was partitioned between DCM and water, and the biphasic solution was passed through a phase separator cartridge. The organic layer was collected, and the solvent was removed. The material was purified by reverse phase HPLC (Sunfire C18 19×150 mm, 10 μm 20-80% MeCN/water+0.1% formic acid, 20 mL/min, rt) and the appropriate fractions were collected and lyophilised to yield the title compound (5 mg, 7%) as an off white solid. LCMS: Method A, m/z=399.3 $(M+H)^+$, RT=4.13 min. $^1H$ NMR (400 MHz, DMSO) δ 8.36-8.32 (m, 1H), 7.95-7.91 (m, 2H), 7.82-7.79 (m, 1H), 7.73-7.70 (m, 3H), 3.89-3.84 (m, 2H), 3.74 (s, 3H), 3.58-3.53 (m, 4H). One signal of two piperazine protons is obscured by water peak.

Example 22: Synthesis of 4-(4-(imidazo[1,2-a]pyridin-5-yl)piperazine-1-carbonyl)-2-methylphthalazin-1(2H)-one (Compound 231)

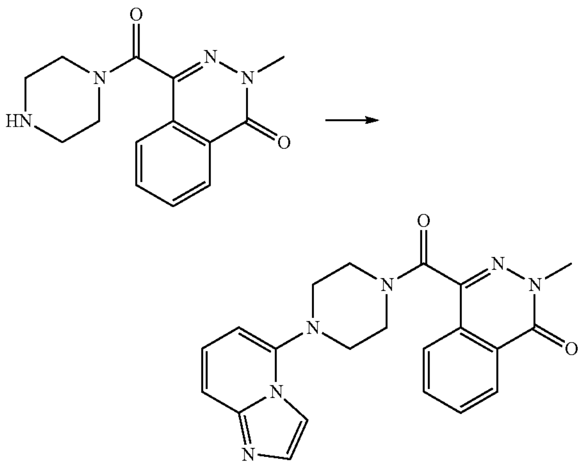

2-Methyl-4-(piperazine-1-carbonyl)phthalazin-1-one (50 mg, 0.18 mmol, 1.0 equiv.) 5-bromoimidazo[1,2-a]pyridine (54 mg, 0.28 mmol, 1.5 equiv.), tris(dibenzylideneacetone) dipalladium (O) (17 mg, 0.018 mmol, 0.1 equiv.), rac-BINAP (11 mg, 0.018 mmol, 0.1 equiv.), and sodium tert-butoxide (35 mg, 0.367 mmol, 2.0 equiv.) were suspended in CPME (1 mL) in a vial. The vial was sealed, evacuated and then flushed with nitrogen three times. The mixture was heated to 110° C. for 16 hrs, then allowed to rt. The mixture was partitioned between DCM and water, and the biphasic solution was passed through a phase separator cartridge. The organic layer was collected, and the solvent was removed. The material was purified by reverse phase HPLC (Luna Phenyl-Hexyl 21.2×150 mm, 10 μm 20-80% MeOH/water+0.1% formic acid, 20 m/min, rt) and the appropriate fractions were collected and lyophilised to yield the title compound (32 mg, 43%) as an off white solid. LCMS: Method A, m/z=389.5 $(M+H)^+$, RT=2.34 min. $^1H$ NMR (400 MHz, DMSO) δ 8.34 (dd, J=1.1, 6.9 Hz, 1H), 8.01-7.91 (m, 2H), 7.84 (d, J=6.5 Hz, 2H), 7.61 (d, J=1.0 Hz, 1H), 7.36-7.33 (m, 1H), 7.26 (dd, J=7.2, 8.9 Hz, 1H), 6.50 (d, J=7.0 Hz, 1H), 4.01 (s, 2H), 3.76 (s, 3H). 3.70 (t, J=5.0 Hz, 2H), 3.03 (t, J=4.2 Hz, 2H). One signal of two piperazine protons is obscured by water peak.

Example 23: Synthesis of 4-(4-(4-cyclopropylpyridin-3-yl)piperazine-1-carbonyl)-6-fluoro-2-methylphthalazin-1(2H)-one (Compound 232)

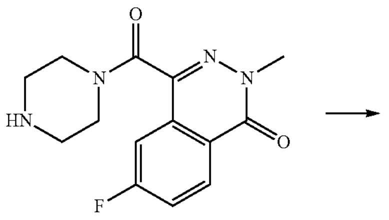

-continued

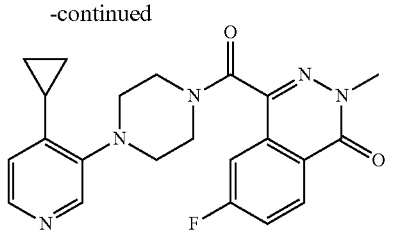

To a vial was added 6-fluoro-2-methyl-4-(piperazine-1-carbonyl)phthalazin-1-one (50 mg, 0.172 mmol, 1.0 equiv.), 3-bromo-4-cyclopropyl-pyridine (44 mg, 0.224 mmol, 1.3 equiv.), RuPhos Pd G3 (14 mg, 0.0172 mmol, 0.1 equiv.) and sodium tert-butoxide (25 mg, 0.258 mmol, 1.5 equiv.). The vial was sealed, and the vial was purged with nitrogen. CPME (1.5 mL) was added to the vial, and the vial purged again with nitrogen. The mixture was stirred at 110° C. for 20 hrs, then allowed to rt. The mixture was partitioned between EtOAc and water, and the phases were separated. The organics were collected and the solvent was removed. The material was purified by SFC (REPROSPHER PEI 100 20×150 mm, 5 μm, 5-15% MeOH (0.1% $NH_4OH$)/$CO_2$, 100 mL/min, 120 bar, 40° C., DAD 295 nm) and the appropriate fractions were collected and lyophilised to yield the title compound (16 mg, 22%) as an off white solid. LCMS: Method B, m/z=408.4 $(M+H)^+$, RT=4.07 mi. $^1H$ NMR (400 MHz, DMSO) δ 8.40 (dd, J=5.3, 8.8 Hz, 1H), 8.23 (s, 1H), 8.14 (d, J=5.1 Hz, 1H), 7.79 (dt, J=2.3, 8.8 Hz, 1H), 7.57 (dd, J=2.7, 9.3 Hz, 1H), 6.76 (d, J=5.2 Hz, 1H), 3.92 (t, J=4.7 Hz, 2H), 3.73 (s, 3H), 3.63 (t, J=4.8 Hz, 2H), 3.18 (t, J=4.8 Hz, 2H), 2.98 (t, J=4.8 Hz, 2H), 2.28-2.20 (m, 1H), 1.08 (dt, J=4.9, 7.3 Hz, 2H), 0.79 (dt, J=3.8, 5.7 Hz, 2H).

The compounds in Table 14 were made according to the method described in Example 23, using appropriate aryl halide reagent.

TABLE 14

Structure and Data for Compound 233.

| Compound No. | Structure | LCMS data | NMR data |
| --- | --- | --- | --- |
| 233 | 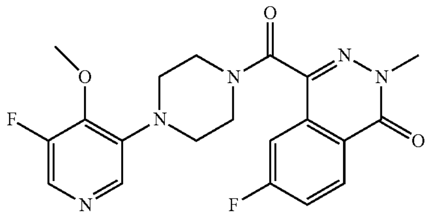 [SMILES: COc1c(F)cncc1N1CCN(C(=O)c2nn(C)c(=O)c3ccc(F)cc23)CC1] | Method A m/z = 416.4 $(M + H)^+$ RT = 3.24 min | $^1H$ NMR (400 MHz, DMSO) δ 8.40 (dd, J = 5.8, 8.8 Hz, 1H), 8.23 (d, J = 2.6 Hz, 1H), 8.06 (s, 1H), 7.78 (dt, J = 3.4, 8.6 Hz, 1H), 7.57 (dd, J = 3.2, 8.8 Hz, 1H), 4.02 (d, J = 2.6 Hz, 3H), 3.90 (t, J = 4.9 Hz, 2H), 3.73 (s, 3H), 3.61 (t, J = 5.5 Hz, 2H), 3.25 (t, J = 5.3 Hz, 2H), 3.05 (t, J = 5.0 Hz, 2H). |

Example 24: Synthesis of 5-(4-(7-fluoro-3-methyl-4-oxo-3,4-dihydrophthalazine-1-carbonyl)piperazin-1-yl)nicotinonitrile (Compound 234)

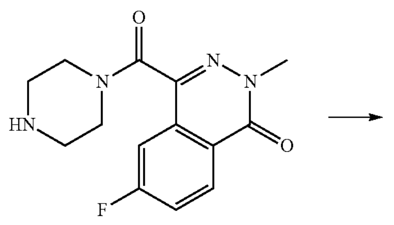

-continued

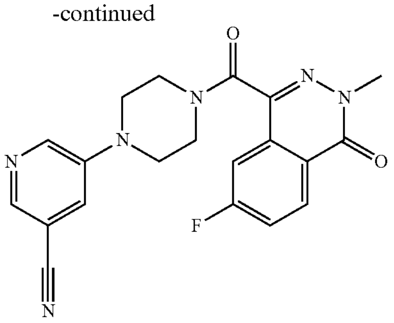

6-fluoro-2-methyl-4-(piperazine-1-carbonyl)phthalazin-1-one (90 mg, 0.310 mmol, 1.0 equiv.), 5-bromo-3-cyano-pyridine (102 mg, 0.558 mmol, 1.8 equiv.), sodium tert-butoxide (45 mg, 0.465 mmol, 1.5 equiv.) and RuPhos Pd G3 (26 mg, 0.031 mmol, 0.1 equiv.) were combined in a vial. The vial was sealed and evacuated, then CPME (2.5 mL) was added. The mixture was stirred for 5 mins and once all reagents were in solution, the vial was filled with nitrogen, then heated at 110° C. for 3.5 hrs. The mixture was allowed to rt then diluted with DCM and filtered through a phase separation cartridge. The filtrate was collected, and the solvent was removed. The material was purified by column chromatography on silica (12 g cartridge, 0-65% [EtOAc: IMS (3:1)]/cyclohexane) and the appropriate fraction were combined and the solvent removed to yield the title compound (15 mg, 12%) as a white solid. LCMS: Method C, m/z=393.2 $(M+H)^+$, RT=3.55 min. $^1H$ NMR (400 MHz, DMSO) δ 8.62 (1H, d, J=2.9 Hz), 8.42-8.37 (2H, m), 7.84-7.84 (1H, m), 7.82-7.75 (1H, m), 7.59 (1H, dd, J=2.4, 9.2 Hz), 3.86 (2H, dd, J=5.1, 5.1 Hz), 3.73 (3H, s), 3.62 (2H, dd, J=4.9, 4.9 Hz), 3.52 (2H, dd, J=5.1, 5.1 Hz), 3.30 (2H, dd, J=5.0, 5.0 Hz)

The compounds in Table 15 were made according to the method described in Example 24, using appropriate aryl halide reagent.

TABLE 15

Structure and Data for Compound 235.

| Compound No. | Structure | LCMS data | NMR data |
|---|---|---|---|
| 235 | 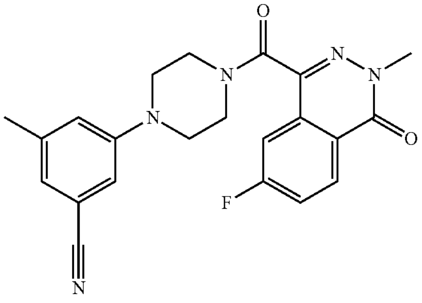 | Method A m/z = 406.2 $(M + H)^+$ RT = 4.62 min | $^1H$ NMR (400 MHz, DMSO) δ 8.33 (dd, J = 5.4, 9.0 Hz, 1H), 7.71 (td, J = 2.5, 8.8 Hz, 1H), 7.50 (dd, J = 2.5, 9.1 Hz, 1H), 7.09 (d, J = 16.7 Hz, 2H), 6.96 (s, 1H), 3.78 (t, J = 5.2 Hz, 2H), 3.54-3.49 (m, 2H), 3.34 (t, J = 5.2 Hz, 2H), 3.13 (t, J = 5.1 Hz, 2H), 2.22 (s, 3H). |

Example 25: Synthesis of 2-ethyl-6-fluoro-4-(4-(4-methoxypyridin-3-yl)piperazine-1-carbonyl)phthalazin-1(2H)-one (Compound 236)

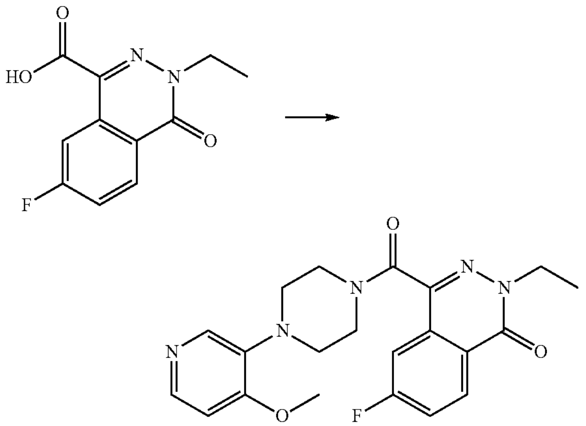

To a suspension of 3-ethyl-7-fluoro-4-oxo-phthalazine-1-carboxylic acid (100 mg, 0.423 mmol, 1.0 equiv.) and 1-(4-methoxy-3-pyridyl)piperazine (86 mg, 0.445 mmol, 1.05 equiv.) in EtOAc (3 mL) was added triethylamine (0.24 mL, 1.69 mmol, 4.0 equiv.) followed by T3P (50% in EtOAc, 0.37 mL, 0.631 mmol, 1.5 equiv.) and the mixture was stirred at rt for 1.5 hrs. The mixture was filtered and the solid washed with a small volume of EtOAc, then water, collected and dried to yield the title compound (130 mg, 74%) as a white solid. LCMS: Method C, m/z=412.1 $(M+H)^+$, RT=2.55 min. $^1$H NMR (400 MHz, DMSO) δ 8.40 (dd, J=5.5, 8.9 Hz, 1H), 8.16 (d, J=5.4 Hz, 1H), 8.06 (s, 1H), 7.78 (td, H=2.6, 838 Hz, 1H), 7.57 (dd, J=2.5, 9.2 Hz, 1H), 7.00 (d, J=5.5 Hz, 1H), 4.18 (q, J=7.2 Hz, 2H), 3.88-3.86 (m, 5H), 3.59 (t, J=4.9 Hz, 2H), 3.32 (s, 2H), 2.99 (t, J=4.9 Hz, 2H), 1.31 (t, J=7.2 Hz, 3H).

The compounds in Table 16 were made according to the method described in Example 25, using the appropriate amine reagent.

TABLE 16

Structure and Data for Compounds 237 to 240.

| Compound No. | Structure | LCMS data | NMR data |
|---|---|---|---|
| 237 | 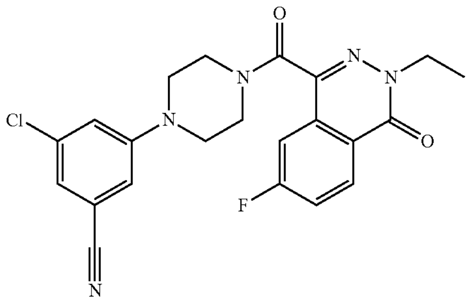 [SMILES: CCn1nc(C(=O)N2CCN(c3cc(Cl)cc(C#N)c3)CC2)c2cc(F)ccc2c1=O] | Method C m/z = 440.3 $(M + H)^+$ RT = 4.93 min | $^1$H NMR (400 MHz, DMSO) δ 8.40 (dd, J = 5.5, 8.9 Hz, 1H), 7.78 (td, J = 2.6, 8.8 Hz, 1H), 7.59 (dd, J = 2.5, 9.2 Hz, 1H), 7.39-7.29 (m, 3H), 4.18 (q, J = 7.2 Hz, 2H), 3.87-3.82 (m, 2H), 3.60 (t, J = 5.1 Hz, 2H), 3.50 (t, J = 5.2 Hz, 2H), 1.31 (t, J = 7.2 Hz, 3H). One signal of two piperazine protons is obscured by water peak. |
| 238 | 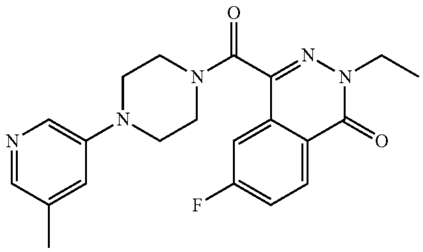 [SMILES: CCn1nc(C(=O)N2CCN(c3cncc(C)c3)CC2)c2cc(F)ccc2c1=O] | Method C m/z = 396.1 $(M + H)^+$ RT = 2.57 min | $^1$H NMR (400 MHz, DMSO) δ 8.40 (dd, J = 5.5, 8.9 Hz, 1H), 8.13 (d, J = 2.8 Hz, 1H), 7.88 (d, J = 1.0 Hz, 1H), 7.78 (td, J = 2.6, 8.7 Hz, 1H), 7.58 (dd, J = 2.4, 9.2 Hz, 1H), 7.19 (s, 1H), 4.18 (q, J = 7.2 Hz, 2H), 3.88 (t, J = 5.2 Hz, 2H), 3.61 (t, J = 5.0 Hz, 2H), 3.37 (t, J = 5.5 Hz, 1H), 3.18 (t, J = 5.9 Hz, 2H), 2.24 (s, 3H), 1.31 (t, J = 7.2 Hz, 3H). |
| 239 | 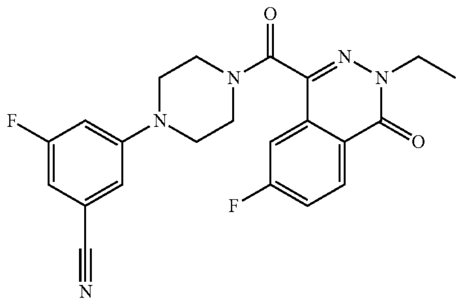 [SMILES: CCn1nc(C(=O)N2CCN(c3cc(F)cc(C#N)c3)CC2)c2cc(F)ccc2c1=O] | Method C m/z = 424.1 $(M + H)^+$ RT = 4.68 min | $^1$H NMR (400 MHz, DMSO) δ 8.40 (dd, J = 5.5, 8.9 Hz, 1H), 7.78 (td, J = 2.5, 8.7 Hz, 1H), 7.59 (dd, J = 2.5, 9.3 Hz, 1H), 7.27 (s, 1H), 7.19-7.10 (m, 2H), 4.18 (q, J = 7.2 Hz, 2H), 3.87-3.82 (m, 2H), 3.62-3.58 (m, 2H), 3.50 (t, J = 5.2 Hz, 2H), 3.32 (s, 2H), 1.31 (t, J = 7.2 Hz, 3H). One signal of two piperazine protons is obscured by water peak. |

TABLE 16-continued

| Structure and Data for Compounds 237 to 240. | | | |
|---|---|---|---|
| Compound No. | Structure | LCMS data | NMR data |
| 240 | 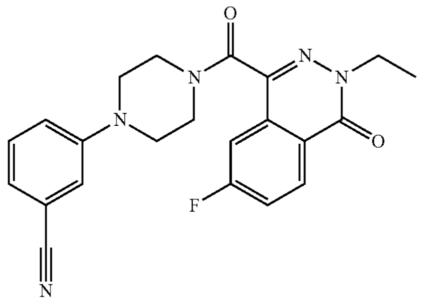 [SMILES: CCn1nc(C(=O)N2CCN(c3cccc(C#N)c3)CC2)c2cc(F)ccc2c1=O] | Method C m/z = 406.1 $(M + H)^+$ RT = 4.43 min | $^1H$ NMR (400 MHz, DMSO) δ 8.40 (dd, J = 5.4, 8.9 Hz, 1H), 7.78 (td, J = 2.5, 8.8 Hz, 1H), 7.59 (dd, J = 2.5, 9.3 Hz, 1H), 7.43-7.37 (m, 2H), 7.31 (dd, J = 1.8, 8.5 Hz, 1H), 7.20 (d, J = 7.5 Hz, 1H), 4.18 (q, J = 7.2 Hz, 2H), 3.87 (t, J = 5.2 Hz, 2H), 3.61 (t, J = 5.0 Hz, 2H), 3.43 (t, J = 5.2 Hz, 2H), 3.24 (t, J = 5.1 Hz, 2H), 1.32 (t, J = 7.2 Hz, 3H). |

Example 26: Synthesis of 3-(4-(2-ethyl-1-oxo-1,2-dihydropyrido[3,4-d]pyridazine-4-carbonyl)piperazin-1-yl)-5-fluorobenzonitrile (Compound 241)

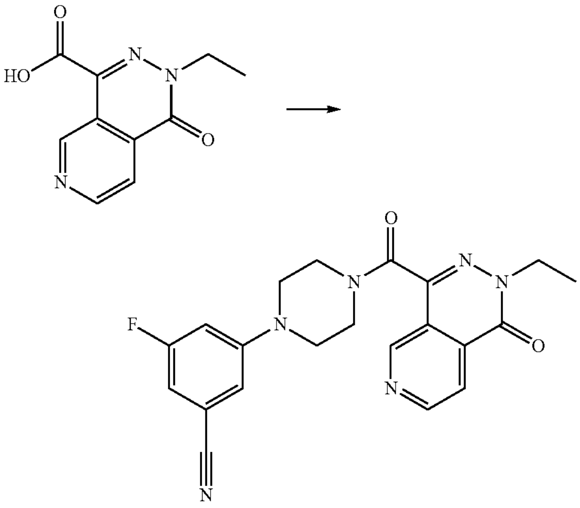

To a suspension of 2-ethyl-1-oxo-pyrido[3,4-d]pyridazine-4-carboxylic acid hydrochloride (70 mg, 0.274 mmol, 1.0 equiv.) and 3-fluoro-5-piperazin-1-yl-benzonitrile (58 mg, 0.282 mmol, 1.03 equiv.) in EtOAc (2 mL) was added triethylamine (0.19 mL, 1.37 mmol, 5.0 equiv.) followed by T3P (50% in EtOAc) (0.24 mL, 0.411 mmol, 1.5 equiv.) and the mixture was stirred at rt for 2 hrs. The mixture was partitioned between DCM and water and the phases separated. The organics were collected, and the solvent removed. The material was purified by SFC (REPROSPHER PEI 100 20×150 mm, 5 μm, 5-15% MeOH+ 0.1% $NH_4OH/CO_2$, 100 mL/min, 120 bar, 40° C., DAD 260 nm) and the appropriate fractions were combined and lyophilized to yield the title compound (44 mg, 40%) as a white solid. LCMS: Method C, m/z=407.3 $(M+H)^+$, RT=4.13 min. $^1H$ NMR (400 MHz, $CDCl_3$) δ 9.33 (d, J=0.7 Hz, 1H), 9.01 (d, J=5.3 Hz, 1H), 8.25 (dd, J=0.9, 5.3 Hz, 1H), 6.94 (s, 1H), 6.88-6.79 (m, 2H), 4.32 (q, J=7.2 Hz, 2H), 4.10-4.05 (m, 2H), 3.78-3.74 (m, 2H), 3.43 (t, J=5.3 Hz, 2H), 3.30 (t, J=5.2 Hz, 2H), 1.43 (t, J=7.2 Hz, 3H).

The compounds in Table 17 were made according to the method described in Example 28, using appropriate amine reagent.

TABLE 17

| Structure and Data for Compounds 242 to 244. | | | |
|---|---|---|---|
| Compound No. | Structure | LCMS data | NMR data |
| 242 | 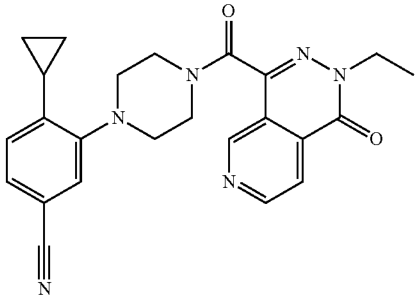 [SMILES: CCn1nc(C(=O)N2CCN(c3cc(C#N)ccc3C3CC3)CC2)c2cnccc2c1=O] | Method A m/z = 429.6 $(M + H)^+$ RT = 4.77 min | $^1H$ NMR (400 MHz, DMSO) δ 9.19 (s, 1H), 9.03 (d, J = 5.3 Hz, 1H), 8.17 (d, J = 5.3 Hz, 1H), 7.46-7.40 (m, 2H), 6.97-6.94 (m, 1H), 4.19 (q, J = 7.1 Hz, 2H), 3.95 (t, J = 4.4 Hz, 2H), 3.69 (t, J= 4.7 Hz, 2H), 3.15 (t, J = 4.8 Hz, 2H), 2.95 (t, J = 4.7 |

TABLE 17-continued

Structure and Data for Compounds 242 to 244.

| Compound No. | Structure | LCMS data | NMR data |
| --- | --- | --- | --- |
| | | | Hz, 2H), 2.36-2.28 (m, 1H), 1.32 (t, J = 7.1 Hz, 3H), 1.12-1.06 (m, 2H), 0.83-0.77 (m, 2H). |
| 243 | 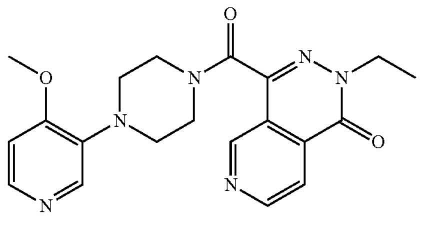 [SMILES: CCn1nc(C(=O)N2CCN(c3cnccc3OC)CC2)c2cnccc2c1=O] | Method A m/z = 395.2 $(M + H)^+$ RT = 2.30 min | $^1H$ NMR (400 MHz, DMSO) δ 9.20 (s, 1H), 9.03 (d, J = 5.4 Hz, 1H), 8.17 (dd, J = 5.1, 5.1 Hz, 2H), 8.07 (s, 1H), 7.01 (d, J = 5.5 Hz, 1H), 4.20 (q, J = 7.1 Hz, 2H), 3.90 (t, J = 5.0 Hz, 2H), 3.87 (s, 3H), 3.66 (t, J = 4.8 Hz, 2H), 3.20 (t, J = 5.1 Hz, 2H), 3.01 (t, J = 4.8 Hz, 2H), 1.33 (t, J = 7.1 Hz, 3H). |
| 244 | 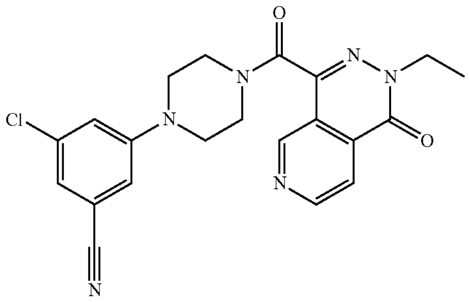 [SMILES: CCn1nc(C(=O)N2CCN(c3cc(Cl)cc(C#N)c3)CC2)c2cnccc2c1=O] | Method A m/z = 423.3 $(M + H)^+$ RT = 4.62 min | $^1H$ NMR (400 MHz, DMSO) δ 9.21 (s, 1H), 9.03 (d, J = 5.3 Hz, 1H), 8.17 (d, J = 5.4 Hz, 1H), 7.40 (s, 1H), 7.35 (dd, J = 2.1, 2.1 Hz, 1H), 7.30 (s, 1H), 4.19 (q, J = 7.2 Hz, 2H), 3.87 (t, J = 5.2 Hz, 2H), 3.69-3.64 (m, 2H), 3.51 (t, J = 5.3 Hz, 2H), 3.32 (s, 2H), 1.33 (t, J = 7.2 Hz, 3H). One signal of two piperazine protons is obscured by water peak. |

Example 27: Synthesis of 6-chloro-2-methyl-4-(4-(5-methylpyridin-3-yl)piperazine-1-carbonyl)phthalazin-1(2H)-one (Compound 245)

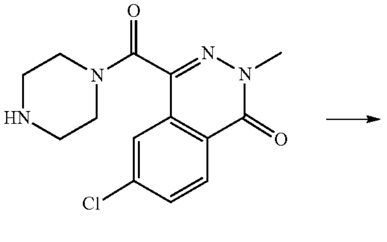

-continued

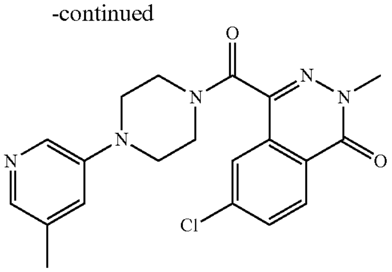

2-Methyl-4-(piperazine-1-carbonyl)phthalazin-1-one (70 mg, 0.257 mmol, 1.0 equiv.), 3-bromo-5-methylpyridine (0.051 mL, 0.440 mmol, 1.8 equiv.), DavePhos Pd G3 (19 mg, 0.0244 mmol, 0.1 equiv.) and sodium tert-butoxide (42 mg, 0.440 mmol, 1.8 equiv.) were suspended in CPME (2 mL) in a vial. The vial was sealed, evacuated and flushed with nitrogen twice. The solution was stirred at 100° C. for 2 hrs then allowed to rt. The mixture was partitioned between DCM and water and the phases separated. The organics were collected, and the solvent was removed. The material was purified by reverse phase HPLC (Luna Phenyl-Hexyl 21.2×150 mm, 10 μm 20-80% MeOH/water+0.1% formic acid, 20 m/min, rt) and the appropriate fractions were combined and lyophilized to yield the title compound (44 mg, 46%) as an off white solid. LCMS: Method A, m/z=398.2 $(M+H)^+$, RT=2.71 min. $^1H$ NMR (400 MHz, DMSO) δ 8.33 (d, J=8.6 Hz, 1H), 8.14 (d, J=2.8 Hz, 1H), 7.95 (dd, J=2.0, 8.6 Hz, 1H), 7.89 (s, 1H), 7.84 (d, J=2.0 Hz, 1H), 7.20 (s, 1H), 3.88 (t, J=5.1 Hz, 2H), 3.74 (s, 3H), 3.66-3.61 (m, 2H), 3.37 (t, J=5.3 Hz, 2H), 3.17 (t, J=4.9 Hz, 2H), 2.25 (s, 3H).

Example 28: Synthesis of 6-chloro-4-(4-(4-methoxypyridin-3-yl)piperazine-1-carbonyl)-2-methylphthalazin-1(2H)-one (Compound 246)

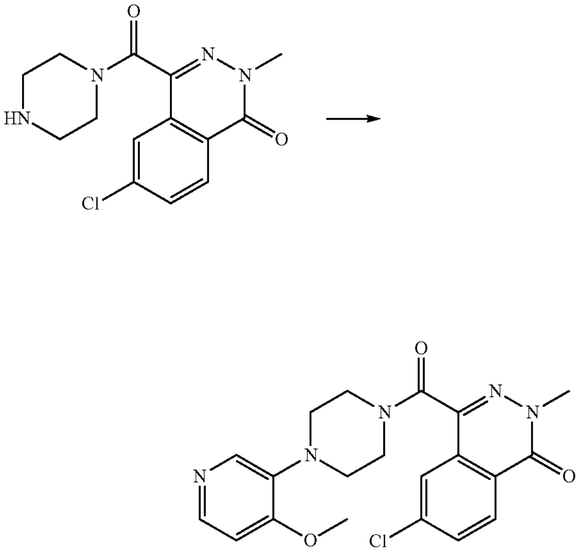

2-Methyl-4-(piperazine-1-carbonyl)phthalazin-1-one (70 mg, 0.257 mmol, 1.0 equiv.), 3-bromo-4-methoxy-pyridine (99 mg, 0.528 mmol, 1.8 equiv.), RuPhos Pd G3 (25 mg, 0.0293 mmol, 0.1 equiv.) and sodium tert-butoxide (51 mg, 0.528 mmol, 1.8 equiv.) were suspended in CPME (2 mL) in a vial. The vial was sealed, evacuated and flushed with nitrogen twice. The solution was stirred at 110° C. for 2 hrs then allowed to rt. The mixture was partitioned between DCM and water and the phases were separated. The organics were collected, and the solvent was removed. The material was purified by column chromatography on silica (12 g cartridge, 15 μM silica, 1-10% methanol/DCM) and the appropriate fractions were combined and the solvent removed to yield the title compound (54 mg, 44%) as an off white solid. LCMS: Method C, m/z=414.2 $(M+H)^+$, RT=2.78 min. $^1H$ NMR (400 MHz, DMSO) δ 8.32 (d, J=8.6 Hz, 1H), 8.16 (d, J=5.4 Hz, 1H), 8.06 (s, 1H), 7.95 (dd, J=2.0, 8.6 Hz, 1H), 7.82 (d, J=2.0 Hz, 1H), 7.01 (d, J=5.5 Hz, 1H), 3.89-3.86 (m, 5H), 3.73 (s, 3H), 3.61 (t, J=4.8 Hz, 2H), 3.17 (t, J=5.2 Hz, 2H), 2.99 (t, J=4.8 Hz, 2H).

Example 29: Synthesis of 4-(4-(2-methoxyphenyl)-1,2,3,6-tetrahydropyridine-1-carbonyl)-2-methylphthalazin-1(2H)-one (Compound 247)

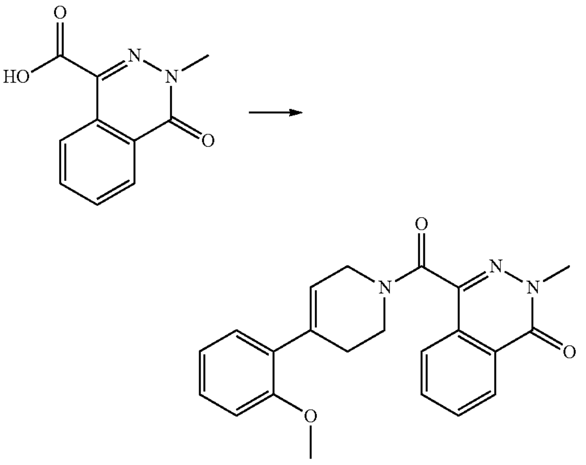

To a solution of 3-methyl-4-oxo-phthalazine-1-carboxylic acid (30 mg, 0.147 mmol, 1.0 equiv.) and 4-(2-methoxyphenyl)piperidin-4-ol (33 mg, 0.162 mmol, 1.1 equiv.) in DMF (2 mL) was added 1-hydroxybenzotriazole (22 mg, 0.162 mmol, 1.1 equiv.) and N-(3-dimethylaminopropyl)-N'-ethylcarbodiimide hydrochloride (34 mg, 0.176 mmol, 1.2 equiv.). The mixture was stirred at rt for 2 hrs. The mixture was partitioned between EtOAc and water and the phases were separated. The organics were collected, and the solvent was removed. The material was purified by reverse phase HPLC (Sunfire C18 19×150 mm, 10 μm 20-80% MeCN/water+0.1% formic acid, 20 mL/min, rt) and the appropriate fraction were combined and lyophilised to yield the title compound (8 mg, 15%) as an off-white solid. LCMS: Method A, m/z=376.1 $(M+H)^+$, RT=4.63 min. $^1H$ NMR (400 MHz, DMSO) δ 8.34 (d, J=7.7 Hz, 1H), 7.98-7.90 (m, 2H), 7.75 (t, J=7.3 Hz, 1H), 7.26 (t, J=7.8 Hz, 1H), 7.14 (dq, J=1.7, 10.2 Hz, 1H), 7.00 (d, J=8.1 Hz, 1H), 6.92 (ddd, J=7.3, 7.3, 7.3 Hz, 1H), 5.76 (d, J=103.6 Hz, 1H), 4.35 (d, J=2.9 Hz, 1H), 4.04 (d, J=3.2 Hz, 1H), 3.92 (t, J=5.7 Hz, 1H), 3.78-3.74 (m, 6H), 3.55 (t, J=5.4 Hz, 1H), 2.63 (d, J=30.2 Hz, 1H), 2.42 (s, 1H).

Example 30: Synthesis of 4-(4-(4-methoxyphenyl)-4-methylpiperidine-1-carbonyl)-2-methylphthalazin-1(2H)-one (Compound 248) and 4-(4-(2-methoxyphenyl)-4-methylpiperidine-1-carbonyl)-2-methylphthalazin-1(2H)-one (Compound 249)

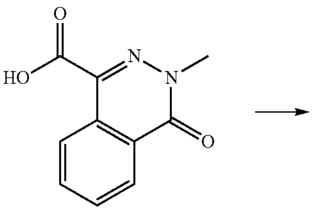

-continued

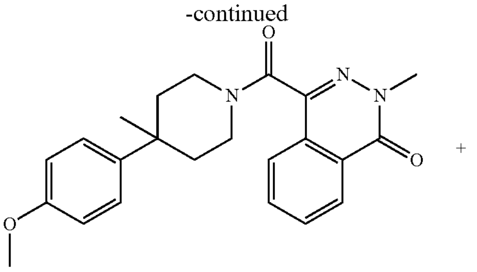

Compound 248

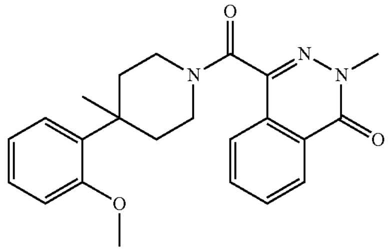

Compound 249

Step 1: Synthesis of 1-benzyl-4-(2-methoxyphenyl)-4-methyl-piperidine and 1-benzyl-4-(4-methoxyphenyl)-4-methyl-piperidine: To a solution of 1-benzyl-4-methylene-piperidine (200 mg, 1.07 mmol, 1.0 equiv.) in anisole (2.0 mL, 18.4 mmol, 17.2 equiv.) was added trifluoromethane-sulfonic acid (3.0 mL, 34.2 mmol, 32.0 equiv.) and the mixture was stirred at rt for 3 hrs. The mixture was poured on ice, then basified with 2 M aq. NaOH. The mixture was extracted with chloroform (2×15 mL) and the organic phases were combined, dried with magnesium sulfate, filtered, the filtrate collected and the solvent was removed. The material was loaded onto an SCX-2 cartridge, washed with DCM, then eluted with 50% (7 M ammonia in MeOH)/DCM. The appropriate fractions were collected and the solvent was removed. The material was redissolved in DCM and washed with brine (25 ml). The organics were dried with magnesium sulfate, filtered, the filtrate collected and the solvent was removed to yield the title compounds (245 mg, 77%) as a yellow oil. The material was used directly to the next step without further purification.

Step 2: Synthesis of 4-(2-methoxyphenyl)-4-methylpiperidine and 4-(4-methoxyphenyl)-4-methylpiperidine: To a solution of 1-benzyl-4-(2-methoxyphenyl)-4-methyl-piperidine (128 mg, 0.432 mmol, 1.0 equiv.) and 1-benzyl-4-(4-methoxyphenyl)-4-methyl-piperidine (128 mg, 0.432 mmol, 1.0 equiv.) in IMS (3 mL) was added a suspension of 10% palladium on carbon (92 mg, 0.0863 mmol, 0.2 equiv.) in EtOAc (3 mL). The flask was evacuated, then flushed with hydrogen and the mixture was stirred under an atmosphere of hydrogen for 18 hrs. The mixture was filtrated through a short pad of Celite™, the filtrate was collected, and the solvent was removed. The material was used directly to the next step without further purification.

Step 3: Synthesis of 4-(4-(4-methoxyphenyl)-4-methylpiperidine-1-carbonyl)-2-methylphthalazin-1(2H)-one and 4-(4-(2-methoxyphenyl)-4-methylpiperidine-1-carbonyl)-2-methylphthalazin-1(2H)-one: To a solution of 3-methyl-4-oxo-phthalazine-1-carboxylic acid (176 mg, 0.863 mmol, 2.0 equiv.), HATU (500 mg, 1.31 mmol, 3.05 equiv.) and DIPEA (0.35 mL, 2.01 mmol, 4.66 equiv.) in DMF (2.5 mL) was added a solution of 4-(2-methoxyphenyl)-4-methylpiperidine and 4-(4-methoxyphenyl)-4-methylpiperidine (the material obtained from the previous step) in DMF (0.5 mL). The mixture was stirred at rt for 20 hrs and then the solvent was removed. The material was purified by column chromatography on silica (0-5% MeOH/DCM) then further purified by reverse phase HPLC (Sunfire C18 19×150 mm, 10 μm, 20-80% MeCN/water+0.1% formic acid, 20 mL/min, rt) and the appropriate fractions were combined and lyophilized to yield the title compounds Example 32 (48 mg, 28%) and Example 33 (80 mg, 47%) as off-white solids.

Compound 248: LCMS: Method B, m/z=392.4 $(M+H)^+$, RT=4.64 min. $^1H$ NMR (400 MHz, DMSO) δ 8.34-8.30 (m, 1H), 7.95-7.88 (m, 2H), 7.73-7.69 (m, 1H), 7.32-7.26 (m, 2H), 6.92-6.87 (m, 2H), 3.84-3.78 (m, 1H) 3.73 (s, 3H), 3.71 (s, 3H), 3.69-3.62 (m, 1H), 3.46-340 (m, 1H), 3.27-3.22 (m, 1H), 2.16-2.07 (m, 1H), 1.94-1.77 (m, 2H), 1.63-1.56 (m, 1H), 1.22 (s, 3H).

Compound 249: LCMS: Method B, m/z=392.4 $(M+H)^+$, RT=4.86 min. $^1H$ NMR (400 MHz, DMSO) δ 8.32 (dd, J=2.0, 6.8 Hz, 1H), 7.95-7.88 (m, 2H), 7.71 (dd, J=1.8, 7.1 Hz, 1H), 7.25-7.20 (m, 2H), 7.03-7.00 (m, 1H), 6.94-6.90 (m, 1H), 3.87-3.81 (m, 1H), 3.78 (s, 3H), 3.73-3.67 (m, 4H), 3.46-3.40 (m, 2H), 2.34-2.24 (m, 1H), 2.12-2.04 (m, 1H), 1.94-1.87 (m, 1H), 1.74-1.69 (m, 1H), 1.35 (s, 3H).

Example 31: Cell Viability Assays

Phthalazinone based modulators as described herein were dispensed into 384 well CulturPlates™ (PerkinElmer) using Echo 555 acoustic dispensing in 10-point dose response curves at a final top concentration of 30 μM following a 1 in 3 dilution series. A2058 (ATCC, CRL-11147) or PA1 (ECACC, 90013101) cells were added directly to a compound at a density of 5000 cells per well in a final volume of 50 μL and incubated for 72 hours at 37° C., 5% $CO_2$. Viability was assessed using Cell Titre Glo® (Promega) according to the manufacturer's instructions (25 μL per well) and $IC_{50}$ curves were generated for each inhibitor using IDBS ActivityBase data analysis software.

Table 18 provides $IC_{50}$ values for cell viability in A2058, or PA1 for selected compounds; with compounds having a $IC_{50}$ of less than or equal to 1 μM as A; 1 μM>B≥10 μM as B; 10 μM>C≥20 μM as C; and greater than 20 μM as D.

TABLE 18

Cell Viability Studies in A2058 and PA1 Cell Lines For Select Compounds

| Compound No. | A2058 $IC_{50}$ (μM) | PA1 $IC_{50}$ (μM) |
|---|---|---|
| 1 | B | B |
| 2 | C | B |
| 3 | B | A |
| 4 | D | C |
| 5 | D | C |
| 6 | D | D |
| 7 | D | D |
| 8 | D | D |
| 9 | B | A |
| 10 | D | D |
| 11 | D | D |
| 12 | C | C |
| 13 | C | B |
| 14 | B | A |
| 15 | B | A |
| 16 | C | B |
| 17 | A | A |
| 18 | D | D |
| 19 | B | A |
| 20 | B | B |
| 21 | D | B |

TABLE 18-continued

| Cell Viability Studies in A2058 and PA1 Cell Lines For Select Compounds | | |
|---|---|---|
| Compound No. | A2058 $IC_{50}$ (μM) | PA1 $IC_{50}$ (μM) |
| 22 | D | D |
| 23 | A | A |
| 24 | D | D |
| 25 | A | A |
| 26 | D | D |
| 27 | B | B |
| 28 | D | D |
| 29 | D | D |
| 30 | B | B |
| 31 | D | D |
| 32 | D | D |
| 33 | A | A |
| 34 | A | A |
| 35 | B | B |
| 36 | D | D |
| 37 | A | A |
| 38 | C | B |
| 40 | B | B |
| 41 | A | A |
| 42 | A | A |
| 43 | B | B |
| 44 | A | A |
| 45 | A | A |
| 46 | B | B |
| 47 | A | A |
| 48 | A | A |
| 49 | A | A |
| 50 | A | A |
| 51 | D | C |
| 52 | A | A |
| 53 | B | B |
| 54 | A | A |
| 55 | D | C |
| 56 | A | A |
| 57 | B | A |
| 58 | B | A |
| 59 | B | B |
| 60 | A | A |
| 61 | A | A |
| 62 | A | A |
| 63 | D | D |
| 64 | D | B |
| 65 | D | D |
| 66 | B | A |
| 67 | A | A |
| 68 | A | A |
| 69 | B | B |
| 70 | A | A |
| 71 | A | A |
| 72 | B | B |
| 73 | B | B |
| 74 | D | D |
| 75 | A | A |
| 76 | C | B |
| 77 | B | B |
| 78 | B | B |
| 79 | C | C |
| 80 | A | A |
| 81 | B | A |
| 82 | D | C |
| 83 | B | A |
| 84 | A | A |
| 85 | B | B |
| 86 | D | D |
| 87 | D | D |
| 88 | A | A |
| 89 | D | D |
| 90 | D | D |
| 91 | D | D |
| 92 | A | A |
| 93 | B | B |
| 94 | C | B |
| 95 | A | A |
| 96 | B | A |

TABLE 18-continued

| Cell Viability Studies in A2058 and PA1 Cell Lines For Select Compounds | | |
|---|---|---|
| Compound No. | A2058 $IC_{50}$ (μM) | PA1 $IC_{50}$ (μM) |
| 97 | D | C |
| 98 | B | B |
| 99 | B | B |
| 100 | B | A |
| 101 | A | A |
| 102 | A | A |
| 103 | A | A |
| 104 | B | B |
| 105 | A | A |
| 106 | B | B |
| 107 | D | D |
| 108 | A | A |
| 109 | B | B |
| 110 | B | B |
| 111 | D | D |
| 112 | D | D |
| 113 | D | D |
| 114 | B | A |
| 115 | A | A |
| 116 | A | A |
| 117 | A | A |
| 118 | A | A |
| 119 | A | A |
| 120 | B | B |
| 121 | A | A |
| 122 | B | A |
| 123 | D | D |
| 124 | A | A |
| 125 | D | C |
| 126 | A | A |
| 127 | D | D |
| 128 | B | A |
| 129 | D | D |
| 130 | A | A |
| 131 | B | B |
| 132 | B | A |
| 133 | D | C |
| 134 | A | A |
| 135 | A | A |
| 136 | C | B |
| 137 | D | C |
| 138 | A | A |
| 139 | D | D |
| 140 | B | B |
| 141 | D | D |
| 142 | A | A |
| 143 | A | A |
| 144 | A | A |
| 145 | B | A |
| 146 | A | A |
| 147 | B | B |
| 148 | A | A |
| 149 | C | B |
| 150 | A | A |
| 151 | C | B |
| 152 | D | D |
| 153 | B | B |
| 154 | B | B |
| 155 | A | A |
| 156 | B | B |
| 157 | A | A |
| 158 | A | A |
| 159 | A | A |
| 161 | D | D |
| 162 | B | A |
| 163 | D | D |
| 164 | D | D |
| 165 | B | B |
| 166 | A | A |
| 167 | A | A |
| 168 | B | A |
| 169 | B | A |
| 170 | D | D |
| 171 | D | D |

TABLE 18-continued

Cell Viability Studies in A2058 and PA1 Cell Lines For Select Compounds

| Compound No. | A2058 $IC_{50}$ (μM) | PA1 $IC_{50}$ (μM) |
|---|---|---|
| 172 | B | B |
| 173 | B | A |
| 174 | C | B |
| 175 | B | A |
| 176 | A | A |
| 177 | A | A |
| 178 | D | D |
| 179 | B | B |
| 180 | B | A |
| 181 | A | A |
| 182 | D | D |
| 183 | D | C |
| 184 | C | B |
| 185 | B | B |
| 186 | A | A |
| 187 | A | A |
| 188 | A | A |
| 189 | A | A |
| 190 | A | A |
| 191 | D | D |
| 192 | C | B |
| 193 | D | D |
| 194 | C | B |
| 195 | C | C |
| 196 | D | D |
| 197 | B | A |
| 198 | A | A |
| 199 | A | A |
| 200 | B | B |
| 201 | A | A |
| 202 | D | D |
| 203 | D | D |
| 204 | D | D |
| 205 | A | A |
| 206 | A | A |
| 207 | A | A |
| 208 | B | A |
| 209 | C | C |
| 210 | B | A |
| 211 | A | A |
| 212 | A | A |
| 213 | A | A |
| 214 | B | A |
| 215 | B | A |
| 216 | A | A |
| 217 | A | A |
| 218 | A | A |
| 219 | B | B |
| 220 | B | B |
| 221 | A | A |
| 222 | A | A |
| 223 | B | A |
| 224 | A | A |
| 225 | A | A |
| 226 | D | D |
| 227 | D | D |
| 228 | C | B |
| 229 | A | A |
| 230 | B | A |
| 231 | D | D |
| 232 | A | A |
| 233 | B | A |
| 234 | D | D |
| 235 | A | A |
| 236 | A | A |
| 237 | A | A |
| 238 | A | A |
| 239 | A | A |
| 240 | A | A |
| 241 | A | A |
| 242 | A | A |
| 243 | B | A |
| 244 | A | A |
| 245 | D | C |
| 246 | B | A |
| 247 | A | A |
| 248 | B | C |
| 249 | B | B |

What is claimed is:

1. A compound represented by the structure of Formula (II):

(II)

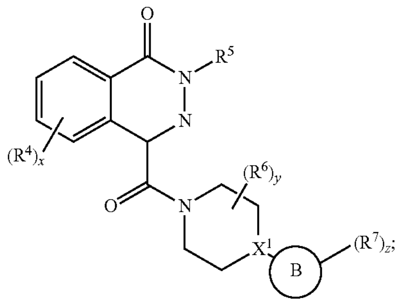

or a pharmaceutically acceptable salt thereof wherein:

$X^1$ is N;

$R^4$ is independently selected at each occurrence from (a), (b), and (c):

(a) halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, and —CN;

(b) $C_{1-6}$ alkyl optionally substituted with one or more substituents independently selected from halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, =S, =O, and —CN; and (c) $C_{3-10}$ carbocycle and 3- to 10-membered heterocycle, any of which is optionally substituted with one or more substituents independently selected from halogen, —$OR^{20}$, —$SR^{20}$, —$N(R^{20})_2$, —$C(O)R^{20}$, —$C(O)OR^{20}$, —$OC(O)R^{20}$, —$OC(O)N(R^{20})_2$, —$C(O)N(R^{20})_2$, —$N(R^{20})C(O)R^{20}$, —$N(R^{20})C(O)OR^{20}$, —$N(R^{20})C(O)N(R^{20})_2$, —$N(R^{20})S(O)_2(R^{20})$, —$S(O)R^{20}$, —$S(O)_2R^{20}$, —$S(O)_2N(R^{20})_2$, —$NO_2$, =S, =O, and —CN;

$R^5$ is $C_{1-6}$ alkyl optionally substituted with one or more substituents independently selected from: halogen, —$OR^{21}$, —$SR^{21}$, —$N(R^{21})_2$, —$C(O)R^{21}$, —$C(O)OR^{21}$, —$OC(O)R^{21}$, —$OC(O)N(R^{21})_2$, —$C(O)N(R^{21})_2$, —$N(R^{21})C(O)R^{21}$, —$N(R^{21})C(O)OR^{21}$, —$N(R^{21})C(O)N(R^{21})_2$, —$N(R^{21})S(O)_2(R^{21})$, —$S(O)R^{21}$, —$S(O)_2R^{21}$, —$S(O)_2N(R^{21})_2$, —$NO_2$, =S, =O, and —CN;

$R^6$ is independently selected at each occurrence from:

$C_{1-6}$ alkyl optionally substituted with one or more substituents independently selected from halogen, —$OR^{22}$, —$SR^{22}$, —$N(R^{22})_2$, —$C(O)R^{22}$,—$C(O)OR^{22}$, —$OC(O)R^{22}$, —$OC(O)N(R^{22})_2$, —$C(O)N(R^{22})_2$, —$N(R^{22})C(O)R^{22}$, —$N(R^{22})C(O)OR^{22}$, —$N(R^{22})C(O)N(R^{22})_2$, —$N(R^{22})S(O)_2(R^{22})$, —$S(O)R^{22}$, —$S(O)_2R^{22}$, —$S(O)_2N(R^{22})_2$, —$NO_2$, =S, =O, and —CN;

Ring B is selected from $C_{3-10}$ carbocycle and 3- to 10-membered heterocycle;

$R^7$ is independently selected at each occurrence from:

halogen, —$OR^{23}$, —$SR^{23}$, —$N(R^{23})_2$, —$C(O)R^{23}$, —$OC(O)R^{23}$, —$OC(O)N(R^{23})_2$, —$C(O)N(R^{23})_2$, —$N(R^{23})C(O)R^{23}$, —$N(R^{23})C(O)OR^{23}$, —$N(R^{23})C(O)N(R^{23})_2$, —$N(R^{23})S(O)_2(R^{23})$, —$S(O)R^{23}$, —$S(O)_2R^{23}$, —$S(O)_2N(R^{23})_2$, —$NO_2$, and —CN; and $C_{1-6}$ alkyl optionally substituted with one or more substituents independently selected from halogen, —$OR^{23}$, —$SR^{23}$, —$N(R^{23})_2$, —$C(O)R^{23}$, —$C(O)OR^{23}$, —$OC(O)R^{23}$, —$OC(O)N(R^{23})_2$, —$C(O)N(R^{23})_2$, —$N(R^{23})C(O)R^{23}$, —$N(R^{23})C(O)OR^{23}$, —$N(R^{23})C(O)N(R^{23})_2$, —$N(R^{23})S(O)_2(R^{23})$, —$S(O)R^{23}$, —$S(O)_2R^{23}$, —$S(O)_2N(R^{23})_2$, —$NO_2$, =S, =O, and —CN;

$R^{20}$, $R^{21}$, $R^{22}$, and $R^{23}$, are each independently selected at each occurrence from (d), (e), and (f):

(d) hydrogen;

(e) $C_{1-6}$ alkyl optionally substituted with one or more substituents independently selected from halogen, —O—$C_{1-6}$ alkyl, —O—$C_{1-6}$ haloalkyl, —$NH_2$, —$NO_2$, =O, —CN, $C_{3-10}$ carbocycle and 3- to 10-membered heterocycle, wherein each $C_{3-10}$ carbocycle and 3- to 10-membered heterocycle are optionally substituted with one or more substituents independently selected from: halogen, —OH, —O—$C_{1-6}$ alkyl, —O—$C_{1-6}$ haloalkyl, —$NH_2$, —$NO_2$, =O, and —CN; and (f) $C_{3-10}$ carbocycle and 3- to 10-membered heterocycle optionally substituted with one or more substituents independently selected from: halogen, —OH, —O—$C_{1-6}$ alkyl, —O—$C_{1-6}$ haloalkyl, —$NH_2$, —$NO_2$, =O, and —CN;

x is selected from 0, 1, 2, 3, and 4;

y is selected from 0, 1, 2, 3, and 4; and z is selected from 0, 1, 2, 3, 4 and 5; wherein at least one of x or y is selected from 1, 2, 3, and 4.

2. The compound or salt of claim 1, wherein x is selected from 0 and 1.

3. The compound or salt of claim 1, wherein $R^4$ is selected from:

halogen, —$OR^{20}$, —$N(R^{20})_2$, —$C(O)R^{20}$, —$NO_2$, and —CN; and $C_{1-3}$ alkyl, $C_{3-6}$ carbocycle, and 3- to 6-membered heterocycle, any of which is optionally substituted with one or more substituents independently selected from: halogen, —$OR^{20}$, —$N(R^{20})_2$, —$C(O)R^{20}$, —$NO_2$, and —CN; and each $R^{20}$ is independently selected from hydrogen, $C_{1-4}$ alkyl, and $C_{1-4}$ haloalkyl.

4. The compound or salt of claim 1, wherein each $R^4$ is independently selected from: fluoro, chloro, bromo, —O—$C_{1-6}$ alkyl, —$N(CH_3)_2$, —CN,

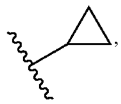, and 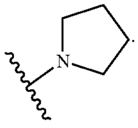.

5. The compound or salt of claim 1, wherein y is selected from 0 and 1.

6. The compound or salt of claim 1, wherein $R^5$ is $C_{1-3}$ alkyl optionally substituted with one or more substituents independently selected from halogen, —$OR^{21}$, —$N(R^{21})_2$, —$C(O)R^{21}$, —$NO_2$, =S, =O, and —CN; and $R^{21}$ is selected from hydrogen and $C_{1-3}$ alkyl.

7. The compound or salt of claim 1, wherein z is selected from 0, 1, and 2.

8. The compound or salt of claim 1, wherein $R^7$ is selected from halogen, —$OR^{23}$, —$N(R^{23})_2$, —$C(O)R^{23}$, —$NO_2$, —CN; and $C_{1-6}$ alkyl optionally substituted with one or more substituents independently selected from halogen, —$OR^{23}$, —$N(R^{23})_2$, —$C(O)R^{23}$, —$NO_2$, and —CN; and $R^{23}$ is selected from hydrogen and $C_{1-3}$ alkyl.

9. The compound or salt of claim 1, wherein

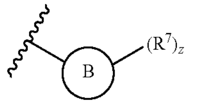

is selected from:

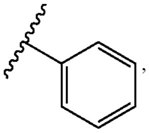, 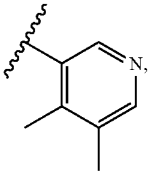, 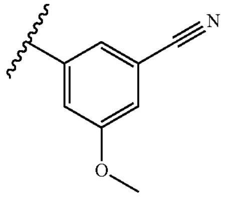,

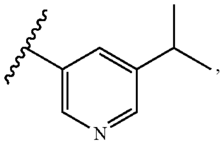, 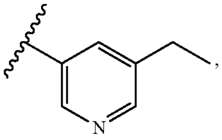,

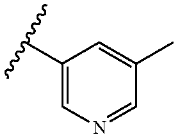, 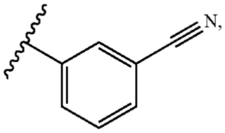,

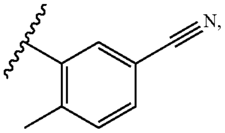, 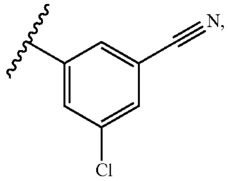,

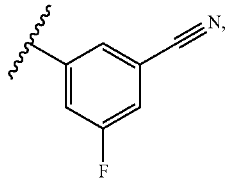, 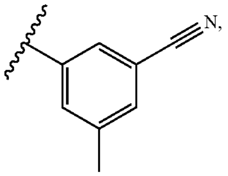,

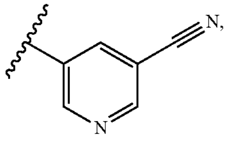, 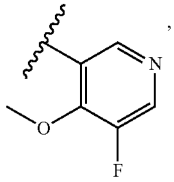,

-continued
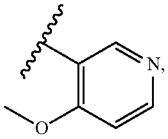 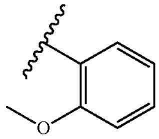,
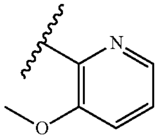, and 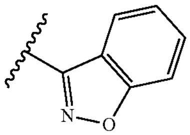.
10. The compound of claim 1, wherein the compound is selected from the group consisting of:
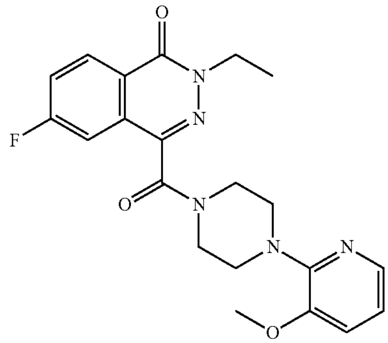,
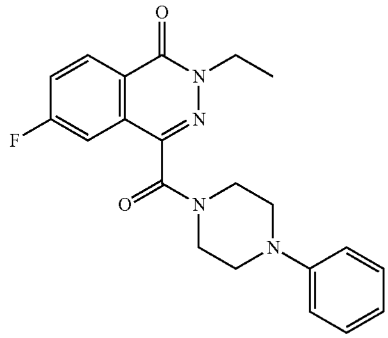,
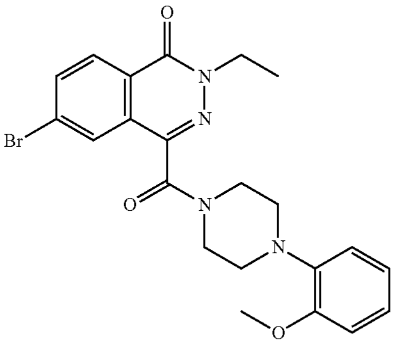,
-continued
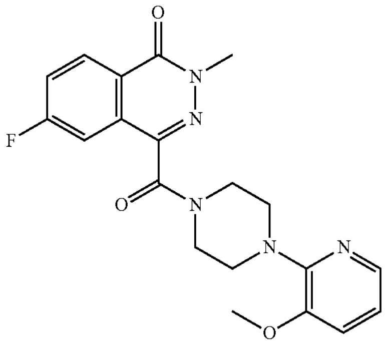,
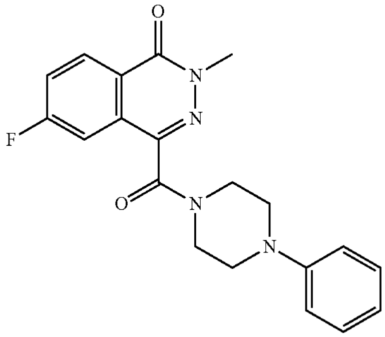,
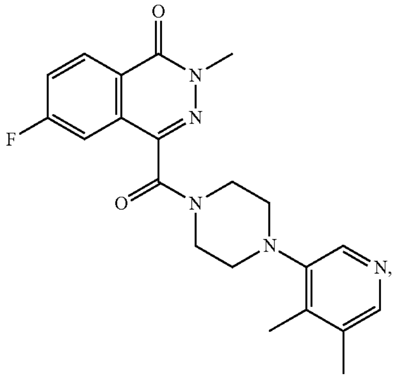
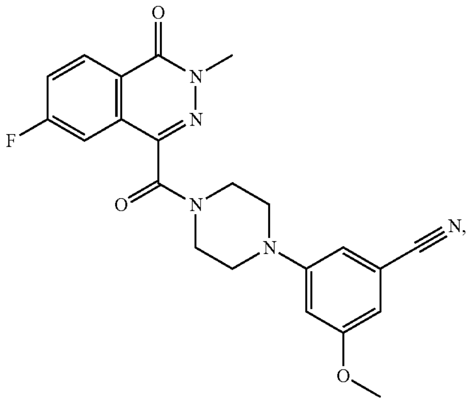

-continued
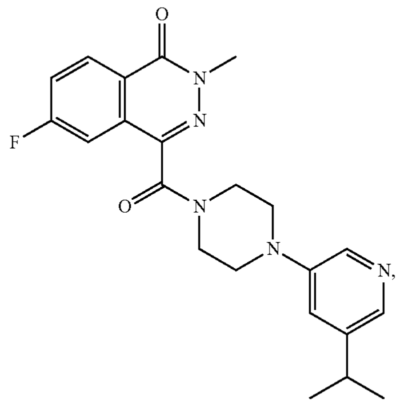
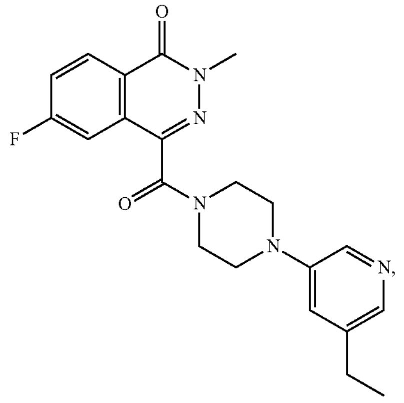
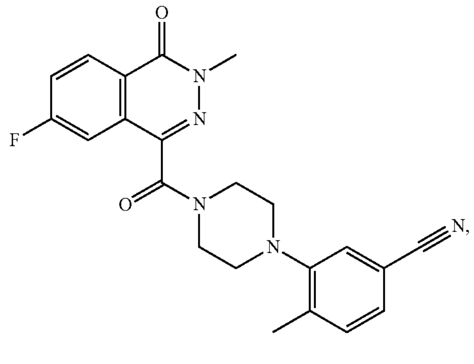
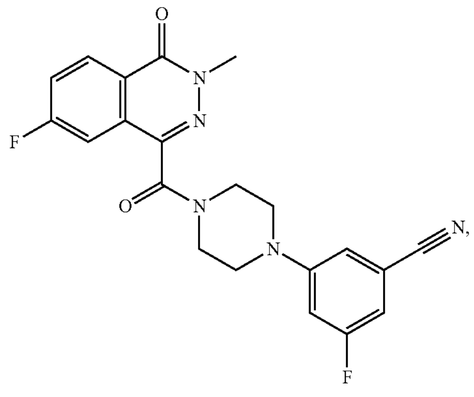
-continued
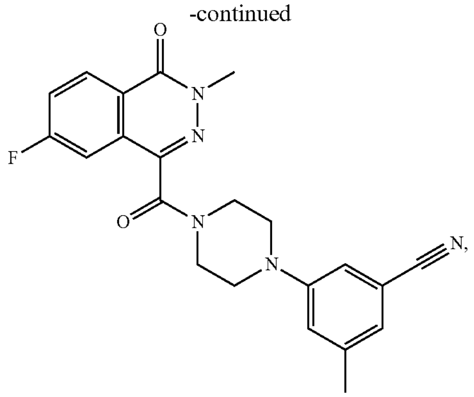
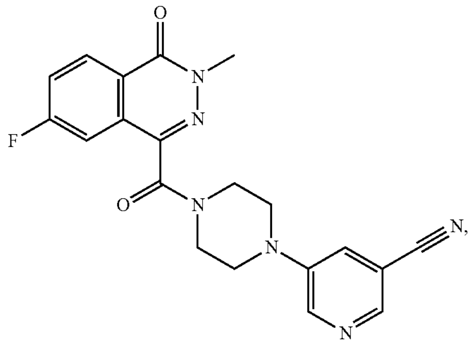
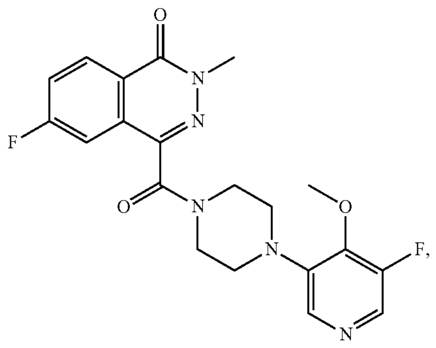
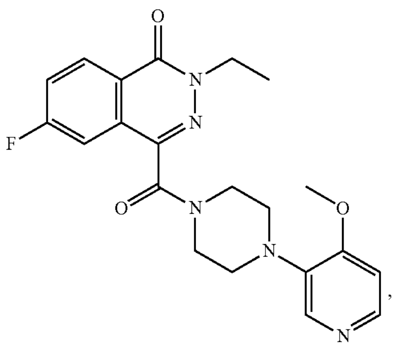

-continued
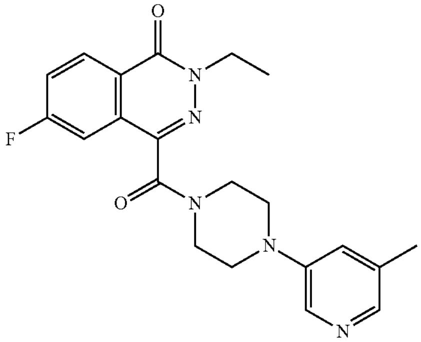
,
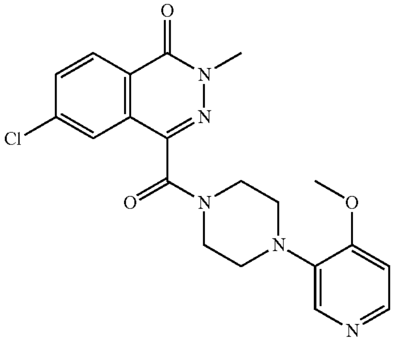
,
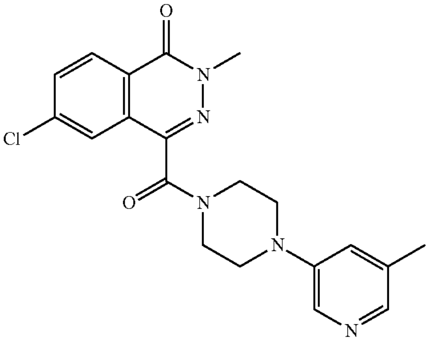
,
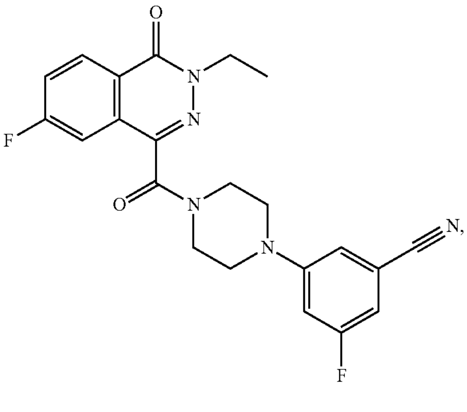
,
-continued
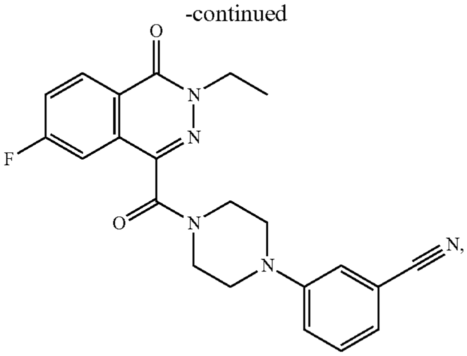
,
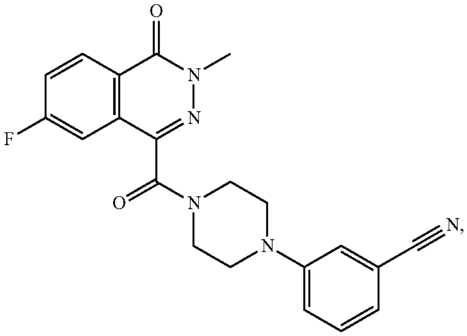
,
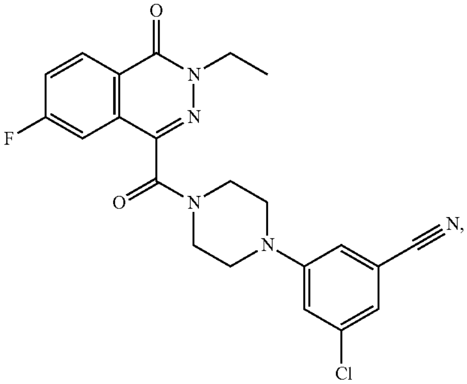
,
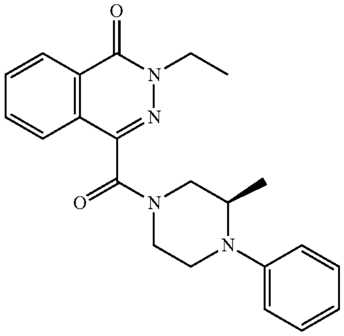
,
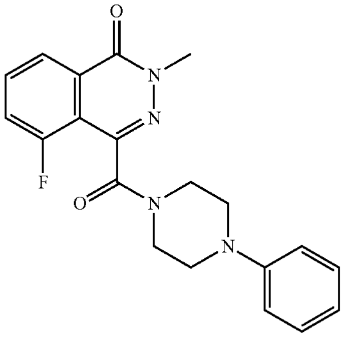
, -continued
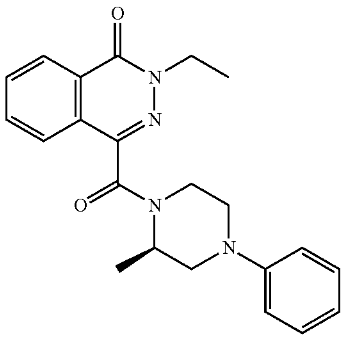
,
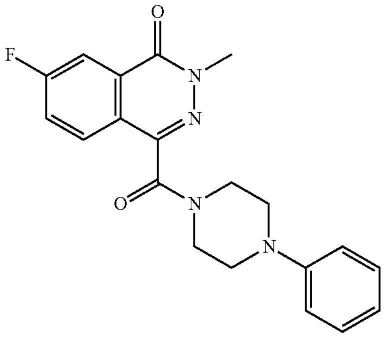
,
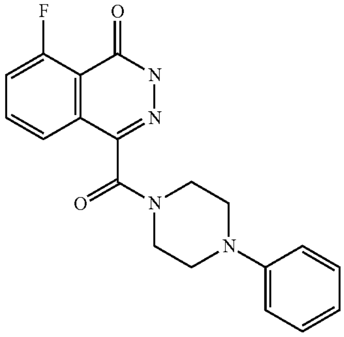
,
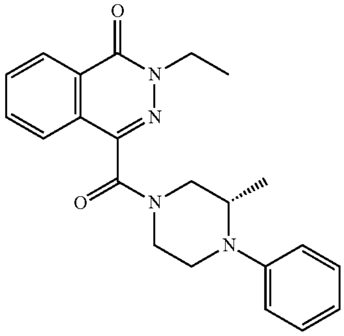
,
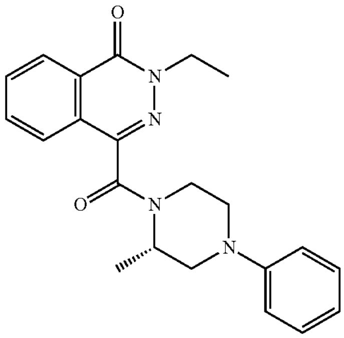
,
-continued
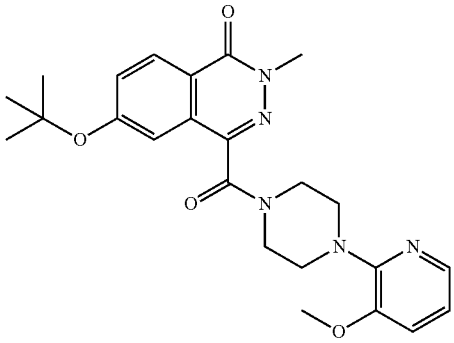
,
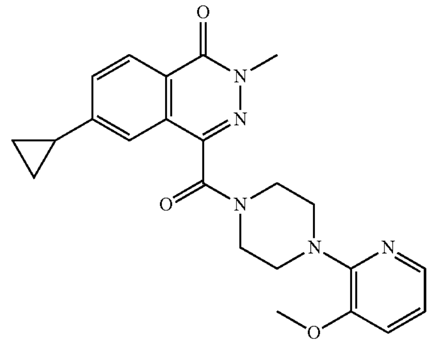
,
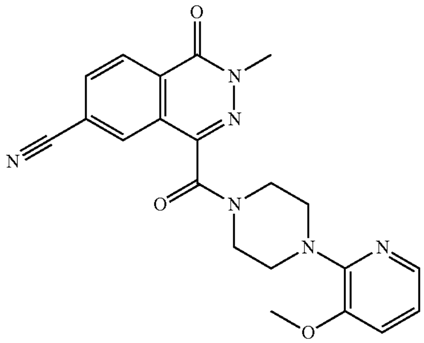
,
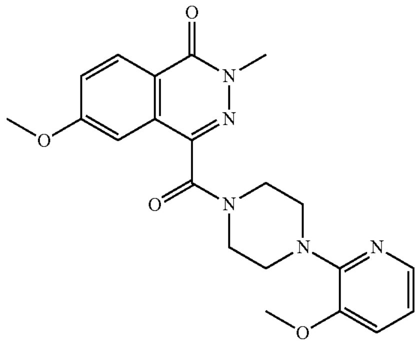
,
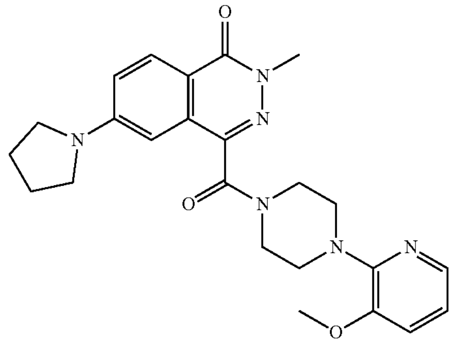
, -continued
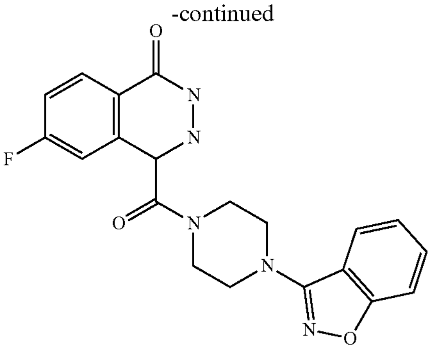
,
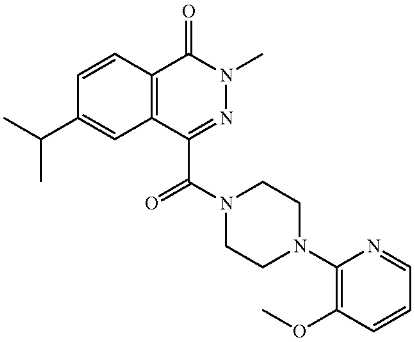
,
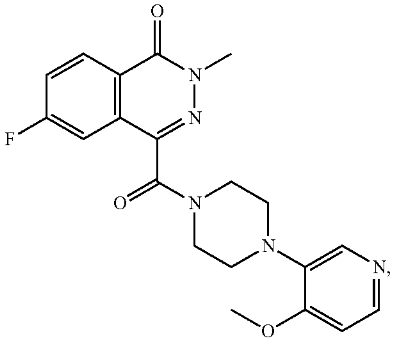
,
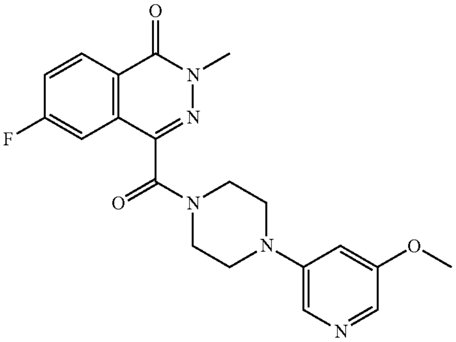
,
-continued
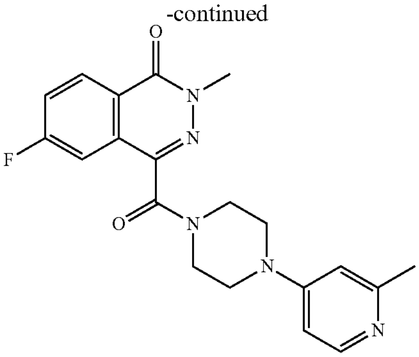
,
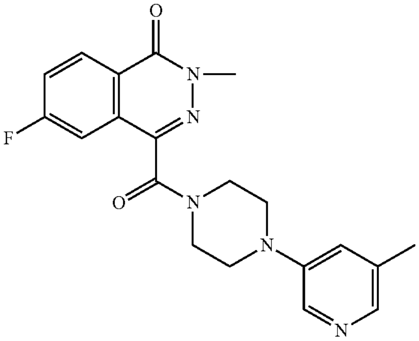
, and
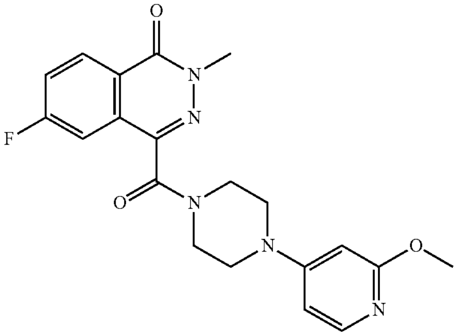
;
or a pharmaceutically acceptable salt of any one thereof.
* * * * *